US011286255B2

(12) United States Patent
Yamaguchi et al.

(10) Patent No.: US 11,286,255 B2
(45) Date of Patent: Mar. 29, 2022

(54) PYRIDONE CARBOXYLIC ACID DERIVATIVE OR SALT THEREOF

(71) Applicant: WAKUNAGA PHARMACEUTICAL CO., LTD., Osaka (JP)

(72) Inventors: Tomonori Yamaguchi, Akitakata (JP); Kenji Itoh, Akitakata (JP); Tatsuya Hirano, Akitakata (JP); Rumiko Shimabara, Akitakata (JP); Yohei Kawakubo, Akitakata (JP); Masayuki Sato, Akitakata (JP); Junpei Yamashita, Akitakata (JP); Akira Yazaki, Akitakata (JP); Taichi Ueshima, Akitakata (JP)

(73) Assignee: WAKUNAGA PHARMACEUTICAL CO., LTD., Osaka (JP)

( * ) Notice: Subject to any disclaimer, the term of this patent is extended or adjusted under 35 U.S.C. 154(b) by 0 days.

(21) Appl. No.: 16/496,145

(22) PCT Filed: Mar. 23, 2018

(86) PCT No.: PCT/JP2018/011848
§ 371 (c)(1),
(2) Date: Sep. 20, 2019

(87) PCT Pub. No.: WO2018/174266
PCT Pub. Date: Sep. 27, 2018

(65) Prior Publication Data

US 2020/0062752 A1 Feb. 27, 2020

(30) Foreign Application Priority Data

Mar. 24, 2017 (JP) ............................. JP2017-059192

(51) Int. Cl.
*C07D 519/00* (2006.01)
*C07D 471/04* (2006.01)
*A61P 35/00* (2006.01)

(52) U.S. Cl.
CPC ......... *C07D 471/04* (2013.01); *C07D 519/00* (2013.01); *A61P 35/00* (2018.01)

(58) Field of Classification Search
CPC ...... C07D 471/04; C07D 519/00; A61P 35/00
(Continued)

(56) References Cited

U.S. PATENT DOCUMENTS 5,412,098 A 5/1995 Yasuhiro et al.
5,817,669 A 10/1998 Tomita et al.

FOREIGN PATENT DOCUMENTS

JP 9-221424 A 9/1997
JP 5079612 B2 11/2012
(Continued)

OTHER PUBLICATIONS

Bisacchi, G.S. et al, "A "Double-Edged" Scaffold: Antitumor Power within the Antibacterial Quinolone," Current Medicinal Chemistry, 2016, vol. 23, No. 6, pp. 520-577.
Hoch, U., et al., "Voreloxin, formerly SNS-595, has potent activity against a broad panel of cancer cell lines and in vivo tumor models," Cancer, Chemotherapy and Pharmacology, 2009, vol. 64, No. 1, pp. 53-65.

(Continued)

*Primary Examiner* — Taylor V Oh

(74) *Attorney, Agent, or Firm* — Oblon, McClelland, Maier & Neustadt, L.L.P.

(57) ABSTRACT

It is intended to provide a novel compound having high antitumor activity and low toxicity to normal cells. The present invention provides a pyridone carboxylic acid derivative represented by the following formula (1) or a salt thereof wherein $R^1$ represents a hydrogen atom, a halogen atom or the like; $R^2$ represents a hydrogen atom, a halogen atom or the like; $R^3$ to $R^6$ each represent a hydrogen atom or the like; $R^7$ represents a hydrogen atom or the like; $R^8$ represents a hydrogen atom, a halogen atom, the following formula (a) (wherein $R^{a1}$ and $R^{a2}$ each represent a hydrogen atom, a hydroxy group, an optionally substituted lower alkyl group or the like) or the like, or $R^7$ and $R^8$ together represent $=N—OR^{10}$ (wherein $R^{10}$ represents a hydrogen atom, an optionally substituted lower alkyl group, or an aralkyl group), or $R^7$ and $R^8$ form an optionally substituted 4- to 6-membered saturated hetero ring together with the adjacent carbon atom, or the like; $R^9$ represents a hydrogen atom or the like; X represents a nitrogen atom or the like; and Y represents a nitrogen atom or the like.

(1)

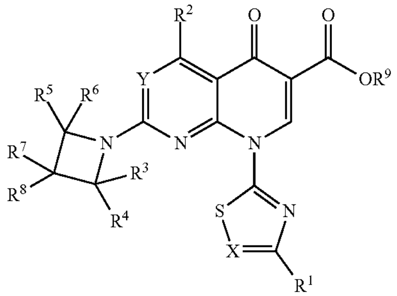

(a)

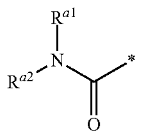

14 Claims, No Drawings

(58) Field of Classification Search
USPC .......................................................... 546/123
See application file for complete search history.

(56) References Cited

FOREIGN PATENT DOCUMENTS

| | | | |
|---|---|---|---|
| WO | WO 93/13091 | | 7/1997 |
| WO | WO 2011/056566 | A2 | 5/2011 |

OTHER PUBLICATIONS

Short, N.J. et al., "The safety and efficacy of vosaroxin in patients with first relapsed or refractory acute myeloid leukemia—a critical review," Expert Review of Hematology, 2016, vol. 9, No. 6, pp. 1-6.
Ravandi, F. et al, "Vosaroxin plus cytarabine versus placebo plus cytarabine in patients with first relapsed or refractory acute myeloid leukaemia (VALOR): a randomised, controlled, double-blind, multinational, phase 3 study," The Lancet Oncology, Jul. 31, 2015, vol. 16, No. 9 pp. 1-12.
Jia, X-D., "Synthesis and in vitro antitumor activity of novel naphthyridinone derivatives," Chinese Chemical Letters, Jul. 25, 2016, vol. 28, No. 2, pp. 235-239.
Tsuzuki, Y. et al, "Synthesis and Structure—Activity Relationships of Novel 7-Substituted 1, 4-Dihydro-4-oxo-1-(2-thiazolyl)-1,8-naphthyridine-3-carboxylic Acids as Antitumor Agents. Part 2," Journal of Medicinal Chemistry, 2004, vol. 47, No. 8 pp. 2097-2109.
International Search Report dated Jun. 5, 2018 in PCT/JP2018/011848 filed on Mar. 23, 2018.
Extended European Search Report dated Oct. 23, 2020 in European Patent Application No. 18770988.6, 9 pages.
Ikee, Y., et al., "Synthesis of New Quinolone Antibiotics Utilizing Azetidine Derivatives Obtained from 1-Azabicyclo[1.1.0]butane", Chem. Pharm. Bull., 2008, vol. 56 No. 3, pp. 346-356.

PYRIDONE CARBOXYLIC ACID DERIVATIVE OR SALT THEREOF

TECHNICAL FIELD

The present invention relates to a pyridone carboxylic acid derivative or a salt thereof which has an excellent cell growth inhibitory effect and is useful as an antitumor agent.

BACKGROUND ART

While pyridone carboxylic acid derivatives are known to have antimicrobial activity, certain pyridone carboxylic acid derivatives are also known to have antitumor activity or anticancer activity (Non Patent Literature 1). For example, it has been reported that pyridone carboxylic acid derivatives having a 2-thiazolyl group have an antitumor effect (Patent Literatures 1 and 2). Among them, 1,4-dihydro-7-(3-methoxy-4-methylamino-1-pyrrolidinyl)-4-oxo-1-(2-thiazolyl)-1,8-naphthyridine-3-carboxylic acid described in Patent Literature 1 has been confirmed to have an excellent antitumor effect in vitro and in vivo on human cancer cells (Non Patent Literatures 2 and 3). It has also been reported that in a phase III trial, the compound used in combination with cytarabine exhibits a significant therapeutic effect on relapsed/refractory acute myeloid leukemia in over-sixties as compared with a placebo group (Non Patent Literature 4).

However, even the compound does not exhibit a significant therapeutic effect in an overall survival targeting all patients, which is a primary endpoint, as compared with a placebo group (Non Patent Literature 5), and thus still has insufficient cell growth inhibitory activity and antitumor effect.

CITATION LIST

Patent Literature

Patent Literature 1: JP-B-5079612
Patent Literature 2: WO 2011/056566 A2

Non Patent Literature

Non Patent Literature 1: Current Medicinal Chemistry 23, 520 (2016)
Non Patent Literature 2: Journal of Medicinal Chemistry 47, 2097 (2004)
Non Patent Literature 3: Cancer Chemotherapy and Pharmacology 64, 53 (2009)
Non Patent Literature 4: Expert Review of Hematology 9, 529 (2016)
Non Patent Literature 5: The Lancet Oncology 16, 1025 (2015)

SUMMARY OF INVENTION

Technical Problem

An object of the present invention is to provide a novel compound having high antitumor activity and low toxicity to normal cells.

Solution to Problem

The present inventors have conducted diligent studies to attain the object and consequently completed the present invention by finding that a pyridone carboxylic acid compound having a substituted azetidinyl group at position 7 has an excellent antitumor effect and is useful as an antitumor agent.

Specifically, the present invention relates to the following [1] to [6].

[1] A pyridone carboxylic acid derivative represented by the following formula (1) or a salt thereof:

(1)

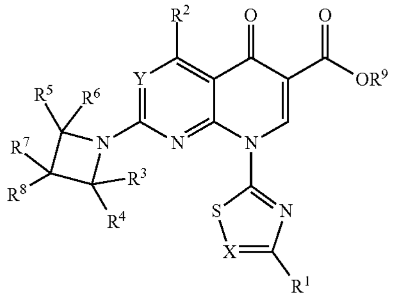

wherein $R^1$ represents a hydrogen atom, a halogen atom, a nitrile group, an optionally substituted lower alkyl group, an optionally substituted lower alkoxy group, an optionally substituted lower alkylamino group, a cyclo lower alkyl group, a cyclic amino group, an optionally substituted aryl group or an optionally substituted heteroaryl group;

$R^2$ represents a hydrogen atom, a halogen atom, a nitro group, a hydroxy group, an optionally substituted lower alkyl group, a lower alkoxy group, an amino group, an optionally substituted lower alkylamino group, a cyclo lower alkyl group, an optionally substituted 4- to 7-membered cyclic amino group or a $C_{1-17}$ alkanoylamino group;

$R^3$ to $R^6$ are the same or different and each represent a hydrogen atom, an optionally substituted lower alkyl group, a carboxy group, a lower alkoxycarbonyl group or an optionally substituted carbamoyl group;

$R^7$ represents a hydrogen atom, a halogen atom, a hydroxy group, an optionally substituted amino group, a carboxy group, a nitrile group, an optionally substituted lower alkyl group or a lower alkoxy group;

$R^8$ represents a hydrogen atom, a halogen atom, a hydroxy group, an optionally substituted lower alkyl group, an optionally substituted lower alkenyl group, an optionally substituted cyclo lower alkyl group, an optionally substituted lower alkoxy group, an optionally substituted lower alkylaminocarbonylalkyl group, a lower alkanoyloxy group, a lower alkanoylthio group, an arylcarbonylthio group, a thiol group, —SS—$R^{8a}$(wherein $R^{8a}$ represents an optionally substituted lower alkyl group) or a group represented by any of the following 1) to 7):

1) the following formula (a):

(a)

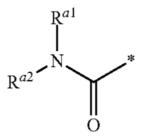

wherein $R^{a1}$ and $R^{a2}$ are the same or different and each represent a hydrogen atom, a hydroxy group, an optionally substituted lower alkyl group, an optionally substituted lower alkenyl group, an optionally substituted lower alkynyl group, an optionally substituted lower alkoxy group, an optionally substituted $C_{2-12}$ alkyl or alkoxy group having an ether bond(s), an optionally substituted heteroarylamino group, an optionally substituted nitrogen-containing bicyclic heteroaryl group, —$R^{a3}$-$Cy^1$ (wherein $R^{a3}$ represents a single bond, an optionally halogen atom-substituted divalent hydrocarbon group or an oxy group, and $Cy^1$ represents an optionally substituted cyclo lower alkyl group, an optionally substituted 4- to 7-membered cyclic ether group, a N-substituted morpholinyl group, an oxazinanyl group or an isoxazolinyl group), an optionally substituted 5- or 6-membered heteroaryl group, an optionally substituted heteroaralkyl group, or the following group:

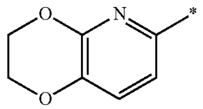

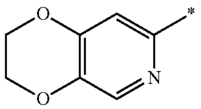

or $R^{a1}$ and $R^{a2}$ form an optionally substituted 4- to 9-membered cyclic amino group together with the adjacent nitrogen atom, and * represents a bonding site;

2) the following formula (b):

$(R^{b1})_m$ Het—* (b)

wherein Het represents a 4- to 6-membered heterocyclyl group, $R^{b1}$ is a substituent on the hetero ring wherein when a plurality of $R^{b1}$ are present, these substitutents are the same or different and each represent a halogen atom, a hydroxy group, an amino group, a nitro group, an amide group, a lower alkylamide group, a carboxy group, an optionally substituted lower alkyl group, an optionally substituted lower alkoxy group, a lower alkoxycarbonyl group, an optionally substituted 4- to 7-membered cyclic ether group, a lower alkylamino group, a lower alkanoylamino group or an oxy group, m represents an integer of 0 to 2, and * represents a bonding site;

3) the following formula (c):

$R^{c2}$—$R^{c1}$—* (C)

wherein $R^{c1}$ represents CO, SO or $SO_2$, $R^{c2}$ represents an optionally substituted lower alkyl group, an optionally substituted lower alkoxy group, an optionally substituted cyclo lower alkyl group, an optionally substituted 5- or 6-membered heteroaryl group, an optionally substituted aralkyl group or an optionally substituted heteroaralkyl group, and * represents a bonding site;

4) the following formula (d):

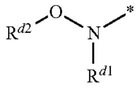

(d)

wherein $R^{d1}$ represents a hydrogen atom, an optionally substituted lower alkyl group or an optionally substituted $C_{1-17}$ alkanoyl group, $R^{d2}$ represents a hydrogen atom, an optionally substituted lower alkyl group, an optionally substituted aralkyl group or an optionally substituted heteroaralkyl group, and * represents a bonding site;

5) the following formula (e):

(e)

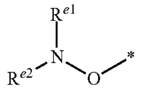

wherein $R^{e1}$ and $R^{e2}$ are the same or different and each represent a hydrogen atom, an optionally substituted lower alkyl group, an optionally substituted lower alkanoyl group, an optionally substituted aralkyl group or an optionally substituted 5- or 6-membered heteroaryl group, and * represents a bonding site;

6) the following formula (f):

(f)

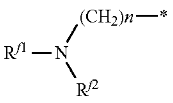

wherein $R^{f1}$ and $R^{f2}$ are the same or different and each represent a hydrogen atom, an optionally substituted lower alkyl group, an optionally substituted lower alkanoyl group or an optionally substituted 5- or 6-membered heteroaryl group, n represents an integer of 0 to 2, and * represents a bonding site; and 7) the following formula (g):

(g)

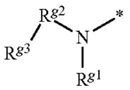

wherein $R^{g1}$ represents a hydrogen atom or an optionally substituted lower alkyl group, $R^{g2}$ represents CO, CS, SO or $SO_2$, $R^{g3}$ represents a hydrogen atom, an optionally substituted $C_{1-17}$ alkyl group, an optionally substituted lower alkoxy group, an optionally substituted lower alkylamino group, an optionally substituted 4- to 7-membered cyclic amino group, an optionally substituted 5- or 6-membered heteroaryl group or an optionally substituted 5- or 6-membered heteroarylamino group, and * represents a bonding site, or $R^7$ and $R^8$ together represent ═N—$OR^{10}$ (wherein $R^{10}$ represents a hydrogen atom, an optionally substituted lower alkyl group, or an aralkyl group) or ═O, or $R^7$ and $R^8$ form an optionally substituted 4- to 6-membered saturated hetero ring together with the adjacent carbon atom;

$R^9$ represents a hydrogen atom or an ester residue;

X represents a nitrogen atom or C—$R^{11}$ (wherein $R^{11}$ represents a hydrogen atom, a halogen atom, a nitrile group, a nitro group, a lower alkyl group, a lower alkoxy group, an optionally substituted thienyl group, or an optionally substituted phenyl group, or $R^1$ and $R^{11}$ forms a benzene ring or a naphthalene ring together with the adjacent carbon atom); and Y represents a nitrogen atom or C—$R^{12}$ (wherein $R^{12}$ represents a hydrogen atom, a halogen atom, a nitrile group or an optionally substituted lower alkyl group), except for the case where $R^7$ is an amino group and $R^8$ is a hydrogen atom and the case where $R^7$ is a hydrogen atom and $R^8$ is a methylamino group.

[2] A medicament comprising the pyridone carboxylic acid derivative according to [1] or a salt thereof and a pharmaceutically acceptable carrier.
[3] An antitumor agent comprising the pyridone carboxylic acid derivative according to [1] or a salt thereof as an active ingredient.
[4] Use of the pyridone carboxylic acid derivative according to [1] or a salt thereof for producing an antitumor agent.
[5] The pyridone carboxylic acid derivative according to [1] or a salt thereof for use in the prevention or treatment of a cancer.
[6] A method for preventing or treating a cancer, comprising administering the pyridone carboxylic acid derivative according to [1] or a salt thereof.

Advantageous Effects of Invention

The pyridone carboxylic acid derivative of the present invention or a salt thereof has an excellent growth inhibitory effect on cancer cell lines of solid and nonsolid tumors and low cytotoxicity to normal cells. Thus, the pyridone carboxylic acid derivative of the present invention or a salt thereof is useful as an antitumor agent for the prevention or treatment of various cancers.

DESCRIPTION OF EMBODIMENTS

Hereinafter, the present invention will be described in detail.

In the present specification, the term "lower" means that the number of carbon atoms in the hydrocarbon moiety of a group with this term is 1 to 12 for the chain hydrocarbon moiety and 3 to 12 for the cyclic hydrocarbon moiety, wherein the chain hydrocarbon moiety may be linear or branched, unless otherwise specified.

In the present specification, the number of carbon atoms (x to y carbon atoms) in the hydrocarbon moiety is abbreviated to "$C_{x-y}$".

The term "optionally substituted" means that a hydrogen atom of the group concerned may be replaced with another group. The number of the substituent may be one or more. When two or more substituents are present, the substituents may be the same or different.

Hereinafter, the symbols used in the formula (1) will be described.

Examples of the "halogen atom" represented by $R^1$ include fluorine, chlorine, bromine and iodine. Fluorine or chlorine is preferred.

The "lower alkyl group" represented by $R^1$ is preferably a $C_{1-7}$ alkyl group, more preferably a $C_{1-4}$ alkyl group such as a methyl group, an ethyl group, a propyl group, an isopropyl group, a butyl group, an isobutyl group, or a tert-butyl group, further preferably a methyl group, an ethyl group, or an isopropyl group.

Examples of the group which may be substituted on the lower alkyl group include a halogen atom (e.g., a fluorine atom), a hydroxy group, a $C_{1-7}$ alkoxy group (e.g., a methoxy group, an ethoxy group, and a propoxy group), a $C_{1-3}$ alkoxy $C_{1-7}$ alkoxy group (e.g., a methoxyethoxy group and an ethoxyethoxy group), an amino group, a $C_{1-7}$ alkylamino group (e.g., a methylamino group, an ethylamino group, a dimethylamino group, and a diethylamino group), a carboxy group, a $C_{1-7}$ alkoxycarbonyl group (e.g., a methoxycarbonyl group and an ethoxycarbonyl group), and a $C_{1-7}$ alkanoyl group (e.g., an acetyl group, an ethylcarbonyl group, a propylcarbonyl group, a butylcarbonyl group, a pentylcarbonyl group, and a hexylcarbonyl group).

The "lower alkoxy group" represented by $R^1$ is preferably a $C_{1-7}$ alkoxy group, more preferably a $C_{1-4}$ alkoxy group such as a methoxy group, an ethoxy group, a propoxy group, an isopropoxy group, or a butoxy group, further preferably a methoxy group, an ethoxy group, or a propoxy group.

Examples of the group which may be substituted on the lower alkoxy group include a halogen atom (e.g., a fluorine atom), a hydroxy group, a $C_{1-7}$ alkoxy group (e.g., a methoxy group, an ethoxy group, and a propoxy group), a carboxy group, an amino group, and a $C_{1-7}$ alkylamino group (e.g., a methylamino group, an ethylamino group, a dimethylamino group, and a diethylamino group).

The "lower alkylamino group" represented by $R^1$ is preferably a mono- or di-$C_{1-7}$ alkylamino group, more preferably, for example, a mono- or di-$C_{1-4}$ alkylamino group such as a methylamino group, an ethylamino group, a propylamino group, a methylethylamino group, a dimethylamino group, or a diethylamino group.

Examples of the group which may be substituted on the lower alkylamino group include a hydroxy group, a $C_{1-7}$ alkoxy group (e.g., a methoxy group, an ethoxy group, and a propoxy group), a carboxy group, an amino group, and a $C_{1-4}$ alkylamino group (e.g., a methylamino group and an ethylamino group).

The "cyclo lower alkyl group" represented by $R^1$ is preferably a cyclo $C_{3-7}$ alkyl group, more preferably a cyclopropyl group, a cyclobutyl group, a cyclopentyl group, or a cyclohexyl group.

Examples of the "cyclic amino group" represented by $R^1$ include a 4- to 7-membered saturated cyclic amino group such as a piperidino group, a morpholino group, a pyrrolidino group, a hexahydroazepino group, and a piperazino group.

Examples of the "aryl group" represented by $R^1$ include a $C_{6-14}$ aryl group such as a phenyl group, a naphthyl group, an indenyl group, and an anthryl group and preferably include a $C_{6-10}$ aryl group, more preferably a phenyl group.

Examples of the "heteroaryl group" represented by $R^1$ include a 5- or 6-membered heteroaryl group such as a pyrrolyl group, a pyrazolyl group, a furyl group, a thienyl group, a pyridyl group, an imidazolyl group, a triazolyl group, a tetrazolyl group, a triazinyl group, a pyridazinyl group, a pyrimidinyl group, a pyrazinyl group, an isoxazolyl group, a thiazolyl group, an isothiazolyl group, a thiadiazolyl group, an oxazolyl group, and an oxadiazolyl group. Among them, a nitrogen-containing heteroaryl group having 1 to 3 nitrogen atoms, such as a pyrrolyl group, a pyrazolyl group, an imidazolyl group, a triazolyl group, a pyridyl group, a pyrimidinyl group, a pyridazinyl group, a pyrazinyl group, or a triazinyl group is preferred, and a (2-, 3- or 4-)pyridyl group or a (4- or 5-)pyrimidinyl group is more preferred.

Examples of the group which may be substituted on the aryl group or the heteroaryl group include a halogen atom (e.g., a fluorine atom), a hydroxy group, a $C_{1-7}$ alkyl group (e.g., a methyl group, an ethyl group, a propyl group, an isopropyl group, a butyl group, an isobutyl group, and a tert-butyl group), a $C_{1-7}$ alkoxy group (e.g., a methoxy group, an ethoxy group, and a propoxy group), an amino group, a $C_{1-7}$ alkylamino group (e.g., a methylamino group, an ethylamino group, a dimethylamino group, and a diethylamino group), and a carboxy group.

$R^1$ is preferably a hydrogen atom, a halogen atom, an optionally substituted lower alkyl group, an optionally substituted lower alkoxy group, an optionally substituted lower alkylamino group, or a cyclic amino group, more preferably a hydrogen atom, a halogen atom, a $C_{1-4}$ alkyl group, a $C_{1-4}$ alkoxy group, or a $C_{1-4}$ alkylamino group, further preferably a hydrogen atom or a halogen atom.

Examples of the "halogen atom" represented by $R^2$ include fluorine, chlorine, bromine, and iodine. A fluorine atom or a chlorine atom is preferred.

The "lower alkyl group" represented by $R^2$ is preferably $C_{1-7}$ alkyl group, more preferably, for example, a $C_{1-4}$ alkyl group such as a methyl group, an ethyl group, a propyl group, an isopropyl group, a butyl group, an isobutyl group, or a tert-butyl group, further preferably a methyl group or an ethyl group. Examples of the group which may be substituted on the lower alkyl group include a halogen atom (e.g., a fluorine atom), a hydroxy group, a $C_{1-7}$ alkoxy group (e.g., a methoxy group, an ethoxy group, and a propoxy group), an amino group, and a $C_{1-7}$ alkylamino group (e.g., a methylamino group, an ethylamino group, a dimethylamino group, and a diethylamino group).

Examples of the "lower alkoxy group", the "lower alkylamino group", and the "cyclo lower alkyl group" represented by $R^2$ include the same as those listed above in $R^1$.

Examples of the group which may be substituted on the lower alkylamino group include a halogen atom (e.g., a fluorine atom), a hydroxy group, and a $C_{1-7}$ alkoxy group (e.g., a methoxy group, an ethoxy group, and a propoxy group).

Examples of the "4- to 7-membered cyclic amino group" represented by $R^2$ include an azetidino group, a pyrrolidino group, a morpholino group, and an isoxazolino group.

Examples of the group which may be substituted on the cyclic amino group include a halogen atom (e.g., a fluorine atom), a hydroxy group, a $C_{1-4}$ alkyl group (e.g., a methyl group, an ethyl group, a propyl group, and an isopropyl group), a halo $C_{1-4}$ alkyl group (e.g., a trifluoromethyl group), a $C_{1-4}$ alkoxy group (e.g., a methoxy group, an ethoxy group, and a propoxy group), an amino group, a $C_{1-4}$ alkylamino group (e.g., a methylamino group, an ethylamino group, a dimethylamino group, and a diethylamino group), and a carboxy group.

Examples of the "$C_{1-17}$ alkanoylamino group" represented by $R^2$ preferably include a $C_{1-7}$ alkanoylamino group such as an acetylamino group, an ethylcarbonylamino group, a propylcarbonylamino group, a butylcarbonylamino group, a pentylcarbonylamino group, and a hexylcarbonylamino group as well as a $C_{15-17}$ alkanoylamino group such as a pentadecanoylamino group, a hexadecanoylamino group, and a heptadecanoylamino group.

$R^2$ is preferably a hydrogen atom, a halogen atom, an optionally substituted lower alkyl group, a hydroxy group, or an amino group, more preferably a hydrogen atom or an optionally substituted $C_{1-7}$ alkyl group.

The "lower alkyl group" represented by $R^3$ to $R^6$ is preferably a $C_{1-7}$ alkyl group, more preferably a $C_{1-4}$ alkyl group such as a methyl group, an ethyl group, a propyl group, an isopropyl group, a butyl group, an isobutyl group, or a tert-butyl group, further preferably a methyl group or an ethyl group.

Examples of the group which may be substituted on the lower alkyl group include a halogen atom (e.g., a fluorine atom), a hydroxy group, a $C_{1-7}$ alkoxy group (e.g., a methoxy group, an ethoxy group, and a propoxy group), and a $C_{1-3}$ alkoxy $C_{1-7}$ alkoxy group (e.g., a methoxyethoxy group and an ethoxyethoxy group).

The "lower alkoxycarbonyl group" represented by $R^3$ to $R^6$ is preferably a $C_{1-7}$ alkoxycarbonyl group, more preferably a methoxycarbonyl group or an ethoxycarbonyl group.

Examples of the group which may be substituted on the carbamoyl group represented by $R^3$ to $R^6$ include those listed as "—$R^{a3}$-$Cy^1$ (wherein $R^{a3}$ represents a single bond or an optionally halogen atom-substituted divalent hydrocarbon group, and $Cy^1$ represents an optionally substituted cyclo lower alkyl group, an optionally substituted 4- to 7-membered cyclic ether group, a N-substituted morpholinyl group, an oxazinanyl group or an isoxazolinyl group)" represented by $R^{a1}$ and $R^{a2}$ when $R^8$ is represented by the formula (a). Preferably, $R^{a3}$ is a divalent hydrocarbon group, and $Cy^1$ is an optionally substituted 4- to 7-membered cyclic ether group.

Each of $R^3$ to $R^6$ is preferably a hydrogen atom or an optionally substituted $C_{1-7}$ alkyl group, more preferably a hydrogen atom.

Examples of the "halogen atom" represented by $R^7$ include fluorine, chlorine, bromine, and iodine. A fluorine atom or a chlorine atom is preferred.

The "lower alkyl group" represented by $R^7$ is preferably a $C_{1-7}$ alkyl group, more preferably a $C_{1-4}$ alkyl group such as a methyl group, an ethyl group, a propyl group, an isopropyl group, a butyl group, an isobutyl group, or a tert-butyl group.

Examples of the group which may be substituted on the lower alkyl group include a halogen atom (e.g., a fluorine atom), a hydroxy group, a $C_{1-7}$ alkoxy group (e.g., a methoxy group, an ethoxy group, and a propoxy group), a $C_{1-3}$ alkoxy $C_{1-7}$ alkoxy group (e.g., a methoxyethoxy group and an ethoxyethoxy group), an amino group, and a $C_{1-7}$ alkylamino group (e.g., a methylamino group, an ethylamino group, a dimethylamino group, and a diethylamino group).

The "lower alkoxy group" represented by $R^7$ is preferably a $C_{1-7}$ alkoxy group, more preferably, for example, a $C_{1-4}$ alkoxy group such as a methoxy group, an ethoxy group, a propoxy group, an isopropyl group, or a butoxy group, further preferably a methoxy group.

Examples of the substituent on the amino group represented by $R^7$ include a $C_{1-4}$ alkyl group (e.g., a methyl group, an ethyl group, a propyl group, an isopropyl group, a butyl group, an isobutyl group, and a tert-butyl group) as well as a hydroxy group- or halogen atom-substituted $C_{1-4}$ alkyl group.

$R^7$ is preferably a hydrogen atom, a halogen atom, or an optionally substituted lower alkyl group, more preferably a hydrogen atom.

Examples of the "halogen atom" represented by $R^8$ preferably include a fluorine atom and a chlorine atom.

The "lower alkyl group" represented by $R^8$ is preferably a $C_{1-7}$ alkyl group, more preferably a $C_{1-4}$ alkyl group such as a methyl group, an ethyl group, a propyl group, an isopropyl group, a butyl group, an isobutyl group, or a tert-butyl group, further preferably a methyl group, an ethyl group, a propyl group, or a butyl group.

Examples of the group which may be substituted on the lower alkyl group include a halogen atom (e.g., a fluorine atom and a chlorine atom), a hydroxy group, a $C_{1-7}$ alkoxy group (e.g., a methoxy group, an ethoxy group, and a propoxy group), a $C_{1-3}$ alkoxy $C_{1-7}$ alkoxy group (e.g., a methoxyethoxy group, an ethoxyethoxy group, and a methoxypropoxy group), a halo $C_{1-7}$ alkoxy group (e.g., fluoromethoxy group, a difluoromethoxy group, a trifluoromethoxy group, and a 2,2,2-trifluoroethoxy group), a hydroxy $C_{1-7}$ alkoxy group (e.g., hydroxyethoxy group, a 2-hydroxypropoxy group, and a 3-hydroxypropoxy group), an amino group, a $C_{1-7}$ alkylamino group (e.g., a methylamino group, an ethylamino group, a dimethylamino group, and a diethylamino group), a 4- to 7-membered cyclic ether $C_{1-3}$ alkoxy group (e.g., a tetrahydrofuranylmethoxy group, a tetrahydropyranylmethoxy group, and a tetrahydropyranylethoxy group), a 4- to 7-membered cyclic ether $C_{1-3}$ alkylamino group (e.g., a tetrahydrofuranylmethylamino group, a tetrahydropyranylmethylamino group, and a tetrahydropyranylethylamino group), a carboxy group, and a group which can be converted to a hydroxy group (e.g., a tert-butyldimethylsilyl group).

The "lower alkenyl group" represented by $R^8$ is preferably a $C_{2-7}$ alkenyl group, more preferably, for example, a vinyl group, a propenyl group, a 2-methyl-1-propenyl group, or a 1-methyl-1-propenyl group.

Examples of the group which may be substituted on the lower alkenyl group include a halogen atom (e.g., a fluorine atom), a hydroxy group, a $C_{1-7}$ alkoxy group (e.g., a methoxy group, an ethoxy group, and a propoxy group), and carboxy.

The "cyclo lower alkyl group" represented by $R^8$ is preferably a cyclo $C_{3-7}$ alkyl group, more preferably a cyclopropyl group, a cyclobutyl group, a cyclopentyl group, or a cyclohexyl group.

Examples of the group which may be substituted on the cyclo lower alkyl group include a halogen atom (e.g., a fluorine atom), a hydroxy group, a carboxy group, and an oxo group.

The "lower alkoxy group" represented by $R^8$ is preferably a $C_{1-7}$ alkoxy group, more preferably, for example, a $C_{1-4}$ alkoxy group such as a methoxy group, an ethoxy group, a propoxy group, an isopropyl group, or a butoxy group, further preferably a methoxy group, an ethoxy group, or a propoxy group.

Examples of the group which may be substituted on the lower alkoxy group include a halogen atom, a hydroxy group, a $C_{1-3}$ alkoxy group (e.g., a methoxy group, an ethoxy group, and a propoxy group), a $C_{1-3}$ alkoxy $C_{1-7}$ alkoxy group (e.g., a methoxyethoxy group and an ethoxyethoxy group), an amino group, a $C_{1-7}$ alkylamino group (e.g., a methylamino group, an ethylamino group, a dimethylamino group, and a diethylamino group), a carboxy group, and a 4 to 6-membered cyclic ether group (e.g., an oxetanyl group, a tetrahydrofuranyl group, a tetrahydropyranyl group, and a dioxanyl group).

The "lower alkylaminocarbonylalkyl group" represented by R is preferably a mono- or di-$C_{1-4}$ alkylaminocarbonyl $C_{1-4}$ alkyl group. Examples thereof include an ethylaminocarbonylmethyl group and an isopropylaminocarbonylmethyl group.

Examples of the group which may be substituted on the lower alkylaminocarbonylalkyl group preferably include a hydroxy group, a $C_{1-3}$ alkoxy group (e.g., a methoxy group, an ethoxy group, and a propoxy group), and a carboxy group.

The "lower alkanoyloxy group" represented by $R^8$ is preferably a $C_{1-4}$ alkanoyloxy group, more preferably, for example, an acetyloxy group, a propanoyloxy group, or an isopropanoyloxy group.

The "lower alkanoylthio group" represented by $R^8$ is preferably a $C_{1-4}$ alkanoylthio group, more preferably, for example, an acetylthio group, a propanoylthio group, or an isopropanoylthio group.

The "lower alkoxycarbonyl group" represented by $R^8$ is preferably a $C_{1-7}$ alkoxycarbonyl group, more preferably a methoxycarbonyl group or an ethoxycarbonyl group.

The "lower alkyl group" represented by $R^{8a}$ is preferably a $C_{1-7}$ alkyl group, more preferably a $C_{1-4}$ alkyl group such as a methyl group, an ethyl group, or a propyl group.

Examples of the group which may be substituted on the lower alkyl group include a hydroxy group, a $C_{1-4}$ alkoxy group (e.g., a methoxy group and an ethoxy group), an amino group, a $C_{1-4}$ alkylamino group (e.g., a methylamino group, an ethylamino group, a dimethylamino group, and a diethylamino group), and a carboxy group.

In the formula (a), the "lower alkyl group" represented by $R^{a1}$ or $R^{a2}$ is preferably a $C_{1-7}$ alkyl group, more preferably a $C_{1-5}$ alkyl group such as a methyl group, an ethyl group, a propyl group, an isopropyl group, a butyl group, an isobutyl group, a tert-butyl group, a pentyl group, an isopentyl group, or a neopentyl group.

Examples of the group which may be substituted on the lower alkyl group include a halogen atom (e.g., a fluorine atom), a nitrile group, a hydroxy group, an amino group, a $C_{1-7}$ alkylamino group (e.g., a methylamino group, an ethylamino group, a dimethylamino group, and a diethylamino group), a carboxy group, a $C_{1-7}$ alkoxycarbonyl group (e.g., a methoxycarbonyl group and an ethoxycarbonyl group), a $C_{1-7}$ alkanoyl group (e.g., an acetyl group, an ethylcarbonyl group, a propylcarbonyl group, a butylcarbonyl group, a pentylcarbonyl group, and a hexylcarbonyl group), a mercapto group, a $C_{1-7}$ alkylsulfenyl group (e.g., a methylsulfenyl group, an ethylsulfenyl group, a propylsulfenyl group, and a butylsulfenyl group), a $C_{1-7}$ alkylsulfinyl group (e.g., a methylsulfinyl group, an ethylsulfinyl group, a propylsulfinyl group, and a butylsulfinyl group), a $C_{1-7}$ alkylsulfonyl group (e.g., a methylsulfonyl group, an ethylsulfonyl group, a propylsulfonyl group, and a butylsulfonyl group), and an aralkyloxy group (e.g., a benzyloxy group, a 1-phenylethyloxy group, and a 2-phenylethyloxy group). A halogen atom, a hydroxy group, a $C_{1-4}$ alkoxy group, a $C_{1-4}$ alkylsulfonyl group, a carboxy group, or a $C_{1-7}$ alkanoyl group is preferred.

The "lower alkenyl group" represented by $R^{a1}$ or $R^{a2}$ is preferably a $C_{2-7}$ alkenyl group, more preferably a $C_{2-4}$ alkenyl group such as a vinyl group, an allyl group, or a 1-propenyl group.

Examples of the group which may be substituted on the lower alkenyl group include a halogen atom (e.g., a fluorine atom), a hydroxy group, and a $C_{1-7}$ alkoxy group (e.g., a methoxy group, an ethoxy group, and a propoxy group).

The "lower alkynyl group" represented by $R^{a1}$ or $R^{a2}$ is preferably a $C_{2-7}$ alkynyl group, more preferably, for example, a $C_{2-4}$ alkynyl group such as an ethynyl group, a 1-propynyl group, or a 1-butynyl group.

Examples of the group which may be substituted on the lower alkynyl group include a halogen atom (e.g., a fluorine atom), a hydroxy group, and a $C_{1-7}$ alkoxy group (e.g., a methoxy group, an ethoxy group, and a propoxy group).

The "lower alkoxy group" represented by $R^{a1}$ or $R^{a2}$ is preferably a $C_{1-7}$ alkoxy group, more preferably, for example, a $C_{1-4}$ alkoxy group such as a methoxy group, an ethoxy group, a propoxy group, an isopropoxy group, or a butoxy group, further preferably a methoxy group, an ethoxy group, or a propoxy group.

Examples of the group which may be substituted on the lower alkoxy group preferably include a halogen atom and a hydroxy group.

Examples of the "$C_{2-12}$ alkyl or alkoxy group having an ether bond(s)" represented by $R^{a1}$ or $R^{a2}$ include a $C_{2-12}$ alkyl group or a $C_{2-12}$ alkoxy group having one or more ether bonds (—C—O—C—) in the substituent. Among them, a $C_{2-7}$ alkyl group or a $C_{2-7}$ alkoxy group having 1 to 3 ether bonds is preferred. The alkyl chain of the $C_{2-7}$ alkyl group or the $C_{2-7}$ alkoxy group may be linear or branched.

Examples of the $C_{2-12}$ alkyl group having an ether bond(s) include the following groups.

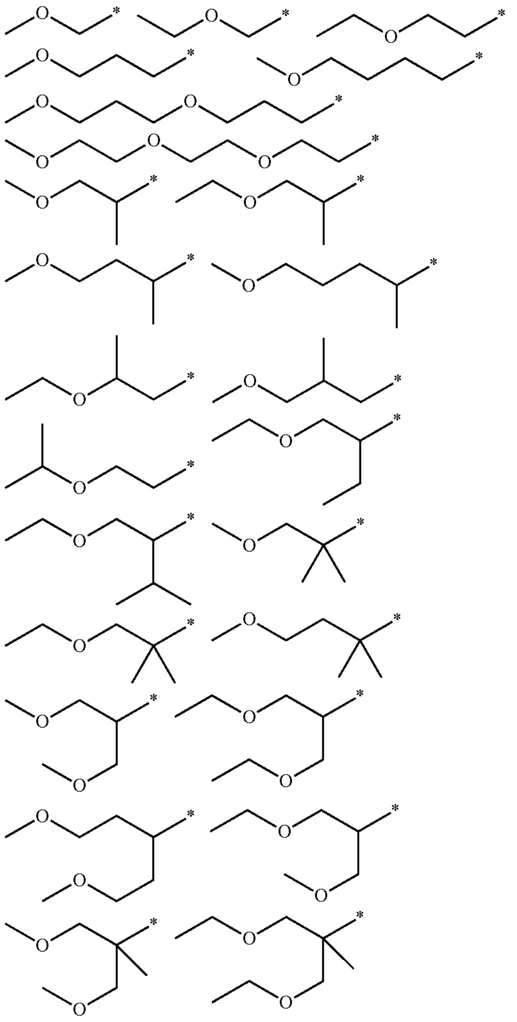
Examples of the $C_{2-12}$ alkoxy group having an ether bond(s) include the following groups.
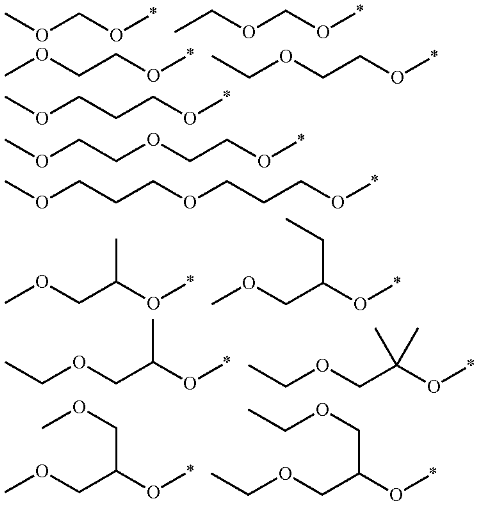
Examples of the group which may be substituted on such a $C_{2-12}$ alkyl or alkoxy group having an ether bond(s) include a hydroxy group and a halogen atom. One example of the substituted $C_{2-12}$ alkyl group having an ether bond(s) will be shown below (wherein Hal represents a halogen atom).
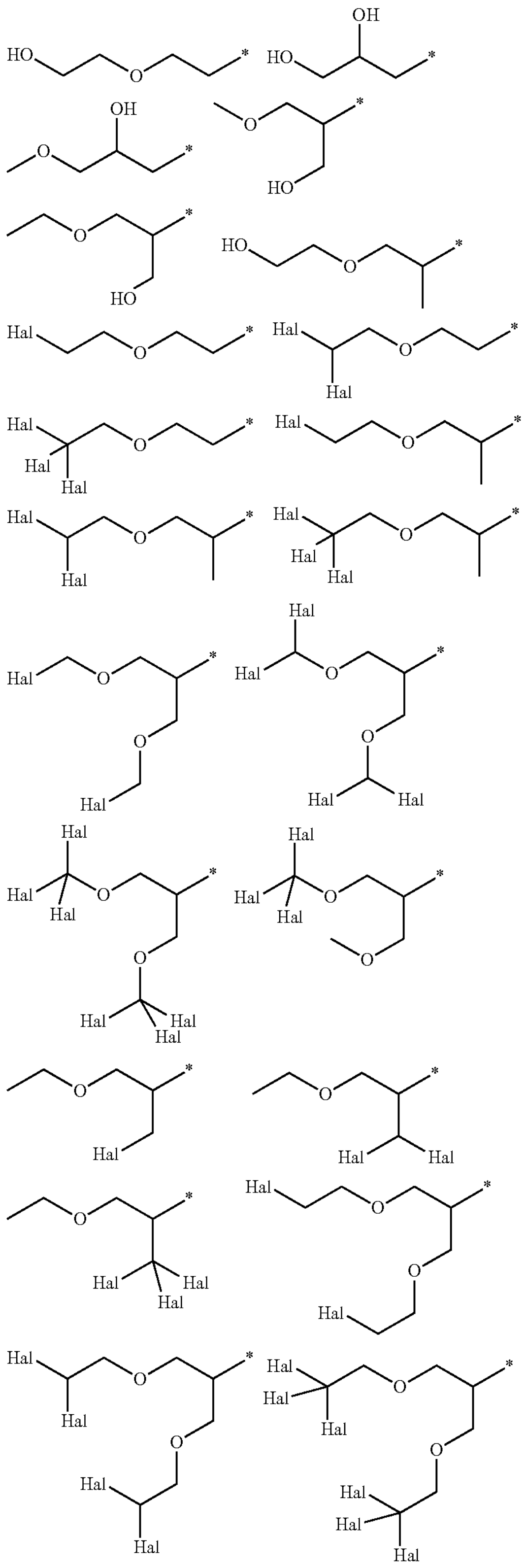

-continued

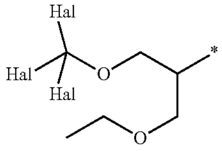
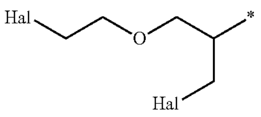
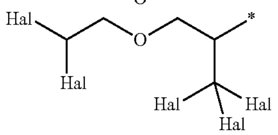
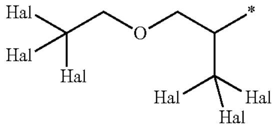
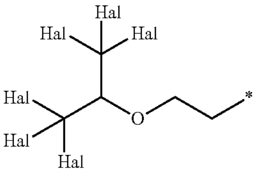
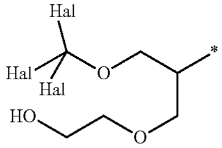
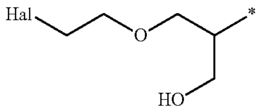
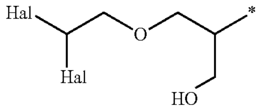
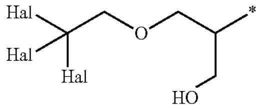
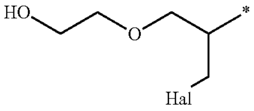
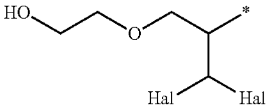
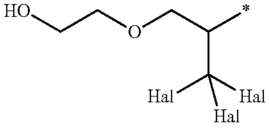

The "$C_{2-12}$ alkyl or alkoxy group having an ether bond(s)" is preferably a $C_{2-7}$ alkyl group having 1 to 3 ether bonds, more preferably any of the following groups.

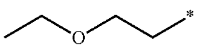
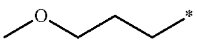
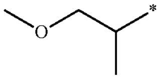
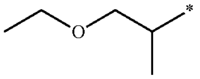
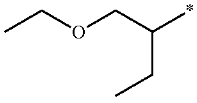
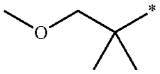
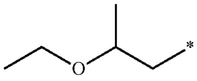
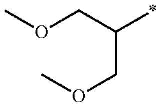

-continued

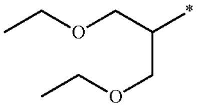

Examples of the heteroaryl in the "heteroarylamino group" represented by $R^{a1}$ or $R^{a2}$ preferably include 5- or 6-membered nitrogen-containing heteroaryl containing 1 to 3 nitrogen atoms, such as pyrrolyl, pyrazolyl, imidazolyl, triazolyl, pyridyl, pyrimidinyl, pyridazinyl, pyrazinyl, and triazinyl. (2-, 3- or 4-)Pyridyl is preferred, and 2-pyridyl is more preferred.

The group which may be substituted on the heteroarylamino group means a group which may be substituted on the hetero ring. Examples of such a substituent include a $C_{1-7}$ alkyl group (e.g., a methyl group and an ethyl group), a halogen atom, a hydroxy group, a $C_{1-7}$ alkoxy group (e.g., a methoxy group, an ethoxy group, and a propoxy group), and a $C_{1-3}$ alkoxy $C_{1-7}$ alkoxy group (e.g., a methoxyethoxy group and an ethoxyethoxy group).

Specific examples of the heterocyclic ring constituting the heteroaryl group in the "nitrogen-containing bicyclic heteroaryl group" represented by $R^{a1}$ or $R^{a2}$ include benzimidazole, purine, isoquinoline, quinoline, and quinoxaline.

Examples of the group which may be substituted on the nitrogen-containing bicyclic heteroaryl include a $C_{1-7}$ alkyl group (e.g., a methyl group and an ethyl group), a halogen atom, a hydroxy group, a $C_{1-7}$ alkoxy group (e.g., a methoxy group, an ethoxy group, and a propoxy group), and a carboxy group.

Examples of the divalent hydrocarbon group represented by $R^{a3}$ in "—$R^{3a}$-$Cy^1$" represented by $R^{a1}$ or $R^4$ include a $C_{1-6}$ alkylene group (e.g., a methylene group, a 1,1-ethylene group, a 1,2-ethylene group, a 1,2-propylene group, a 1,3-propylene group, a 1,4-butylene group, a 1,2-butylene group, a 1,2-pentylene group, a 1,2-hexylene group, a 2,3-butylene group, and a 2,4-pentylene group), a $C_{2-6}$ alkenylene group (e.g., a 1,1-ethenylene group, a 1,2-ethenylene group, a 1,2-ethenylenemethylene group, a 1-methyl-1,2-ethenylene group, a 1,2-ethenylene-1,1-ethylene group, a 1,2-ethenylene-1,2-ethylene group, a 1,2-ethenylene-1,2-propylene group, a 1,2-ethenylene-1,3-propylene group, a 1,2-ethenylene-1,4-butylene group, and a 1,2-ethenylene-1,2-butylene group), and a $C_{2-4}$ alkynylene group (e.g., an ethynylene group, an ethynylenemethylene group, an ethynylene-1,1-ethylene group, an ethynylene-1,2-ethylene group, an ethynylene-1,2-propylene group, an ethynylene-1,3-propylene group, an ethynylene-1,4-butylene group, and an ethynylene-1,2-butylene group).

The divalent hydrocarbon group may be substituted by a halogen atom (e.g., a fluorine atom and a chlorine atom). Examples of the halogen atom-substituted divalent hydrocarbon group include a fluoromethylene group, a chloromethylene group, a difluoromethylene group, a chlorofluoromethylene group, a difluoroethylene group, a fluoro-1,1-ethenylene group, a fluoro-1,4-butylene group, a 1,2-ethenylene-fluoro-1,2-ethylene group, a 1,2-ethenylene-3,3,3-trifluoro-1,2-propylene group, an ethynylene-3,3,3-trifluoro-1,2-propylene group, an ethynylene-4-fluoro-1,4-butylene group, and an ethynylene-4,4,4-trifluoro-1,2-butylene group.

The "cyclo lower alkyl group" represented by $Cy^1$ is preferably a cyclo $C_{3-6}$ alkyl group, more preferably a cyclopropyl group, a cyclobutyl group, a cyclopentyl group, or a cyclohexyl group.

Examples of the group which may be substituted on the cyclo lower alkyl group preferably include a halogen atom, a hydroxy group, a $C_{1-7}$ alkyl group (e.g., a methyl group and an ethyl group), a $C_{1-7}$ alkoxy group (e.g., a methoxy group, an ethoxy group, a propoxy group, and an isopropoxy group), a $C_{1-4}$ alkoxy $C_{1-4}$ alkyl group (e.g., a methoxymethyl group, an ethoxymethyl group, a methoxyethyl group, a methoxyisopropyl group, an isopropoxymethyl group, and an isopropoxyethyl group), an amino group, and a $C_{1-7}$ alkylamino group (e.g., a methylamino group, an ethylamino group, a dimethylamino group, and a diethylamino group).

Examples of the "4- to 7-membered cyclic ether group" represented by $Cy^1$ include an oxetanyl group, a tetrahydrofuranyl group, a tetrahydropyranyl group, a dihydropyranyl group, a dioxolanyl group, a dioxanyl group, an oxepanyl group, and a dioxepanyl group. A 3-oxetanyl group, a (2- or 3-)tetrahydrofuranyl group, a (2-, 3- or 4-)tetrahydropyranyl group, or a 2-(1,4-dioxanyl) group is preferred.

Examples of the group which may be substituted on the cyclic ether group include a $C_{1-7}$ alkyl group (e.g., a methyl group and an ethyl group), a halogen atom, a hydroxy group, a $C_{1-7}$ alkoxy group (e.g., a methoxy group, an ethoxy group, and a propoxy group), a $C_{1-4}$ alkoxy $C_{1-4}$ alkyl group (e.g., a methoxymethyl group and an ethoxymethyl group), a halo $C_{1-7}$ alkyl group (a fluoromethyl group, a difluoromethyl group, a trifluoromethyl group, and a 2,2,2-trifluoroethyl group), an amino group, and an oxy group.

The "N-substituted morpholinyl group" represented by $Cy^1$ means a morpholinyl group in which a nitrogen atom of the morpholine ring is substituted by a $C_{1-4}$ alkyl group, an aralkyl group such as benzyl, an optionally substituted $C_{1-4}$ alkanoyl group (substituent: a halogen atom, a hydroxy group or the like), or an aroyl group such as benzoyl. Examples thereof preferably include a N-methylmorpholinyl group, a N-benzylmorpholinyl group, a N-acetylmorpholinyl group, and N-benzoylmorpholinyl.

In "—$R^{3a}$-$Cy^1$", $R^{a3}$ is preferably a $C_{1-6}$ alkylene group, and $Cy^1$ is preferably a 4- to 7-membered cyclic ether group (preferably a tetrahydropyranyl group, a tetrahydrofuranyl group or the like).

The "optionally substituted 5- or 6-membered heteroaryl group" represented by $R^{a1}$ or $R^{a2}$ is preferably a 5- or 6-membered heteroaryl group having 1 to 4 heteroatoms selected from the group consisting of a nitrogen atom, an oxygen atom and a sulfur atom. Examples thereof include: a 5-membered heteroaryl group such as a pyrrolyl group, a furyl group, a thienyl group, an imidazolyl group, a pyrazolyl group, an oxazolyl group, an isoxazolyl group, a thiazolyl group, an isothiazolyl group, a triazolyl group, a tetrazolyl group, an oxadiazolyl group, and a thiadiazolyl group; and a 6-membered heteroaryl group such as a pyridyl group, a pyrazinyl group, a pyrimidinyl group, a pyridazinyl group, a triazinyl group, and a tetrazinyl group. Among them, a nitrogen-containing heteroaryl group having 1 to 4 nitrogen atoms, such as a pyrrolyl group, a pyrazolyl group, an imidazolyl group, a triazolyl group, a tetrazolyl group, an oxazolyl group, an isoxazolyl group, a thiazolyl group, an isothiazolyl group, a pyridyl group, a pyrimidinyl group, a pyridazinyl group, a pyrazinyl group, a triazinyl group, or a tetrazinyl group is preferred, and a (2-, 3- or 4-)pyridyl group, a 2-oxazolyl group, a 2-thiazolyl group, a 3-pyrazolyl group, or a 3-isoxazolyl group is more preferred.

Examples of the group which may be substituted on the heteroaryl group include: a halogen atom (e.g., a fluorine atom); a hydroxy group; a $C_{1-7}$ alkyl group (e.g., a methyl group and an ethyl group); a $C_{1-7}$ alkyl group substituted by one or more groups selected from the group consisting of a halogen atom (e.g., a fluorine atom), a hydroxy group, an amino group, a $C_{1-4}$ alkylamino group and a carboxy group (e.g., a fluoromethyl group, a difluoromethyl group, a trifluoromethyl group, a 2,2,2-trifluoroethyl group, a hydroxymethyl group, a hydroxyethyl group, a hydroxypropyl group, a dimethylaminomethyl group, a dimethylaminoethyl group, a methoxy-1,1-difluoroethyl group, an ethoxy-1,1-difluoroethyl group, a methoxy-1,1-difluoropropyl group, a hydroxy-1,1-difluoroethyl group, a hydroxy-1,1-difluoropropyl group, and a methylamino-1,1-difluoroethyl group); a $C_{1-7}$ alkoxy group (e.g., a methoxy group, an ethoxy group, and a propoxy group); a $C_{1-7}$ alkoxy group substituted by one or more groups selected from the group consisting of a halogen atom (e.g., a fluorine atom), a hydroxy group, an amino group, a $C_{1-4}$ alkylamino group and a carboxy group (e.g., a trifluoromethoxy group, a hydroxyethoxy group, a dimethylaminoethoxy group, a 3-fluoro-2-hydroxypropoxy group, a 2-amino-3-fluoropropoxy group, a 4,4,4-trifluoro-2-hydroxybutoxy group, and a 4,4,4-trifluoro-2-methoxybutoxy group); a $C_{1-4}$ alkylamino group optionally substituted by one or more groups selected from the group consisting of a halogen atom (e.g., a fluorine atom) and a hydroxy group (e.g., a hydroxyethylamino group, a hydroxypropylamino group, a trifluoroethylamino group, a (3-fluoro-2-hydroxypropyl)amino group, and a (4,4,4-trifluoro-2-hydroxybutyl)amino group); a cyclo $C_{3-7}$ alkyl group; a $C_{3-7}$ alkyl or alkoxy group having an ether bond(s) (e.g., $—O(CH_2)_2OCH_3$, $—O(CH_2)_2O(CH_2)_2OCH_3$, $—O(CH_2)_2O(CH_2)_2O(CH_2)_2OCH_3$, $—O(CH_2)_3OCH_3$, $—O(CH_2)_3O(CH_2)_3OCH_3$, $—(CH_2)_2OCH_3$, and $—OCH_2OCH_3$); an amino group; an amino group substituted by a $C_{1-7}$ alkyl group (e.g., a methyl group and an ethyl group) and/or a $C_{2-7}$ alkyl group having an ether bond(s) (e.g., $—(CH_2)_3O(CH_2)_2CH_3$, $—(CH_2)_2O(CH_2)_2OCH_3$, $—(CH_2)_2OCH_3$, and $—(CH_2)_3OCH_3$); a mercapto group; a $C_{1-7}$ alkylsulfenyl group (e.g., a methylsulfenyl group, an ethylsulfenyl group, a propylsulfenyl group, and a butylsulfenyl group); a $C_{1-7}$ alkylsulfinyl group (e.g., a methylsulfinyl group, an ethylsulfinyl group, a propylsulfinyl group, and a butylsulfinyl group); a $C_{1-7}$ alkylsulfonyl group (e.g., a methylsulfonyl group, an ethylsulfonyl group, a propylsulfonyl group, and a butylsulfonyl group); a carboxy group; a $C_{1-7}$ alkoxycarbonyl group (e.g., a methoxycarbonyl group and an ethoxycarbonyl group); and a $C_{1-7}$ alkanoyl group (e.g., an acetyl group, an ethylcarbonyl group, a propylcarbonyl group, a butylcarbonyl group, a pentylcarbonyl group, and a hexylcarbonyl group).

Examples of the "heteroaralkyl group" represented by $R^{a1}$ or $R^{a2}$ include a heteroaralkyl group having a 5- or 6-membered heteroaryl moiety and an alkyl moiety having 1 or 2 carbon atoms (5- or 6-membered heteroaryl $C_{1-2}$ alkyl group). Examples of the 5- or 6-membered heteroaryl include the same as those listed above. Among them, furyl, pyridyl, pyrazolyl, thiazolyl, oxazolyl or the like is preferred.

Examples of the group which may be substituted on the heteroaralkyl group include those listed above as the group which may be substituted on the heteroaryl group and preferably include a halogen atom (e.g., a fluorine atom), a hydroxy group, a $C_{1-7}$ alkyl group (e.g., a methyl group and an ethyl group), a halo $C_{1-7}$ alkyl group (a fluoromethyl group, a difluoromethyl group, a trifluoromethyl group, and a pentafluoroethyl group), a $C_{1-7}$ alkoxy halo $C_{1-7}$ alkyl group (e.g., an ethoxydifluoroethyl group and a methoxyethoxydifluoroethyl group), a hydroxy $C_{1-7}$ alkyl group (a hydroxymethyl group, a hydroxyethyl group, and a hydroxypropyl group), a $C_{1-4}$ alkoxy $C_{1-4}$ alkyl group (e.g., a methoxymethyl group and an ethoxymethyl group), a $C_{1-7}$ alkoxy group (e.g., a methoxy group, an ethoxy group, a propoxy group, and an isopropoxy group), a $C_{1-3}$ alkoxy $C_{1-7}$ alkoxy group (e.g., a methoxyethoxy group and an ethoxyethoxy group), a carboxy $C_{1-7}$ alkyl group, an amino group, a $C_{1-7}$ alkylamino group (e.g., a methylamino group, an ethylamino group, a dimethylamino group, and a diethylamino group), a $C_{1-4}$ alkoxy $C_{1-4}$ alkylamino group (e.g., a methoxymethylamino group and an ethoxymethylamino group), a $C_{1-7}$ alkylsulfonyl group (e.g., a methylsulfonyl group, an ethylsulfonyl group, a propylsulfonyl group, and a butylsulfonyl group), a carboxy group, and a $C_{1-7}$ alkanoyl group (e.g., an acetyl group, an ethylcarbonyl group, a propylcarbonyl group, a butylcarbonyl group, a pentylcarbonyl group, and a hexylcarbonyl group).

Examples of the "heteroaralkyl group" preferably include a 2-pyridylmethyl group and a 2-furylmethyl group.

Examples of the 4- to 9-membered cyclic amino group which is formed by $R^{a1}$ and $R^{a2}$ together with the adjacent nitrogen atom include an azetidino group, a pyrrolidino group, a piperidino group, a piperazino group, a morpholino group, an oxazolino group, and an isoxazolino group as well as the following spiro azetidino groups.

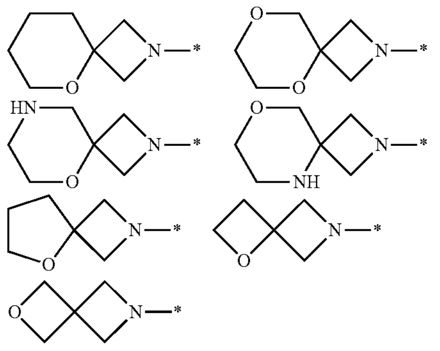

Examples of the group which may be substituted on the cyclic amino group include a halogen atom (e.g., a fluorine atom), a hydroxy group, a $C_{1-7}$ alkyl group (e.g., a methyl group and an ethyl group), a $C_{1-7}$ alkoxy group (e.g., a methoxy group, an ethoxy group, a propoxy group, and an isopropoxy group), a 4- to 6-membered cyclic amino group (e.g., piperidino group and a morpholino group), a carboxy group, an acyl group, and an oxy group.

In the group represented by the formula (a), preferably, any one of $R^{a1}$ and $R^{a2}$ is a hydrogen atom, and the other moiety is an optionally substituted $C_{1-7}$ alkyl group, an optionally substituted $C_{2-12}$ alkyl or alkoxy group having an ether bond(s), —$R^3$-$Cy^1$, an optionally substituted 5- or 6-membered heteroaryl group, or an optionally substituted heteroaralkyl group, more preferably an optionally substituted $C_{2-12}$ alkyl group having an ether bond(s), —$R^{83}$-$Cy^1$, or an optionally substituted 5- or 6-membered heteroaryl group.

In the formula (b), examples of the hetero ring constituting the "4- to 6-membered heterocyclyl group" represented by Het include a hetero ring containing one or more atoms selected from the group consisting of a nitrogen atom, an oxygen atom and a sulfur atom. Examples thereof include: an aliphatic hetero ring such as azetidine, oxetane, pyrrolidine, pyrazolidine, imidazolidine, pyrroline, pyrazoline, imidazoline, piperidine, piperidine, piperazine, triazinane, tetrahydropyran, 1,3-dioxane, 1,4-dioxane, morpholine, oxazolidine, and isoxazolidine; and a 6n-electron system hetero ring such as pyrrole, pyrazole, imidazole, triazole, tetrazole, pyridine, pyridazine, pyrimidine, pyrazine, triazine, tetrazine, oxazole, isoxazole, oxadiazole, thiazole, isothiazole, and thiadiazole.

Among them, a nitrogen-containing hetero ring containing at least one nitrogen atom is preferred, a 6n-electron system nitrogen-containing hetero ring is more preferred, and pyrazole, oxazole, thiazole, or pyridine is further preferred.

One preferred example of Het will be shown below.

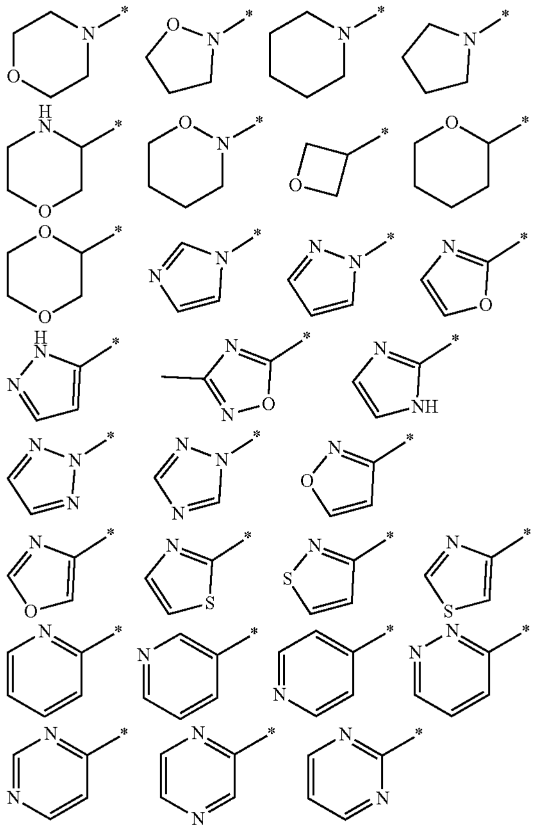

Examples of the "halogen atom" represented by $R^{b1}$ include fluorine, chlorine, bromine and iodine. Fluorine or chlorine is preferred.

The "lower alkyl group" represented by $R^{b1}$ is preferably a $C_{1-7}$ alkyl group, more preferably a $C_{1-4}$ alkyl group such as a methyl group, an ethyl group, a propyl group, an isopropyl group, a butyl group, an isobutyl group, or a tert-butyl group, further preferably a methyl group, an ethyl group, or an isopropyl group.

Examples of the group which may be substituted on the lower alkyl group include a halogen atom (e.g., a fluorine atom), a hydroxy group, a $C_{1-7}$ alkoxy group (e.g., a methoxy group, an ethoxy group, and a propoxy group), an amino group, a $C_{1-7}$ alkylamino group (e.g., a methylamino group, an ethylamino group, a dimethylamino group, and a diethylamino group), a carboxy group, a $C_{1-7}$ alkoxycarbonyl group (e.g., a methoxycarbonyl group and an ethoxycarbonyl group), a $C_{1-7}$ alkanoyl group (e.g., an acetyl group, an ethylcarbonyl group, a propylcarbonyl group, a butylcarbonyl group, a pentylcarbonyl group, and a hexylcarbonyl group), and a 4- to 7-membered cyclic ether group (oxetanyl, tetrahydrofuranyl group, and a tetrahydropyranyl group).

The "lower alkoxy group" represented by $R^{b1}$ is preferably a $C_{1-7}$ alkoxy group, more preferably a $C_{1-4}$ alkoxy group such as a methoxy group, an ethoxy group, a propoxy group, an isopropoxy group, or a butoxy group, further preferably a methoxy group, an ethoxy group, or a propoxy group.

Examples of the group which may be substituted on the lower alkoxy group include a hydroxy group, a $C_{1-7}$ alkoxy group (e.g., a methoxy group, an ethoxy group, and a propoxy group), a carboxy group, an amino group, and a $C_{1-7}$ alkylamino group (e.g., a methylamino group, an ethylamino group, a dimethylamino group, and a diethylamino group).

The "lower alkylamide group" represented by $R^{b1}$ is preferably a $C_{1-7}$ alkylamide group, more preferably a methylamide group, an ethylamide group, or a dimethylamide group.

The "lower alkoxycarbonyl group" represented by $R^{b1}$ is preferably a $C_{1-7}$ alkoxycarbonyl group, more preferably a methoxycarbonyl group or an ethoxycarbonyl group.

The "lower alkylamino group" represented by $R^{b1}$ is preferably a mono- or di-$C_{1-7}$ alkylamino group, more preferably, for example, a mono- or di-$C_{1-4}$ alkylamino group such as a methylamino group, an ethylamino group, a propylamino group, a methylethylamino group, a dimethylamino group, or a diethylamino group.

The "lower alkanoylamino group" represented by $R^{b1}$ is preferably a $C_{1-7}$ alkanoylamino group. Examples thereof include an acetylamino group, an ethylcarbonylamino group, a propylcarbonylamino group, a butylcarbonylamino group, a pentylcarbonylamino group, and a hexylcarbonylamino group.

Examples of the "4- to 7-membered cyclic ether group" represented by $R^{b1}$ include an oxetanyl group, a tetrahydrofuranyl group, a tetrahydropyranyl group, a dihydropyranyl group, a dioxolanyl group, and a dioxanyl group and preferably include a 3-oxetanyl group, a (2- or 3-)tetrahydrofuranyl group, a (2-, 3- or 4-)tetrahydropyranyl group, and a 2-(1,4-dioxanyl) group. Examples of the group which may be substituted on the cyclic ether group include a $C_{1-7}$ alkyl group (e.g., a methyl group and an ethyl group), a halogen atom, a hydroxy group, and a $C_{1-7}$ alkoxy group (e.g., a methoxy group, an ethoxy group, and a propoxy group).

$R^{b1}$ is preferably an optionally substituted $C_{1-7}$ alkyl group, an optionally substituted $C_{1-7}$ alkoxy group, or a mono- or di-$C_{1-4}$ alkylamino group.

m is preferably 0 or 1.

In the formula (c), CO, SO and $SO_2$ represented by $R^{c1}$ represent carbonyl, sulfinyl and sulfonyl, respectively. Among them, carbonyl is preferred.

The optionally substituted lower alkyl group represented by $R^{c2}$ is preferably a $C_{1-7}$ alkyl group, more preferably a $C_{1-4}$ alkyl group such as a methyl group, an ethyl group, a propyl group, an isopropyl group, a butyl group, an isobutyl group, or a tert-butyl group, further preferably a methyl group, an ethyl group, or an isopropyl group.

Examples of the group which may be substituted on the lower alkyl group include a halogen atom (e.g., a fluorine atom), a hydroxy group, a $C_{1-7}$ alkoxy group (e.g., a methoxy group, an ethoxy group, and a propoxy group), an amino group, a $C_{1-7}$, alkylamino group (e.g., a methylamino group, an ethylamino group, a dimethylamino group, and a diethylamino group), a carboxy group, a $C_{1-7}$ alkoxycarbonyl group (e.g., a methoxycarbonyl group and an ethoxycarbonyl group), a $C_{1-7}$ alkanoyl group (e.g., an acetyl group, an ethylcarbonyl group, a propylcarbonyl group, a butylcarbonyl group, a pentylcarbonyl group, and a hexylcarbonyl group), and an oxazinanyl group.

The "lower alkoxy group" represented by $R^{c2}$ is preferably a $C_{1-7}$ alkoxy group, more preferably a $C_{1-4}$ alkoxy group such as a methoxy group, an ethoxy group, a propoxy group, an isopropoxy group, or a butoxy group, further preferably a methoxy group, an ethoxy group, or a propoxy group.

Examples of the group which may be substituted on the lower alkoxy group include a halogen atom (e.g., a fluorine atom), a hydroxy group, a carboxy group, and an amino group.

The "cyclo lower alkyl group" represented by $R^{c2}$ is preferably a cyclo $C_{3-7}$ alkyl group, more preferably a cyclopropyl group, a cyclobutyl group, a cyclopentyl group, or a cyclohexyl group.

Examples of the group which may be substituted on the cyclo lower alkyl group include a halogen atom (e.g., a fluorine atom), a hydroxy group, a $C_{1-7}$ alkyl group (e.g., a methyl group and an ethyl group), and an oxy group.

Examples of the "5- or 6-membered heteroaryl group" represented by $R^{c2}$ include a pyrrolyl group, a pyrazinyl group, a pyrazolyl group, a tetrazolyl group, a furyl group, a thienyl group, a pyridyl group, an imidazolyl group, a triazolyl group, a triazinyl group, a pyridazinyl group, a pyrimidinyl group, an isoxazolyl group, a thiazolyl group, an isothiazolyl group, a thiadiazolyl group, an oxazolyl group, and an oxadiazolyl group. Among them, a 6-membered nitrogen-containing heteroaryl group such as a pyridyl group is preferred.

Examples of the group which may be substituted on the heteroaryl group include a halogen atom (e.g., a fluorine atom), a hydroxy group, a $C_{1-7}$ alkyl group (e.g., a methyl group, an ethyl group, a propyl group, an isopropyl group, a butyl group, an isobutyl group, and a tert-butyl group), and a $C_{1-7}$ alkoxy group (e.g., a methoxy group, an ethoxy group, and a propoxy group).

The "aralkyl group" represented by $R^{c2}$ is preferably an aralkyl group having an aryl moiety having 6 to 12 carbon atoms, and an alkyl moiety having 1 to 7 carbon atoms ($C_{6-12}$ aryl $C_{1-7}$ alkyl group). Examples thereof include a benzyl group, a 2-phenylpropan-2-yl group, a 1-phenylethyl group, a 2-phenylethyl group, a 1-phenylisopropyl group, a 2-phenylisopropyl group, a phenyl-tert-butyl group, an α-naphthylmethyl group, a 1-α-naphthylethyl group, a 2-α-naphthylethyl group, a 1-α-naphthylisopropyl group, a 2-α-naphthylisopropyl group, a β-naphthylmethyl group, a 1-β-naphthylethyl group, a 2-β-naphthylethyl group, a 1-β-naphthylisopropyl group, and a 2-β-naphthylisopropyl group. A benzyl group is preferred.

The "heteroaralkyl group" represented by $R^{c2}$ is preferably a heteroaralkyl group having a 5- or 6-membered heteroaryl moiety, and an alkyl moiety having 1 or 2 carbon atoms (5- or 6-membered heteroaryl $C_{1-2}$ alkyl group). Examples of the 5- or 6-membered heteroaryl include the same as those listed above.

Examples of the group which may be substituted on the aralkyl group or the heteroaralkyl group include those listed above as the group which may be substituted on the heteroaryl group and preferably include a halogen atom (e.g., a fluorine atom), a hydroxy group, a $C_{1-7}$ alkyl group (e.g., a methyl group and an ethyl group), a halo $C_{1-7}$ alkyl group (e.g., a fluoromethyl group, a difluoromethyl group, a trifluoromethyl group, and a pentafluoroethyl group), a $C_{1-7}$ alkoxy group (e.g., a methoxy group, an ethoxy group, and a propoxy group), a $C_{1-7}$ alkylamino group (e.g., a methylamino group, an ethylamino group, a dimethylamino group, and a diethylamino group), and a $C_{1-7}$ alkanoyl group (e.g., an acetyl group, an ethylcarbonyl group, a propylcarbonyl group, a butylcarbonyl group, a pentylcarbonyl group, and a hexylcarbonyl group).

$R^{c2}$ is preferably an optionally substituted $C_{1-7}$ alkyl group, an optionally substituted cyclo $C_{3-7}$ alkyl group, or an optionally substituted heteroaralkyl group.

In the formula (d), the "lower alkyl group" represented by $R^{d1}$ is preferably a $C_{1-7}$ alkyl group, more preferably a $C_{1-4}$ alkyl group such as a methyl group, an ethyl group, a propyl group, an isopropyl group, a butyl group, an isobutyl group, or a tert-butyl group, further preferably a methyl group or an ethyl group.

Examples of the group which may be substituted on the lower alkyl group include a hydroxy group, a $C_{1-7}$ alkoxy group (e.g., a methoxy group, an ethoxy group, and a propoxy group), an amino group, a carboxy group, a $C_{1-7}$ alkoxycarbonyl group (e.g., a methoxycarbonyl group and an ethoxycarbonyl group), and a $C_{1-7}$ alkanoyl group (e.g., an acetyl group, an ethylcarbonyl group, a propylcarbonyl group, a butylcarbonyl group, a pentylcarbonyl group, and a hexylcarbonyl group).

Examples of the "$C_{1-17}$ alkanoyl group" represented by $R^{d1}$ preferably include a $C_{1-7}$ alkanoyl group such as an acetyl group, an ethylcarbonyl group, a propylcarbonyl group, a butylcarbonyl group, a pentylcarbonyl group, and a hexylcarbonyl group as well as a $C_{5-17}$ alkanoyl group such as a pentadecanoyl group, a hexadecanoyl group, and a heptadecanoyl group.

Examples of the group which may be substituted on the $C_{1-17}$ alkanoyl group include an amino group and an aryl group (e.g., a phenyl group).

Examples of the "lower alkyl group" represented by $R^{d1}$ include the same lower alkyl groups as those listed for $R^{d1}$. A $C_{1-7}$ alkyl group is preferred.

Examples of the group which may be substituted on the lower alkyl group include a halogen atom (e.g., a fluorine atom), a hydroxy group, a $C_{1-7}$ alkoxy group (e.g., a methoxy group, an ethoxy group, a propoxy group, and an isopropoxy group), an amino group, a carboxy group, a $C_{1-7}$ alkoxycarbonyl group (e.g., a methoxycarbonyl group and an ethoxycarbonyl group), a $C_{1-7}$ alkanoyl group (e.g., an acetyl group, an ethylcarbonyl group, a propylcarbonyl group, a butylcarbonyl group, a pentylcarbonyl group, and a hexylcarbonyl group), a halo $C_{1-7}$ alkoxy group (e.g., a fluoromethoxy group, a difluoromethoxy group, a trifluoromethoxy group, a 2,2,2-trifluoroethoxy group, and a pentafluoroethoxy group), a hydroxy $C_{1-7}$ alkoxy group (e.g., hydroxyethoxy group, a 2-hydroxypropoxy group, and a 3-hydroxypropoxy group), a 5- or 6-membered heterocyclyl group having one or more nitrogen atoms (those listed as Het in the formula (b); e.g., pyrrole, pyrazole, oxazole, isoxazole, thiazole, isothiazole, pyridine, and pyrimidine), and a 4- to 7-membered cyclic ether group (oxetanyl, tetrahydrofuranyl group, and a tetrahydropyranyl group).

Examples of the "optionally substituted aralkyl group" represented by $R^{d2}$ include the same as those listed for $R^{c2}$.

Examples of the "optionally substituted heteroaralkyl group" represented by $R^{d2}$ include the same as those listed for $R^{c2}$.

In the formula (d), preferably, $R^{d1}$ is a hydrogen atom, and $R^{d2}$ is an optionally substituted lower alkyl group, more preferably, $R^{d1}$ is a hydrogen atom, and $R^{2}$ is a $C_{1-7}$ alkyl group.

In the formula (e), the "lower alkyl group" represented by $R^{e1}$ or $R^{e2}$ is preferably a $C_{1-7}$ alkyl group, more preferably a $C_{1-4}$ alkyl group such as a methyl group, an ethyl group, a propyl group, an isopropyl group, a butyl group, an isobutyl group, or a tert-butyl group, further preferably a methyl group, an ethyl group, or a propyl group.

Examples of the group which may be substituted on the lower alkyl group include a hydroxy group, a $C_{1-7}$ alkoxy group (e.g., a methoxy group, an ethoxy group, and a propoxy group), a carboxy group, a $C_{1-7}$ alkoxycarbonyl group (e.g., a methoxycarbonyl group and an ethoxycarbonyl group), and a 5- or 6-membered heterocyclyl group having one or more nitrogen atoms (those listed as Het in the formula (b); e.g., a pyrrolidinyl group, a morpholinyl group, a pyrrolyl group, a pyrazolyl group, a pyridyl group, a pyrimidinyl group, an oxazolyl group, an isoxazolyl group, a thiazolyl group, an isothiazolyl group, a thiadiazolyl group, and an oxadiazolyl group), and a 4- to 7-membered cyclic ether group (an oxetanyl group, a tetrahydrofuranyl group, and a tetrahydropyranyl group).

Examples of the "lower alkanoyl group" represented by $R^{e1}$ or $R^{e2}$ preferably include a $C_{1-7}$ alkanoyl group such as an acetyl group, an ethylcarbonyl group, a propylcarbonyl group, a butylcarbonyl group, a pentylcarbonyl group, and a hexylcarbonyl group.

Examples of the group which may be substituted on the lower alkanoyl group include a hydroxy group, a $C_{1-7}$ alkoxy group (e.g., a methoxy group, an ethoxy group, and a propoxy group), a halo $C_{1-7}$ alkoxy group (e.g., a fluoromethoxy group, a difluoromethoxy group, a trifluoromethoxy group, and a pentafluoroethoxy group), an aralkylcarbonylamino group (e.g., a benzylcarbonylamino group and a 1-phenylethylcarbonylamino group), a $C_{1-7}$ alkoxycarbonylamino group (e.g., a methoxycarbonylamino group, an ethoxycarbonylamino group, and a propoxycarbonylamino group), an amino group, and a carboxy group.

Examples of the "optionally substituted aralkyl group" represented by $R^{e1}$ or $R^{e2}$ include the same as those listed for $R^{c2}$.

Examples of the "5- or 6-membered heteroaryl group" represented by $R^{e1}$ or $R^{e2}$ include the same as those listed for $R^{2}$. Among them, a nitrogen-containing heteroaryl group such as a pyrazolyl group, a thiazolyl group, or a pyridyl group is preferred.

Examples of the group which may be substituted on the heteroaryl group include a halogen atom (e.g., a fluorine atom), a hydroxy group, a $C_{1-7}$ alkyl group (e.g., a methyl group, an ethyl group, a propyl group, an isopropyl group, a butyl group, an isobutyl group, and a tert-butyl group), and a $C_{1-7}$ alkoxy group (e.g., a methoxy group, an ethoxy group, and a propoxy group).

In the formula (e), preferably, $R^{e1}$ is a hydrogen atom or an optionally substituted lower alkyl group, and $R^{e2}$ is an optionally substituted lower alkyl group, more preferably, $R^{e1}$ is a hydrogen atom, and $R^{8}$ is a $C_{1-7}$ alkyl group.

In the formula (f), the "lower alkyl group" represented by $R^{f1}$ or $R^{f2}$ is preferably a $C_{1-7}$ alkyl group, more preferably a $C_{1-4}$ alkyl group such as a methyl group, an ethyl group, a propyl group, an isopropyl group, a butyl group, an isobutyl group, or a tert-butyl group, further preferably a methyl group, an ethyl group, or a propyl group.

Examples of the group which may be substituted on the lower alkyl group include a hydroxy group, a $C_{1-7}$ alkoxy group (e.g., a methoxy group, an ethoxy group, and a propoxy group), a halo $C_{1-7}$ alkoxy group (a fluoromethoxy group, a difluoromethoxy group, a trifluoromethoxy group, and a pentafluoroethoxy group), an amino group, a carboxy group, a $C_{1-7}$ alkoxycarbonyl group (e.g., a methoxycarbonyl group and an ethoxycarbonyl group), and a $C_{1-7}$ alkanoyl group (e.g., an acetyl group, an ethylcarbonyl group, a propylcarbonyl group, a butylcarbonyl group, a pentylcarbonyl group, and a hexylcarbonyl group).

Examples of the "lower alkanoyl group" represented by $R^{f1}$ or $R^{f2}$ preferably include a $C_{1-7}$ alkanoyl group such as an acetyl group, an ethylcarbonyl group, a propylcarbonyl group, a butylcarbonyl group, a pentylcarbonyl group, and a hexylcarbonyl group.

Examples of the group which may be substituted on the lower alkanoyl group include the same as those listed above as the group which may be substituted on the lower alkyl group represented by $R^{f1}$ or $R^{f2}$.

Examples of the "5- or 6-membered heteroaryl group" represented by $R^{f1}$ or $R^{f2}$ include the same as those listed for $R^{c2}$. Among them, a nitrogen-containing heteroaryl group such as a pyrazolyl group, a thiazolyl group, a pyridyl group, or a pyrimidinyl group is preferred.

Examples of the group which may be substituted on the heteroaryl group include a halogen atom (e.g., a fluorine atom and a chlorine atom), a hydroxy group, a $C_{1-7}$ alkyl group (e.g., a methyl group, an ethyl group, a propyl group, an isopropyl group, a butyl group, an isobutyl group, and a tert-butyl group), a $C_{1-7}$ alkoxy group (e.g., a methoxy group, an ethoxy group, and a propoxy group), a $C_{1-7}$ alkoxycarbonyl group (e.g., a methoxycarbonyl group and an ethoxycarbonyl group), a $C_{1-7}$ alkanoyl group (e.g., an acetyl group, an ethylcarbonyl group, a propylcarbonyl group, a butylcarbonyl group, a pentylcarbonyl group, and a hexylcarbonyl group), and a halo $C_{1-7}$ alkyl group (a fluoromethyl group, a difluoromethyl group, a trifluoromethyl group, and a 2,2,2-trifluoroethyl group).

In the formula (f), preferably, $R^{f1}$ is a hydrogen atom, and $R^{f2}$ is an optionally substituted $C_{1-7}$ alkyl group or an optionally substituted 5- or 6-membered heteroaryl group, more preferably, $R^{f1}$ is a hydrogen atom, and $R^{f2}$ is an optionally substituted 6-membered heteroaryl group.

n is preferably 0 or 1.

In the formula (g), CO, CS, SO and $SO_2$ represented by $R^{g2}$ represent carbonyl, thiocarbonyl, sulfinyl and sulfonyl, respectively. Among them, carbonyl is preferred.

The "lower alkyl group" represented by $R^{g1}$ is preferably a $C_{1-7}$ alkyl group, more preferably a $C_{1-4}$ alkyl group such as a methyl group, an ethyl group, a propyl group, an isopropyl group, a butyl group, an isobutyl group, or a tert-butyl group, further preferably a methyl group.

Examples of the group which may be substituted on the lower alkyl group include a halogen atom (e.g., a fluorine atom), a hydroxy group, and a $C_{1-7}$ alkoxy group (e.g., a methoxy group, an ethoxy group, and a propoxy group).

Examples of the "$C_{1-17}$ alkyl group" represented by $R^{93}$ preferably include a $C_{1-4}$ alkyl group such as a methyl group, an ethyl group, a propyl group, an isopropyl group, a butyl group, an isobutyl group, and a tert-butyl group as well as a $C_{15-17}$ alkyl group such as a pentadecanyl group, a hexadecanyl group, and heptadecanyl.

Examples of the group which may be substituted on the $C_{1-17}$ alkyl group include a halogen atom (e.g., a fluorine atom), a hydroxy group, an amino group, a $C_{1-4}$ alkylamino group (e.g., a methylamino group, an ethylamino group, and a dimethylamino group), a $C_{1-7}$ alkoxy group (e.g., a methoxy group, an ethoxy group, and a propoxy group), a $C_{1-7}$ alkoxycarbonyl group (e.g., a methoxycarbonyl group and an ethoxycarbonyl group), a $C_{1-7}$ alkoxycarbonylamino group (e.g., a methoxycarbonylamino group, an ethoxycarbonylamino group, and a tert-butoxycarbonylamino group), a $C_{1-7}$ alkanoyl group (e.g., an acetyl group, an ethylcarbonyl group, a propylcarbonyl group, a butylcarbonyl group, a pentylcarbonyl group, and a hexylcarbonyl group), an aryl group, and a 4- to 7-membered cyclic ether group (e.g., a tetrahydrofuranyl group, and a tetrahydropyranyl group).

The "lower alkoxy group" represented by $R^{93}$ is preferably a $C_{1-7}$ alkoxy group, more preferably a $C_{1-4}$ alkoxy group such as a methoxy group, an ethoxy group, a propoxy group, an isopropoxy group, or a butoxy group, further preferably a methoxy group, an ethoxy group, or a propoxy group.

Examples of the group which may be substituted on the lower alkoxy group include a halogen atom (e.g., a fluorine atom), a hydroxy group, a $C_{1-7}$ alkoxy group (e.g., a methoxy group, an ethoxy group, and a propoxy group), a carboxy group, an amino group, and a $C_{1-7}$ alkylamino group (e.g., a methylamino group, an ethylamino group, a dimethylamino group, and a diethylamino group).

The "lower alkylamino group" represented by $R^{g3}$ is preferably a mono- or di-$C_{1-7}$ alkylamino group, more preferably, for example, a mono- or di-$C_{1-4}$ alkylamino group such as a methylamino group, an ethylamino group, a propylamino group, a methylethylamino group, a dimethylamino group, or a diethylamino group.

Examples of the group which may be substituted on the lower alkylamino group include a hydroxy group, a $C_{1-7}$ alkoxy group (e.g., a methoxy group, an ethoxy group, and a propoxy group), a carboxy group, an amino group, and a $C_{1-4}$ alkylamino group (e.g., a methylamino group and an ethylamino group).

Examples of the "5- or 6-membered heteroaryl group" represented by $R^{g3}$ include the same as those listed for $R^{c2}$. Among them, a 6-membered nitrogen-containing heteroaryl group such as a pyridyl group or a pyrimidinyl group is preferred.

Examples of the "5- or 6-membered heteroarylamino group" represented by $R^{g3}$ include an amino group mono- or di-substituted by the heteroaryl group described above.

Examples of the group which may be substituted on the heteroaryl group include a halogen atom (e.g., a fluorine atom and a chlorine atom), a hydroxy group, a $C_{1-7}$ alkyl group (e.g., a methyl group, an ethyl group, a propyl group, an isopropyl group, a butyl group, an isobutyl group, and a tert-butyl group), a $C_{1-7}$ alkoxy group (e.g., a methoxy group, an ethoxy group, and a propoxy group), a $C_{1-7}$ alkoxycarbonyl group (e.g., a methoxycarbonyl group and an ethoxycarbonyl group), a $C_{1-7}$ alkanoyl group (e.g., an acetyl group, an ethylcarbonyl group, a propylcarbonyl group, a butylcarbonyl group, a pentylcarbonyl group, and a hexylcarbonyl group), an amino group, a $C_{1-7}$ alkylamino group (e.g., a methylamino group, an ethylamino group, a dimethylamino group, and a diethylamino group), a halo $C_{1-7}$ alkyl group (e.g., a fluoromethyl group, a difluoromethyl group, a trifluoromethyl group, and a 2,2,2-trifluoroethyl group), a hydroxy $C_{1-7}$ alkyl group (e.g., a hydroxymethyl group, a hydroxyethyl group, and a hydroxypropyl group), a halo $C_{1-7}$ alkoxy group (e.g., a fluoromethoxy group, a difluoromethoxy group, a trifluoromethoxy group, and a 2,2,2-trifluoroethoxy group), and a hydroxy $C_{1-7}$ alkoxy group (e.g., a hydroxyethoxy group, a 2-hydroxypropoxy group, and a 3-hydroxypropoxy group).

Examples of the "4- to 7-membered cyclic amino group" represented by $R^{93}$ include an azetidino group, a pyrrolidino group, a morpholino group, an isoxazolino group, a piperidino group, and an oxazinano group.

Examples of the group which may be substituted on the cyclic amino group include a halogen atom (e.g., a fluorine atom), a hydroxy group, a $C_{1-4}$ alkyl group (e.g., a methyl group, an ethyl group, a propyl group, and an isopropyl group), a halo $C_{1-4}$ alkyl group (e.g., a trifluoromethyl group), a $C_{1-4}$ alkoxy group (e.g., a methoxy group, an ethoxy group, and a propoxy group), an amino group, a $C_{1-4}$ alkylamino group (e.g., a methylamino group, an ethylamino group, a dimethylamino group, and a diethylamino group), and a carboxy group.

In the formula (g), preferably, $R^8$ is a hydrogen atom, $R^{g2}$ is carbonyl, and $R^{g3}$ is an optionally substituted 5- or 6-membered heteroaryl group.

When $R^7$ and $R^8$ form oxime (═N—$OR^{10}$), the lower alkyl group represented by $R^{10}$ is preferably a $C_{1-4}$ alkyl group, more preferably a methyl group, an ethyl group, a propyl group, an isopropyl group, a butyl group, an isobutyl group, or a tert-butyl group. Examples of the group which may be substituted on the lower alkyl group include a hydroxy group and a 4- to 6-membered cyclic ether group (e.g., an oxetanyl group, a tetrahydrofuranyl group, a tetrahydropyranyl group, and a dioxanyl group). The aralkyl group represented by $R^{10}$ is preferably an aralkyl group having an aryl moiety having 6 to 12 carbon atoms, and an alkyl moiety having 1 or 2 carbon atoms ($C_{6-12}$ aryl $C_{1-2}$ alkyl group). Examples thereof include a benzyl group, a 1-phenylethyl group, and a 2-phenylethyl group.

When $R^7$ and $R^8$ form an optionally substituted 4- to 6-membered saturated hetero ring together with the adjacent carbon atom, examples of the hetero ring include a saturated hetero ring containing an oxygen atom and/or a nitrogen atom, for example, oxetane, pyrrolidine, pyrazolidine, imidazolidine, pyrroline, pyrazoline, imidazoline, piperidine, piperidine, piperazine, triazinane, morpholine, oxazolidine, isoxazolidine, tetrahydrofuran, and tetrahydropyran.

The hetero ring forms an azaspiro ring together with an azetidine ring.

Examples of the group which may be substituted on the hetero ring include a halogen atom (e.g., a fluorine atom), a hydroxy group, a $C_{1-7}$ alkyl group (e.g., a methyl group and an ethyl group), a $C_{1-7}$ alkoxy group (e.g., a methoxy group, an ethoxy group, and a propoxy group), an amino group, a $C_{1-7}$ alkylamino group (e.g., a methylamino group, an ethylamino group, a dimethylamino group, and a diethylamino group), and an oxo group.

Examples of the "ester residue" represented by $R^9$ include any residue which is relatively easily cleaved to generate the corresponding free carboxy group. Examples thereof include groups which are eliminated by treatment under mild conditions such as hydrolysis or catalytic reduction, including: a $C_{1-7}$ alkyl group such as a methyl group, an ethyl group, a propyl group, an isopropyl group, a butyl group, an isobutyl group, a tert-butyl group, a pentyl group, a hexyl group, and a heptyl group; a $C_{2-7}$ alkenyl group such as a vinyl group, an allyl group, a 1-propenyl group, a butenyl group, a pentenyl group, a hexenyl group, and a heptenyl group; an aralkyl group such as a benzyl group; and an aryl group such as a phenyl group and a naphthyl group, and groups which are eliminated in vivo, including: a $C_{1-7}$ alkanoyloxy $C_{1-4}$ lower alkyl group such as an acetoxymethyl group and a pivaloyloxymethyl group; a $C_{1-4}$ alkoxycarbonyloxy $C_{1-4}$ alkyl group such as a methoxycarbonyloxymethyl group and a 1-ethoxycarbonyloxyethyl group; a $C_{1-4}$ alkoxymethyl group such as a methoxymethyl group; a lactonyl group such as a phthalidyl group; a di-$C_{1-4}$ alkylamino $C_{1-4}$ alkyl group such as a 1-dimethylaminoethyl group; $R^{1s}O—(CH_2CH_2O)_p—R^{19}—$ (wherein $R^{18}$ represents a $C_{1-4}$ alkyl group, $R^{19}$ represents a $C_{1-4}$ alkylene group, and p represents an integer of 0 to 4) such as a methoxyethoxyethoxyethyl group; and a (5-methyl-2-oxo-1,3-dioxol-4-yl)methyl group. The compound of the present invention in which $R^9$ is an ester residue which is eliminated in vivo functions as a so-called prodrug.

$R^9$ is preferably a hydrogen atom.

When X is C—$R^{11}$, the "halogen atom" represented by $R^{11}$ means fluorine, chlorine, bromine or iodine and is preferably fluorine or chlorine, more preferably fluorine.

Examples of the "lower alkyl group" and the "lower alkoxy group" represented by $R^{11}$ include the same as those listed for $R^1$.

Examples of the group which may be substituted on the "thienyl group" or the "phenyl group" represented by $R^{11}$ include a halogen atom (e.g., a fluorine atom and a bromine atom), a hydroxy group, and a nitro group.

When Y is C—$R^{12}$, the "halogen atom" represented by $R^{12}$ is preferably a fluorine atom or a chlorine atom, more preferably a fluorine atom.

When Y is C—$R^{12}$, examples of the "optionally substituted lower alkyl group" represented by $R^{12}$ include the same as those listed for $R^1$ and preferably include a $C_{1-4}$ alkyl group such as a methyl group, an ethyl group, a propyl group, an isopropyl group, a butyl group, an isobutyl group, and a tert-butyl group as well as a halogen atom-substituted $C_{1-4}$ alkyl group (e.g., a fluoromethyl group, a difluoromethyl group, a trifluoromethyl group, and a 2,2,2-trifluoroethyl group).

In the pyridone carboxylic acid derivative described above, particularly preferably, $R^1$ is a hydrogen atom or a halogen atom (preferably a fluorine atom or a chlorine atom), $R^2$ is a hydrogen atom or an optionally substituted $C_{1-7}$ alkyl group (preferably a methyl group or an ethyl group), each of $R^3$ to $R^6$ is a hydrogen atom, $R^7$ is a hydrogen atom, $R^9$ is a hydrogen atom, X is a nitrogen atom or C—$R^{11}$ (wherein $R^{11}$ is preferably a hydrogen atom or a halogen atom), Y is C—$R^{12}$ (wherein $R^{12}$ is preferably a hydrogen atom or a halogen atom), and $R^8$ is any of the following:

1) $R^8$ is a group represented by the formula (a) wherein any one of $R^{a1}$ and $R^{a2}$ is a hydrogen atom, and the other moiety is an optionally substituted $C_{2-12}$ alkyl group having an ether bond(s) (preferably a 1-ethoxy-2-propanyl group, a 1,3-dimethoxy-2-propanyl group, or a 1,3-diethoxy-2-propanyl group); any one of $R^{a1}$ and $R^{a2}$ is a hydrogen atom, and the other moiety is —$R^{a3}$-$Cy^1$ ($R^{a3}$: preferably an optionally halogen atom-substituted $C_{1-6}$ alkylene group, $Cy^1$: preferably an optionally substituted 4- to 7-membered cyclic ether group (preferably a tetrahydropyranyl group); or any one of $R^{a1}$ and $R^{a2}$ is a hydrogen atom, and the other moiety is an optionally substituted 5- or 6-membered heteroaryl group (preferably a pyridyl group);

2) $R^8$ is a group represented by the formula (b) wherein m is 0, and Het is a 6π-electron system nitrogen-containing heterocyclyl group (preferably a pyrazolyl group);

3) $R^8$ is a group represented by the formula (d) wherein $R^{d1}$ is a hydrogen atom, and $R^{d2}$ is an optionally substituted $C_{1-7}$ alkyl group (preferably a methyl group or a tetrahydropyranylmethyl group); and 4) $R^8$ is a group represented by the formula (e) wherein $R^{e1}$ is a hydrogen atom, and $R^{e2}$ is an optionally substituted $C_{1-7}$ alkyl group (preferably a methyl group).

The pyridone carboxylic acid derivative of the present invention can form a base-addition salt. This salt also includes a chelate salt formed with a boron compound. Examples of the base-addition salt can include (A) a salt with an alkali metal such as sodium and potassium, (B) a salt with an alkaline earth metal such as calcium and magnesium, (C) an ammonium salt, (D) a salt with a nitrogen-containing organic base such as trimethylamine, triethylamine, tributylamine, pyridine, N,N-dimethylaniline, N-methylpiperidine, N-methylmorpholine, diethylamine, 2-aminoethan-1-ol, N-methylaminoethanol, N,N-dimethylaminoethanol, 1,1,3,3-tetramethylguanidine, diethanolamine, triethanolamine, dicyclohexylamine, cyclohexylamine, procaine, dibenzylamine, N-benzyl-β-phenethylamine, 1-ephenamine, N,N'-dibenzylethylenediamine, glucamine, N-methylglucamine, and 1-carbamimidamido-N,N-dimethylmethanimidamide, and (E) a salt with a basic amino acid such as arginine, lysine, and ornithine. Examples of the boron compound include boron halide such as boron fluoride, and lower acyloxyboron such as acetoxyboron.

The pyridone carboxylic acid derivative of the present invention or a salt thereof can exist not only in an unsolvated form but as a hydrate or a solvate. Thus, the pyridone carboxylic acid derivative of the present invention or a salt thereof includes every crystal form and hydrate or solvate thereof.

The pyridone carboxylic acid derivative of the present invention or a salt thereof may exist as an optical isomer. Such an optical isomer is also included in the compound of the present invention. Further, the pyridone carboxylic acid derivative of the present invention or a salt thereof may exist as different stereoisomers (cis and trans forms). These stereoisomers are also encompassed by the present invention.

The pyridone carboxylic acid derivative of the present invention or a salt thereof can basically be produced by methods of the following processes 1 to 3 and can be produced according to any method appropriate therefor by appropriately modifying the method through the type of a substituent, etc.

(Process 1)

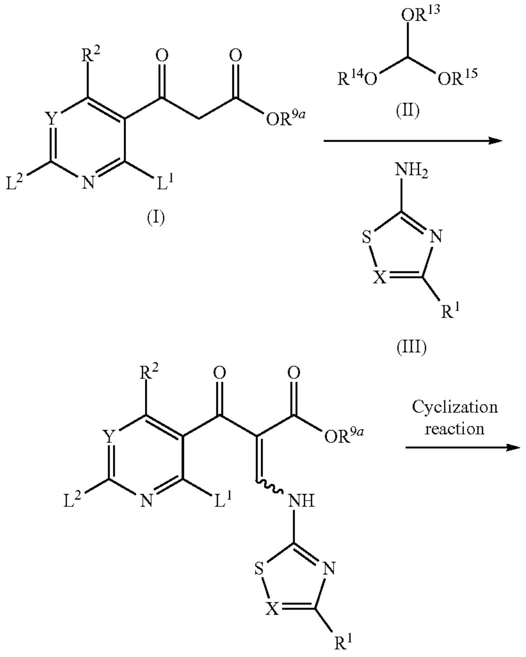

(I) (II) (III) (IV)

-continued

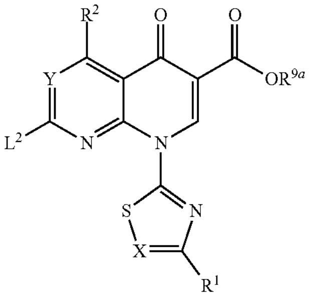

(V)

In the formulae, $R^{9a}$ represents a lower alkyl group, a lower alkenyl group or an aralkyl group, $R^{13}$, $R^{14}$ and $R^{13}$ each represent a lower alkyl group, $L^1$ represents a halogen atom, $L^2$ represents a halogen atom, a sulfide group or a sulfoxide group, and $R^1$, $R^2$, X and Y are as defined above.

Specifically, compound (I) is reacted with orthoformic acid ester (II) such as ethyl orthoformate or methyl orthoformate, and the obtained compound is reacted with aromatic amine (III) and thereby converted into compound (IV), which is then subjected to cyclization reaction to obtain compound (V).

In this context, the "lower alkyl group" represented by $R^{9a}$ is preferably a $C_{1-4}$ alkyl group, more preferably a methyl group, an ethyl group, or a tert-butyl group. The "lower alkenyl group" is preferably a $C_{2-4}$ alkenyl group, more preferably a vinyl group, an allyl group, a 1-propenyl group or the like. The "aralkyl group" is preferably a $C_{7-14}$ aralkyl group, more preferably a benzyl group, a phenethyl group, or a benzhydryl group.

The "lower alkyl group" represented by $R^{13}$, $R^{14}$ and $R^{15}$ is preferably a $C_{1-3}$ alkyl group, more preferably an ethyl group.

Examples of the "halogen atom" represented by $L^1$ and $L^2$ preferably include a fluorine atom and a chlorine atom.

The reaction of the compound (I) with the orthoformic acid ester (II) is usually performed at 0 to 160° C., preferably 50 to 150° C. The reaction time is usually 10 minutes to 48 hours, preferably 1 to 10 hours. The amount of the orthoformic acid ester used is equimolar or more, in particular, preferably approximately 1- to 10-fold mol, with respect to the compound (I).

The reaction with the aromatic amine (III) is performed in an appropriate reaction solvent. In this context, the solvent used can be any solvent which does not influence the reaction. Examples thereof include: aromatic hydrocarbons such as toluene and xylene; ethers such as diethyl ether, tetrahydrofuran, and dioxane; aliphatic hydrocarbons such as pentane and hexane; halogenated hydrocarbons such as methylene chloride, chloroform, and carbon tetrachloride; aprotic polar solvents such as acetonitrile, N,N-dimethylformamide, dimethyl sulfoxide, and N-methylpyrrolidin-2-one; and alcohols such as methanol, ethanol, and propanol. This reaction is usually performed at 0 to 150° C., preferably 0 to 100° C. The reaction time is usually 10 minutes to 48 hours, preferably 1 to 10 hours.

The cyclization reaction of the compound (IV) is performed in an appropriate solvent in the presence or absence of a basic compound. The solvent for use in this reaction can be any solvent which does not influence the reaction. Examples thereof include: aromatic hydrocarbons such as toluene and xylene; ethers such as diethyl ether, tetrahydrofuran, and dioxane; aliphatic hydrocarbons such as pentane and hexane; halogenated hydrocarbons such as methylene chloride, chloroform, and carbon tetrachloride; aprotic polar solvents such as N,N-dimethylformamide and dimethyl sulfoxide; and alcohols such as methanol, ethanol, and propanol. Examples of the basic compound used include: alkali metals such as sodium metal and potassium metal; metal hydrides such as sodium hydride and calcium hydride; inorganic bases such as sodium hydroxide, potassium hydroxide, sodium carbonate, potassium carbonate, and sodium bicarbonate; alkoxides such as sodium methoxide, sodium ethoxide, and potassium tert-butoxide; metal fluorides such as sodium fluoride and potassium fluoride; and organic bases such as triethylamine, N-methylpyrrolidine, 1,1,3,3-tetramethylguanidine, and 1,8-diazabicyclo[5.4.0]undec-7-ene (DBU). This reaction is usually performed at 0 to 200° C., preferably room temperature to 120° C. The reaction time to complete the reaction is usually 10 minutes to 48 hours.

The compound (I) for use as a starting material may be a commercially available product which can be purchased and used, or may be produced by methods described in the following literatures or methods equivalent thereto.

1) JP-A-2-282384

2) JP-A-2006-514964

(Process 2)

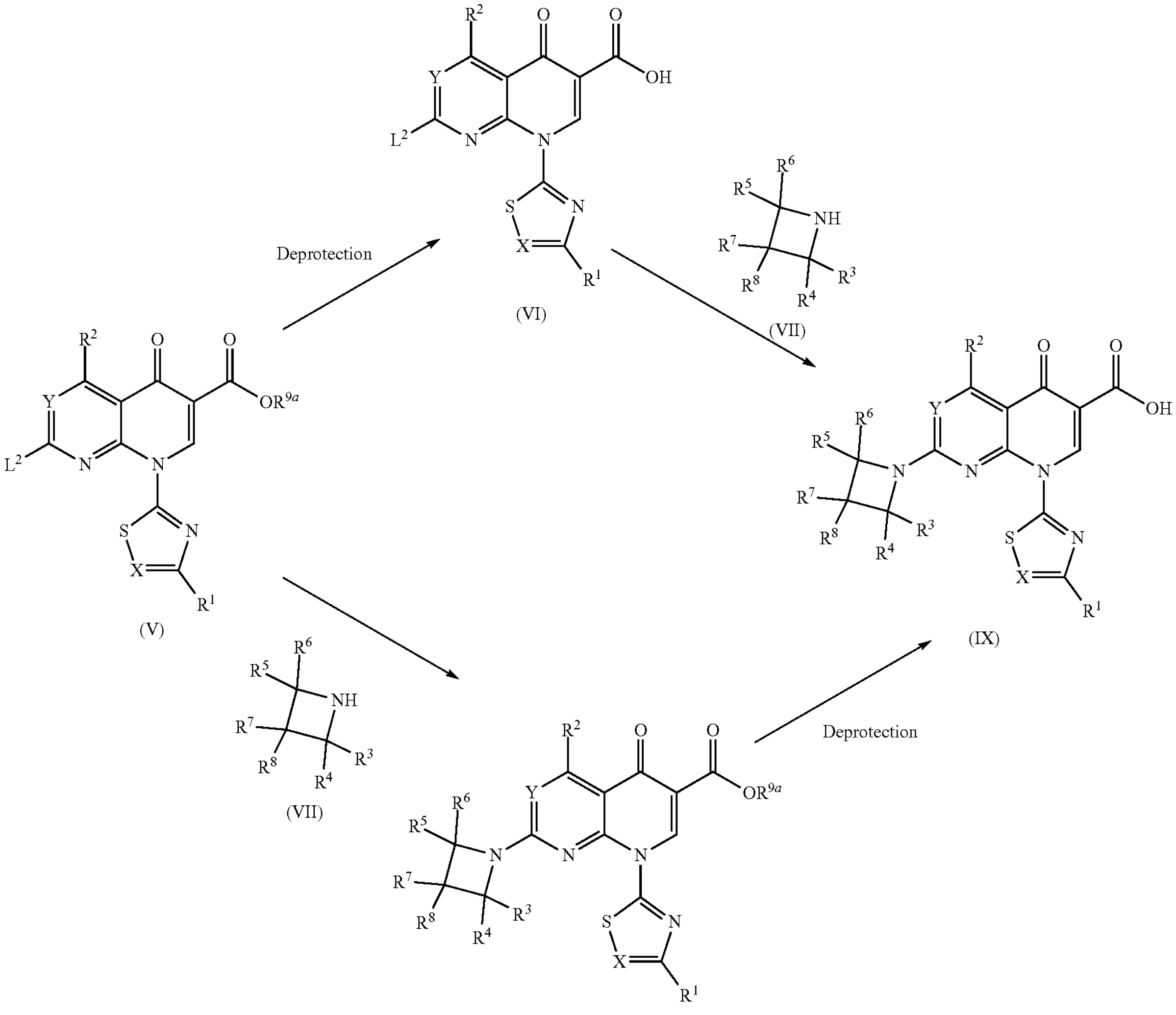

(VI)
(VII)
(V)
(IX)
(VII)
(VIII)

In the formulae, $R^1$, $R^2$, $R^3$, $R^4$, $R^5$, $R^6$, $R^7$, $R^8$, $R^{9a}$, $L^2$, X and Y are as defined above.

Specifically, a protective group of $R^{9a}$ on compound (V) is eliminated to prepare compound (VI), which is then subjected to aromatic substitution reaction with compound (VII) to obtain compound (IX). In another method, after the same substitution reaction as above of compound (V) with compound (VII), a protective group of $R^{9a}$ may be eliminated to obtain compound (IX).

The aromatic substitution reaction is usually performed at 0 to 80° C., preferably 0° C. to room temperature in a solvent which does not influence the reaction, for example, esters such as ethyl acetate, aromatic hydrocarbons, ethers, aliphatic hydrocarbons, halogenated hydrocarbons, aprotic polar solvents or alcohols, in the presence of, if necessary, a deoxidant, for example, sodium carbonate, calcium carbonate, sodium bicarbonate, potassium carbonate, sodium hydroxide, triethylamine, 1,8-diazabicyclo[5.4.0]undec-7-ene, N-methylpyrrolidine, 1,1,3,3-tetramethylguanidine, or sodium hydride. The reaction time to complete the reaction is a few minutes to 48 hours.

The amount of the compound (VII) used is preferably equimolar to 5-fold mol with respect to the compound (V) or the compound (VI). Alternatively, this reaction may be performed in the presence of a lithium salt such as lithium chloride as a weak Lewis acid.

For the introduction of an azetidinyl group, aromatic substitution reaction may be performed using compound (VII) having a protective group. In the case of introducing, for example, tert-butyl 2,6-diazaspiro[3.3]heptane-2-carboxylate or tert-butyl 1,6-diazaspiro[3.3]heptane-1-carboxylate, a tert-butoxycarbonyl (Boc) group is eliminated with an acidic compound to obtain a compound in which the azetidinyl group of interest is introduced. Examples of the acidic compound used include inorganic acids such as hydrochloric acid, and organic acids such as trifluoroacetic acid (TFA). This reaction is usually performed at 0 to 80° C., preferably 0° C. to room temperature. The reaction time is usually a few minutes to 48 hours.

The deprotection reaction of the compound (VIII) can be performed by the application of, for example, hydrolysis reaction generally used, and can be performed, for example, in an alcohol solution using an inorganic base such as sodium hydroxide or potassium hydroxide. This reaction is usually performed at 0 to 150° C., preferably room temperature to 100° C. The reaction time is usually 10 minutes to 48 hours.

Another deprotection reaction of the compound (VIII) is as follows.

Specifically, for example, a methyl group, an ethyl group or a tert-butyl group is eliminated with an acidic compound in an acetic acid solution to obtain the compound of interest. Examples of the acidic compound used include inorganic acids such as hydrochloric acid, and organic acids such as trifluoroacetic acid (TFA). This reaction is usually performed at room temperature to 150° C. The reaction time is usually a few hours to 3 days.

The deprotection reaction of the compound (V) can be performed by the application of, for example, hydrolysis reaction generally used, and, for example, a methyl group, an ethyl group or a tert-butyl group is eliminated with an acidic compound in an acetic acid solution to obtain the compound of interest. Examples of the acidic compound used include inorganic acids such as hydrochloric acid, and organic acids such as trifluoroacetic acid (TFA). This reaction is usually performed at room temperature to 150° C. The reaction time is usually a few hours to 3 days.

(Process 3)

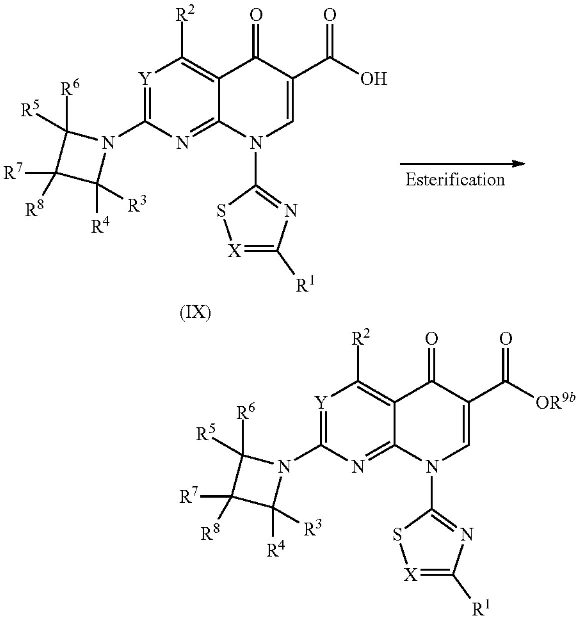

(IX)

(X)

In the formulae, $R^{9b}$ represents an ester residue, and $R^1$, $R^2$, $R^3$, $R^4$, $R^5$, $R^6$, $R^7$, $R^8$, X and Y are as defined above.

In this context, examples of the "ester residue" represented by $R^{9b}$ include any residue which is relatively easily cleaved to generate the corresponding free carboxy group. Examples thereof include groups which are eliminated by treatment under mild conditions such as hydrolysis or catalytic reduction, including: a $C_{1-7}$ alkyl group such as a methyl group, an ethyl group, a propyl group, an isopropyl group, a butyl group, an isobutyl group, a tert-butyl group, a pentyl group, a hexyl group, and a heptyl group; a $C_{2-7}$ alkenyl group such as a vinyl group, an allyl group, a 1-propenyl group, a butenyl group, a pentenyl group, a hexenyl group, and a heptenyl group; an aralkyl group such as a benzyl group and a diphenylmethyl (benzhydryl) group; and an aryl group such as a phenyl group and a naphthyl group, and groups which are eliminated in vivo, including: a $C_{1-7}$ alkanoyloxy $C_{1-4}$ lower alkyl group such as an acetoxymethyl group and a pivaloyloxymethyl group; a $C_{1-4}$ alkoxycarbonyloxy $C_{1-4}$ alkyl group such as a methoxycarbonyloxymethyl group and a 1-ethoxycarbonyloxyethyl group; a $C_{1-4}$ alkoxymethyl group such as a methoxymethyl group; a lactonyl group such as a phthalidyl group; a di-$C_{1-4}$ alkylamino $C_{1-4}$ alkyl group such as a 1-dimethylaminoethyl group; $R^{18}O—(CH_2CH_2O)_p—R^{19}—$ (wherein $R^{18}$ represents a $C_{1-4}$ alkyl group, $R^{19}$ represents a $C_{1-4}$ alkylene group, and p represents an integer of 0 to 4) such as a methoxyethoxyethoxyethyl group; and (5-methyl-2-oxo-1,3-dioxol-4-yl)methyl group.

Specifically, compound (IX) is subjected to the introduction of an ester residue (esterification) to obtain compound (X).

Examples of the esterification reaction can include methods described in Theodora W. Greene, Peter G. M. Wuts, "Protective Groups in Organic Synthesis" 4th. ed., John Wiley & Sons, Inc., 2007. Examples of the esterifying agent include alkyl halide or 4-halomethyl-5-methyl-2-oxo-1,3-dioxolane, acetoxymethyl halide, and pivaloyloxymethyl halide.

This reaction may be performed by the addition of a basic compound.

Examples of the basic compound include: metal hydrides such as sodium hydride and calcium hydride; inorganic bases such as sodium hydroxide, potassium hydroxide, sodium carbonate, and potassium carbonate; and organic bases such as triethylamine, N,N-diisopropylethylamine, N-methylmorpholine, N-methylpyrrolidine, 1,1,3,3-tetramethylguanidine, and 1,8-diazabicyclo[5.4.0]undec-7-ene.

The solvent for use in this reaction can be any solvent which does not influence the reaction. Examples thereof include aromatic hydrocarbons, ethers, esters, aliphatic hydrocarbons, halogenated hydrocarbons, and aprotic polar solvents. This reaction is usually performed at room temperature to 100° C. The reaction time is a few minutes to 48 hours.

(Process 4-1)

Compound (III-1) corresponding to the aromatic amine (III) for use as a starting material wherein X is a nitrogen atom may be a commercially available product which can be purchased and used, or can be produced by any method. One example of the production method is as follows.

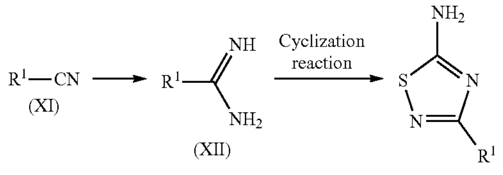

(XI) (XII) (III-1)

In the formulae, $R^1$ is as defined above.

Specifically, nitrile (XI) is reacted with alkoxide and then reacted with ammonium chloride to obtain carboxamidine (XII), which is then subjected to cyclization reaction to obtain aromatic amine (III). In another method, nitrile (XI) is reacted with hydrogen halide and then reacted with ammonia gas to obtain carboxamidine (XII), which is then subjected to cyclization reaction to obtain aromatic amine (III-1).

The solvent for use in the reaction with the alkoxide can be any solvent which does not influence the reaction. Examples thereof include ethers, aprotic polar solvents and alcohols and preferably include alcohols. This reaction is usually performed at −30 to 80° C., preferably −20 to 40° C. The reaction time is usually 10 minutes to 48 hours.

The solvent for use in the reaction with the hydrogen halide can be any solvent which does not influence the reaction. Examples thereof include halogenated hydrocarbons, ethers, aprotic polar solvents and alcohols and preferably include halogenated hydrocarbons, ethers and alcohols. Examples of the hydrogen halide for use in this reaction include hydrogen fluoride, hydrogen chloride, hydrogen bromide, and hydrogen iodide and preferably include hydrogen chloride. This reaction is usually performed at −30 to 80° C., preferably −20 to 40° C. The reaction time is usually a few hours to 5 days.

The solvent for use in the cyclization reaction can be any solvent which does not influence the reaction. Examples thereof include halogenated hydrocarbons, ethers, aprotic polar solvents and alcohols and preferably include alcohols. This reaction is usually performed at −30 to 80° C., preferably −20 to 40° C. The reaction time is usually 10 minutes to 48 hours.

(Process 4-2)

Compound (111-2) corresponding to the aromatic amine (III) wherein X is C—$R^{11}$ may be a commercially available product which can be purchased and used, or can be produced by any method. One example of the production method is as follows.

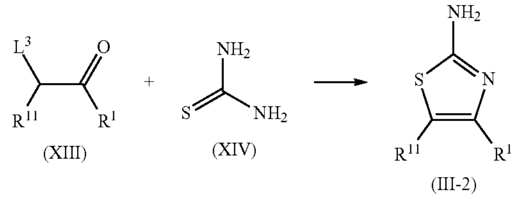

(XIII) (XIV) (III-2)

In the formulae, $L^3$ represents a halogen atom, a mesylate group, a tosylate group or a triflate group, and $R^1$ and $R^{11}$ are as defined above.

Specifically, compound (XIII) and compound (XIV) are subjected to cyclization reaction to obtain aromatic amine (III-2).

In this context, examples of the "halogen atom" represented by $L^3$ preferably include a chlorine atom, a bromine atom and an iodine atom.

The solvent for use in this reaction can be any solvent which does not influence the reaction. Examples thereof include ethers, aprotic polar solvents, halogenated hydrocarbons and alcohols and preferably include ethanol, methanol, N,N-dimethylformamide, and chloroform.

This reaction may be performed by the addition of a basic compound.

Examples of the basic compound include organic bases such as triethylamine and N,N-diisopropylethylamine, and inorganic bases such as potassium carbonate and sodium bicarbonate.

The amount of the basic compound used can be 1- to 5-fold mol with respect to the compound (XIII) or a salt thereof.

This reaction is usually performed at 0 to 120° C. The reaction time is usually a few minutes to 10 hours.

(Process 5)

The starting material compound (VII) can be produced by any method. One example of the production method is as follows.

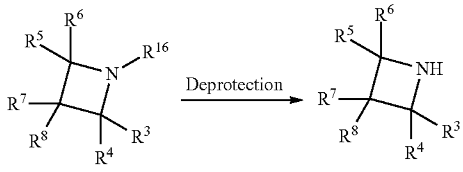

(XV) (VII)

In the formulae, $R^{16}$ represents an amino-protective group, and $R^3$, $R^4$, $R^5$, $R^6$, $R^7$ and $R^8$ are as defined above.

Specifically, a protective group $R^{16}$ on compound (XV) can be eliminated to obtain compound (VII).

In this context, examples of the "amino-protective group" represented by $R^{16}$ include an amino-protective group which is usually used in the field of organic synthetic chemistry. Examples thereof include a lower alkoxycarbonyl group, a benzyloxycarbonyl group, a benzyl group, a p-methoxybenzyl group, a 2,4-dimethoxybenzyl group, and a benzhydryl group and preferably include a tert-butoxycarbonyl group and a benzhydryl group.

Examples of the deprotection reaction of the compound (XV) can include methods described in Theodora W. Greene, Peter G. M. Wuts, "Protective Groups in Organic Synthesis" 4th. ed., John Wiley & Sons, Inc., 2007. In the case of, for example, a tert-butoxycarbonyl group, the deprotection reaction can be performed in a solvent in the presence of an acid. In the case of a benzhydryl group, the deprotection reaction can be performed in a solvent in the presence or absence of an acid and in the presence of a metal catalyst in a hydrogen gas atmosphere.

The solvent for use in this reaction can be any solvent which does not influence the reaction. Examples thereof include aliphatic hydrocarbons, aprotic polar solvents, ethers, halogenated hydrocarbons, esters, and alcohols and preferably include ethers, halogenated hydrocarbons, esters, and alcohols.

Examples of the acid include trifluoroacetic acid, hydrofluoric acid, hydrochloric acid, hydrobromic acid, methanesulfonic acid and trifluoromethanesulfonic acid and preferably include trifluoroacetic acid, hydrochloric acid and hydrobromic acid.

The amount of the acid used is 1 to 30 equivalents, preferably 1 to 15 equivalents, with respect to the compound (XV). The reaction is performed at −30 to 120° C., preferably 0 to 80° C. The reaction time is usually 10 minutes to 48 hours, preferably 1 to 12 hours.

Examples of the metal catalyst include palladium catalysts and platinum catalysts and preferably include palladium catalysts.

The compound (XV) for use as a starting material may be a commercially available product which can be purchased and used, or may be produced by methods described in the following literatures or methods equivalent thereto.

1) WO 2000/063168 A1

2) Chemical Reviews 108, 3988 (2008)

3) Chemical and Pharmaceutical Bulletin 56, 346 (2008)

4) Science 351, 241 (2016)

(Process 6-1)

Compound (XV-1) corresponding to the compound (XV) wherein $R^7$ or $R^8$ is an optionally substituted lower alkoxy group can be produced by any method. One example of the production method is as follows.

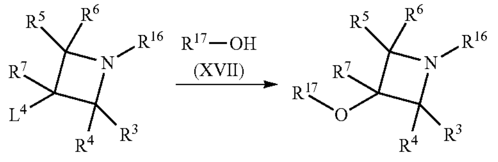

(XVI) (XV-1)

In the formulae, $R^{17}$ represents a lower alkyl group appropriate for the optionally substituted lower alkoxy group of $R^8$, $L^4$ represents a halogen atom, a mesylate group, a tosylate group or a triflate group, and $R^3$, $R^4$, $R^5$, $R^6$, $R^7$ and $R^{16}$ are as defined above.

Specifically, compound (XVI) and compound (XVII) can be subjected to substitution reaction to obtain compound (XV-1).

In this context, examples of the "lower alkyl group" represented by $R^{17}$ preferably include a $C_{1-5}$ alkyl group, more preferably a methyl group, an ethyl group, a propyl group, an isopropyl group, a butyl group, an isobutyl group, a sec-butyl group and a tert-butyl group, further preferably a methyl group, an ethyl group and a propyl group.

Examples of the "halogen atom" represented by $L^4$ preferably include a chlorine atom, a bromine atom and an iodine atom.

The solvent for use in the substitution reaction can be any solvent which does not influence the reaction. Examples thereof include ethers and aprotic polar solvents.

This reaction may be performed by the addition of a basic compound.

Examples of the basic compound include sodium carbonate, calcium carbonate, sodium bicarbonate, potassium carbonate, triethylamine, N,N-diisopropylethylamine, N-methylmorpholine, 1,8-diazabicyclo[5.4.0]undec-7-ene, 1,1,3,3-tetramethylguanidine and sodium hydride and preferably include sodium hydride.

The amount of the basic compound used can be 1- to 20-fold mol, preferably 1- to 5-fold mol, with respect to the compound (XVII) or a salt thereof.

This reaction is usually performed at −30 to 150° C., preferably −10 to 100° C. The reaction time is usually a few minutes to 48 hours.

(Process 6-2)

Compound (XV-2) corresponding to the compound (XV) wherein $R^7$ and $R^8$ together form an oxime group can be produced by any method. One example of the production method is as follows.

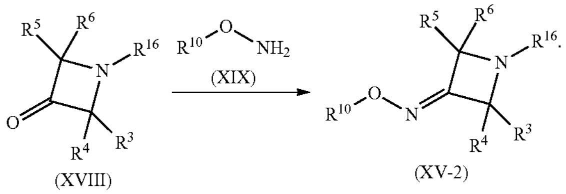

(XVIII) (XV-2)

In the formulae, $R^3$, $R^4$, $R^5$, $R^6$, $R^{10}$ and $R^{16}$ are as defined above.

Specifically, compound (XVIII) and compound (XIX) or a salt thereof are subjected to condensation reaction to obtain compound (XV-2).

The solvent for use in this reaction can be any solvent which does not influence the reaction. Examples thereof include aromatic hydrocarbons, esters, ethers, aliphatic hydrocarbons, halogenated hydrocarbons, protic polar solvents and aprotic polar solvents and preferably include halogenated hydrocarbons, protic polar solvents and aprotic polar solvents.

This reaction may be performed by the addition of an acidic compound.

Examples of the acidic compound include formic acid, acetic acid, and hydrochloric acid and preferably include acetic acid.

The amount of the acidic compound used can be 0.05- to 1-fold mol with respect to the compound (XIX) or a salt thereof.

This reaction may be performed by the addition of a basic compound.

Examples of the basic compound include inorganic bases such as sodium hydroxide, potassium hydroxide, sodium carbonate, potassium carbonate, and sodium acetate.

The amount of the basic compound used can be 1- to 10-fold mol with respect to the compound (XIX) or a salt thereof.

This reaction is usually performed at 0 to 110° C., preferably room temperature to 80° C. The reaction time is usually a few hours to 8 days.

(Process 6-3)

When $R^8$ in the compound (XV) is a group represented by the formula (a), the starting material compound (XV-a) can be produced by any method. One example of the production method is as follows.

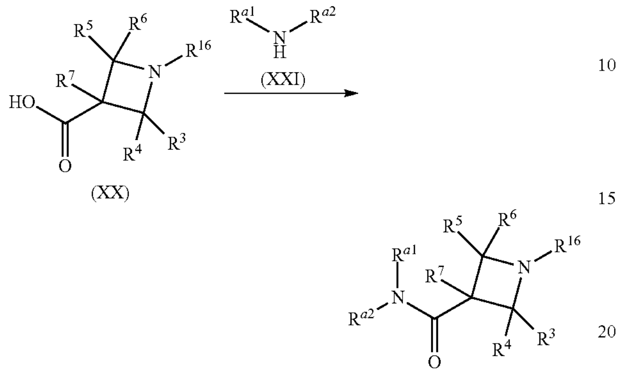

(XX)
(XV-a)

In the formulae, $R^3$, $R^4$, $R^8$, $R^6$, $R^7$, $R^{a1}$, $R^{a2}$ and $R^{16}$ are as defined above.

Specifically, compound (XX) and compound (XXI) or a salt thereof can be subjected to condensation reaction to obtain compound (XV-a).

The solvent for use in this reaction can be any solvent which does not influence the reaction. Examples thereof include aromatic hydrocarbons, ethers, aliphatic hydrocarbons, halogenated hydrocarbons, aprotic polar solvents, and alcohols and preferably include halogenated hydrocarbons and aprotic polar solvents, more preferably amides.

The amount of the solvent used is not particularly limited and can be 1 to 500 times (v/w) the amount of the compound (XX).

The amount of the compound (XXI) or a salt thereof used can be 1- to 50-fold mol, preferably 1- to 5-fold mol, with respect to the compound (XX).

Examples of the condensing agent for use in this reaction include: carbodiimides such as N,N'-diisopropylcarbodiimide (DIC), N,N'-di-tert-butylcarbodiimide, N,N'-dicyclohexylcarbodiimide (DCC), N-(tert-butyl)-N'-ethylcarbodiimide (BEC), N-cyclohexyl-N'-(2-morpholinoethyl)carbodiimide (CMC) and N-(3-dimethylaminopropyl)-N'-ethylcarbodiimide (EDC); imidazoliums such as 1,1'-carbonyldiimidazole (CDI) and 1,1'-carbonyldi(1,2,4-triazole) (CDT); uroniums such as O-(benzotriazol-1-yl)-N,N,N',N'-tetramethyluronium hexafluorophosphate (HBTU), O-(7-azabenzotriazol-1-yl)-N, N, N',N'-tetramethyluronium hexafluorophosphate (HATU), O-(benzotriazol-1-yl)-N,N,N',N'-bis(tetramethylene) uronium hexafluorophosphate (HBPyU), O-(benzotriazol-1-yl)-N,N,N',N'-bis(pentamethylene) uronium hexafluorophosphate (HBPipU), O-(6-chlorobenzotriazol-1-yl)-N,N,N',N'-tetramethyluronium hexafluorophosphate (HCTU), O-(3,4-dihydro-4-oxo-1,2,3-benzotriazin-3-yl)-N, N,N',N'-tetramethyluronium hexafluorophosphate (HDBTU), O-(2-oxo-1-(2H)pyridyl)-N,N,N',N'-tetramethyluronium hexafluorophosphate (TPTU), O-{(ethoxycarbonyl)cyanomethylenamino}-N,N,N',N'-tetramethyluronium hexafluorophosphate (HOTU), O-{(ethoxycarbonyl)cyanomethylenamino}-N,N,N',N'-tetramethyluronium tetrafluoroborate (TOTU), N,N,N',N'-tetramethyl-O—(N-succinimidyl)uronium hexafluorophosphate (HSTU), N,N,N',N'-tetramethyl-O—(N-succinimidyl)uronium tetrafluoroborate (TSTU), dipyrrolidino(N-succinimidyloxy)carbenium hexafluorophosphate (HSPyU), S-(1-oxido-2-pyridyl)-N,N,N',N'-tetramethylthiouronium tetrafluoroborate (TOTT) and ([{(1-cyano-2-ethoxy-2-oxoethylidene) amino}oxy]-4-morpholinomethylene)dimethylammonium hexafluorophosphate (COMU); phosphoniums such as 1H-benzotriazol-1-yloxytris(dimethylamino)phosphonium hexafluorophosphate (BOP), 1H-benzotriazol-1-yloxytripyrrolidinophosphonium hexafluorophosphate (PyBOP), (7-azabenzotriazol-1-yloxy)tripyrrolidinophosphonium hexafluorophosphate (PyAOP), chlorotripyrrolidinophosphonium hexafluorophosphate (PyCloP), bromotris(dimethylamino)phosphonium hexafluorophosphate (Brop), 3-(diethoxyphosphoryloxy)-1,2,3-benzotriazin-4(3H)-one (DEPBT) and (ethylcyano(hydroxyimino) acetato-O 2)-tri-(1-pyrrolidinyl)phosphonium hexafluorophosphate (PyOxim); and triazines such as 2,4, 6-trichloro-1,3,5-triazine (TCT), chlorodimethoxytriazine (CDMT), N-(3,5-dimethoxytriazinyl)-N-methylmorpholinium chloride (DMT-MM) and dichloromethoxytriazine (DCMT) and preferably include carbodiimides, imidazoliums, uroniums and triazines, more preferably carbodiimides, uroniums and triazines, further preferably EDC, COMU and DMT-MM.

The amount of the condensing agent used can be 1- to 50-fold mol, preferably 1- to 5-fold mol, with respect to the compound (XX).

This reaction may be performed by the addition of a basic compound.

Examples of the basic compound include triethylamine, N,N-diisopropylethylamine and N-methylmorpholine.

The amount of the basic compound used can be 1- to 50-fold mol, preferably 1- to 5-fold mol, with respect to the compound (XXI) or a salt thereof.

In the case of using a carbodiimide as the condensing agent, it is preferred to add an additive.

Examples of the additive include 1-hydroxybenzotriazole (HOBt), 1-hydroxy-7-azabenzotriazole (HOAt), 6-chloro-1-hydroxybenzotriazole (6-Cl-HOBt), 1-hydroxy-6-nitrobenzotriazole (6-NO2-HOBt), 6-trifluoromethyl-1-hydroxybenzotriazole (6-CF3-HOBt), 3,4-dihydro-3-hydroxy-4-oxo-1, 2,3-benzotriazine (HODhbt), 3-hydroxy-4-oxo-3,4-dihydro-5-azabenzo-1,2,3-triazene (HODhat), N-hydroxysuccinimide (HOSu), N-hydroxy-5-norbornene-2,3-dicarboximide (HONB) and ethyl(hydroxyimino) cyanoacetate (Oxyma) and preferably include HOBt.

The amount of the additive used can be 1- to 50-fold mol, preferably 1- to 5-fold mol, with respect to the compound of the formula (XX).

This reaction can be carried out at −50 to 100° C., preferably 0 to 50° C., for 15 minutes to 48 hours.

Another example of the method for producing the compound (XV-a) includes the following method.

Specifically, compound (XX) is mixed with an acid halide, an acid anhydride or 2-ethoxy-1-ethoxycarbonyl-1, 2-dihydroquinoline (EEDQ), and the mixture can then be reacted with compound (XXI) or a salt thereof to obtain compound (XV-a).

The solvent for use in the condensation reaction can be any solvent which does not influence the reaction. Examples thereof include aromatic hydrocarbons, ethers, aliphatic hydrocarbons, halogenated hydrocarbons, and aprotic polar solvents and preferably include ethers and aprotic polar solvents, more preferably ethers.

The amount of the solvent used is not particularly limited and can be 1 to 500 times (v/w) the amount of the compound (XX).

The amount of the compound (XXI) or a salt thereof used can be 1- to 50-fold mol, preferably 1- to 5-fold mol, with respect to the compound (XX).

Examples of the acid halide for use in the condensation reaction include: chloroformic acid esters such as methyl chloroformate, ethyl chloroformate, propyl chloroformate, butyl chloroformate and isobutyl chloroformate; and sulfonic acid chlorides such as methanesulfonic acid chloride, ethanesulfonic acid chloride, benzenesulfonic acid chloride and p-toluenesulfonic acid chloride.

Examples of the acid anhydride for use in the condensation reaction include: carboxylic anhydrides such as acetic anhydride; and carbonic acid esters such as di-tert-butyl dicarbonate ($(Boc)_2O$).

The acid halide or the acid anhydride for use in the reaction is preferably an acid halide, more preferably a chloroformic acid ester or a sulfonic acid chloride, further preferably ethyl chloroformate or isobutyl chloroformate, particularly preferably isobutyl chloroformate.

The amount of the acid halide or the acid anhydride used can be 1- to 50-fold mol, preferably 1- to 5-fold mol, with respect to the compound (XX).

For this reaction, it is preferred to add a basic compound.

Examples of the basic compound include triethylamine, N,N-diisopropylethylamine, pyridine, N-methylmorpholine, 1-methylimidazole and N,N-dimethylbenzylamine and preferably include N-methylmorpholine.

The amount of the basic compound used can be 1- to 50-fold mol, preferably 1- to 5-fold mol, with respect to the compound (XX).

This reaction can be carried out at −50 to 100° C., preferably −30 to 50° C., for a few minutes to 5 days, preferably 10 minutes to 72 hours.

(Process 6-4)

Compound (XV-b) corresponding to the compound (XV) wherein $R^8$ is a group represented by the formula (b) can be produced by any method. One example of the production method is as follows.

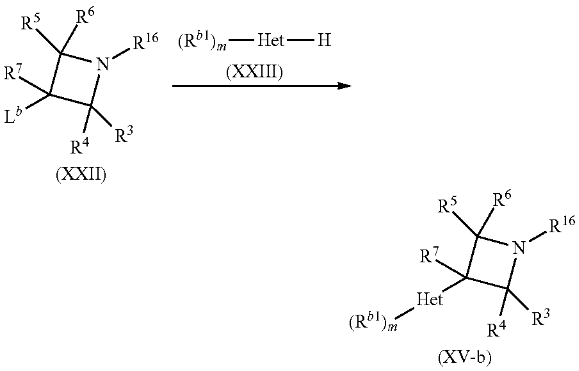

(XXII)

(XV-b)

In the formulae, $L^b$ represents a halogen atom, a mesylate group, a tosylate group or a triflate group, and Het, $R^{b1}$, $R^3$, $R^4$, $R^5$, $R^6$, $R^7$, $R^{16}$ and m are as defined above.

Specifically, compound (XXII) and compound (XXIII) or a salt thereof can be subjected to substitution reaction to obtain compound (XV-b).

In this context, examples of the "halogen atom" represented by $L^b$ preferably include a chlorine atom, a bromine atom and an iodine atom.

The solvent for use in the substitution reaction can be any solvent which does not influence the reaction. Examples thereof include ethers and aprotic polar solvents.

This reaction may be performed by the addition of a basic compound.

Examples of the basic compound include sodium carbonate, calcium carbonate, sodium bicarbonate, potassium carbonate, triethylamine, N,N-diisopropylethylamine, N-methylmorpholine, 1,8-diazabicyclo[5.4.0]undec-7-ene, 1,1,3,3-tetramethylguanidine and sodium hydride and preferably include sodium hydride.

The amount of the basic compound used can be 1- to 20-fold mol, preferably 1- to 5-fold mol, with respect to the compound (XXIII) or a salt thereof.

This reaction can be carried out at −30 to 150° C., preferably −10 to 100° C., for a few minutes to 48 hours.

(Process 6-5)

Compound (XV-c1) corresponding to the compound (XV) wherein $R^8$ is a group represented by the formula (c) (wherein $R^{c1}$ is CO) can be produced by any method. One example of the production method is as follows.

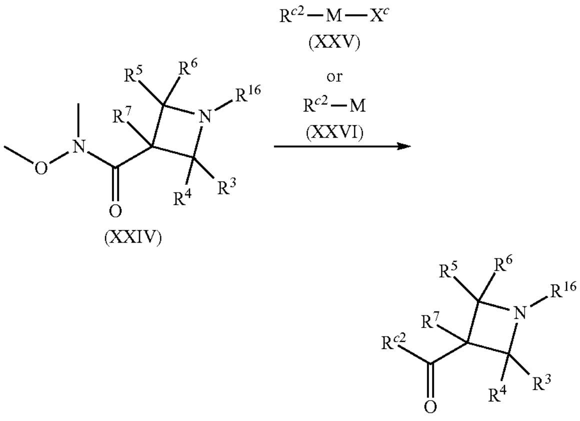

(XXIV)

(XV-c1)

In the formulae, M represents a metal, $X^c$ represents a halogen atom, and $R^{c2}$, $R^3$, $R^4$, $R^5$, $R^6$, $R^7$ and $R^{16}$ are as defined above.

Specifically, compound (XXIV) can be reacted with organometallic reagent (XXV) or organometallic reagent (XXVI) to obtain compound (XV-c1).

In this context, examples of the "halogen atom" represented by $X^c$ preferably include a chlorine atom, a bromine atom and an iodine atom.

Examples of the solvent for use in this reaction include aromatic hydrocarbons, ethers and aliphatic hydrocarbons and preferably include ethers, more preferably tetrahydrofuran.

The organometallic reagent for use in this reaction may be produced by a method described in HANDBOOK OF GRIGNARD REAGENTS, 1996, etc. Examples thereof include organomagnesium reagents such as Grignard reagents, and organolithium reagents and preferably include alkyl magnesium halide, cyclyl magnesium halide, heterocyclyl magnesium halide, aryl magnesium halide, heteroaryl magnesium halide, alkyllithium and aryllithium, more preferably alkyl magnesium chloride, alkyl magnesium bromide, aryl magnesium chloride, aryl magnesium bromide, and alkyllithium, further preferably methyl magnesium bromide, ethyl magnesium bromide, cyclopentyl magnesium bromide, pyridyl magnesium chloride, benzyl magnesium bromide, and n-butyllithium.

This reaction can be carried out at −100 to 50° C., preferably −80 to 30° C., for a few minutes to 24 hours.

(Process 6-6)

Compound (XV-c2) corresponding to the compound (XV) wherein $R^8$ is a group represented by the formula (c) (wherein $R^{c1}$ is SO or $SO_2$) can be produced by any method. One example of the production method is as follows.

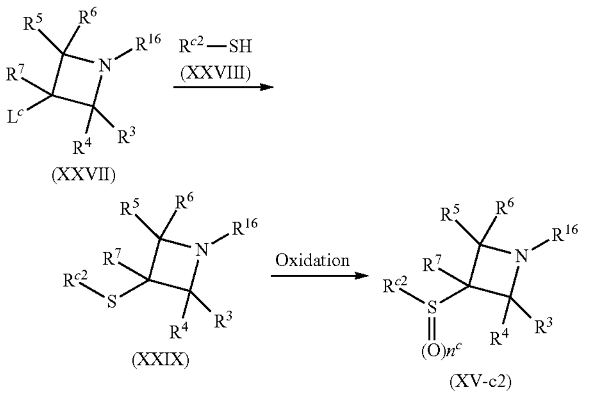

(XXVII)

(XXIX)

(XV-c2)

In the formulae, $L^e$ represents a halogen atom, a mesylate group, a tosylate group or a triflate group, $n^c$ represents an integer of 1 or 2, and $R^{c2}$, $R^3$, $R^4$, $R^5$, $R^6$, $R^7$ and $R^{16}$ are as defined above.

Specifically, compound (XXVII) and compound (XXVIII) are subjected to substitution reaction to prepare compound (XXIX), which is then subjected to oxidation reaction to obtain compound (XV-c2).

In this context, examples of the "halogen atom" represented by $L^c$ preferably include a chlorine atom, a bromine atom and an iodine atom.

The solvent for use in the substitution reaction can be any solvent which does not influence the reaction. Examples thereof include ethers and aprotic polar solvents.

The substitution reaction may be performed by the addition of a basic compound.

Examples of the basic compound include sodium carbonate, calcium carbonate, sodium bicarbonate, potassium carbonate, triethylamine, N,N-diisopropylethylamine, N-methylmorpholine, 1,8-diazabicyclo[5.4.0]undec-7-ene, 1,1,3,3-tetramethylguanidine and sodium hydride and preferably include sodium hydride.

The amount of the basic compound used can be 1- to 20-fold mol, preferably 1- to 5-fold mol, with respect to the compound (XXVIII).

This reaction can be carried out at −30 to 150° C., preferably −10 to 100° C., for a few minutes to 48 hours.

The solvent for use in the oxidation reaction can be any solvent which does not influence the reaction. Examples thereof include halogenated hydrocarbons, ethers, protic polar solvents and aprotic polar solvents and preferably include halogenated hydrocarbons, ethers, alcohols and acetic acid. Examples of the oxidizing agent for use in this reaction include mCPBA, Oxone, hydrogen peroxide, and 3-phenyl-2-(phenylsulfonyl)-1,2-oxaziridine.

This reaction is usually performed at 0 to 110° C., preferably room temperature to 80° C. The reaction time is usually a few hours to 8 days.

(Process 6-7)

Compound (XV-d) corresponding to the compound (XV) wherein $R^8$ is a group represented by the formula (d) can be produced by any method. One example of the production method is as follows.

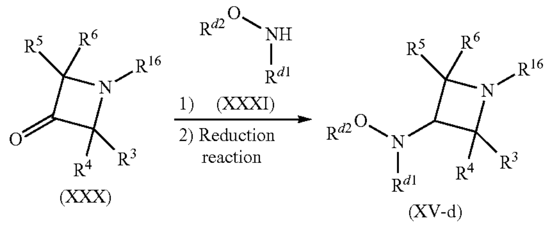

(XXX)

(XV-d)

In the formulae, $R^{d1}$, $R^{d2}$, $R^3$, $R^4$, $R^5$, $R^6$ and $R^{16}$ are as defined above.

Specifically, compound (XXX) and amine (XXXI) or a salt thereof are subjected to condensation reaction, and the reduction reaction of the obtained oxime can be performed to obtain compound (XV-d).

The solvent for use in the condensation reaction can be any solvent which does not influence the reaction. Examples thereof include aromatic hydrocarbons, esters, ethers, aliphatic hydrocarbons, halogenated hydrocarbons, protic polar solvents and aprotic polar solvents and preferably include halogenated hydrocarbons, protic polar solvents and aprotic polar solvents, more preferably alcohols and halogenated hydrocarbons.

The condensation reaction may be performed by the addition of an acidic compound.

Examples of the acidic compound include formic acid, acetic acid, and hydrochloric acid and preferably include acetic acid.

The amount of the acid used can be 0.05- to 1-fold mol with respect to the compound (XXX).

This reaction may be performed by the addition of a basic compound.

Examples of the basic compound include inorganic bases such as sodium hydroxide, potassium hydroxide, sodium carbonate, potassium carbonate, and sodium acetate.

The amount of the basic compound used can be 1- to 10-fold mol with respect to the compound (XXXI) or a salt thereof.

The condensation reaction is usually performed at 0 to 120° C., preferably 0 to 80° C. The reaction time is usually 10 minutes to 48 hours, preferably 1 to 24 hours.

The solvent for use in the reduction reaction can be any solvent which does not influence the reaction. Examples thereof include aromatic hydrocarbons, halogenated hydrocarbons, ethers, esters, aprotic polar solvents, and alcohols and preferably include alcohols and halogenated hydrocarbons.

Examples of the reducing agent for use in the reduction reaction include lithium borohydride, sodium borohydride, lithium aluminum hydride, sodium cyanoborohydride, sodium triacetoxyborohydride and hydride sources and preferably include sodium borohydride and sodium triacetoxyborohydride.

The amount of the reducing agent used is equimolar or more, in particular, preferably approximately 1- to 10-fold mol, with respect to the compound (XXX).

The reduction reaction is usually performed at 0 to 120° C., preferably 0 to 80° C. The reaction time is usually 10 minutes to 72 hours, preferably 1 to 48 hours.

(Process 6-8)

Compound (XV-e1), compound (XV-e2) or compound (XV-e3) each corresponding to the compound (XV) wherein $R^8$ is a group represented by the formula (e) can be produced by any method. One example of the production method is as follows.

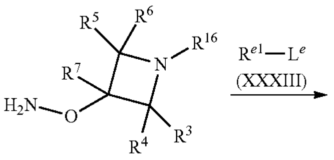

(XXXII)

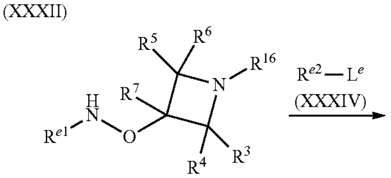

(XV-e1)

or

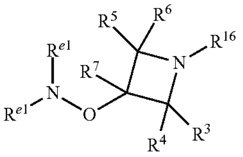

(XV-e2)

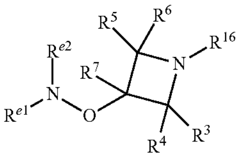

(XV-e3)

In the formulae, $L^e$ represents a halogen atom, a mesylate group, a tosylate group or a triflate group, and $R^{e1}$, $R^{e2}$, $R^3$, $R^4$, $R^5$, $R^6$, $R^7$ and $R^{16}$ are as defined above.

Specifically, compound (XXXII) and compound (XXXIII) are subjected to substitution reaction to obtain compound (XV-e1) or compound (XV-e2), and the compound (XV-e1) and compound (XXXIV) can be subjected to substitution reaction to obtain compound (XV-e3).

In this context, examples of the "halogen atom" represented by $L^e$ preferably include a chlorine atom, a bromine atom and an iodine atom.

The solvent for use in this reaction can be any solvent which does not influence the reaction. Examples thereof include aliphatic hydrocarbons, aprotic polar solvents, ethers, and halogenated hydrocarbons and preferably include ethers and aprotic polar solvents, more preferably aprotic polar solvents.

For this reaction, it is preferred to add a basic compound.

Examples of the basic compound include: alkali metals such as metal sodium and metal potassium; metal hydrides such as sodium hydride and calcium hydride; inorganic bases such as sodium hydroxide, potassium hydroxide, sodium carbonate, and potassium carbonate; alkoxides such as sodium methoxide, sodium ethoxide, and potassium tert-butoxide; metal fluorides such as sodium fluoride and potassium fluoride; and organic bases such as triethylamine, N-methylpyrrolidine, 1,1,3,3-tetramethylguanidine, and 1,8-diazabicyclo[5.4.0]undec-7-ene and preferably include sodium hydride, potassium carbonate and triethylamine.

The amount of the basic compound used is equimolar or more, in particular, preferably approximately 1- to 10-fold mol, with respect to the compounds (XXXII) and (XV-e1).

The substitution reaction is usually performed at 0 to 120° C., preferably 0 to 80° C. The reaction time is usually 10 minutes to 48 hours, preferably 1 to 24 hours.

(Process 6-9) Compound (XV-f1), compound (XV-f2) or compound (XV-f3) each corresponding to the compound (XV) wherein $R^8$ is a group represented by the formula (f) can be produced by any method. One example of the production method is as follows.

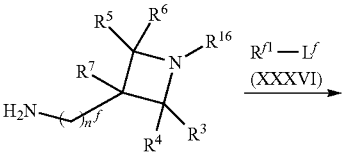

(XXXV)

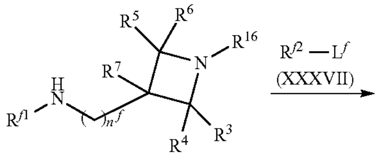

(XV-f1)

or

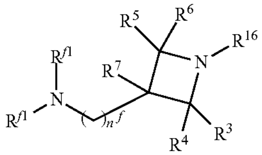

(XV-f2)

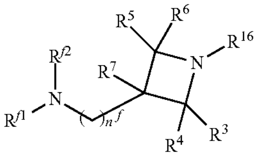

(XV-f3)

In the formulae, $L^f$ represents a halogen atom or a triflate group, $n^f$ represents an integer of 0, 1 or 2, and $R^{f1}$, $R^{f2}$, $R^3$, $R^4$, $R^5$, $R^6$, $R^7$ and $R^{16}$ are as defined above.

Specifically, compound (XXXV) and compound (XXXVI) are subjected to substitution reaction in the presence of a metal catalyst to obtain compound (XV-f1) or compound (XV-f2), and the compound (XV-f1) and compound (XXXVII) can be subjected to substitution reaction in the presence of a metal catalyst to obtain compound (XV-f3).

In this context, examples of the "halogen atom" represented by $L^f$ preferably include a chlorine atom, a bromine atom and an iodine atom, more preferably a bromine atom and an iodine atom.

The solvent for use in this reaction can be any solvent which does not influence the reaction. Examples thereof include aromatic hydrocarbons, aliphatic hydrocarbons, aprotic polar solvents, ethers, esters, halogenated hydrocarbons, and alcohols and preferably include aromatic hydrocarbons.

Examples of the metal catalyst include palladium catalysts such as tetrakis(triphenylphosphine)palladium, tris(dibenzylideneacetone)dipalladium, bis(dibenzylideneacetone)palladium(0), palladium acetate, palladium chloride, bis(benzonitrile)dichloropalladium and bis-(diphenylphosphinoferrocene) palladium dichloride-dichloromethane complexes, and copper catalysts and preferably include palladium acetate.

The amount of the metal catalyst used can be 0.005- to 1-fold mol with respect to the compound (XXXV).

This reaction may be performed by the addition of a phosphine compound.

Examples of the phosphine compound include 2,2'-bis (diphenylphosphino)-1,1'-binaphthalene (BINAP), Xantphos™ (Strem Chemicals Inc.) and related phosphine-based ligands and preferably include BINAP.

The amount of the phosphine compound used can be 0.01- to 1-fold mol with respect to the compound (XXXV).

For this reaction, it is preferred to add a basic compound.

Examples of the basic compound include: alkali metals such as metal sodium and metal potassium; metal hydrides such as sodium hydride and calcium hydride; inorganic bases such as sodium hydroxide, potassium hydroxide, sodium carbonate, and potassium carbonate; alkoxides such as sodium methoxide, sodium ethoxide, and potassium tert-butoxide; metal fluorides such as sodium fluoride and potassium fluoride; and organic bases such as triethylamine and 1,8-diazabicyclo[5.4.0]undec-7-ene and preferably include potassium tert-butoxide.

The amount of the basic compound used is equimolar or more, in particular, preferably approximately 1- to 10-fold mol, with respect to the compound (XXXV).

This reaction is usually performed at 0 to 150° C., preferably 50 to 120° C. The reaction time is usually 10 minutes to 72 hours, preferably 1 to 48 hours.

(Process 6-10-1)

Compound (XV-g1) or compound (XV-g2) each corresponding to the compound (XV) wherein $R^8$ is a group represented by the formula (g) can be produced by any method. One example of the production method is as follows.

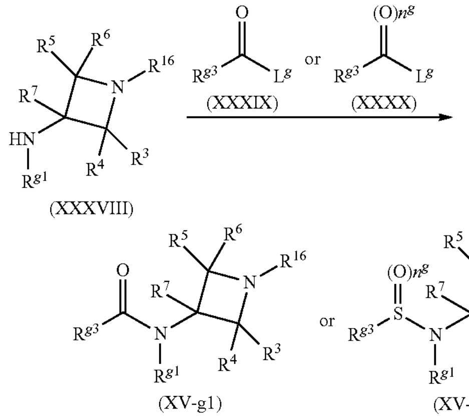

(XXXVIII) (XXXIX) or (XXXX)

(XV-g1) or (XV-g2)

In the formulae, ng represents an integer of 1 or 2, $L^g$ represents a halogen atom, and $R^{g1}$, $R^{g3}$, $R^3$, $R^4$, $R^5$, $R^6$, $R^7$ and $R^{16}$ are as defined above.

Specifically, compound (XXXVIII) or a salt thereof and compound (XXXIX) or compound (XXXX) can be subjected to condensation reaction to obtain compound (XV-g1) or compound (XV-g2).

In this context, examples of the "halogen atom" represented by $L^9$ preferably include a chlorine atom, a bromine atom and an iodine atom, more preferably a chlorine atom.

The solvent for use in the condensation reaction can be any solvent which does not influence the reaction. Examples thereof include aromatic hydrocarbons, ethers, esters, aliphatic hydrocarbons, halogenated hydrocarbons, aprotic polar solvents, and alcohols and preferably include halogenated hydrocarbons and amides.

The amount of the compound (XXXIX) or the compound (XXXX) used is equimolar or more, in particular, preferably approximately 1- to 10-fold mol, with respect to the compound (XXXVIII) or a salt thereof.

This reaction may be performed by the addition of a basic compound.

Examples of the basic compound include organic bases such as triethylamine, N,N-diisopropylethylamine and N-methylmorpholine, and inorganic bases such as sodium hydroxide, potassium hydroxide, sodium carbonate, and potassium carbonate.

The amount of the basic compound used can be 1- to 50-fold mol, preferably 1- to 5-fold mol, with respect to the compound (XXXVIII) or a salt thereof.

This reaction is usually performed at −30 to 80° C., preferably −20 to 40° C. The reaction time is usually 10 minutes to 72 hours, preferably 1 to 48 hours.

(Process 6-10-2)

Another method for producing the compound (XV-g1) is as follows.

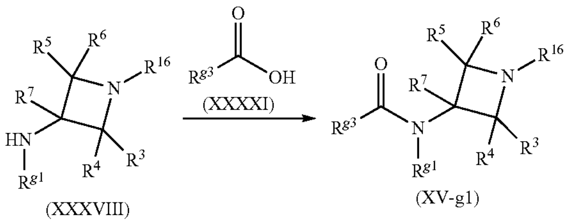

(XXXVIII) (XXXXI) (XV-g1)

In the formulae, $R^{g1}$, $R^{g3}$, $R^3$, $R^4$, $R^5$, $R^6$, $R^7$ and $R^{16}$ are as defined above.

Specifically, compound (XXXVIII) or a salt thereof and compound (XXXXI) can be subjected to condensation reaction to obtain compound (XV-g1).

The solvent for use in the condensation reaction can be any solvent which does not influence the reaction. Examples thereof include aromatic hydrocarbons, ethers, esters, aliphatic hydrocarbons, halogenated hydrocarbons, aprotic polar solvents, and alcohols and preferably include halogenated hydrocarbons and amides.

The amount of the compound (XXXXI) used is equimolar or more, in particular, preferably approximately 1- to 10-fold mol, with respect to the compound (XXXVIII) or a salt thereof.

Examples of the condensing agent for use in the condensation reaction include the same as above and preferably include carbodiimides, more preferably EDC.

The amount of the condensing agent used is equimolar or more, in particular, preferably approximately 1- to 10-fold mol, with respect to the compound (XXXVIII) or a salt thereof.

This reaction may be performed by the addition of a basic compound.

Examples of the basic compound include organic bases such as triethylamine, N,N-diisopropylethylamine and N-methylmorpholine, and inorganic bases such as sodium hydroxide, potassium hydroxide, sodium carbonate, and potassium carbonate.

The amount of the basic compound used can be 1- to 50-fold mol, preferably 1- to 5-fold mol, with respect to the compound (XXXVIII) or a salt thereof.

This reaction is usually performed at −30 to 80° C., preferably −20 to 40° C. The reaction time is usually 10 minutes to 72 hours, preferably 1 to 48 hours.

A further alternative method for producing the compound (XV-g1) is as follows.

Specifically, compound (XXXXI) is mixed with an acid halide, an acid anhydride or 2-ethoxy-1-ethoxycarbonyl-1,2-dihydroquinoline (EEDQ), and the mixture can then be reacted with compound (XXXVIII) or a salt thereof to obtain compound (XV-a).

The solvent for use in the condensation reaction can be any solvent which does not influence the reaction. Examples thereof include aromatic hydrocarbons, ethers, aliphatic hydrocarbons, halogenated hydrocarbons, and aprotic polar solvents and preferably include ethers and aprotic polar solvents, more preferably ethers.

The amount of the compound (XXXXI) used can be 1- to 50-fold mol, preferably 1- to 5-fold mol, with respect to the compound (XXXVIII) or a salt thereof.

Examples of the acid halide or the acid anhydride for use in the condensation reaction include the same as above and preferably include chloroformic acid esters, more preferably isobutyl chloroformate.

The amount of the acid halide or the acid anhydride used can be 1- to 50-fold mol, preferably 1- to 5-fold mol, with respect to the compound (XXXXI).

For this reaction, it is preferred to add a basic compound.

Examples of the basic compound include triethylamine, N,N-diisopropylethylamine, pyridine, N-methylmorpholine, 1-methylimidazole and N,N-dimethylbenzylamine and preferably include N-methylmorpholine.

The amount of the basic compound used can be 1- to 50-fold mol, preferably 1- to 5-fold mol, with respect to the compound (XXXXI).

This reaction is performed at −50 to 100° C., preferably −30 to 50° C. The reaction time is usually a few minutes to 72 hours, preferably 10 minutes to 48 hours.

(Process 6-10-3)

Compound (XV-g3) corresponding to the compound (XV) wherein $R^8$ is a group represented by the formula (g) (wherein $R^{g2}$ is CO or CS) can be produced by any method. One example of the production method is as follows.

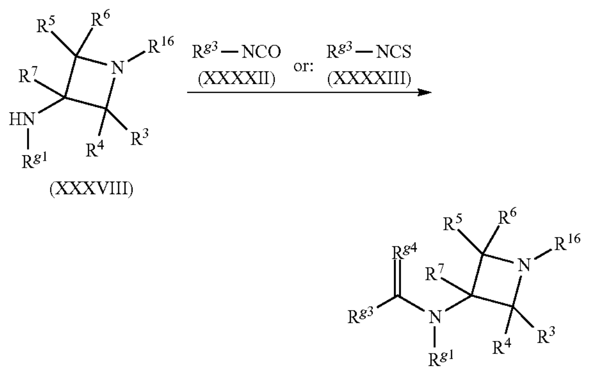

(XXXVIII)

(XV-g3)

In the formulae, $R^{g4}$ represents O or S, and $R^{g1}$, $R^{g3}$, $R^3$, $R^4$, $R^5$, $R^6$, $R^7$ and $R^{16}$ are as defined above.

Specifically, compound (XXXVIII) can be reacted with compound (XXXXII) or compound (XXXXIII) to obtain compound (XV-g3).

The solvent for use in this reaction can be any solvent which does not influence the reaction. Examples thereof include aromatic hydrocarbons, ethers, esters, aliphatic hydrocarbons, halogenated hydrocarbons, aprotic polar solvents, and protic polar solvents and preferably include halogenated hydrocarbons.

The amount of the compound (XXXXII) or the compound (XXXXIII) used is equimolar or more, in particular, preferably approximately 1- to 10-fold mol, with respect to the compound (XXXVIII) or a salt thereof.

This reaction may be performed by the addition of a basic compound.

Examples of the basic compound include: organic bases such as triethylamine, pyridine, N,N-diisopropylethylamine, 1,8-diazabicyclo[5.4.0]undec-7-ene and N-methylmorpholine; inorganic bases such as sodium hydroxide, potassium hydroxide, sodium bicarbonate, sodium carbonate, and potassium carbonate; organometallic reagents such as n-butyllithium; and alkoxides such as potassium tert-butoxide.

The amount of the basic compound used can be 1- to 50-fold mol, preferably 1- to 5-fold mol, with respect to the compound (XXXVIII) or a salt thereof.

This reaction is usually performed at −30 to 80° C., preferably −20 to 40° C. The reaction time is usually 10 minutes to 72 hours, preferably 1 to 48 hours.

The starting material compound for use in each of the production methods described above may be a commercially available product which can be used as it is, or may be produced by the application of a method described in production examples mentioned later, a method obvious to those skilled in the art, or a modified method thereof using a commercially available product.

The compound (IX) or a synthetic intermediate compound is isolated and purified as a free compound, a salt thereof, a hydrate, a solvate, or a crystalline polymorphic substance. A salt of the compound (IX) or the synthetic intermediate compound may be produced by being subjected to a salt-forming reaction according to a routine method.

The isolation and purification are performed by the application of usual chemical operations such as extraction, fractionated crystallization, various fractionation chromatography techniques, evaporation, drying, filtration, and centrifugation.

Various isomers can be produced by the selection of an appropriate starting material compound or can be isolated through the use of difference in physicochemical property between isomers. For example, optical isomers are obtained by a general optical resolution method for racemates (e.g., fractionated crystallization which induces diastereomer salts with an optically active base or acid, and chromatography using chiral columns or the like) and can also be produced from an appropriate optically active starting material compound.

The pyridone carboxylic acid derivative of the present invention or a salt thereof thus obtained has excellent antitumor activity against a human non-small cell lung cancer cell line and a human acute myeloid leukemia cell line and exerts an excellent tumor growth inhibitory effect on human prostate cancer cell line xenograft tumor models, as shown in test examples mentioned later. On the other hand, the pyridone carboxylic acid derivative of the present invention or a salt thereof has low cytotoxicity to normal human cells.

Thus, the pyridone carboxylic acid derivative of the present invention or a salt thereof is capable of serving as a highly safe antitumor agent useful in the prevention or treatment of various cancers.

Examples of the cancer which the antitumor agent can be applied to the treatment or prevention of include, but are not particularly limited to, carcinoma, lymphoma, blastoma, sarcoma and leukemia or lymphoid malignancies. More specific examples thereof include neuroblastoma, intestine cancer, for example, rectal cancer, large intestine cancer, familial polyposis coli and hereditary non-polyposis, and colorectal cancer, esophageal cancer, lip cancer, larynx cancer, hypopharynx cancer, tongue cancer, salivary gland cancer, stomach cancer, malignant adenocarcinoma, medullary thyroid cancer, papillary thyroid cancer, kidney cancer, stromal cancer of the kidney, ovary cancer, head and neck cancer, uterine corpus cancer, endometrial cancer, chorionic cancer, pancreatic cancer, prostate cancer, testicular cancer, breast cancer, urinary organ cancer, malignant melanoma, brain tumor, for example, glioblastoma, astrocytoma, meningioma, medulloblastoma and peripheral neuroectodermal tumor, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, diffuse large B-cell lymphoma (DLBCL), myelodysplastic syndrome (MDS), hepatocellular carcinoma, gallbladder cancer, cancer associated with bronchial asthma, small-cell lung cancer, non-small cell lung cancer, multiple myeloma, basalioma, teratoma, retinoblastoma, choroidal malignant melanoma, seminoma, rhabdomyosarcoma, craniopharyngioma, osteosarcoma, chondrosarcoma, myosarcoma, liposarcoma, fibrosarcoma, Ewing's sarcoma, plasmacytoma, and cancer of unknown primary.

In the case of using the pyridone carboxylic acid derivative of the present invention or a salt thereof as a medicament (pharmaceutical composition), the pyridone carboxylic acid derivative according to the present invention or a salt thereof can be formulated into a composition together with a pharmaceutically acceptable carrier for parenteral administration such as injection or transrectal administration, or oral administration in a solid, semisolid or liquid form.

Examples of the form of the composition according to the present invention for injections include pharmaceutically acceptable aseptic water, nonaqueous solutions, suspensions and emulsions. Examples of an appropriate nonaqueous carrier, diluent solvent or vehicle include propylene glycol, polyethylene glycol, plant oils such as olive oil, and an injectable organic ester such as ethyl oleate. Such a composition can also contain a pharmaceutical aid such as an antiseptic, a humectant, an emulsifier, and a dispersant. These compositions can be sterilized, for example, by filtration through a bacterial retention filter, or by mixing with a sterilizing agent in the form of an aseptic solid composition which is dissolvable in aseptic water or a small amount of other sterile injectable medium immediately before use.

Examples of the solid formulation for oral administration include capsules, tablets, pills, troches, powders, and granules. For the preparation of this solid formulation, the compound of the present invention is generally mixed with at least one inert diluent, for example, sucrose, lactose, or starch. This formulation can contain an additional substance other than the inert diluent in the preparation of usual formulations, for example, a lubricant (e.g., magnesium stearate). The capsules, the tablets and the pills may contain a buffer. The tablets and the pills may be further coated with an enteric coating.

Examples of the liquid formulation for oral administration include an inert diluent which is commonly used by those skilled in the art, for example, water-containing and pharmaceutically acceptable emulsions, solutions, suspensions, syrups, and elixirs. In addition to such an inert diluent, the composition can also be supplemented with aids such as a humectant, an emulsifier, a suspending agent, a sweetener, a seasoning agent, and a flavor. The formulation for transrectal administration preferably contains an excipient such as cacao butter or suppository wax, in addition to the compound of the present invention.

The dose of the pyridone carboxylic acid derivative of the present invention or a salt thereof depends on the properties of the compound to be administered, an administration route, a desired treatment period and other factors and is generally preferably approximately 0.1 to 1000 mg/m$^2$ (body surface area) per day for intravenous administration, approximately 1 to 1000 mg/m$^2$ (body surface area) per day for intramuscular administration, and approximately 5 to 500 mg/m$^2$ (body surface area) per day for oral administration. This daily dose may be administered in 2 to 4 divided portions, if desired.

Hereinafter, the present invention will be described further specifically with reference to Reference Examples and Examples. Compounds containing tautomeric groups are indicated by use of a notation method, i.e., designation and formula, for one of the tautomers for the sake of convenience.

EXAMPLES

Reference Example 001

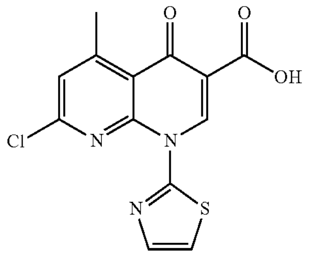 [SMILES: Cc1cc(Cl)nc2c1c(=O)c(C(=O)O)cn2-c1nccs1]

7-Chloro-5-methyl-4-oxo-1-(1,3-thiazol-2-yl)-1,4-dihydro-1,8-naphthyridine-3-carboxylic acid (1) To a mixture of orthoformic acid ethyl ester (500 μL) and ethyl 3-(2,6-dichloro-4-methylpyridin-3-yl)-3-oxopropanoate (457 mg) obtained by the method described in JP-A-2006-514964 or a method equivalent thereto was added acetic anhydride (500 μL), and the mixture was stirred at 130° C. for 2 hours. The reaction mixture was cooled down to room temperature and concentrated. To a solution of the residue in diisopropyl ether (3 mL) was added 1,3-thiazol-2-amine (170 mg), and the mixture was stirred overnight at room temperature. The resulting solid was collected by filtration. To a solution of the obtained solid in 1,4-dioxane (4 mL) was added potassium carbonate (1.0 g), and the mixture was stirred overnight at 60° C. The reaction mixture was cooled down to room temperature, and the reaction solution was poured into water. The resulting solid was collected by filtration to obtain 369 mg of ethyl 7-chloro-5-methyl-4-oxo-1-(1,3-thiazol-2-yl)-1,4-dihydro-1,8-naphthyridine-3-carboxylate.

1H-NMR (CDCl3): δ 1.43 (3H, t, J=7.5 Hz), 2.99 (3H, s), 4.44 (2H, q, J=7.5 Hz), 7.35 (1H, d, J=3.5 Hz), 7.73 (1H, d, J=3.5 Hz), 9.91 (1H, s)

(2) To a solution of ethyl 7-chloro-5-methyl-4-oxo-1-(1,3-thiazol-2-yl)-1,4-dihydro-1,8-naphthyridine-3-carboxylate (200 mg) obtained in the preceding section in acetic acid was added 6 mol/L hydrochloric acid (500 μL), and the mixture was stirred at 100° C. for 2 hours. The reaction mixture was cooled down to room temperature, and the reaction solution was poured into ice water. The resulting solid was collected by filtration to obtain 162 mg of the title compound.

1H-NMR (DMSO-d6): δ 2.93 (3H, s), 7.79 (1H, s), 7.86 (1H, d, J=3.5 Hz), 7.88 (1H, d, J=3.5 Hz), 9.89 (1H, s)

Reference Example 002

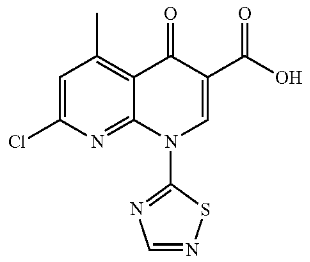 [SMILES: Cc1cc(Cl)nc2c1c(=O)c(C(=O)O)cn2-c1ncns1]

7-Chloro-5-methyl-4-oxo-1-(1,2,4-thiadiazol-5-yl)-1,4-dihydro-1,8-naphthyridine-3-carboxylic acid (1) Ethyl 7-chloro-5-methyl-4-oxo-1-(1,2,4-thiadiazol-5-yl)-1,4-dihydro-1,8-naphthyridine-3-carboxylate was obtained by the method described in Reference Example 001-(1) or a method equivalent thereto using ethyl 3-(2,6-dichloro-4-methylpyridin-3-yl)-3-oxopropanoate obtained by the method described in JP-A-2006-514964 or a method equivalent thereto, and 1,2,4-thiadiazol-5-amine.

1H-NMR (CDCl3): δ 1.45 (3H, t, J=7.5 Hz), 3.01 (3H, s), 4.46 (2H, q, J=7.5 Hz), 7.35 (1H, s), 8.56 (1H, s), 9.90 (1H, s)

(2) The title compound was obtained by the method described in Reference Example 001-(2) or a method equivalent thereto from ethyl 7-chloro-5-methyl-4-oxo-1-(1,2,4-thiadiazol-5-yl)-1,4-dihydro-1,8-naphthyridine-3-carboxylate obtained in the preceding section.

1H-NMR (DMSO-d6): δ 2.93 (3H, s), 7.87 (1H, s), 8.86 (1H, s), 9.82 (1H, s), 13.61 (1H, brs)

Reference Example 003

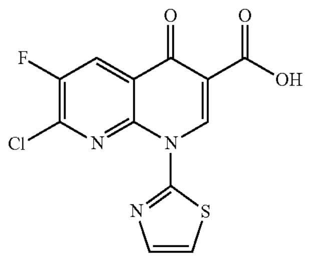 [SMILES: O=C(O)c1cn(-c2nccs2)c2nc(Cl)c(F)cc2c1=O]

7-Chloro-6-fluoro-4-oxo-1-(1,3-thiazol-2-yl)-1,4-dihydro-1,8-naphthyridine-3-carboxylic acid (1) Ethyl 7-chloro-6-fluoro-4-oxo-1-(1,3-thiazol-2-yl)-1,4-dihydro-1,8-naphthyridine-3-carboxylate was obtained by the method described in Reference Example 001-(1) or a method equivalent thereto using ethyl 3-(2,6-dichloro-5-fluoropyridin-3-yl)-3-oxopropanoate and 1,3-thiazol-2-amine.

1H-NMR (CDCl3): δ 1.17 (3H, t, J=7.5 Hz), 4.15 (2H, q, J=7.5 Hz), 7.10 (1H, d, J=3.5 Hz), 7.42 (1H, d, J=7.5 Hz), 7.54 (1H, d, J=3.5 Hz), 8.96 (1H, d, J=12.5 Hz)

(2) The title compound was obtained by the method described in Reference Example 001-(2) or a method equivalent thereto from ethyl 7-chloro-6-fluoro-4-oxo-1-(1,3-thiazol-2-yl)-1,4-dihydro-1,8-naphthyridine-3-carboxylate obtained in the preceding section.

1H-NMR (DMSO-d6): δ 7.88 (1H, d, J=3.5 Hz), 7.89 (1H, d, J=3.5 Hz), 8.79 (1H, d, J=7.5 Hz), 9.85 (1H, s), 13.50 (1H, brs)

Reference Example 004

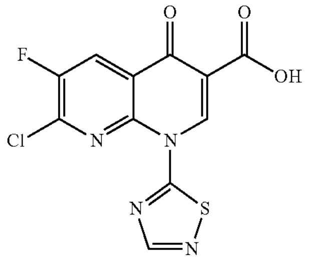 [SMILES: O=C(O)c1cn(-c2ncns2)c2nc(Cl)c(F)cc2c1=O]

7-Chloro-6-fluoro-4-oxo-1-(1,2,4-thiadiazol-5-yl)-1,4-dihydro-1,8-naphthyridine-3-carboxylic acid (1) Using ethyl 3-(2,6-dichloro-5-fluoropyridin-3-yl)-3-oxopropanoate and 1,2,4-thiadiazol-5-amine, ethyl 7-chloro-6-fluoro-4-oxo-1-(1,2,4-thiadiazol-5-yl)-1,4-dihydro-1,8-naphthyridine-3-carboxylate was obtained by the method described in Reference Example 001-(1) or a method equivalent thereto.

1H-NMR (DMSO-d6): δ 1.33 (3H, t, J=7.0 Hz), 4.35 (2H, q, J=7.0 Hz), 8.72 (1H, d, J=7.5 Hz), 8.85 (1H, s), 9.74 (1H, s)

(2) The title compound was obtained from ethyl 7-chloro-6-fluoro-4-oxo-1-(1,2,4-thiadiazol-5-yl)-1,4-dihydro-1,8-naphthyridine-3-carboxylate obtained in the preceding section by the method described in Reference Example 001-(2) or a method equivalent thereto.

1H-NMR (DMSO-d6): δ 8.82 (1H, d, J=7.5 Hz), 8.87 (1H, s), 9.82 (1H, s), 13.33 (1H, brs)

Reference Example 005

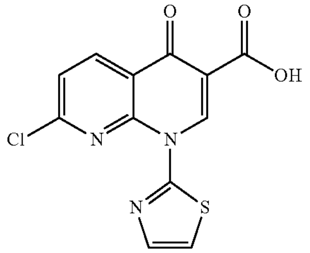 [SMILES: O=C(O)c1cn(-c2nccs2)c2nc(Cl)ccc2c1=O]

7-Chloro-4-oxo-1-(1,3-thiazol-2-yl)-1,4-dihydro-1,8-naphthyridine-3-carboxylic acid (1) Using ethyl 3-(2,6-dichloropyridin-3-yl)-3-oxopropanoate and 1,3-thiazol-2-amine, ethyl 7-chloro-4-oxo-1-(1,3-thiazol-2-yl)-1,4-dihydro-1,8-naphthyridine-3-carboxylate was obtained by the method described in Reference Example 001-(1) or a method equivalent thereto.

1H-NMR (DMSO-d6): δ 1.32 (3H, t, J=7.0 Hz), 4.31 (2H, q, J=7.0 Hz), 7.79 (1H, d, J=8.5 Hz), 7.81 (1H, d, J=3.5 Hz), 7.85 (1H, d, J=3.5 Hz), 8.66 (1H, d, J=8.5 Hz), 9.76 (1H, s)

(2) The title compound was obtained from ethyl 7-chloro-4-oxo-1-(1,3-thiazol-2-yl)-1,4-dihydro-1,8-naphthyridine-3-carboxylate obtained in the preceding section by the method described in Reference Example 001-(2) or a method equivalent thereto.

1H-NMR (DMSO-d6): δ 7.88 (1H, d, J=3.5 Hz), 7.89 (1H, d, J=3.5 Hz), 7.90 (1H, d, J=8.5 Hz), 8.80 (1H, d, J=8.5 Hz), 9.90 (1H, s), 13.66 (1H, brs)

Reference Example 006

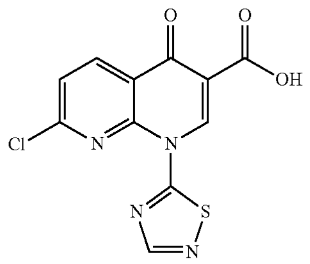 [SMILES: O=C(O)c1cn(-c2ncns2)c2nc(Cl)ccc2c1=O]

7-Chloro-4-oxo-1-(1,2,4-thiadiazol-5-yl)-1,4-dihydro-1,8-naphthyridine-3-carboxylic acid (1) Using ethyl 3-(2,6-dichloropyridin-3-yl)-3-oxopropanoate and 1,2,4-thiadiazol-5-amine, ethyl 7-chloro-4-oxo-1-(1,2,4-thiadiazol-5-yl)-1,4-dihydro-1,8-naphthyridine-3-carboxylate was obtained by the method described in Reference Example 001-(1) or a method equivalent thereto.

1H-NMR (CDCl3): δ 1.46 (3H, t, J=7.5 Hz), 4.47 (2H, q, J=7.5 Hz), 7.60 (1H, d, J=8.0 Hz), 8.58 (1H, s), 8.80 (1H, d, J=8.0 Hz), 9.99 (1H, s)

(2) The title compound was obtained from ethyl 7-chloro-4-oxo-1-(1,2,4-thiadiazol-5-yl)-1,4-dihydro-1,8-naphthyridine-3-carboxylate obtained in the preceding section by the method described in Reference Example 001-(2) or a method equivalent thereto.

1H-NMR (DMSO-d6): δ 7.94 (1H, d, J=8.0 Hz), 8.80 (1H, d, J=8.0 Hz), 8.87 (1H, s), 9.83 (1H, s), 13.40 (1H, brs)

Reference Example 007

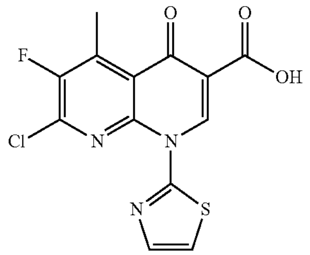 [SMILES: Cc1c(F)c(Cl)nc2c1c(=O)c(C(=O)O)cn2-c1nccs1]

7-Chloro-6-fluoro-5-methyl-4-oxo-1-(1,3-thiazol-2-yl)-1,4-dihydro-1,8-naphthyridine-3-carboxylic acid (1) Ethyl 7-chloro-6-fluoro-5-methyl-4-oxo-1-(1,3-thiazol-2-yl)-1,4-dihydro-1,8-naphthyridine-3-carboxylate was obtained by the method described in Reference Example 001-(1) or a method equivalent using 1,3-thiazol-2-amine and ethyl 3-(2,6-dichloro-5-fluoro-4-methylpyridin-3-yl)-3-oxopropanoate obtained by the method as claimed in JP-A-2-282384 or a method equivalent thereto.

1H-NMR (DMSO-d6): δ 1.31 (3H, t, J=7.0 Hz), 2.83 (3H, d, J=2.5 Hz), 4.30 (2H, q, J=7.0 Hz), 7.80 (1H, d, J=3.5 Hz), 7.85 (1H, d, J=3.6 Hz), 9.64 (1H, s)

(2) The title compound was obtained from ethyl 7-chloro-6-fluoro-5-methyl-4-oxo-1-(1,3-thiazol-2-yl)-1,4-dihydro-1,8-naphthyridine-3-carboxylate obtained in the preceding section by the method described in Reference Example 001-(2) or a method equivalent thereto.

1H-NMR (DMSO-d6): δ 2.90 (3H, d, J=2.5 Hz), 7.88 (1H, d, J=3.5 Hz), 7.90 (1H, d, J=3.5 Hz), 9.84 (1H, s), 13.83 (1H, brs)

Reference Example 008

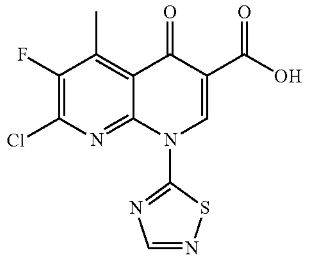 [SMILES: Cc1c(F)c(Cl)nc2c1c(=O)c(C(=O)O)cn2-c1ncns1]

7-Chloro-6-fluoro-5-methyl-4-oxo-1-(1,2,4-thiadiazol-5-yl)-1,4-dihydro-1,8-naphthyridine-3-carboxylic acid (1) Ethyl 7-chloro-6-fluoro-5-methyl-4-oxo-1-(1,2,4-thiadiazol-5-yl)-1,4-dihydro-1,8-naphthyridine-3-carboxylate was obtained using ethyl 3-(2,6-dichloro-5-fluoro-4-methylpyridin-3-yl)-3-oxopropanoate obtained by the method as claimed in JP-A-2-282384 or a method equivalent thereto and 1,2,4-thiadiazol-5-amine by the method described in Reference Example 001-(1) or a method equivalent.

1H-NMR (DMSO-d6): δ 1.32 (3H, t, J=7.0 Hz), 2.85 (3H, d, J=2.5 Hz), 4.32 (2H, q, J=7.0 Hz), 8.83 (1H, s), 9.65 (1H, s)

(2) The title compound was obtained from ethyl 7-chloro-6-fluoro-5-methyl-4-oxo-1-(1,2,4-thiadiazol-5-yl)-1,4-dihydro-1,8-naphthyridine-3-carboxylate obtained in the preceding section by the method described in Reference Example 001-(2) or a method equivalent.

1H-NMR (DMSO-d6): δ 2.89 (3H, d, J=2.5 Hz), 8.87 (1H, s), 9.80 (1H, s), 13.46 (1H, s)

Reference Example 009

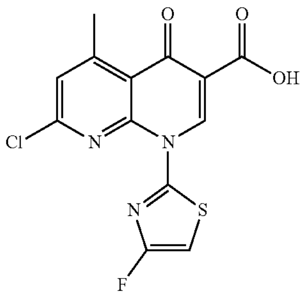 [SMILES: Cc1cc(Cl)nc2c1c(=O)c(C(=O)O)cn2-c1nc(F)cs1]

7-Chloro-1-(4-fluoro-1,3-thiazol-2-yl)-5-methyl-4-oxo-1,4-dihydro-1,8-naphthyridine-3-carboxylic acid (1) Ethyl 7-chloro-1-(4-fluoro-1,3-thiazol-2-yl)-5-methyl-4-oxo-1,4-dihydro-1,8-naphthyridine-3-carboxylate was obtained from ethyl 7-chloro-5-methyl-4-oxo-1-(1,3-thiazol-2-yl)-1,4-dihydro-1,8-naphthyridine-3-carboxylate obtained in Reference Example 001-(1) by the method described in the JP-B-5079612 or a method equivalent thereto.

1H-NMR (CDCl3): δ 1.43 (3H, t, J=7.0 Hz), 2.99 (3H, s), 4.44 (2H, q, J=7.0 Hz), 7.27 (1H, s), 7.34 (1H, d, J=3.0 Hz), 9.79 (1H, s)

(2) The title compound was obtained from ethyl 7-chloro-1-(4-fluoro-1,3-thiazol-2-yl)-5-methyl-4-oxo-1,4-dihydro-1,8-naphthyridine-3-carboxylate obtained in the preceding section by the method described in Reference Example 001-(2) or a method equivalent thereto.

1H-NMR (DMSO-d6): δ 2.92 (3H, s), 7.80 (1H, d, J=3.0 Hz), 7.80 (1H, s), 9.73 (1H, s)

Reference Example 010

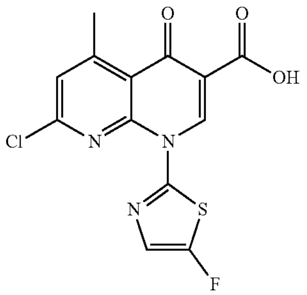 [SMILES: Cc1cc(Cl)nc2c1c(=O)c(C(=O)O)cn2-c1ncc(F)s1]

7-Chloro-1-(5-fluoro-1,3-thiazol-2-yl)-5-methyl-4-oxo-1,4-dihydro-1,8-naphthyridine-3-carboxylic acid (1) Ethyl 7-chloro-1-(5-fluoro-1,3-thiazol-2-yl)-5-methyl-4-oxo-1,4-dihydro-1,8-naphthyridine-3-carboxylate was obtained using ethyl 3-(2,6-dichloro-4-methylpyridin-3-yl)-3-oxopropanoate obtained by the method described in JP-A-2006-514964 or a method equivalent thereto and 5-fluoro-1,3-thiazol-2-amine hydrochloride by the method described in Reference Example 001-(1) or a method equivalent thereto.

1H-NMR (DMSO-d6): δ 1.30 (3H, t, J=7.0 Hz), 2.85 (3H, s), 4.29 (2H, q, J=7.0 Hz), 7.67 (1H, s), 7.74 (1H, d, J=3.0 Hz), 9.51 (1H, s)

(2) The title compound was obtained from ethyl 7-chloro-1-(5-fluoro-1,3-thiazol-2-yl)-5-methyl-4-oxo-1,4-dihydro-1,8-naphthyridine-3-carboxylate obtained in the preceding section by the method described in Reference Example 001-(2) or a method equivalent thereto.

1H-NMR (DMSO-d6): δ 2.92 (3H, s), 7.81 (1H, d, J=2.5 Hz), 7.81 (1H, s), 9.73 (1H, s)

Reference Example 011

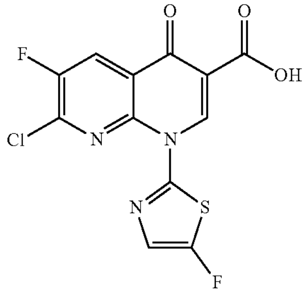 [SMILES: O=C(O)c1cn(-c2ncc(F)s2)c2nc(Cl)c(F)cc2c1=O]

7-Chloro-6-fluoro-1-(5-fluoro-1,3-thiazol-2-yl)-4-oxo-1,4-dihydro-1,8-naphthyridine-3-carboxylic acid (1) Ethyl 7-chloro-6-fluoro-1-(5-fluoro-1,3-thiazol-2-yl)-4-oxo-1,4-dihydro-1,8-naphthyridine-3-carboxylate was obtained using ethyl 3-(2,6-dichloro-5-fluoropyridin-3-yl)-3-oxopropanoate and 5-fluoro-1,3-thiazol-2-amine hydrochloride by the method described in Reference Example 001-(1) or a method equivalent thereto.

1H-NMR (CDCl3): δ 1.45 (3H, t, J=7.0 Hz), 4.46 (2H, q, J=7.0 Hz), 7.36 (1H, d, J=3.0 Hz), 8.55 (1H, d, J=7.5 Hz), 9.86 (1H, s)

(2) The title compound was obtained from ethyl 7-chloro-6-fluoro-1-(5-fluoro-1,3-thiazol-2-yl)-4-oxo-1,4-dihydro-1,8-naphthyridine-3-carboxylate obtained in the preceding section by the method described in Reference Example 001-(2) or a method equivalent thereto.

1H-NMR (DMSO-d6): δ 7.82 (1H, d, J=3.0 Hz), 8.79 (1H, d, J=8.0 Hz), 9.69 (1H, s), 13.47 (1H, brs)

Reference Example 012

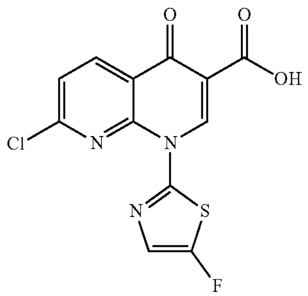 [SMILES: O=C(O)c1cn(-c2ncc(F)s2)c2nc(Cl)ccc2c1=O]

7-Chloro-1-(5-fluoro-1,3-thiazol-2-yl)-4-oxo-1,4-dihydro-1,8-naphthyridine-3-carboxylic acid (1) Ethyl 7-chloro-1-(5-fluoro-1,3-thiazol-2-yl)-4-oxo-1,4-dihydro-1,8-naphthyridine-3-carboxylate was obtained using ethyl 3-(2,6-dichloropyridin-3-yl)-3-oxopropanoate and 5-fluoro-1,3-thiazol-2-amine hydrochloride by the method described in Reference Example 001-(1) or a method equivalent thereto.

1H-NMR (CDCl3): δ 1.43 (3H, t, J=7.5 Hz), 4.44 (2H, q, J=7.5 Hz), 7.34 (1H, d, J=3.5 Hz), 7.51 (1H, d, J=8.0 Hz), 8.76 (1H, d, J=8.0 Hz), 9.86 (1H, s)

(2) The title compound was obtained from ethyl 7-chloro-1-(5-fluoro-1,3-thiazol-2-yl)-4-oxo-1,4-dihydro-1,8-naphthyridine-3-carboxylate obtained in the preceding section by the method described in Reference Example 001-(2) or a method equivalent thereto.

1H-NMR (DMSO-d6): δ 7.81 (1H, d, J=3.0 Hz), 7.89 (1H, d, J=8.5 Hz), 8.79 (1H, d, J=8.5 Hz), 9.74 (1H, s), 13.59 (1H, brs)

Reference Example 013

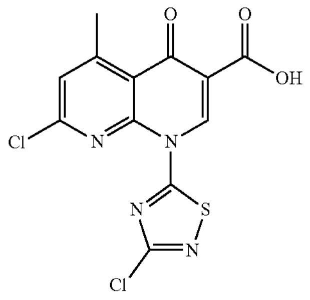 [SMILES: Cc1cc(Cl)nc2c1c(=O)c(C(=O)O)cn2-c1nc(Cl)ns1]

7-Chloro-1-(3-chloro-1,2,4-thiadiazol-5-yl)-5-methyl-4-oxo-1,4-dihydro-1,8-naphthyridine-3-carboxylic acid (1) Ethyl 7-chloro-1-(3-chloro-1,2,4-thiadiazol-5-yl)-5-methyl-4-oxo-1,4-dihydro-1,8-naphthyridine-3-carboxylate was obtained using ethyl 3-(2,6-dichloro-4-methylpyridin-3-yl)-3-oxopropanoate obtained by the method described in JP-A-2006-514964 or a method equivalent thereto and 3-chloro-1,2,4-thiadiazol-5-amine by the method described in Reference Example 001-(1) or a method equivalent thereto.

1H-NMR (CDCl3): δ 1.45 (3H, t, J=7.0 Hz), 3.01 (3H, s), 4.47 (2H, q, J=7.0 Hz), 7.37 (1H, s), 9.71 (1H, s)

(2) The title compound was obtained from ethyl 7-chloro-1-(3-chloro-1,2,4-thiadiazol-5-yl)-5-methyl-4-oxo-1,4-dihydro-1,8-naphthyridine-3-carboxylate obtained in the preceding section by the method described in Reference Example 001-(2) or a method equivalent thereto.

1H-NMR (DMSO-d6): δ 2.91 (3H, s), 7.88 (1H, S), 9.55 (1H, s), 13.48 (1H, brs)

Reference Example 014

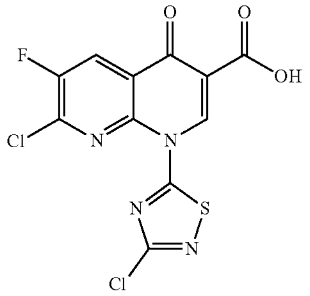 [SMILES: O=C(O)c1cn(-c2nc(Cl)ns2)c2nc(Cl)c(F)cc2c1=O]

7-Chloro-1-(3-chloro-1,2,4-thiadiazol-5-yl)-6-fluoro-4-oxo-1,4-dihydro-1,8-naphthyridine-3-carboxylic acid (1) Ethyl 7-chloro-1-(3-chloro-1,2,4-thiadiazol-5-yl)-6-fluoro-4-oxo-1,4-dihydro-1,8-naphthyridine-3-carboxylate was obtained using ethyl 3-(2,6-dichloro-5-fluoropyridin-3-yl)-3-oxopropanoate and 3-chloro-1,2,4-thiadiazol-5-amine by the method described in Reference Example 001-(1) or a method equivalent thereto.

1H-NMR (CDCl3): δ 1.46 (3H, t, J=7.0 Hz), 4.48 (2H, q, J=7.0 Hz), 8.57 (1H, d, J=7.0 Hz), 9.82 (1H, s)

(2) The title compound was obtained from ethyl 7-chloro-1-(3-chloro-1,2,4-thiadiazol-5-yl)-6-fluoro-4-oxo-1,4-dihydro-1,8-naphthyridine-3-carboxylate obtained in the preceding section by the method described in Reference Example 001-(2) or a method equivalent thereto.

1H-NMR (DMSO-d6): δ 8.82 (1H, d, J=7.5 Hz), 9.56 (1H, s), 13.36 (1H, brs)

Reference Example 015

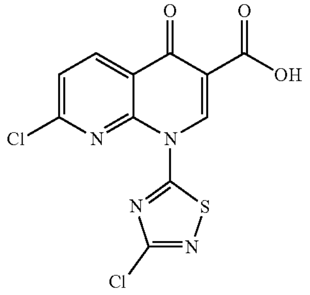 [SMILES: O=C(O)c1cn(-c2nc(Cl)ns2)c2nc(Cl)ccc2c1=O]

7-Chloro-1-(3-chloro-1,2,4-thiadiazol-5-yl)-4-oxo-1,4-dihydro-1,8-naphthyridine-3-carboxylic acid (1) Ethyl 7-chloro-1-(3-chloro-1,2,4-thiadiazol-5-yl)-4-oxo-1,4-dihydro-1,8-naphthyridine-3-carboxylate was obtained using ethyl 3-(2,6-dichloropyridin-3-yl)-3-oxopropanoate and 3-chloro-1,2,4-thiadiazol-5-amine by the method described in Reference Example 001-(1) or a method equivalent thereto.

1H-NMR (CDCl3): δ 1.46 (3H, t, J=7.0 Hz), 4.48 (2H, q, J=7.0 Hz), 7.61 (1H, d, J=8.0 Hz), 8.79 (1H, d, J=8.0 Hz), 9.80 (1H, s)

(2) The title compound was obtained from ethyl 7-chloro-1-(3-chloro-1,2,4-thiadiazol-5-yl)-4-oxo-1,4-dihydro-1,8-naphthyridine-3-carboxylate obtained in the preceding section by the method described in Reference Example 001-(2) or a method equivalent thereto.

1H-NMR (DMSO-d6): δ 7.94 (1H, d, J=8.0 Hz), 8.78 (1H, d, J=8.0 Hz), 9.57 (1H, s), 13.37 (1H, s)

Reference Example 016

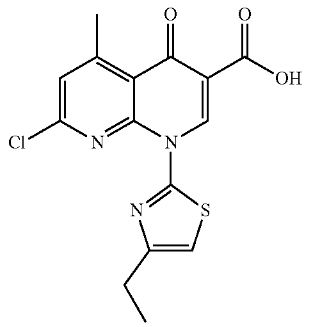 [SMILES: CCc1csc(-n2cc(C(=O)O)c(=O)c3c(C)cc(Cl)nc32)n1]

7-Chloro-1-(4-ethyl-1,3-thiazol-2-yl)-5-methyl-4-oxo-1,4-dihydro-1,8-naphthyridine-3-carboxylic acid (1) Ethyl 7-chloro-1-(4-ethyl-1,3-thiazol-2-yl)-5-methyl-4-oxo-1,4-dihydro-1,8-naphthyridine-3-carboxylate was obtained using ethyl 3-(2,6-dichloro-4-methylpyridin-3-yl)-3-oxopropanoate obtained by the method described in JP-A-2006-514964 or a method equivalent thereto and 4-ethyl-1,3-thiazol-2-amine by the method described in Reference Example 001-(1) or a method equivalent thereto.

1H-NMR (CDCl3): δ 1.35 (3H, t, J=7.5 Hz), 1.44 (3H, t, J=7.0 Hz), 2.83 (2H, q, J=7.5 Hz), 2.99 (3H, s), 4.46 (2H, q, J=7.0 Hz), 6.91 (1H, s), 7.25 (1H, s), 9.91 (1H, s)

(2) The title compound was obtained from ethyl 7-chloro-1-(4-ethyl-1,3-thiazol-2-yl)-5-methyl-4-oxo-1,4-dihydro-1,8-naphthyridine-3-carboxylate obtained in the preceding section by the method described in Reference Example 001-(2) or a method equivalent thereto.

1H-NMR (DMSO-d6): δ 1.28 (3H, t, J=7.5 Hz), 2.80 (2H, q, J=7.5 Hz), 2.93 (3H, s), 7.43 (1H, s), 7.80 (1H, s), 9.88 (1H, s)

Reference Example 017

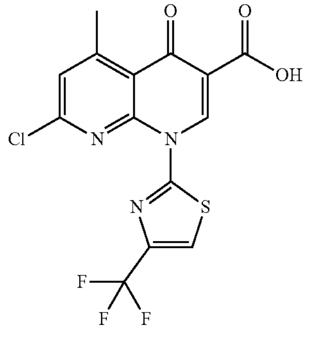 [SMILES: Cc1cc(Cl)nc2c1c(=O)c(C(=O)O)cn2-c1nc(C(F)(F)F)cs1]

7-Chloro-5-methyl-4-oxo-1-[4-(trifluoromethyl)-1,3-thiazol-2-yl]-1,4-dihydro-1,8-naphthyridine-3-carboxylic acid (1) Ethyl 7-chloro-1-[4-(trifluoromethyl)-1,3-thiazol-2-yl]-5-methyl-4-oxo-1,4-dihydro-1,8-naphthyridine-3-carboxylate was obtained using ethyl 3-(2,6-dichloro-4-methylpyridin-3-yl)-3-oxopropanoate obtained by the method described in JP-A-2006-514964 or a method equivalent thereto and 4-(trifluoromethyl)-1,3-thiazol-2-amine by the method described in Reference Example 001-(1) or a method equivalent thereto.

1H-NMR (CDCl3): δ 1.45 (3H, t, J=7.0 Hz), 3.00 (3H, s), 4.47 (2H, q, J=7.0 Hz), 7.31 (1H, s), 7.74 (1H, s), 9.89 (1H, s)

(2) The title compound was obtained from ethyl 7-chloro-1-[4-(trifluoromethyl)-1,3-thiazol-2-yl]-5-methyl-4-oxo-1,4-dihydro-1,8-naphthyridine-3-carboxylate obtained in the preceding section by the method described in Reference Example 001-(2) or a method equivalent thereto.

1H-NMR (DMSO-d6): δ 2.93 (3H, s), 7.84 (1H, s), 8.54 (1H, s), 9.79 (1H, s), 13.83 (1H, brs)

Reference Example 018

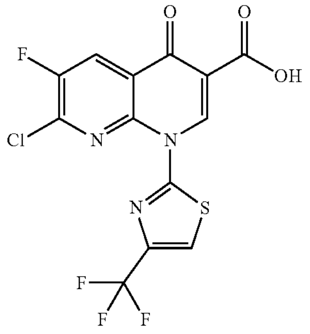 [SMILES: O=C(O)c1cn(-c2nc(C(F)(F)F)cs2)c2nc(Cl)c(F)cc2c1=O]

7-Chloro-6-fluoro-4-oxo-1-[4-(trifluoromethyl)-1,3-thiazol-2-yl]-1,4-dihydro-1,8-naphthyridine-3-carboxylic acid (1) Ethyl 7-chloro-6-fluoro-4-oxo-1-[4-(trifluoromethyl)-1,3-thiazol-2-yl]-1,4-dihydro-1,8-naphthyridine-3-carboxylate was obtained using ethyl 3-(2,6-dichloro-5-fluoropyridin-3-yl)-3-oxopropanoate and 4-(trifluoromethyl)-1,3-thiazol-5-amine by the method described in Reference Example 001-(1) or a method equivalent thereto.

1H-NMR (CDCl3): δ 1.46 (3H, t, J=7.0 Hz), 4.48 (2H, q, J=7.0 Hz), 7.78 (1H, s), 8.57 (1H, d, J=7.0 Hz), 9.98 (1H, s)

(2) The title compound was obtained from ethyl 7-chloro-6-fluoro-4-oxo-1-[4-(trifluoromethyl)-1,3-thiazol-2-yl]-1,4-dihydro-1,8-naphthyridine-3-carboxylate obtained in the preceding section by the method described in Reference Example 001-(2) or a method equivalent thereto.

1H-NMR (DMSO-d6): δ 8.56 (1H, s), 8.80 (1H, d, J=7.5 Hz), 9.76 (1H, s), 13.43 (1H, brs)

Reference Example 019

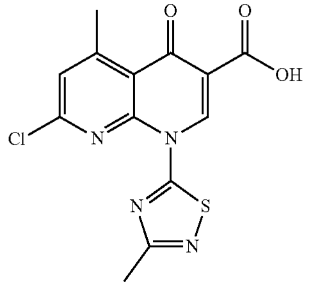 [SMILES: Cc1nsc(-n2cc(C(=O)O)c(=O)c3c(C)cc(Cl)nc32)n1]

7-Chloro-5-methyl-1-(3-methyl-1,2,4-thiadiazol-5-yl)-4-oxo-1,4-dihydro-1,8-naphthyridine-3-carboxylic acid (1) Ethyl 7-chloro-1-(3-methyl-1,2,4-thiadiazol-5-yl)-5-methyl-4-oxo-1,4-dihydro-1,8-naphthyridine-3-carboxylate was obtained using ethyl 3-(2,6-dichloro-4-methylpyridin-3-yl)-3-oxopropanoate obtained by the method described in JP-A-2006-514964 or a method equivalent thereto and 3-methyl-1,2,4-thiadiazol-5-amine by the method described in Reference Example 001-(1) or a method equivalent thereto.

1H-NMR (CDCl3): δ 1.46 (3H, t, J=7.0 Hz), 2.68 (3H, s), 3.00 (3H, s), 4.47 (2H, q, J=7.0 Hz), 7.33 (1H, s), 9.88 (1H, s)

(2) The title compound was obtained from ethyl 7-chloro-1-(3-methyl-1,2,4-thiadiazol-5-yl)-5-methyl-4-oxo-1,4-dihydro-1,8-naphthyridine-3-carboxylate obtained in the preceding section by the method described in Reference Example 001-(2) or a method equivalent thereto.

1H-NMR (DMSO-d6): 2.63 (3H, s), 2.92 (3H, s), 7.86 (1H, s), 9.79 (1H, s), 13.65 (1H, brs)

Reference Example 020

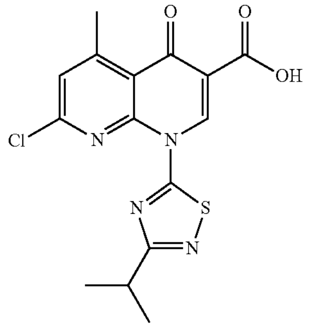 [SMILES: Cc1cc(Cl)nc2c1c(=O)c(C(=O)O)cn2-c1nc(C(C)C)ns1]

7-Chloro-5-methyl-4-oxo-1-[3-(propan-2-yl)-1,2,4-thiadiazol-5-yl]-1,4-dihydro-1,8-naphthyridine-3-carboxylic acid (1) Ethyl 7-chloro-5-methyl-4-oxo-1-[3-(propan-2-yl)-1,2,4-thiadiazol-5-yl]-1,4-dihydro-1,8-naphthyridine-3-carboxylate was obtained using ethyl 3-(2,6-dichloro-4-methylpyridin-3-yl)-3-oxopropanoate obtained by the method described in JP-A-2006-514964 or a method equivalent thereto and 3-(propan-2-yl)-1,2,4-thiadiazol-5-amine by the method described in Reference Example 001-(1) or a method equivalent thereto.

1H-NMR (CDCl3): δ 1.44 (6H, d, J=7.0 Hz), 1.46 (3H, t, J=7.0 Hz), 3.00 (3H, s), 3.30 (1H, sep, J=7.0 Hz), 4.48 (2H, q, J=7.0 Hz), 7.32 (1H, s), 9.91 (1H, s)

(2) The title compound was obtained from ethyl 7-chloro-1-(3-methyl-1,2,4-thiadiazol-5-yl)-5-methyl-4-oxo-1,4-dihydro-1,8-naphthyridine-3-carboxylate obtained in the preceding section by the method described in Reference Example 001-(2) or a method equivalent thereto.

1H-NMR (DMSO-d6): δ 1.37 (6H, d, J=6.5 Hz), 2.92 (3H, s), 3.23-3.44 (1H, m), 7.85 (1H, s), 9.82 (1H, s), 13.7 (1H, s)

Reference Example 021

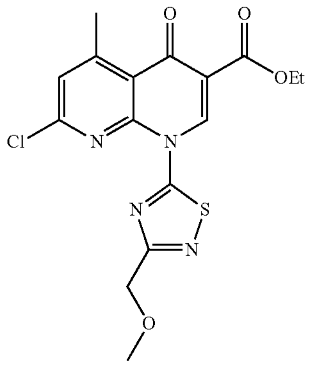 [SMILES: CCOC(=O)c1cn(-c2nc(COC)ns2)c2nc(Cl)cc(C)c2c1=O]

Ethyl 7-chloro-1-[3-(methoxymethyl)-1,2,4-thiadiazol-5-yl]-5-methyl-4-oxo-1,4-dihydro-1,8-naphthyridine-3-carboxylate The title compound was obtained using ethyl 3-(2,6-dichloro-4-methylpyridin-3-yl)-3-oxopropanoate obtained by the method described in JP-A-2006-514964 or a method equivalent thereto and 3-(methoxymethyl)-1,2,4-thiadiazol-5-amine by the method described in Reference Example 001-(1) or a method equivalent thereto.

1H-NMR (CDCl3): δ 1.45 (3H, t, J=7.0 Hz), 3.01 (3H, s), 3.58 (3H, s), 4.47 (2H, q, J=7.0 Hz), 4.74 (2H, s), 7.34 (1H, s), 9.87 (1H, s)

Reference Example 022

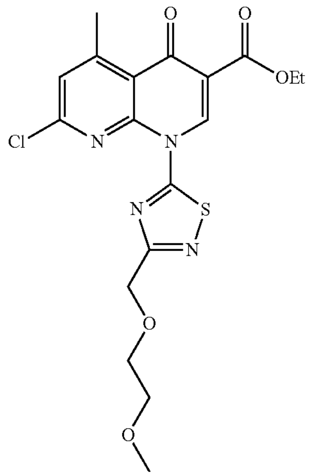 [SMILES: CCOC(=O)c1cn(-c2nc(COCCOC)ns2)c2nc(Cl)cc(C)c2c1=O]

Ethyl 7-chloro-1-{3-[(2-methoxyethoxy)methyl]-1,2,4-thiadiazol-5-yl}-5-methyl-4-oxo-1,4-dihydro-1,8-naphthyridine-3-carboxylate (1) To 2-methoxyethan-1-ol (22 mL) was added 55% sodium hydride (910 mg), and the mixture was stirred at room temperature for 15 minutes. Then, chloroacetonitrile (630 μL) was added thereto, and the mixture was stirred at room temperature for 1 day. To the reaction solution was added ammonium chloride (1.1 g). Insoluble material was filtered off, and the filtrate was then concentrated. To the residue was added isopropyl ether, and the mixture was stirred, followed by removal of the supernatant. To the residue was added acetone, and the supernatant was concentrated to obtain crude 2-(2-methoxyethoxy)ethanimidamide hydrochloride.

(2) To a solution of crude 2-(2-methoxyethoxy) ethanimidamide hydrochloride obtained in the preceding section in methanol (20 mL) were added triethylamine (1.9 mL), bromine (248 μL) and a solution of potassium thiocyanate (549 mg) in methanol (7 mL) under ice cooling, and the mixture was stirred at the same temperature for 2 hours. Insoluble material was filtered off, and the filtrate was then concentrated. To the residue was added ethyl acetate. Insoluble material was filtered off, and the filtrate was then concentrated. The residue was purified by silica gel column chromatography (eluent: methanol/methylene chloride) to obtain 456 mg of 3-[(2-methoxyethoxy)methyl]-1,2,4-thiadiazol-5-amine.

1H-NMR (CDCl3): δ 3.41 (3H, s), 3.59-3.66 (2H, m), 3.71-3.78 (2H, m), 4.58 (2H, s), 6.14 (1H, brs)

(3) The title compound was obtained by the method described in Reference Example 001-(1) or a method equivalent thereto using ethyl 3-(2,6-dichloro-4-methylpyridin-3-yl)-3-oxopropanoate obtained by the method described in JP-A-2006-514964 or a method equivalent thereto, and 3-[(2-methoxyethoxy)methyl]-1,2,4-thiadiazol-5-amine obtained in the preceding section.

1H-NMR (CDCl3): δ 1.45 (3H, t, J=7.5 Hz), 3.01 (3H, s), 3.43 (3H, s), 3.65-3.69 (2H, m), 3.84-3.88 (2H, m), 4.47 (2H, q, J=7.5 Hz), 4.86 (2H, s), 7.34 (1H, s), 9.87 (1H, s)

Reference Example 023

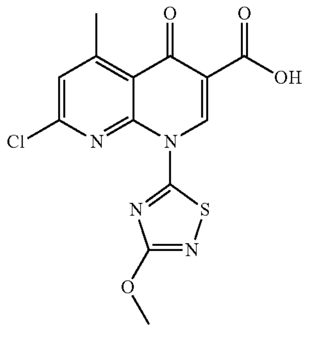 [SMILES: COc1nsc(-n2cc(C(=O)O)c(=O)c3c(C)cc(Cl)nc32)n1]

7-Chloro-1-(3-methoxy-1,2,4-thiadiazol-5-yl)-5-methyl-4-oxo-1,4-dihydro-1,8-naphthyridine-3-carboxylic acid (1) Ethyl chloro-1-(3-methoxy-1,2,4-thiadiazol-5-yl)-5-methyl-4-oxo-1,4-dihydro-1,8-naphthyridine-3-carboxylate was obtained ethyl 3-(2,6-dichloro-4-methylpyridin-3-yl)-3-oxopropanoate obtained by the method described in JP-A-2006-514964 or a method equivalent thereto and 3-methoxy-1,2,4-thiadiazol-5-amine by the method described in Reference Example 001-(1) or a method equivalent thereto.

1H-NMR (CDCl3): δ 1.43 (3H, t, J=7.0 Hz), 2.99 (3H, s), 4.14 (3H, s), 4.44 (2H, q, J=7.0 Hz), 7.33 (1H, s), 9.75 (1H, s)

(2) The title compound was obtained from ethyl 7-chloro-1-(3-methoxy-1,2,4-thiadiazol-5-yl)-5-methyl-4-oxo-1,4-dihydro-1,8-naphthyridine-3-carboxylate obtained in the preceding section by the method described in Reference Example 001-(2) or a method equivalent thereto.

1H-NMR (DMSO-d6): δ 2.91 (3H, s), 4.05 (3H, s), 7.85 (1H, s), 9.63 (1H, s), 13.56 (1H, s)

Reference Example 024

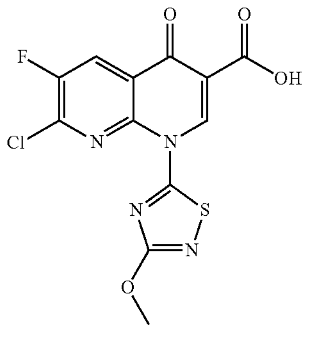 [SMILES: COc1nsc(-n2cc(C(=O)O)c(=O)c3cc(F)c(Cl)nc32)n1]

7-Chloro-6-fluoro-1-(3-methoxy-1,2,4-thiadiazol-5-yl)-4-oxo-1,4-dihydro-1,8-naphthyridine-3-carboxylic acid (1) Ethyl 7-chloro-6-fluoro-1-(3-methoxy-1,2,4-thiadiazol-5-yl)-4-oxo-1,4-dihydro-1,8-naphthyridine-3-carboxylate was obtained using ethyl 3-(2,6-dichloro-5-fluoropyridin-3-yl)-3-oxopropanoate and 3-methoxy-1,2,4-thiadiazol-5-amine by the method described in Reference Example 001-(1) or a method equivalent thereto.

1H-NMR (CDCl3): δ 1.44 (3H, t, J=7.0 Hz), 4.16 (3H, s), 4.45 (2H, q, J=7.0 Hz), 8.55 (1H, d, J=7.0 Hz), 9.86 (1H, s)

(2) The title compound was obtained from ethyl 7-chloro-6-fluoro-1-(3-methoxy-1,2,4-thiadiazol-5-yl)-4-oxo-1,4-dihydro-1,8-naphthyridine-3-carboxylate obtained in the preceding section by the method described in Reference Example 001-(2) or a method equivalent thereto.

1H-NMR (DMSO-d6): δ 4.06 (3H, s), 8.79 (1H, d, J=7.5 Hz), 9.63 (1H, s), 13.32 (1H, brs)

Reference Example 025

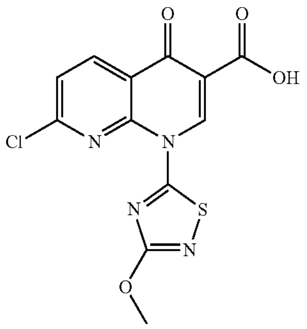 [SMILES: COc1nsc(-n2cc(C(=O)O)c(=O)c3ccc(Cl)nc32)n1]

7-Chloro-1-(3-methoxy-1,2,4-thiadiazol-5-yl)-4-oxo-1,4-dihydro-1,8-naphthyridine-3-carboxylic acid (1) Ethyl 7-chloro-1-(3-methoxy-1,2,4-thiadiazol-5-yl)-4-oxo-1,4-dihydro-1,8-naphthyridine-3-carboxylate was obtained using ethyl 3-(2,6-dichloropyridin-3-yl)-3-oxopropanoate and 3-methoxy-1,2,4-thiadiazol-5-amine by the method described in Reference Example 001-(1) or a method equivalent thereto.

1H-NMR (CDCl3): δ 1.44 (3H, t, J=7.0 Hz), 4.15 (3H, s), 4.45 (2H, q, J=7.0 Hz), 7.57 (1H, d, J=8.5 Hz), 8.77 (1H, d, J=8.5 Hz), 9.84 (1H, s)

(2) The title compound was obtained from ethyl 7-chloro-1-(3-methoxy-1,2,4-thiadiazol-5-yl)-4-oxo-1,4-dihydro-1,8-naphthyridine-3-carboxylate obtained in the preceding section by the method described in Reference Example 001-(2) or a method equivalent thereto.

1H-NMR (DMSO-d6): δ 4.05 (3H, s), 7.91 (1H, d, J=8.5 Hz), 8.77 (1H, d, J=8.5 Hz), 9.64 (1H, s), 13.37 (1H, s)

Reference Example 026

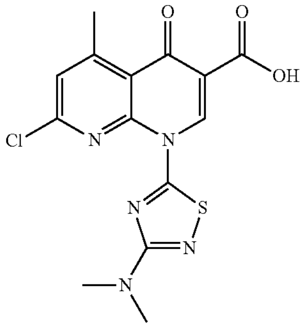 [SMILES: Cc1cc(Cl)nc2c1c(=O)c(C(=O)O)cn2-c1nc(N(C)C)ns1]

7-Chloro-1-[3-(dimethylamino)-1,2,4-thiadiazol-5-yl]-5-methyl-4-oxo-1,4-dihydro-1,8-naphthyridine-3-carboxylic acid (1) Ethyl 7-chloro-1-[3-(dimethylamino)-1,2,4-thiadiazol-5-yl]-5-methyl-4-oxo-1,4-dihydro-1,8-naphthyridine-3-carboxylate was obtained using 3-(dimethylamino)-1,2,4-thiadiazol-5-amine obtained by the method described in Chemische Berichte 88, 1071 (1955) or a method equivalent thereto and ethyl 3-(2,6-dichloro-4-methylpyridin-3-yl)-3-oxopropanoate obtained by the method described in JP-A-2006-514964 or a method equivalent thereto by the method described in Reference Example 001-(1) or a method equivalent thereto.

1H-NMR (CDCl3): δ 1.45 (3H, t, J=7.0 Hz), 2.99 (3H, s), 3.23 (6H, s), 4.46 (2H, q, J=7.0 Hz), 7.29 (1H, s), 9.84 (1H, s)

(2) The title compound was obtained from ethyl 7-chloro-1-[3-(dimethylamino)-1,2,4-thiadiazol-5-yl]-5-methyl-4-oxo-1,4-dihydro-1,8-naphthyridine-3-carboxylate obtained in the preceding section by the method described in Reference Example 001-(2) or a method equivalent thereto.

1H-NMR (DMSO-d6): δ 2.91 (3H, s), 3.14 (6H, s), 7.83 (1H, s), 9.76 (1H, s), 13.71 (1H, s)

Reference Example 027

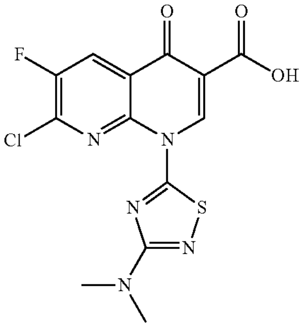 [SMILES: CN(C)c1nsc(-n2cc(C(=O)O)c(=O)c3cc(F)c(Cl)nc32)n1]

7-Chloro-1-[3-(dimethylamino)-1,2,4-thiadiazol-5-yl]-6-fluoro-4-oxo-1,4-dihydro-1,8-naphthyridine-3-carboxylic acid (1) Ethyl 7-chloro-1-[3-(dimethylamino)-1,2,4-thiadiazol-5-yl]-6-fluoro-4-oxo-1,4-dihydro-1,8-naphthyridine-3-carboxylate was obtained using 3-(dimethylamino)-1,2,4-thiadiazol-5-amine obtained by the method described in ChemischeBerichte 88, 1071 (1955) or a method equivalent thereto and ethyl 3-(2,6-dichloro-5-fluoropyridin-3-yl)-3-oxopropanoate by the method described in Reference Example 001-(1) or a method equivalent thereto.

1H-NMR (CDCl3): δ 1.46 (3H, t, J=7.0 Hz), 3.24 (6H, s), 4.47 (2H, q, J=7.0 Hz), 8.52 (1H, d, J=7.5 Hz), 9.94 (1H, s)

(2) The title compound was obtained from ethyl 7-chloro-1-[3-(dimethylamino)-1,2,4-thiadiazol-5-yl]-6-fluoro-4-oxo-1,4-dihydro-1,8-naphthyridine-3-carboxylate obtained in the preceding section by the method described in Reference Example 001-(2) or a method equivalent thereto.

1H-NMR (DMSO-d6): δ 3.15 (6H, s), 8.78 (1H, d, J=7.5 Hz), 9.76 (1H, s)

Reference Example 028

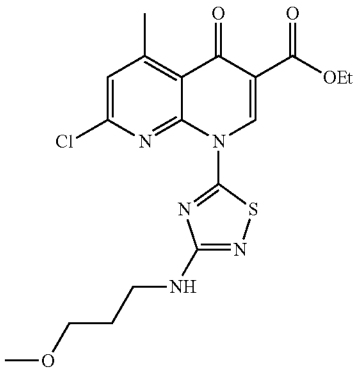 [SMILES: CCOC(=O)c1cn(-c2nc(NCCCOC)ns2)c2nc(Cl)cc(C)c2c1=O]

Ethyl 7-chloro-1-{3-[(3-methoxypropyl)amino]-1,2,4-thiadiazol-5-yl}-5-methyl-4-oxo-1,4-dihydro-1,8-naphthyridine-3-carboxylate (1) A mixture of 2,4-dichloro-1,2,4-thiadiazole (4.5 g), 2,4-dimethoxybenzylamine (4.8 mL), N,N-diisopropylethylamine (15 mL), and 2-propanol (145 mL) was stirred at 80° C. The reaction solution was concentrated. The residue was dispersed in methanol, and the solid was then collected by filtration to obtain 5.6 g of 3-chloro-N-[(2,4-dimethoxyphenyl)methyl]-1,2,4-thiadiazol-5-amine.

1H-NMR (CDCl3): δ 3.82 (3H, s), 3.84 (3H, s), 4.34 (2H, d, J=6.0 Hz), 6.36 (1H, brs), 6.43-6.51 (2H, m), 7.17 (1H, d, J=8.5 Hz)

(2) A mixture of 3-chloro-N-[(2,4-dimethoxyphenyl)methyl]-1,2,4-thiadiazol-5-amine (1.8 g) obtained in the preceding section, 3-methoxypropan-1-amine (1.6 mL), zinc dichloride (1.3 g), N,N-diisopropylethylamine (2.7 mL), and 2-propanol (14 mL) was stirred at 120° C. for 6 hours under microwave irradiation. The reaction solution was concentrated, and the residue was purified by silica gel column chromatography (eluent: methanol/chloroform) to obtain 2.1 g of N5-[(2,4-dimethoxyphenyl)methyl]-N3-(3-methoxypropyl)-1,2,4-thiadiazole-3,5-diamine.

1H-NMR (CDCl3): δ 1.78-1.87 (2H, m), 3.33 (3H, s), 3.35-3.42 (1H, m), 3.44 (2H, t, J=6.0 Hz), 3.80 (3H, s), 3.84 (3H, s), 4.17-4.25 (2H, m), 6.41-6.49 (2H, m), 7.13 (1H, d, J=8.5 Hz)

(3) A mixture of N5-[(2,4-dimethoxyphenyl)methyl]-N3-(3-methoxypropyl)-1,2,4-thiadiazole-3,5-diamine (2.1 g) obtained in the preceding section, 1,4-dioxane (10 mL), and a 4 mol/L solution of hydrochloric acid in 1,4-dioxane (20 mL) was stirred overnight at room temperature. To the reaction solution was added methanol, and the resulting solid was filtered off. The filtrate was concentrated, to the residue was added an aqueous sodium bicarbonate solution, and the mixture was extracted with chloroform. The organic layer was dried over sodium sulfate and concentrated to obtain 916 mg of N3-(3-methoxypropyl)-1,2,4-thiadiazole-3,5-diamine.

1H-NMR (CD3OD): δ 1.83 (2H, q, J=6.5 Hz), 3.32 (2H, t, J=6.5 Hz), 3.48 (2H, t, J=6.5 Hz)

(4) The title compound was obtained by the method described in Reference Example 001-(1) or a method equivalent thereto using ethyl 3-(2,6-dichloro-4-methylpyridin-3-yl)-3-oxopropanoate obtained by the method described in JP-A-2006-514964 or a method equivalent thereto, and N3-(3-methoxypropyl)-1,2,4-thiadiazole-3,5-diamine obtained in the preceding section.

1H-NMR (CDCl3): δ 1.44 (3H, t, J=7.0 Hz), 1.95 (2H, q, J=6.5 Hz), 2.98 (3H, s), 3.39 (3H, s), 3.54-3.58 (4H, m), 4.45 (2H, q, J=7.0 Hz), 5.40 (1H, t, J=5.5 Hz), 7.28 (1H, s), 9.77 (1H, s)

Reference Example 029

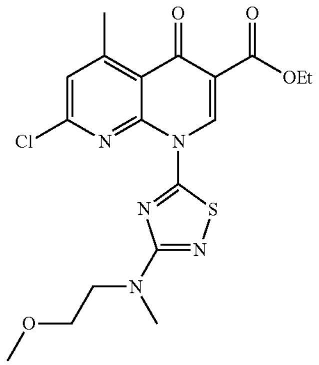 [SMILES: CCOC(=O)c1cn(-c2nc(N(C)CCOC)ns2)c2nc(Cl)cc(C)c2c1=O]

Ethyl 7-chloro-1-{3-[(2-methoxyethyl) (methyl)amino]-1,2,4-thiadiazol-5-yl}-5-methyl-4-oxo-1,4-dihydro-1,8-naphthyridine-3-carboxylate The title compound was obtained using N3-(2-methoxyethyl)-N3-methyl-1,2,4-thiadiazole-3,5-diamine obtained from (2-methoxyethyl) (methyl)amine by the method described in Reference Example 028-(2),(3) or a method equivalent thereto and ethyl 3-(2,6-dichloro-4-methylpyridin-3-yl)-3-oxopropanoate obtained by the method described in JP-A-2006-514964 or a method equivalent thereto by the method described in Reference Example 001-(1) or a method equivalent thereto.

1H-NMR (CDCl3): δ 1.44 (3H, t, J=7.5 Hz), 2.99 (3H, s), 3.28 (3H, s), 3.40 (3H, s), 3.67 (2H, t, J=5.5 Hz), 3.82 (2H, t, J=5.5 Hz), 4.46 (2H, q, J=7.5 Hz), 7.29 (1H, s), 9.82 (1H, s)

Reference Example 030

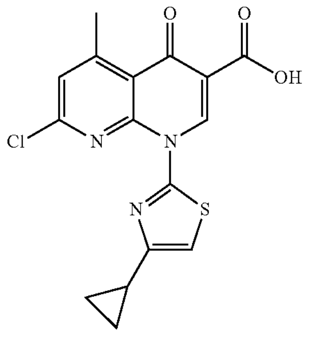 [SMILES: Cc1cc(Cl)nc2c1c(=O)c(C(=O)O)cn2-c1nc(C2CC2)cs1]

7-Chloro-1-(4-cyclopropyl-1,3-thiazol-2-yl)-5-methyl-4-oxo-1,4-dihydro-1,8-naphthyridine-3-carboxylic acid (1) Ethyl 7-chloro-1-(4-cyclopropyl-1,3-thiazol-2-yl)-5-methyl-4-oxo-1,4-dihydro-1,8-naphthyridine-3-carboxylate was obtained using ethyl 3-(2,6-dichloro-4-methylpyridin-3-yl)-3-oxopropanoate obtained by the method described in JP-A-2006-514964 or a method equivalent thereto and 4-cyclopropyl-1,3-thiazol-2-amine by the method described in Reference Example-001-(l) or a method equivalent thereto.

1H-NMR (CDCl3): δ 0.94-1.01 (4H, m), 1.45 (3H, t, J=7.0 Hz), 2.04-2.11 (1H, m), 4.45 (2H, q, J=7.0 Hz), 6.88 (1H, s), 7.25 (1H, s), 9.85 (1H, s)

(2) The title compound was obtained from ethyl 7-chloro-1-(4-cyclopropyl-1,3-thiazol-2-yl)-5-methyl-4-oxo-1,4-dihydro-1,8-naphthyridine-3-carboxylate obtained in the preceding section by the method described in Reference Example 001-(2) or a method equivalent thereto.

1H-NMR (DMSO-d6): δ 0.82-0.87 (2H, m), 0.95-1.01 (2H, m), 2.13-2.20 (1H, m), 2.92 (1H, s), 7.42 (1H, s), 7.79 (1H, s), 9.82 (1H, s)

Reference Example 031

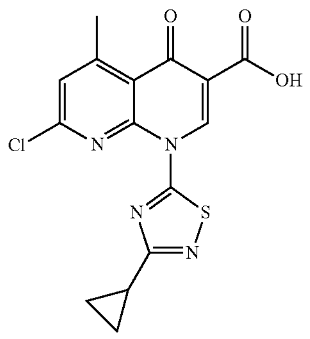 [SMILES: Cc1cc(Cl)nc2c1c(=O)c(C(=O)O)cn2-c1nc(C2CC2)ns1]

7-Chloro-1-(3-cyclopropyl-1,2,4-thiadiazol-5-yl)-5-methyl-4-oxo-1,4-dihydro-1,8-naphthyridine-3-carboxylic acid (1) Ethyl 7-chloro-1-(3-cyclopropyl-1,2,4-thiadiazol-5-yl)-5-methyl-4-oxo-1,4-dihydro-1,8-naphthyridine-3-carboxylate was obtained using ethyl 3-(2,6-dichloro-4-methylpyridin-3-yl)-3-oxopropanoate obtained by the method described in JP-A-2006-514964 or a method equivalent thereto and 3-cyclopropyl-1,2,4-thiadiazol-5-amine by the method described in Reference Example 001-(1) or a method equivalent thereto.

1H-NMR (CDCl3): δ 1.09-1.14 (2H, m), 1.17-1.23 (2H, m), 1.46 (3H, t, J=7.0 Hz), 2.30-2.37 (1H, m), 3.00 (3H, s), 4.47 (2H, q, J=7.0 Hz), 7.32 (1H, s), 9.82 (1H, s)

(2) The title compound was obtained from ethyl 7-chloro-1-(3-cyclopropyl-1,2,4-thiadiazol-5-yl)-5-methyl-4-oxo-1,4-dihydro-1,8-naphthyridine-3-carboxylate obtained in the preceding section by the method described in Reference Example 001-(2) or a method equivalent thereto.

1H-NMR (DMSO-d6): δ 1.04-1.09 (2H, m), 1.09-1.15 (2H, m), 2.32-2.40 (1H, m), 2.91 (3H, s), 7.85 (1H, s), 9.74 (1H, s), 13.66 (1H, brs)

Reference Example 032

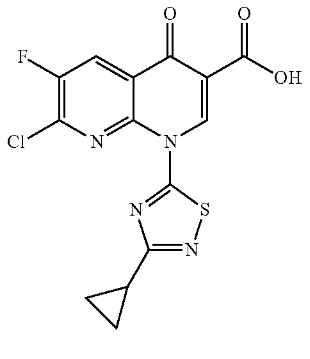 [SMILES: O=C(O)c1cn(-c2nc(C3CC3)ns2)c2nc(Cl)c(F)cc2c1=O]

7-Chloro-1-(3-cyclopropyl-1,2,4-thiadiazol-5-yl)-6-fluoro-4-oxo-1,4-dihydro-1,8-naphthyridine-3-carboxylic acid (1) Ethyl 7-chloro-1-(3-cyclopropyl-1,2,4-thiadiazol-5-yl)-6-fluoro-4-oxo-1,4-dihydro-1,8-naphthyridine-3-carboxylate was obtained using ethyl 3-(2,6-dichloro-5-fluoropyridin-3-yl)-3-oxopropanoate and 3-cyclopropyl-1,2,4-thiadiazol-5-amine by the method described in Reference Example 001-(1) or a method equivalent thereto.

1H-NMR (CDCl3): δ 1.10-1.17 (2H, m), 1.18-1.24 (2H, m), 1.46 (3H, t, J=7.0 Hz), 2.31-2.40 (1H, m), 4.48 (2H, q, J=7.0 Hz), 8.55 (1H, d, J=7.0 Hz), 9.92 (1H, 8)

(2) The title compound was obtained from ethyl 7-chloro-1-(3-cyclopropyl-1,2,4-thiadiazol-5-yl)-6-fluoro-4-oxo-1,4-dihydro-1,8-naphthyridine-3-carboxylate obtained in the preceding section by a method described in Reference Example 001-(2) or a method equivalent thereto.

1H-NMR (DMSO-d6): δ 1.04-1.17 (4H, m), 2.33-2.42 (1H, m), 8.80 (1H, d, J=7.5 Hz), 9.74 (1H, s), 13.34 (1H, brs)

Reference Example 033

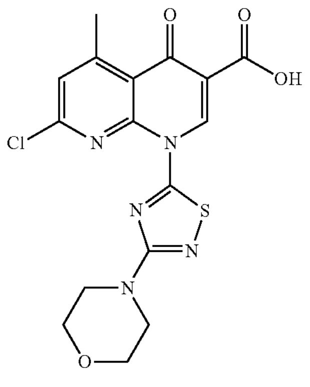 [SMILES: Cc1cc(Cl)nc2c1c(=O)c(C(=O)O)cn2-c1nc(N2CCOCC2)ns1]

7-Chloro-5-methyl-1-[3-(morpholin-4-yl)-1,2,4-thiadiazol-5-yl]-4-oxo-1,4-dihydro-1,8-naphthyridine-3-carboxylic acid (1) Ethyl 7-chloro-5-methyl-[3-(morpholin-4-yl)-1,2,4-thiadiazol-5-yl]-4-oxo-1,4-dihydro-1,8-naphthyridine-3-carboxylate was obtained using ethyl 3-(2,6-dichloro-4- methylpyridin-3-yl)-3-oxopropanoate obtained by the method described in JP-A-2006-514964 or a method equivalent thereto and 3-(morpholin-4-yl)-1,2,4-thiadiazol-5-amine by the method described in Reference Example 001-(1) or a method equivalent thereto.

1H-NMR (CDCl3): δ 1.44 (3H, t, J=7.0 Hz), 2.99 (3H, s), 3.72 (4H, t, J=5.0 Hz), 3.84 (4H, t, J=5.0 Hz), 4.47 (2H, q, J=7.0 Hz), 7.31 (1H, s), 9.79 (1H, s)

(2) The title compound was obtained from ethyl 7-chloro-5-methyl-1-[3-(morpholin-4-yl)-1,2,4-thiadiazol-5-yl]-4-oxo-1,4-dihydro-1,8-naphthyridine-3-carboxylate obtained in the preceding section by the method described in Reference Example 001-(2) or a method equivalent thereto.

1H-NMR (DMSO-d6): δ 2.91 (3H, s), 3.60 (4H, t, J=5.0 Hz), 3.72 (4H, t, J=5.0 Hz), 7.83 (1H, s), 9.73 (1H, s), 13.68 (1H, brs)

Reference Example 034

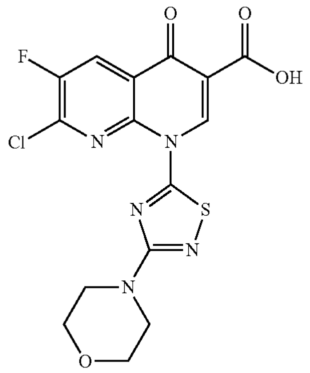 [SMILES: O=C(O)c1cn(-c2nc(N3CCOCC3)ns2)c2nc(Cl)c(F)cc2c1=O]

7-Chloro-6-fluoro-1-[3-(morpholin-4-yl)-1,2,4-thiadiazol-5-yl]-4-oxo-1,4-dihydro-1,8-naphthyridine-3-carboxylic acid (1) Ethyl 7-chloro-6-fluorol-[3-(morpholin-4-yl)-1,2,4-thiadiazol-5-yl]-4-oxo-1,4-dihydro-1,8-naphthyridine-3-carboxylate was obtained using ethyl 3-(2,6-dichloro-5-fluoropyridin-3-yl)-3-oxopropanoate and 3-(morpholin-4-yl)-1,2,4-thiadiazol-5-amine by a method described in Reference Example 001-(1) or a method equivalent thereto.

1H-NMR (CDCl3): δ 1.46 (3H, t, J=7.0 Hz), 3.73 (4H, t, J=5.0 Hz), 3.84 (4H, t, J=5.0 Hz), 4.48 (2H, q, J=7.0 Hz), 8.53 (1H, d, J=7.0 Hz), 9.89 (1H, s)

(2) The title compound was obtained from ethyl 7-chloro-6-fluoro-1-[3-(morpholin-4-yl)-1,2,4-thiadiazol-5-yl]-4-oxo-1,4-dihydro-1,8-naphthyridine-3-carboxylate obtained in the preceding section by the method described in Reference Example 001-(2) or a method equivalent thereto.

1H-NMR (DMSO-d6): δ 3.61 (4H, t, J=5.0 Hz), 3.72 (4H, t, J=5.0 Hz), 8.79 (1H, d, J=7.5 Hz), 9.73 (1H, s), 13.35 (1H, brs)

Reference Example 035

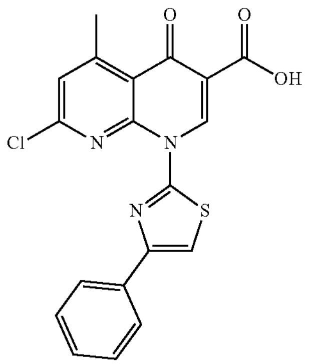 [SMILES: Cc1cc(Cl)nc2c1c(=O)c(C(=O)O)cn2-c1nc(-c2ccccc2)cs1]

7-Chloro-5-methyl-4-oxo-1-(4-phenyl-1,3-thiazol-2-yl)-1,4-dihydro-1,8-naphthyridine-3-carboxylic acid (1) Ethyl 7-chloro-5-methyl-4-oxo-1-(4-phenyl-1,3-thiazol-2-yl)-1,4-dihydro-1,8-naphthyridine-3-carboxylate was obtained using ethyl 3-(2,6-dichloro-4-methylpyridin-3-yl)-3-oxopropanoate obtained by the method described in JP-A-2006-514964 or a method equivalent thereto and 4-phenyl-1,3-thiazol-2-amine by a method described in Reference Example 001-(1) or a method equivalent thereto.

1H-NMR (CDCl3): δ 1.47 (3H, t, J=7.0 Hz), 3.01 (3H, s), 4.48 (2H, q, J=7.0 Hz), 7.28 (1H, s), 7.39 (1H, t, J=7.5 Hz), 7.48 (2H, t, J=7.5 Hz), 7.51 (1H, s), 7.98 (2H, d, J=7.5 Hz), 10.10 (1H, s)

(2) The title compound was obtained from ethyl 7-chloro-5-methyl-4-oxo-1-(4-phenyl-1,3-thiazol-2-yl)-1,4-dihydro-1,8-naphthyridine-3-carboxylate obtained in the preceding section by a method described in Reference Example 001-(2) or a method equivalent thereto.

1H-NMR (DMSO-d6): δ 2.94 (3H, s), 7.41 (1H, t, J=7.5 Hz), 7.52 (2H, t, J=7.5 Hz), 7.82 (1H, s), 8.01 (2H, d, J=7.5 Hz), 8.24 (1H, s), 10.03 (1H, s)

Reference Example 036

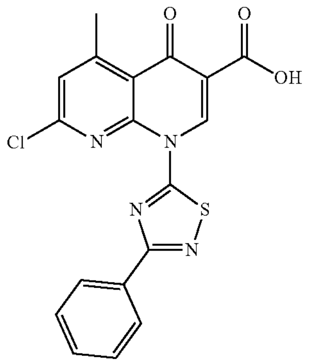 [SMILES: Cc1cc(Cl)nc2c1c(=O)c(C(=O)O)cn2-c1nc(-c2ccccc2)ns1]

7-Chloro-5-methyl-4-oxo-1-(3-phenyl-1,2,4-thiadiazol-5-yl)-1,4-dihydro-1,8-naphthyridine-3-carboxylic acid (1) Ethyl 7-chloro-5-methyl-4-oxo-1-(3-phenyl-1,2,4-thiadiazol-5-yl)-1,4-dihydro-1,8-naphthyridine-3-carboxylate was obtained using ethyl 3-(2,6-dichloro-4-methylpyridin-3-yl)-3-oxopropanoate obtained by the method described in JP-A-2006-514964 or a method equivalent thereto and 3-phenyl-1,2,4-thiadiazol-5-amine by the method described in Reference Example 001-(1) or a method equivalent thereto.

1H-NMR (CDCl3): δ 1.49 (3H, t, J=7.0 Hz), 3.02 (3H, s), 4.51 (2H, q, J=7.0 Hz), 7.35 (1H, s), 7.51-7.56 (3H, m), 8.36-8.38 (2H, m), 10.04 (1H, s)

(2) The title compound was obtained from ethyl 7-chloro-5-methyl-4-oxo-1-(3-phenyl-1,2,4-thiadiazol-5-yl)-1,4-dihydro-1,8-naphthyridine-3-carboxylate obtained in the preceding section by the method described in Reference Example 001-(2) or a method equivalent thereto.

1H-NMR (DMSO-d6): δ 2.93 (3H, s), 7.58-7.68 (2H, m), 7.88 (1H, s), 8.29 (2H, dd, J=8.5, 2.0 Hz), 9.94 (1H, s), 13.65 (1H, s)

Reference Example 037

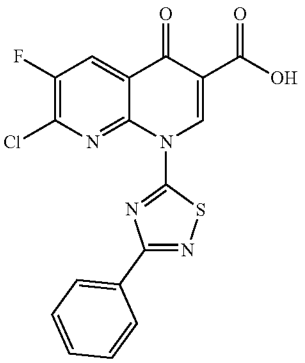 [SMILES: O=C(O)c1cn(-c2nc(-c3ccccc3)ns2)c2nc(Cl)c(F)cc2c1=O]

7-Chloro-6-fluoro-4-oxo-1-(3-phenyl-1,2,4-thiadiazol-5-yl)-1,4-dihydro-1,8-naphthyridine-3-carboxylic acid (1) Ethyl 7-chloro-6-fluoro-4-oxo-1-(3-phenyl-1,2,4-thiadiazol-5-yl)-1,4-dihydro-1,8-naphthyridine-3-carboxylate was obtained using ethyl 3-(2,6-dichloro-5-fluoropyridin-3-yl)-3-oxopropanoate and 3-phenyl-1,2,4-thiadiazol-5-amine by the method described in Reference Example 001-(1) or a method equivalent thereto.

1H-NMR (CDCl3): δ 1.49 (3H, t, J=7.0 Hz), 4.52 (2H, q, J=7.0 Hz), 7.53-7.56 (3H, m), 8.37-8.39 (2H, m), 8.58 (1H, d, J=7.0 Hz), 10.14 (1H, s)

(2) The title compound was obtained from ethyl 7-chloro-6-fluoro-4-oxo-1-(3 phenyl-1,2,4-thiadiazol-5-yl)-1,4-dihydro-1,8-naphthyridine-3-carboxylate obtained in the preceding section by the method described in Reference Example 001-(2) or a method equivalent thereto.

1H-NMR (DMSO-d6): δ 7.59-7.63 (3H, m), 8.30 (2H, dd, J=8.0, 2.0 Hz), 8.83 (1H, d, J=8.0 Hz), 9.94 (1H, s)

Reference Example 038

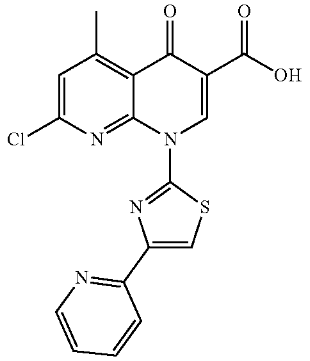

7-Chloro-5-methyl-4-oxo-1-[4-(pyridin-2-yl)-1,3-thiazol-2-yl]-1,4-dihydro-1,8-naphthyridine-3-carboxylic acid (1) Ethyl 7-chloro-5-methyl-4-oxo-1-[4-(pyridin-2-yl)-1,3-thiazol-2-yl]-1,4-dihydro-1,8-naphthyridine-3-carboxylate was obtained using ethyl 3-(2,6-dichloro-4-methylpyridin-3-yl)-3-oxopropanoate obtained by the method described in JP-A-2006-514964 or a method equivalent thereto and 4-(pyridin-2-yl)-1,3-thiazol-2-amine by the method described in Reference Example 001-(1) or a method equivalent thereto.

1H-NMR (CDCl3): δ 1.48 (3H, t, J=7.0 Hz), 3.01 (3H, s), 4.49 (2H, q, J=7.0 Hz), 7.28-7.31 (1H, m), 7.84 (2H, td, J=8.0, 2.0 Hz), 8.12 (1H, s), 8.20 (1H, d, J=8.0 Hz), 8.66 (1H, dd, J=5.0, 2.0 Hz), 10.09 (1H, s)

(2) The title compound was obtained from ethyl 7-chloro-5-methyl-4-oxo-1-[4-(pyridin-2-yl)-1,3-thiazol-2-yl]-1,4-dihydro-1,8-naphthyridine-3-carboxylate obtained in the preceding section by the method described in Reference Example 001-(2) or a method equivalent thereto.

1H-NMR (DMSO-d6): δ 2.94 (3H, s), 7.44 (1H, ddd, J=7.5, 5.0, 1.0 Hz), 7.83 (1H, d, J=1.0 Hz), 8.01 (1H, td, J=7.5, 1.5 Hz), 8.13 (1H, d, J=7.5 Hz), 8.42 (1H, s), 8.67 (1H, ddd, J=5.0, 1.5, 1.0 Hz), 10.03 (1H, s)

Reference Example 039

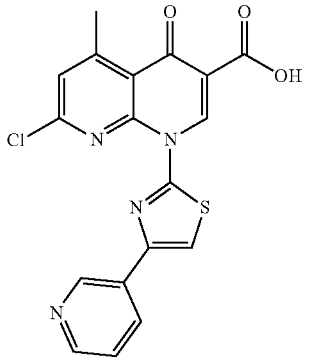 [SMILES: Cc1cc(Cl)nc2c1c(=O)c(C(=O)O)cn2-c1nc(-c2cccnc2)cs1]

7-Chloro-5-methyl-4-oxo-1-[4-(pyridin-3-yl)-1,3-thiazol-2-yl]-1,4-dihydro-1,8-naphthyridine-3-carboxylic acid (1) Ethyl 7-chloro-5-methyl-4-oxo-1-[4-(pyridin-3-yl)-1,3-thiazol-2-yl]-1,4-dihydro-1,8-naphthyridine-3-carboxylate obtained using ethyl 3-(2,6-dichloro-4-methylpyridin-3-yl)-3-oxopropanoate obtained by the method described in JP-A-2006-514964 or a method equivalent thereto and 4-(pyridin-3-yl)-1,3-thiazol-2-amine by the method described in Reference Example 001-(1) or a method equivalent thereto.

1H-NMR (CDCl3): δ 1.47 (3H, t, J=7.0 Hz), 3.02 (3H, s), 4.48 (2H, q, J=7.0 Hz), 7.30 (1H, s), 7.42 (1H, ddd, J=8.0, 5.0, 1.0 Hz), 7.60 (1H, s), 8.27 (1H, dt, J=8.0, 2.0 Hz), 8.63 (1H, dd, J=5.0, 2.0 Hz), 9.21 (1H, dd, J=2.0, 1.0 Hz), 10.07 (1H, s)

(2) The title compound was obtained from ethyl 7-chloro-5-methyl-4-oxo-1-[4-(pyridin-3-yl)-1,3-thiazol-2-yl]-1,4-dihydro-1,8-naphthyridine-3-carboxylate obtained in the preceding section by the method described in Reference Example 001-(2) or a method equivalent thereto.

1H-NMR (DMSO-d6): δ 2.94 (3H, s), 7.69 (1H, brs), 7.83 (1H, s), 8.46 (1H, s), 8.53 (1H, brs), 8.67 (1H, d, J=4.5 Hz), 9.29 (1H, s), 10.01 (1H, s)

Reference Example 040

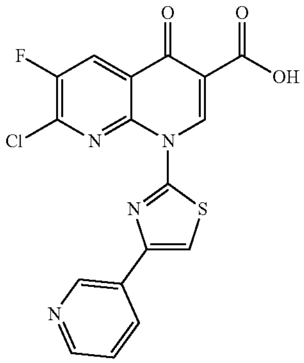 [SMILES: O=C(O)c1cn(-c2nc(-c3cccnc3)cs2)c2nc(Cl)c(F)cc2c1=O]

7-Chloro-6-fluoro-4-oxo-1-[4-(pyridin-3-yl)-1,3-thiazol-2-yl]-1,4-dihydro-1,8-naphthyridine-3-carboxylic acid (1) Ethyl 7-chloro-6-fluoro-4-oxo-1-[4-(pyridin-3-yl)-1,3-thiazol-2-yl]-1,4-dihydro-1,8-naphthyridine-3-carboxylate was obtained using ethyl 3-(2,6-dichloro-5-fluoropyridin-3-yl)-3-oxopropanoate and 4-(pyridin-3-yl)-1,3-thiazol-2-amine by the method described in Reference Example 001-(1) or a method equivalent thereto.

1H-NMR (CDCl3): δ 1.47 (3H, t, J=7.5 Hz), 4.49 (2H, q, J=7.0 Hz), 7.43 (1H, dd, J=8.0, 5.0, 1.0 Hz), 7.63 (1H, s), 8.28 (1H, dt, J=8.0, 2.0 Hz), 8.57 (1H, d, J=7.0 Hz), 8.65 (1H, dd, J=5.0, 2.0 Hz), 9.21 (1H, dd, J=2.0, 1.0 Hz), 10.14 (1H, s)

(2) The title compound was obtained from 7-chloro-6-fluoro-4-oxo-1-[4-(pyridin-3-yl)-1,3-thiazol-2-yl]-1,4-dihydro-1,8-naphthyridine-3-carboxylate obtained in the preceding section by a method described in Reference Example 001-(2) or a method equivalent thereto.

1H-NMR (DMSO-d6): δ 7.69 (1H, dd, J=7.5, 5.0 Hz), 8.48 (1H, s), 8.54 (1H, d, J=7.5 Hz), 8.68 (1H, dd, J=5.0, 1.5 Hz), 8.81 (1H, d, J=7.5 Hz), 9.30 (1H, d, J=1.5 Hz), 9.98 (1H, s)

Reference Example 041

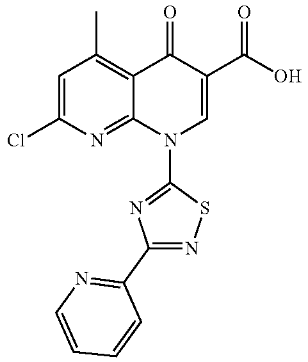 [SMILES: Cc1cc(Cl)nc2c1c(=O)c(C(=O)O)cn2-c1nc(-c2ccccn2)ns1]

7-Chloro-5-methyl-4-oxo-1-[3-(pyridin-2-yl)-1,2,4-thiadiazol-5-yl]-1,4-dihydro-1,8-naphthyridine-3-carboxylic acid (1) Ethyl 7-chloro-5-methyl-4-oxo-1-[3-(pyridin-2-yl)-1,2,4-thiadiazol-5-yl]-1,4-dihydro-1,8-naphthyridine-3-carboxylate was obtained using ethyl 3-(2,6-dichloro-4-methylpyridin-3-yl)-3-oxopropanoate obtained by the method described in JP-A-2006-514964 or a method equivalent thereto and 3-(pyridin-2-yl)-1,2,4-thiadiazol-5-amine by the method equivalent thereto in Reference Example 001-(1) or a method equivalent thereto.

1H-NMR (CDCl3): δ 1.47 (3H, t, J=7.0 Hz), 3.02 (3H, s), 4.49 (2H, q, J=7.0 Hz), 7.37 (1H, s), 7.45 (1H, ddd, J=8.0, 4.5, 1.0 Hz), 7.92 (1H, td, J=8.0, 2.0 Hz), 8.42 (1H, d, J=8.0 Hz), 8.85 (1H, d, J=4.5 Hz), 10.02 (1H, s)

(2) The title compound was obtained from ethyl 7-chloro-5-methyl-4-oxo-1-[3-(pyridin-2-yl)-1,2,4-thiadiazol-5-yl]-1,4-dihydro-1,8-naphthyridine-3-carboxylate obtained in the preceding section by the method described in Reference Example 001-(2) or a method equivalent thereto.

1H-NMR (DMSO-d6): δ 2.94 (3H, s), 7.60 (1H, dd, J=7.5, 5.0 Hz), 7.89 (1H, s), 8.06 (1H, td, J=7.5, 1.5 Hz), 8.37 (1H, d, J=7.5 Hz), 8.81 (1H, d, J=5.0 Hz), 9.94 (1H, s)

Reference Example 042

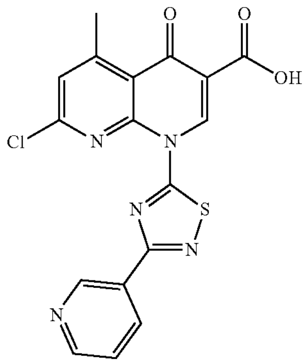 [SMILES: Cc1cc(Cl)nc2c1c(=O)c(C(=O)O)cn2-c1nc(-c2cccnc2)ns1]

7-Chloro-5-methyl-4-oxo-1-[3-(pyridin-3-yl)-1,2,4-thiadiazol-5-yl]-1,4-dihydro-1,8-naphthyridine-3-carboxylic acid (1) Ethyl 7-chloro-5-methyl-4-oxo-1-[3-(pyridin-3-yl)-1,2,4-thiadiazol-5-yl]-1,4-dihydro-1,8-naphthyridine-3-carboxylate was obtained using ethyl 3-(2,6-dichloro-4-methylpyridin-3-yl)-3-oxopropanoate obtained by the method described in JP-A-2006-514964 or a method equivalent thereto and 3-(pyridin-3-yl)-1,2,4-thiadiazol-5-amine by the method described in Reference Example 001-(1) or a method equivalent thereto.

1H-NMR (CDCl3): δ 1.48 (3H, t, J=7.0 Hz), 3.03 (3H, a), 4.50 (2H, q, J=7.0 Hz), 7.37 (1H, s), 7.47 (1H, dd, J=8.0, 5.0 Hz), 8.62 (1H, dt, J=8.0, 2.0 Hz), 8.76 (1, dd, J=5.0, 2.0 Hz), 9.59 (1H, d, J=2.0 Hz), 10.00 (1H, s)

(2) The title compound was obtained from ethyl 7-chloro-5-methyl-4-oxo-1-[3-(pyridin-3-yl)-1,2,4-thiadiazol-5-yl]-1,4-dihydro-1,8-naphthyridine-3-carboxylate obtained in the preceding section by the method described in Reference Example 001-(2) or a method equivalent thereto.

1H-NMR (DMSO-d6): δ 2.93 (3H, s), 7.67 (1H, dd, J=8.0, 5.0 Hz), 7.88 (1H, s), 8.65 (1H, dt, J=8.0, 1.5 Hz), 8.78 (1H, dd, J=5.0, 1.5 Hz), 9.46 (1H, d, J=1.5 Hz), 9.92 (1H, s)

Reference Example 043

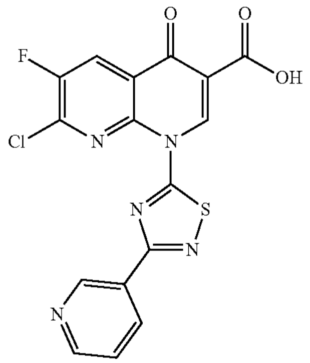 [SMILES: O=C(O)c1cn(-c2nc(-c3cccnc3)ns2)c2nc(Cl)c(F)cc2c1=O]

7-Chloro-6-fluoro-4-oxo-1-[3-(pyridin-3-yl)-1,2,4-thiadiazol-5-yl]-1,4-dihydro-1,8-naphthyridine-3-carboxylic acid (1) Ethyl 7-chloro-6-fluoro-4-oxo-1-[3-(pyridin-3-yl)-1,2,4-thiadiazol-5-yl]-1,4-dihydro-1,8-naphthyridine-3-carboxylate obtained using ethyl 3-(2,6-dichloro-5-fluoropyridin-3-yl)-3-oxopropanoate and 3-(pyridin-3-yl)-1,2,4-thiadiazol-5-amine by the method described in Reference Example 001-(1) or a method equivalent thereto.

1H-NMR (CDCl3): δ 1.36 (3H, t, J=7.0 Hz), 4.37 (2H, q, J=7.0 Hz), 7.64 (1H, ddd, J=8.0, 5.0, 0.5 Hz), 8.62 (1H, td, J=8.0, 2.0 Hz), 8.75 (1H, d, J=8.0 Hz), 8.77 (1H, dd, J=5.0, 2.0 Hz), 9.47 (1H, dd, J=2.0, 0.5 Hz), 9.86 (1H, s)

(2) The title compound was obtained from ethyl 7-chloro-6-fluoro-4-oxo-1-[3 (pyridin-3-yl)-1,2,4-thiadiazol-5-yl]-1,4-dihydro-1,8-naphthyridine-3-carboxylate obtained in the preceding section by the method described in Reference Example 001-(2) or a method equivalent thereto.

1H-NMR (DMSO-d6): δ 7.65 (1H, ddd, J=8.0, 4.5, 1.0 Hz), 8.63 (1H, td, J=8.0, 1.5 Hz), 8.78 (1H, dd, J=4.5, 1.5 Hz), 8.83 (1H, d, J=7.5 Hz), 9.46 (1H, d, J=1.5 Hz); 9.94 (1H, s)

Reference Example 044

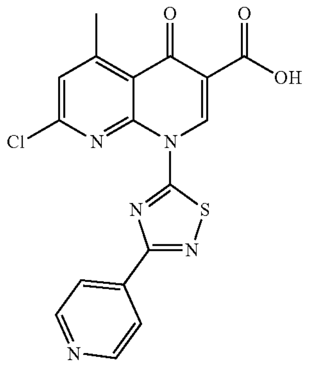 [SMILES: Cc1cc(Cl)nc2c1c(=O)c(C(=O)O)cn2-c1nc(-c2ccncc2)ns1]

7-Chloro-5-methyl-4-oxo-1-[3-(pyridin-4-yl)-1,2,4-thiadiazol-5-yl]-1,4-dihydro-1,8-naphthyridine-3-carboxylic acid (1) Ethyl 7-chloro-5-methyl-4-oxo-1-[3-(pyridin-4-yl)-1,2,4-thiadiazol-5-yl]-1,4-dihydro-1,8-naphthyridine-3-carboxylate was obtained using ethyl 3-(2,6-dichloro-4-methylpyridin-3-yl)-3-oxopropanoate obtained by the method described in JP-A-2006-514964 or a method equivalent thereto and 3-(pyridin-4-yl)-1,2,4-thiadiazol-5-amine by the method described in Reference Example 001-(1) or a method equivalent thereto.

1H-NMR (CDCl3): δ 1.49 (3H, t, J=7.0 Hz), 3.03 (3H, s), 4.52 (2H, q, J=7.0 Hz), 7.38 (1H, s), 8.21 (2H, dd, J=4.5, 1.5 Hz), 8.82 (2H, dd, J=4.5, 1.5 Hz), 9.98 (1H, s)

(2) The title compound was obtained from ethyl 7-chloro-5-methyl-4-oxo-1-[3-(pyridin-4-yl)-1,2,4-thiadiazol-5-yl]-1,4-dihydro-1,8-naphthyridine-3-carboxylate obtained in the preceding section by the method described in Reference Example 001-(2) or a method equivalent thereto.

1H-NMR (DMSO-d6): δ 2.93 (3H, s), 7.89 (1H, s), 8.28 (2H, d, J=5.5 Hz), 8.88 (2H, d, J=5.5 Hz), 9.90 (1H, s)

Reference Example 045

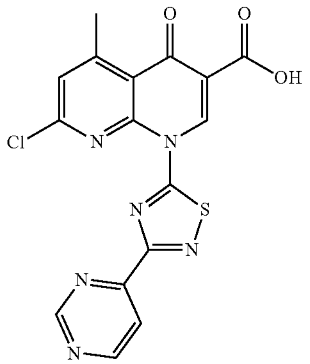 [SMILES: Cc1cc(Cl)nc2c1c(=O)c(C(=O)O)cn2-c1nc(-c2ccncn2)ns1]

7-Chloro-5-methyl-4-oxo-1-[3-(pyrimidin-4-yl)-1,2,4-thiadiazol-5-yl]-1,4-dihydro-1,8-naphthyridine-3-carboxylic acid (1) Ethyl 7-chloro-5-methyl-4-oxo-1-[3-(pyrimidin-4-yl)-1,2,4-thiadiazol-5-yl]-1,4-dihydro-1,8-naphthyridine-3-carboxylate was obtained using ethyl 3-(2,6-dichloro-4-methylpyridin-3-yl)-3-oxopropanoate obtained by the method described in JP-A-2006-514964 or a method equivalent thereto and 3-(pyrimidin-4-yl)-1,2,4-thiadiazol-5-amine obtained from pyrimidine-4-carboximidamide by the method described in Reference Example 022-(2) or method equivalent thereto by the method described in Reference Example 001-(1) or a method equivalent thereto.

1H-NMR (CDCl3): δ 1.48 (3H, t, J=7.5 Hz), 3.03 (3H, s), 4.50 (2H, q, J=7.5 Hz), 7.39 (1H, s), 8.34 (1H, dd, J=5.0, 1.5 Hz), 9.02 (1H, d, J=5.0 Hz), 9.48 (1H, d, J=1.5 Hz), 9.96 (1H, s)

(2) The title compound was obtained from ethyl 7-chloro-5-methyl-4-oxo-1-[3-(pyrimidin-4-yl)-1,2,4-thiadiazol-5-yl]-1,4-dihydro-1,8-naphthyridine-3-carboxylate obtained in the preceding section by the method described in Reference Example 001-(2) or a method equivalent thereto.

1H-NMR (DMSO-d6): δ 2.94 (3H, s), 7.90 (1H, s), 8.38 (1H, dd, J=5.0, 1.5 Hz), 9.10 (1H, d, J=5.0 Hz), 9.44 (1H, d, J=1.5 Hz), 9.90 (1H, s)

Reference Example 046

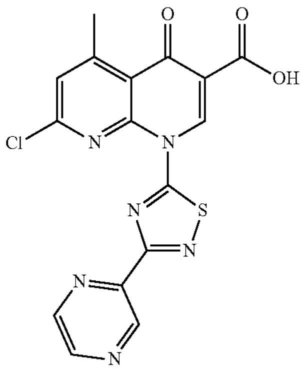 [SMILES: Cc1cc(Cl)nc2c1c(=O)c(C(=O)O)cn2-c1nc(-c2cnccn2)ns1]

7-Chloro-5-methyl-4-oxo-1-[3-(pyrazin-2-yl)-1,2,4-thiadiazol-5-yl]-1,4-dihydro-1,8-naphthyridine-3-carboxylic acid (1) Ethyl 7-chloro-5-methyl-4-oxo-1-[3-(pyrazin-2-yl)-1,2,4-thiadiazol-5-yl]-1,4-dihydro-1,8-naphthyridine-3-carboxylate was obtained using ethyl 3-(2,6-dichloro-4-methylpyridin-3-yl)-3-oxopropanoate obtained by the method described in JP-A-2006-514964 or a method equivalent thereto and 3-(pyrazin-2-yl)-1,2,4-thiadiazol-5-amine by the method described in Reference Example 001-(1) or a method equivalent thereto.

1H-NMR (CDCl3): δ 1.48 (3H, t, J=7.0 Hz), 3.03 (3H, s), 4.50 (2H, q, J=7.0 Hz), 7.39 (1H, s), 8.74 (1H, d, J=2.5 Hz), 8.81 (1H, dd, J=2.5, 1.5 Hz), 9.65 (1H, d, J=1.5 Hz), 9.98 (1H, s)

(2) The title compound was obtained using ethyl 7-chloro-5-methyl-4-oxo-1-[3-(pyrazin-2-yl)-1,2,4-thiadiazol-5-yl]-1,4-dihydro-1,8-naphthyridine-3-carboxylate obtained in the preceding section by the method described in Reference Example 001-(2) or a method to equivalent thereto.

1H-NMR (DMSO-d6): δ 2.94 (3H, s), 7.90 (1H, s), 8.85 (1H, d, J=2.5 Hz), 8.90 (1H, dd, J=2.5, 1.5 Hz), 9.55 (1H, d, J=1.5 Hz), 9.92 (1H, s)

Reference Example 047

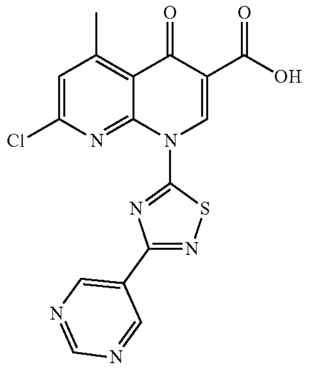 [SMILES: Cc1cc(Cl)nc2c1c(=O)c(C(=O)O)cn2-c1nc(-c2cncnc2)ns1]

7-Chloro-5-methyl-4-oxo-1-[3-(pyrimidin-5-yl)-1,2,4-thiadiazol-5-yl]-1,4-dihydro-1,8-naphthyridine-3-carboxylic acid (1) Ethyl 7-chloro-5-methyl-4-oxo-1-[3-(pyrimidin-5-yl)-1,2,4-thiadiazol-5-yl]-1,4-dihydro-1,8-naphthyridine-3-carboxylate was obtained using ethyl 3-(2,6-dichloro-4-methylpyridin-3-yl)-3-oxopropanoate obtained by the method described in JP-A-2006-514964 or a method equivalent thereto and 3-(pyrimidin-5-yl)-1,2,4-thiadiazol-5-amine by the method described in Reference Example 001-(1) or a method equivalent thereto.

1H-NMR (CDCl3): δ 1.49 (3H, t, J=7.0 Hz), 3.03 (3H, s), 4.51 (2H, q, J=7.0 Hz), 7.39 (1H, s), 9.36 (1H, s), 9.64 (2H, s), 9.95 (1H, s)

(2) The title compound was obtained from ethyl 7-chloro-5-methyl-4-oxo-1-[3-(pyrimidin-5-yl)-1,2,4-thiadiazol-5-yl]-1,4-dihydro-1,8-naphthyridine-3-carboxylate obtained in the preceding section by the method described in Reference Example 001-(2) or a method equivalent thereto.

1H-NMR (DMSO-d6): δ 2.93 (3H, s), 7.89 (1H, s), 9.39 (1H, s), 9.61 (2H, s), 9.91 (1H, s)

Reference Example 048

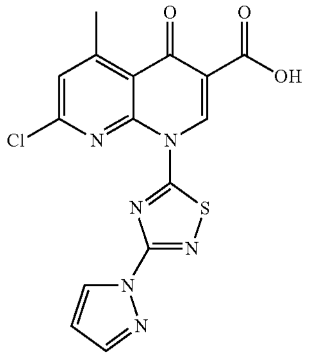 [SMILES: Cc1cc(Cl)nc2c1c(=O)c(C(=O)O)cn2-c1nc(-n2cccn2)ns1]

7-Chloro-5-methyl-4-oxo-1-[3-(1H-pyrazol-1-yl)-1,2,4-thiadiazol-5-yl]-1,4-dihydro-1,8-naphthyridine-3-carboxylic acid (1) Ethyl 7-chloro-5-methyl-4-oxo-1-[3-(1H-pyrazol-1-yl)-1,2,4-thiadiazol-5-yl]-1,4-dihydro-1,8-naphthyridine-3-carboxylate was obtained using 3-(1H-pyrazol-1-yl)-1,2,4-thiadiazol-5-amine obtained from 1H-pyrazole-1-carboximidamide by the method described in Reference Example 022-(2) or a method equivalent thereto and ethyl 3-(2,6-dichloro-4-methylpyridin-3-yl)-3-oxopropanoate obtained by the method described in JP-A-2006-514964 or a method equivalent thereto by the method described in Reference Example 001-(1) or a method equivalent thereto.

1H-NMR (CDCl3): δ 1.46 (3H, t, J=7.0 Hz), 3.02 (3H, s), 4.48 (2H, q, J=7.0 Hz), 6.55 (1H, dd, J=3.0, 1.5 Hz), 7.38 (1H, d, J=1.0 Hz), 7.87 (1H, d, J=1.0 Hz), 8.47 (1H, d, J=3.0 Hz), 9.84 (1H, s)

(2) The title compound was obtained from ethyl 7-chloro-5-methyl-4-oxo-1-[3-(1H-pyrazol-1-yl)-1,2,4-thiadiazol-5-yl]-1,4-dihydro-1,8-naphthyridine-3-carboxylate obtained in the preceding section by the method described in Reference Example 001-(2) or a method equivalent thereto.

1H-NMR (DMSO-d6): δ 2.93 (3H, s), 6.65 (1H, dd, J=2.5, 1.5 Hz), 7.89 (1H, s), 7.91 (1H, d, J=1.5 Hz), 8.68 (1H, d, J=2.5 Hz), 9.77 (1H, s)

Reference Example 049

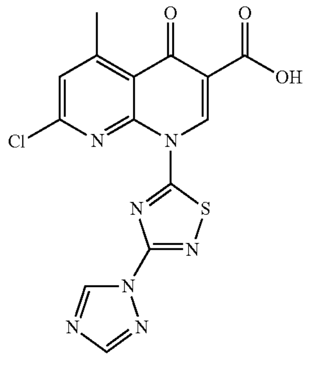 [SMILES: Cc1cc(Cl)nc2c1c(=O)c(C(=O)O)cn2-c1nc(-n2cncn2)ns1]

7-Chloro-5-methyl-4-oxo-1-[3-(1H-1,2,4-triazol-1-yl)-1,2,4-thiadiazol-5-yl]-1,4-dihydro-1,8-naphthyridine-3-carboxylic acid (1) Ethyl 7-chloro-5-methyl-4-oxo-1-[3-(1H-1,2,4-triazol-1-yl)-1,2,4-thiadiazol-5-yl]-1,4-dihydro-1,8-naphthyridine-3-carboxylate was obtained using 3-(1H-1,2,4-triazol-1-yl)-1,2,4-thiadiazol-5-amine obtained from 1H-1,2,4-triazole-1-carboximidamide by the method described in Reference Example 022-(2) or a method equivalent thereto and ethyl 3-(2,6-dichloro-4-methylpyridin-3-yl)-3-oxopropanoate obtained by the method described in JP-A-2006-514964 or a method equivalent thereto by the method described in Reference Example 001-(1) or a method equivalent thereto.

1H-NMR (CDCl3): δ 1.47 (3H, t, J=7.5 Hz), 3.03 (3H, s), 4.49 (2H, q, J=7.5 Hz), 7.40 (1H, s), 8.22 (1H, s), 9.12 (1H, s), 0.9.79 (1H, s)

(2) The title compound was obtained from ethyl 7-chloro-5-methyl-4-oxo-1-[3-(1H-1,2,4-triazol-1-yl)-1,2,4-thiadiazol-5-yl]-1,4-dihydro-1,8-naphthyridine-3-carboxylate obtained in the preceding section by the method described in Reference Example 001-(2) or a method equivalent thereto.

1H-NMR (DMSO-d6): δ 2.93 (3H, s), 7.89 (1H, s), 8.39 (1H, s), 9.61 (1H, s), 9.75 (1H, s), 13.54 (1H, brs)

Reference Example 050

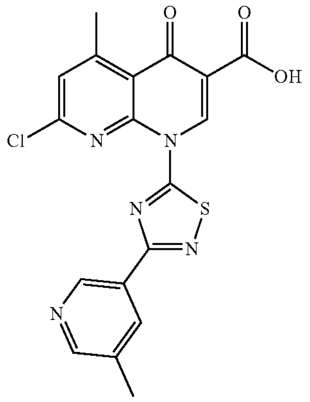 [SMILES: Cc1cncc(-c2nsc(-n3cc(C(=O)O)c(=O)c4c(C)cc(Cl)nc43)n2)c1]

7-Chloro-5-methyl-1-[3-(5-methylpyridin-3-yl)-1,2,4-thiadiazol-5-yl]-4-oxo-1,4-dihydro-1,8-naphthyridine-3-carboxylic acid (1) A mixture of 5-methylpyridine-3-carbonitrile (5.0 g), a solution of 28% sodium methoxide in methanol (11 mL), and methanol (40 mL) was stirred at 30° C. for 8 hours. To the reaction solution was added ammonium chloride (5.5 g), and the mixture was stirred overnight at 30° C. Insoluble material was filtered off, and the filtrate was concentrated. The residue was dispersed in diethyl ether, and the solid was then collected by filtration to obtain crude 5-methylpyridine-3-carboximidamide.

(2) Ethyl 7-chloro-5-methyl-1-[3-(5-methylpyridin-3-yl)-1,2,4-thiadiazol-5-yl]-4-oxo-1,4-dihydro-1,8-naphthyridine-3-carboxylate was obtained by the method described in Reference Example 001-(1) or a method equivalent thereto using ethyl 3-(2,6-dichloro-4-methylpyridin-3-yl)-3-oxopropanoate obtained by the method described in JP-A-2006-514964 or a method equivalent thereto, and 3-(5-methylpyridin-3-yl)-1,2,4-thiadiazol-5-amine obtained by the method described in Reference Example 022-(2) or a method equivalent thereto from crude 5-methylpyridine-3-carboximidamide obtained in the preceding section.

1H-NMR (CDCl3): δ 1.49 (3H, t, J=7.5 Hz), 2.49 (3H, s), 3.03 (3H, s), 4.51 (2H, q, J=7.5 Hz), 7.37 (1H, s), 8.43 (1H, d, J=1.5 Hz), 8.58 (1H, d, J=1.5 Hz), 9.39 (1H, d, J=1.5 Hz), 10.00 (1H, s)

(3) The title compound was obtained by the method described in Reference Example 001-(2) or a method equivalent thereto from ethyl 7-chloro-5-methyl-1-[3-(5-methylpyridin-3-yl)-1,2,4-thiadiazol-5-yl]-4-oxo-1,4-dihydro-1,8-naphthyridine-3-carboxylate obtained in the preceding section.

1H-NMR (DMSO-d6): δ 2.47 (3H, s), 2.93 (3H, s), 7.89 (1H, s), 8.52 (1H, s), 8.65 (1H, s), 9.29 (1H, s), 9.91 (1H, s)

Reference Example 051

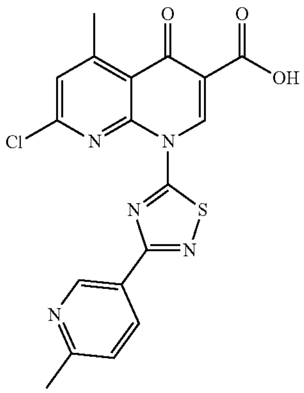 [SMILES: Cc1ccc(-c2nsc(-n3cc(C(=O)O)c(=O)c4c(C)cc(Cl)nc43)n2)cn1]

7-Chloro-5-methyl-1-[3-(6-methylpyridin-3-yl)-1,2,4-thiadiazol-5-yl]-4-oxo-1,4-dihydro-1,8-naphthyridine-3-carboxylic acid (1) Ethyl 7-chloro-5-methyl-1-[3-(6-methylpyridin-3-yl)-1,2,4-thiadiazol-5-yl]-4-oxo-1,4-dihydro-1,8-naphthyridine-3-carboxylate was obtained using ethyl 3-(2,6-dichloro-4-methylpyridin-3-yl)-3-oxopropanoate obtained by the method described in JP-A-2006-514964 or a method equivalent thereto and 3-(6-methylpyridin-3-yl)-1,2,4-thiadiazol-5-amine by the method described in Reference Example 001-(1) or a method equivalent thereto.

1H-NMR (CDCl3): δ 1.48 (3H, t, J=7.0 Hz), 2.68 (3H, s), 3.02 (3H, s), 4.50 (2H, q, J=7.0 Hz), 7.32 (1H, d, J=8.0 Hz), 7.36 (1H, s), 8.50 (1H, dd, J=8.0, 2.0 Hz), 9.46 (1H, d, J=2.0 Hz), 10.00 (1H, s)

(2) The title compound was obtained from ethyl 7-chloro-5-methyl-1-[3-(6-methylpyridin-3-yl)-1,2,4-thiadiazol-5-yl]-4-oxo-1,4-dihydro-1,8-naphthyridine-3-carboxylate obtained in the preceding section by the method described in Reference Example 001-(2) or a method equivalent thereto.

1H-NMR (DMSO-d6): δ 2.64 (3H, s), 2.93 (3H, s), 7.59-7.70 (1H, m), 7.88 (1H, s), 8.61-8.72 (1H, m), 9.37 (1H, s), 9.90 (1H, s)

Reference Example 052

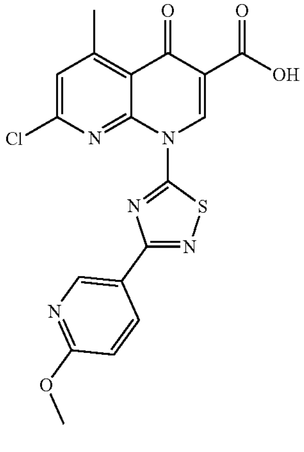 [SMILES: COc1ccc(-c2nsc(-n3cc(C(=O)O)c(=O)c4c(C)cc(Cl)nc43)n2)cn1]

7-Chloro-1-[3-(6-methoxypyridin-3-yl)-1,2,4-thiadiazol-5-yl]-5-methyl-4-oxo-1,4-dihydro-1,8-naphthyridine-3-carboxylic acid (1) Ethyl 7-chloro-1-[3-(6-methoxypyridin-3-yl)-1,2,4-thiadiazol-5-yl]-5-methyl-4-oxo-1,4-dihydro-1,8-naphthyridine-3-carboxylate was obtained using ethyl 3-(2,6-dichloro-4-methylpyridin-3-yl)-3-oxopropanoate obtained by the method described in JP-A-2006-514964 or a method equivalent thereto and 3-(6-methoxypyridin-3-yl)-1,2,4-thiadiazol-5-amine by the method described in Reference Example 001-(1) or a method equivalent thereto.

1H-NMR (CDCl3): δ 1.48 (3H, t, J=7.5 Hz), 3.02 (3H, s), 4.05 (3H, s), 4.50 (2H, q, J=7.5 Hz), 6.89 (1H, d, J=8.5 Hz), 7.36 (1H, s), 8.49 (1H, dd, J=8.5, 2.0 Hz), 9.18 (1H, d, J=2.0 Hz), 9.98 (1H, s)

(2) The title compound was obtained from ethyl 7-chloro-1-[3-(6-methoxypyridin-3-yl)-1,2,4-thiadiazol-5-yl]-5-methyl-4-oxo-1,4-dihydro-1,8-naphthyridine-3-carboxylate obtained in the preceding section by the method described in Reference Example 001-(2) or a method equivalent thereto.

1H-NMR (DMSO-d6): δ 2.93 (3H, s), 3.96 (3H, s), 7.03 (1H, d, J=8.5 Hz), 7.88 (1H, s), 8.51 (1H, dd, J=8.5, 2.0 Hz), 9.08 (1H, d, J=2.0 Hz), 9.92 (1H, s)

Example 001

Compound 001

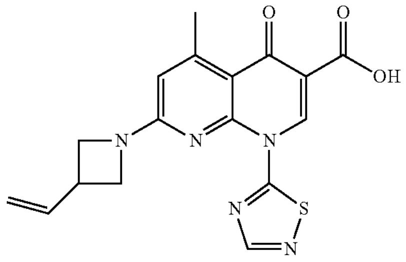

7-(3-Ethenylazetidin-1-yl)-5-methyl-4-oxo-1-(1,2,4-thiadiazol-5-yl)-1,4-dihydro-1,8-naphthyridine-3-carboxylic acid (1) To a solution of methyltriphenylphosphonium bromide (492 mg) in THF (2 mL) was added n-butyllithium (1.6 mol/L solution in n-hexane, 844 μL) under ice cooling in a nitrogen atmosphere, and the mixture was stirred at the same temperature for 10 minutes. A solution of tert-butyl 3-formylazetidine-1-carboxylate (50 mg) in THF (1 mL) was added thereto at the same temperature, and the mixture was stirred overnight at room temperature. To the reaction solution was added an aqueous ammonium chloride solution, and the mixture was extracted with ethyl acetate. The organic layer was washed with water and brine, dried over sodium sulfate, and concentrated. The residue was purified by silica gel column chromatography (eluent: ethyl acetate/n-hexane) to obtain 46 mg of tert-butyl 3-ethenylazetidine-1-carboxylate.

1H-NMR (CDCl3): δ 1.45 (9H, s), 3.14-3.25 (1H, m), 3.75 (2H, dd, J=6.0, 9.5 Hz), 4.09 (2H, J=9.5 Hz), 5.08-5.09 (1H, m), 5.10-5.12 (1H, m), 5.95-6.06 (1H, m)

(2) To a solution of tert-butyl 3-ethenylazetidine-1-carboxylate (46 mg) obtained in the preceding section in methylene chloride (500 μL) was added a 4 mol/L solution of hydrochloric acid in ethyl acetate (500 μL), and the mixture was stirred at room temperature for 5 days. The reaction solution was concentrated to obtain 42 mg of 3-ethenylazetidine hydrochloride.

1H-NMR (CDCl3): δ 3.57-3.69 (1H, m), 3.93-4.03 (2H, m), 4.17-4.26 (2H, m), 5.20 (1H, d, J=17.0 Hz), 5.23 (1H, d, J=10.5 Hz), 5.93-6.04 (1H, m)

(3) To a suspension of 3-ethenylazetidine hydrochloride (5 mg) obtained in the preceding section, 7-chloro-5-methyl-4-oxo-1-(1,2,4-thiadiazol-5-yl)-1,4-dihydro-1,8-naphthyridine-3-carboxylic acid (8 mg) obtained in Reference Example 002-(2), and lithium chloride (8 mg) in dimethyl sulfoxide (150 μL) was added 1,1,3,3-tetramethylguanidine (13 μL), and the mixture was stirred overnight at room temperature. To the reaction solution was added diethyl ether, and the mixture was stirred, followed by removal of the supernatant (5 times). The residue was dispersed in an aqueous citric acid solution, and the solid was then collected by filtration to obtain 7 mg of the title compound.

1H-NMR (DMSO-d6): δ 2.72 (3H, s), 3.54-3.66 (1H, m), 4.04-4.67 (4H, m), 5.18 (1H, d, J=10.0 Hz), 5.28 (1H, d, J=17.0 Hz), 6.13-6.26 (1H, m), 6.50 (1H, s), 8.79 (1H, s), 9.67 (1H, s)

Example 002

Compound 002

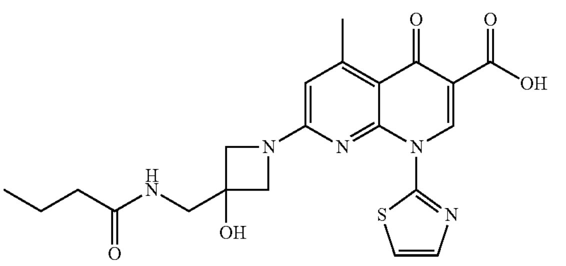

7-[3-(Butanamidomethyl)-3-hydroxyazetidin-1-yl]-5-methyl-4-oxo-1-(1,3-thiazol-2-yl)-1,4-dihydro-1,8-naphthyridine-3-carboxylic acid (1) To a solution of 3-(aminomethyl)-1-(diphenylmethyl)azetidin-3-ol (268 mg) obtained by the method described in WO 2016/042452 A or a method equivalent thereto in methylene chloride (5 mL) were added 1,1,3,3-tetramethylguanidine (377 μL) and butanoyl chloride (262 μL) under ice cooling, and the mixture was stirred at room temperature for 3 days. To the reaction solution was added an aqueous sodium bicarbonate solution, and the mixture was extracted with methylene chloride. The organic layer was washed with brine, dried over sodium sulfate, and concentrated. The residue was purified by silica gel column chromatography (eluent: methanol/methylene chloride) to obtain 379 mg of N-{[1-(diphenylmethyl)-3-hydroxyazetidin-3-yl]methyl}butanamide.

1H-NMR (CDCl3): δ 0.93 (3H, t, J=7.5 Hz), 1.61-1.71 (2H, m), 2.19 (2H, t, J=7.0 Hz), 2.88-2.91 (2H, m), 3.22-3.26 (2H, m), 3.68 (1H, d, J=7.0 Hz), 4.38 (1H, s), 6.01-6.08 (1H, m), 7.15-7.21 (2H, m), 7.23-7.29 (4H, m), 7.36-7.40 (4H, m)

(2) To a solution of N-{[1-(diphenylmethyl)-3-hydroxyazetidin-3-yl]methyl}butanamide (338 mg) obtained in the preceding section in methanol (10 mL) was added 10% palladium carbon (25 mg), and the mixture was hydrogenated at room temperature to 50° C. for 2 days. The catalyst was filtered off, and the filtrate was then concentrated. To the residue was added water, and the mixture was washed with chloroform. Then, the aqueous layer was concentrated to obtain crude N-[(3-hydroxyazetidin-3-yl)methyl]butanamide.

(3) To a suspension of crude N-[(3-hydroxyazetidin-3-yl)methyl]butanamide acetate (36 mg) obtained in the preceding section, 7-chloro-5-methyl-4-oxo-1-(1,3-thiazol-5-yl)-1,4-dihydro-1,8-naphthyridine-3-carboxylic acid (25 mg) obtained in Reference Example 001-(2), and lithium chloride (26 mg) in dimethyl sulfoxide (311 μL) was added 1,1,3,3-tetramethylguanidine (34 μL), and the mixture was stirred at room temperature for 4 hours. The reaction solution was dispersed in 0.5 mol/L hydrochloric acid, and the solid was collected by filtration and dried to obtain 31 mg of the title compound.

1H-NMR (DMSO-d6): δ 0.76 (3H, t, J=7.5 Hz), 1.40-1.49 (2H, m), 2.06 (2H, t, J=7.0 Hz), 2.78 (3H, s), 3.94-4.14 (2H, m), 4.20-4.41 (2H, m), 6.14 (1H, s), 6.56 (1H, s), 7.78 (1H, d, J=3.5 Hz), 7.85 (1H, d, J=3.5 Hz), 8.07 (1H, brt, J=6.0 Hz), 9.84 (1H, s)

Example 003

Compound 003

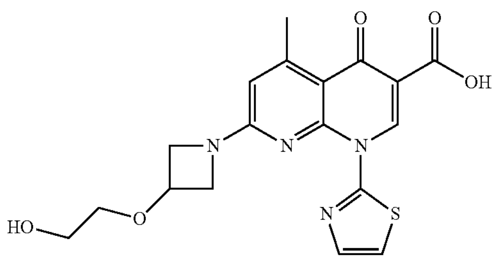

7-[3-(2-Hydroxyethoxy) azetidin-1-yl]-5-methyl-4-oxo-1-(1,3-thiazol-2-yl)-1,4-dihydro-1,8-naphthyridine-3-carboxylic acid (1) To ethane-1,2-diol (12 mL) was added sodium hydride (55%, 385 mg) under ice cooling, and the mixture was stirred at room temperature for 30 minutes. 1-(diphenylmethyl)azetidin-3-yl methanesulfonate (2.0 g) was added thereto, and the mixture was stirred overnight at 60° C. Water was added thereto, and the mixture was extracted with ethyl acetate. The organic layer was dried over sodium sulfate and concentrated. The residue was subjected to silica gel column chromatography (elution: ethyl acetate/n-hexane) to obtain crude 2-{[1-(diphenylmethyl)azetidin-3-yl]oxy}ethan-1-ol.

(2) 1.0 g of 2-(azetidin-3-yloxy)ethan-1-ol acetate was obtained by the method described in Example 002-(2) or a method equivalent thereto from crude 2-{[1-(diphenylmethyl)azetidin-3-yl]oxy}ethan-1-ol obtained in the preceding section.

1H-NMR (D2O): δ 3.49-3.52 (2H, m), 3.61-3.65 (2H, m), 3.94-4.02 (2H, m), 4.19-4.29 (2H, m), 4.42-4.50 (1H, m)

(3) The title compound was obtained by the method described in Example 002-(3) or a method equivalent thereto using 2-(azetidin-3-yloxy)ethan-1-ol acetate obtained in the preceding section, and 7-chloro-5-methyl-4-oxo-1-(1,3-thiazol-2-yl)-1,4-dihydro-1,8-naphthyridine-3-carboxylic acid obtained in Reference Example 001-(2).

1H-NMR (DMSO-d6): δ 2.78 (3H, s), 3.46-3.58 (3H, m), 4.00-4.21 (2H, m), 4.39-4.63 (2H, m), 4.70 (1H, brs), 6.54 (1H, s), 7.76 (1H, d, J=3.5 Hz), 7.84 (1H, d, J=3.5 Hz), 9.85 (1H, s)

Example 004

Compound 004

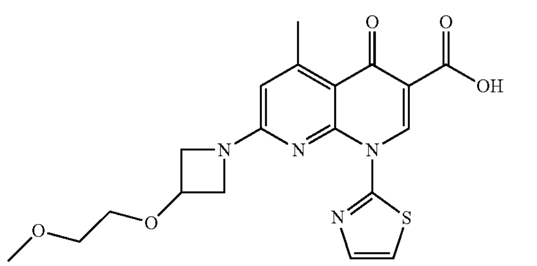

7-[3-(2-Methoxyethoxy) azetidin-1-yl]-5-methyl-4-oxo-1-(1,3-thiazol-2-yl)-1,4-dihydro-1,8-naphthyridine-3-carboxylic acid (1) To a solution of 1-(diphenylmethyl)azetidin-3-ol (479 mg) in N,N-dimethylformamide (100 μL) was added 55% sodium hydride under ice cooling, and the mixture was stirred at room temperature for 15 minutes. To the reaction solution was added 1-chloro-2-methoxyethane (364 μL) under ice cooling, and the mixture was stirred overnight at room temperature. To the reaction solution was added an aqueous sodium bicarbonate solution, and the mixture was extracted with methylene chloride. The organic layer was dried over sodium sulfate and concentrated. The residue was subjected to silica gel column chromatography (eluent: methanol/methylene chloride) to obtain crude 1-(diphenylmethyl)-3-(2-methoxyethoxy) azetidine.

(2) Crude 3-(2-methoxyethoxy)azetidine acetate was obtained by the method described in Example 002-(2) or a method equivalent thereto from crude 1-(diphenylmethyl)-3-(2-methoxyethoxy)azetidine obtained in the preceding section.

(3) The title compound was obtained by the method described in Example 002-(3) or a method equivalent thereto using crude 3-(2-methoxyethoxy)azetidine acetate obtained in the preceding section, and 7-chloro-5-methyl-4-oxo-1-(1,3-thiazol-2-yl)-1,4-dihydro-1,8-naphthyridine-3-carboxylic acid obtained in Reference Example 001-(2).

1H-NMR (DMSO-d6): δ 2.78 (3H, s), 3.28 (3H, s), 3.48-3.52 (2H, m), 3.59-3.64 (2H, m), 4.00-4.22 (2H, m), 4.42-4.63 (3H, m), 6.55 (1H, s), 7.76 (1H, d, J=3.5 Hz), 7.84 (1H, d, J=3.5 Hz), 9.86 (1H, s)

Example 005

Compound 005

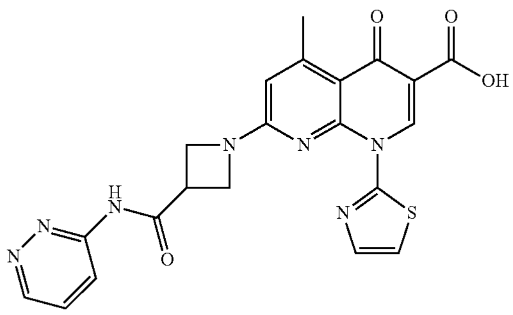

5-Methyl-4-oxo-7-{3-[(pyridazin-3-yl)carbamoyl]azetidin-1-yl}-1-(1,3-thiazol-2-yl)-1,4-dihydro-1,8-naphthyridine-3-carboxylic acid (1) A mixture of pyridazin-3-amine (95 mg), 1-[(tert-butoxy)carbonyl]azetidine-3-carboxylic acid (241 mg), HOBt monohydrate (15 mg), EDC (383 mg), and N,N-dimethylformamide (1 mL) was stirred at room temperature for 26 hours. To the reaction solution was added a saturated aqueous solution of sodium bicarbonate, and the mixture was extracted with ethyl acetate. The organic layer was washed with water and brine, dried over sodium sulfate, and concentrated to obtain 196 mg of tert-butyl 3-[(pyridazin-3-yl)carbamoyl]azetidine-1-carboxylate.

1H-NMR (DMSO-d6): δ 1.38 (9H, s), 3.62-3.70 (1H, m), 3.92-4.04 (4H, m), 7.69 (1H, dd, J=5.0, 9.0 Hz), 8.33 (1H, d, J=9.0 Hz), 8.96 (1H, dd, J=1.5, 5.0 Hz), 11.20 (1H, brs)

(2) The title compound was obtained by the method described in Example 001-(3) or a method equivalent thereto using N-(pyridazin-3-yl)azetidine-3-carboxamide hydrochloride obtained by the method described in Example 001-(2) or a method equivalent thereto from tert-butyl 3-[(pyridazin-3-yl)carbamoyl]azetidine-1-carboxylate obtained in the preceding section, and 7-chloro-5-methyl-4-oxo-1-(1,3-thiazol-2-yl)-1,4-dihydro-1,8-naphthyridine-3-carboxylic acid obtained in Reference Example 001-(2).

1H-NMR (D2O+NaOD): δ 2.43 (3H, s), 3.19-3.28 (1H, m), 3.77-3.85 (4H, m), 5.73 (1H, s), 6.94 (1H, dd, J=9.0, 1.0 Hz), 7.22 (1H, d, J=3.5 Hz), 7.30 (1H, dd, J=9.5, 5.0 Hz), 7.48 (1H, d, J=4.0 Hz), 8.35 (1H, dd, J=4.5, 1.0 Hz), 8.91 (1H, s)

Example 006

Compound 006

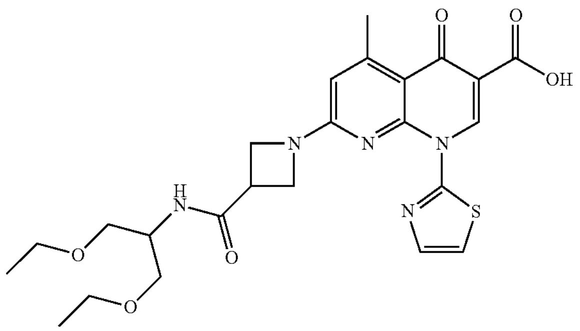

7-{3-[(1,3-Diethoxypropan-2-yl)carbamoyl]azetidin-1-yl}-5-methyl-4-oxo-1-(1,3-thiazol-2-yl)-1,4-dihydro-1,8-naphthyridine-3-carboxylic acid (1) Crude tert-butyl 3-[(1,3-dihydroxypropan-2-yl)carbamoyl]azetidine-1-carboxylate was obtained from 2-aminopropane-1,3-diol (1.1 g) by the method described in Example 005-(1) or a method equivalent thereto.

(2) To a solution of 55% sodium hydride (570 mg) in N,N-dimethylformamide (25 mL) was added a solution of crude tert-butyl 3-[(1,3-dihydroxypropan-2-yl)carbamoyl]azetidine-1-carboxylate obtained in the preceding section in N,N-dimethylformamide (5 mL), and the mixture was stirred at room temperature for 10 minutes. To the reaction solution was added ethyl iodide (1.0 mL), and the mixture was stirred at room temperature for 6 hours. To the reaction solution was added water, and the mixture was extracted with ethyl acetate. The organic layer was washed with water, dried over sodium sulfate, and concentrated. The residue was purified by silica gel column chromatography (eluent: ethyl acetate/n-hexane) to obtain 830 mg of tert-butyl 3-[(1,3-diethoxypropan-2-yl)carbamoyl]azetidine-1-carboxylate.

1H-NMR (CDCl3): δ 1.19 (6H, t, J=7.0 Hz), 1.45 (9H, s), 3.13-3.23 (1H, m), 3.42-3.60 (8H, m), 4.01-4.08 (2H, m), 4.08-4.16 (2H, m), 4.18-4.28 (1H, m)

(3) The title compound was obtained by the method described in Example 001-(3) or a method equivalent thereto using N-(1,3-diethoxypropan-2-yl)azetidine-3-carboxamide hydrochloride obtained by the method described in Example 001-(2) or a method equivalent thereto from tert-butyl 3-[(1,3-diethoxypropan-2-yl)carbamoyl]azetidine-1-carboxylate obtained in the preceding section, and 7-chloro-5-methyl-4-oxo-1-(1,3-thiazol-2-yl)-1,4-dihydro-1,8-naphthyridine-3-carboxylic acid obtained in Reference Example 001-(2).

1H-NMR (DMSO-d6): δ 1.11 (6H, t, J=7.0 Hz), 2.76 (3H, s), 3.36-3.47 (8H, m), 3.60-3.67 (1H, m), 4.02-4.08 (1H, m), 4.18-4.48 (4H, m), 6.52 (1H, d, J=1.0 Hz), 7.75 (1H, d, J=3.5 Hz), 7.83 (1H, d, J=3.5 Hz), 8.10 (1H, d, J=8.2 Hz), 9.82 (1H, s), 15.39 (1H, brs)

Example 007

Compound 007

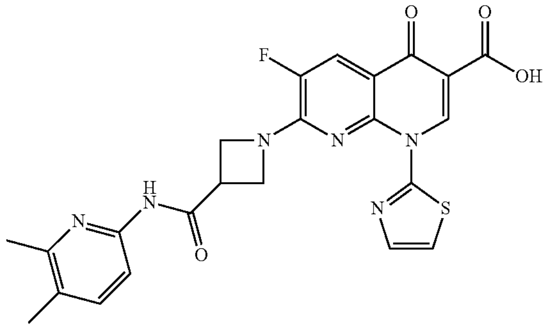

7-{3-[(5,6-Dimethylpyridin-2-yl)carbamoyl]azetidin-1-yl}-6-fluoro-4-oxo-1-(1,3-thiazol-2-yl)-1,4-dihydro-1,8-naphthyridine-3-carboxylic acid (1) To a solution of 1-[(tert-butoxy)carbonyl]azetidine-3-carboxylic acid (402 mg) and N-methylmorpholine (221 μL) in THF was added isobutyl chloroformate (262 μL) at −10° C., and the mixture was stirred at the same temperature for 20 minutes. Insoluble material was filtered off. To the residue was added 5,6-dimethylpyridin-2-amine (122 mg) at −10° C., and the mixture was stirred at room temperature for 3 days. To the reaction solution was added ethyl acetate, and the mixture was washed with water, an aqueous sodium bicarbonate solution, and brine, dried over sodium sulfate, and concentrated to obtain crude tert-butyl 3-[(5,6-dimethylpyridin-2-yl)carbamoyl]azetidine-1-carboxylate.

(2) The title compound was obtained by the method described in Example 001-(3) or a method equivalent thereto using N-(5,6-dimethylpyridin-2-yl)azetidine-3-carboxamide hydrochloride obtained by the method described in Example 001-(2) or a method equivalent thereto from crude tert-butyl 3-[(5,6-dimethylpyridin-2-yl)carbamoyl]azetidine-1-carboxylate obtained in the preceding section, and 7-chloro-6-fluoro-4-oxo-1-(1,3-thiazol-2-yl)-1,4-dihydro-1,8-naphthyridine-3-carboxylic acid obtained in Reference Example 003-(2).

1H-NMR (DMSO-d6): δ 2.31 (3H, s), 2.37 (3H, s), 3.91-4.03 (1H, m), 4.47-4.80 (4H, m), 7.53 (1H, d, J=8.5 Hz), 7.79 (1H, d, J=3.5 Hz), 7.83-7.89 (2H, m), 8.12 (1H, d, J=11.5 Hz), 9.83 (1H, s), 10.59 (1H, s), 14.79 (1H, brs)

Example 008

Compound 008

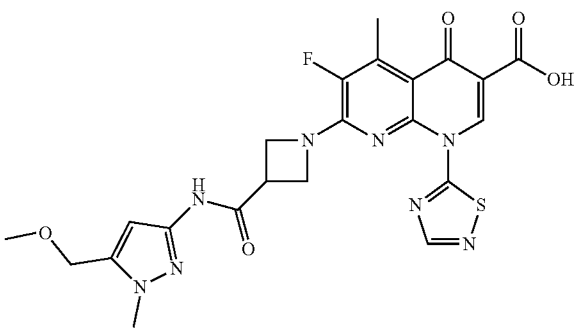

6-Fluoro-7-(3-{[5-(methoxymethyl)-1-methyl-1H-pyrazol-3-yl]carbamoyl}azetidin-1-yl)-5-methyl-4-oxo-1-(1,2,4-thiadiazol-5-yl)-1,4-dihydro-1,8-naphthyridine-3-carboxylic acid To a suspension of N-[5-(methoxymethyl)-1-methyl-1H-pyrazol-3-yl]azetidine-3-carboxamide hydrochloride (7.8 mg) obtained from 5-(methoxymethyl)-1-methyl-1H-pyrazol-3-amine by the methods described in Examples 007-(1) and 001-(2) or methods equivalent thereto, 7-chloro-6-fluoro-5-methyl-4-oxo-1-(1,2,4-thiadiazol-5-yl)-1,4-dihydro-1,8-naphthyridine-3-carboxylic acid (6.8 mg) obtained in Reference Example 008-(2), and lithium chloride (6.6 mg) in dimethyl sulfoxide (95 μL) was added 1,1,3,3-tetramethylguanidine (10 μL), and the mixture was stirred at 25° C. for 4 days. To the reaction solution was added methanol, and the mixture was neutralized with acetic acid and stirred at room temperature for 3 hours. The resulting solid was collected by filtration to obtain 4.1 mg of the title compound.

1H-NMR (DMSO-d6): δ 2.70 (3H, d, J=2.5 Hz), 3.25 (3H, s), 3.69 (3H, s), 3.77-3.84 (1H, m), 3.87 (2H, t, J=6.5 Hz), 4.54-4.89 (4H, m), 6.56 (1H, s), 8.84 (1H, s), 9.76 (1H, s), 10.68 (1H, s), 14.86 (1H, brs)

Example 009

Compound 009

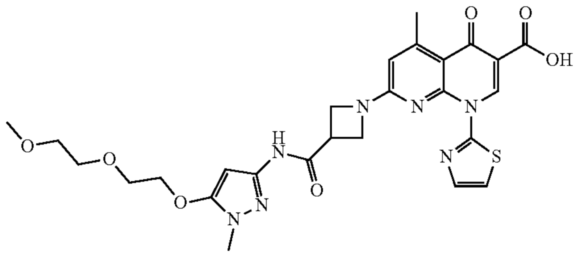

7-[3-({5-[2-(2-Methoxyethoxy)ethoxy]-1-methyl-1H-pyrazol-3-yl}carbamoyl)azetidin-1-yl]-5-methyl-4-oxo-1-(1,3-thiazol-2-yl)-1,4-dihydro-1,8-naphthyridine-3-carboxylic acid (1) To a solution of methyl 5-hydroxy-1-methyl-1H-pyrazole-3-carboxylate (1.0 g) in acetone (20 mL) were added potassium carbonate (1.3 g) and 1-bromo-2-(2-methoxyethoxy)ethane (1.3 mL), and the mixture was refluxed for 5 days. The reaction mixture was cooled down to room temperature. Insoluble material was filtered off, and the filtrate was concentrated. The residue was purified by silica gel column chromatography (eluent: ethyl acetate/n-hexane) to obtain 432 mg of methyl 5-[2-(2-methoxyethoxy)ethoxy]-1-methyl-1H-pyrazole-3-carboxylate.

1H-NMR (DMSO-d6): δ 3.23 (3H, s), 3.42-3.45 (2H, m), 3.55-3.59 (2H, m), 3.62 (3H, s), 3.70-3.74 (2H, m), 3.75 (3H, s), 4.19-4.27 (2H, m), 6.20 (1H, s)

(2) To a solution of methyl 5-[2-(2-methoxyethoxy)ethoxy]-1-methyl-1H-pyrazole-3-carboxylate (430 mg) obtained in the preceding section in THF (3.5 mL) was added a 1 mol/L aqueous sodium hydroxide solution (3.4 mL), and the mixture was stirred at room temperature to 40° C. for 1 day. The reaction solution was concentrated. Then, to the residue was added water, and the mixture was washed with chloroform and neutralized. After extraction with chloroform, the organic layer was dried over sodium sulfate and concentrated to obtain 383 mg of 5-[2-(2-methoxyethoxy)ethoxy]-1-methyl-1H-pyrazole-3-carboxylic acid.

1H-NMR (DMSO-d6): δ 3.24 (3H, s), 3.42-3.45 (2H, m), 3.55-3.59 (2H, m), 3.62 (3H, s), 3.70-3.74 (2H, m), 4.19-4.27 (2H, m), 6.13 (1H, s), 12.51 (1H, brs)

(3) To a solution of 5-[2-(2-methoxyethoxy)ethoxy]-1-methyl-1H-pyrazole-3-carboxylic acid (383 mg) obtained in the preceding section in toluene were added triethylamine (276 μL) and diphenylphosphoryl azide (406 μL), and the mixture was stirred at 90° C. for 3 hours. To the reaction solution was added tert-butanol (5.4 mL), and the mixture was stirred at the same temperature for 3 hours. To the reaction solution was added ethyl acetate, and the mixture was washed with brine. The organic layer was concentrated. To the residue was added a 4 mol/L solution of hydrochloric acid in ethyl acetate, and the mixture was stirred overnight at room temperature. To the reaction solution was added water, and the mixture was washed with chloroform and then neutralized. After extraction with chloroform, the organic layer was dried over sodium sulfate and concentrated to obtain 60 mg of 5-[2-(2-methoxyethoxy)ethoxy]-1-methyl-1H-pyrazol-3-amine.

1H-NMR (DMSO-d6): δ 3.24 (3H, s), 3.28 (3H, s), 3.42-3.45 (2H, m), 3.55-3.59 (2H, m), 3.66-3.71 (2H, m), 4.04-4.09 (2H, m), 4.89 (1H, s)

(4) The title compound was obtained by the method described in Example 008 or a method equivalent thereto using N-{5-[2-(2-methoxyethoxy)ethoxy]-1-methyl-1H-pyrazol-3-yl}azetidine-3-carboxamide hydrochloride obtained by the methods described in Examples 007-(1) and 001-(2) or methods equivalent thereto from 5-[2-(2-methoxyethoxy)ethoxy]-1-methyl-1H-pyrazol-3-amine obtained in the preceding section, and 7-chloro-5-methyl-4-oxo-1-(1,3-thiazol-2-yl)-1,4-dihydro-1,8-naphthyridine-3-carboxylic acid obtained in Reference Example 001-(2).

1H-NMR (DMSO-d6): δ 2.78 (3H, s), 3.24 (3H, s), 3.42-3.45 (2H, m), 3.46 (3H, s), 3.54-3.59 (2H, m), 3.69-3.73 (2H, m), 3.74-3.81 (1H, m), 4.14-4.19 (2H, m), 4.24-4.55 (4H, m), 6.00 (1H, s), 6.57 (1H, brs), 7.74 (1H, d, J=3.5 Hz), 7.84 (1H, d, J=3.5 Hz), 9.86 (1H, s), 10.55 (1H, s), 15.41 (1H, brs)

Example 010

Compound 010

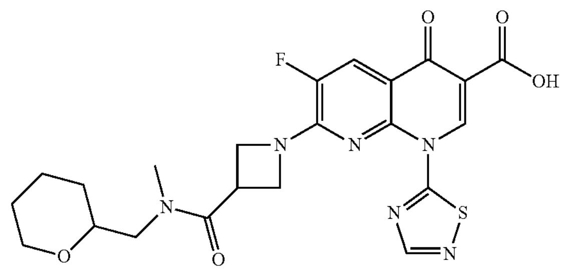

6-Fluoro-7-{3-[methyl(oxan-2-ylmethyl)carbamoyl] azetidin-1-yl}-4-oxo-1-(1,2,4-thiadiazol-5-yl)-1,4-dihydro-1,8-naphthyridine-3-carboxylic acid (1) To a solution of tert-butyl 3-[(oxan-2-ylmethyl)carbamoyl]azetidine-1-carboxylate (164 mg) obtained from (oxan-2-yl)methylamine by the method described in Example 005-(1) or a method equivalent thereto in N,N-dimethylformamide (2.2 mL) was added 55% sodium hydride (48 mg) under ice cooling, and the mixture was stirred at room temperature for 15 minutes. To the reaction solution was added methyl iodide (69 L) under ice cooling, and the mixture was stirred at room temperature for 1 day. To the reaction solution was added water, and the mixture was extracted with chloroform. The organic layer was washed with brine, dried over sodium sulfate, and concentrated. The residue was subjected to silica gel column chromatography (eluent: methanol/methylene chloride) to obtain crude tert-butyl 3-[methyl(oxan-2-ylmethyl)carbamoyl]azetidine-1-carboxylate.

(2) The title compound was obtained by the method described in Example 002-(3) or a method equivalent thereto using N-methyl-N-(oxan-2-ylmethyl)azetidine-3-carboxamide trifluoroacetate obtained by the method described in Example 001-(2) or a method equivalent thereto from crude tert-butyl 3-{methyl(oxan-2-ylmethyl)carbamoyl}azetidine-1-carboxylate obtained in the preceding section, and 7-chloro-6-fluoro-4-oxo-1-(1,2,4-thiadiazol-5-yl)-1,4-dihydro-1,8-naphthyridine-3-carboxylic acid obtained in Reference Example 004-(2).

1H-NMR (DMSO-d6): δ 1.11-1.28 (1H, m), 1.38-1.66 (4H, m), 1.71-1.87 (1H, m), 2.90 (2H, s), 2.99 (1H, s), 3.46-3.53 (1H, m), 3.83-3.98 (1H, m), 4.01-4.17 (1H, m), 4.44-4.93 (4H, m), 8.15 (1H, dd, J=2.5, 11.5 Hz), 8.85 (1H, d, J=3.0 Hz), 9.75 (1H, d, J=4.0 Hz), 14.49 (1H, brs)

Example 011

Compound 011

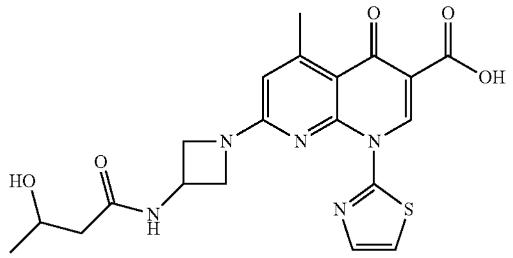

7-[3-(3-Hydroxybutanamido)azetidin-1-yl]-5-methyl-4-oxo-1-(1,3-thiazol-2-yl)-1,4-dihydro-1,8-naphthyridine-3-carboxylic acid (1) To a solution of 1-(diphenylmethyl)azetidin-3-amine (238 mg) obtained by the method described in U.S. Pat. No. 6,143,750 or a method equivalent thereto in N,N-dimethylformamide (1 mL) was added 4-methyloxetan-2-one (122 μL), and the mixture was stirred at room temperature for 3 days. The reaction solution was concentrated, and the residue was subjected to silica gel column chromatography (eluent: methanol/methylene chloride) to obtain crude N-[1-(diphenylmethyl)azetidin-3-yl]-3-hydroxybutanamide.

(2) Crude N-(azetidin-3-yl)-3-hydroxybutanamide was obtained by the method described in Example 002-(2) or a method equivalent thereto from crude N-[1-(diphenylmethyl)azetidin-3-yl]-3-hydroxybutanamide obtained in the preceding section.

(3) The title compound was obtained by the method described in Example 002-(3) or a method equivalent thereto using crude N-(azetidin-3-yl)-3-hydroxybutanamide acetate obtained in the preceding section, and 7-chloro-5-methyl-4-oxo-1-(1,3-thiazol-2-yl)-1,4-dihydro-1,8-naphthyridine-3-carboxylic acid obtained in Reference Example 001-(2).

1H-NMR (DMSO-d6): δ 1.08 (3H, d, J=6.5 Hz), 2.11-2.27 (2H, m), 2.78 (3H, s), 3.95-4.03 (1H, m), 4.04-4.31 (2H, m), 4.42-4.64 (2H, m), 4.65-4.73 (1H, m), 6.56 (1H, s), 7.77 (1H, d, J=3.5 Hz), 7.84 (1H, d, J=3.5 Hz), 8.60 (1H, brd, J=6.5 Hz), 9.85 (1H, s)

Example 012

Compound 012

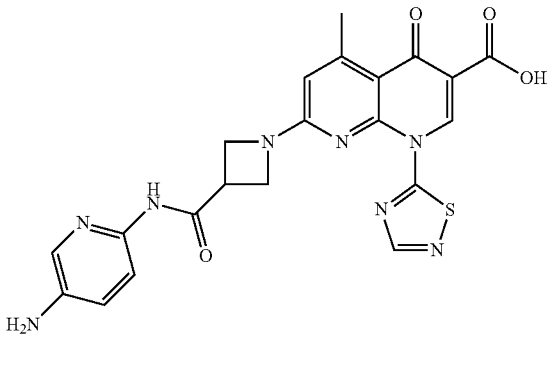

7-{3-[(5-Aminopyridin-2-yl)carbamoyl]azetidin-1-yl}-5-methyl-4-oxo-1-(1,2,4-thiadiazol-5-yl)-1,4-dihydro-1,8-naphthyridine-3-carboxylic acid (1) To a solution of tert-butyl 3-[(5-nitropyridin-2-yl) carbamoyl]azetidine-1-carboxylate (967 mg) obtained from 5-nitropyridin-2-amine by the method described in Example 007-(1) or a method equivalent thereto in THF (30 mL) was added 10% palladium carbon (30 mg), and the mixture was hydrogenated overnight at room temperature. The catalyst was filtered off, and the filtrate was then concentrated. The residue was subjected to silica gel column chromatography (eluent: ethyl acetate/n-hexane) to obtain crude tert-butyl 3-[(5-aminopyridin-2-yl)carbamoyl]azetidine-1-carboxylate.

(2) The title compound was obtained by the method described in Example 002-(3) or a method equivalent thereto using N-(5-aminopyridin-2-yl)azetidine-3-carboxamide trifluoroacetate obtained by the method described in Example 001-(2) or a method equivalent thereto from crude tert-butyl 3-[(5-aminopyridin-2-yl)carbamoyl]azetidine-1-carboxylate obtained in the preceding section, and 7-chloro-5-methyl-4-oxo-1-(1,2,4-thiadiazol-5-yl)-1,4-dihydro-1,8-naphthyridine-3-carboxylic acid obtained in Reference Example 002-(2).

1H-NMR (DMSO-d6): δ 2.79 (3H, s), 3.83-3.93 (1H, m), 4.17-4.68 (4H, m), 5.11 (2H, s), 6.62 (1H, s), 6.96-7.00 (1H, m), 7.68-7.71 (1H, m), 7.80-7.83 (1H, m), 8.82 (1H, s), 9.76 (1H, s), 10.33 (1H, s)

Example 013

Compound 013

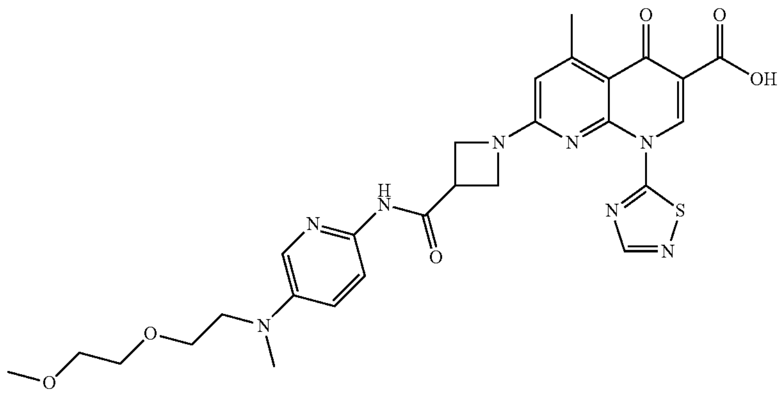

7-{3-[(5-{[2-(2-Methoxyethoxy)ethyl](methyl) amino}pyridin-2-yl)carbamoyl]azetidin-1-yl}-5-methyl-4-oxo-1-(1,2,4-thiadiazol-5-yl)-1,4-dihydro-1,8-naphthyridine-3-carboxylic acid (1) To a solution of [2-(2-methoxyethoxy)ethyl](methyl) amine (3.3 g) in ethanol (10 mL) was added 5-bromo-2-nitropyridine (1.0 g), and the mixture was stirred at room temperature for 4 days. The reaction solution was concentrated, and the residue was purified by silica gel column chromatography (eluent: ethyl acetate/n-hexane) to obtain 1.0 g of crude N-[2-(2-methoxyethoxy)ethyl]-N-methyl-6-nitropyridin-3-amine.

(2) To a solution of crude N-[2-(2-methoxyethoxy)ethyl]-N-methyl-6-nitropyridin-3-amine (1.0 g) obtained in the preceding section in methanol (34 mL) was added 10% palladium carbon (40 mg), and the mixture was hydrogenated at room temperature for 1 day. The catalyst was filtered off, and the filtrate was then concentrated. The residue was subjected to silica gel column chromatography (eluent: methanol/methylene chloride) to obtain 808 mg of N5-[2-(2-methoxyethoxy)ethyl]-N5-methylpyridine-2,5-diamine.

1H-NMR (CDCl3): δ 2.89 (3H, s), 3.39 (3H, s), 3.40 (2H, t, J=6.0 Hz), 3.52-3.55 (2H, m), 3.59-3.61 (2H, m), 3.63 (2H, t, J=6.0 Hz), 4.03 (2H, brs), 6.49 (1H, dd, J=0.5, 9.0 Hz), 7.08 (1H, dd, J=3.0, 9.0 Hz), 7.67 (1H, d, J=3.0 Hz)

(3) The title compound was obtained by the method described in Example 002-(3) or a method equivalent thereto using N-(5-{[2-(2-methoxyethoxy)ethyl](methyl) amino}pyridin-2-yl)azetidine-3-carboxamide trifluoroacetate obtained from N5-[2-(2-methoxyethoxy)ethyl]-N5-methylpyridine-2,5-diamine by the methods described in Examples 007-(1) and 001-(2) or methods equivalent thereto, and 7-chloro-5-methyl-4-oxo-1-(1,2,4-thiadiazol-5-yl)-1,4-dihydro-1,8-naphthyridine-3-carboxylic acid obtained in Reference Example 002-(2).

1H-NMR (DMSO-d6): δ 2.77 (3H, s), 2.92 (3H, s), 3.22 (3H, s), 3.39-3.43 (2H, m), 3.49-3.52 (4H, m), 3.52-3.58 (2H, m), 3.86-3.95 (1H, m), 4.33-4.70 (4H, m), 6.61 (1H, s), 7.19 (1H, dd, J=9.0, 3.0 Hz), 7.83 (1H, d, J=3.0 Hz), 7.94 (1H, d, J=9.0 Hz), 8.82 (1H, s), 9.74 (1H, s), 10.45 (1H, s), 15.09 (1H, s)

Example 014

Compound 014

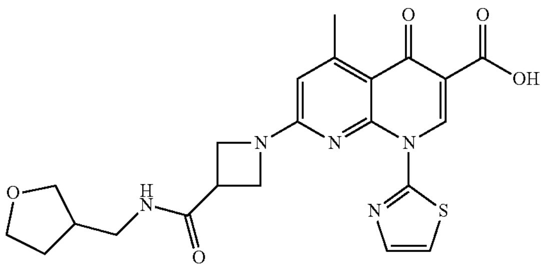

5-Methyl-4-oxo-7-{3-[(oxolan-3-ylmethyl)carbamoyl]azetidin-1-yl}-1-(1,3-thiazol-2-yl)-1,4-dihydro-1,8-naphthyridine-3-carboxylic acid To a suspension of N-(oxolan-3-ylmethyl)azetidine-3-carboxamide hydrochloride (16 mg) obtained from oxolan-3-ylmethylamine by the methods described in Examples 005-(1) and 001-(2) or methods equivalent thereto, 7-chloro-5-methyl-4-oxo-1-(1,3-thiazol-2-yl)-1,4-dihydro-1,8-naphthyridine-3-carboxylic acid (16 mg) obtained in Reference Example 001-(2), and lithium chloride (20 mg) in dimethyl sulfoxide (100 L) was added N-methylpyrrolidine (40 μL), and the mixture was stirred at room temperature for 18 hours. Diethyl ether was added to the reaction solution, and the mixture was stirred, followed by removal of the supernatant (5 times). The residue was dispersed in an aqueous citric acid solution, and the solid was then collected by filtration to obtain 8 mg of the title compound.

1H-NMR (DMSO-d6): δ 1.48-1.59 (1H, m), 1.87-1.97 (1H, m), 2.33-2.39 (1H, m), 2.78 (3H, s), 3.05-3.16 (2H, m), 3.35-3.42 (1H, m), 3.53-3.64 (2H, m), 3.64-3.75 (2H, m), 4.16-4.53 (4H, m), 6.54 (1H, s), 7.62 (1H, dd, J=2.0, 8.5 Hz), 7.74 (1H, d, J=3.5 Hz), 7.83 (1H, d, J=3.5 Hz), 8.25 (1H, t, J=5.5 Hz), 9.84 (1H, s), 15.41 (1H, brs)

Example 015

Compound 015

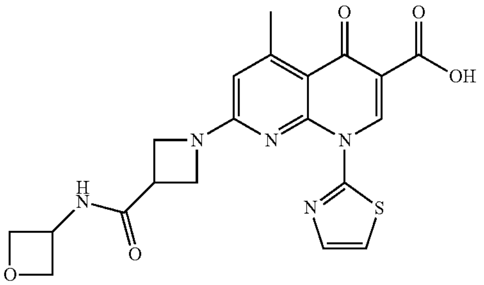

5-Methyl-7-{3-[(oxetan-3-yl)carbamoyl]azetidin-1-yl}-4-oxo-1-(1,3-thiazol-2-yl)-1,4-dihydro-1,8-naphthyridine-3-carboxylic acid (1) A mixture of 1-[(benzyloxy) carbonyl]azetidine-3-carboxylic acid (470 mg), l-hydroxypyrrolidine-2,5-dione (345 mg), EDC (573 mg), and methylene chloride (10 mL) was stirred overnight at room temperature. The reaction solution was washed with diluted hydrochloric acid, water and brine, and concentrated. The residue was dissolved in methylene chloride to obtain a 1 mol/L solution of 1-benzyl 3-(2,5-dioxopyrrolidin-1-yl)azetidine-1,3-dicarboxylate in methylene chloride.

(2) A mixture of the 1 mol/L solution of 1-benzyl 3-(2,5-dioxopyrrolidin-1-yl)azetidine-1,3-dicarboxylate in methylene chloride (1 mL) obtained in the preceding section, oxetan-3-amine (140 μL), methylene chloride (4 mL), and triethylamine (140 μL) was stirred overnight at room temperature. The reaction solution was subjected to silica gel column chromatography (eluent: methanol/methylene chloride) to obtain crude benzyl 3-[(oxetan-3-yl)carbamoyl]azetidine-1-carboxylate.

(3) The title compound was obtained by the method described in Example 014 or a method equivalent thereto using N-(oxetan-3-yl)azetidine-3-carboxamide hydrochloride obtained by the method described in Example 002-(2) or a method equivalent thereto from crude benzyl 3-[(oxetan-3-yl)carbamoyl]azetidine-1-carboxylate obtained in the preceding section, and 7-chloro-5-methyl-4-oxo-1-(1,3-thiazol-2-yl)-1,4-dihydro-1,8-naphthyridine-3-carboxylic acid obtained in Reference Example 001-(2).

1H-NMR (DMSO-d6): δ 2.72 (3H, s), 3.43-3.74 (4H, m), 4.20-4.53 (4H, m), 6.55 (1H, s), 7.76 (1H, d, J=4.4 Hz), 7.82 (1H, d, J=4.4 Hz), 9.78 (1H, s), 15.34 (1H, brs)

Example 016

Compound 016

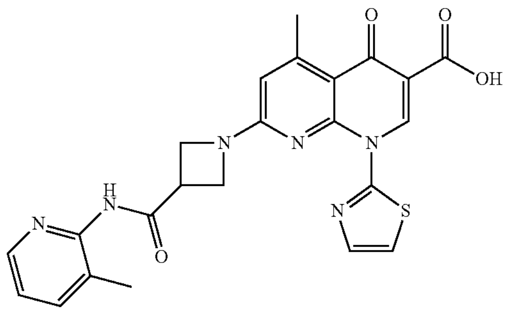

5-Methyl-7-{3-[(3-methylpyridin-2-yl)carbamoyl]azetidin-1-yl}-4-oxo-1-(1,3-thiazol-2-yl)-1,4-dihydro-1,8-naphthyridine-3-carboxylic acid To a suspension of crude N-(3-methylpyridin-2-yl)azetidine-3-carboxamide hydrochloride obtained from 3-methylpyridin-2-amine by the methods described in Examples 005-(1) and 001-(2) or methods equivalent thereto, 7-chloro-5-methyl-4-oxo-1-(1,3-thiazol-2-yl)-1,4-dihydro-1,8-naphthyridine-3-carboxylic acid (6 mg) obtained in Reference Example 001-(2), and lithium chloride (7 mg) in dimethyl sulfoxide (350 μL) was added N-methylpyrrolidine (14 μL), and the mixture was stirred overnight at room temperature. The reaction solution was purified by preparative HPLC (elution: acetonitrile/0.1 mol/L aqueous ammonium carbonate solution) using an ODS column to obtain 0.4 mg of the title compound.

1H-NMR (DMSO-d6): δ 2.25 (3H, s), 2.79 (3H, s), 3.87-3.96 (1H, m), 4.29-4.56 (4H, m), 6.58 (1H, s), 7.62 (1H, dd, J=2.0, 9.0 Hz), 7.74 (1H, d, J=3.5 Hz), 7.83 (1H, d, J=3.5 Hz), 8.00-8.06 (1H, m), 8.17 (1H, d, J=2.0 Hz), 9.85 (1H, s), 10.68 (1H, s), 8.01 (1H, dd, J=7.5, 1.5 Hz)

Example 017

Compound 017

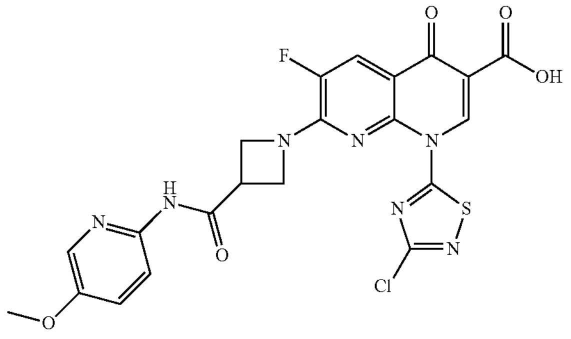

1-(3-Chloro-1,2,4-thiadiazol-5-yl)-6-fluoro-7-{3-[(5-methoxypyridin-2-yl)carbamoyl]azetidin-1-yl}-4-oxo-1,4-dihydro-1,8-naphthyridine-3-carboxylic acid (1) N-(5-Methoxypyridin-2-yl)azetidine-3-carboxamide hydrochloride was obtained from 5-methoxypyridin-2-amine by the methods described in Examples 005-(1) and 001-(2) or methods equivalent thereto.

1H-NMR (DMSO-d6): δ 3.81 (3H, s), 3.81-3.87 (1H, m), 4.00-4.22 (4H, m), 7.47 (1H, dd, J=9.0, 3.0 Hz), 8.04-8.07 (2H, s), 8.80 (1H, brs), 9.01 (1H, brs), 10.59 (1H, 8)

(2) A suspension of N-(5-methoxypyridin-2-yl)azetidine-3-carboxamide hydrochloride (10 mg) obtained in the preceding section, 7-chloro-1-(3-chloro-1,2,4-thiadiazol-5-yl)-6-fluoro-4-oxo-1,4-dihydro-1,8-naphthyridine-3-carboxylic acid (10 mg) obtained in Reference Example 014, triethylamine (16 μL), and lithium chloride (9 mg) in dimethyl sulfoxide (150 μL) was stirred overnight at room temperature. To the reaction solution was added diethyl ether, and the mixture was stirred, followed by removal of the supernatant (5 times). The residue was dispersed in an aqueous citric acid solution, and the solid was then collected by filtration to obtain 12 mg of the title compound.

1H-NMR (DMSO-d6): δ 3.33-3.45 (1H, m), 3.68 (3H, s), 4.10-4.28 (2H, m), 4.29-4.43 (2H, m), 6.95 (1H, d, J=12.0 Hz), 7.05 (1H, dt, J=9.0, 3.0 Hz), 7.43 (1H, dt, J=9.0, 4.0 Hz), 7.77 (1H, dd, J=4.0, 3.0 Hz), 8.56 (1H, a)

Example 018

Compound 018

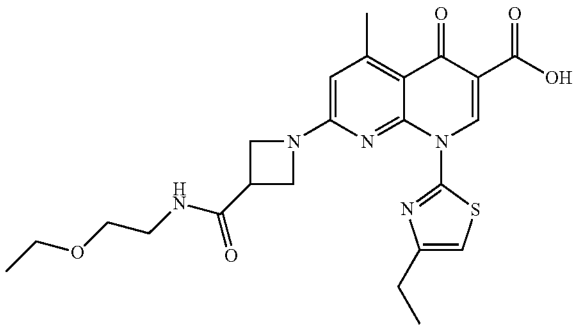

7-{3-[(2-Ethoxyethyl)carbamoyl]azetidin-1-yl}-1-(4-ethyl-1,3-thiazol-2-yl)-5-methyl-4-oxo-1,4-dihydro-1,8-naphthyridine-3-carboxylic acid (1) N-(2-Ethoxyethyl)azetidine-3-carboxamide hydrochloride was obtained from 2-ethoxyethan-1-amine by the methods described in Examples 007-(1) and 001-(2) or methods equivalent thereto.

1H-NMR (DMSO-d6): δ 1.10 (3H, t, J=7.0 Hz), 3.24 (2H, dd, J=5.7, 5.4 Hz), 3.38 (2H, t, J=5.7 Hz), 3.42 (2H, q, J=7.0 Hz), 3.52-3.59 (1H, m), 3.93-4.02 (4H, m), 8.23 (1H, t, J=5.4 Hz), 8.88 (1H, brs), 9.23 (1H, brs)

(2) A solution of N-(2-ethoxyethyl)azetidine-3-carboxamide hydrochloride (16 mg) obtained in the preceding section from 2-ethoxyethan-1-amine, 7-chloro-1-(4-ethyl-1,3-thiazol-2-yl)-5-methyl-4-oxo-1,4-dihydro-1,8-naphthyridine-3-carboxylic acid (15 mg) obtained in Reference Example 016-(2), and DBU (28 μL) in N,N-dimethylformamide (200 μL) was stirred overnight at room temperature. To the reaction solution was added diethyl ether, and the mixture was stirred, followed by removal of the supernatant (5 times). The residue was dispersed in an aqueous citric acid solution, and the solid was then collected by filtration to obtain 12 mg of the title compound.

1H-NMR (DMSO-d6): δ 1.11 (3H, t, J=7.0 Hz), 1.27 (3H, t, J=7.5 Hz), 2.78 (3H, s), 3.38-3.46 (8H, m), 3.55-3.64 (1H, m), 4.13-4.49 (4H, m), 6.54 (1H, s), 7.31 (1H, s), 8.23 (1H, t, J=5.5 Hz), 9.83 (1H, s)

Example 019

Compound 019

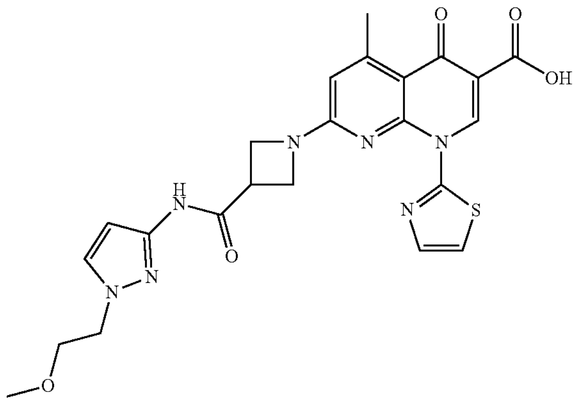

7-(3-{[1-(2-Methoxyethyl)-1H-pyrazol-3-yl] carbamoyl}azetidin-1-yl)-5-methyl-4-oxo-1-(1,3-thiazol-2-yl)-1,4-dihydro-1,8-naphthyridine-3-carboxylic acid A solution of N-[1-(2-methoxyethyl)-1H-pyrazol-3-yl] azetidine-3-carboxamide hydrochloride (6.3 mg) obtained from 1-(2-methoxyethyl)-1H-pyrazol-3-amine by the methods described in Examples 007-(1) and 001-(2) or methods equivalent thereto, 7-chloro-5-methyl-4-oxo-1-(1,3-thiazol-2-yl)-1,4-dihydro-1,8-naphthyridine-3-carboxylic acid (6.4 mg) obtained in Reference Example 001-(2), and DBU (12 μL) in N,N-dimethylformamide (80 μL) was stirred at room temperature for 22 hours. To the reaction solution was added 2-propanol (800 μL), and the mixture was refluxed for 1 hour. The reaction mixture was cooled down to room temperature, and the resulting solid was collected by filtration to obtain 3.9 mg of the title compound.

1H-NMR (DMSO-d6): δ 2.79 (3H, s), 3.22 (3H, s), 3.64 (2H, t, J=5.5 Hz), 3.75-3.83 (1H, m), 4.15 (2H, t, J=5.5 Hz), 4.22-4.56 (4H, m), 6.49 (1H, d, J=2.0 Hz), 6.58 (1H, s), 7.58 (1H, d, J=2.0 Hz), 7.74 (1H, d, J=3.5 Hz), 7.84 (1H, d, J=3.5 Hz), 9.86 (1H, s), 10.71 (1H, s), 15.41 (1H, brs)

Example 020

Compound 020

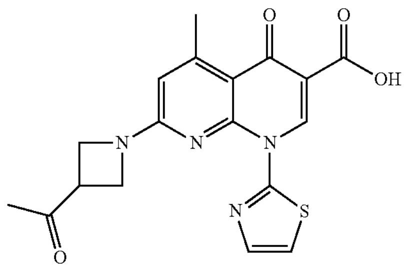

7-(3-Acetylazetidin-1-yl)-5-methyl-4-oxo-1-(1,3-thiazol-2-yl)-1,4-dihydro-1,8-naphthyridine-3-carboxylic acid (1) To a solution of tert-butyl 3-[methoxy(methyl)carbamoyl]azetidine-1-carboxylate (120 mg) obtained from methoxy(methyl)amine by the method described in Example 005-(1) or a method equivalent thereto in THF (2.5 mL) was added a 3 mol/L solution of methyl magnesium bromide in diethyl ether (250 μL) at −20° C., and the mixture was stirred at the same temperature for 135 minutes. To the reaction solution was added an aqueous ammonium chloride solution, and the mixture was extracted with ethyl acetate. The organic layer was washed with water and brine, dried over sodium sulfate, and concentrated. The residue was subjected to silica gel column chromatography (eluent: ethyl acetate/n-hexane) to obtain crude tert-butyl 3-acetylazetidine-1-carboxylate.

(2) 49 mg of 1-(azetidin-3-yl)ethan-1-one hydrochloride was obtained by the method described in Example 001-(2) or a method equivalent thereto using crude tert-butyl 3-acetylazetidine-1-carboxylate obtained in the preceding section.

1H-NMR (CDCl3): δ 1.45 (9H, s), 2.19 (3H, s), 3.38-3.48 (1H, m), 4.00-4.10 (4H, m)

(3) The title compound was obtained by the method described in Example 001-(3) or a method equivalent thereto using 1-(azetidin-3-yl)ethan-1-one hydrochloride obtained in the preceding section, and 7-chloro-5-methyl-4-oxo-1-(1,3-thiazol-5-yl)-1,4-dihydro-1,8-naphthyridine-3-carboxylic acid obtained in Reference Example 001-(2).

1H-NMR (DMSO-d6): δ 2.24 (3H, s), 2.75 (3H, s), 3.38-3.48 (2H, m), 3.84-3.91 (1H, m), 4.29-4.50 (4H, m), 6.51 (1H, d, J=0.9 Hz), 7.76 (1H, d, J=3.5 Hz), 7.83 (1H, d, J=3.5 Hz), 9.81 (1H, s), 15.35 (1H, brs)

Example 021

Compound 021

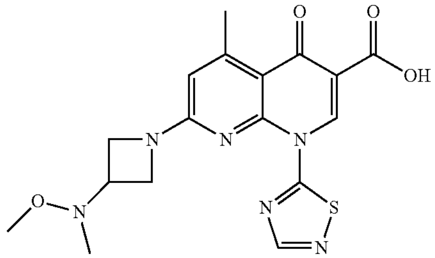

7-{3-[Methoxy(methyl)amino]azetidin-1-yl}-5-methyl-4-oxo-1-(1,2,4-thiadiazol-5-yl)-1,4-dihydro-1,8-naphthyridine-3-carboxylic acid (1) To a solution of methoxy(methyl)amine hydrochloride (107 mg) and tert-butyl 3-oxoazetidine-1-carboxylate (170 mg) in methylene chloride (1 mL) was added acetic acid, and the mixture was stirred at room temperature for 1 day. The reaction solution was concentrated. To a suspension of the residue in methylene chloride (1 mL) was added sodium triacetoxyborohydride (212 mg), and the mixture was stirred at room temperature for 3 days. To the reaction solution was added an aqueous sodium bicarbonate solution, and the mixture was extracted with methylene chloride. The organic layer was washed with brine, dried over sodium sulfate, and concentrated. The residue was purified by silica gel column chromatography (eluent: ethyl acetate/n-hexane) to obtain 146 mg of tert-butyl 3-[methoxy(methyl)amino]azetidine-1-carboxylate.

1H-NMR (CDCl3): δ 1.45 (9H, s), 2.49 (3H, s), 3.44-3.49 (1H, m), 3.57 (3H, s), 3.85-3.98 (4H, m)

(2) The title compound was obtained by the method described in Example 001-(3) or a method equivalent thereto using N-methoxy-N-methylazetidin-3-amine trifluoroacetate obtained by the method described in Example 001-(2) or a method equivalent thereto from tert-butyl 3-[methoxy(methyl)amino]azetidine-1-carboxylate obtained in the preceding section, and 7-chloro-5-methyl-4-oxo-1-(1,2,4-thiadiazol-5-yl)-1,4-dihydro-1,8-naphthyridine-3-carboxylic acid obtained in Reference Example 002-(2).

1H-NMR (DMSO-d6): δ 2.77 (3H, d, J=0.9 Hz), 3.12-3.23 (3H, m), 3.45 (1H, td, J=11.0, 2.7 Hz), 3.52-3.65 (4H, m), 3.68-3.75 (2H, m), 4.19-4.49 (4H, m), 6.54 (1H, d, J=0.9 Hz), 7.75 (1H, d, J=3.5 Hz), 7.84 (1H, d, J=3.5 Hz), 8.27 (1H, t, J=5.9 Hz), 9.84 (1H, s), 15.41 (1H, brs)

Example 022

Compound 022

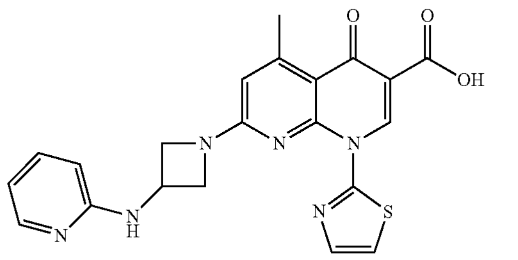

5-Methyl-4-oxo-7-{3-[(pyridin-2-yl)amino]azetidin-1-yl}-1-(1,3-thiazol-2-yl)-1,4-dihydro-1,8-naphthyridine-3-carboxylic acid (1) To a solution of 2-bromopyridine (316 mg) and tert-butyl 3-aminoazetidine-1-carboxylate (516 mg) in toluene (5 mL) were added tris(dibenzylideneacetone)dipalladium (37 mg), rac-2,2'-bis(diphenylphosphino)-1,1'-binaphthyl (25 mg), and sodium tert-butoxide (364 mg), and the mixture was stirred overnight at 80° C. Insoluble material was filtered off, and the filtrate was purified by silica gel column chromatography (eluent: ethyl acetate/n-hexane) to obtain 55 mg of tert-butyl 3-[(pyridin-2-yl)amino]azetidine-1-carboxylate.

1H-NMR (CDCl3): δ 1.45 (9H, s), 3.76 (2H, dd, J=9.0, 5.0 Hz), 4.32 (2H, dd, J=8.5, 7.5 Hz), 4.48-4.57 (1H, m), 6.35 (1H, d, J=8.0 Hz), 6.65 (1H, dd, J=7.5, 5.0 Hz), 7.44 (1H, ddd, J=8.0, 7.5, 2.0 Hz), 8.11 (1H, dd, J=5.0, 2.0 Hz), (2) To a suspension of 3-[(pyridin-2-yl)amino]azetidine trifluoroacetate (18 mg) obtained by the method described in Example 001-(2) or a method equivalent thereto from tert-butyl 3-[(pyridin-2-yl)amino]azetidine-1-carboxylate obtained in the preceding section, and 7-chloro-5-methyl-4-oxo-1-(1,3-thiazol-2-yl)-1,4-dihydro-1,8-naphthyridine-3-carboxylic acid (13 mg) obtained in Reference Example 001-(2) in N,N-dimethylformamide (200 μL) was added 1,1,3,3-tetramethylguanidine (50 μL), and the mixture was stirred at room temperature for 4 days. To the reaction solution was added diethyl ether, and the mixture was stirred, followed by removal of the supernatant (5 times). The residue was dispersed in 1 mol/L hydrochloric acid, and the solid was then collected by filtration to obtain 17 mg of the title compound.

1H-NMR (DMSO-d6): δ 2.80 (3H, s), 4.20-4.35 (2H, m), 4.62-4.79 (2H, m), 4.78-4.85 (1H, m), 6.63 (1H, s), 6.76-6.95 (2H, m), 7.72-7.77 (1H, m), 7.78 (1H, d, J=3.5 Hz), 7.85 (1H, d, J=3.5 Hz), 8.01-8.04 (1H, m), 9.86 (1H, s), 15.35 (1H, brs)

Example 023

Compound 023

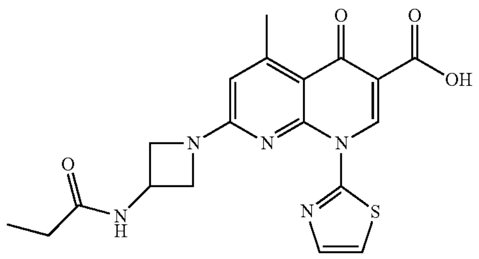

5-Methyl-4-oxo-7-(3-propanamidoazetidin-1-yl)-1-(1,3-thiazol-2-yl)-1,4-dihydro-1,8-naphthyridine-3-carboxylic acid (1) To a solution of 1-(diphenylmethyl)azetidin-3-amine (238 mg) in methylene chloride (10 mL) was added propanoyl chloride (131 μL), and the mixture was stirred overnight at room temperature. Methylene chloride was added thereto, and the mixture was washed with an aqueous sodium bicarbonate solution. The organic layer was dried over sodium sulfate and concentrated to obtain crude N-[1-(diphenylmethyl)azetidin-3-yl]propanamide.

(2) The title compound was obtained by the method described in Example 002-(3) or a method equivalent thereto using crude N-(azetidin-3-yl)propanamide acetate obtained by the method described in Example 002-(2) or a method equivalent thereto from crude N-[1-(diphenylmethyl)azetidin-3-yl]propanamide obtained in the preceding section, and 7-chloro-5-methyl-4-oxo-1-(1,3-thiazol-2-yl)-1,4-dihydro-1,8-naphthyridine-3-carboxylic acid obtained in Reference Example 001-(2).

1H-NMR (DMSO-d6): δ 1.02 (3H, t, J=7.5 Hz), 2.13 (2H, q, J=7.5 Hz), 2.78 (3H, s), 4.01-4.23 (2H, m), 4.47-4.65 (2H, m), 4.66-4.73 (1H, m), 6.56 (1H, s), 7.76 (1H, d, J=3.5 Hz), 7.84 (1H, d, J=3.5 Hz), 8.55 (1H, brd, J=7.0 Hz), 9.85 (1H, s)

Example 024

Compound 024

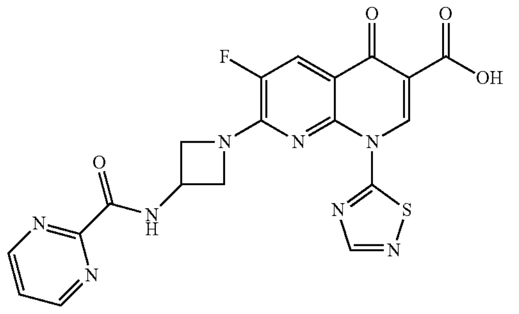

6-Fluoro-4-oxo-7-[3-(pyrimidin-2-amido)azetidin-1-yl]-1-(1,2,4-thiadiazol-5-yl)-1,4-dihydro-1,8-naphthyridine-3-carboxylic acid (1) A mixture of pyrimidine-2-carboxylic acid (124 mg), tert-butyl 3-aminoazetidine-1-carboxylate (207 mg), HOBt monohydrate (230 mg), EDC (288 mg), and N,N-dimethylformamide (7 mL) was stirred at room temperature for 3 days. Ethyl acetate was added thereto, and the mixture was extracted with an aqueous sodium bicarbonate solution, water and brine. The aqueous layers were combined and extracted with ethyl acetate. The organic layer was washed with an aqueous sodium bicarbonate solution and brine, dried over sodium sulfate, and concentrated to obtain crude tert-butyl 3-(pyrimidin-2-amido) azetidine-1-carboxylate.

(2) The title compound was obtained by the method described in Example 002-(3) or a method equivalent thereto using N-(azetidin-3-yl)pyrimidine-2-carboxamide hydrochloride obtained by the method described in Example 001-(2) or a method equivalent thereto using crude tert-butyl 3-(pyrimidin-2-amido) azetidine-1-carboxylate obtained in the preceding section, and 7-chloro-6-fluoro-4-oxo-1-(1,2,4-thiadiazol-5-yl)-1,4-dihydro-1,8-naphthyridine-3-carboxylic acid obtained in Reference Example 004-(2).

1H-NMR (DMSO-d6): δ 4.60-4.78 (2H, m), 4.79-4.99 (2H, m), 5.00-5.09 (1H, m), 7.71 (1H, dd, J=5.0, 5.0 Hz), 8.14 (1H, d, J=11.5 Hz), 8.82 (1H, s), 9.00 (2H, d, J=5.0 Hz), 9.71 (1H, s), 9.77 (1H, d, J=7.0 Hz), 13.30 (1H, brs)

Example 025

Compound 025

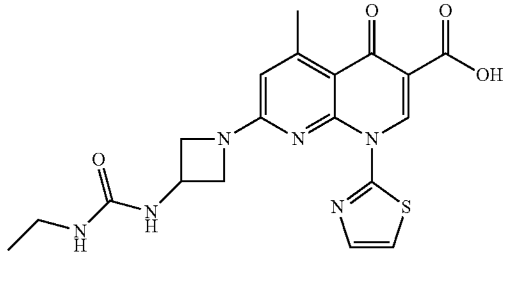

7-{3-[(Ethylcarbamoyl)amino]azetidin-1-yl}-5-methyl-4-oxo-1-(1,3-thiazol-2-yl)-1,4-dihydro-1,8-naphthyridine-3-carboxylic acid (1) To a solution of tert-butyl 3-aminoazetidine-1-carboxylate (54 mg) in methylene chloride was added ethyl isocyanate (32 μL) under ice cooling, and the mixture was stirred overnight at the same temperature. Methylene chloride was added thereto, and the mixture was washed with water and brine. The organic layer was dried over sodium sulfate and concentrated to obtain crude tert-butyl 3-[(ethylcarbamoyl)amino]azetidine-1-carboxylate.

(2) To a solution of crude 1-(azetidin-3-yl)-3-ethylurea hydrochloride obtained by the method described in Example 001-(2) or a method equivalent thereto from crude tert-butyl 3-[(ethylcarbamoyl)amino]azetidine-1-carboxylate obtained in the preceding section in dimethyl sulfoxide were added 1,1,3,3-tetramethylguanidine (63 ILL), 7-chloro-5-methyl-4-oxo-1-(1,3-thiazol-2-yl)-1,4-dihydro-1,8-naphthyridine-3-carboxylic acid (32 mg) obtained in Reference Example 001-(2), and lithium chloride (34 mg), and the mixture was stirred overnight at room temperature. To the reaction solution was added cyclopentyl methyl ether, and the mixture was stirred, followed by removal of the supernatant (5 times). The residue was dispersed in water, and the solid was then collected by filtration to obtain 45 mg of the title compound.

1H-NMR (DMSO-d6): δ 1.00 (3H, t, J=7.0 Hz), 2.76 (3H, s), 2.99-3.06 (2H, m), 3.95-4.23 (2H, m), 4.36-4.67 (3H, m), 6.00-6.10 (1H, m), 6.51 (1H, brs), 6.64-6.71 (1H, m), 7.71-7.76 (1H, m), 7.82 (1H, d, J=3.0 Hz), 9.83 (1H, s)

Example 026

Compound 026

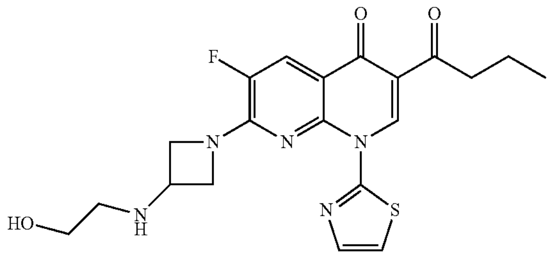

Ethyl 6-fluoro-7-{3-[(2-hydroxyethyl)amino]azetidin-1-yl}-4-oxo-1-(1,3-thiazol-2-yl)-1,4-dihydro-1,8-naphthyridine-3-carboxylate (1) To a solution of 2-aminoethan-1-ol (11.89 g) in ethanol was added 1-(diphenylmethyl)azetidin-3-yl methanesulfonate (1.72 g), and the mixture was refluxed for 18 hours. The reaction solution was concentrated, and to the residue was added water, and the mixture was extracted with chloroform. The organic layer was concentrated, and the residue was purified by silica gel column chromatography (eluent: methanol/chloroform) to obtain 847 mg of 2-{[1-(diphenylmethyl)azetidin-3-yl]amino}ethan-1-ol.

1H-NMR (CDCl3): δ 2.67-2.71 (2H, m), 3.45-3.51 (5H, m), 3.59-3.63 (2H, m), 4.32 (1H, s), 7.16-7.21 (2H, m), 7.24-7.29 (4H, m), 7.37-7.41 (4H, m)

(2) 435 mg of 2-[(azetidin-3-yl)amino]ethan-1-ol hydrochloride was obtained by the method described in Example 002-(2) or a method equivalent thereto from 2-{[1-(diphenylmethyl)azetidin-3-yl]amino}ethan-1-ol obtained in the preceding section.

1H-NMR (DMSO-d6): δ 2.53 (2H, t, J=5.5 Hz), 3.38 (2H, t, J=5.5 Hz), 3.57-3.72 (2H, m), 3.87-4.01 (2H, m), 4.41-4.77 (1H, m)

(3) To a suspension of 2-[(azetidin-3-yl)amino]ethan-1-ol hydrochloride (193 mg) obtained in the preceding section, and ethyl 6,7-difluoro-4-oxo-1-(1,3-thiazol-2-yl)-1,4-dihydro-1,8-naphthyridine-3-carboxylate (120 mg) obtained in Reference Example 003-(1) in acetonitrile (2.4 mL) was added 1,1,3,3-tetramethylguanidine (255 μL), and the mixture was stirred at room temperature for 2 hours. The resulting solid was collected by filtration to obtain 130 mg of the title compound.

1H-NMR (DMSO-d6): δ 1.30 (3H, t, J=7.5 Hz), 2.58-2.66 (2H, m), 3.46 (2H, dt, J=5.5, 5.5 Hz), 3.75-3.86 (1H, m), 4.08-4.17 (2H, m), 4.28 (2H, q, J=7.5 Hz), 4.51 (1H, t, J=5.5 Hz), 4.52-4.61 (2H, m), 7.70 (1H, d, J=3.5 Hz), 7.80 (1H, d, J=3.5 Hz), 7.92 (1H, d, J=11.5 Hz), 9.63 (1H, s)

Example 027

Compound 027

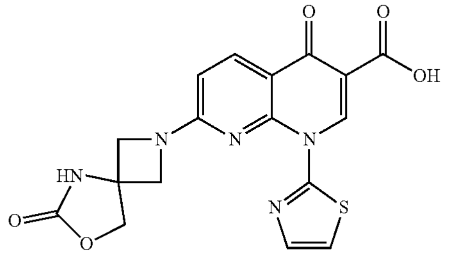

4-Oxo-7-{6-oxo-7-oxa-2,5-diazaspiro[3.4]octan-2-yl}-1-(1,3-thiazol-2-yl)-1,4-dihydro-1,8-naphthyridine-3-carboxylic acid (1) To a solution of 4,4-bis(hydroxymethyl)-1,3-oxazolidin-2-one (29 g) obtained by the method described in U.S. 2014/94495 A1 or a method equivalent thereto in pyridine (400 mL) was added p-toluenesulfonyl chloride (83 g) under ice cooling, and the mixture was stirred at room temperature for 22 hours. The reaction solution was poured into 1 mol/L hydrochloric acid, and precipitates were collected by filtration. To a solution of the obtained solid (71 g) in acetonitrile (1.5 L) was added benzylamine (51 mL), and the mixture was refluxed for 6 hours. The reaction mixture was cooled down to room temperature and concentrated. A solution of the residue in chloroform was washed with an aqueous sodium carbonate solution, dried and concentrated. The residue was subjected to silica gel column chromatography (eluent: methanol/chloroform), and the obtained crude powder was washed with diisopropyl ether and diethyl ether and then collected by filtration to obtain 8.0 g of 2-benzyl-7-oxa-2,5-diazaspiro[3.4]octan-6-one.

1H-NMR (CDCl3): δ 3.24-3.29 (2H, m), 3.40-3.47 (2H, m), 3.58 (2H, s), 4.53 (2H, s), 7.21-7.35 (5H, m)

(2) To a solution of 2-benzyl-7-oxa-2,5-diazaspiro[3.4]octan-6-one (470 mg) obtained in the preceding section in methanol (40 mL) were added 20% palladium hydroxide on carbon (50 mg) and acetic acid (3 mL), and the mixture was hydrogenated at 40 to 50° C. for 23 hours. The catalyst was filtered off, and the filtrate was then concentrated. The residue was dispersed in diethyl ether, and the solid was then collected by filtration to obtain crude 7-oxa-2,5-diazaspiro[3.4]octan-6-one acetate.

(3) To a suspension of ethyl 7-chloro-4-oxo-1-(1,3-thiazol-2-yl)-1,4-dihydro-1,8-naphthyridine-3-carboxylate (40 mg) obtained in Reference Example 005-(1) in acetonitrile (850 μL) were added crude 7-oxa-2,5-diazaspiro[3.4]octan-6-one acetate (25 mg) obtained in the preceding section, and 1,1,3,3-tetramethylguanidine (36 μL), and the mixture was stirred at room temperature for 4 days. Precipitates were collected by filtration to obtain 52 mg of ethyl 4-oxo-7-{6-oxo-7-oxa-2,5-diazaspiro(3.4)octan-2-yl}-1-(1,3-thiazol-2-yl)-1,4-dihydro-1,8-naphthyridine-3-carboxylate.

1H-NMR (DMSO-d6): δ 1.30 (3H, t, J=7.0 Hz), 4.28 (2H, q, J=7.0 Hz), 4.33-4.43 (2H, m), 4.46-4.56 (2H, m), 4.62 (2H, s), 6.66 (1H, d, J=9.0), 7.68 (1H, d, J=3.5 Hz), 7.80 (1H, d, J=3.5 Hz), 8.28 (1H, d, J=9.0 Hz), 8.54 (1H, s), 9.67 (1H, s)

(4) A mixture of ethyl 4-oxo-7-{6-oxo-7-oxa-2,5-diazaspiro(3.4)octan-2-yl}-1-(1,3-thiazol-2-yl)-1,4-dihydro-1,8-naphthyridine-3-carboxylate (40 mg) obtained in the preceding section, and 6 mol/L hydrochloric acid (780 μL) was refluxed overnight. The reaction mixture was cooled down to room temperature, and the resulting solid was collected by filtration to obtain 34 mg of the title compound.

1H-NMR (DMSO-d6): δ 3.72 (1H, dd, J=14.0, 5.0 Hz), 3.86 (2H, dt, J=11.5, 9.5 Hz), 4.07-4.16 (1H, m), 4.24 (2H, dt, J=9.5, 9.0 Hz), 7.00 (1H, d, J=9.0), 7.82 (1H, d, J=3.5 Hz), 7.87 (1H, d, J=3.5 Hz), 8.05 (1H, s), 8.31 (1H, d, J=9.0 Hz), 8.55-8.61 (1H, m), 9.75 (1H, 8)

Example 028

Compound 028

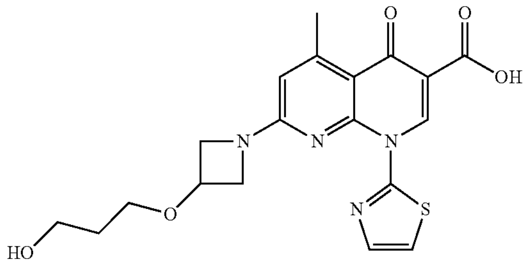

7-[3-(3-Hydroxypropoxy)azetidin-1-yl]-5-methyl-4-oxo-1-(1,3-thiazol-2-yl)-1,4-dihydro-1,8-naphthyridine-3-carboxylic acid (1) To a solution of 3-(azetidin-3-yloxy)propan-1-ol hydrochloride (20 mg) obtained from propane-1,3-diol by the methods described in Examples 003-(1) and 002-(2) or methods equivalent thereto in acetonitrile (613 L) were added 1,1,3,3-tetramethylguanidine (43 μL) and ethyl 7-chloro-5-methyl-4-oxo-1-(1,3-thiazol-2-yl)-1,4-dihydro-1,8-naphthyridine-3-carboxylate (30 mg) obtained in Reference Example 001-(1), and the mixture was stirred at room temperature for 3 days. The reaction solution was concentrated, and the residue was purified by silica gel column chromatography (eluent: methanol/methylene chloride) to obtain 13 mg of ethyl 7-[3-(3-hydroxypropoxy) azetidin-1-yl]-5-methyl-4-oxo-1-(1,3-thiazol-2-yl)-1,4-dihydro-1,8-naphthyridine-3-carboxylate.

1H-NMR (CDCl3): δ 1.41 (3H, J=7.0 Hz), 1.86-1.94 (2H, m), 2.88 (3H, s), 3.65 (2H, t, J=6.0 Hz), 3.81 (2H, dt, J=5.5, 5.5 Hz), 4.07-4.20 (2H, m), 4.41 (2H, q, J=7.0 Hz), 4.41-4.48 (2H, m), 4.48-4.55 (1H, m), 6.09 (1H, s), 7.23 (1H, J=3.5 Hz), 7.68 (1H, J=3.5 Hz), 9.78 (1H, s)

(2) To a solution of ethyl 7-[3-(3-hydroxypropoxy) azetidin-1-yl]-5-methyl-4-oxo-1-(1,3-thiazol-2-yl)-1,4-dihydro-1,8-naphthyridine-3-carboxylate (13 mg) obtained in the preceding section in ethanol (286 μL) was added a 1 mol/L aqueous sodium hydroxide solution (34 L), and the mixture was stirred at room temperature to 50° C. for 4 hours. The reaction mixture was cooled down to room temperature, and 6 mol/L hydrochloric acid was added thereto. The resulting solid was collected by filtration to obtain 9 mg of the title compound.

1H-NMR (DMSO-d6): δ 1.67-1.74 (2H, m), 2.78 (3H, s), 3.46-3.56 (2H, m), 3.83-4.27 (6H, m), 4.36-4.62 (2H, m), 6.54 (1H, s), 7.74-7.77 (1H, m), 7.83-7.85 (1H, m), 9.87 (1H, s)

Example 029

Compound 029

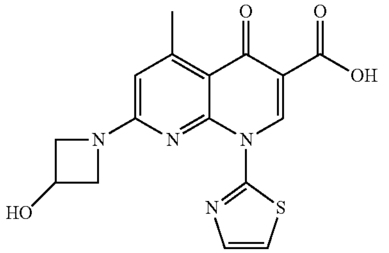

7-(3-Hydroxyazetidin-1-yl)-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001 and azetidin-3-ol hydrochloride by the method described in Example 019 or a method equivalent thereto.

1H-NMR (DMSO-d6): δ 2.73 (3H, s), 3.87-4.16 (2H, m), 4.36-4.59 (2H, m), 4.64-4.75 (1H, m), 5.94 (1H, d, J=6.5 Hz), 6.46 (1H, d, J=1.0 Hz), 7.74 (1H, d, J=3.5 Hz), 7.82 (1H, d, J=3.5 Hz), 9.80 (1H, s)

Example 030

Compound 030

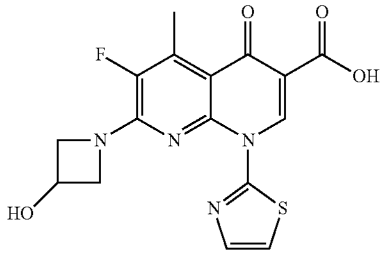

6-Fluoro-7-(3-hydroxyazetidin-1-yl)-5-methyl-4-oxo-1-(1,3-thiazol-2-yl)-1,4-dihydro-1,8-naphthyridine-3-carboxylic acid The title compound was obtained using 7-chloro-6-fluoro-5-methyl-4-oxo-1-(1,3-thiazol-2-yl)-1,4-dihydro-1,8-naphthyridine-3-carboxylic acid obtained in Reference Example 007-(2) and azetidin-3-ol hydrochloride by the method described in Example 019 or a method equivalent thereto.

1H-NMR (DMSO-d6): δ 2.66 (3H, s), 4.05-4.32 (2H, m), 4.60-4.77 (3H, m), 5.95 (1H, d, J=5.0 Hz), 7.76 (1H, d, J=3.5 Hz), 7.83 (1H, d, J=3.5 Hz), 9.78 (1H, s)

Example 031

Compound 031

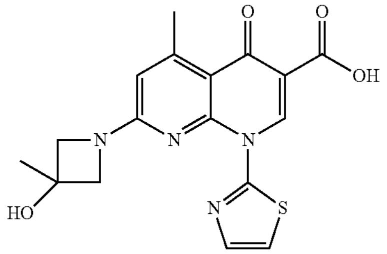

7-(3-Hydroxy-3-methylazetidin-1-yl)-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and 3-methylazetidin-3-ol hydrochloride by the method described in Example 019 or a method equivalent thereto.

1H-NMR (DMSO-d6): δ 1.52 (3H, s), 2.72 (3H, s), 3.92-4.34 (4H, m), 6.46 (1H, s), 7.73 (1H, d, J=3.5 Hz), 7.81 (1H, d, J=3.5 Hz), 9.79 (1H, s)

Example 032

Compound 032

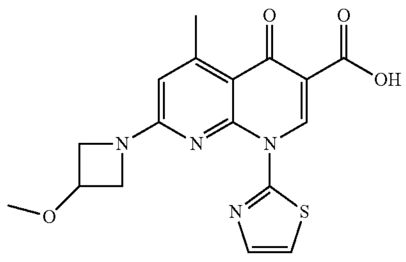

7-(3-Methoxyazetidin-1-yl)-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and 3-methoxyazetidine hydrochloride by the method described in Example 019 or a method equivalent thereto.

1H-NMR (DMSO-d6): δ 2.71 (3H, s), 3.32 (3H, s), 4.01-4.16 (2H, m), 4.36-4.52 (3H, m), 6.43 (1H, s), 7.72 (1H, d, J=3.5 Hz), 7.81 (1H, d, J=3.5 Hz), 9.77 (1H, s)

Example 033

Compound 033

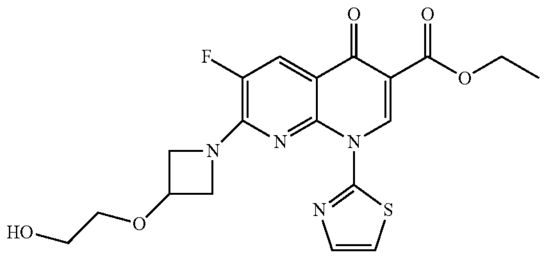

Ethyl 6-fluoro-7-[3-(2-hydroxyethoxy)azetidin-1-yl]-4-oxo-1-(1,3-thiazol-2-yl)-1,4-dihydro-1,8-naphthyridine-3-carboxylate The title compound was obtained using ethyl 7-chloro-6-fluoro-4-oxo-1-(1,3-thiazol-2-yl)-1,4-dihydro-1,8-naphthyridine-3-carboxylate obtained in Reference Example 003-(1) and 2-(azetidin-3-yloxy) ethan-1-ol acetate obtained in Example 003-(2) by the method described in Example 028-(1) or a method equivalent thereto.

Property: yellow solid;

ESI-MS (m/z): 435 [M+H]+

Example 034

Compound 034

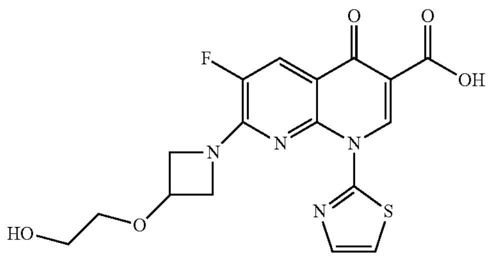

6-Fluoro-7-[3-(2-hydroxyethoxy)azetidin-1-yl]-4-oxo-1-(1,3-thiazol-2-yl)-1,4-dihydro-1,8-naphthyridine-3-carboxylic acid The title compound was obtained from ethyl 6-fluoro-7-[3-(2-hydroxyethoxy)azetidin-1-yl]-4-oxo-1-(1,3-thiazol-2-yl)-1,4-dihydro-1,8-naphthyridine-3-carboxylate obtained in Example 033 by the method described in Example 028-(2) or a method equivalent thereto.

Property: pale orange solid;

ESI-MS (m/z): 407 [M+H]+

Example 035

Compound 035

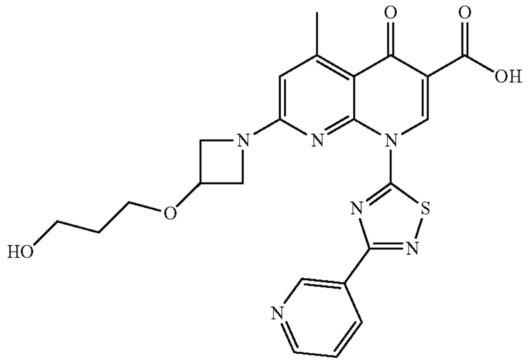

7-[3-(3-Hydroxypropoxy)azetidin-1-yl]-5-methyl-4-oxo-1-[3-(pyridin-3-yl)-1,2,4-thiadiazol-5-yl]-1,4-dihydro-1,8-naphthyridine-3-carboxylic acid The title compound was obtained using 7-chloro-5-methyl-4-oxo-1-[3-(pyridin-3-yl)-1,2,4-thiadiazol-5-yl]-1,4-dihydro-1,8-naphthyridine-3-carboxylic acid obtained in Reference Example 042-(2) and 3-(3-hydroxypropoxy) azetidine hydrochloride obtained in Example 028-(1) by the method described in Example 018-(2) or a method equivalent thereto.

1H-NMR (DMSO-d6): δ 1.70-1.75 (2H, m), 2.89 (3H, s), 3.45-3.63 (4H, m), 4.06-4.33 (2H, m), 4.45-4.58 (2H, m), 4.64-4.77 (1H, m), 6.57 (1H, d, J=1.0 Hz), 7.64 (1H, ddd, J=8.0, 5.0, 1.0 Hz), 8.57 (1H, ddd, J=8.0, 2.0, 1.5 Hz), 8.76 (1H, dd, J=5.0, 1.5 Hz), 9.40 (1H, dd, J=2.0, 0.5 Hz), 9.82 (1H, s)

Example 036

Compound 036

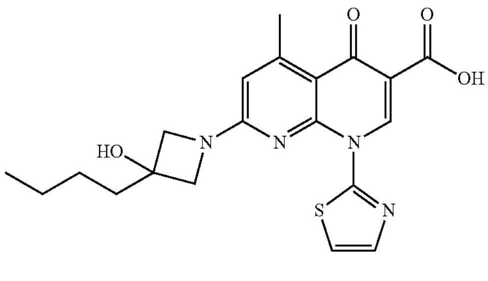

7-(3-Butyl-3-hydroxyazetidin-1-yl)-5-methyl-4-oxo-1-(1,3-thiazol-2-yl)-1,4-dihydro-1,8-naphthyridine-3-carboxylic acid (1) To a solution of 1-(diphenylmethyl)azetidin-3-one (237 mg) in THF (250 mL) was added n-butyllithium (1.6 mol/L solution in hexane, 1.6 mL) at −78° C., and the mixture was stirred at the same temperature for 150 minutes. To the reaction solution was added water, and the mixture was extracted with methylene chloride. The organic layer was washed with brine, dried over sodium sulfate, and concentrated to obtain crude 3-butyl-1-(diphenylmethyl) azetidin-3-ol.

(2) 3-Butylazetidin-3-ol acetate was obtained by the method described in Example 002-(2) or a method equivalent thereto from crude 3-butyl-1-(diphenylmethyl)azetidin-3-ol obtained in the preceding section.

(3) The title compound was obtained by the method described in Example 002-(3) or a method equivalent thereto using crude 3-butylazetidin-3-ol acetate obtained in the preceding section, and 7-chloro-5-methyl-4-oxo-1-(1,3-thiazol-2-yl)-1,4-dihydro-1,8-naphthyridine-3-carboxylic acid obtained in Reference Example 001-(2).

1H-NMR (DMSO-d6): δ 0.90 (3H, t, J=7.0 Hz), 1.27-1.45 (4H, m), 1.74 (2H, t, J=8.0 Hz), 2.77 (3H, s), 3.95-4.30 (4H, m), 5.80 (1H, brs), 6.53 (1H, d, J=1.0 Hz), 7.76 (1H, d, J=3.5 Hz), 7.83 (1H, d, J=3.5 Hz), 9.85 (1H, s)

Example 037

Compound 037

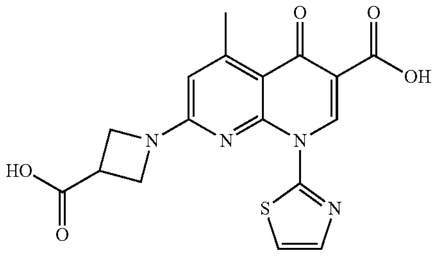

7-(3-Carboxyazetidin-1-yl)-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and azetidine-3-carboxylic acid hydrochloride by the method described in Example 002-(3) or a method equivalent thereto.

1H-NMR (DMSO-d6): δ 2.78 (3H, s), 3.63-3.74 (1H, m), 4.24-4.62 (4H, m), 6.58 (1H, s), 7.76 (1H, d, J=3.5 Hz), 7.84 (1H, d, J=3.5 Hz), 9.85 (1H, s), 12.88 (1H, brs)

Example 038

Compound 038

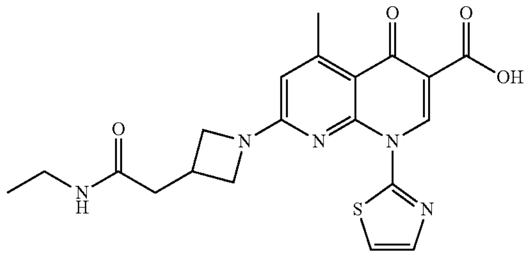

7-{3-[(Ethylcarbamoyl)methyl]azetidin-1-yl}-5-methyl-4-oxo-1-(1,3-thiazol-2-yl)-1,4-dihydro-1,8-naphthyridine-3-carboxylic acid (1) To a solution of ethyl diethylphosphonoacetate (2.0 mL) in THF (20 mL) was added 55% sodium hydride (404 mg) under ice cooling, and the mixture was stirred at room temperature for 20 minutes. To the reaction solution was added 1-(diphenylmethyl)azetidin-3-one (2.0 g), and the mixture was stirred at room temperature for 18 hours. The reaction solution was washed with an aqueous ammonium chloride solution, and the organic layer was then concentrated. The residue was purified by silica gel column chromatography (eluent: ethyl acetate/n-hexane) to obtain 2.6 g of ethyl 2-[1-(diphenylmethyl)azetidin-3-ylidene]acetate.

Property: pale yellow oil (2) To a solution of ethyl 2-[1-(diphenylmethyl)azetidin-3-ylidene]acetate (2.6 g) obtained in the preceding section in methanol (30 mL) was added 10% palladium carbon (200 mg), and the mixture was hydrogenated at room temperature for 150 minutes. The catalyst was filtered off, and the filtrate was then concentrated to obtain 2.5 g of ethyl 2-[1-(diphenylmethyl)azetidin-3-yl]acetate.

Property: pale yellow oil (3) A mixture of 2-[1-(diphenylmethyl)azetidin-3-yl]acetic acid (56 mg) obtained by the method described in Example 028-(2) or a method equivalent thereto from ethyl 2-[1-(diphenylmethyl)azetidin-3-yl]acetate obtained in the preceding section, ethanamine hydrochloride (49 mg), HOBt monohydrate (46 mg), EDC (58 mg), triethylamine (84 μL), and N,N-dimethylformamide (1 mL) was stirred overnight at room temperature. To the reaction solution were added ethyl acetate and n-hexane, and the mixture was washed with an aqueous sodium bicarbonate solution, water and brine. The organic layer was dried over sodium sulfate and concentrated to obtain crude 2-[1-(diphenylmethyl)azetidin-3-yl]-N-ethylacetamide.

(2) The title compound was obtained by the method described in Example 002-(3) or a method equivalent thereto using 2-(azetidin-3-yl)-N-ethylacetamide hydrochloride obtained by the method described in Example 002-(2) or a method equivalent thereto from crude 2-[1-(diphenylmethyl)azetidin-3-yl]-N-ethylacetamide obtained in the preceding section, and 7-chloro-5-methyl-4-oxo-1-(1,3-thiazol-2-yl)-1,4-dihydro-1,8-naphthyridine-3-carboxylic acid obtained in Reference Example 002-(2).

Property: pale brown solid;

Melting point: 214-216° C.

Example 039

Compound 039

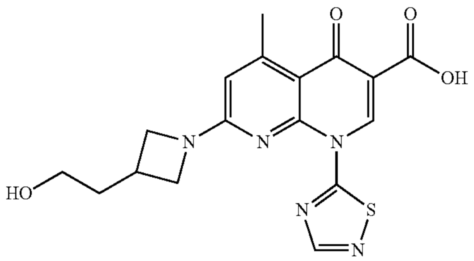

7-[3-(2-Hydroxyethyl)azetidin-1-yl]-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and 2-(azetidin-3-yl)ethan-1-ol hydrochloride by the method described in Example 002-(3) or a method equivalent thereto.

1H-NMR (DMSO-d6): δ 1.34-1.72 (3H, m), 2.82 (3H, s), 3.60-3.67 (2H, m), 3.73-3.78 (2H, m), 3.79-3.87 (2H, m), 7.77 (1H, s), 8.84 (1H, s), 9.82 (1H, s)

Example 040

Compound 040

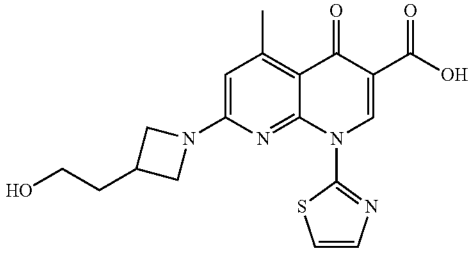

7-[3-(2-Hydroxyethyl)azetidin-1-yl]-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and 2-(azetidin-3-yl)ethan-1-ol hydrochloride by the method described in Example 002-(3) or a method equivalent thereto.

Property: dark brown solid;

ESI-MS (m/z): 385 [M−H]−

Example 041

Compound 041

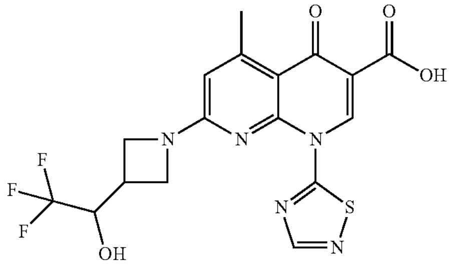

5-Methyl-4-oxo-1-(1,2,4-thiadiazol-5-yl)-7-[3-(2,2,2-trifluoro-1-hydroxyethyl)azetidin-1-yl]-1,4-dihydro-1,8-naphthyridine-3-carboxylic acid (1) To a solution of tert-butyl 3-formylazetidine-1-carboxylate (191 mg) and a 0.5 mol/L solution of (trifluoromethyl)trimethylsilane in THF (2.8 mL) was added a 1 mol/L solution of tetrabutylammonium fluoride in THF (1.4 mL) under ice cooling, and the mixture was stirred at room temperature for 3 days. The reaction solution was poured into diluted hydrochloric acid, and the mixture was extracted with diethyl ether. The organic layer was washed with brine, dried over sodium sulfate, and concentrated. The residue was purified by silica gel column chromatography (eluent: ethyl acetate/n-hexane) to obtain 133 mg of tert-butyl 3-(2,2,2-trifluoro-1-hydroxyethyl)azetidine-1-carboxylate.

1H-NMR (CDCl3): δ 1.45 (9H, s), 2.55 (1H, brs), 2.88-2.96 (1H, m), 3.89 (1H, dd, J=8.5, 6.0 Hz), 4.00-4.08 (3H, m), 4.11 (1H, q, J=6.0 Hz)

(2) The title compound was obtained by the method described in Example 001-(3) or a method equivalent thereto using 1-(azetidin-3-yl)-2,2,2-trifluoroethan-1-ol hydrochloride obtained by the method described in Example 001-(2) or a method equivalent thereto from tert-butyl 3-(2,2,2-trifluoro-1-hydroxyethyl)azetidine-1-carboxylate obtained in the preceding section, and 7-chloro-5-methyl-4-oxo-1-(1,2,4-thiadiazol-5-yl)-1,4-dihydro-1,8-naphthyridine-3-carboxylic acid obtained in Reference Example 002-(2).

1H-NMR (DMSO-d6): δ 2.73 (3H, s), 3.18-3.28 (1H, m), 4.12-4.59 (5H, m), 6.57 (1H, brs), 6.75 (1H, brs), 8.80 (1H, s), 9.68 (1H, s)

Example 042

Compound 042

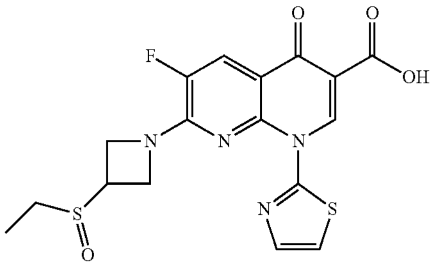

7-[3-(Ethanesulfinyl)azetidin-1-yl]-6-fluoro-4-oxo-(1,3-thiazol-2-yl)-1,4-dihydro-1,8-naphthyridine-3-carboxylic acid (1) A suspension of tert-butyl 3-(ethylsulfanyl)azetidine-1-carboxylate (133 mg) obtained from ethanethiol by the method described in Example 003-(1) or a method equivalent thereto, and a 30% aqueous hydrogen peroxide solution (670 μL) in acetic acid (700 μL) was stirred at room temperature for 5 days. To the reaction solution was added an aqueous sodium thiosulfate solution, and the mixture was extracted with ethyl acetate. The organic layer was washed with an aqueous sodium bicarbonate solution and brine, dried over sodium sulfate, and concentrated. The residue was purified by silica gel column chromatography (eluent: ethyl acetate/n-hexane) to obtain 147 mg of tert-butyl 3-(ethanesulfinyl)azetidine-1-carboxylate.

1H-NMR (CDCl3): δ 1.35 (3H, t, J=7.5 Hz), 1.45 (9H, s), 2.61 (2H, qd, J=7.5, 2.5 Hz), 3.50-3.59 (1H, m), 4.06-4.13 (1H, m), 4.13 (1H, t, J=8.5 Hz), 4.18 (1H, t, J=8.5 Hz), 4.45 (1H, dd, J=9.5, 5.5 Hz)

(2) The title compound was obtained by the method described in Example 001-(3) or a method equivalent thereto using 3-(ethanesulfinyl)azetidine hydrochloride obtained by the method described in Example 001-(2) or a method equivalent thereto from tert-butyl 3-(ethanesulfinyl)azetidine-1-carboxylate obtained in the preceding section, and 7-chloro-6-fluoro-4-oxo-1-(1,3-thiazol-2-yl)-1,4-dihydro-1,8-naphthyridine-3-carboxylic acid obtained in Reference Example 003-(2).

1H-NMR (DMSO-d6): δ 1.22 (3H, t, J=7.5 Hz), 3.25-3.37 (2H, m), 4.16 (1H, m), 4.40-5.00 (4H, m), 7.78 (1H, d, J=3.5 Hz), 7.85 (1H, d, J=3.5 Hz), 8.12 (1H, d, J=11.5 Hz), 9.80 (1H, s)

Example 043

Compound 043

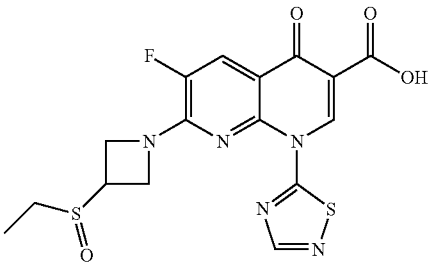

7-[3-(Ethanesulfinyl)azetidin-1-yl]-6-fluoro-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and 3-(ethanesulfinyl)azetidine hydrochloride obtained in Example 042-(2) by the method described in Example 001-(3) or a method equivalent thereto.

1H-NMR (DMSO-d6): δ 1.22 (3H, t, J=7.5 Hz), 3.26-3.41 (2H, m), 4.13-4.22 (1H, m), 4.54-5.06 (4H, m), 8.19 (1H, d, J=11.5 Hz), 8.85 (1H, s), 9.75 (1H, s)

Example 044

Compound 044

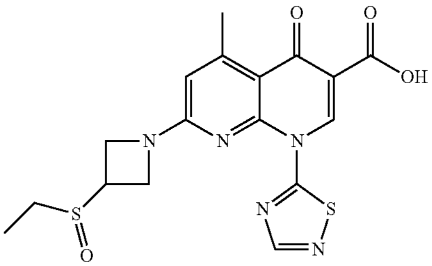

7-[3-(Ethanesulfinyl)azetidin-1-yl]-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and 3-(ethanesulfinyl)azetidine hydrochloride obtained in Example 042-(2) by the method described in Example 001-(3) or a method equivalent thereto.

1H-NMR (DMSO-d6): δ 1.22 (3H, t, J=7.5 Hz), 2.79 (3H, s), 3.18-3.41 (2H, m), 4.00-4.90 (5H, m), 7.77 (1H, s), 8.83 (1H, s), 9.77 (1H, s)

Example 045

Compound 045

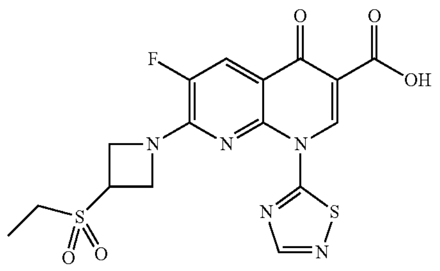

7-[3-(Ethanesulfonyl)azetidin-1-yl]-6-fluoro-4-oxo-1-(1,2,4-thiadiazol-5-yl)-1,4-dihydro-1,8-naphthyridine-3-carboxylic acid (1) tert-Butyl 3-(ethanesulfonyl)azetidine-1-carboxylate was obtained from tert-butyl 3-(ethanesulfinyl)azetidine-1-carboxylate obtained in Example 042-(1) by the method described in Example 042-(1) or a method equivalent thereto.

1H-NMR (CDCl3): δ 1.46 (9H, s), 1.41 (3H, t, J=7.5 Hz), 2.99 (2H, q, J=7.5 Hz), 3.87-3.96 (1H, m), 4.19 (2H, t, J=9.0 Hz), 4.32 (2H, dd, J=9.0, 5.5 Hz)

(2) The title compound was obtained using 7-chloro-6-fluoro-4-oxo-1-(1,2,4-thiadiazol-2-yl)-1,4-dihydro-1,8 naphthyridine-3-carboxylic acid obtained in Reference Example 004-(2) and 3-(ethanesulfonyl)azetidine hydrochloride obtained from tert-butyl 3-(ethanesulfonyl)azetidine-1-carboxylate obtained in the preceding section by the method described in Example 001-(2) or a method equivalent thereto by the method described in Example 001-(3) or a method equivalent thereto.

1H-NMR (DMSO-d6): δ 1.27 (3H, t, J=7.5 Hz), 3.26-3.41 (2H, m), 4.60-4.69 (1H, m), 4.69-5.03 (4H, m), 8.22 (1H, d, J=11.0 Hz), 8.85 (1H, s), 9.75 (1H, s)

Example 046

Compound 046

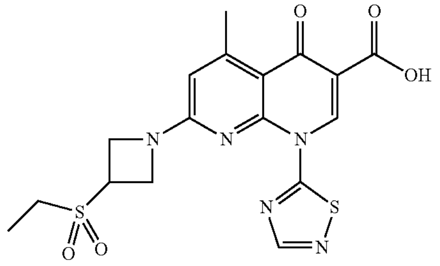

7-[3-(Ethanesulfonyl)azetidin-1-yl]-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8- naphthyridine-3-carboxylic acid obtained in Reference Example 002-(2) and 3-(ethanesulfonyl)azetidine hydrochloride obtained in Example 045-(2) by the method described in Example 001-(3) or a method equivalent thereto.

1H-NMR (DMSO-d6): δ 1.27 (3H, t, J=7.0 Hz), 2.79 (3H, s), 3.24-3.39 (2H, m), 4.41-4.86 (5H, m), 6.68 (1H, s), 8.82 (1H, s), 9.76 (1H, s)

Example 047

Compound 047

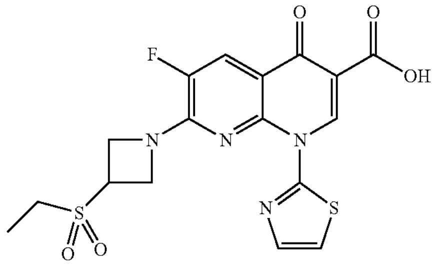

7-[3-(Ethanesulfonyl)azetidin-1-yl]-6-fluoro-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and 3-(ethanesulfonyl)azetidine hydrochloride obtained in Example 045-(2) by the method as claimed in Example 001-(3) or a method equivalent thereto.

1H-NMR (DMSO-d6): δ 1.26 (3H, t, J=7.5 Hz), 3.23-3.41 (2H, m), 4.56-4.99 (5H, m), 7.80 (1H, d, J=3.5 Hz), 7.86 (1H, d, J=3.5 Hz), 8.18 (1H, d, J=11.0 Hz), 9.82 (1H, s)

Example 048

Compound 048

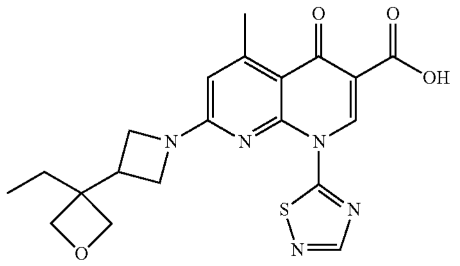

7-[3-(3-Ethyloxetan-3-yl)azetidin-1-yl]-5-methyl-4-oxo-1-(1,2,4-thiadiazol-5-yl)-1,4-dihydro-1,8-naphthyridine-3-carboxylic acid (1) To a suspension of (methoxymethyl)triphenylphosphonium chloride (5.1 g) in THF (20 mL) was added a solution of n-butyllithium in n-hexane (1.6 mol/L, 8.8 mL) under ice cooling, and the mixture was stirred at the same temperature for 10 minutes. A solution of tert-butyl 3-propanoylazetidine-1-carboxylate (1.0 g) in THF (10 mL) obtained by the method described in Example 020-(1) or a method equivalent thereto using tert-butyl 3-[methoxy(methyl)carbamoyl]azetidine-1-carboxylate and ethyl magnesium bromide was added to the reaction solution under ice cooling, and the mixture was stirred at room temperature for 7 hours. To the reaction solution was added an aqueous ammonium chloride solution, and the mixture was extracted with ethyl acetate. The organic layer was washed with water and brine, dried over sodium sulfate, and concentrated. The residue was purified by silica gel column chromatography (eluent: ethyl acetate/n-hexane), and a mixture of the obtained tert-butyl 3-[1-(methyloxo)but-1-en-2-yl]azetidine-1-carboxylate (1.2 g), water (20 mL), and acetic acid (10 mL) was stirred at 50° C. for 1 day. The reaction solution was concentrated, and the residue was purified by silica gel column chromatography (eluent: ethyl acetate/n-hexane) to obtain 180 mg of tert-butyl 3-(1-oxobutan-2-yl)azetidine-1-carboxylate.

1H-NMR (CDCl3): δ 0.94 (3H, t, J=7.5 Hz), 1.43 (9H, s), 1.61-1.70 (2H, m), 2.51-2.57 (1H, m), 2.69-2.78 (1H, m), 3.62-3.70 (2H, m), 4.02-4.10 (2H, m), 9.65 (1H, d, J=1.9 Hz)

(2) To a solution of tert-butyl 3-(1-oxobutan-2-yl)azetidine-1-carboxylate (175 mg) obtained in the preceding section, and 37% formalin (70 μL) in methanol (1 mL) was added a 1 mol/L aqueous sodium hydroxide solution (80 μL), and the mixture was stirred at room temperature for 14 days. To the reaction solution was added water, and the mixture was extracted with ethyl acetate. The organic layer was washed with water and brine, dried over sodium sulfate, and concentrated. The residue was purified by silica gel column chromatography (eluent: ethyl acetate/n-hexane). To a solution of the obtained tert-butyl 3-[2-(hydroxymethyl)-1-oxobutan-2-yl]azetidine-1-carboxylate (60 mg) in a methanol/methylene chloride mixed solvent (50%, 2 mL) was added sodium borohydride (26 mg) under ice cooling, and the mixture was stirred at room temperature for 1 day. To the reaction solution was added an aqueous sodium bicarbonate solution, and the mixture was extracted with ethyl acetate. The organic layer was washed with water and brine, dried over sodium sulfate, and concentrated. The residue was purified by silica gel column chromatography (eluent: ethyl acetate/n-hexane) to obtain 31 mg of tert-butyl 3-(2-ethyl-1,3-dihydroxypropan-2-yl)azetidine-1-carboxylate.

1H-NMR (CDCl3): δ 0.85 (3H, t, J=7.7 Hz), 1.41 (9H, s), 2.15-2.20 (2H, m), 2.79-2.86 (1H, m), 3.68-3.74 (4H, m), 3.88-3.96 (4H, m)

(3) To a solution of tert-butyl 3-(2-ethyl-1,3-dihydroxypropan-2-yl)azetidine-1-carboxylate (30 mg) obtained in the preceding section in toluene (1 mL) were added carbon tetrabromide (56 mg) and triphenylphosphine (44 mg) under ice cooling, and the mixture was stirred at 100° C. for 1 day. To the reaction solution was added an aqueous ammonium chloride solution, and the mixture was extracted with ethyl acetate. The organic layer was washed with water, dried over sodium sulfate, and concentrated. The residue was purified by silica gel column chromatography (eluent: ethyl acetate/n-hexane). To a solution of the obtained tert-butyl 3-[2-(bromomethyl)-1-hydroxybutan-2-yl]azetidine-1-carboxylate (23 mg) in THF was added 55% sodium hydride (4 mg), and the mixture was stirred overnight at room temperature. To the reaction solution was added water, and the mixture was extracted with ethyl acetate. The organic layer was washed with water and brine, dried over sodium sulfate, and concentrated. The residue was purified by silica gel column chromatography (eluent: ethyl acetate/n-hexane) to obtain 13 mg of tert-butyl 3-(3-ethyloxetan-3-yl)azetidine-1-carboxylate.

1H-NMR (CDCl3): δ 0.89 (3H, t, J=7.5 Hz), 1.45 (9H, s), 1.63 (2H, q, J=7.5 Hz), 2.67-2.74 (1H, m), 3.76-4.02 (2H, m), 4.04 (2H, d, J=8.8 Hz), 4.45 (2H, d, J=6.3 Hz), 4.39-4.59 (2H, m)

(4) The title compound was obtained by the method described in Example 002-(3) or a method equivalent thereto using 3-(3-ethyloxetan-3-yl)azetidine trifluoroacetate obtained by the method described in Example 001-(2) or a method equivalent thereto from tert-butyl 3-(3-ethyloxetan-3-yl)azetidine-1-carboxylate obtained in the preceding section, and 7-chloro-5-methyl-4-oxo-1-(1,2,4-thiadiazol-5-yl)-1,4-dihydro-1,8-naphthyridine-3-carboxylic acid obtained in Reference Example 002-(2).

1H-NMR (DMSO-d6): δ 0.92 (3H, t, J=7.5 Hz), 1.68 (2H, q, J=7.5 Hz), 2.76 (3H, d, J=0.9 Hz), 3.09-3.17 (1H, m), 4.20-4.26 (1H, m), 4.34-4.45 (5H, m), 4.48-4.53 (1H, m), 4.58-4.64 (1H, m), 6.60 (1H, d, J=0.9 Hz), 8.82 (1H, s), 9.72 (1H, s), 15.11 (1H, brs)

Example 049

Compound 049

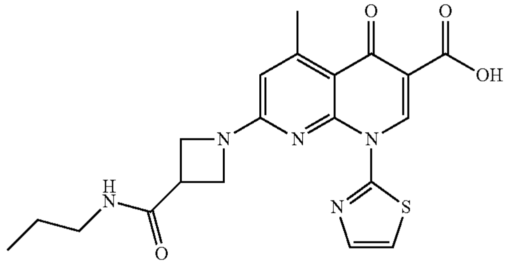

5-Methyl-4-oxo-7-[3-(propylcarbamoyl)azetidin-1-yl]-1-(1,3-thiazol-2-yl)-1,4-dihydro-1,8-naphthyridine-3-carboxylic acid The title compound was obtained by the method described in Example 001-(3) or a method equivalent thereto using 7-chloro-5-methyl-4-oxo-1-(1,3-thiazol-2-yl)-1,4-dihydro-1,8-naphthyridine-3-carboxylic acid obtained in Reference Example 001-(2) and N-propylazetidine-3-carboxamide hydrochloride obtained from propan-1-amine by the methods described in Examples 005-(1) and 001-(2) or methods equivalent thereto.

1H-NMR (DMSO-d6): δ 0.86 (3H, t, J=7.5 Hz), 1.39-1.49 (2H, m), 2.76 (3H, s), 3.02-3.12 (2H, m), 3.52-3.60 (1H, m), 4.16-4.52 (4H, m), 6.52 (1H, s), 7.74 (1H, d, J=3.5 Hz), 7.83 (1H, d, J=3.5 Hz), 8.12 (1H, brt, J=5.5 Hz), 9.84 (1H, s)

Example 050

Compound 050

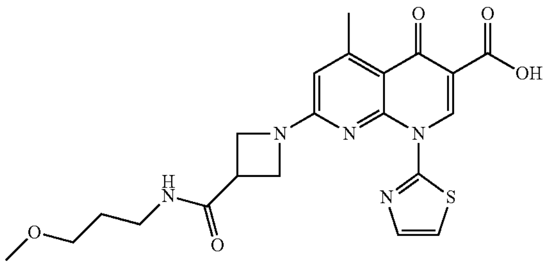

7-{3-[(3-Methoxypropyl)carbamoyl]azetidin-1-yl}-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-(3-methoxypropyl)azetidine-3-carboxamide hydrochloride obtained from 3-methoxypropan-1-amine by the method described in Example 005-(l) and Example 001-(2) or a method equivalent thereto by the method as claimed in Example 002-(3) or a method equivalent thereto.

1H-NMR (DMSO-d6): δ 1.61-1.70 (2H, m), 2.78 (3H, s), 3.10-3.19 (2H, m), 3.22 (3H, s), 3.51-3.60 (1H, m), 4.17-4.52 (4H, m), 6.55 (1H, s), 7.75 (1H, d, J=3.5 Hz), 7.84 (1H, d, J=3.5 Hz), 8.14 (1H, brt, J=5.5 Hz), 9.85 (1H, s)

Example 051

Compound 051

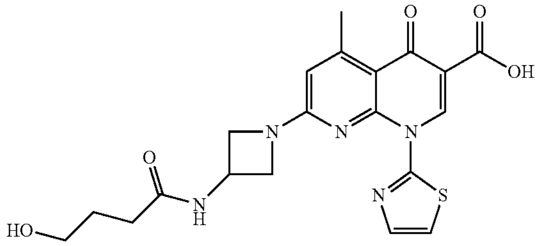

7-[3-(4-Hydroxybutanamido)azetidin-1-yl]-5-methyl-4-oxo-1-(1,3-thiazol-2-yl)-1,4-dihydro-1,8-naphthyridine-3-carboxylic acid (1) Crude N-[1-(diphenylmethyl)azetidin-3-yl]-4-hydroxybutanamide was obtained from oxolan-2-one by the method described in Example 011-(1) or a method equivalent thereto.

(2) Crude N-(azetidin-3-yl)-4-hydroxybutanamide was obtained by the method described in Example 002-(2) or a method equivalent thereto from crude N-[1-(diphenylmethyl)azetidin-3-yl]-4-hydroxybutanamide obtained in the preceding section.

(3) The title compound was obtained by the method described in Example 002-(3) or a method equivalent thereto using 7-chloro-5-methyl-4-oxo-1-(1,3-thiazol-2-yl)-1,4-dihydro-1,8-naphthyridine-3-carboxylic acid obtained in Reference Example 001-(2) and crude N-(azetidin-3-yl)-4-hydroxybutanamide acetate obtained in the preceding section.

1H-NMR (DMSO-d6): δ 1.60-1.70 (2H, m), 2.12-2.19 (2H, m), 2.78 (3H, s), 3.93-4.73 (6H, m), 6.57 (1H, s), 7.72-7.89 (2H, m), 8.54-8.63 (1H, m), 9.85 (1H, s)

Example 052

Compound 052

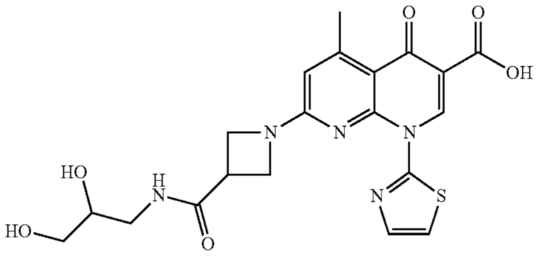

7-{3-[(2,3-Dihydroxypropyl)carbamoyl]azetidin-1-yl}-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-(2,3-dihydroxypropyl)azetidine-3-carboxamide hydrochloride obtained from (2,2-dimethyl-1,3-dioxolan-4-yl)methylamine by the method described in Example 005-(1) and Example 001-(2) or a method equivalent thereto by the method described in Example 002-(3) or a method equivalent thereto.

1H-NMR (DMSO-d6): δ 3.41-3.86 (5H, m), 2.78 (3H, s), 4.22-4.62 (5H, m), 6.58 (1H, s), 7.74-7.78 (1H, m), 7.84 (1H, d, J=3.5 Hz), 7.88 (1H, dd, J=7.5, 3.5 Hz), 9.85 (1H, s)

Example 053

Compound 053

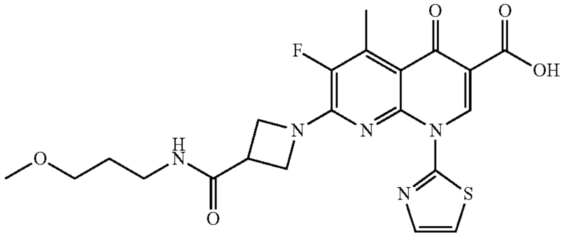

6-Fluoro-7-{(3-[(3-methoxypropyl)carbamoyl]azetidin-1-yl}-5-methyl-4-oxo-1-(1,3-thiazol-2-yl)-1,4-dihydro-1,8-naphthyridine-3-carboxylic acid The title compound was obtained using 7-chloro-6-fluoro-5-methyl-4-oxo-1-(1,3-thiazol-2-yl)-1,4-dihydro-1,8-naphthyridine-3-carboxylic acid obtained in Reference Example 007-(2) and N-(3-methoxypropyl)azetidine-3-carboxamide hydrochloride obtained in Example 050 by the method described in Example 002-(3) or a method equivalent thereto.

1H-NMR (DMSO-d6): δ 1.63-1.69 (2H, m), 2.69 (1H, d, J=3.0 Hz), 3.22-3.23 (5H, m), 3.54-3.63 (1H, m), 4.15-4.34 (2H, m), 4.35-4.77 (4H, m), 7.77 (1H, d, J=3.5 Hz), 7.85 (1H, d, J=3.5 Hz), 8.14 (1H, t, J=5.5 Hz), 9.81 (1H, s)

Example 054

Compound 054

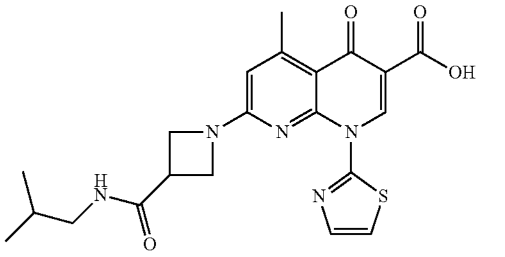

5-Methyl-7-{3-[(2-methylpropyl)carbamoyl]azetidin-1-yl}-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-(2-methylpropyl)azetidine-3-carboxamide hydrochloride obtained from 2-methylpropan-1-amine by the method described in Example 005-(1) and Example 001-(2) or a method equivalent thereto by the method described in Example 002-(3) or a method equivalent thereto.

1H-NMR (DMSO-d6): δ 0.86 (6H, d, J=6.5 Hz), 1.66-1.75 (1H, m), 2.78 (3H, s), 2.90-3.01 (2H, m), 3.56-3.64 (1H, m), 4.17-4.51 (4H, m), 6.54 (1H, s), 7.75 (1H, d, J=3.5 Hz), 7.84 (1H, d, J=3.5 Hz), 8.12 (1H, brt, J=6.0 Hz), 9.85 (1H, s)

Example 055

Compound 055

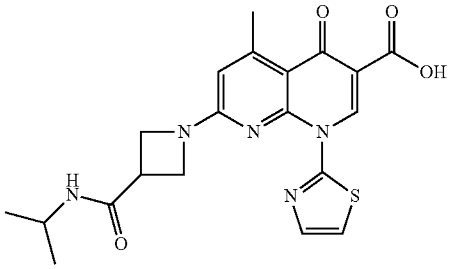

5-Methyl-4-oxo-7-{3-[(propan-2-yl)carbamoyl]azetidin-1-yl}-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-(propan-2-yl)azetidine-3-carboxamide hydrochloride obtained from propan-2-amine by the method described in Example 005-(1) and Example 001-(2) or a method equivalent thereto by the method described in Example 002-(3) or a method equivalent thereto.

1H-NMR (DMSO-d6): δ 1.08 (6H, d, J=6.5 Hz), 2.77 (3H, s), 3.48-3.57 (1H, m), 3.84-3.93 (1H, m), 4.18-4.48 (4H, m), 6.53 (1H, s), 7.74 (1H, d, J=3.5 Hz), 7.83 (1H, d, J=3.5 Hz), 8.02 (1H, brd, J=7.5 Hz), 9.84 (1H, s)

Example 056

Compound 056

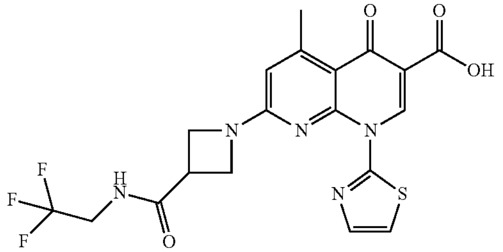

5-Methyl-4-oxo-1-(1,3-thiazol-2-yl)-7-{3-[(2,2,2-trifluoroethyl)carbamoyl]azetidin-1-yl}-1,4-dihydro-1,8-naphthyridine-3-carboxylic acid The title compound was obtained by the method described in Example 002-(3) or a method equivalent thereto using N-(2,2,2-trifluoroethyl)azetidine-3-carboxamide hydrochloride obtained from 2,2,2-trifluoroethan-1-amine by the methods described in Examples 005-(1) and 001-(2) or methods equivalent thereto, and 7-chloro-5-methyl-4-oxo-1-(1,3-thiazol-2-yl)-1,4-dihydro-1,8-naphthyridine-3-carboxylic acid obtained in Reference Example 001-(2).

1H-NMR (DMSO-d6): δ 2.78 (3H, s), 3.63-3.74 (1H, m), 3.92-4.05 (2H, m), 4.19-4.55 (4H, m), 6.57 (1H, s), 7.76 (1H, d, J=3.5 Hz), 7.84 (1H, d, J=3.5 Hz), 8.85 (1H, t, J=6.5 Hz), 9.85 (1H, s)

Example 057

Compound 057

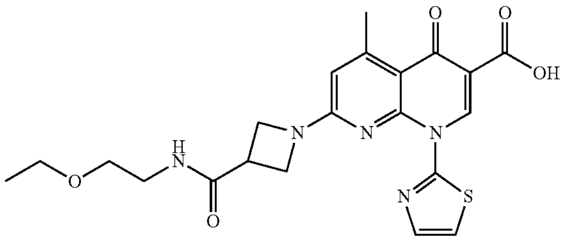

7-{3-[(2-Ethoxyethyl)carbamoyl]azetidin-1-yl}-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-(2-ethoxyethyl)azetidine-3-carboxamide hydrochloride obtained in Example 018-(1) by the method described in Example 002-(3) or a method equivalent thereto.

1H-NMR (DMSO-d6): δ 1.12 (3H, q, J=5.5 Hz), 2.76 (3H, s), 3.25-3.30 (2H, m), 3.38-3.47 (4H, m), 3.57-3.64 (1H, m), 4.18-4.50 (4H, m), 6.51 (1H, s), 7.74 (1H, d, J=3.5 Hz), 7.83 (1H, d, J=3.5 Hz), 8.24 (1H, t, J=5.5 Hz), 9.82 (1H, s)

Example 058

Compound 058

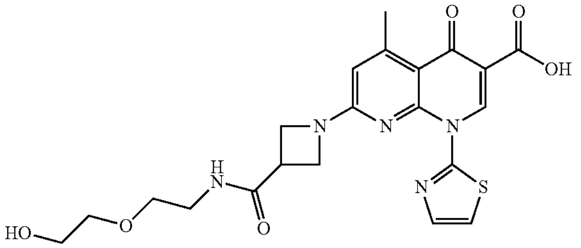

7-(3-{[2-(2-Hydroxyethoxy)ethyl] carbamoyl}azetidin-1-yl)-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-[2-(2-hydroxyethoxy)ethyl]azetidine-3-carboxamide hydrochloride obtained from 2-(2-aminoethoxy)ethan-1-ol by the method described in Example 005-(1) and Example 001-(2) or a method equivalent thereto by the method described in Example 002-(3) or a method equivalent thereto.

1H-NMR (DMSO-d6): δ 2.76 (3H, s), 3.28 (2H, dt, J=6.0, 5.5 Hz), 3.43 (2H, t, J=5.0 Hz), 3.45 (2H, t, J=5.5 Hz), 3.50 (2H, dt, J=5.0 Hz), 3.57-3.64 (1H, m), 4.12-4.55 (4H, m), 6.53 (1H, s), 7.74 (1H, d, J=3.5 Hz), 7.83 (1H, d, J=3.5 Hz), 8.22 (1H, t, J=6.0 Hz), 9.84 (1H, s)

Example 059

Compound 059

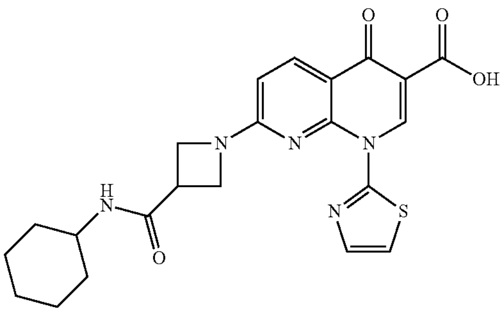

7-[3-(Cyclohexylcarbamoyl)azetidin-1-yl]-4-oxo-1-(1,3-thiazol-2-yl)-1,4-dihydro-1,8-naphthyridine-3-carboxylic acid The title compound was obtained using 7-chloro-4-oxo-1-(1,3-thiazol-2-yl)-1,4-dihydro-1,8-naphthyridine-3-carboxylic acid obtained in Reference Example 001-(2) and N-cyclohexylazetidine-3-carboxamide hydrochloride obtained from cyclohexanamine by the method described in Example 005-(1) and Example 001-(2) or a method equivalent thereto by the method described in Example 002-(3) or a method to equivalent thereto.

1H-NMR (DMSO-d6): δ 1.08-1.34 (5H, m), 1.50-1.60 (1H, m), 1.63-1.72 (2H, m), 1.72-1.81 (2H, m), 3.53-3.64 (1H, m), 4.18-4.53 (4H, m), 6.75 (1H, d, J=8.5 Hz), 7.77 (1H, d, J=3.5 Hz), 7.85 (1H, d, J=3.5 Hz), 8.02 (1H, d, J=7.5 Hz), 8.34 (1H, d, J=8.5 Hz), 9.85 (1H, s)

Example 060

Compound 060

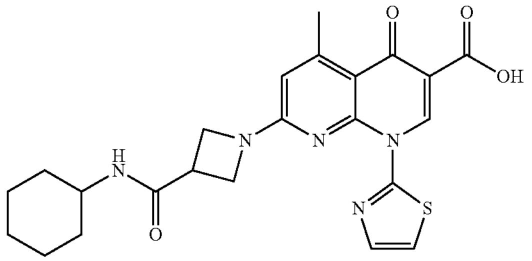

7-[3-(Cyclohexylcarbamoyl)azetidin-1-yl]-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-cyclohexylazetidine-3-carboxamide hydrochloride obtained in Example 059 by the method described in Example 002-(3) or a method equivalent thereto.

1H-NMR (DMSO-d6): δ 1.09-1.33 (5H, m), 1.50-1.81 (5H, m), 2.76 (3H, s), 3.51-3.64 (2H, m), 4.11-4.51 (4H, m), 6.52 (1H, s), 7.74 (1H, d, J=3.5 Hz), 7.83 (1H, d, J=3.5 Hz), 8.02 (1H, d, J=8.0 Hz), 9.83 (1H, s)

Example 061

Compound 061

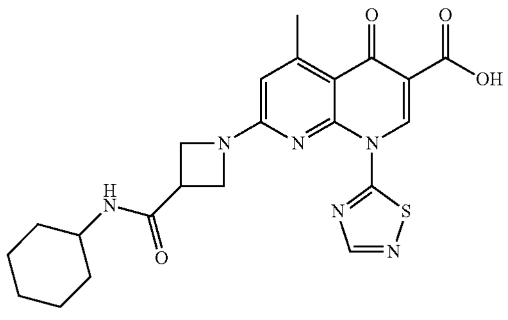

7-[3-(Cyclohexylcarbamoyl)azetidin-1-yl]-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-cyclohexylazetidine-3-carboxamide hydrochloride obtained in Example 059 by the method described in Example 002-(3) or a method equivalent thereto.

1H-NMR (DMSO-d6): δ 1.08-1.83 (10H, m), 2.77 (3H, s), 2.85-3.08 (1H, m), 3.54-3.66 (1H, m), 4.22-4.63 (4H, m), 6.58 (1H, s), 8.03 (1H, d, J=8.0 Hz), 8.81 (1H, s), 9.75 (1H, s)

Example 062

Compound 062

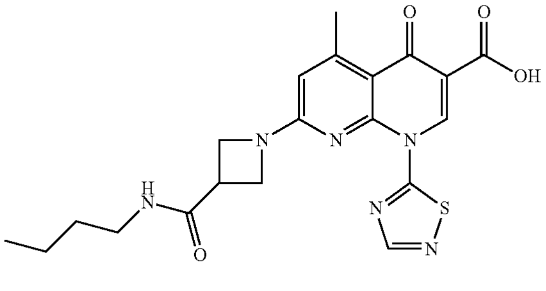

7-[3-(Butylcarbamoyl)azetidin-1-yl]-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-butylazetidine-3-carboxamide hydrochloride obtained from butan-1-amine by the method described in Example 005-(1) and Example 001-(2) or a method equivalent thereto by the method described in Example 002-(3) or a method equivalent thereto.

1H-NMR (DMSO-d6): δ 0.88 (3H, t, J=7.5 Hz), 1.30 (2H, td, J=7.5, 7.5 Hz), 1.42 (2H, dd, J=7.5, 7.5 Hz), 2.77 (3H, s), 3.07-3.17 (2H, m), 3.55-3.63 (1H, m), 4.18-4.65 (4H, m), 6.58 (1H, s), 8.13 (1H, t, J=6.0 Hz), 8.81 (1H, s), 9.74 (1H, s)

Example 063

Compound 063

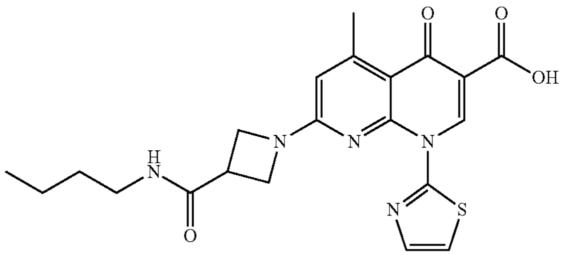

7-[3-(Butylcarbamoyl)azetidin-1-yl]-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-butylazetidine-3-carboxamide hydrochloride obtained in Example 062 by the method described in Example 002-(3) or a method equivalent thereto.

1H-NMR (DMSO-d6): δ 0.89 (1H, t, J=7.5 Hz), 1.25-1.34 (2H, m), 1.38-1.45 (2H, m), 2.78 (3H, s), 3.08-3.15 (2H, m), 3.52-3.60 (1H, m), 4.17-4.51 (4H, m), 6.55 (1H, d, J=1.0 Hz), 7.75 (1H, d, J=3.5 Hz), 7.84 (1H, d, J=3.5 Hz), 8.11 (1H, t, J=5.5 Hz), 9.85 (1H, s)

Example 064

Compound 064

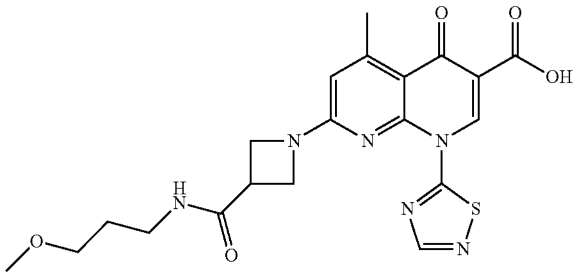

7-{3-[(3-Methoxypropyl)carbamoyl]azetidin-1-yl}-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-(3-methoxypropyl)azetidine-3-carboxamide hydrochloride obtained in Example 050 by the method described in Example 002-(3) or a method equivalent thereto.

1H-NMR (DMSO-d6): δ 1.67 (2H, quin, J=6.5 Hz), 2.73 (3H, s), 3.16 (2H, q, J=6.5 Hz), 3.23 (3H, s), 3.27-3.49 (2H, m), 3.55-3.63 (1H, m), 4.20-4.60 (4H, m), 6.53 (1H, s), 8.17 (1H, t, J=5.5 Hz), 8.79 (1H, s), 9.67 (1H, s)

Example 065

Compound 065

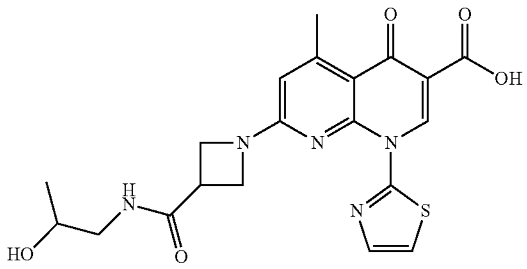

7-{3-[(2-Hydroxypropyl)carbamoyl]azetidin-1-yl}-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-(2-hydroxypropyl)azetidine-3-carboxamide hydrochloride obtained from 1-aminopropan-2-ol by the method described in Example 005-(1) and Example 001-(2) or a method equivalent thereto by the method described in Example 002-(3) or a method equivalent thereto.

1H-NMR (DMSO-d6): δ 0.99-1.09 (3H, m), 2.77 (3H, d, J=2.0 Hz), 2.85-3.13 (2H, m), 3.57-3.83 (2H, m), 4.21-4.58 (4H, m), 6.51-6.58 (1H, m), 7.74-7.77 (1H, m), 7.84 (1H, d, J=3.5 Hz), 8.13 (1H, t, J=6.0 Hz), 9.84 (1H, d, J=2.0 Hz)

Example 066

Compound 066

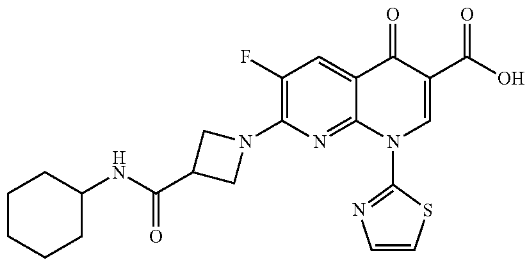

7-[3-(Cyclohexylcarbamoyl)azetidin-1-yl]-6-fluoro-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-cyclohexylazetidine-3-carboxamide hydrochloride obtained in Example 059 by the method described in Example 002-(3) or a method equivalent thereto.

1H-NMR (DMSO-d6): δ 1.10-1.33 (5H, m), 1.51-1.81 (5H, m), 3.53-3.64 (2H, m), 4.24-4.81 (4H, m), 7.79 (1H, d, J=3.0 Hz), 7.86 (1H, d, J=3.0 Hz), 8.01 (1H, d, J=8.0 Hz), 8.11 (1H, d, J=11.0 Hz), 9.83 (1H, s), 14.81 (1H, brs)

Example 067

Compound 067

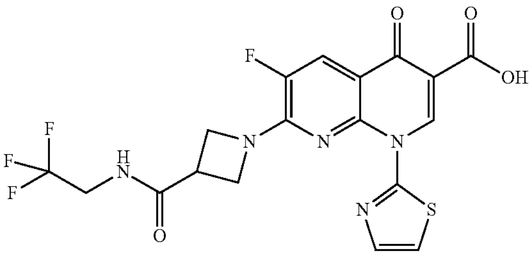

6-Fluoro-4-oxo-1-(1,3-thiazol-2-yl)-7-{3-[(2,2,2-trifluoroethyl)carbamoyl]azetidin-1-yl}-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-(2,2,2-trifluoroethyl)azetidine-3-carboxamide hydrochloride obtained in Example 056 by the method described in Example 002-(3) or a method equivalent thereto.

1H-NMR (DMSO-d6): δ 3.66-3.78 (1H, m), 3.94-4.05 (2H, m), 4.42-4.84 (4H, m), 7.80 (1H, d, J=11.5 Hz), 7.86 (1H, d, J=3.5 Hz), 8.12 (1H, d, J=3.5 Hz), 8.85 (1H, t, J=6.0 Hz), 9.83 (1H, s)

Example 068

Compound 068

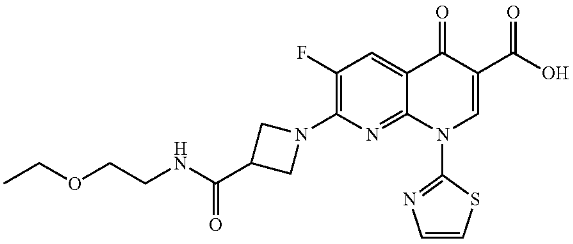

7-{3-[(2-Ethoxyethyl)carbamoyl]azetidin-1-yl}-6-fluoro-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-(2-ethoxyethyl)azetidine-3-carboxamide hydrochloride obtained in Example 018-(1) by the method described in Example 002-(3) or a method equivalent thereto.

1H-NMR (DMSO-d6): δ 1.13 (3H, t, J=7.0 Hz), 3.26-3.30 (2H, m), 3.40-3.48 (4H, m), 3.60-3.70 (1H, m), 4.34-4.83 (4H, m), 7.77 (1H, d, J=3.0 Hz), 7.85 (1H, d, J=3.0 Hz), 8.07 (1H, d, J=11.5 Hz), 8.25 (1H, t, J=5.0 Hz), 9.78 (1H, s), 14.73 (1H, brs)

Example 069

Compound 069

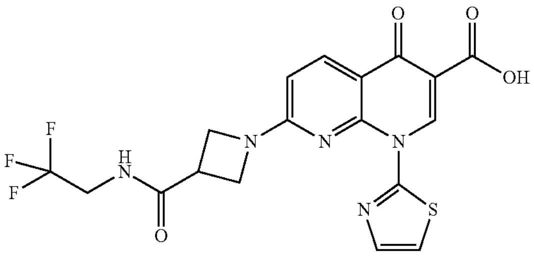

4-Oxo-1-(1,3-thiazol-2-yl)-7-{3-[(2,2,2-trifluoroethyl)carbamoyl]azetidin-1-yl}-1,4-dihydro-1,8-naphthyridine-3-carboxylic acid The title compound was obtained using 7-chloro-4-oxo-1-(1,3-thiazol-2-yl)-1,4-dihydro-1,8-naphthyridine-3-carboxylic acid obtained in Reference Example 005-(2) and N-(2,2,2-trifluoroethyl)azetidine-3-carboxamide hydrochloride obtained in Example 056 by the method described in Example 002-(3) or a method equivalent thereto.

1H-NMR (DMSO-d6): δ 3.66-3.75 (1H, m), 3.94-4.04 (2H, m), 4.23-4.57 (4H, m), 6.79 (1H, d, J=9.0 Hz), 7.79 (1H, d, J=3.5 Hz), 7.86 (1H, d, J=3.5 Hz), 8.36 (1H, d, J=9.0 Hz), 8.87 (1H, t, J=6.5 Hz), 9.87 (1H, s), 14.99 (1H, brs)

Example 070

Compound 070

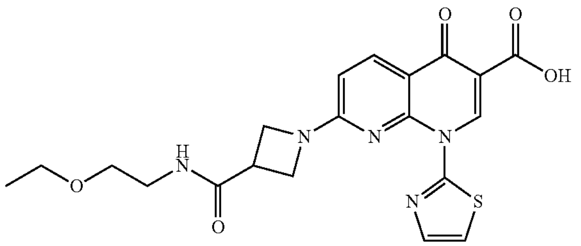

7-{3-[(2-Ethoxyethyl)carbamoyl]azetidin-1-yl}-4-oxo-1-(1,3-thiazol-2-yl)-1,4-dihydro-1,8-naphthyridine-3-carboxylic acid The title compound was obtained using 7-chloro-4-oxo-1-(1,3-thiazol-2-yl)-1,4-dihydro-1,8-naphthyridine-3-carboxylic acid obtained in Reference Example 005-(2) and N-(2-ethoxyethyl)azetidine-3-carboxamide hydrochloride obtained in Example 018-(1) by the method described in Example 002-(3) or a method equivalent thereto.

1H-NMR (DMSO-d6): δ 1.13 (1H, t, J=7.0 Hz), 3.25-3.30 (2H, m), 3.39-3.47 (4H, m), 3.56-3.67 (1H, m), 4.22-4.54 (4H, m), 6.75 (1H, d, J=9.0 Hz), 7.77 (1H, d, J=3.0 Hz), 7.85 (1H, d, J=3.0 Hz), 8.25 (1H, t, J=5.0 Hz), 8.33 (1H, d, J=9.0 Hz), 9.84 (1H, s), 15.00 (1H, brs)

Example 071

Compound 071

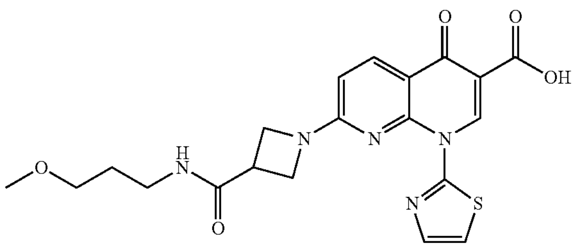

7-{3-[(3-Methoxypropyl)carbamoyl]azetidin-1-yl}-4-oxo-1-(1,3-thiazol-2-yl)-1,4-dihydro-1,8-naphthyridine-3-carboxylic acid The title compound was obtained using 7-chloro-4-oxo-1-(1,3-thiazol-2-yl)-1,4-dihydro-1,8-naphthyridine-3-carboxylic acid obtained in Reference Example 005-(2) and N-(3-methoxypropyl)azetidine-3-carboxamide hydrochloride obtained in Example 050 by the method described in Example 002-(3) or a method equivalent thereto.

1H-NMR (DMSO-d6): δ 1.63-1.70 (2H, m), 3.16 (2H, q, J=6.5 Hz), 3.23 (3H, s), 3.53-3.63 (1H, m), 4.24-4.51 (4H, m), 6.76 (1H, d, J=9.0 Hz), 7.77 (1H, d, J=3.5 Hz), 7.85 (1H, d, J=3.5 Hz), 8.16 (1H, t, J=5.5 Hz), 8.34 (1H, d, J=9.0 Hz), 9.85 (1H, s), 15.01 (1H, brs)

Example 072

Compound 072

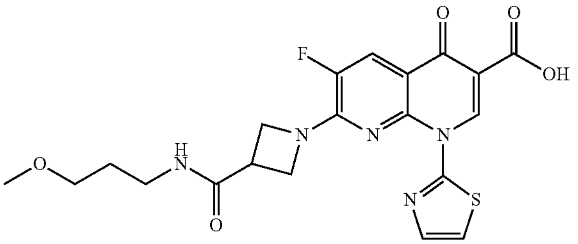

6-Fluoro-7-{3-[(3-methoxypropyl)carbamoyl]azetidin-1-yl}-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-(3-methoxypropyl)azetidine-3-carboxamide hydrochloride obtained in Example 050 by the method described in Example 002-(3) or a method equivalent thereto.

1H-NMR (DMSO-d6): δ 1.63-1.70 (2H, m), 3.13-3.19 (2H, m), 3.23 (3H, s), 3.56-3.66 (1H, m), 4.36-4.79 (4H, m), 7.79 (1H, d, J=3.0 Hz), 7.86 (1H, d, J=3.0 Hz), 8.07-8.18 (2H, m), 9.83 (1H, s), 14.80 (1H, brs)

Example 073

Compound 073

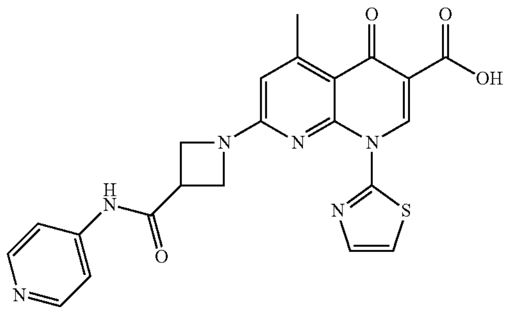

5-Methyl-4-oxo-7-{3-[(pyridin-4-yl)carbamoyl]azetidin-1-yl}-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-(pyridin-4-yl)azetidine-3-carboxamide hydrochloride obtained from pyridin-4-amine by the method described in Example 005-(1) and Example 001-(2) or a method equivalent thereto by the method described in Example 002-(3) or a method equivalent thereto.

1H-NMR (DMSO-d6): δ 2.79 (3H, s), 3.96-4.06 (1H, m), 4.35-4.63 (4H, m), 7.77 (1H, d, J=3.4 Hz), 7.80 (1H, s), 7.85 (1H, d, J=3.4 Hz), 8.16 (2H, d, J=6.8 Hz), 8.73 (2H, d, J=6.8 Hz), 9.85 (1H, s), 11.93 (1H, s), 15.13 (1H, brs)

Example 074

Compound 074

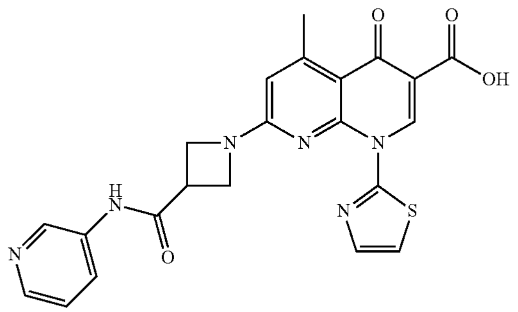

5-Methyl-4-oxo-7-{3-[(pyridin-3-yl)carbamoyl]azetidin-1-yl}-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-(pyridin-3-yl)azetidine-3-carboxamide hydrochloride obtained from pyridin-3-amine by the method described in Example 005-(1) and Example 001-(2) or a method equivalent thereto by the method described in Example 002-(3) or a method equivalent thereto.

Property: pale yellow solid;

ESI-MS (m/z): 463 [M+H]+

Example 075

Compound 075

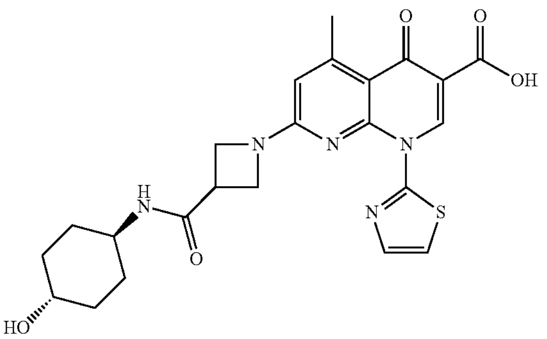

5-Methyl-4-oxo-7-{3-[(trans-4-hydroxycyclohexyl)carbamoyl]azetidin-1-yl}-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-(trans-4-hydroxycyclohexyl)azetidine-3-carboxamide hydrochloride obtained from trans-4-aminocyclohexane-1-ol by the method described in Example 005-(l) and Example 001-(2) or a method equivalent thereto by the method described in Example 002-(3) or a method equivalent thereto.

1H-NMR (D2O+NaOD): δ 1.19-1.32 (4H, m), 1.81 (2H, d, J=11.0 Hz), 1.88 (2H, d, J=11.0 Hz), 2.24 (3H, s), 3.24 (1H, quin, J=7.0 Hz), 3.46-3.68 (6H, m), 5.37 (1H, a), 6.92 (1H, d, J=3.5 Hz), 7.28 (1H, d, J=3.5 Hz), 8.81 (1H, s)

Example 076

Compound 076

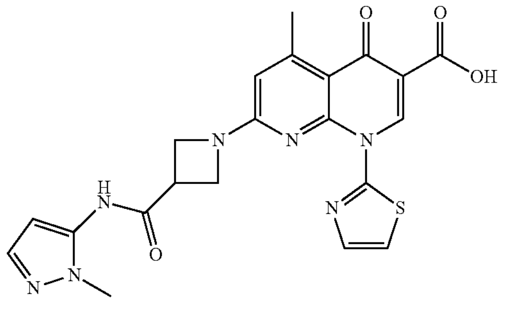

5-Methyl-7-{3-[(1-methyl-1H-pyrazol-5-yl)carbamoyl]azetidin-1-yl}-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-(1-methyl-1H-pyrazol-5-yl)azetidine-3-carboxamide hydrochloride obtained from 1-methyl-1H-pyrazol-5-amine by the method described in Example 005-(1) and Example 001-(2) or a method equivalent thereto by the method described in Example 002-(3) or a method equivalent thereto.

1H-NMR (DMSO-d6): δ 2.73 (3H, s), 3.70 (3H, s), 3.86-3.95 (1H, m), 4.30-4.55 (4H, m), 6.25 (1H, d, J=1.5 Hz), 6.50 (1H, s), 7.34 (1H, d, J=2.0 Hz), 7.73 (1H, d, J=3.5 Hz), 7.81 (1H, d, J=3.5 Hz), 9.78 (1H, s), 10.30 (1H, s)

Example 077

Compound 077

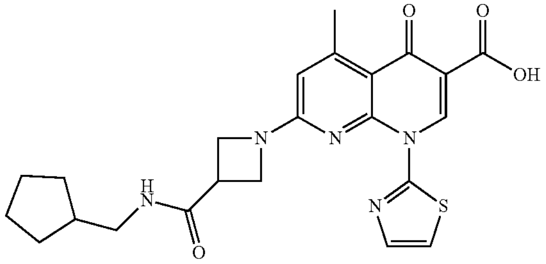

7-{3-[(Cyclopentylmethyl)carbamoyl]azetidin-1-yl}-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-(cyclopentylmethyl)azetidine-3-carboxamide hydrochloride obtained from cyclopentylmethylamine by the method described in Example 005-(1) and Example 001-(2) or a method to equivalent thereto by the method as claimed in Example 002-(3) or a method equivalent thereto.

1H-NMR (DMSO-d6): δ 1.14-1.21 (2H, m), 1.45-1.52 (2H, m), 1.53-1.60 (2H, m), 1.62-1.70 (2H, m), 2.00 (1H, quin, J=7.5 Hz), 2.77 (3H, s), 2.87-3.11 (2H, m), 3.52-3.64 (1H, m), 4.20-4.48 (4H, m), 6.54 (1H, s), 7.75 (1H, d, J=3.5 Hz), 7.83 (1H, d, J=3.5 Hz), 8.14 (1H, t, J=5.5 Hz), 9.84 (1H, s)

Example 078

Compound 078

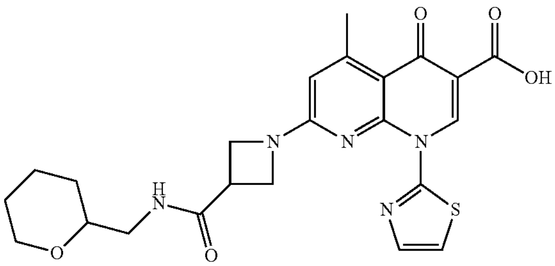

5-Methyl-7-{3-[(oxan-2-ylmethyl)carbamoyl]azetidin-1-yl}-4-oxo-1-(1,3-thiazol-2-yl)-1,4-dihydro-1,8-naphthyridine-3-carboxylic acid (1) N-(Oxan-2-yl)methylazetidine-3-carboxamide hydrochloride was obtained from oxan-2-ylmethylamine by the methods described in Examples 005-(1) and 001-(2) or methods equivalent thereto.

1H-NMR (DMSO-d6): δ 1.09-1.18 (1H, m), 1.37-1.48 (3H, m), 1.50-1.56 (1H, m), 1.71-1.80 (1H, m), 3.02-3.08 (1H, m), 3.13-3.18 (1H, m), 3.24-3.34 (2H, m), 3.53-3.61 (1H, m), 3.83-3.88 (1H, m), 3.91-4.03 (4H, m), 8.21 (1H, t, J=5.7 Hz), 8.80 (1H, brs), 9.12 (1H, brs)

(2) The title compound was obtained by the method described in Example 002-(3) or a method equivalent thereto using N-(oxan-2-yl)methylazetidine-3-carboxamide hydrochloride obtained in the preceding section, and 7-chloro-5-methyl-4-oxo-1-(1,3-thiazol-2-yl)-1,4-dihydro-1,8-naphthyridine-3-carboxylic acid obtained in Reference Example 001-(2).

1H-NMR (DMSO-d6): δ 1.10-1.20 (1H, m), 1.39-1.49 (3H, m), 1.52-1.59 (1H, m), 1.72-1.81 (1H, m), 2.75 (3H, s), 3.00-3.24 (4H, m), 3.58-3.66 (1H, m), 3.84-3.90 (1H, m), 4.16-4.48 (4H, m), 6.51 (1H, s), 7.73 (1H, d, J=3.5 Hz), 7.82 (1H, d, J=3.5 Hz), 8.22 (1H, t, J=5.5 Hz), 9.82 (1H, s)

Example 079

Compound 079

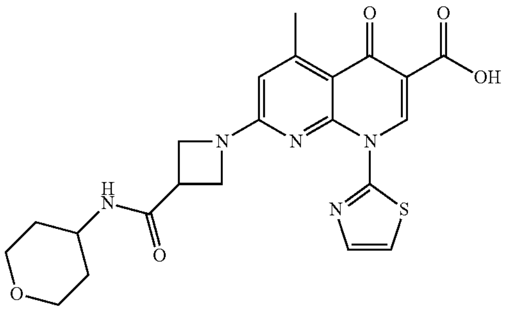

5-Methyl-7-{3-[(oxan-4-yl)carbamoyl]azetidin-1-yl}-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-(oxan-4-yl)azetidine-3-carboxamide hydrochloride obtained from oxane-4-amine by the method described in Example 005-(1) and Example 001-(2) or a method equivalent thereto by the method described in Example 002-(3) or a method equivalent thereto.

1H-NMR (DMSO-d6): δ 1.36-1.45 (2H, m), 1.70-1.77 (2H, m), 2.74 (3H, s), 3.23-3.45 (1H, m), 3.52-3.60 (1H, m), 3.76-3.86 (3H, m), 4.17-4.49 (4H, m), 6.49 (1H, s), 7.73 (1H, d, J=3.5 Hz), 7.82 (1H, d, J=3.5 Hz), 8.15 (1H, d, J=7.5 Hz), 9.80 (1H, s)

Example 080

Compound 080

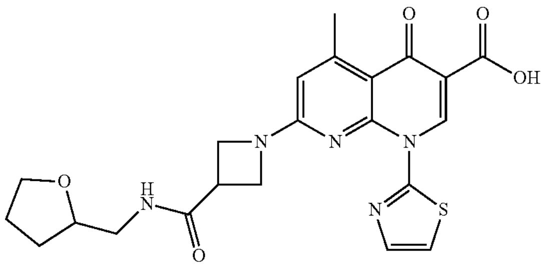

5-Methyl-4-oxo-7-{3-[(oxolan-2-ylmethyl)carbamoyl]azetidin-1-yl}-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-(oxolan-2-yl)methylazetidine-3-carboxamide hydrochloride obtained from oxolan-2-ylmethylamine by the method described in Example 005-(1) and Example 001-(2) or a method equivalent thereto by the method as claimed in Example 002-(3) or a method equivalent thereto.

1H-NMR (DMSO-d6): δ 1.43-1.96 (4H, m), 2.78 (3H, s), 3.57-3.68 (2H, m), 3.70-3.81 (1H, m), 3.81-3.91 (1H, m), 4.14-4.58 (4H, m), 6.55 (1H, s), 7.75 (1H, d, J=3.5 Hz), 7.84 (1H, d, J=3.5 Hz), 8.21-8.27 (1H, m), 9.86 (1H, s), 15.41 (1H, brs)

Example 081

Compound 081

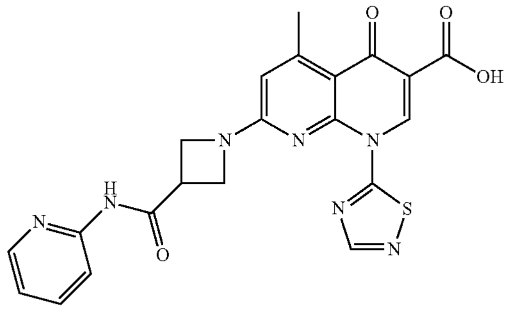

5-Methyl-4-oxo-7-{3-[(pyridin-2-yl)carbamoyl]azetidin-1-yl}-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-(pyridin-2-yl)azetidine-3-carboxamide hydrochloride obtained from pyridin-2-amine by the method described in Example 005-(1) and Example 001-(2) or a method equivalent thereto by the method described in Example 002-(3) or a method equivalent thereto.

1H-NMR (DMSO-d6): δ 2.76 (3H, s), 3.93-4.01 (1H, m), 4.35-4.70 (4H, m), 6.60 (1H, s), 7.15 (1H, ddd, J=7.5, 5.0, 1.0 Hz), 7.83 (1H, dd, J=7.5, 2.0 Hz), 8.08-8.15 (1H, m), 8.35 (1H, ddd, J=5.0, 2.0, 1.0 Hz), 8.80 (1H, s), 9.72 (1H, s), 10.86 (1H, brs)

Example 082

Compound 082

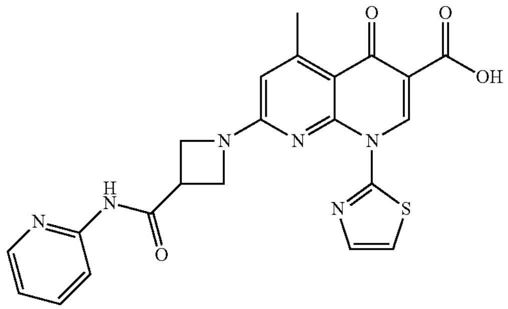

5-Methyl-4-oxo-7-{3-[(pyridin-2-yl)carbamoyl]azetidin-1-yl}-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-(pyridin-2-yl)azetidine-3-carboxamide hydrochloride obtained in Example 081 by the method described in Example 002-(3) or a method equivalent thereto.

1H-NMR (DMSO-d6): δ 2.79 (3H, s), 3.89-4.01 (1H, m), 4.34-4.57 (4H, m), 6.59 (1H, S), 7.15 (1H, t, J=5.5 Hz), 7.75 (1H, d, J=3.5 Hz), 7.84 (2H, d, d, J=3.5 Hz), 8.11 (1H, brs), 8.34 (1H, d, J=5.0 Hz), 9.86 (1H, s), 10.84 (1H, brs)

Example 083

Compound 083

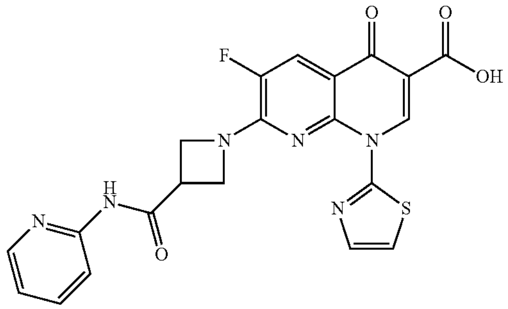

6-Fluoro-4-oxo-7-{3-[(pyridin-2-yl)carbamoyl]azetidin-1-yl}-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-(pyridin-2-yl)azetidine-3-carboxamide hydrochloride obtained in Example 081 by the method described in Example 002-(3) or a method equivalent thereto.

1H-NMR (DMSO-d6): δ 3.29-3.40 (1H, m), 3.92-4.32 (4H, m), 6.57 (1H, d, J=8.0 Hz), 6.65 (1H, ddd, J=7.0, 5.0, 1.0 Hz), 7.27 (1H, d, J=3.5 Hz), 7.46 (1H, ddd, J=8.0, 7.0, 2.0 Hz), 7.51-7.53 (1H, m), 7.57 (1H, d, J=12.0 Hz), 7.83 (1H, ddd, J=5.0, 2.0, 1.0 Hz), 9.06 (1H, s)

Example 084

Compound 084

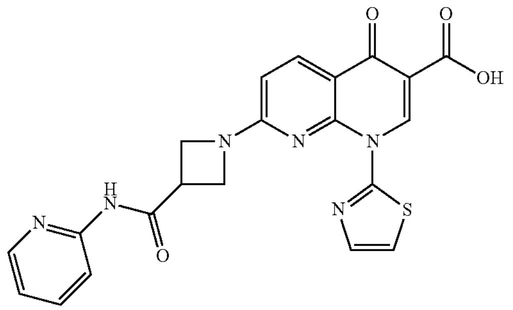

4-Oxo-7-{3-[(pyridin-2-yl)carbamoyl]azetidin-1-yl}-1-(1,3-thiazol-2-yl)-1,4-dihydro-1,8-naphthyridine-3-carboxylic acid The title compound was obtained using 7-chloro-4-oxo-1-(1,3-thiazol-2-yl)-1,4-dihydro-1,8-naphthyridine-3-carboxylic acid obtained in Reference Example 005-(2) and N-(pyridin-2-yl)azetidine-3-carboxamide hydrochloride obtained in Example 081 by the method described in Example 002-(3) or a method equivalent thereto.

1H-NMR (DMSO-d6): δ 3.91-4.03 (1H, m), 4.37-4.57 (4H, m), 6.79 (1H, d, J=9.5 Hz), 7.15 (1H, ddd, J=7.5, 5.0, 1.0 Hz), 7.77 (1H, d, J=3.5 Hz), 7.83-7.85 (2H, m), 8.11 (1H, d, J=6.5 Hz), 8.32-8.37 (2H, m), 9.84 (1H, s), 10.86 (1H, s)

Example 085

Compound 085

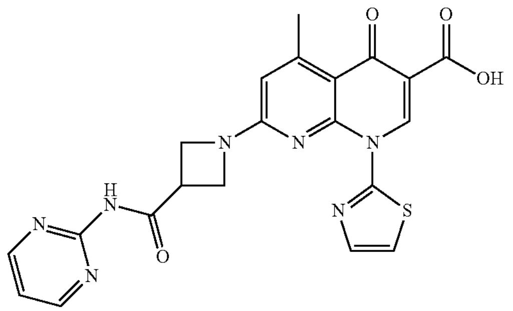

5-Methyl-4-oxo-7-{3-[(pyrimidin-2-yl)carbamoyl]azetidin-1-yl}-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-(pyrimidin-2-yl)azetidine-3-carboxamide hydrochloride obtained from pyrimidin-2-amine by the method described in Example 005-(1) and Example 001-(2) or a method equivalent thereto by the method described in Example 002-(3) or a method equivalent thereto.

Property: green solid;

ESI-MS (m/z): 464 [M+H]+

Example 086

Compound 086

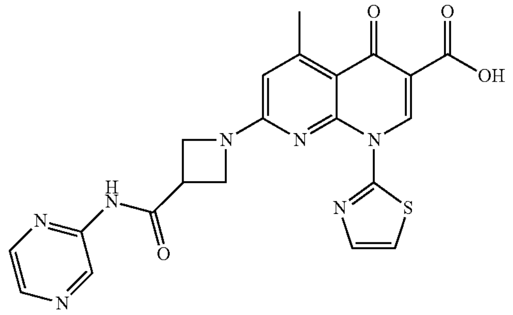

5-Methyl-4-oxo-7-{3-[(pyrazin-2-yl)carbamoyl]azetidin-1-yl}-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-(pyrazin-2-yl)azetidine-3-carboxamide hydrochloride obtained from pyrazin-2-amine by the method described in Example 005-(1) and Example 001-(2) or a method equivalent thereto by the method described in Example 002-(3) or a method equivalent thereto.

1H-NMR (DMSO-d6): δ 2.77 (3H, s), 3.89-4.01 (1H, m), 4.26-4.58 (4H, m), 6.56 (1H, s), 7.73-7.76 (1H, m), 7.78-7.84 (2H, m), 7.86 (1H, d, J=3.5 Hz), 7.88 (1H, d, J=3.5 Hz), 9.82 (1H, s), 11.07 (1H, brs)

Example 087

Compound 087

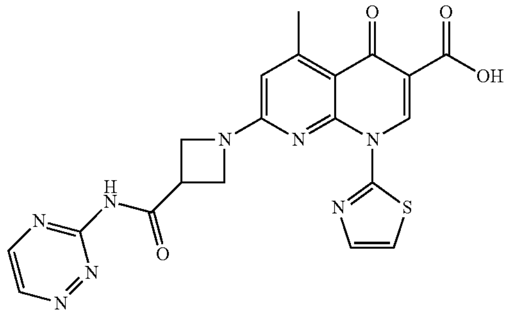

5-Methyl-4-oxo-1-(1,3-thiazol-2-yl)-7-{3-[(1,2,4-triazin-3-yl)carbamoyl]azetidin-1-yl}-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-(1,2,4-triazine-3-yl)azetidine-3-carboxamide hydrochloride obtained from 1,2,4-triazine-3-amine by the method described in Example 005-(1) and Example 001-(2) or a method equivalent thereto by the method described in Example 002-(3) or a method equivalent thereto.

1H-NMR (DMSO-d6): δ 2.75 (3H, s), 4.02-4.59 (5H, m), 6.49-6.58 (1H, m), 7.69-7.89 (4H, m), 9.81 (1H, s)

Example 088

Compound 088

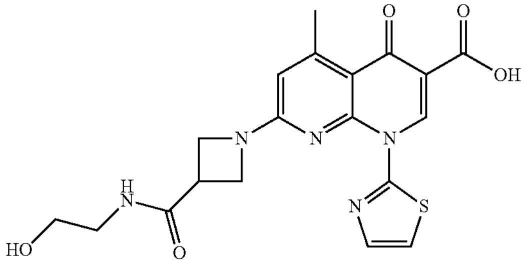

7-{3-[(2-Hydroxyethyl)carbamoyl]azetidin-1-yl}-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-(2-hydroxyethyl)azetidine-3-carboxamide hydrochloride obtained from 2-aminoethan-1-ol by the method described in Example 005-(1) and Example 001-(2) or a method equivalent thereto by the method described in Example 002-(3) or a method equivalent thereto.

1H-NMR (DMSO-d6): δ 2.74 (3H, s), 3.42-3.47 (2H, m), 3.65-3.72 (2H, m), 4.15-4.57 (5H, m), 6.47-6.53 (1H, m), 7.72-7.76 (1H, m), 7.81-7.84 (1H, m), 7.86-7.89 (1H, m), 8.17-8.50 (1H, m), 9.79 (1H, s)

Example 089

Compound 089

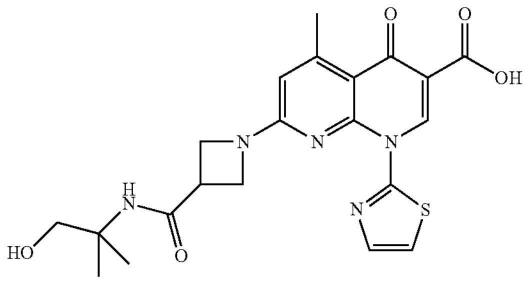

7-{3-[(1-Hydroxy-2-methylpropan-2-yl)carbamoyl]azetidin-1-yl}-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-(1-hydroxy-2-methylpropan-2-yl)azetidine-3-carboxamide hydrochloride obtained from 2-amino-2-methylpropan-1-ol by the method described in Example 005-(1) and Example 001-(2) or a method equivalent thereto by the method described in Example 002-(3) or a method equivalent thereto.

1H-NMR (DMSO-d6): δ 1.13-1.35 (6H, m), 2.75-2.79 (3H, m), 3.66-4.04 (2H, m), 4.13-4.22 (1H, m), 4.26-4.64 (4H, m), 6.50-6.57 (1H, m), 7.75-7.78 (1H, m), 7.82-7.86 (1H, m), 8.14 (1H, brs), 9.83 (1H, s)

Example 090

Compound 090

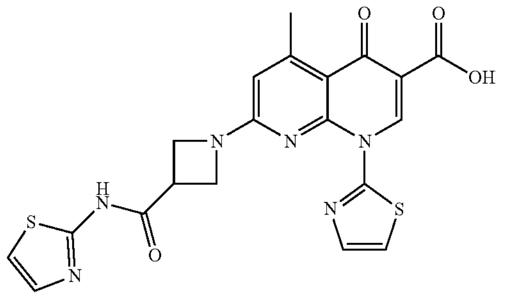

5-Methyl-4-oxo-1-(1,3-thiazol-2-yl)-7-{3-[(1,3-thiazol-2-yl)carbamoyl]azetidin-1-yl}-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-(1,3-thiazol-2-yl)azetidine-3-carboxamide hydrochloride obtained from 1,3-thiazol-2-amine by the method described in Example 005-(1) and Example 001-(2) or a method equivalent thereto by the method described in Example 002-(3) or a method equivalent thereto.

1H-NMR (D2O+NaOD): δ 2.46 (3H, s), 3.42-3.51 (1H, m), 3.93-4.01 (4H, m), 5.83 (1H, s), 6.88 (1H, d, J=3.5 Hz), 7.17 (1H, d, J=3.5 Hz), 7.28 (1H, d, J=3.5 Hz), 7.44 (1H, d, J=3.5 Hz), 8.92 (1H, s)

Example 091

Compound 091

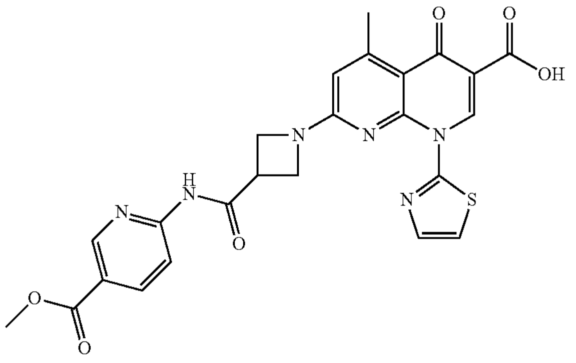

7-(3-{[5-(Methoxycarbonyl)pyridin-2-yl]carbamoyl}azetidin-1-yl)-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and methyl 6-(azetidine-3-amide)pyridine-3-carboxylate hydrochloride obtained from methyl 6-aminopyridine-3-carboxylate by the method described in Example 007-(1) and Example 001-(2) or a method equivalent thereto by the method described in Example 014 or a method equivalent thereto.

1H-NMR (DMSO-d6): δ 2.79 (3H, s), 3.86 (3H, s), 3.94-4.01 (1H, m), 4.33-4.58 (4H, m), 6.57 (1H, s), 7.70-7.76 (1H, m), 7.81-7.84 (1H, m), 8.23-8.29 (1H, m), 8.29-8.34 (1H, m), 8.85-8.89 (1H, m), 9.84 (1H, s), 11.19 (1H, s), 15.38 (1H, brs)

Example 092

Compound 092

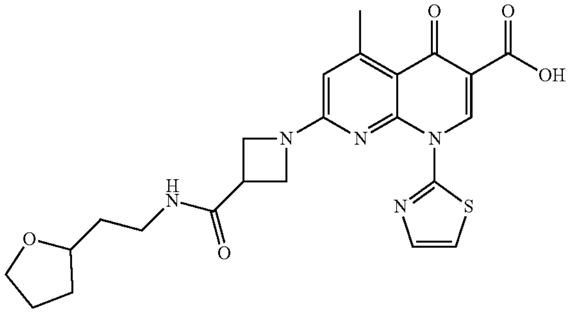

5-Methyl-4-oxo-7-(3-{[2-(oxolan-2-yl)ethyl]carbamoyl}azetidin-1-yl)-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-[2-(oxolan-2-yl)ethyl]azetidine-3-carboxamide hydrochloride obtained from 2-(oxolan-2-yl)ethan-1-amine by the method described in Example 005-(1) and Example 001-(2) or a method equivalent thereto by the method described in Example 014 or a method equivalent thereto.

1H-NMR (DMSO-d6): δ 1.36-1.43 (1H, m), 1.57-1.63 (2H, m), 1.75-1.85 (2H, m), 1.91-1.98 (1H, m), 2.75-2.79 (3H, m), 3.09-3.24 (2H, m), 3.50-3.61 (2H, m), 3.70-3.78 (2H, m), 4.16-4.53 (4H, m), 6.51-6.56 (1H, m), 7.73-7.76 (1H, m), 7.82-7.85 (1H, m), 8.14 (1H, t, J=5.5 Hz), 9.83-9.86 (1H, m), 15.41 (1H, brs)

Example 093

Compound 093

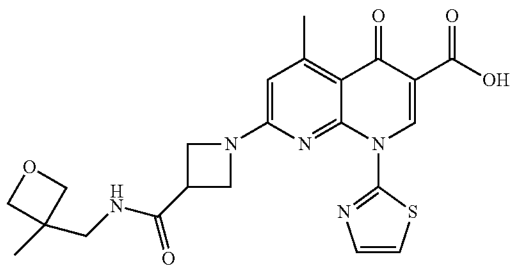

5-Methyl-7-(3-{[(3-methyloxetan-3-yl)methyl]carbamoyl}azetidin-1-yl)-4-oxo-1-(1,3-thiazol-2-yl)-1,4-dihydro-1,8-naphthyridine-3-carboxylic acid (1) Crude benzyl 3-{[(3-methyloxetan-3-yl)methyl]carbamoyl}azetidine-1-carboxylate was obtained using (3-methyl oxetan-3-yl)methylamine and 1-[(benzyloxy) carbonyl]azetidine-3-carboxylic acid by the method described in Example 005-(1) or a method equivalent thereto.

(2) The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-[(3-methyloxetan-3-yl)methyl]azetidine-3-carboxamide obtained from crude benzyl 3-{[(3-methyloxetan-3-yl)methyl]carbamoyl}azetidine-1-carboxylate obtained in the preceding section by the method described in Example 002-(2) or a method equivalent thereto by the method described in Example 014 or a method equivalent thereto.

1H-NMR (DMSO-d6): δ 0.83 (3H, s), 2.77 (3H, s), 3.99-4.52 (6H, m), 6.57 (1H, s), 7.63 (1H, brs), 7.74-7.88 (3H, m), 9.83 (1H, s), 15.22 (1H, brs)

Example 094

Compound 094

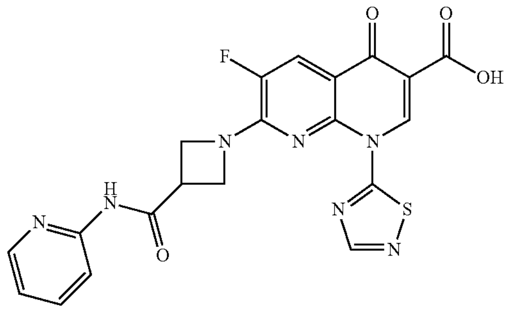

6-Fluoro-4-oxo-7-{3-[(pyridin-2-yl)carbamoyl]azetidin-1-yl}-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and N-(pyridin-2-yl)azetidine-3-carboxamide hydrochloride obtained in Example 081 by the method described in Example 001-(3) or a method equivalent thereto.

Property: pale yellow solid;

ESI-MS (m/z): 468 [M+H]+

Example 095

Compound 095

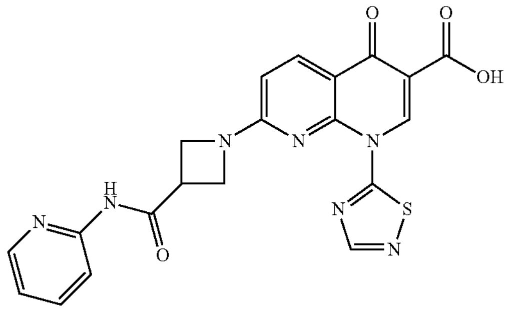

4-Oxo-7-{3-[(pyridin-2-yl)carbamoyl]azetidin-1-yl}-1-(1,2,4-thiadiazol-5-yl)-1,4-dihydro-1,8-naphthyridine-3-carboxylic acid The title compound was obtained using 7-chloro-4-oxo-1-(1,2,4-thiadiazol-5-yl)-1,4-dihydro-1,8-naphthyridine-3-carboxylic acid obtained in Reference Example 006-(2) and N-(pyridin-2-yl)azetidine-3-carboxamide hydrochloride obtained in Example 081 by the method described in Example 001-(3) or a method equivalent thereto.

Property: pale yellow solid;

ESI-MS (m/z): 450 [M+H]+

Example 096

Compound 096

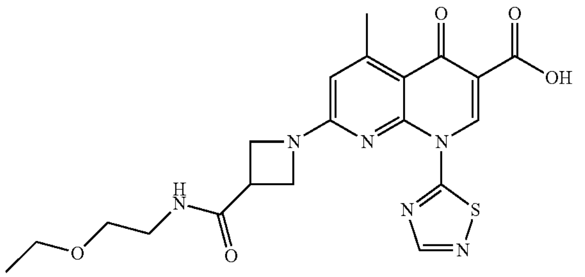

7-{3-[(2-Ethoxyethyl)carbamoyl]azetidin-1-yl}-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-(2-ethoxyethyl)azetidine-3-carboxamide hydrochloride obtained in Example 018-(1) by the method described in Example 001-(3) or a method equivalent thereto.

1H-NMR (D2O+NaOD): δ 1.08 (3H, t, J=7.0 Hz), 2.30 (3H, s), 3.35 (2H, t, J=5.0 Hz), 3.43-3.57 (5H, m), 3.68-4.00. (4H, m), 5.61 (1H, s), 8.24 (1H, s), 8.74 (1H, 8)

Example 097

Compound 097

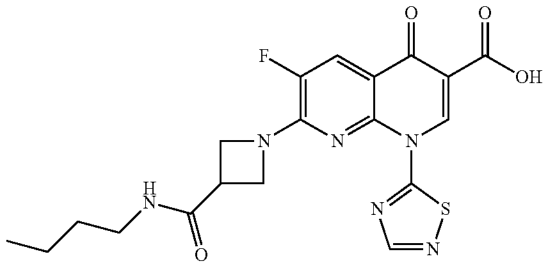

7-[3-(Butylcarbamoyl)azetidin-1-yl]-6-fluoro-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and N-butyl azetidine-3-carboxamide hydrochloride obtained in Example 062 by the method described in Example 001-(3) or a method equivalent thereto.

1H-NMR (D2O+NaOD): δ 0.80 (3H, t, J=7.5 Hz), 1.24 (2H, sext, J=7.5 Hz), 1.43 (2H, quin, J=7.5 Hz), 3.16 (2H, t, J=7.5 Hz), 3.59-3.68 (1H, m), 4.30-4.83 (4H, m), 7.76 (1H, d, J=11.5 Hz), 8.44 (1H, s), 9.20 (1H, s)

Example 098

Compound 098

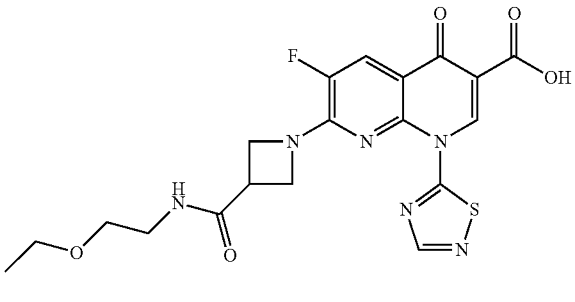

7-{3-[(2-Ethoxyethyl)carbamoyl]azetidin-1-yl}-6-fluoro-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and N-(2-ethoxyethyl)azetidine-3-carboxamide hydrochloride obtained in Example 018-(1) by the method described in Example 001-(3) or a method equivalent thereto.

1H-NMR (CD3OD): δ 1.21 (3H, t, J=7.0 Hz), 3.45 (2H, t, J=5.5 Hz), 3.55 (2H, q, J=7.0 Hz), 3.56 (2H, t, J=5.5 Hz), 3.71-3.79 (1H, m), 4.64-4.94 (4H, m), 8.06 (1H, d, J=11.5 Hz), 8.62 (1H, s), 9.82 (1H, s)

Example 099

Compound 099

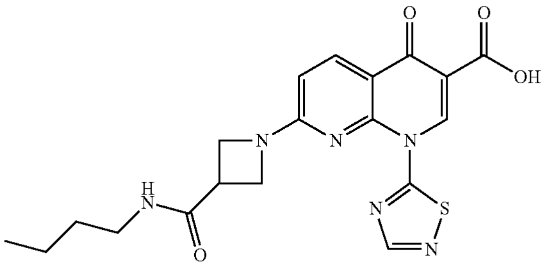

7-[3-(Butylcarbamoyl)azetidin-1-yl]-4-oxo-1-(1,2,4-thiadiazol-5-yl)-1,4-dihydro-1,8-naphthyridine-3-carboxylic acid The title compound was obtained using 7-chloro-4-oxo-1-(1,2,4-thiadiazol-5-yl)-1,4-dihydro-1,8-naphthyridine-3-carboxylic acid obtained in Reference Example 006-(2) and N-butyl azetidine-3-carboxamide hydrochloride obtained in Example 062 by the method described in Example 001-(3) or a method equivalent thereto.

1H-NMR (D2O+NaOD): δ 0.81 (3H, t, J=7.5 Hz), 1.26 (2H, sext, J=7.5 Hz), 1.44 (2H, quin, J=7.5 Hz), 3.16 (2H, t, J=7.5 Hz), 3.51-3.59 (1H, m), 3.93-4.19 (4H, m), 6.10 (1H, d, J=9.0 Hz), 7.83 (1H, d, J=9.0 Hz), 8.34 (1H, s), 8.98 (1H, s)

Example 100

Compound 100

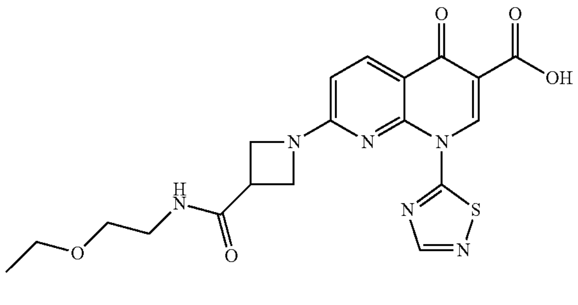

7-{3-[(2-Ethoxyethyl)carbamoyl]azetidin-1-yl}-4-oxo-1-(1,2,4-thiadiazol-5-yl)-1,4-dihydro-1,8-naphthyridine-3-carboxylic acid The title compound was obtained using 7-chloro-4-oxo-1-(1,2,4-thiadiazol-5-yl)-1,4-dihydro-1,8-naphthyridine-3-carboxylic acid obtained in Reference Example 006-(2) and N-(2-ethoxyethyl)azetidine-3-carboxamide hydrochloride obtained in Example 018-(1) by the method described in Example 001-(3) or a method equivalent thereto.

1H-NMR (D2O+NaOD): δ 1.09 (3H, t, J=7.5 Hz), 3.37 (2H, t, J=5.5 Hz), 3.47-3.59 (5H, m), 3.76-4.10 (4H, m), 5.98 (1H, d, J=8.5 Hz), 7.71 (1H, d, J=8.5 Hz), 8.29 (1H, s), 8.84 (1H, s)

Example 101

Compound 101

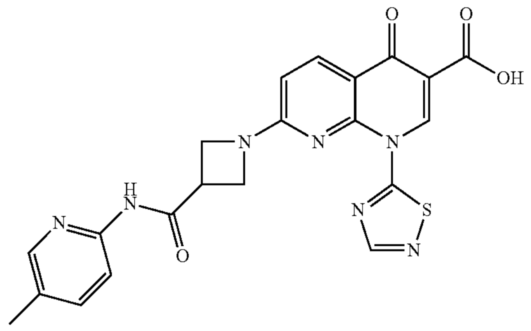

7-{3-[(5-Methylpyridin-2-yl)carbamoyl]azetidin-1-yl}-4-oxo-1-(1,2,4-thiadiazol-5-yl)-1,4-dihydro-1,8-naphthyridine-3-carboxylic acid The title compound was obtained using 7-chloro-4-oxo-1-(1,2,4-thiadiazol-5-yl)-1,4-dihydro-1,8-naphthyridine-3-carboxylic acid obtained in Reference Example 006-(2) and N-(5-methylpyridin-2-yl)azetidine-3-carboxamide hydrochloride obtained from 5-methylpyridin-2-amine by the method described in Example 005-(1) and Example 001-(2) or a method equivalent thereto by the method described in Example 014 or a method equivalent thereto.

1H-NMR (DMSO-d6): δ 2.27 (3H, s), 3.92-4.00 (1H, m), 4.38-4.70 (4H, m), 6.81 (1H, d, J=9.0 Hz), 7.62 (1H, dd, J=8.0, 2.0 Hz), 8.04 (1H, d, J=8.0 Hz), 8.17 (1H, d, J=2.0 Hz), 8.35 (1H, d, J=9.0 Hz), 8.83 (1H, s), 9.74 (1H, s), 10.70 (1H, s), 14.61 (1H, brs)

Example 102

Compound 102

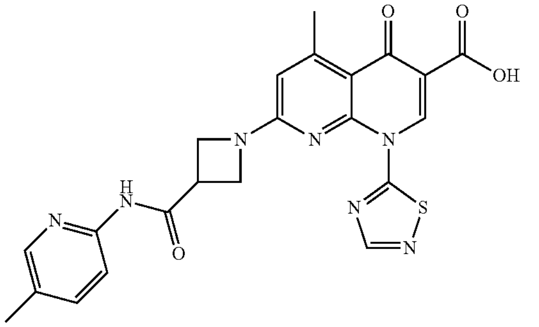

5-Methyl-7-{3-[(5-methylpyridin-2-yl)carbamoyl]azetidin-1-yl}-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-(5-methylpyridin-2-yl)azetidine-3-carboxamide hydrochloride obtained in Example 101 by the method described in Example 014 or a method equivalent thereto.

1H-NMR (DMSO-d6): δ 2.26 (3H, s), 2.77 (3H, s), 3.87-4.00 (1H, m), 4.27-4.69 (4H, m), 6.54 (1H, s), 7.62 (1H, dd, J=8.0, 2.0 Hz), 8.04 (1H, d, J=8.0 Hz), 8.17 (1H, d, J=2.0 Hz), 8.76 (1H, s), 9.65 (1H, s), 10.68 (1H, s)

Example 103

Compound 103

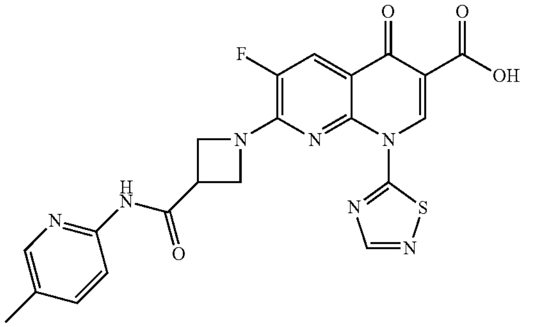

6-Fluoro-7-{3-[(5-methylpyridin-2-yl)carbamoyl]azetidin-1-yl}-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and N-(5-methylpyridin-2-yl)azetidine-3-carboxamide hydrochloride obtained in Example 101 by the method described in Example 014 or a method equivalent thereto.

1H-NMR (DMSO-d6): δ 2.26 (3H, s), 3.90-4.07 (1H, m), 4.57-4.87 (4H, m), 7.63 (1H, dd, J=8.0, 2.0 Hz), 8.05 (1H, d, J=8.0 Hz), 8.14 (1H, d, J=11.0 Hz), 8.18 (1H, d, J=2.0 Hz), 8.84 (1H, s), 9.74 (1H, s), 10.68 (1H, s)

Example 104

Compound 104

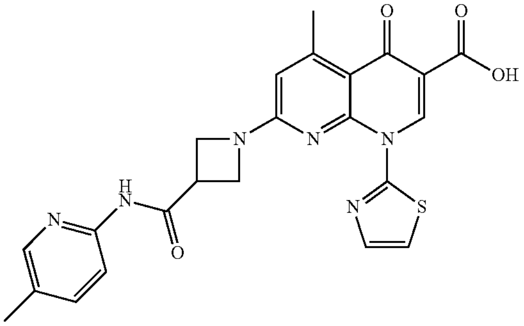

5-Methyl-7-{3-[(5-methylpyridin-2-yl)carbamoyl]azetidin-1-yl}-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-(5-methylpyridin-2-yl)azetidine-3-carboxamide hydrochloride obtained in Example 101 by the method described in Example 014 or a method equivalent thereto.

1H-NMR (DMSO-d6): δ 2.25 (3H, s), 2.77 (3H, s), 3.85-3.97 (1H, m), 4.28-4.56 (4H, m), 6.56 (1H, s), 7.62 (1H, dd, J=8.5, 2.0 Hz), 7.74 (1H, d, J=3.5 Hz), 7.83 (1H, d, J=3.5 Hz), 8.03 (1H, d, J=8.5 Hz), 8.17 (1H, d, J=2.0 Hz), 9.84 (1H, s), 10.69 (1H, s), 15.38 (1H, brs)

Example 105

Compound 105

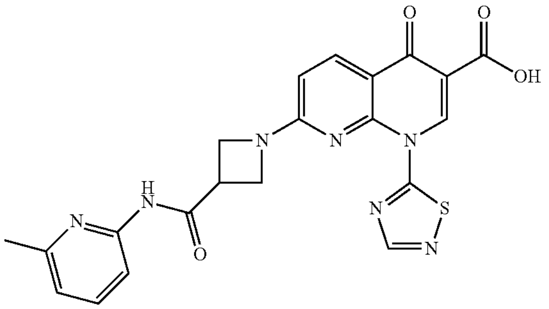

7-{3-[(6-Methylpyridin-2-yl)carbamoyl]azetidin-1-yl}-4-oxo-1-(1,2,4-thiadiazol-5-yl)-1,4-dihydro-1,8-naphthyridine-3-carboxylic acid The title compound was obtained using 7-chloro-4-oxo-1-(1,2,4-thiadiazol-5-yl)-1,4-dihydro-1,8-naphthyridine-3-carboxylic acid and N-(6-methylpyridin-2-yl)azetidine-3-carboxamide hydrochloride obtained from 6-methylpyridin-2-amine by the method described in Example 007-(1) and Example 001-(2) or a method equivalent thereto by the method described in Example 014 or a method equivalent thereto.

1H-NMR (DMSO-d6): δ 2.42 (3H, s), 3.93-4.01 (1H, m), 4.38-4.70 (4H, m), 6.82 (1H, d, J=9.0 Hz), 6.99 (1H, d, J=8.0 Hz), 7.69 (1H, t, J=8.0 Hz), 7.91-7.98 (1H, m), 8.37 (1H, d, J=9.0 Hz), 8.84 (1H, brs), 9.76 (1H, s), 10.73 (1H, s), 14.66 (1H, brs)

Example 106

Compound 106

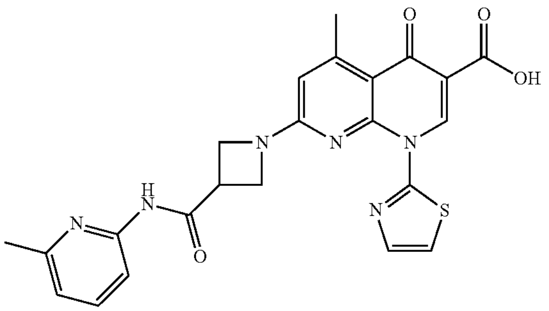

5-Methyl-7-{3-[(6-methylpyridin-2-yl)carbamoyl]azetidin-1-yl}-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-(6-methylpyridin-2-yl)azetidine-3-carboxamide hydrochloride obtained in Example 105 by the method described in Example 014 or a method equivalent thereto.

1H-NMR (DMSO-d6): δ 2.41 (3H, s), 2.77 (3H, s), 3.88-3.99 (1H, m), 4.29-4.56 (4H, m), 6.56 (1H, s), 6.99 (1H, d, J=7.5 Hz), 7.68 (1H, dd, J=7.5, 7.5 Hz), 7.74 (1H, d, J=3.5 Hz), 7.83 (1H, d, J=3.5 Hz), 7.94 (1H, d, J=7.5 Hz), 9.84 (1H, s), 10.70 (1H, s), 15.39 (1H, brs)

Example 107

Compound 107

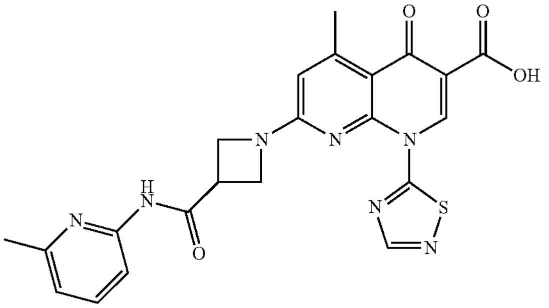

5-Methyl-7-{3-[(6-methylpyridin-2-yl)carbamoyl]azetidin-1-yl}-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-(6-methylpyridin-2-yl)azetidine-3-carboxamide hydrochloride obtained in Example 105 by the method described in Example 014 or a method equivalent thereto.

1H-NMR (DMSO-d6): δ 2.42 (3H, s), 2.79 (3H, s), 3.90-3.99 (1H, m), 4.33-4.71 (4H, m), 6.61 (1H, s), 6.99 (1H, d, J=8.0 Hz), 7.68 (1H, t, J=8.0 Hz), 7.91-7.99 (1H, m), 8.80 (1H, s), 9.71 (1H, s), 10.72 (1H, s)

Example 108

Compound 108

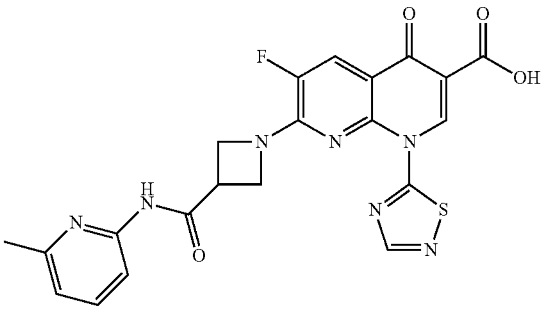

6-Fluoro-7-{3-[(6-methylpyridin-2-yl)carbamoyl] azetidin-1-yl}-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) N-(6-methylpyridin-2-yl)azetidine-3-carboxamide hydrochloride obtained in Example 105 by the method described in Example 014 or a method equivalent thereto.

1H-NMR (DMSO-d6): δ 2.42 (3H, s), 3.90-4.07 (1H, m), 4.57-4.87 (4H, m), 6.96-6.98 (1H, m), 6.99 (1H, d, J=8.0 Hz), 7.69 (1H, t, J=8.0 Hz), 7.91-7.98 (1H, m), 8.16 (1H, d, J=9.0 Hz), 8.85 (1H, s), 9.76 (1H, s), 10.71 (1H, s), 14.40 (1H, brs)

Example 109

Compound 109

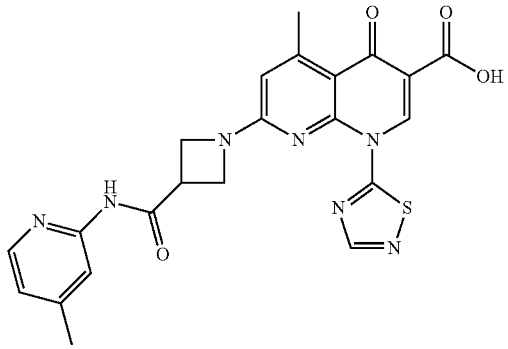

5-Methyl-7-{3-[(4-methylpyridin-2-yl)carbamoyl] azetidin-1-yl}-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-(4-methylpyridin-2-yl)azetidine-3-carboxamide hydrochloride obtained from 4-methylpyridin-2-amine by the method described in Example 007-(1) and Example 001-(2) or a method equivalent thereto by the method described in Example 014 or a method equivalent thereto.

1H-NMR (DMSO-d6): δ 2.31 (3H, s), 2.79 (3H, s), 3.91-4.00 (1H, m), 4.33-4.71 (4H, m), 6.63 (1H, s), 6.96-6.98 (1H, m), 8.00 (1H, brs), 8.19 (1H, d, J=5.0 Hz), 8.82 (1H, s), 9.76 (1H, s), 10.70 (1H, s), 15.08 (1H, brs)

Example 110

Compound 110

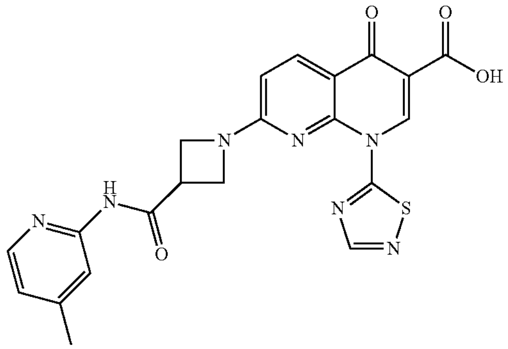

7-{3-[(4-Methylpyridin-2-yl)carbamoyl]azetidin-1-yl}-4-oxo-1-(1,2,4-thiadiazol-5-yl)-1,4-dihydro-1,8-naphthyridine-3-carboxylic acid The title compound was obtained using 7-chloro-4-oxo-1-(1,2,4-thiadiazol-5-yl)-1,4-dihydro-1,8-naphthyridine-3-carboxylic acid obtained in Reference Example 006-(2) and N-(4-methylpyridin-2-yl)azetidine-3-carboxamide hydrochloride obtained in Example 109 by the method described in Example 014 or a method equivalent thereto.

1H-NMR (DMSO-d6): δ 2.31 (3H, s), 3.93-4.01 (1H, m), 4.38-4.70 (4H, m), 6.82 (1H, d, J=9.0 Hz), 6.96-6.98 (1H, m), 8.00 (1H, brs), 8.19 (1H, d, J=5.0 Hz), 8.35 (1H, d, J=9.0 Hz), 8.82 (1H, s), 9.74 (1H, s), 10.71 (1H, s), 14.70 (1H, brs)

Example 111

Compound 111

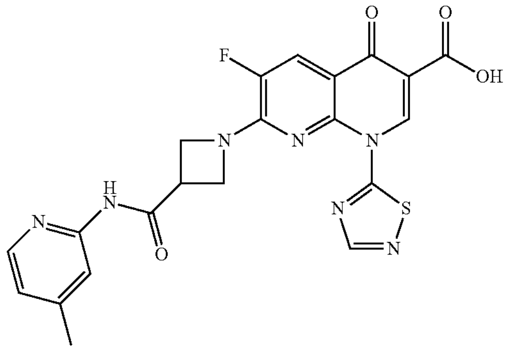

6-Fluoro-7-{3-[(4-methylpyridin-2-yl)carbamoyl] azetidin-1-yl}-4-oxo-1-(1,2,4-thiadiazol-5-yl)-1,4-dihydro-1,8-naphthyridine-3-carboxylic acid The title compound was obtained using 7-chloro-6-fluoro-4-oxo-(1,2,4-thiadiazol-5-yl)-1,4-dihydro-1,8-naphthyridine-3-carboxylic acid obtained in Reference Example 004-(2) and N-(4-methylpyridin-2-yl)azetidine-3-carboxamide hydrochloride obtained in Example 109 by the method described in Example 014 or a method equivalent thereto.

1H-NMR (DMSO-d6): δ 2.32 (3H, s), 3.90-4.07 (1H, m), 4.53-4.95 (4H, m), 6.96-6.98 (1H, m), 8.01 (1H, brs), 8.17 (1H, d, J=11.5 Hz), 8.19 (1H, d, J=5.0 Hz), 8.35 (1H, d, J=9.0 Hz), 8.85 (1H, s), 9.76 (1H, s), 10.69 (1H, s), 15.80 (1H, brs)

Example 112

Compound 112

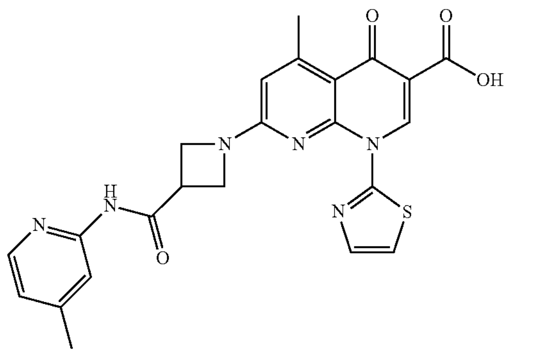

5-Methyl-7-{3-[(4-methylpyridin-2-yl)carbamoyl] azetidin-1-yl}-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-(4-methylpyridin-2-yl)azetidine-3-carboxamide hydrochloride obtained in Example 109 by the method described in Example 014 or a method equivalent thereto.

1H-NMR (DMSO-d6): δ 2.32 (3H, s), 2.78 (3H, s), 3.88-4.01 (1H, m), 4.28-4.60 (4H, m), 6.56 (1H, s), 6.99 (1H, d, J=5.0 Hz), 7.74 (1H, d, J=3.5 Hz), 7.83 (1H, d, J=3.5 Hz), 7.97 (1H, brs), 8.19 (1H, d, J=5.0 Hz), 9.85 (1H, s), 10.76 (1H, s), 15.39 (1H, brs)

Example 113

Compound 113

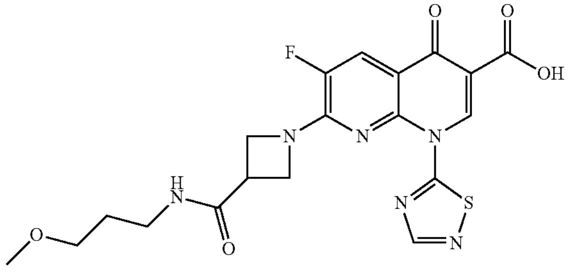

6-Fluoro-7-{3-[(3-methoxypropyl)carbamoyl]azetidin-1-yl}-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8- naphthyridine-3-carboxylic acid obtained in Reference Example 004-(2) and N-(3-methoxypropyl)azetidine-3-carboxamide hydrochloride obtained in Example 050 by the method described in Example 001-(3) or a method equivalent thereto.

1H-NMR (D2O+NaOD): δ 1.71-1.77 (2H, m), 3.20-3.29 (5H, m), 3.44 (2H, t, J=6.5 Hz), 3.54-3.62 (1H, m), 3.88-4.56 (4H, m), 7.54 (1H, d, J=11.5 Hz), 8.34 (1H, s), 8.98 (1H, s)

Example 114

Compound 114

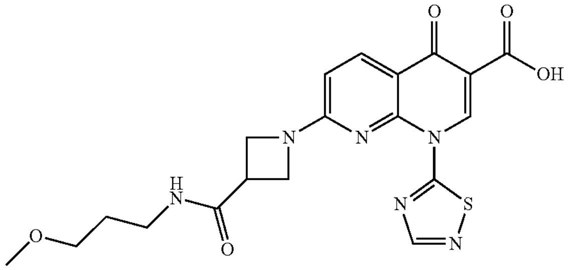

7-{3-[(3-Methoxypropyl)carbamoyl]azetidin-1-yl}-4-oxo-1-(1,2,4-thiadiazol-5-yl)-1,4-dihydro-1,8-naphthyridine-3-carboxylic acid The title compound was obtained using 7-chloro-4-oxo-1-(1,2,4-thiadiazol-5-yl)-1,4-dihydro-1,8-naphthyridine-3-carboxylic acid obtained in Reference Example 006-(2) and N-(3-methoxypropyl)azetidine-3-carboxamide hydrochloride obtained in Example 050 by the method described in Example 001-(3) or a method equivalent thereto.

1H-NMR (D2O+NaOD): δ 1.74 (2H, quin, J=6.5 Hz), 3.24 (2H, t, J=6.5 Hz), 3.26 (3H, s), 3.44 (2H, t, J=6.5 Hz), 3.49-3.57 (1H, m), 3.83-4.14 (4H, m), 6.04 (1H, d, J=9.0 Hz), 7.77 (1H, d, J=9.0 Hz), 8.32 (1H, s), 8.92 (1H, 8)

Example 115

Compound 115

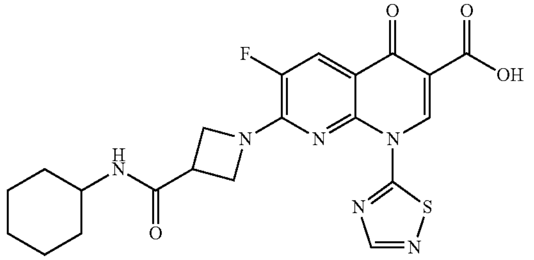

7-[3-(Cyclohexylcarbamoyl)azetidin-1-yl]-6-fluoro-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8- naphthyridine-3-carboxylic acid obtained in Reference Example 004-(2) and N-cyclohexylazetidine-3-carboxamide hydrochloride obtained in Example 059 by the method described in Example 002-(3) or a method equivalent thereto.

1H-NMR (DMSO-d6): δ 1.08-1.33 (5H, m), 1.52-1.81 (5H, m), 3.55-3.66 (2H, m), 4.42-4.80 (4H, m), 8.03 (1H, d, J=8.0 Hz), 8.14 (1H, d, J=11.5 Hz), 8.85 (1H, s), 9.75 (1H, s), 14.49 (1H, brs)

Example 116

Compound 116

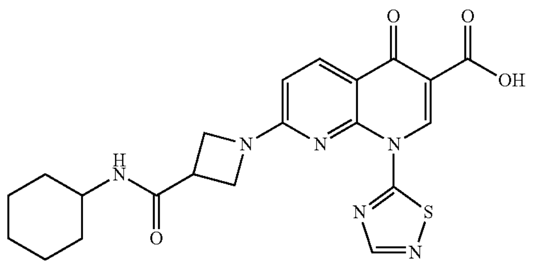

7-[3-(Cyclohexylcarbamoyl)azetidin-1-yl]-4-oxo-1-(1,2,4-thiadiazol-5-yl)-1,4-dihydro-1,8-naphthyridine-3-carboxylic acid The title compound was obtained using 7-chloro-4-oxo-1-(1,2,4-thiadiazol-5-yl)-1,4-dihydro-1,8-naphthyridine-3-carboxylic acid obtained in Reference Example 006-(2) and N-cyclohexylazetidine-3-carboxamide hydrochloride obtained in Example 059 by the method described in Example 002-(3) or a method equivalent thereto.

1H-NMR (DMSO-d6): δ 1.06-1.37 (5H, m), 1.51-1.85 (5H, m), 3.54-3.64 (2H, m), 4.25-4.64 (4H, m), 6.79 (1H, d, J=9.0 Hz), 8.06 (1H, d, J=8.0 Hz), 8.35 (1H, d, J=9.0 Hz), 8.83 (1H, s), 9.75 (1H, s), 14.72 (1H, brs)

Example 117

Compound 117

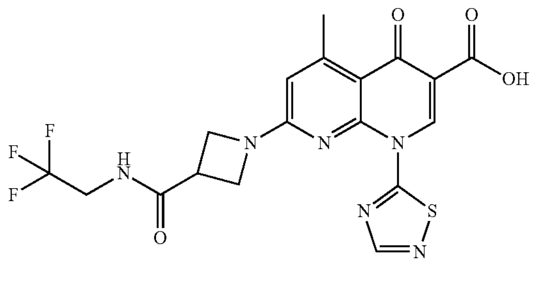

5-Methyl-4-oxo-1-(1,2,4-thiadiazol-5-yl)-7-{3-[(2,2,2-trifluoroethyl)carbamoyl]azetidin-1-yl}-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-(2,2,2-trifluoroethyl)azetidine-3-carboxamide hydrochloride obtained in Example 056 by the method described in Example 002-(3) or a method equivalent thereto.

1H-NMR (DMSO-d6): δ 2.78 (3H, s), 3.67-3.78 (1H, m), 3.91-4.01 (2H, m), 4.23-4.70 (4H, m), 6.61 (1H, s), 8.82 (1H, s), 8.87 (1H, t, J=6.5 Hz), 9.75 (1H, s), 15.06 (1H, brs)

Example 118

Compound 118

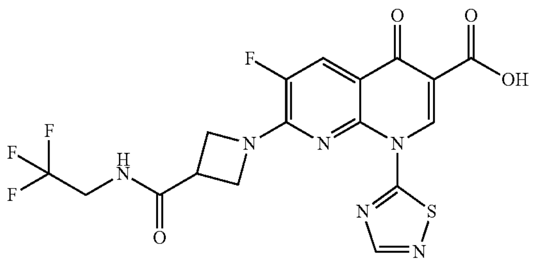

6-Fluoro-4-oxo-1-(1,2,4-thiadiazol-5-yl)-7-{3-[(2,2,2-trifluoroethyl)carbamoyl]azetidin-1-yl}-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and N-(2,2,2,2-trifluoroethyl)azetidine-3-carboxamide hydrochloride obtained in Example 056 by the method described in Example 002-(3) or a method equivalent thereto.

1H-NMR (DMSO-d6): δ 3.72-3.80 (1H, m), 3.91-4.07 (2H, m), 4.48-4.88 (4H, m), 8.16 (1H, d, J=11.5 Hz), 8.83-8.88 (2H, m), 9.76 (1H, s), 14.47 (1H, brs)

Example 119

Compound 119

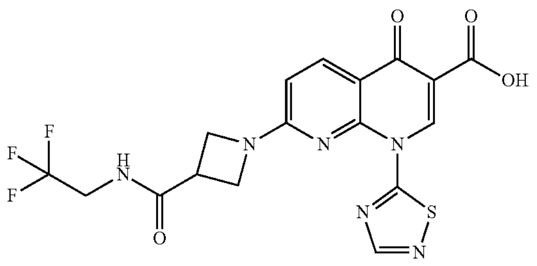

4-Oxo-1-(1,2,4-thiadiazol-5-yl)-7-{3-[(2,2,2-trifluoroethyl)carbamoyl]azetidin-1-yl}-1,4-dihydro-1,8-naphthyridine-3-carboxylic acid The title compound was obtained using 7-chloro-4-oxo-1-(1,2,4-thiadiazol-5-yl)-1,4-dihydro-1,8-naphthyridine-3-carboxylic acid obtained in Reference Example 006-(2) and N-(2,2,2-trifluoroethyl)azetidine-3-carboxamide hydrochloride obtained in Example 056 by the method described in Example 002-(3) or a method equivalent thereto.

1H-NMR (DMSO-d6): δ 3.69-3.79 (1H, m), 3.90-4.10 (2H, m), 4.25-4.76 (4H, m), 6.81 (1H, d, J=9.0 Hz), 8.36 (1H, d, J=9.0 Hz), 8.83 (1H, s), 8.90 (1H, t, J=6.5 Hz), 9.75 (1H, s), 14.69 (1H, brs)

Example 120

Compound 120

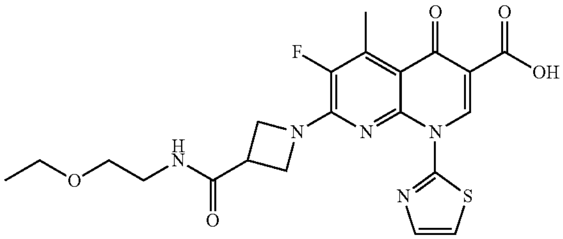

7-{3-[(2-Ethoxyethyl)carbamoyl]azetidin-1-yl}-6-fluoro-5-methyl-4-oxo-1-(1,3-thiazol-2-yl)-1,4-dihydro-1,8-naphthyridine-3-carboxylic acid The title compound was obtained using 7-chloro-6-fluoro-5-methyl-4-oxo-1-(1,3-thiazol-2-yl)-1,4-dihydro-1,8-naphthyridine-3-carboxylic acid obtained in Reference Example 007-(2) and N-(2-ethoxyethyl)azetidine-3-carboxamide hydrochloride obtained in Example 018-(1) by the method described in Example 002-(3) or a method equivalent thereto.

1H-NMR (DMSO-d6): δ 1.12 (3H, t, J=7.0 Hz), 2.68 (3H, d, J=3.5 Hz), 3.25-3.30 (2H, m), 3.39-3.47 (4H, m), 3.57-3.67 (1H, m), 4.34-4.80 (4H, m), 7.77 (1H, d, J=3.5 Hz), 7.85 (1H, d, J=3.5 Hz), 8.23 (1H, t, J=5.5 Hz), 9.80 (1H, s), 15.17 (1H, brs)

Example 121

Compound 121

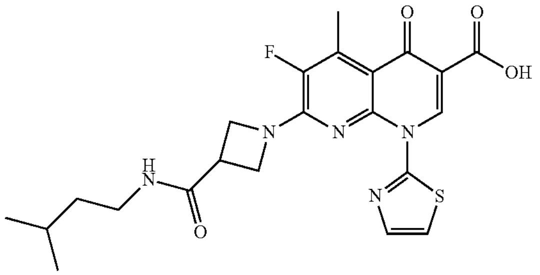

6-Fluoro-5-methyl-7-{3-[(3-methylbutyl)carbamoyl]azetidin-1-yl}-4-oxo-1-(1,3-thiazol-2-yl)-1,4-dihydro-1,8-naphthyridine-3-carboxylic acid The title compound was obtained using 7-chloro-6-fluoro-5-methyl-4-oxo-1-(1,3-thiazol-2-yl)-1,4-dihydro-1,8-naphthyridine-3-carboxylic acid obtained in Reference Example 007-(2) and N-(3-methylbutyl)azetidine-3-carboxamide hydrochloride obtained from 3-methylbutan-1-amine by the method described in Example 005-(1) and Example 001-(2) or a method equivalent thereto by the method described in Example 002-(3) or a method equivalent thereto.

1H-NMR (DMSO-d6): δ 0.88 (6H, d, J=6.5 Hz), 1.32 (2H, dt, J=7.5, 6.5 Hz), 1.53-1.63 (1H, m), 2.70 (3H, d, J=2.5 Hz), 2.89 (3H, s), 3.12 (2H, dt, J=6.5, 6.5 Hz), 3.52-3.62 (1H, m), 4.31-4.79 (4H, m), 7.77 (1H, d, J=3.5 Hz), 7.85 (1H, d, J=3.5 Hz), 8.08 (1H, t, J=6.5 Hz), 9.82 (1H, s), 15.18 (1H, s)

Example 122

Compound 122

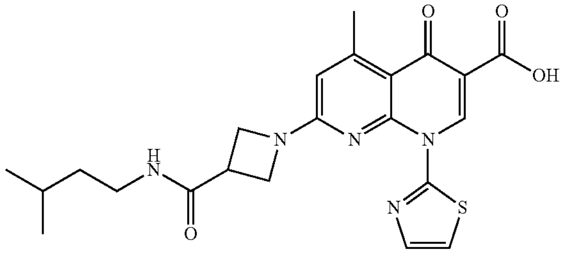

5-Methyl-7-{3-[(3-methylbutyl)carbamoyl]azetidin-1-yl}-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-(3-methylbutyl)azetidine-3-carboxamide hydrochloride obtained in Example 121 by the method described in Example 002-(3) or a method equivalent thereto.

1H-NMR (DMSO-d6): δ 0.88 (6H, d, J=6.5 Hz), 1.29-1.36 (2H, m), 1.54-1.63 (1H, m), 2.78 (3H, s), 3.09-3.16 (2H, m), 3.52-3.59 (1H, m), 4.18-4.51 (4H, m), 6.54 (1H, s), 7.75 (1H, d, J=3.5 Hz), 7.84 (1H, d, J=3.5 Hz), 8.10 (1H, t, J=5.5 Hz), 9.85 (1H, s)

Example 123

Compound 123

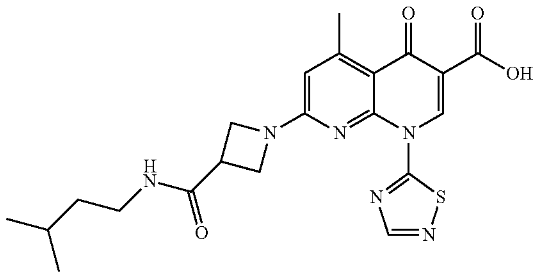

5-Methyl-7-{3-[(3-methylbutyl)carbamoyl]azetidin-1-yl}-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-(3-methylbutyl)azetidine-3-carboxamide hydrochloride obtained in Example 121 by the method described in Example 002-(3) or a method equivalent thereto.

1H-NMR (DMSO-d6): δ 0.88 (6H, d, J=7.0 Hz), 1.34 (2H, q, J=7.0 Hz), 1.60 (1H, sep, J=7.0 Hz), 2.75 (3H, s), 3.10-3.17 (2H, m), 3.55-3.63 (1H, m), 4.20-4.63 (4H, m), 6.56 (1H, s), 8.12 (1H, t, J=5.5 Hz), 8.80 (1H, s), 9.71 (1H, s)

Example 124

Compound 124

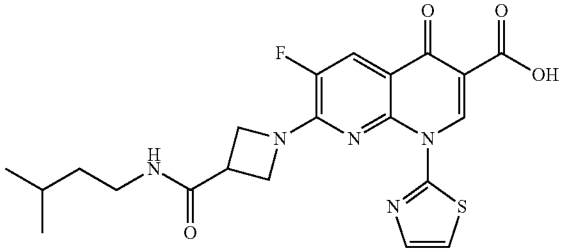

6-Fluoro-7-{3-[(3-methylbutyl)carbamoyl]azetidin-1-yl}-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-(3-methylbutyl)azetidine-3-carboxamide hydrochloride obtained in Example 121 by the method described in Example 002-(3) or a method equivalent thereto.

1H-NMR (DMSO-d6): δ 0.88 (6H, d, J=6.5 Hz), 1.30-1.36 (2H, m), 1.53-1.64 (1H, m), 3.09-3.17 (2H, m), 3.56-3.64 (1H, m), 4.36-4.81 (4H, m), 7.79 (1H, d, J=3.5 Hz), 7.86 (1H, d, J=3.5 Hz), 8.08-8.13 (2H, m), 9.82 (1H, s)

Example 125

Compound 125

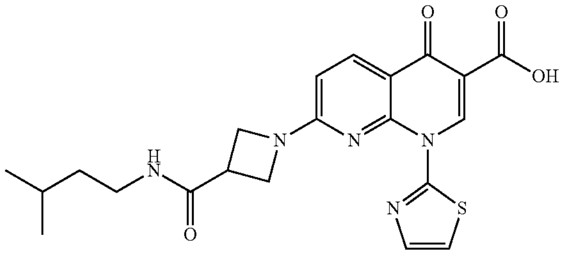

7-{3-[(3-Methylbutyl)carbamoyl]azetidin-1-yl}-4-oxo-1-(1,3-thiazol-2-yl)-1,4-dihydro-1,8-naphthyridine-3-carboxylic acid The title compound was obtained using 7-chloro-4-oxo-1-(1,3-thiazol-2-yl)-1,4-dihydro-1,8-naphthyridine-3-carboxylic acid obtained in Reference Example 005-(2) and N-(3-methylbutyl)azetidine-3-carboxamide hydrochloride obtained in Example 121 by the method described in Example 002-(3) or a method equivalent thereto.

Property: yellowish-brown solid;

ESI-MS (m/z): 442 [M+H]+

Example 126

Compound 126

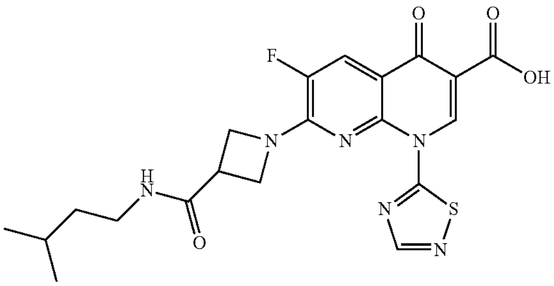

6-Fluoro-7-{3-[(3-methylbutyl)carbamoyl]azetidin-1-yl}-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and N-(3-methylbutyl)azetidine-3-carboxamide hydrochloride obtained in Example 121 by the method described in Example 001-(3) or a method equivalent thereto.

1H-NMR (D2O+NaOD): δ 0.80 (6H, d, J=6.5 Hz), 1.29-1.38 (2H, m), 1.47-1.56 (1H, m), 3.18 (2H, t, J=7.0 Hz), 3.58-3.66 (1H, m), 4.20-4.77 (4H, m), 7.78 (1H, d, J=12.0 Hz), 8.44 (1H, s), 9.21 (1H, s)

Example 127

Compound 127

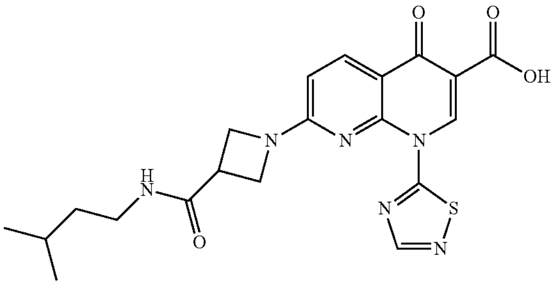

7-{3-[(3-Methylbutyl)carbamoyl]azetidin-1-yl}-4-oxo-1-(1,2,4-thiadiazol-5-yl)-1,4-dihydro-1,8-naphthyridine-3-carboxylic acid The title compound was obtained using 7-chloro-4-oxo-1-(1,2,4-thiadiazol-5-yl)-1,4-dihydro-1,8-naphthyridine-3-carboxylic acid obtained in Reference Example 006-(2) and N-(3-methylbutyl)azetidine-3-carboxamide hydrochloride obtained in Example 121 by the method described in Example 001-(3) or a method equivalent thereto.

1H-NMR (D2O+NaOD): δ 0.81 (6H, d, J=6.5 Hz), 1.32-1.38 (2H, m), 1.49-1.57 (1H, m), 3.19 (2H, t, J=7.0 Hz), 3.52-3.60 (1H, m), 4.04-4.19 (4H, m), 6.18 (1H, d, J=8.5 Hz), 7.91 (1H, d, J=8.5 Hz), 8.38 (1H, s), 9.06 (1H, s)

Example 128

Compound 128

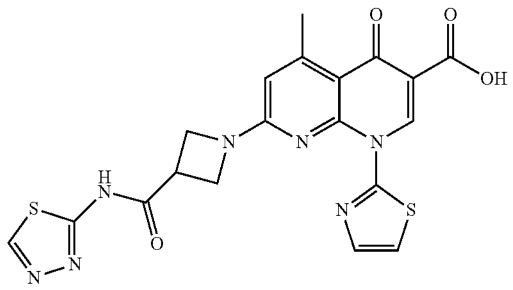

5-Methyl-4-oxo-7-{3-[(1,3,4-thiadiazol-2-yl)carbamoyl]azetidin-1-yl}-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-(1,3,4-thiadiazol-2-yl)azetidine-3-carboxamide hydrochloride obtained from 1,3,4-thiadiazol-2-amine by the method described in Example 005-(1) and Example 001-(2) or a method equivalent thereto by the method described in Example 002-(3) or a method equivalent thereto.

1H-NMR (DMSO-d6): δ 2.78 (3H, s), 3.94-4.03 (1H, m), 4.30-4.63 (4H, m), 6.59 (1H, s), 7.75 (1H, d, J=3.5 Hz), 7.84 (1H, d, J=3.5 Hz), 9.19 (1H, s), 9.84 (1H, s), 12.83 (1H, s), 15.35 (1H, brs)

Example 129

Compound 129

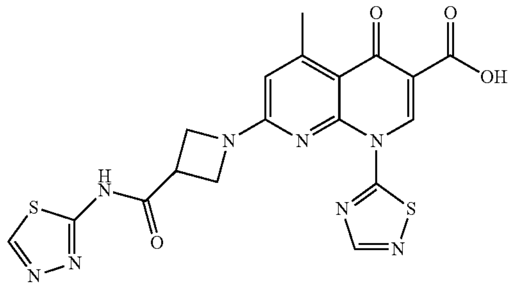

5-Methyl-4-oxo-7-{3-[(1,3,4-thiadiazol-2-yl)carbamoyl]azetidin-1-yl}-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-(1,3,4-thiadiazol-2-yl)azetidine-3-carboxamide hydrochloride obtained in Example 128 by the method described in Example 002-(3) or a method equivalent thereto.

1H-NMR (DMSO-d6): δ 2.78 (3H, s), 3.99-4.06 (1H, m), 4.36-4.76 (4H, m), 6.63 (1H, s), 7.79 (1H, s), 8.82 (1H, a), 9.75 (1H, s), 12.84 (1H, s), 15.06 (1H, brs)

Example 130

Compound 130

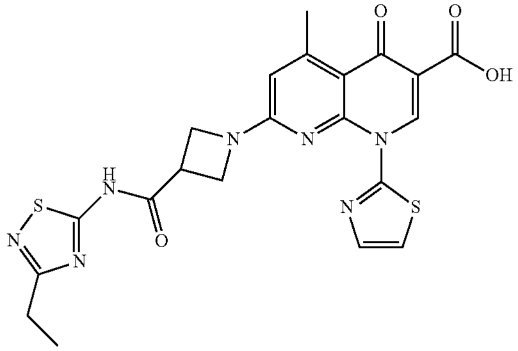

7-{3-[(3-Ethyl-1,2,4-thiadiazol-5-yl)carbamoyl]azetidin-1-yl}-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and (3-ethyl-1,2,4-thiadiazol-5-yl)azetidine-3-carboxamide hydrochloride obtained from 3-ethyl-1,2,4-thiadiazol-5-amine by the method described in Example 005-(1) and Example 001-(2) or a method equivalent thereto by the method described in Example 002-(3) or a method equivalent thereto.

1H-NMR (DMSO-d6): δ 1.26 (3H, t, J=7.5 Hz), 2.77-2.83 (5H, m), 3.95-4.04 (1H, m), 4.32-4.62 (4H, m), 6.60 (1H, s), 7.75 (1H, d, J=3.5 Hz), 7.84 (1H, d, J=3.5 Hz), 9.85 (1H, s), 13.10 (1H, s), 15.36 (1H, brs)

Example 131

Compound 131

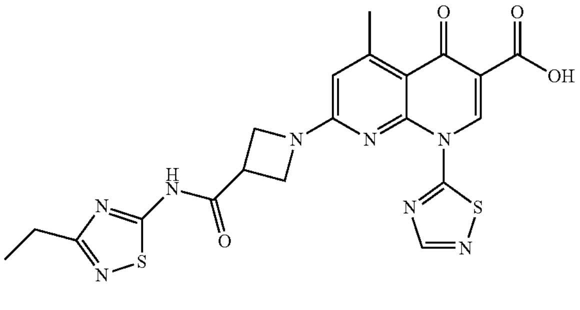

7-{3-[(3-Ethyl-1,2,4-thiadiazol-5-yl)carbamoyl]azetidin-1-yl}-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and (3-ethyl-1,2,4-thiadiazol-5-yl)azetidine-3-carboxamide hydrochloride obtained in Example 130 by the method described in Example 002-(3) or a method equivalent thereto.

1H-NMR (DMSO-d6): δ 1.27 (3H, t, J=7.5 Hz), 2.73-2.84 (5H, m), 3.97-4.08 (1H, m), 4.41-4.76 (4H, m), 6.64 (1H, s), 8.82 (1H, s), 9.76 (1H, s), 13.11 (1H, s), 15.04 (1H, brs)

Example 132

Compound 132

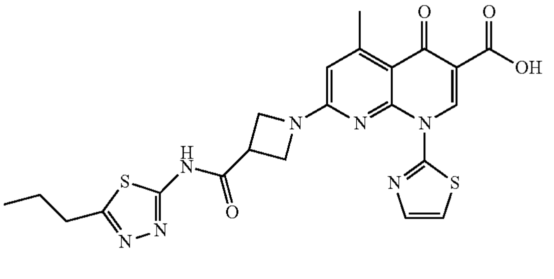

5-Methyl-4-oxo-7-{3-[(5-propyl-1,3,4-thiadiazol-2-yl)carbamoyl]azetidin-1-yl}-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-(5-propyl-1,3,4-thiadiazol-2-yl)azetidine-3-carboxamide hydrochloride obtained from 5-propyl-1,3,4-thiadiazol-2-amine by the method described in Example 005-(1) and Example 001-(2) or a method equivalent thereto by the method described in Example 002-(3) or a method equivalent thereto.

1H-NMR (DMSO-d6): δ 0.94 (3H, t, J=7.5 Hz), 1.67-1.76 (2H, m), 2.78 (3H, s), 2.94 (2H, t, J=7.5 Hz), 3.91-4.00 (1H, m), 4.30-4.60 (4H, m), 6.58 (1H, s), 7.75 (1H, d, J=3.5 Hz), 7.84 (1H, d, J=3.5 Hz), 9.84 (1H, s), 12.66 (1H, 9), 15.37 (1H, brs)

Example 133

Compound 133

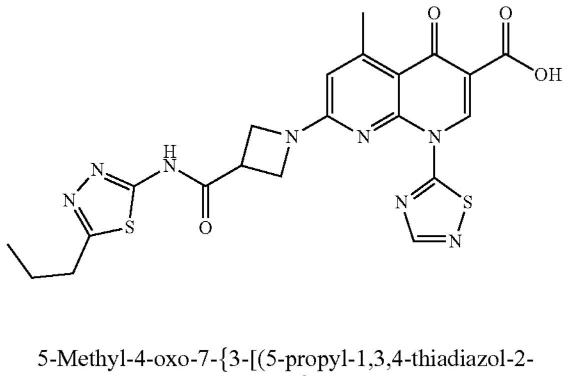

5-Methyl-4-oxo-7-{3-[(5-propyl-1,3,4-thiadiazol-2-yl)carbamoyl]azetidin-1-yl}-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-(5-propyl-1,3,4-thiadiazol-2-yl)azetidine-3-carboxamide hydrochloride obtained in Example 132 by the method described in Example 002-(3) or a method equivalent thereto.

1H-NMR (DMSO-d6): δ 0.94 (3H, t, J=7.5 Hz), 1.67-1.77 (2H, m), 2.76 (3H, s), 2.96 (2H, t, J=7.5 Hz), 3.96-4.05 (1H, m), 4.37-4.70 (4H, m), 6.59 (1H, s), 7.84 (1H, s), 8.80 (1H, s), 9.70 (1H, s), 12.69 (1H, brs)

Example 134

Compound 134

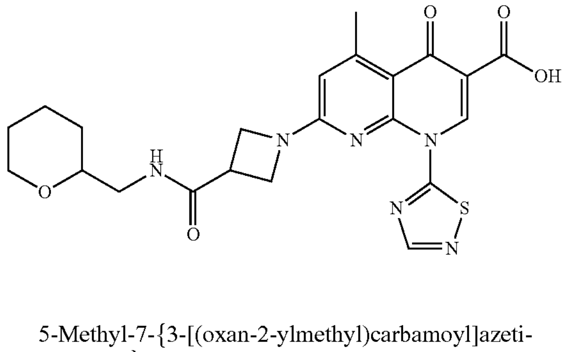

5-Methyl-7-{3-[(oxan-2-ylmethyl)carbamoyl]azetidin-1-yl}-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-(oxan-2-ylmethyl)azetidine-3-carboxamide hydrochloride obtained in Example 078-(1) by the method described in Example 002-(3) or a method equivalent thereto.

1H-NMR (DMSO-d6): δ 1.12-1.21 (1H, m), 1.39-1.50 (3H, m), 1.53-1.59 (1H, m), 1.74-1.81 (1H, m), 2.77 (3H, 8), 3.06-3.14 (1H, m), 3.16-3.23 (1H, m), 3.62-3.69 (1H, m), 3.85-3.91 (1H, m), 4.23-4.62 (4H, m), 6.58 (1H, s), 8.25 (1H, t, J=5.7 Hz), 8.81 (1H, s), 9.73 (1H, s), 15.04 (1H, brs)

Example 135

Compound 135

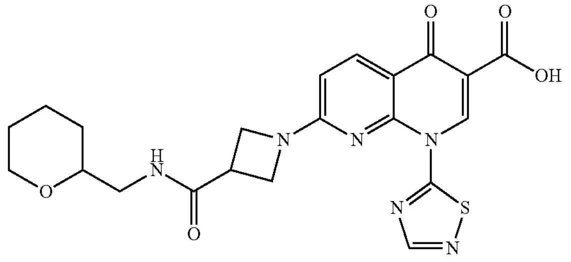

7-{3-[(Oxan-2-ylmethyl)carbamoyl]azetidin-1-yl}-4-oxo-1-(1,2,4-thiadiazol-5-yl)-1,4-dihydro-1,8-naphthyridine-3-carboxylic acid The title compound was obtained using 7-chloro-4-oxo-1-(1,2,4-thiadiazol-5-yl)-1,4-dihydro-1,8-naphthyridine-3-carboxylic acid obtained in Reference Example 006-(2) and N-(oxan-2-ylmethyl)azetidine-3-carboxamide hydrochloride obtained in Example 078-(1) by the method described in Example 002-(3) or a method equivalent thereto.

1H-NMR (DMSO-d6): δ 1.11-1.20 (1H, m), 1.39-1.49 (3H, m), 1.53-1.59 (1H, m), 1.73-1.79 (1H, m), 3.06-3.13 (1H, m), 3.16-3.22 (1H, m), 3.62-3.69 (1H, m), 3.85-3.90 (1H, m), 4.19-4.59 (4H, m), 6.63 (1H, d, J=8.9 Hz), 8.25 (1H, t, J=5.8 Hz), 8.30 (1H, d, J=8.9 Hz), 8.73 (1H, s), 9.67 (1H, s)

Example 136

Compound 136

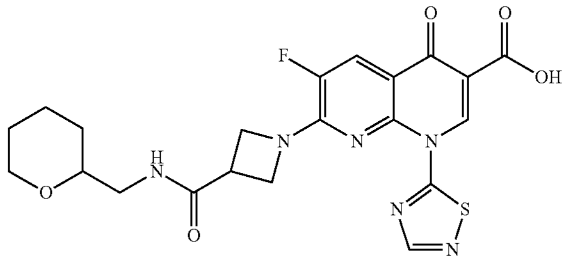

6-Fluoro-7-{3-[(oxan-2-ylmethyl)carbamoyl]azetidin-1-yl}-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and N-(oxan-2-ylmethyl)azetidine-3-carboxamide hydrochloride obtained in Example 078-(1) by the method described in Example 002-(3) or a method equivalent thereto.

1H-NMR (DMSO-d6): δ 1.11-1.21 (1H, m), 1.39-1.49 (3H, m), 1.54-1.59 (1H, m), 1.73-1.80 (1H, m), 3.07-3.13 (1H, m), 3.16-3.23 (1H, m), 3.64-3.71 (1H, m), 3.85-3.90 (1H, m), 4.47-4.53 (2H, m), 4.61-4.68 (2H, m), 8.02 (1H, d, J=11.6 Hz), 8.24 (1H, t, J=5.7 Hz), 8.75 (1H, s), 9.66 (1H, s)

Example 137

Compound 137

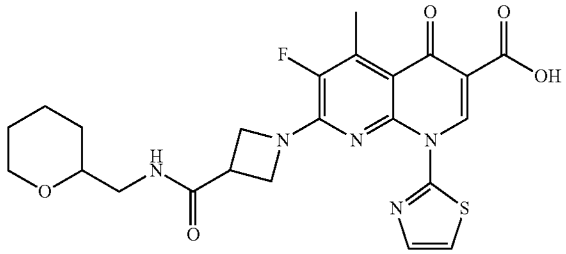

6-Fluoro-5-methyl-7-{3-[(oxan-2-ylmethyl)carbamoyl]azetidin-1-yl}-4-oxo-1-(1,3-thiazol-2-yl)-1,4-dihydro-1,8-naphthyridine-3-carboxylic acid The title compound was obtained using 7-chloro-6-fluoro-5-methyl-4-oxo-1-(1,3-thiazol-2-yl)-1,4-dihydro-1,8-naphthyridine-3-carboxylic acid obtained in Reference Example 007-(2) and N-(oxan-2-ylmethyl)azetidine-3-carboxamide hydrochloride obtained in Example 078-(1) by the method described in Example 002-(3) or a method equivalent thereto.

Property: white solid;

ESI-MS (m/z): 502 [M+H]+

Example 138

Compound 138

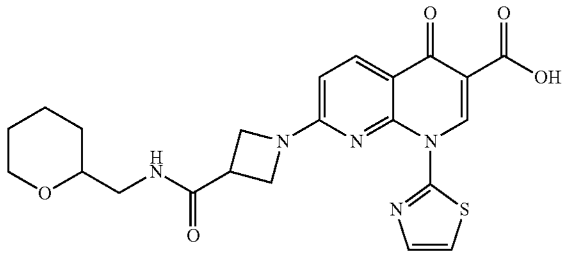

7-{3-[(Oxan-2-ylmethyl)carbamoyl]azetidin-1-yl}-4-oxo-1-(1,3-thiazol-2-yl)-1,4-dihydro-1,8-naphthyridine-3-carboxylic acid The title compound was obtained using 7-chloro-4-oxo-1-(1,3-thiazol-2-yl)-1,4-dihydro-1,8-naphthyridine-3-carboxylic acid in Reference Example 005-(2) and N-(oxan-2-ylmethyl)azetidine-3-carboxamide hydrochloride obtained in Example 078-(1) by the method described in Example 002-(3) or a method equivalent thereto.

Property: yellow solid;

ESI-MS (m/z): 470 [M+H]+

Example 139

Compound 139

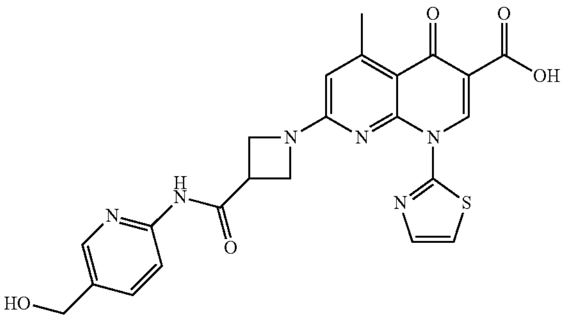

7-(3-{[5-(Hydroxymethyl)pyridin-2-yl]carbamoyl}azetidin-1-yl)-5-methyl-4-oxo-1-(1,3-thiazol-2-yl)-1,4-dihydro-1,8-naphthyridine-3-carboxylic acid (1) A suspension of methyl 6-{1-[(tert-butoxy) carbonyl]azetidin-3-amido}pyridine-3-carboxylate (134 mg) obtained from methyl 6-aminopyridine-3-carboxylate by the method described in Example 007-(1) or a method equivalent thereto, and lithium iodide (104 mg) in pyridine (2.0 mL) was stirred at 150° C. for 3 hours under microwave irradiation. The reaction solution was concentrated, and the residue was then dissolved in an aqueous sodium carbonate solution and washed with chloroform. The aqueous layer was neutralized, and the mixture was extracted with chloroform. The organic layer was dried over sodium sulfate and concentrated to obtain 57 mg of 6-{1-[(tert-butoxy) carbonyl]azetidin-3-amido}pyridine-3-carboxylic acid.

1H-NMR (CDCl3): δ 1.45 (9H, s), 3.32-3.42 (1H, m), 4.11-4.18 (2H, m), 4.19-4.26 (2H, m), 4.69-4.73 (2H, m), 7.77 (1H, dd, J=8.5, 2.5 Hz), 7.90 (1H, brs), 8.24 (1H, brd, J=8.5 Hz), 8.28 (1H, d, J=2.0 Hz)

(2) To a solution of 6-{l-[(tert-butoxy) carbonyl]azetidin-3-amido}pyridine-3-carboxylic acid (45 mg) obtained in the preceding section, and N-methylmorpholine (18 μL) in THF was added isobutyl chloroformate (18 μL) at −10° C., and the mixture was stirred at the same temperature for 10 minutes. Insoluble material was filtered off. To the residue was added 1 mol/L sodium borohydride (420 μL) under ice cooling, and the mixture was stirred at the same temperature for 100 minutes. The reaction solution was concentrated, and the residue was subjected to silica gel column chromatography (eluent: ethyl acetate/n-hexane) to obtain crude tert-butyl 3-{[5-(hydroxymethyl)pyridin-2-yl]carbamoyl}azetidine-1-carboxylate.

(3) The title compound was obtained by the method described in Example 014 or a method equivalent thereto using N-[5-(hydroxymethyl)pyridin-2-yl]azetidine-3-carboxamide hydrochloride obtained by the method described in Example 001-(2) or a method equivalent thereto from crude tert-butyl 3-{[5-(hydroxymethyl)pyridin-2-yl]carbamoyl}azetidine-1-carboxylate obtained in the preceding section, and 7-chloro-5-methyl-4-oxo-1-(1,3-thiazol-2-yl)-1,4-dihydro-1,8-naphthyridine-3-carboxylic acid obtained in Reference Example 001-(2).

1H-NMR (DMSO-d6): δ 2.79 (3H, s), 3.88-4.01 (1H, m), 4.34-4.58 (4H, m), 4.48 (2H, d, J=6.0 Hz), 5.23 (1H, t, J=6.0 Hz), 6.59 (1H, s), 7.72-7.76 (2H, m), 7.83 (1H, d, J=3.5 Hz), 8.10 (1H, d, J=9.0 Hz), 8.27 (1H, d, J=2.0 Hz), 9.86 (1H, s), 10.75 (1H, s), 15.41 (1H, s)

Example 140

Compound 140

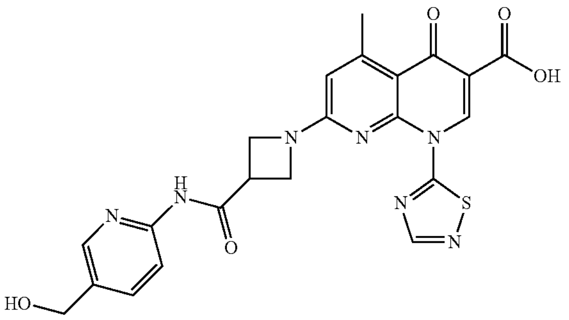

7-(3-{[5-(Hydroxymethyl)pyridin-2-yl]carbamoyl}azetidin-1-yl)-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-[5-(hydroxymethyl)pyridin-2-yl]azetidine-3-carboxamide hydrochloride obtained in Example 139-(3) by the method described in Example 014 or a method equivalent thereto.

1H-NMR (DMSO-d6): δ 2.79 (3H, s), 3.91-4.00 (1H, m), 4.35-4.69 (4H, m), 4.48 (2H, d, J=6.0 Hz), 5.24 (1H, t, J=6.0 Hz), 6.63 (1H, s), 7.74 (1H, dd, J=9.0, 2.0 Hz), 8.11 (1H, d, J=9.0 Hz), 8.28 (1H, d, J=2.0 Hz), 8.82 (1H, s), 9.76 (1H, s), 10.77 (1H, s), 15.08 (1H, s)

Example 141

Compound 141

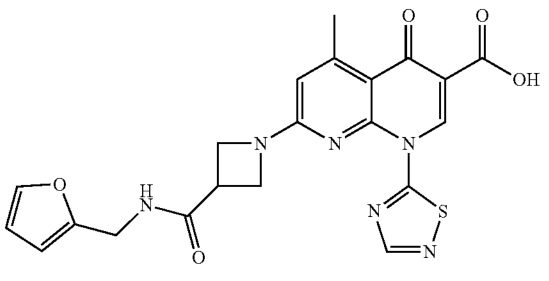

7-{3-[(Furan-2-ylmethyl)carbamoyl]azetidin-1-yl}-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-(furan-2-ylmethyl)azetidine-3-carboxamide hydrochloride obtained from furan-2-ylmethylamine by the method described in Example 005-(1) and Example 001-(2) or a method equivalent thereto by the method described in Example 002-(3) or a method equivalent thereto.

1H-NMR (DMSO-d6): δ 2.77 (3H, s), 3.60-3.71 (1H, m), 4.18-4.51 (6H, m), 6.29 (1H, dd, J=3.0, 0.5 Hz), 6.40 (1H, dd, J=3.0, 2.0 Hz), 6.59 (1H, d, J=1.0 Hz), 7.59 (1H, dd, J=2.0, 0.5 Hz), 8.65 (1H, t, J=5.5 Hz), 8.81 (1H, s), 9.74 (1H, s), 15.06 (1H, brs)

Example 142

Compound 142

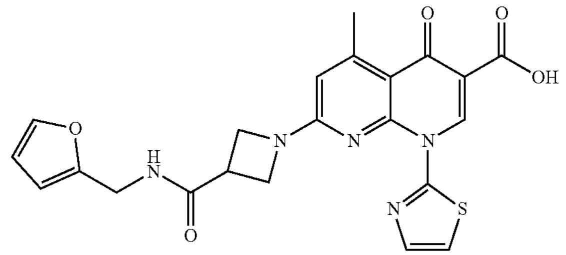

7-{3-[(Furan-2-ylmethyl)carbamoyl]azetidin-1-yl}-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-(furan-2-ylmethyl)azetidine-3-carboxamide hydrochloride obtained in Example 141 by the method described in Example 002-(3) or a method equivalent thereto.

1H-NMR (DMSO-d6): δ 2.79 (3H, s), 3.58-3.66 (1H, m), 4.19-4.52 (6H, m), 6.29 (1H, dd, J=3.0, 1.0 Hz), 6.41 (1H, dd, J=3.0, 2.0 Hz), 6.56 (1H, s), 7.59 (1H, dd, J=2.0, 1.0 Hz), 7.75 (1H, d, J=3.5 Hz), 7.84 (1H, d, J=3.5 Hz), 8.63 (1H, t, J=6.0 Hz), 9.86 (1H, s), 15.41 (1H, brs)

Example 143

Compound 143

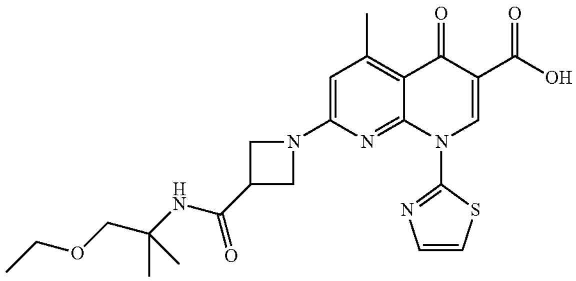

7-{3-[(1-Ethoxy-2-methylpropan-2-yl)carbamoyl]azetidin-1-yl}-5-methyl-4-oxo-1-(1,3-thiazol-2-yl)-1,4-dihydro-1,8-naphthyridine-3-carboxylic acid The title compound was obtained by the method described in Example 002-(3) or a method equivalent thereto using N-(1-ethoxy-2-methylpropan-2-yl)azetidine-3-carboxamide hydrochloride obtained from 2-amino-2-methylpropan-1-ol by the methods described in Examples 005-(1), 006-(2) and 001-(2) or methods equivalent thereto, and 7-chloro-5-methyl-4-oxo-1-(1,3-thiazol-2-yl)-1,4-dihydro-1,8-naphthyridine-3-carboxylic acid obtained in Reference Example 001-(2).

1H-NMR (DMSO-d6): δ 1.11 (3H, t, J=7.0 Hz), 1.24 (6H, s), 2.76 (3H, d, J=1.0 Hz), 3.56-3.63 (1H, m), 4.15-4.45 (4H, m), 6.52 (1H, d, J=1.0 Hz), 7.66 (1H, brs), 7.75 (1H, d, J=3.5 Hz), 7.83 (1H, d, J=3.5 Hz), 9.83 (1H, s)

Example 144

Compound 144

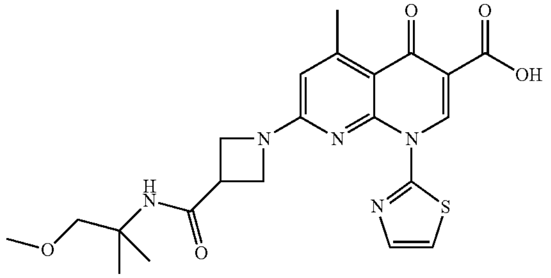

7-{3-[(1-Methoxy-2-methylpropan-2-yl)carbamoyl]azetidin-1-yl}-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl-1,4-dihydro-1,8-naphthyridine-3-carboxylic acid obtained in Reference Example 001-(2) and N-(1-methoxy-2-methylpropane-2-yl)azetidine-3-carboxamide hydrochloride obtained from 2-amino-2-methylpropan-1-ol by the method described in Example 005-(1), Example 006-(2) and Example 001-(2) or a method equivalent thereto by the method described in Example 002-(3) or a method equivalent thereto.

1H-NMR (DMSO-d6): δ 1.11 (3H, t, J=7.0 Hz), 1.24 (6H, s), 2.76 (3H, d, J=1.0 Hz), 3.56-3.63 (1H, m), 4.15-4.45 (4H, m), 6.52 (1H, d, J=1.0 Hz), 7.66 (1H, brs), 7.75 (1H, d, J=3.5 Hz), 7.83 (1H, d, J=3.5 Hz), 9.83 (1H, s)

Example 145

Compound 145

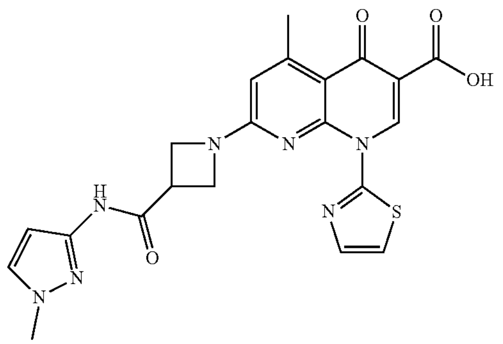

5-Methyl-7-{3-[(1-methyl-1H-pyrazol-3-yl)carbamoyl]azetidin-1-yl}-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-(1-methyl-1H-pyrazol-3-yl)azetidine-3-carboxamide hydrochloride obtained from 1-methyl-1H-pyrazol-3-amine by the method described in Example 007-(1) and Example 001-(2) or a method equivalent thereto by the method described in Example 014 or a method equivalent thereto.

1H-NMR (DMSO-d6): δ 2.77 (3H, s), 3.74 (3H, s), 3.75-3.83 (1H, m), 4.27-4.56 (4H, m), 6.48 (1H, d, J=2.0 Hz), 6.56 (1H, brs), 7.56 (1H, d, J=2.0 Hz), 7.74 (1H, d, J=3.5 Hz), 7.83 (1H, d, J=3.5 Hz), 9.84 (1H, a), 10.66 (1H, s), 15.38 (1H, brs)

Example 146

Compound 146

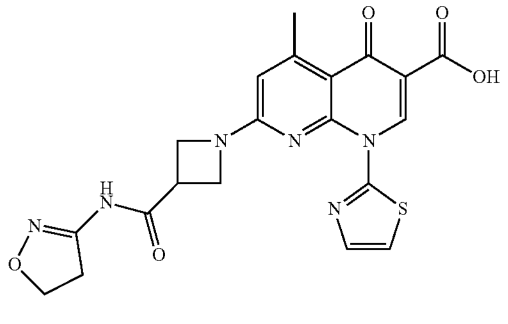

7-{3-[(4,5-Dihydro-1,2-oxazol-3-yl)carbamoyl]azetidin-1-yl}-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-(4,5-dihydro-1,2-oxazol-3-yl)azetidine-3-carboxamide hydrochloride obtained from 4,5-dihydro-1,2-oxazol-3-amine by the method described in Example 005-(1) and Example 001-(2) or a method equivalent thereto by the method described in Example 002-(3) or a method equivalent thereto.

1H-NMR (DMSO-d6): δ 2.78 (3H, s), 3.40 (2H, t, J=9.0 Hz), 3.74-3.84 (1H, m), 4.24 (2H, t, J=9.0 Hz), 4.27-4.55 (4H, m), 6.57 (1H, d, J=1.0 Hz), 7.76 (1H, d, J=3.5 Hz), 7.84 (1H, d, J=3.5 Hz), 9.86 (1H, s), 10.94 (1H, s), 15.38 (1H, brs)

Example 147

Compound 147

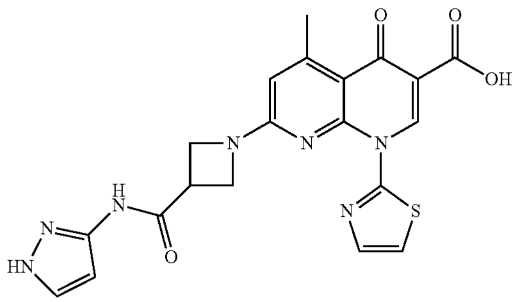

5-Methyl-4-oxo-7-{3-[(1H-pyrazol-3-yl)carbamoyl]azetidin-1-yl}-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-(1H-pyrazol-3-yl)azetidine-3-carboxamide hydrochloride obtained from 1H-pyrazol-3-amine by the method described in Example 005-(1) and Example 001-(2) or a method equivalent thereto by the method described in Example 002-(3) or a method equivalent thereto.

1H-NMR (DMSO-d6): δ 2.76 (3H, s), 3.93-4.11 (1H, m), 4.29-4.57 (4H, m), 6.54 (1H, d, J=2.5 Hz), 6.55 (1H, s), 7.73 (1H, d, J=3.5 Hz), 7.83 (1H, d, J=3.5 Hz), 9.84 (1H, s), 10.69 (1H, s)

Example 148

Compound 148

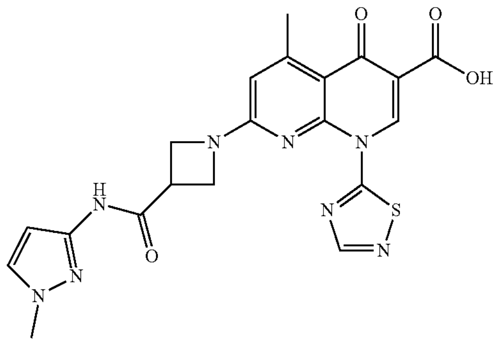

5-Methyl-7-{3-[(1-methyl-1H-pyrazol-3-yl)carbamoyl]azetidin-1-yl}-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-(1-methyl-1H-pyrazol-3-yl)azetidine-3-carboxamide hydrochloride obtained in Example 145 by the method described in Example 019 or a method equivalent thereto.

1H-NMR (DMSO-d6): δ 2.78 (3H, s), 3.74 (3H, s), 3.75-3.83 (1H, m), 4.27-4.71 (4H, m), 6.49 (1H, d, J=2.0 Hz), 6.62 (1H, brs), 7.56 (1H, d, J=2.0 Hz), 8.81 (1H, s), 9.75 (1H, s), 10.69 (1H, s), 15.11 (1H, brs)

Example 149

Compound 149

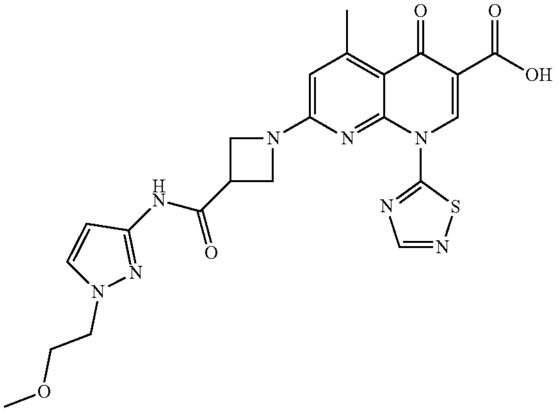

7-(3-{[1-(2-Methoxyethyl)-1H-pyrazol-3-yl]carbamoyl)}azetidin-1-yl)-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-[1-(2-methoxyethyl)-1H-pyrazol-3-yl]azetidine-3-carboxamide hydrochloride obtained in Example 019 by the method described in Example 019 or a method equivalent thereto.

1H-NMR (DMSO-d6): δ 2.78 (3H, s), 3.22 (3H, s), 3.65 (2H, t, J=5.5 Hz), 3.76-3.86 (1H, m), 4.15 (2H, t, J=5.5 Hz), 4.26-4.70 (4H, m), 6.50 (1H, d, J=2.0 Hz), 6.61 (1H, s), 7.59 (1H, d, J=2.0 Hz), 8.81 (1H, s), 9.76 (1H, s), 10.75 (1H, s), 15.07 (1H, brs)

Example 150

Compound 150

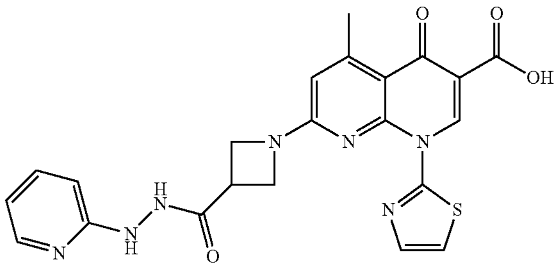

5-Methyl-4-oxo-7-{3-[N'-(pyridin-2-yl)hydrazinecarbonyl]azetidin-1-yl}-1-(1,3-thiazol-2-yl)-1,4-dihydro-1,8-naphthyridine-3-carboxylic acid The title compound was obtained by the method described in Example 002-(3) or a method equivalent thereto using N'-(pyridin-2-yl)azetidine-3-carbohydrazide hydrochloride obtained from 2-hydrazinylpyridine by the methods described in Examples 005-(1) and 001-(2) or methods equivalent thereto, and 7-chloro-5-methyl-4-oxo-1-(1,3-thiazol-2-yl)-1,4-dihydro-1,8-naphthyridine-3-carboxylic acid obtained in Reference Example 001-(2).

1H-NMR (DMSO-d6): δ 2.77 (3H, s), 4.19-4.71 (4H, m), 6.58 (1H, s), 7.07 (1H, dd, J=7.0, 7.0 Hz), 7.19 (1H, d, J=8.0 Hz), 7.77 (1H, d, J=3.5 Hz), 7.85 (1H, d, J=3.5 Hz), 8.02-8.11 (2H, m), 9.83 (1H, s), 10.68 (1H, brs), 10.79 (1H, brs), 15.31 (1H, brs)

Example 151

Compound 151

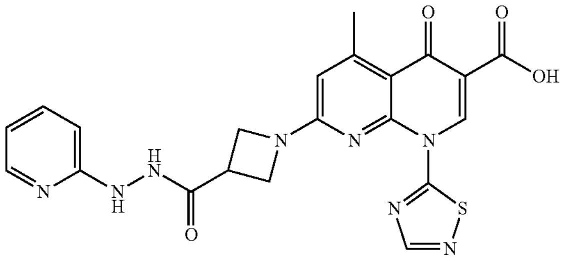

5-Methyl-4-oxo-7-{3-[N'-(pyridin-2-yl)hydrazinecarbonyl]azetidin-1-yl}-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N'-(pyridin-2-yl)azetidine-3-carbohydrazide hydrochloride obtained in Example 150 by the method described in Example 002-(3) or a method equivalent thereto.

1H-NMR (DMSO-d6): δ 2.79 (3H, s), 3.82-3.87 (1H, m), 4.33-4.77 (4H, m), 6.64 (1H, s), 7.07 (1H, t, J=6.5 Hz), 7.19 (1H, d, J=8.0 Hz), 8.00-8.10 (2H, m), 8.83 (1H, s), 9.75 (1H, s), 10.26-11.01 (2H, m)

Example 152

Compound 152

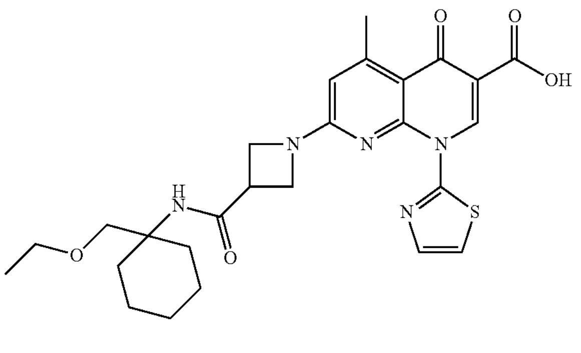

7-(3-{[1-(Ethoxymethyl)cyclohexyl]carbamoyl}azetidin-1-yl)-5-methyl-4-oxo-1-(1,3-thiazol-2-yl)-1,4-dihydro-1,8-naphthyridine-3-carboxylic acid The title compound was obtained by the method described in Example 019 or a method equivalent thereto using N-[1-(ethoxymethyl)cyclohexyl]azetidine-3-carboxamide hydrochloride obtained from (1-aminocyclohexyl)methanol by the methods described in Examples 005-(1), 006-(2) and 001-(2) or methods equivalent thereto, and 7-chloro-5-methyl-4-oxo-1-(1,3-thiazol-2-yl)-1,4-dihydro-1,8-naphthyridine-3-carboxylic acid obtained in Reference Example 001-(2).

1H-NMR (DMSO-d6): δ 1.09 (3H, t, J=7.0 Hz), 1.14-1.57 (7H, m), 2.03-2.14 (3H, m), 2.78 (3H, s), 3.40 (2H, q, J=7.0 Hz), 3.48 (2H, s), 3.61-3.70 (1H, m), 4.16-4.47 (4H, m), 6.56 (1H, s), 7.43 (1H, brs), 7.77 (1H, d, J=3.5 Hz), 7.85 (1H, d, J=3.5 Hz), 9.85 (1H, s), 15.43 (1H, brs)

Example 153

Compound 153

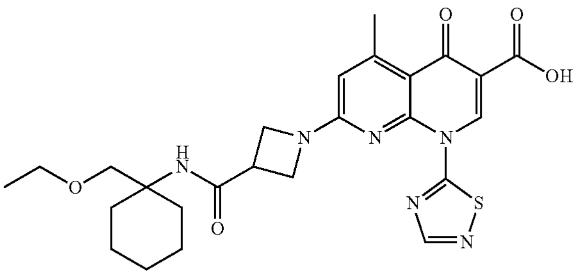

7-(3-{[1-(Ethoxymethyl)cyclohexyl]carbamoyl}azetidin-1-yl)-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-[l-(ethoxymethyl)cyclohexyl]azetidine-3-carboxamide hydrochloride obtained in Example 152 by the method described in Example 019 or a method equivalent thereto.

Property: orange solid;

ESI-MS (m/z): 527 [M+H]+

Example 154

Compound 154

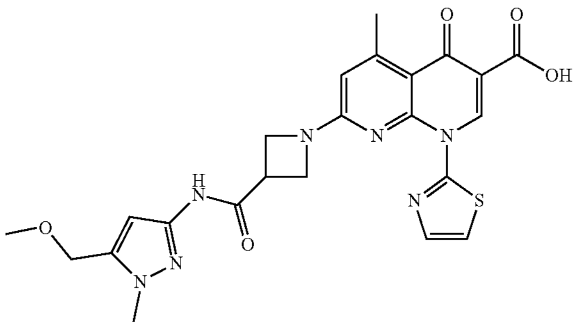

7-(3-{[5-(Methoxymethyl)-1-methyl-1H-pyrazol-3-yl]carbamoyl}azetidin-1-yl)-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-[5-(methoxymethyl)-1-methyl-1H-pyrazol-3-yl]azetidine-3-carboxamide hydrochloride obtained in Example 008 by the method described in Example 019 or a method equivalent thereto.

1H-NMR (DMSO-d6): δ 2.78 (3H, s), 3.25 (3H, s), 3.68 (3H, s), 3.74-3.84 (1H, m), 4.26-4.55 (6H, m), 6.54 (1H, s), 6.57 (1H, brs), 7.74 (1H, d, J=3.5 Hz), 7.84 (1H, d, J=3.5 Hz), 7.95 (1H, brs), 9.86 (1H, s), 10.66 (1H, s), 15.39 (1H, brs)

Example 155

Compound 155

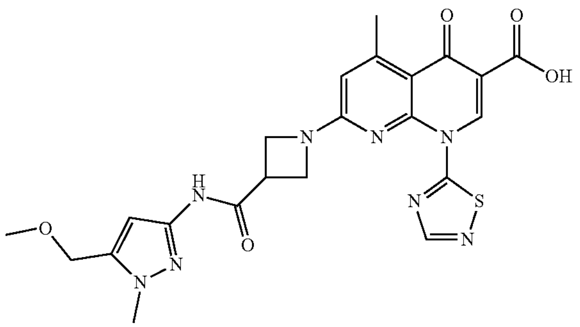

7-(3-{[5-(Methoxymethyl)-1-methyl-1H-pyrazol-3-yl]carbamoyl}azetidin-1-yl)-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-[5-(methoxymethyl)-1-methyl-1H-pyrazol-3-yl]azetidine-3-carboxamide hydrochloride obtained in Example 008 by the method described in Example 019 or a method equivalent thereto.

1H-NMR (DMSO-d6): δ 2.78 (3H, s), 3.25 (3H, s), 3.69 (3H, s), 3.76-3.87 (1H, m), 4.26-4.55 (6H, m), 6.54 (1H, s), 6.61 (1H, brs), 8.81 (1H, brs), 9.72-9.76 (1H, m), 10.68 (1H, s), 14.99 (1H, brs)

Example 156

Compound 156

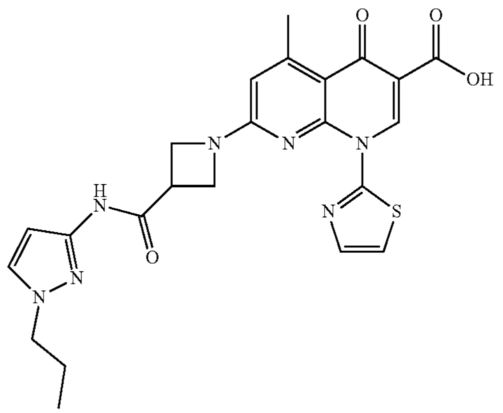

5-Methyl-4-oxo-7-{3-[(1-propyl-1H-pyrazol-3-yl)carbamoyl]azetidin-1-yl}-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-(1-propyl-1H-pyrazol-3-yl)azetidine-3-carboxamide hydrochloride obtained from 1-propyl-1H-pyrazol-3-amine by the method described in Example 007-(1) and Example 001-(2) or a method equivalent thereto by the method described in Example 019 or a method equivalent thereto.

1H-NMR (DMSO-d6): δ 0.80 (3H, t, J=7.5 Hz), 1.70-0.79 (2H, m), 2.77 (3H, s), 3.74-3.84 (1H, m), 3.95 (2H, t, J=7.0 Hz), 4.17-4.58 (4H, m), 6.49 (1H, d, J=2.0 Hz), 6.53-6.59 (1H, m), 7.60 (1H, d, J=2.0 Hz), 7.71-7.77 (1H, m), 7.81-7.85 (1H, m), 9.83-9.85 (1H, m), 10.72 (1H, s), 15.39 (1H, brs)

Example 157

Compound 157

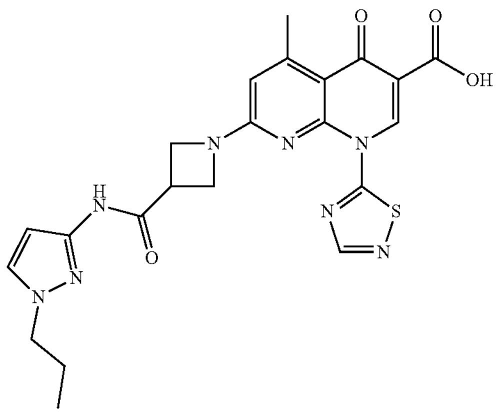

5-Methyl-4-oxo-7-{3-[(1-propyl-1H-pyrazol-3-yl)carbamoyl]azetidin-1-yl}-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-(1-propyl-1H-pyrazol-3-yl)azetidine-3-carboxamide hydrochloride obtained in Example 156 by the method described in Example 019 or a method equivalent thereto.

1H-NMR (DMSO-d6): δ 0.81 (3H, t, J=7.5 Hz), 1.70-1.79 (2H, m), 2.77 (3H, s), 3.77-3.86 (1H, m), 3.96 (2H, t, J=7.0 Hz), 4.17-4.69 (4H, m), 6.50 (1H, d, J=2.0 Hz), 6.58-6.61 (1H, m), 7.60 (1H, d, J=2.0 Hz), 8.80-8.82 (1H, m), 9.70-9.76 (1H, m), 10.73 (1H, s), 14.79 (1H, brs)

Example 158

Compound 158

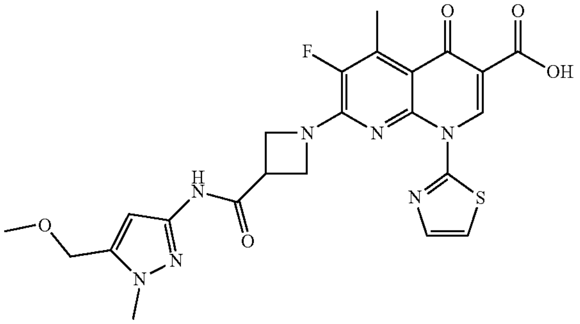

6-Fluoro-7-(3-{[5-(methoxymethyl)-1-methyl-1H-pyrazol-3-yl]carbamoyl}azetidin-1-yl)-5-methyl-4-oxo-1-(1,3-thiazol-2-yl)-1,4-dihydro-1,8-naphthyridine-3-carboxylic acid The title compound was obtained using 7-chloro-6-fluoro-5-methyl-4-oxo-1-(1,3-thiazol-2-yl)-1,4-dihydro-1, 8-naphthyridine-3-carboxylic acid obtained in Reference Example 007-(2) and N-[5-(methoxymethyl)-1-methyl-1H-pyrazol-3-yl]azetidine-3-carboxamide hydrochloride obtained in Example 008 by the method described in Example 019 or a method equivalent thereto.

1H-NMR (DMSO-d6): δ 2.70 (3H, d, J=2.5 Hz), 3.25 (3H, s), 3.68 (3H, s), 3.76-3.86 (1H, m), 4.35-4.76 (6H, m), 6.54 (1H, s), 7.76 (1H, d, J=3.5 Hz), 7.85 (1H, d, J=3.5 Hz), 9.82 (1H, s), 10.64 (1H, s), 15.18 (1H, brs)

Example 159

Compound 159

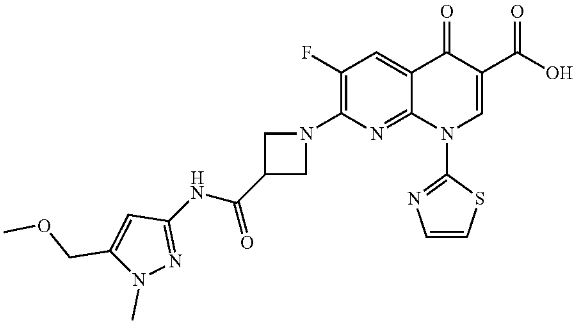

6-Fluoro-7-(3-{[5-(methoxymethyl)-1-methyl-1H-pyrazol-3-yl]carbamoyl}azetidin-1-yl)-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-[5-(methoxymethyl)-1-methyl-1H-pyrazol-3-yl]azetidine-3-carboxamide hydrochloride obtained in Example 008 by the method described in Example 019 or a method equivalent thereto.

1H-NMR (DMSO-d6): δ 3.25 (3H, s), 3.68 (3H, s), 3.78-3.88 (1H, m), 4.42 (2H, s), 4.44-4.82 (4H, m), 6.55 (1H, B), 7.77 (1H, d, J=3.5 Hz), 7.85 (1H, d, J=3.5 Hz), 8.10 (1H, d, J=11.5 Hz), 9.82 (1H, s), 10.66 (1H, s), 14.75 (1H, brs)

Example 160

Compound 160

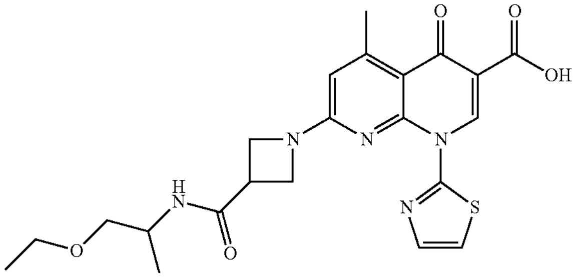

7-{3-[(1-Ethoxypropan-2-yl)carbamoyl]azetidin-1-yl}-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-(1-ethoxypropan-2-yl)azetidine-3-carboxamide hydrochloride obtained from 2-aminopropan-1-ol by the method described in Example 005-(1), Example 006-(2) and Example 001-(2) or a method equivalent thereto by the method described in Example 019 or a method equivalent thereto.

1H-NMR (DMSO-d6): δ 1.07 (3H, d, J=6.8 Hz), 1.11 (3H, t, J=7.0 Hz), 2.76 (3H, s), 3.24 (1H, dd, J=9.6, 5.9 Hz), 3.41-3.47 (2H, m), 3.54-3.61 (1H, m), 3.94-4.00 (1H, m), 4.18-4.48 (4H, m), 6.52 (1H, s), 7.75 (1H, d, J=3.5 Hz), 7.83 (1H, d, J=3.5 Hz), 8.05 (1H, d, J=8.0 Hz), 9.83 (1H, s), 15.40 (1H, brs)

Example 161

Compound 161

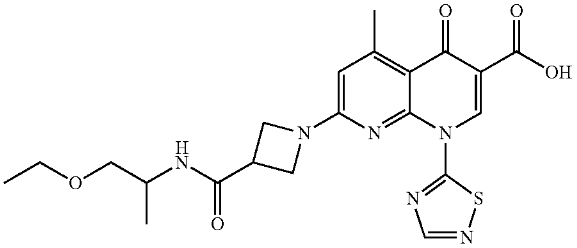

7-{3-[(1-Ethoxypropan-2-yl)carbamoyl]azetidin-1-yl}-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-(1-ethoxypropan-2-yl)azetidine-3-carboxamide hydrochloride obtained in Example 160 by the method described in Example 019 or a method equivalent thereto.

1H-NMR (DMSO-d6): δ 1.08 (3H, d, J=6.7 Hz), 1.11 (3H, t, J=7.0 Hz), 2.76 (3H, s), 3.23-3.28 (1H, m), 3.40-3.49 (2H, m), 3.57-3.64 (1H, m), 3.94-4.03 (1H, m), 4.23-4.62 (4H, m), 6.58 (1H, s), 8.07 (1H, d, J=8.1 Hz), 8.81 (1H, s), 9.73 (1H, s), 15.08 (1H, brs)

Example 162

Compound 162

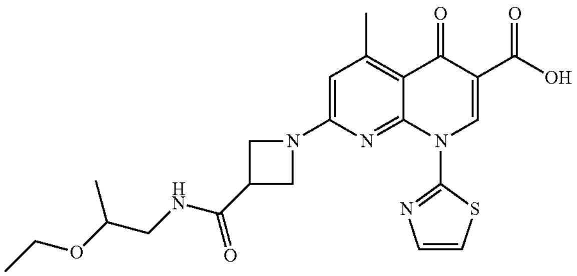

7-{3-[(2-Ethoxypropyl)carbamoyl]azetidin-1-yl}-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-(2-ethoxypropyl)azetidine-3-carboxamide hydrochloride obtained from 1-aminopropan-2-ol by the method described in Example 005-(1), Example 006-(2) and Example 001-(2) or a method equivalent thereto by the method described in Example 019 or a method equivalent thereto.

1H-NMR (DMSO-d6): δ 1.05 (3H, d, J=6.3 Hz), 1.10 (3H, t, J=7.0 Hz), 2.78 (3H, s), 3.12-3.20 (2H, m), 3.41-3.50 (3H, m), 3.60-3.67 (1H, m), 4.16-4.51 (4H, m), 6.55 (1H, s), 7.75 (1H, d, J=3.5 Hz), 7.84 (1H, d, J=3.5 Hz), 8.16 (1H, t, J=5.8 Hz), 9.85 (1H, s), 15.41 (1H, brs)

Example 163

Compound 163

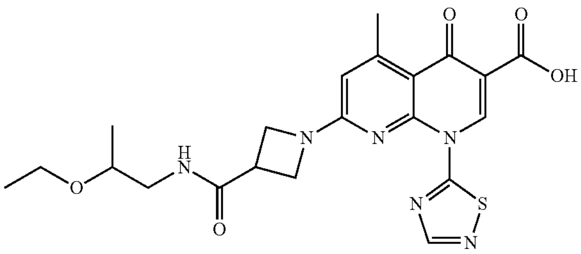

7-{3-[(2-Ethoxypropyl)carbamoyl]azetidin-1-yl}-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-(2-ethoxypropyl)azetidine-3-carboxamide hydrochloride obtained in Example 162 by the method described in Example 019 or a method equivalent thereto.

Property: orange solid;
ESI-MS (m/z): 473 [M+H]+

Example 164

Compound 164

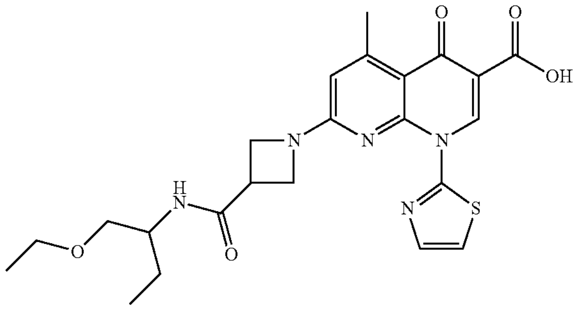

7-{3-[(1-Ethoxybutan-2-yl)carbamoyl]azetidin-1-yl}-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-(1-ethoxybutan-2-yl)azetidine-3-carboxamide hydrochloride obtained from 2-aminobutan-1-ol by the method described in Example 005-(1), Example 006-(2) and Example 001-(2) or a method equivalent thereto by the method described in Example 019 or a method equivalent thereto.

1H-NMR (DMSO-d6): δ 0.85 (3H, t, J=7.4 Hz), 1.10 (3H, t, J=7.0 Hz), 1.31-1.41 (1H, m), 1.52-1.61 (1H, m), 2.75 (3H, s), 3.27-3.37 (2H, m), 3.38-3.48 (2H, m), 3.57-3.64 (1H, m), 3.78-3.86 (1H, m), 4.18-4.48 (4H, m), 6.52 (1H, d, J=0.8 Hz), 7.75 (1H, d, J=3.5 Hz), 7.83 (1H, d, J=3.5 Hz), 7.96 (1H, d, J=10.7 Hz), 9.82 (1H, s)

Example 165

Compound 165

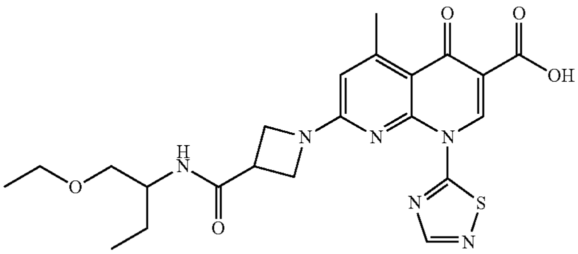

7-{3-[(1-Ethoxybutan-2-yl)carbamoyl]azetidin-1-yl}-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-(1-ethoxybutan-2-yl)azetidine-3- carboxamide hydrochloride obtained in Example 164 by the method described in Example 019 or a method equivalent thereto.

1H-NMR (DMSO-d6): δ 0.86 (3H, t, J=7.5 Hz), 1.10 (3H, t, J=7.0 Hz), 1.31-1.42 (1H, m), 1.53-1.63 (1H, m), 2.76 (3H, s), 3.40-3.47 (2H, m), 3.61-3.68 (1H, m), 3.79-3.87 (1H, m), 4.23-4.63 (4H, m), 6.58 (1H, d, J=1.0 Hz), 7.99 (1H, d, J=8.6 Hz), 8.81 (1H, s), 9.72 (1H, s), 15.07 (1H, s)

Example 166

Compound 166

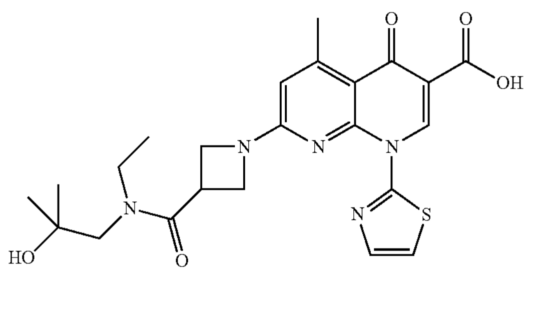

7-{3-[Ethyl(2-hydroxy-2-methylpropyl)carbamoyl]azetidin-1-yl}-5-methyl-4-oxo-1-(1,3-thiazol-2-yl)-1,4-dihydro-1,8-naphthyridine-3-carboxylic acid The title compound was obtained by the method described in Example 019 or a method equivalent thereto using N-ethyl-N-(2-hydroxy-2-methylpropyl)azetidine-3-carboxamide hydrochloride obtained from 1-amino-2-methylpropan-2-ol by the methods described in Examples 005-(1), 006-(2) and 001-(2) or methods equivalent thereto, and 7-chloro-5-methyl-4-oxo-1-(1,3-thiazol-2-yl)-1,4-dihydro-1,8-naphthyridine-3-carboxylic acid obtained in Reference Example 001-(2).

1H-NMR (DMSO-d6): δ 1.03 (3H, t, J=7.0 Hz), 1.07 (6H, s), 2.74 (3H, s), 3.45-3.52 (2H, m), 3.99-4.06 (1H, m), 4.16-4.54 (6H, m), 6.52 (1H, s), 7.76 (1H, d, J=3.5 Hz), 7.83 (1H, d, J=3.5 Hz), 9.81 (1H, s), 15.29 (1H, brs)

Example 167

Compound 167

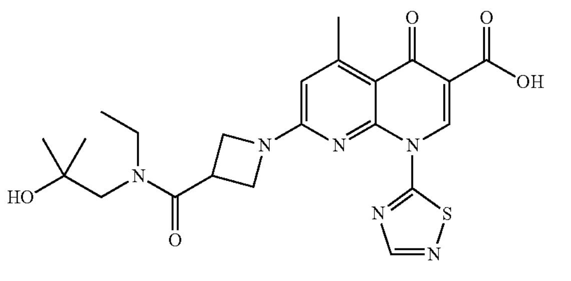

7-{3-[Ethyl(2-hydroxy-2-methylpropyl)carbamoyl]azetidin-1-yl}-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-ethyl-N-(2-hydroxy-2-methylpropyl)azetidine-3-carboxamide hydrochloride obtained in Example 166 by the method described in Example 019 or a method equivalent thereto.

Property: yellow solid;

ESI-MS (m/z): 487 [M+H]+

Example 168

Compound 168

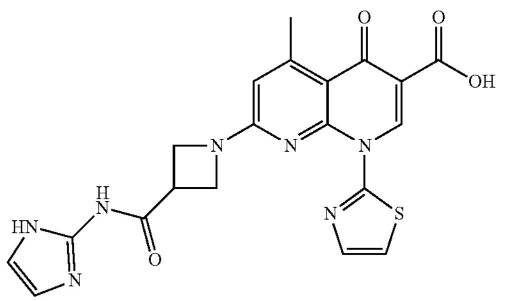

7-{3-[(1H-Imidazol-2-yl)carbamoyl]azetidin-1-yl}-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-(1H-imidazol-2-yl)azetidine-3-carboxamide hydrochloride obtained from 1H-imidazol-2-amine by the method described in Example 005-(1) and Example 001-(2) or a method equivalent thereto by the method described in Example 019 or a method equivalent thereto.

1H-NMR (DMSO-d6): δ 2.78 (3H, s), 3.79-3.88 (1H, m), 4.22-4.56 (4H, m), 6.59 (1H, s), 6.77 (2H, brs), 7.75 (1H, d, J=3.5 Hz), 7.84 (1H, d, J=3.5 Hz), 9.85 (1H, s), 11.39 (1H, brs), 11.64 (1H, brs), 15.39 (1H, brs)

Example 169

Compound 169

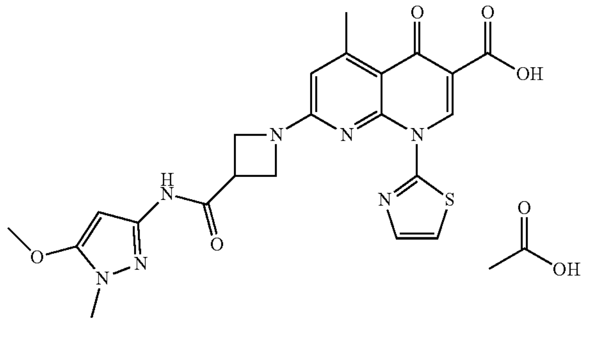

7-{3-[(5-Methoxy-1-methyl-1H-pyrazol-3-yl)carbamoyl]azetidin-1-yl}-5-methyl-4-oxo-1-(1,3-thiazol-2-yl)-1,4-dihydro-1,8-naphthyridine-3-carboxylic acid acetate The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-(5-methoxy-1-methyl-1H-pyrazol-3-yl)azetidine-3-carboxamide hydrochloride obtained from 5-methoxy-1-methyl-1H-pyrazol-3-amine by the method described in Example 005-(1) and Example 001-(2) or a method equivalent thereto by the method described in Example 019 or a method equivalent thereto.

1H-NMR (DMSO-d6): δ 1.90 (3H, s), 2.76 (3H, s), 3.45 (3H, s), 3.74-3.84 (1H, m), 3.85 (3H, s), 4.17-4.54 (4H, m), 6.00 (1H, s), 6.54 (1H, brs), 7.73 (1H, d, J=3.5 Hz), 7.83 (1H, d, J=3.5 Hz), 9.82 (1H, s), 10.56 (1H, brs), 15.29 (1H, brs)

Example 170

Compound 170

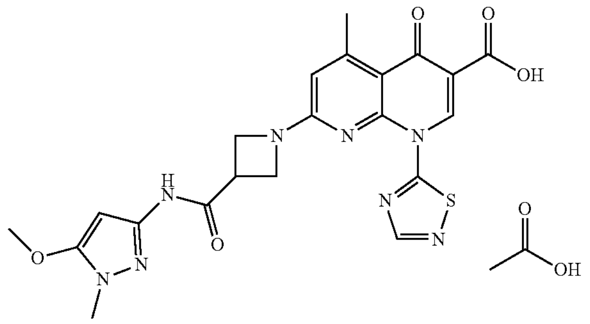

7-{3-[(5-Methoxy-1-methyl-1H-pyrazol-3-yl)carbamoyl]azetidin-1-yl}-5-methyl-4-oxo-1-(1,2,4-thiadiazol-5-yl)-1,4-dihydro-1,8-naphthyridine-3-carboxylic acid acetate The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-(5-methoxy-1-methyl-1H-pyrazol-3-yl)azetidine-3-carboxamide hydrochloride obtained in Example 169 by the method described in Example 019 or a method equivalent thereto.

1H-NMR (DMSO-d6): δ 1.91 (3H, s), 2.79 (3H, s), 3.46 (3H, s), 3.74-3.84 (1H, m), 3.85 (3H, s), 4.23-4.70 (4H, m), 6.01 (1H, s), 6.62 (1H, s), 8.82 (1H, s), 9.76 (1H, s), 10.58 (1H, s)

Example 171

Compound 171

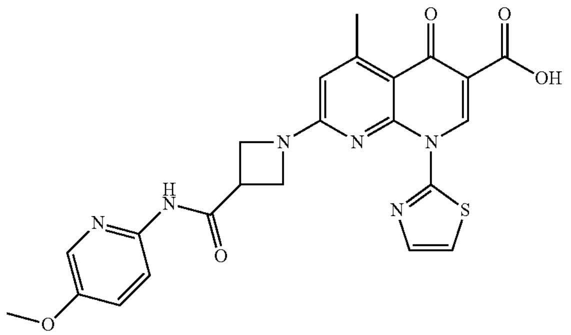

7-{3-[(5-Methoxypyridin-2-yl)carbamoyl]azetidin-1-yl}-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-(5-methoxypyridin-2-yl)azetidine-3-carboxamide hydrochloride obtained in Example 017 by the method described in Example 019 or a method equivalent thereto.

1H-NMR (DMSO-d6): δ 2.79 (3H, s), 3.81 (3H, s), 3.86-3.95 (1H, m), 4.28-4.57 (4H, m), 6.58 (1H, s), 7.45 (1H, dd, J=3.0, 9.0 Hz), 7.74 (1H, d, J=3.5 Hz), 7.84 (1H, d, J=3.5 Hz), 8.05 (1H, d, J=3.0 Hz), 8.08 (1H, d, J=9.0 Hz), 9.85 (1H, s), 10.64 (1H, brs), 15.36 (1H, brs)

Example 172

Compound 172

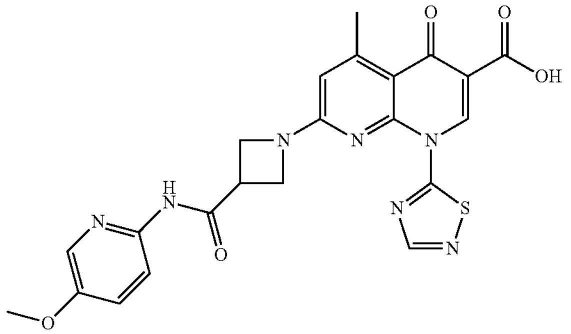

7-{3-[(5-Methoxypyridin-2-yl)carbamoyl]azetidin-1-yl}-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-(5-methoxypyridin-2-yl)azetidine-3-carboxamide hydrochloride obtained in Example 017 by the method described in Example 019 or a method equivalent thereto.

1H-NMR (DMSO-d6): δ 2.79 (3H, s), 3.80 (3H, s), 3.85-4.00 (1H, m), 4.23-4.70 (4H, m), 6.62 (1H, s), 7.45 (1H, dd, J=9.0, 3.0 Hz), 8.05 (1H, d, J=3.0 Hz), 8.08 (1H, d, J=9.0 Hz), 8.82 (1H, s), 9.77 (1H, s), 10.67 (1H, brs), 15.11 (1H, brs)

Example 173

Compound 173

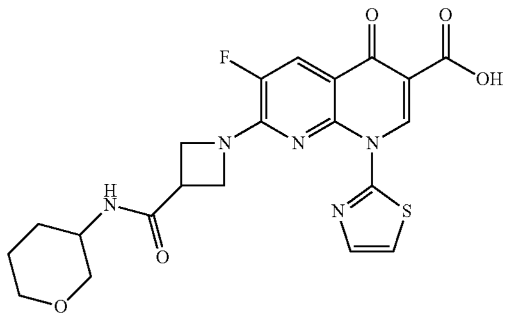

6-Fluoro-7-{3-[(oxan-2-ylmethyl)carbamoyl]azetidin-1-yl}-4-oxo-1-(1,3-thiazol-2-yl)-1,4-dihydro-1,8-naphthyridine-3-carboxylic acid The title compound was obtained by the method described in Example 002-(3) or a method equivalent thereto using N-(oxan-2-ylmethyl)azetidine-3-carboxamide hydrochloride obtained in Example 078-(1), and 7-chloro-6-fluoro-4-oxo-1-(1,3-thiazol-2-yl)-1,4-dihydro-1,8-naphthyridine-3-carboxylic acid obtained in Reference Example 003-(2).

1H-NMR (DMSO-d6): δ 1.10-1.20 (1H, m), 1.37-1.49 (3H, m), 1.52-1.59 (1H, m), 1.71-1.80 (1H, m), 3.02-3.12 (1H, m), 3.14-3.22 (1H, m), 3.60-3.71 (1H, m), 3.82-3.91 (1H, m), 4.31-4.85 (6H, m), 7.79 (1H, d, J=3.5 Hz), 7.86 (1H, d, J=3.5 Hz), 8.11 (1H, d, J=11.5 Hz), 8.22 (1H, t, J=5.5 Hz), 9.82 (1H, s), 14.82 (1H, brs)

Example 174

Compound 174

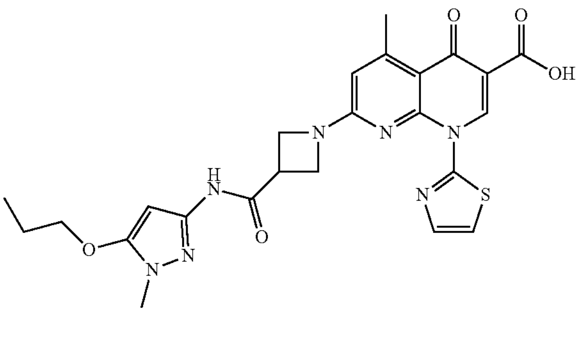

5-Methyl-7-{3-[(1-methyl-5-propoxy-1H-pyrazol-3-yl)carbamoyl]azetidin-1-yl}-4-oxo-1-(1,3-thiazol-2-yl)-1,4-dihydro-1,8-naphthyridine-3-carboxylic acid (1) 1-Methyl-5-propoxy-1H-pyrazol-3-amine was obtained by the methods described in Examples 009-(1) to 009-(3) or methods equivalent thereto using methyl 5-hydroxy-1-methyl-1H-pyrazole-3-carboxylate and propyl iodide.

Property: yellow oil (2) The title compound was obtained by the method described in Example 019 or a method equivalent thereto using N-(1-methyl-5-propoxy-1H-pyrazol-3-yl)azetidine-3-carboxamide hydrochloride obtained by the methods described in Examples 007-(1) and 001-(2) or methods equivalent thereto from 1-methyl-5-propoxy-1H-pyrazol-3-amine obtained in the preceding section, and 7-chloro-5-methyl-4-oxo-1-(1,3-thiazol-2-yl)-1,4-dihydro-1,8-naphthyridine-3-carboxylic acid obtained in Reference Example 001-(2).

1H-NMR (DMSO-d6): δ 0.96 (3H, t, J=7.5 Hz), 1.68-1.76 (2H, m), 2.78 (3H, s), 3.46 (3H, s), 3.72-3.82 (1H, m), 4.00 (2H, t, J=7.0 Hz), 4.20-4.57 (4H, m), 5.98 (1H, s), 6.57 (1H, brs), 7.74 (1H, d, J=3.5 Hz), 7.84 (1H, d, J=3.5 Hz), 9.85 (1H, s), 10.55 (1H, s), 15.36 (1H, brs)

Example 175

Compound 175

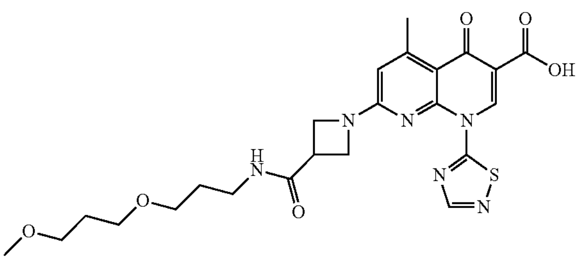

7-(3-{[3-(3-Methoxypropoxy)propyl]carbamoyl}azetidin-1-yl)-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-[3-(3-methoxypropoxy)propyl]azetidine-3-carboxamide hydrochloride obtained from 1-(3-aminopropoxy)-3-methoxypropane by the method described in Example 005-(1) and Example 001-(2) or a method equivalent thereto by the method described in Example 002-(3) or a method equivalent thereto.

1H-NMR (DMSO-d6): δ 0.88-1.11 (6H, m), 2.77 (3H, s), 3.24 (3H, s), 3.47-3.66 (2H, m), 3.86-3.99 (1H, m), 4.16-4.66 (4H, m), 6.58 (1H, s), 8.01-8.05 (1H, m), 8.81 (1H, s), 9.73 (1H, s)

Example 176

Compound 176

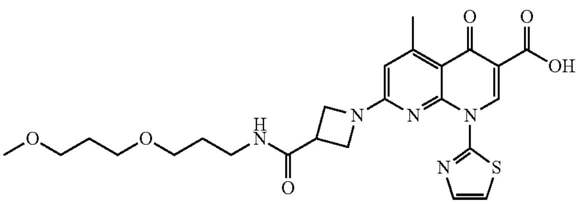

7-(3-{[3-(3-Methoxypropoxy) propyl] carbamoyl}azetidin-1-yl)-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-[3-(3-methoxypropoxy) propyl]azetidine-3-carboxamide hydrochloride obtained in Example 175 by the method described in Example 002-(3) or a method equivalent thereto.

1H-NMR (DMSO-d6): δ 1.02-1.08 (4H, m), 2.78 (3H, s), 3.22-3.23 (4H, m), 3.37-3.44 (2H, m), 3.52-3.61 (2H, m), 3.86-3.95 (1H, m), 4.17-4.51 (4H, m), 6.55 (1H, s), 7.75 (1H, d, J=3.5 Hz), 7.84 (1H, d, J=3.5 Hz), 8.01 (1H, dd, J=8.0, 2.5 Hz), 9.85 (1H, s)

Compound 177

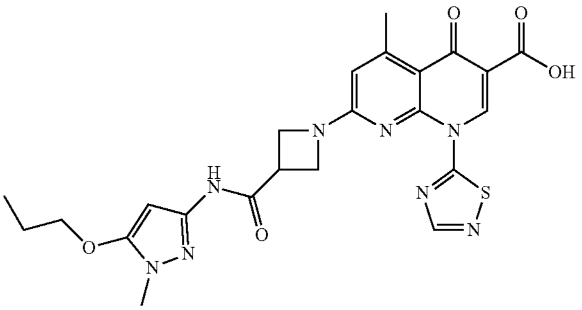

5-Methyl-7-{3-[(1-methyl-5-propoxy-1H-pyrazol-3-yl)carbamoyl]azetidin-1-yl}-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-(1-methyl-5-propoxy-1H-pyrazol-3-yl)azetidine-3-carboxamide hydrochloride obtained in Example 174-(2) by the method described in Example 019 or a method equivalent thereto.

1H-NMR (DMSO-d6): δ 0.96 (3H, t, J=7.5 Hz), 1.68-1.76 (2H, m), 2.78 (3H, s), 3.46 (3H, s), 3.72-3.82 (1H, m), 4.01 (2H, t, J=7.0 Hz), 4.22-4.60 (4H, m), 5.99 (1H, a), 6.60 (1H, brs), 8.82 (1H, s), 9.73 (1H, s), 10.56 (1H, brs), 15.36 (1H, brs)

Example 178

Compound 178

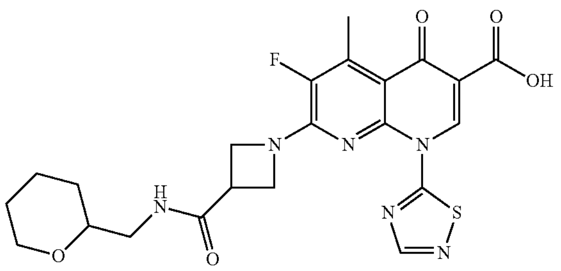

6-Fluoro-5-methyl-7-{3-[(oxan-2-ylmethyl)carbamoyl]azetidin-1-yl}-4-oxo-1-(1,2,4-thiadiazol-5-yl)-1,4-dihydro-1,8-naphthyridine-3-carboxylic acid The title compound was obtained using 7-chloro-6-fluoro-5-methyl-4-oxo-1-(1,2,4-thiadiazol-5-yl)-1,4-dihydro-1,8-naphthyridine-3-carboxylic acid obtained in Reference Example 008-(2) and N-(oxan-2-ylmethyl)azetidine-3-carboxamide hydrochloride obtained in Example 078-(1) by the method described in Example 008 or a method equivalent thereto.

1H-NMR (DMSO-d6): δ 1.10-1.20 (1H, m), 1.37-1.49 (3H, m), 1.52-1.59 (1H, m), 1.71-1.80 (1H, m), 2.62 (3H, s), 3.05-3.14 (1H, m), 3.15-3.22 (1H, m), 3.60-3.71 (1H, m), 3.82-3.91 (1H, m), 4.40-4.52 (2H, m), 4.52-4.60 (2H, m), 8.27 (1H, brs), 8.71 (1H, s), 9.55 (1H, s), 14.82 (1H, brs)

Example 179

Compound 179

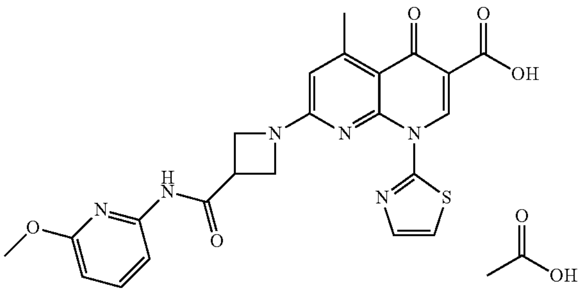

7-{3-[(6-Methoxypyridin-2-yl)carbamoyl]azetidin-1-yl}-5-methyl-4-oxo-1-(1,3-thiazol-2-yl)-1,4-dihydro-1,8-naphthyridine-3-carboxylic acid acetate The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-(6-methoxypyridin-2-yl)azetidine-3-carboxamide hydrochloride obtained from 6-methoxypyridin-2-amine by the method described in Example 005-(1) and Example 001-(2) or a method equivalent thereto by the method described in Example 019 or a method equivalent thereto.

1H-NMR (DMSO-d6): δ 1.91 (3H, s), 2.74 (3H, s), 3.86 (3H, s), 3.91-4.00 (1H, m), 4.31-4.57 (4H, m), 6.51 (1H, s), 6.54 (1H, d, J=8.75 Hz), 7.68-7.77 (3H, m), 7.82 (1H, d, J=3.5 Hz), 9.80 (1H, s), 10.56 (1H, brs), 11.95 (1H, brs), 15.36 (1H, brs)

Example 180

Compound 180

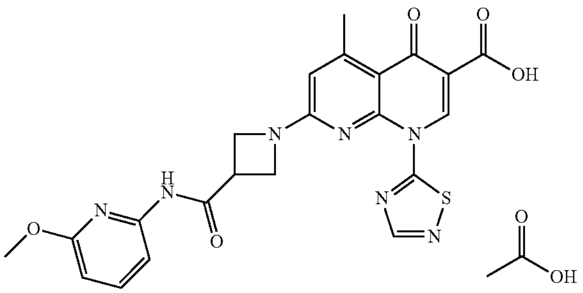

7-{3-[(6-Methoxypyridin-2-yl)carbamoyl]azetidin-1-yl}-5-methyl-4-oxo-1-(1,2,4-thiadiazol-5-yl)-1,4-dihydro-1,8-naphthyridine-3-carboxylic acid acetate The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-(6-methoxypyridin-2-yl)azetidine-3-carboxamide hydrochloride obtained in Example 179 by the method described in Example 019 or a method equivalent thereto.

1H-NMR (DMSO-d6): δ 1.91 (3H, s), 2.75 (3H, s), 3.87 (3H, s), 3.94-4.03 (1H, m), 4.36-4.67 (4H, m), 6.55 (1H, d, J=8.7 Hz), 6.58 (1H, s), 7.68-7.77 (2H, m), 8.81 (1H, s), 9.69 (1H, s), 10.57 (1H, brs), 11.95 (1H, brs), 15.04 (1H, brs)

Example 181

Compound 181

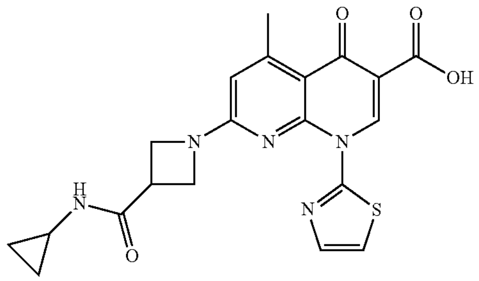

7-[3-(Cyclopropylcarbamoyl)azetidin-1-yl]-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-cyclopropylazetidine-3-carboxamide hydrochloride obtained from cyclopropaneamine by the method described in Example 005-(1) and Example 001-(2) or a method equivalent thereto by the method described in Example 001-(3) or a method equivalent thereto.

1H-NMR (DMSO-d6): δ 0.41-0.46 (2H, m), 0.61-0.67 (2H, m), 2.65-2.71 (1H, m), 2.74 (3H, s), 3.45-3.53 (1H, m), 4.20-4.44 (4H, m), 6.48 (1H, s), 7.72 (1H, d, J=3.5 Hz), 7.81 (1H, d, J=3.5 Hz), 8.22 (1H, d, J=4.5 Hz), 9.80 (1H, s)

Example 182

Compound 182

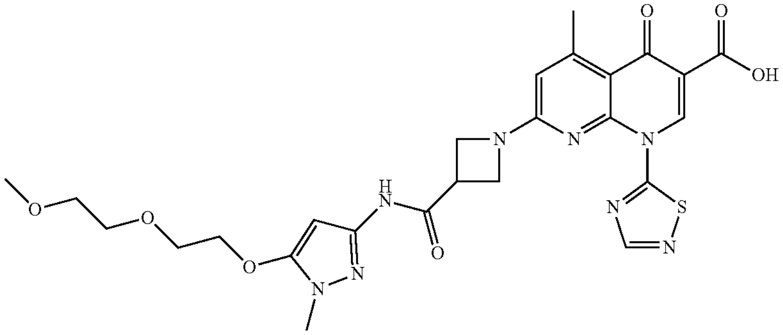

7-[3-({5-[2-(2-Methoxyethoxy)ethoxy]-1-methyl-1H-pyrazol-3-yl}carbamoyl)azetidin-1-yl]-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-{5[2-(2-methoxyethoxy)ethoxy]-1-methyl-1H-pyrazol-3-yl}azetidine-3-carboxamide hydrochloride obtained in Example 009-(4) by the method described in Example 008 or a method equivalent thereto.

1H-NMR (DMSO-d6): δ 2.78 (3H, s), 3.24 (3H, s), 3.42-3.45 (2H, m), 3.46 (3H, s), 3.54-3.59 (2H, m), 3.69-3.73 (2H, m), 3.76-3.84 (1H, m), 4.14-4.19 (2H, m), 4.29-4.68 (4H, m), 6.01 (1H, s), 6.61 (1H, brs), 8.82 (1H, s), 9.76 (1H, s), 10.57 (1H, s), 15.07 (1H, brs)

Example 183

Compound 183

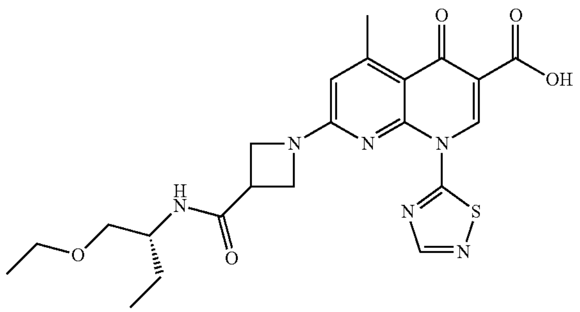

7-(3-{[(2R)-1-Ethoxybutan-2-yl]carbamoyl}azetidin-1-yl)-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-[(2R)-1-ethoxybutan-2-yl]azetidine-3-carboxamide hydrochloride obtained from (2R)-1-ethoxybutan-2-amine by the method described in Example 005-(1), Example 006-(2) and Example 001-(2) or a method equivalent thereto by the method described in Example 019 or a method equivalent thereto.

1H-NMR (DMSO-d6): δ 0.86 (3H, t, J=7.4 Hz), 1.10 (3H, t, J=6.9 Hz), 1.32-1.42 (1H, m), 1.53-1.62 (1H, m), 2.77 (3H, s), 3.38-3.48 (2H, m), 3.60-3.68 (1H, m), 3.79-3.87 (1H, m), 4.24-4.63 (4H, m), 6.60 (1H, s), 7.99 (1H, d, J=8.7 Hz), 8.82 (1H, s), 9.74 (1H, s)

Example 184

Compound 184

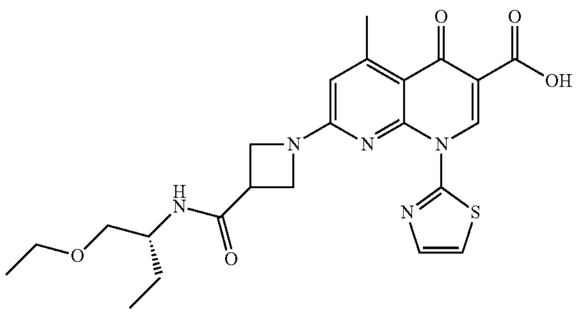

7-(3-{[(2R)-1-Ethoxybutan-2-yl]carbamoyl}azetidin-1-yl)-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-[(2R)-1-ethoxybutan-2-yl]azetidine-3-carboxamide hydrochloride obtained in Example 183 by the method described in Example 019 or a method equivalent thereto.

1H-NMR (DMSO-d6): δ 0.85 (3H, t, J=7.4 Hz), 1.10 (3H, t, J=6.9 Hz), 1.31-1.40 (1H, m), 1.52-1.61 (1H, m), 2.77 (3H, s), 3.38-3.48 (2H, m), 3.58-3.64 (1H, m), 3.78-3.86 (1H, m), 4.18-4.49 (4H, m), 6.54 (1H, s), 7.75 (1H, d, J=3.5 Hz), 7.84 (1H, d, J=3.5 Hz), 7.96 (1H, d, J=8.6 Hz), 9.84 (1H, s)

Example 185

Compound 185

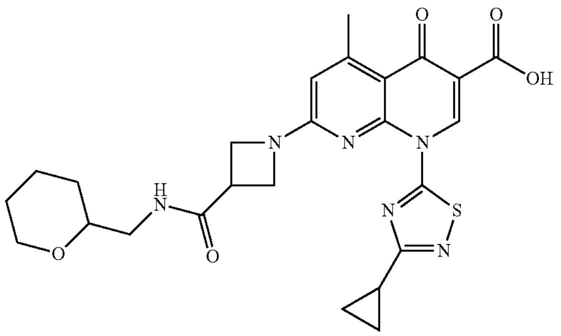

1-(3-Cyclopropyl-1,2,4-thiadiazol-5-yl)-5-methyl-7-{3-[(oxan-2-ylmethyl)carbamoyl]azetidin-1-yl}-4-oxo-1,4-dihydro-1,8-naphthyridine-3-carboxylic acid The title compound was obtained using 7-chloro-1-(3-cyclopropyl-1,2,4-thiadiazol-5-yl)-5-methyl-4-oxo-1,4-dihydro-1,8-naphthyridine-3-carboxylic acid obtained in Reference Example 031-(2) and N-(oxan-2-ylmethyl)azetidine-3-carboxamide hydrochloride obtained in Example 078-(1) by the method described in Example 001-(3) or a method equivalent thereto.

1H-NMR (DMSO-d6): δ 1.00-1.21 (5H, m), 1.37-1.49 (3H, m), 1.52-1.60 (1H, m), 1.72-1.81 (1H, m), 2.28-2.38 (1H, m), 2.75 (3H, s), 3.03-3.13 (2H, m), 3.14-3.23 (2H, m), 3.59-3.68 (1H, m), 3.83-3.92 (1H, m), 4.25-4.52 (4H, m), 6.55 (1H, s), 8.23 (1H, t, J=6.0 Hz), 9.63 (1H, s)

Example 186

Compound 186

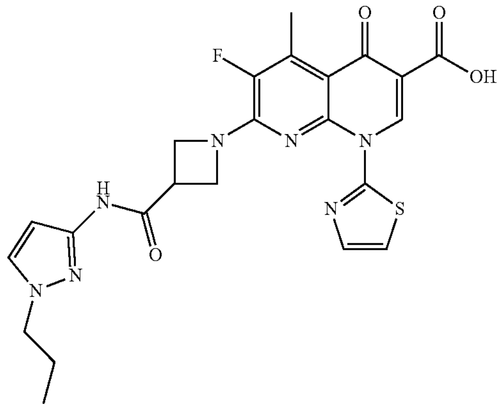

6-Fluoro-5-methyl-4-oxo-7-{3-[(1-propyl-1H-pyrazol-3-yl)carbamoyl]azetidin-1-yl}-1-(1,3-thiazol-2-yl)-1,4-dihydro-1,8-naphthyridine-3-carboxylic acid The title compound was obtained using 7-chloro-6-fluoro-5-methyl-4-oxo-1-(1,3-thiazol-2-yl)-1,4-dihydro-1,8-naphthyridine-3-carboxylic acid obtained in Reference Example 007-(2) and N-(1-propyl-1H-pyrazol-3-yl)azetidine-3-carboxamide hydrochloride obtained in Example 156 by the method described in Example 008 or a method equivalent thereto.

1H-NMR (DMSO-d6): δ 0.80 (3H, t, J=7.5 Hz), 1.66-1.76 (2H, m), 2.69 (3H, d, J=2.5 Hz), 3.76-3.86 (1H, m), 3.95 (2H, t, J=6.5 Hz), 4.40-4.81 (4H, m), 6.50 (1H, d, J=2.5 Hz), 7.60 (1H, d, J=2.5 Hz), 7.76 (1H, d, J=3.5 Hz), 7.84 (1H, d, J=3.5 Hz), 9.83 (1H, s), 10.70 (1H, s), 15.16 (1H, brs)

Example 187

Compound 187

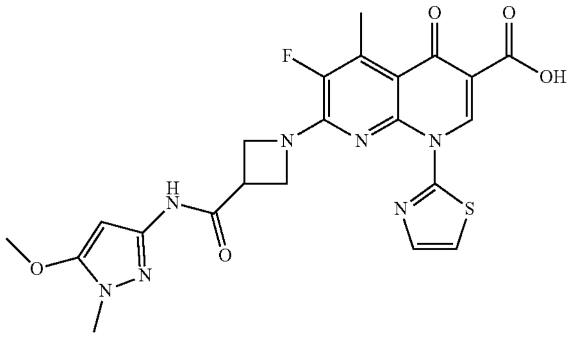

6-Fluoro-7-{3-[(5-methoxy-1-methyl-1H-pyrazol-3-yl)carbamoyl]azetidin-1-yl}-5-methyl-4-oxo-1-(1,3-thiazol-2-yl)-1,4-dihydro-1,8-naphthyridine-3-carboxylic acid The title compound was obtained using 7-chloro-6-fluoro-5-methyl-4-oxo-1-(1,3-thiazol-2-yl)-1,4-dihydro-1,8-naphthyridine-3-carboxylic acid obtained in Reference Example 007-(2) and N-(5-methoxy-1-methyl-1H-pyrazol-3-yl)azetidine-3-carboxamide hydrochloride obtained in Example 169 by the method described in Example 008 or a method equivalent thereto.

1H-NMR (DMSO-d6): δ 2.70 (3H, d, J=2.5 Hz), 2.88 (3H, s), 3.45 (3H, s), 3.75-3.83 (1H, m), 3.85 (3H, s), 4.40-4.81 (4H, m), 6.02 (1H, s), 7.77 (1H, d, J=3.5 Hz), 7.85 (1H, d, J=3.5 Hz), 9.81 (1H, s), 10.55 (1H, s), 15.14 (1H, brs)

Example 188

Compound 188

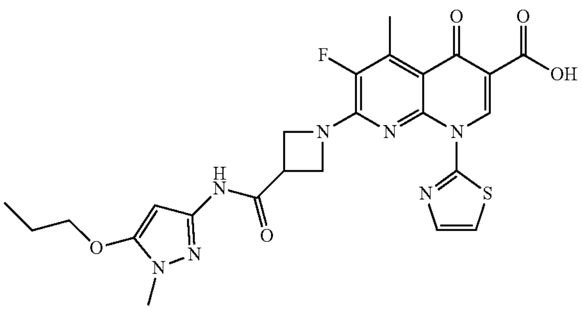

6-Fluoro-5-methyl-7-{3-[(1-methyl-5-propoxy-1H-pyrazol-3-yl)carbamoyl]azetidin-1-yl}-4-oxo-1-(1,3-thiazol-2-yl)-1,4-dihydro-1,8-naphthyridine-3-carboxylic acid The title compound was obtained using 7-chloro-6-fluoro-5-methyl-4-oxo-(1,3-thiazol-2-yl)-1,4-dihydro-1,8-naphthyridine-3-carboxylic acid obtained in Reference Example 007-(2) and N-(1-methyl-5-propoxy-1H-pyrazol- 3-yl)azetidine-3-carboxamide hydrochloride obtained in Example 174-(2) by the method described in Example 008 or a method equivalent thereto.

1H-NMR (DMSO-d6): δ 0.96 (3H, t, J=7.5 Hz), 1.66-1.79 (2H, m), 2.68 (3H, brs), 3.46 (3H, s), 4.01 (2H, t, J=6.5 Hz), 4.30-4.86 (4H, m), 5.98 (1H, s), 7.66-7.96 (2H, m), 9.79 (1H, s), 10.55 (1H, brs), 15.11 (1H, brs)

Example 189

Compound 189

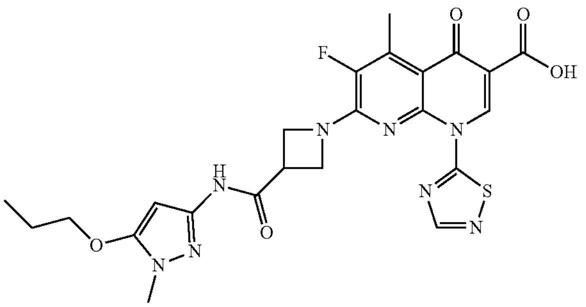

6-Fluoro-5-methyl-7-{3-[(1-methyl-5-propoxy-1H-pyrazol-3-yl)carbamoyl]azetidin-1-yl}-4-oxo-1-(1,2,4-thiadiazol-5-yl)-1,4-dihydro-1,8-naphthyridine-3-carboxylic acid The title compound was obtained using 7-chloro-6-fluoro-5-methyl-4-oxo-1-(1,2,4-thiadiazol-5-yl)-1,4-dihydro-1,8-naphthyridine-3-carboxylic acid obtained in Reference Example 008-(2) N-(1-methyl-5-propoxy-1H-pyrazol-3-yl)azetidine-3-carboxamide hydrochloride obtained in Example 174-(2) by the method described in Example 008 or a method equivalent thereto.

1H-NMR (DMSO-d6): δ 0.96 (3H, t, J=7.5 Hz), 1.66-1.79 (2H, m), 2.68 (3H, brs), 3.46 (3H, s), 4.01 (2H, t, J=6.5 Hz), 4.41-4.86 (4H, m), 6.00 (1H, s), 8.69 (1H, s), 9.63 (1H, s), 10.57 (1H, brs)

Example 190

Compound 190

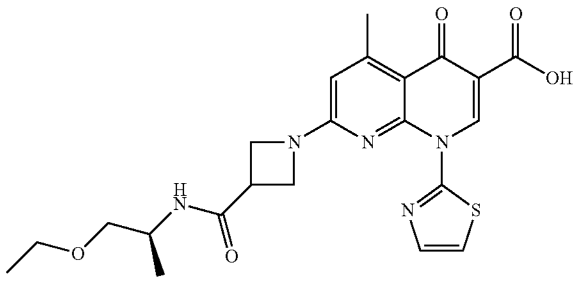

7-(3-{[(2S)-1-Ethoxypropan-2-yl]carbamoyl}azetidin-1-yl)-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-[(2S)-1-ethoxypropan-2-yl]azetidine-3-carboxamide hydrochloride obtained from (2S)-1-ethoxypropan-2-amine by the method described in Example 005-(1) and Example 001-(2) or a method equivalent thereto by the method described in Example 019 or a method equivalent thereto.

1H-NMR (DMSO-d6): δ 1.07 (3H, d, J=6.8 Hz), 1.11 (3H, t, J=7.0 Hz), 2.77 (3H, s), 3.24 (1H, dd, J=9.6, 5.9 Hz), 3.33-3.36 (1H, m), 3.39-3.48 (2H, m), 3.53-3.62 (1H, m), 3.92-4.01 (1H, m), 4.19-4.50 (4H, m), 6.54 (1H, s), 7.75 (1H, d, J=3.5 Hz), 7.84 (1H, d, J=3.5 Hz), 8.05 (1H, d, J=8.0 Hz), 9.84 (1H, s), 15.41 (1H, brs)

Example 191

Compound 191

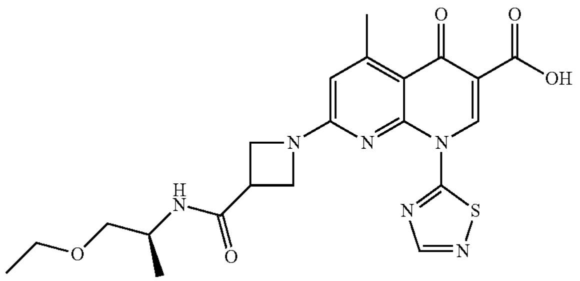

7-(3-{[(2S)-1-Ethoxypropan-2-yl]carbamoyl}azetidin-1-yl)-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-[(2S)-1-ethoxypropan-2-yl]azetidine-3-carboxamide hydrochloride obtained in Example 190 by the method described in Example 019 or a method equivalent thereto.

1H-NMR (DMSO-d6): δ 1.08 (3H, d, J=6.8 Hz), 1.11 (3H, t, J=7.0 Hz), 2.78 (3H, s), 3.23-3.38 (1H, m), 3.39-3.49 (2H, m), 3.57-3.64 (1H, m), 3.95-4.01 (1H, m), 4.23-4.64 (4H, m), 6.60 (1H, s), 8.07 (1H, d, J=8.2 Hz), 8.82 (1H, s), 9.75 (1H, s), 15.10 (1H, brs)

Example 192

Compound 192

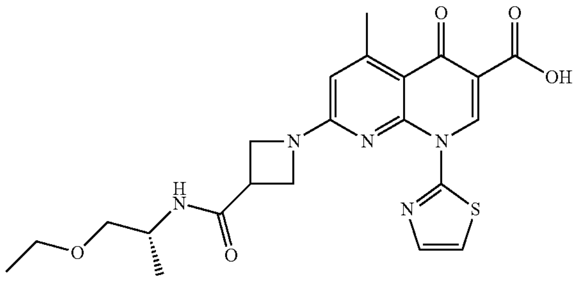

7-(3-{[(2R)-1-Ethoxypropan-2-yl]carbamoyl}azetidin-1-yl)-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-[(2R)-1-ethoxypropan-2-yl]azetidine-3-carboxamide hydrochloride obtained from (2R)-1-ethoxypropan-2-amine by the method described in Example 005-(1) and Example 001-(2) or a method equivalent thereto by the method described in Example 019 or a method equivalent thereto.

1H-NMR (DMSO-d6): δ 1.07 (3H, d, J=6.8 Hz), 1.10 (3H, t, J=7.0 Hz), 2.77 (3H, s), 3.22 (1H, dd, J=9.6, 5.9 Hz), 3.32-3.34 (1H, m), 3.41-3.47 (2H, m), 3.54-3.61 (1H, m), 3.93-4.01 (1H, m), 4.18-4.49 (4H, m), 6.54 (1H, s), 7.75 (1H, d, J=3.5 Hz), 7.84 (1H, d, J=3.5 Hz), 8.05 (1H, d, J=7.8 Hz), 9.84 (1H, s), 15.41 (1H, brs)

Example 193

Compound 193

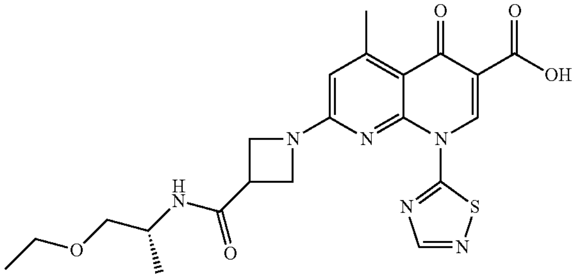

7-(3-{[(2R)-1-Ethoxypropan-2-yl]carbamoyl}azetidin-1-yl)-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-[(2R)-1-ethoxypropan-2-yl]azetidine-3-carboxamide hydrochloride obtained in Example 192 by the method described in Example 019 or a method equivalent thereto.

1H-NMR (DMSO-d6): δ 1.08 (3H, d, J=6.8 Hz), 1.11 (3H, t, J=7.0 Hz), 2.77 (3H, s), 3.23-3.38 (1H, m), 3.39-3.49 (2H, m), 3.57-3.64 (1H, m), 3.95-4.01 (1H, m), 4.23-4.64 (4H, m), 6.59 (1H, s), 8.07 (1H, d, J=8.2 Hz), 8.82 (1H, s), 9.74 (1H, s)

Example 194

Compound 194

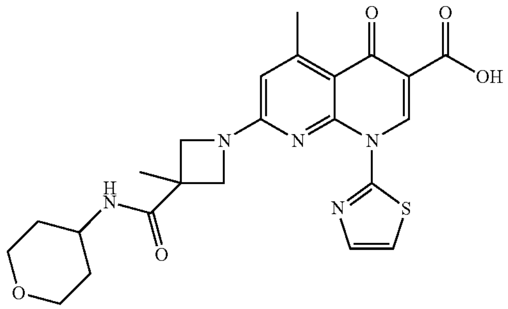

5-Methyl-7-{3-methyl-3-[(oxan-4-yl)carbamoyl]azetidin-1-yl}-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and 3-methyl-N-(oxan-4-yl)azetidine-3-carboxamide hydrochloride obtained from oxane-4-amine and 1-[(tert-butoxy)carbonyl]-3-methylazetidine-3-carboxylic acid by the method described in Example 005-(1) and Example 001-(2) or a method equivalent thereto by the method described in Example 001-(3) or a method equivalent thereto.

1H-NMR (DMSO-d6): δ 1.40-1.52 (2H, m), 1.58 (3H, s), 1.66-1.74 (2H, d, J=10.5 Hz), 2.74 (3H, s), 3.25-3.39 (2H, m), 3.77-3.86 (3H, m), 3.97 (1H, d, J=8.0 Hz), 4.07 (1H, d, J=9.5 Hz), 4.41 (1H, d, J=8.0 Hz), 4.50 (1H, d, J=9.5 Hz), 6.48 (1H, s), 7.77 (1H, d, J=4.0 Hz), 7.83 (1H, d, J=4.0 Hz), 7.95 (1H, d, J=8.0 Hz), 9.79 (1H, s)

Example 195

Compound 195

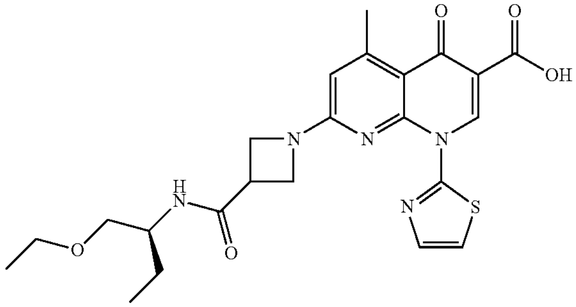

7-(3-{[(2S)-1-Ethoxybutan-2-yl]carbamoyl}azetidin-1-yl)-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-[(2S)-1-ethoxybutan-2-yl]azetidine-3-carboxamide hydrochloride obtained from (2S)-1-ethoxybutan-2-amine by the method described in Example 005-(1) and Example 001-(2) or a method equivalent thereto by the method described in Example 019 or a method equivalent thereto.

1H-NMR (DMSO-d6): δ 0.85 (3H, t, J=7.5 Hz), 1.10 (3H, t, J=7.0 Hz), 1.31-1.40 (1H, m), 1.52-1.61 (1H, m), 2.77 (3H, s), 3.38-3.48 (2H, m), 3.57-3.64 (1H, m), 3.78-3.85 (1H, m), 4.18-4.51 (4H, m), 6.55 (1H, s), 7.76 (1H, d, J=3.5 Hz), 7.84 (1H, d, J=3.5 Hz), 7.96 (1H, d, J=8.5 Hz), 9.84 (1H, s), 15.40 (1H, brs)

Example 196

Compound 196

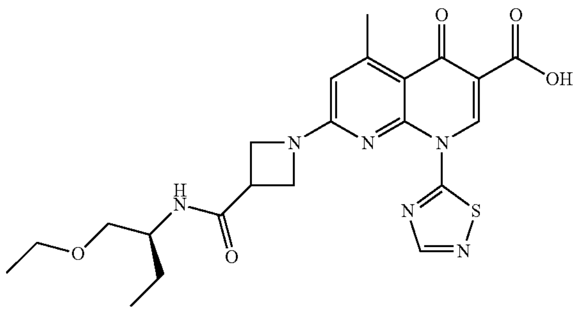

7-(3-({[(2S)-1-Ethoxybutan-2-yl]carbamoyl}azetidin-1-yl)-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-[(2S)-1-ethoxybutan-2-yl]azetidine-3-carboxamide hydrochloride obtained in Example 195 by the method described in Example 019 or a method equivalent thereto.

1H-NMR (DMSO-d6): δ 0.86 (3H, t, J=7.4 Hz), 1.10 (3H, t, J=6.9 Hz), 1.31-1.42 (1H, m), 1.52-1.62 (1H, m), 2.77 (3H, s), 3.38-3.48 (2H, m), 3.60-3.68 (1H, m), 3.78-3.87 (1H, m), 4.23-4.64 (4H, m), 6.60 (1H, s), 7.98 (1H, d, J=8.7 Hz), 8.82 (1H, s), 9.74 (1H, s), 15.09 (1H, brs)

Example 197

Compound 197

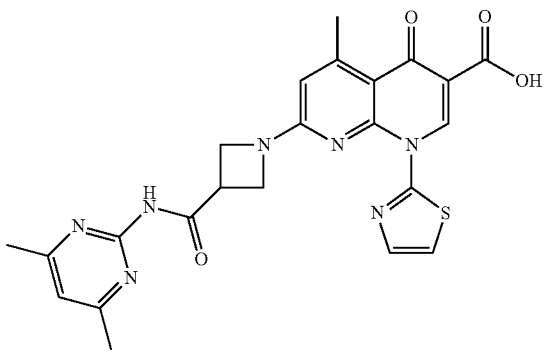

7-{3-[(4,6-Dimethylpyrimidin-2-yl)carbamoyl]azetidin-1-yl}-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-(4,6-dimethylpyrimidin-2-yl)azetidine-3-carboxamide trifluoroacetate obtained from 4,6-dimethylpyrimidin-2-amine by the method described in Example 005-(1) and Example 001-(2) or a method equivalent thereto by the method described in Example 002-(3) or a method equivalent thereto.

Property: pale yellow solid;

ESI-MS (m/z): 492 [M+H]+

Example 198

Compound 198

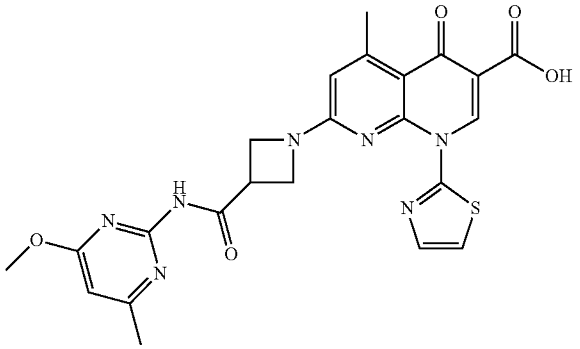

7-{3-[(4-Methoxy-6-methylpyrimidin-2-yl)carbamoyl]azetidin-1-yl}-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-(4-methoxy-6-methylpyrimidin-2-yl)azetidine-3-carboxamide trifluoroacetate obtained from 4-methoxy-6-methylpyrimidin-2-amine by the method described in Example 005-(1) and Example 001-(2) or a method equivalent thereto by the method described in Example 002-(3) or a method equivalent thereto.

1H-NMR (DMSO-d6): δ 2.78 (3H, s), 2.93 (3H, s), 3.76-3.83 (1H, m), 3.91 (1H, s), 4.29-4.61 (4H, m), 6.52 (1H, s), 7.81 (1H, s), 7.87 (1H, d, J=3.5 Hz), 7.89 (1H, d, J=3.5 Hz), 9.89 (1H, s), 10.68 (1H, s)

Example 199

Compound 199

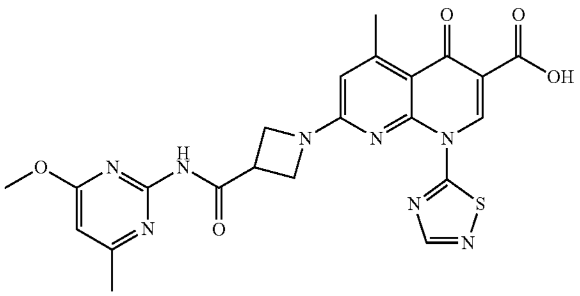

7-{3-[(4-Methoxy-6-methylpyrimidin-2-yl)carbamoyl]azetidin-1-yl}-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-(4-methoxy-6-methylpyrimidin-2-yl)azetidine-3-carboxamide trifluoroacetate obtained in Example 198 by the method described in Example 002-(3) or a method equivalent thereto.

1H-NMR (DMSO-d6): δ 2.79 (6H, s), 2.89 (3H, s), 3.78-3.85 (1H, m), 4.36-4.71 (4H, m), 6.52 (1H, s), 6.65 (1H, s), 8.83 (1H, s), 9.78 (1H, d, J=1.0 Hz), 10.69 (1H, s), 15.08 (1H, brs)

Example 200

Compound 200

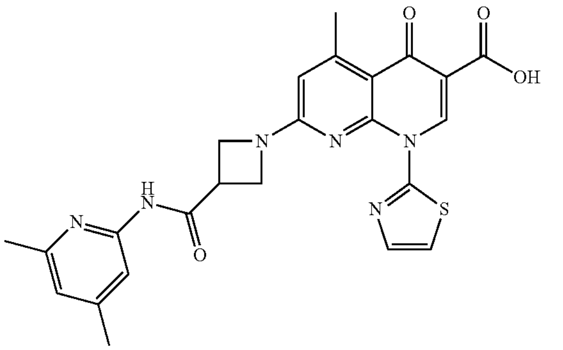

7-{3-[(4,6-Dimethylpyridin-2-yl)carbamoyl]azetidin-1-yl}-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-(4,6-dimethylpyridin-2-yl)azetidine-3-carboxamide trifluoroacetate obtained from 4,6-dimethylpyridin-2-amine by the method described in Example 005-(1) and Example 001-(2) or a method equivalent thereto by the method described in Example 002-(3) or a method equivalent thereto.

1H-NMR (DMSO-d6): δ 2.54 (3H, s), 2.78 (3H, s), 2.80 (3H, d, J=1.0 Hz), 4.27-4.61 (5H, m), 6.56-6.59 (1H, m), 6.88 (1H, d, J=1.0 Hz), 7.76-7.77 (1H, m), 7.82-7.86 (1H, m), 7.87-7.89 (1H, m), 9.71 (1H, s), 9.85 (1H, s), 15.38 (1H, brs)

Example 201

Compound 201

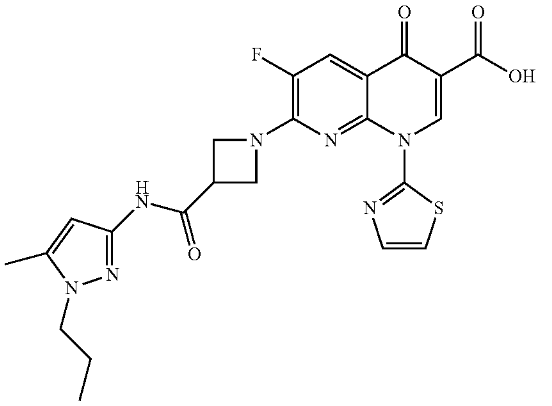

6-Fluoro-7-{3-[(5-methyl-1-propyl-1H-pyrazol-3-yl)carbamoyl]azetidin-1-yl}-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-(5-methyl-1-propyl-1H-pyrazol-3-yl)azetidine-3-carboxamide hydrochloride obtained from 5-methyl-1-propyl-1H-pyrazol-3-amine by the method described in Example 007-(1) and Example 001-(2) or a method equivalent thereto by the method described in Example 008 or a method equivalent thereto.

1H-NMR (DMSO-d6): δ 0.82 (3H, t, J=7.5 Hz), 1.66-1.76 (2H, m), 2.22 (3H, s), 3.76-3.85 (1H, m), 3.87 (2H, t, J=6.5 Hz), 4.38-4.86 (4H, m), 6.34 (1H, s), 7.78 (1H, d, J=3.5 Hz), 7.86 (1H, d, J=3.5 Hz), 8.12 (1H, d, J=11.0 Hz), 9.84 (1H, s), 10.59 (1H, s), 14.81 (1H, s)

Example 202

Compound 202

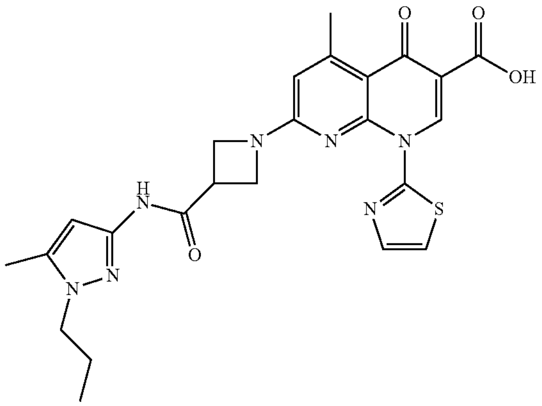

5-Methyl-7-{3-[(5-methyl-1-propyl-1H-pyrazol-3-yl)carbamoyl]azetidin-1-yl}-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-(5-methyl-1-propyl-1H-pyrazol-3-yl)azetidine-3-carboxamide hydrochloride obtained in Example 201 by the method described in Example 008 or a method equivalent thereto.

1H-NMR (DMSO-d6): δ 0.82 (3H, t, J=7.5 Hz), 1.66-1.76 (2H, m), 2.22 (3H, s), 2.76 (3H, s), 3.73-3.79 (1H, m), 3.86 (2H, t, J=6.5 Hz), 4.21-4.51 (4H, m), 6.32 (1H, s), 6.43 (1H, s), 7.63 (1H, d, J=3.5 Hz), 7.78 (1H, d, J=3.5 Hz), 9.75 (1H, s), 10.58 (1H, s), 15.40 (1H, brs)

Example 203

Compound 203

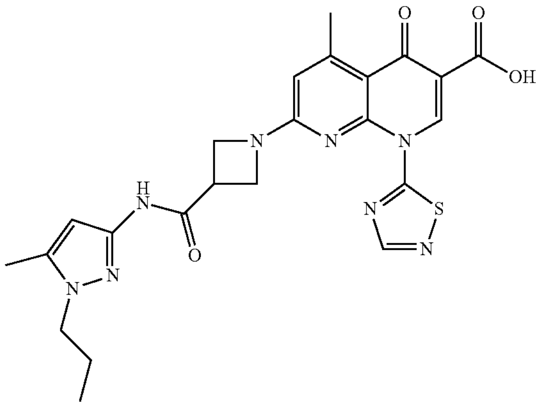

5-Methyl-7-{3-[(5-methyl-1-propyl-1H-pyrazol-3-yl)carbamoyl]azetidin-1-yl}-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-(5-methyl-1-propyl-1H-pyrazol-3-yl)azetidine-3-carboxamide hydrochloride obtained in Example 201 by the method described in Example 008 or a method equivalent thereto.

1H-NMR (DMSO-d6): δ 0.82 (3H, t, J=7.5 Hz), 1.66-1.76 (2H, m), 2.22 (3H, s), 2.77 (3H, s), 3.77-3.84 (1H, m), 3.87 (2H, t, J=6.5 Hz), 4.29-4.68 (4H, m), 6.34 (1H, s), 6.61 (1H, s), 8.81 (1H, s), 9.74 (1H, s), 10.63 (1H, s), 15.06 (1H, brs)

Example 204

Compound 204

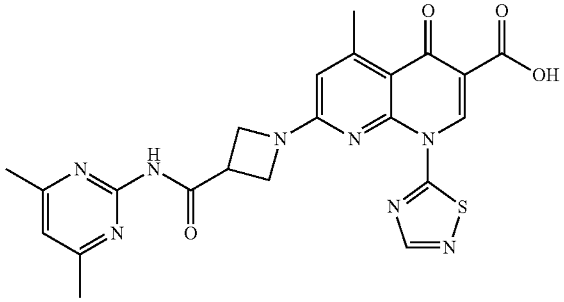

7-{3-[(4,6-Dimethylpyrimidin-2-yl)carbamoyl]azetidin-1-yl}-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-(4,6-dimethyl pyrimidin-2-yl)azetidine-3-carboxamide trifluoroacetate obtained in Example 197 by the method described in Example 002-(3) or a method equivalent thereto.

1H-NMR (DMSO-d6): δ 2.40 (6H, s), 2.79 (3H, s), 4.12-4.23 (1H, m), 4.37-4.74 (4H, m), 6.65 (1H, s), 6.99 (1H, s), 8.83 (1H, s), 9.77 (1H, s), 10.69 (1H, s), 15.12 (1H, brs)

Example 205

Compound 205

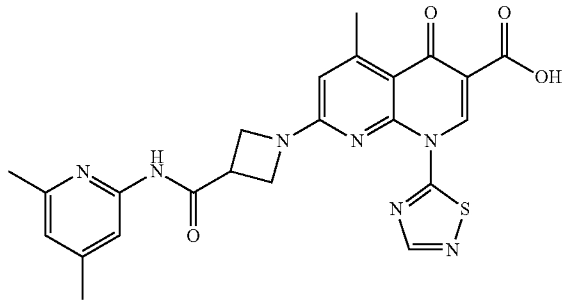

7-{3-[(4,6-Dimethylpyridin-2-yl)carbamoyl]azetidin-1-yl}-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-(4,6-dimethylpyridin-2-yl)azetidine-3-carboxamide trifluoroacetate obtained in Example 200 by the method described in Example 002-(3) or a method equivalent thereto.

1H-NMR (DMSO-d6): δ 2.78 (6H, s), 2.89 (3H, s), 4.13-4.74 (5H, m), 6.62 (1H, s), 6.81 (1H, s), 6.99 (1H, s), 7.88 (1H, s), 8.82 (1H, d, J=1.5 Hz), 9.75 (1H, d, J=3.5 Hz), 10.71 (1H, s)

Example 206

Compound 206

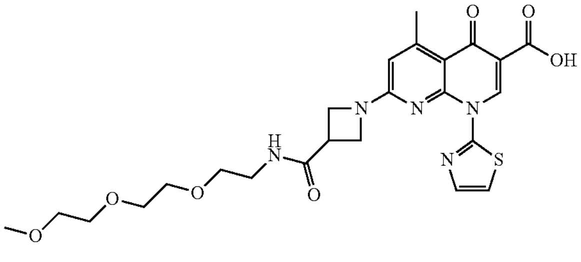

7-[3-({2-[2-(2-Methoxyethoxy)ethoxy]ethyl}carbamoyl)azetidin-1-yl]-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-{2-[2-(2-methoxyethoxy)ethoxy]ethyl}azetidine-3-carboxamide hydrochloride obtained from 1-[2-(2-aminoethoxy)ethoxy]-2-methoxyethane by the method described in Example 005-(1) and Example 001-(2) or a method equivalent thereto by the method described in Example 002-(3) or a method equivalent thereto.

Property: yellow solid;
ESI-MS (m/z): 532 [M+H]+

Example 207

Compound 207

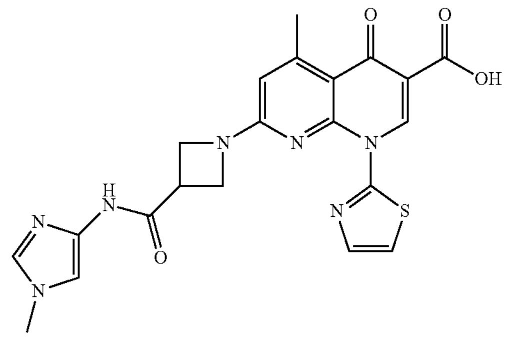

5-Methyl-7-{3-[(1-methyl-1H-imidazol-4-yl)carbamoyl]azetidin-1-yl}-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-(1-methyl-1H-imidazol-4-yl)azetidine-3-carboxamide hydrochloride obtained from 1-methyl-1H-imidazol-4-amine by the method described in Example 005-(1) and Example 001-(2) or a method equivalent thereto by the method described in Example 001-(3) or a method equivalent thereto.

1H-NMR (DMSO-d6): δ 2.75 (3H, s), 3.77-3.85 (1H, m), 4.21-4.54 (4H, m), 6.52 (1H, s), 7.24 (1H, d, J=1.5 Hz), 7.41 (1H, s), 7.72 (1H, d, J=3.5 Hz), 7.82 (1H, d, J=3.5 Hz), 9.81 (1H, s), 10.56 (1H, s)

Example 208

Compound 208

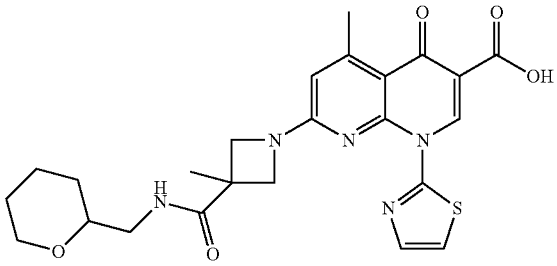

5-Methyl-7-{3-methyl-3-[(oxan-2-ylmethyl)carbamoyl]azetidin-1-yl}-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and 3-methyl-N-(oxan-2-ylmethyl)azetidine-3-carboxamide hydrochloride obtained from (oxan-2-yl)methylamine and 1-[(tert-butoxy) carbonyl]-3-methylazetidine-3-carboxylic acid by the method described in Example 005-(1) and Example 001-(2) or a method equivalent thereto by the method described in Example 019 or a method equivalent thereto.

1H-NMR (DMSO-d6): δ 1.08-1.17 (1H, m), 1.38-1.48 (3H, m), 1.52-1.58 (4H, m), 1.73-1.78 (1H, m), 2.78 (3H, d, J=0.9 Hz), 2.90-3.20 (4H, m), 3.84-3.88 (1H, m), 3.97-4.13 (2H, m), 4.38-4.57 (2H, m), 6.54 (1H, d, J=0.9 Hz), 7.79 (1H, d, J=3.5 Hz), 7.86 (1H, d, J=3.5 Hz), 8.13 (1H, t, J=5.8 Hz), 9.84 (1H, s)

Example 209

Compound 209

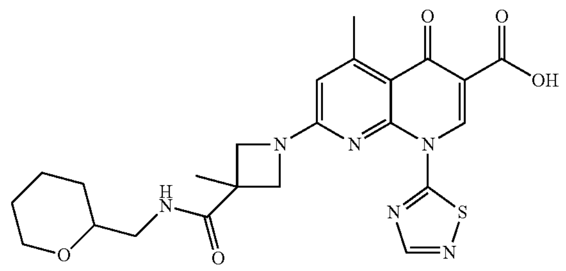

5-Methyl-7-{3-methyl-3-[(oxan-2-ylmethyl)carbamoyl]azetidin-1-yl}-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and 3-methyl-N-(oxan-2-ylmethyl)azetidine-3-carboxamide hydrochloride obtained in Example 208 by the method described in Example 019 or a method equivalent thereto.

1H-NMR (DMSO-d6): δ 1.09-1.20 (1H, m), 1.38-1.48 (3H, m), 1.50-1.68 (4H, m), 1.73-1.80 (1H, m), 2.78 (3H, s), 2.90-3.22 (4H, m), 3.84-4.65 (5H, m), 6.59 (1H, d, J=1.0 Hz), 8.14-8.23 (1H, m), 8.83 (1H, s), 9.75 (1H, s), 15.09 (1H, brs)

Example 210

Compound 210

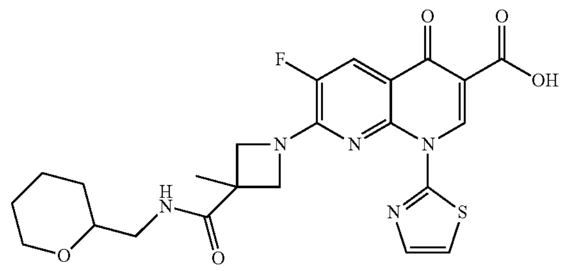

6-Fluoro-7-{3-methyl-3-[(oxan-2-ylmethyl)carbamoyl]azetidin-1-yl}-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and 3-methyl-N-(oxan-2-ylmethyl)azetidine-3-carboxamide hydrochloride obtained in Example 208 by the method described in Example 019 or a method equivalent thereto.

1H-NMR (DMSO-d6): δ 1.09-1.19 (1H, m), 1.38-1.48 (3H, m), 1.53-1.61 (4H, m), 1.73-1.80 (1H, m), 2.90-3.20 (3H, m), 3.84-3.89 (1H, m), 4.07-4.80 (1H, m), 7.82 (1H, d, J=3.5 Hz), 7.87 (1H, d, J=3.5 Hz), 8.07 (1H, d, J=11.4 Hz), 8.14 (1H, t, J=5.9 Hz), 9.80 (1H, s), 14.78 (1H, brs)

Example 211

Compound 211

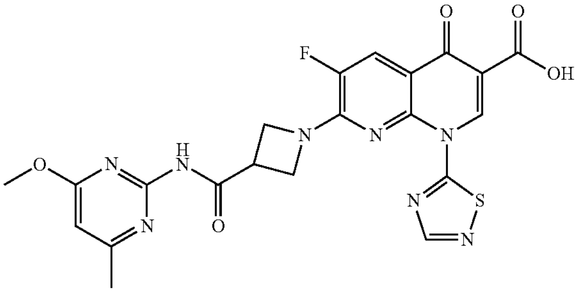

6-Fluoro-7-{3-[(4-methoxy-6-methylpyrimidin-2-yl)carbamoyl]azetidin-1-yl}-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and N-(4-methoxy-6-methylpyrimidin-2-yl)azetidine-3-carboxamide trifluoroacetate obtained in Example 198 by the method described in Example 002-(3) or a method equivalent thereto.

1H-NMR (DMSO-d6): δ 2.35 (3H, s), 3.73 (3H, s), 3.80-3.88 (1H, m), 3.92 (3H, s), 4.55-4.89 (4H, m), 6.53 (1H, s), 8.18 (1H, d, J=10.0 Hz), 8.88 (1H, s), 9.76 (1H, d, J=2.0 Hz), 10.70 (1H, s), 14.47 (1H, brs)

Example 212

Compound 212

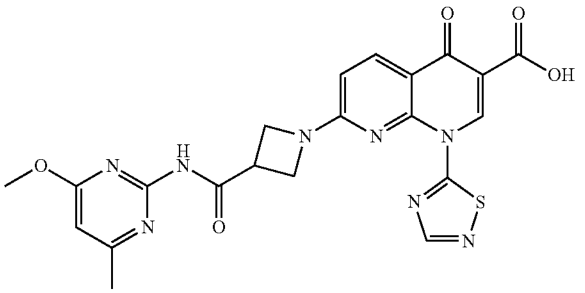

7-{3-[(4-Methoxy-6-methylpyrimidin-2-yl)carbamoyl]azetidin-1-yl}-4-oxo-1-(1,2,4-thiadiazol-5-yl)-1,4-dihydro-1,8-naphthyridine-3-carboxylic acid The title compound was obtained using 7-chloro-4-oxo-1-(1,2,4-thiadiazol-5-yl)-1,4-dihydro-1,8-naphthyridine-3-carboxylic acid obtained in Reference Example 006-(2) and N-(4-methoxy-6-methylpyrimidin-2-yl)azetidine-3-carboxamide trifluoroacetate obtained in Example 198 by the method described in Example 002-(3) or a method equivalent thereto.

1H-NMR (DMSO-d6): δ 2.36 (3H, s), 3.80-3.87 (1H, m), 3.92 (3H, s), 4.35-4.76 (4H, m), 6.53 (1H, s), 6.80-6.85 (1H, m), 8.34-8.39 (1H, m), 8.84 (1H, s), 9.75 (1H, s), 10.70 (1H, s), 14.70 (1H, brs)

Example 213

Compound 213

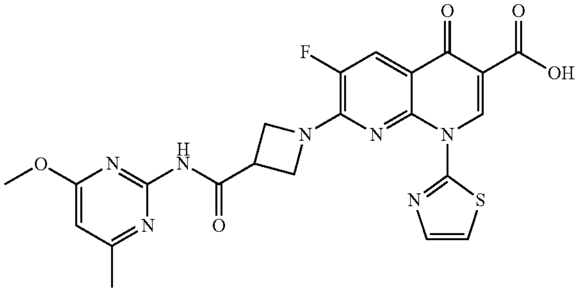

6-Fluoro-7-{3-[(4-methoxy-6-methylpyrimidin-2-yl)carbamoyl]azetidin-1-yl}-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-(4-methoxy-6-methylpyrimidin-2-yl)azetidine-3-carboxamide trifluoroacetate obtained in Example 198 by the method described in Example 002-(3) or a method equivalent thereto.

Property: pale yellow solid;

ESI-MS (m/z): 512 [M+H]+

Example 214

Compound 214

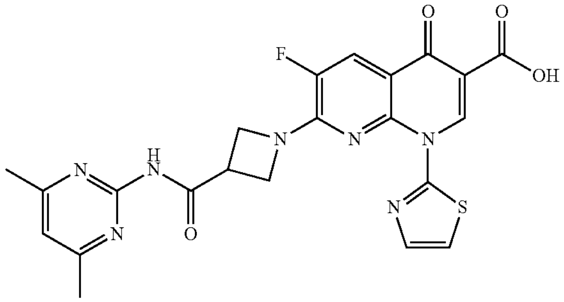

7-{3-[(4,6-Dimethylpyrimidin-2-yl)carbamoyl]azetidin-1-yl}-6-fluoro-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-(4,6-dimethylpyrimidin-2-yl)azetidine-3-carboxamide trifluoroacetate obtained in Example 197 by the method described in Example 002-(3) or a method equivalent thereto.

Property: pale orange solid;

ESI-MS (m/z): 496 [M+H]+

Example 215

Compound 215

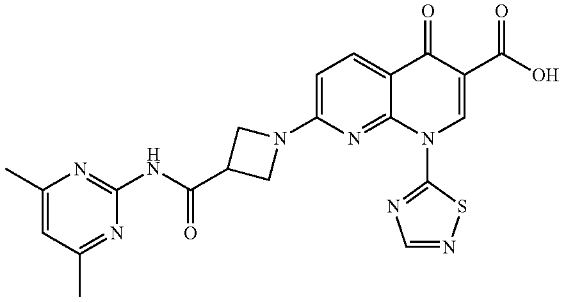

7-{3-[(4,6-Dimethylpyrimidin-2-yl)carbamoyl]azetidin-1-yl}-4-oxo-1-(1,2,4-thiadiazol-5-yl)-1,4-dihydro-1,8-naphthyridine-3-carboxylic acid The title compound was obtained using 7-chloro-4-oxo-1-(1,2,4-thiadiazol-5-yl)-1,4-dihydro-1,8-naphthyridine-3-carboxylic acid obtained in Reference Example 006-(2) and N-(4,6-dimethylpyrimidin-2-yl)azetidine-3-carboxamide trifluoroacetate obtained in Example 197 by the method described in Example 002-(3) or a method equivalent thereto.

Property: dark reddish-brown solid; ESI-MS (m/z): 479 [M+H]+

Example 216

Compound 216

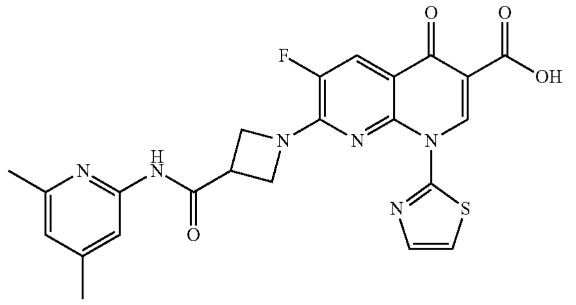

7-{3-[(4,6-Dimethylpyridin-2-yl)carbamoyl]azetidin-1-yl}-6-fluoro-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-(4,6-dimethylpyridin-2-yl)azetidine-3-carboxamide trifluoroacetate obtained in Example 200 by the method described in Example 002-(3) or a method equivalent thereto.

Property: yellowish-brown solid; Melting point: 235-238° C. (decomposition)

Example 217

Compound 217

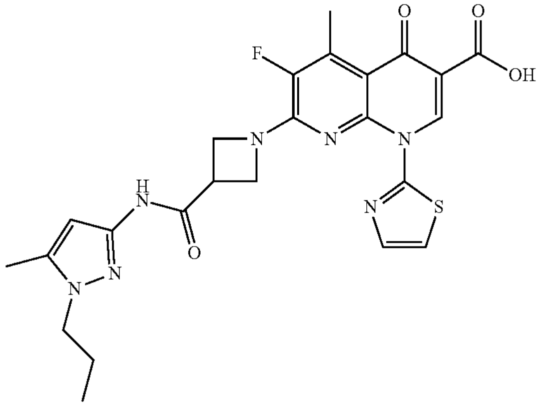

6-Fluoro-5-methyl-7-{3-[(5-methyl-1-propyl-1H-pyrazol-3-yl)carbamoyl]azetidin-1-yl}-4-oxo-1-(1,3-thiazol-2-yl)-1,4-dihydro-1,8-naphthyridine-3-carboxylic acid The title compound was obtained using 7-chloro-6-fluoro-5-methyl-4-oxo-1-(1,3-thiazol-2-yl)-1,4-dihydro-1,8-naphthyridine-3-carboxylic acid obtained in Reference Example 007-(2) and N-(5-methyl-1-propyl-1H-pyrazol-3-yl)azetidine-3-carboxamide hydrochloride obtained in Example 201 by the method described in Example 008 or a method equivalent thereto.

1H-NMR (DMSO-d6): δ 0.82 (3H, t, J=7.5 Hz), 1.66-1.76 (2H, m), 2.22 (3H, s), 2.69 (3H, d, J=2.5 Hz), 3.74-3.83 (1H, m), 3.86 (2H, t, J=6.5 Hz), 4.38-4.75 (4H, m), 6.34 (1H, s), 7.71 (1H, d, J=3.5 Hz), 7.81 (1H, d, J=3.5 Hz), 9.76 (1H, s), 10.58 (1H, s), 15.19 (1H, brs)

Example 218

Compound 218

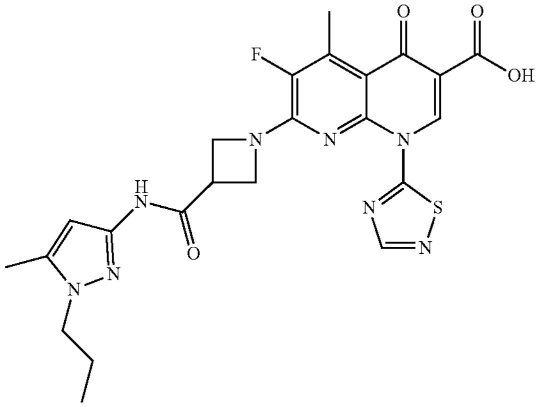

6-Fluoro-5-methyl-7-{3-[(5-methyl-1-propyl-1H-pyrazol-3-yl)carbamoyl]azetidin-1-yl}-4-oxo-1-(1,2,4-thiadiazol-5-yl)-1,4-dihydro-1,8-naphthyridine-3-carboxylic acid The title compound was obtained using 7-chloro-6-fluoro-5-methyl-4-oxo-1-(1,2,4-thiadiazol-5-yl)-1,4-dihydro-1,8-naphthyridine-3-carboxylic acid obtained in Reference Example 008-(2) and N-(5-methyl-1-propyl-1H-pyrazol-3-yl)azetidine-3-carboxamide hydrochloride obtained in Example 201 by the method described in Example 008 or a method equivalent thereto.

1H-NMR (DMSO-d6): δ 0.82 (3H, t, J=7.5 Hz), 1.66-1.76 (2H, m), 2.22 (3H, s), 2.70 (3H, d, J=2.5 Hz), 3.77-3.84 (1H, m), 3.87 (2H, t, J=6.5 Hz), 4.50-4.85 (4H, m), 6.34 (1H, s), 8.85 (1H, s), 9.78 (1H, s), 10.61 (1H, s), 14.86 (1H, s)

Example 219

Compound 219

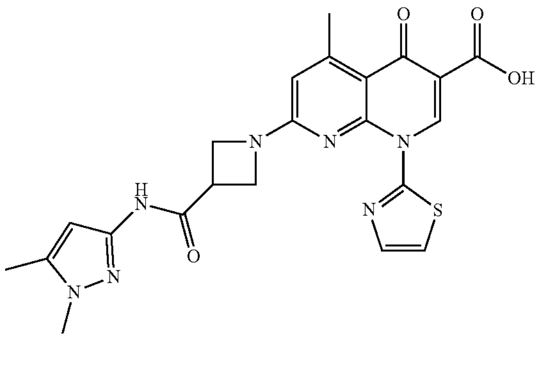

7-{3-[(1,5-Dimethyl-1H-pyrazol-3-yl)carbamoyl]azetidin-1-yl}-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-(1,5-dimethyl-1H-pyrazol-3-yl)azetidine-3-carboxamide hydrochloride obtained from 1,5-dimethyl-1H-pyrazol-3-amine by the method described in Example 007-(1) and Example 001-(2) or a method equivalent thereto by the method described in Example 008 or a method equivalent thereto.

1H-NMR (DMSO-d6): δ 2.22 (3H, s), 2.80 (3H, s), 3.62 (3H, s), 3.74-3.82 (1H, m), 4.24-4.56 (4H, m), 6.32 (1H, s), 6.57 (1H, s), 7.74 (1H, d, J=3.5 Hz), 7.84 (1H, d, J=3.5 Hz), 9.85 (1H, s), 10.54 (1H, s), 15.40 (1H, brs)

Example 220

Compound 220

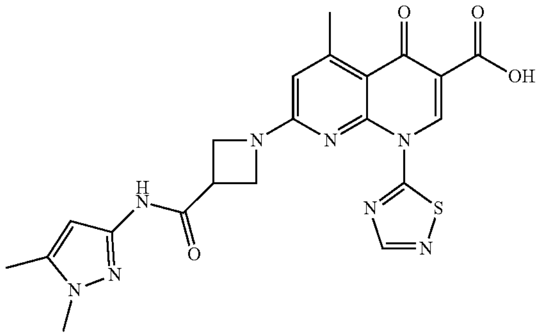

7-{3-[(1,5-Dimethyl-1H-pyrazol-3-yl)carbamoyl]azetidin-1-yl}-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-(1,5-dimethyl-1H-pyrazol-3-yl)azetidine-3-carboxamide hydrochloride obtained in Example 219 by the method described in Example 008 or a method equivalent thereto.

1H-NMR (DMSO-d6): δ 2.21 (3H, s), 2.77 (3H, s), 3.62 (3H, s), 3.77-3.85 (1H, m), 4.29-4.72 (4H, m), 6.34 (1H, s), 6.59 (1H, s), 7.81 (1H, s), 9.74 (1H, s), 10.56 (1H, a), 15.00 (1H, brs)

Example 221

Compound 221

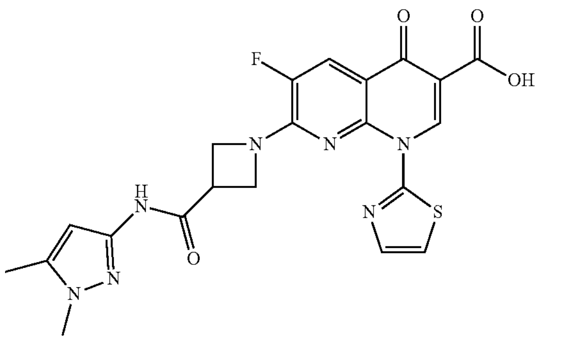

7-{3-[(1,5-Dimethyl-1H-pyrazol-3-yl)carbamoyl]azetidin-1-yl}-6-fluoro-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-(1,5-dimethyl-1H-pyrazol-3-yl)azetidine-3-carboxamide hydrochloride obtained in Example 219 by the method described in Example 008 or a method equivalent thereto.

1H-NMR (DMSO-d6): δ 2.22 (3H, s), 3.62 (3H, s), 3.77-3.85 (1H, m), 4.46-4.75 (4H, m), 6.34 (1H, s), 6.57 (1H, s), 7.74 (1H, d, J=3.5 Hz), 7.84 (1H, d, J=3.5 Hz), 8.09 (1H, d, J=11.5 Hz), 9.76 (1H, s), 10.54 (1H, s), 14.68 (1H, brs)

Example 222

Compound 222

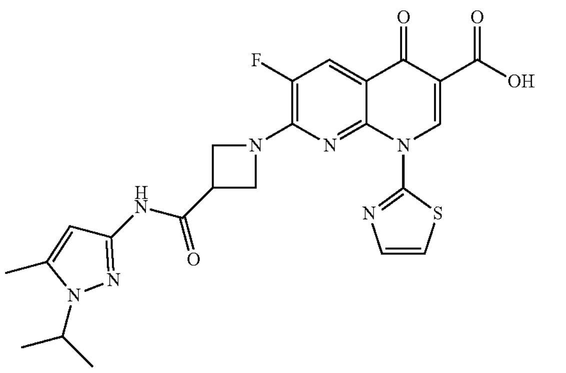

6-Fluoro-7-(3-{[5-methyl-1-(propan-2-yl)-1H-pyrazol-3-yl]carbamoyl}azetidin-1-yl)-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-[5-methyl-1-(propan-2-yl)-1H-pyrazol-3-yl]azetidine-3-carboxamide hydrochloride obtained from 5-methyl-1-(propan-2-yl)-1H-pyrazol-3-amine by the method described in Example 007-(1) and Example 001-(2) or a method equivalent thereto by the method described in Example 008 or a method equivalent thereto.

1H-NMR (DMSO-d6): δ 1.32 (6H, d, J=6.5 Hz), 2.23 (3H, s), 3.74-3.93 (1H, m), 4.38-4.84 (5H, m), 6.32 (1H, s), 7.70-7.92 (2H, m), 8.11 (1H, d, J=11.5 Hz), 9.84 (1H, s), 10.64 (1H, s), 14.74 (1H, brs)

Example 223

Compound 223

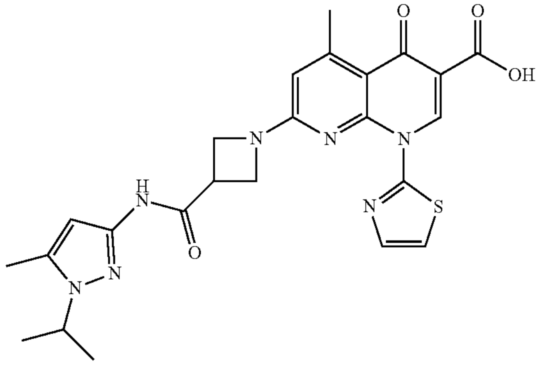

5-Methyl-7-(3-{[5-methyl-1-(propan-2-yl)-1H-pyrazol-3-yl]carbamoyl}azetidin-1-yl)-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-[5-methyl-1-(propan-2-yl)-1H-pyrazol-3-yl]azetidine-3-carboxamide hydrochloride obtained in Example 222 by the method described in Example 008 or a method equivalent thereto.

1H-NMR (DMSO-d6): δ 1.32 (6H, d, J=6.5 Hz), 2.23 (3H, s), 2.79 (3H, brs), 3.70-3.85 (1H, m), 4.20-4.60 (5H, m), 6.31 (1H, s), 6.57 (1H, brs), 7.68-7.87 (2H, m), 9.86 (1H, s), 10.65 (1H, s), 15.41 (1H, brs)

Example 224

Compound 224

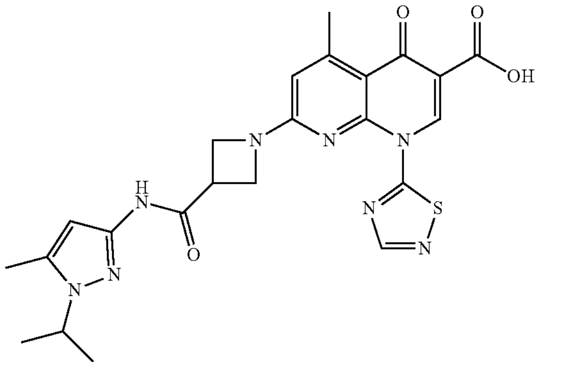

5-Methyl-7-(3-{[5-methyl-1-(propan-2-yl)-1H-pyrazol-3-yl]carbamoyl}azetidin-1-yl)-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-[5-methyl-1-(propan-2-yl)-1H-pyrazol-3-yl]azetidine-3-carboxamide hydrochloride obtained in Example 222 by the method described in Example 008 or a method equivalent thereto.

1H-NMR (DMSO-d6): δ 1.32 (6H, d, J=6.5 Hz), 2.23 (3H, s), 2.79 (3H, brs), 3.62 (3H, s), 3.73-3.90 (1H, m), 4.24-4.72 (5H, m), 6.32 (1H, s), 6.62 (1H, brs), 8.83 (1H, s), 9.76 (1H, s), 10.68 (1H, s), 15.08 (1H, brs)

Example 225

Compound 225

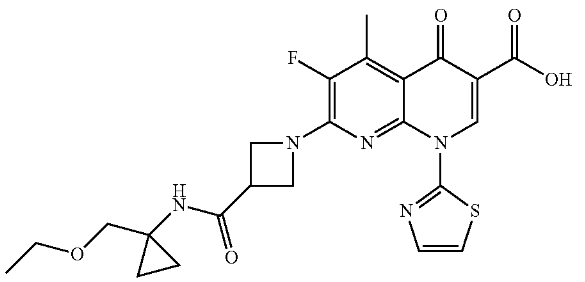

7-(3-{[1-(Ethoxymethyl)cyclopropyl]carbamoyl}azetidin-1-yl)-6-fluoro-5-methyl-4-oxo-1-(1,3-thiazol-2-yl)-1,4-dihydro-1,8-naphthyridine-3-carboxylic acid The title compound was obtained by the method described in Example 019 or a method equivalent thereto using N-[1-(ethoxymethyl)cyclopropyl]azetidine-3-carboxamide hydrochloride obtained from 1-(ethoxymethyl)cyclopropan-1-amine by the methods described in Examples 005-(1) and 001-(2) or methods equivalent thereto, and 7-chloro-6-fluoro-5-methyl-4-oxo-1-(1,3-thiazol-2-yl)-1,4-dihydro-1,8-naphthyridine-3-carboxylic acid obtained in Reference Example 007-(2).

1H-NMR (DMSO-d6): δ 0.64-0.71 (4H, m), 1.10 (3H, t, J=7.0 Hz), 2.69 (3H, d, J=2.8 Hz), 3.41-3.46 (4H, m), 3.49-3.56 (1H, m), 4.36-4.71 (4H, m), 7.78 (1H, d, J=3.5 Hz), 7.85 (1H, d, J=3.5 Hz), 8.44 (1H, s), 9.81 (1H, s), 15.19 (1H, brs)

Example 226

Compound 226

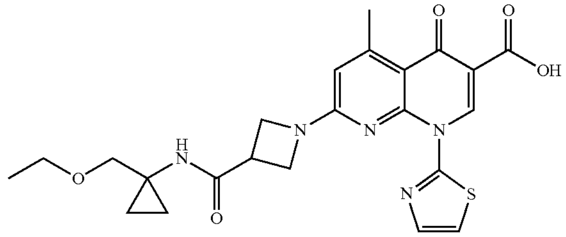

7-(3-{[1-(Ethoxymethyl)cyclopropyl]carbamoyl}azetidin-1-yl)-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-[1-(ethoxymethyl)cyclopropyl]azetidine-3-carboxamide hydrochloride obtained in Example 225 by the method described in Example 019 or a method equivalent thereto.

1H-NMR (DMSO-d6): δ 0.63-0.71 (4H, m), 1.10 (3H, t, J=7.0 Hz), 2.75 (3H, s), 3.41-3.47 (4H, m), 3.47-3.54 (1H, m), 4.15-4.45 (4H, m), 6.51 (1H, s), 7.74 (1H, d, J=3.5 Hz), 7.83 (1H, d, J=3.5 Hz), 8.47 (1H, s), 9.82 (1H, s), 15.39 (1H, s)

Example 227

Compound 227

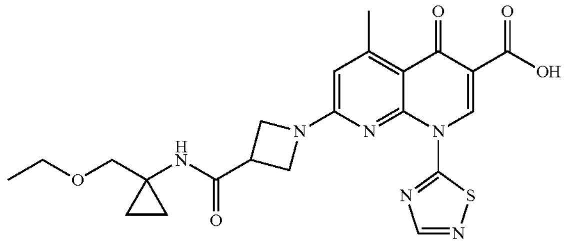

7-(3-{[1-(Ethoxymethyl)cyclopropyl]carbamoyl}azetidin-1-yl)-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-[1-(ethoxymethyl)cyclopropyl]azetidine-3-carboxamide hydrochloride obtained in Example 225 by the method described in Example 019 or a method equivalent thereto.

1H-NMR (DMSO-d6): δ 0.65-0.71 (4H, m), 1.10 (3H, t, J=7.0 Hz), 2.78 (3H, s), 3.41-3.47 (4H, m), 3.51-3.57 (1H, m), 4.23-4.60 (4H, m), 6.59 (1H, s), 8.48 (1H, s), 8.82 (1H, s), 9.75 (1H, s), 15.09 (1H, s)

Example 228

Compound 228

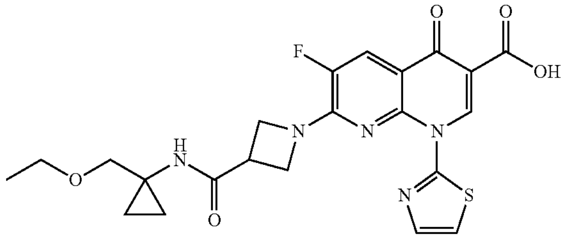

7-(3-{[1-(Ethoxymethyl)cyclopropyl]carbamoyl}azetidin-1-yl)-6-fluoro-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) N-[1-(ethoxymethyl)cyclopropyl]azetidine-3-carboxamide hydrochloride obtained in Example 225 by the method described in Example 019 or a method equivalent thereto.

1H-NMR (DMSO-d6): δ 0.64-0.71 (4H, m), 1.10 (3H, t, J=7.0 Hz), 3.41-3.47 (4H, m), 3.51-3.58 (1H, m), 4.36-4.76 (4H, m), 7.80 (1H, d, J=3.5 Hz), 7.86 (1H, d, J=3.5 Hz), 8.11 (1H, d, J=11.4 Hz), 8.45 (1H, s), 9.82 (1H, s), 14.80 (1H, brs)

Example 229

Compound 229

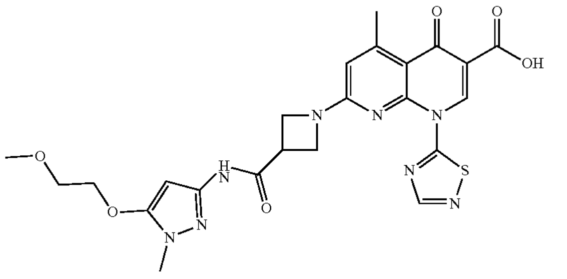

7-(3-{[5-(2-Methoxyethoxy)-1-methyl-1H-pyrazol-3-yl]carbamoyl}azetidin-1-yl)-5-methyl-4-oxo-1-(1,2,4-thiadiazol-5-yl)-1,4-dihydro-1,8-naphthyridine-3-carboxylic acid The title compound was obtained by the method described in Example 008 or a method equivalent thereto using N-[5-(2-methoxyethoxy)-1-methyl-1H-pyrazol-3-yl]azetidine-3-carboxamide hydrochloride obtained by the methods described in Examples 007-(1) and 001-(2) or methods equivalent thereto using 5-(2-methoxyethoxy)-1-methyl-1H-pyrazol-3-amine obtained by the methods described in Examples 009-(1) to 009-(3) or methods equivalent thereto, and 7-chloro-5-methyl-4-oxo-1-(1,2,4-thiadiazol-5-yl)-1,4-dihydro-1,8-naphthyridine-3-carboxylic acid obtained in Reference Example 002-(2).

1H-NMR (DMSO-d6): δ 2.36 (3H, brs), 2.77 (3H, brs), 3.47 (3H, brs), 3.56-3.69 (2H, m), 3.70-3.91 (1H, m), 4.10-4.22 (2H, m), 4.21-4.71 (4H, m), 6.02 (1H, s), 6.56 (1H, brs), 8.77 (1H, s), 9.60 (1H, s), 10.57 (1H, brs)

Example 230

Compound 230

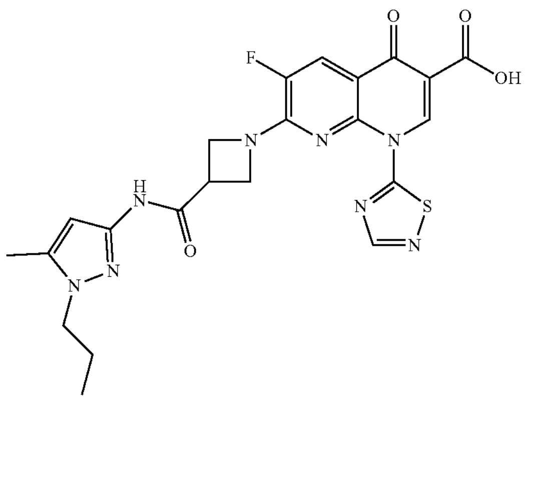

6-Fluoro-7-{3-[(5-methyl-1-propyl-1H-pyrazol-3-yl)carbamoyl]azetidin-1-yl}-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and N-(5-methyl-1-propyl-1H-pyrazol-3-yl)azetidine-3-carboxamide hydrochloride obtained in Example 201 by the method described in Example 008 or a method equivalent thereto.

1H-NMR (DMSO-d6): δ 0.82 (3H, t, J=7.5 Hz), 1.66-1.76 (2H, m), 2.22 (3H, s), 3.77-3.84 (1H, m), 3.87 (2H, t, J=6.5 Hz), 4.54-4.74 (4H, m), 6.33 (1H, s), 8.04 (1H, d, J=12.0 Hz), 8.76 (1H, s), 9.68 (1H, s), 10.59 (1H, s)

Example 231

Compound 231

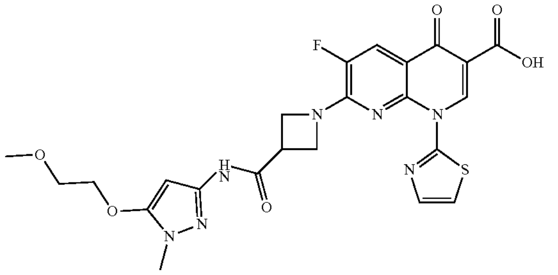

6-Fluoro-7-(3-{[5-(2-methoxyethoxy)-1-methyl-1H-pyrazol-3-yl]carbamoyl}azetidin-1-yl)-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-[5-(2-methoxyethoxy)-1-methyl-1H-pyrazol-3-yl]azetidine-3-carboxamide hydrochloride obtained in Example 229 by the method described in Example 008 or a method equivalent thereto.

1H-NMR (DMSO-d6): δ 2.96 (3H, brs), 3.46 (3H, brs), 3.64 (2H, brs), 3.71-3.84 (1H, m), 4.17 (2H, brs), 4.30-4.61 (4H, m), 6.02 (1H, s), 7.60-7.89 (3H, m), 9.47 (1H, brs), 10.58 (1H, brs)

Example 232

Compound 232

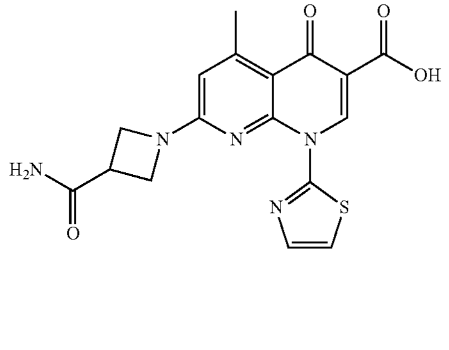

7-(3-Carbamoylazetidin-1-yl)-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and azetidine-3-carboxamide hydrochloride by the method described in Example 002-(3) or a method equivalent thereto.

1H-NMR (DMSO-d6): δ 2.78 (3H, d, J=1.0 Hz), 3.65-3.73 (1H, m), 4.24-4.60 (4H, m), 6.57 (1H, d, J=1.0 Hz), 7.76 (1H, d, J=3.5 Hz), 7.84 (2H, d, J=3.5 Hz), 9.85 (1H, s), 12.89 (1H, brs)

Example 233

Compound 233

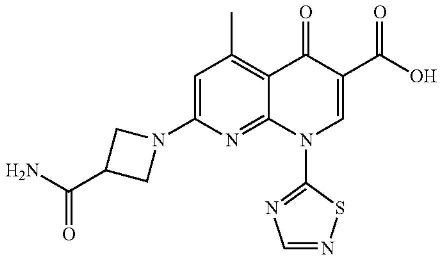

7-(3-Carbamoylazetidin-1-yl)-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and azetidine-3-carboxamide hydrochloride by the method described in Example 002-(3) or a method equivalent thereto.

1H-NMR (DMSO-d6): δ 2.78 (3H, d, J=1.0 Hz), 3.67-3.75 (1H, m), 4.24-4.73 (4H, m), 6.61 (1H, d, J=1.0 Hz), 8.82 (1H, s), 9.75 (1H, s), 12.91 (2H, brs)

Example 234

Compound 234

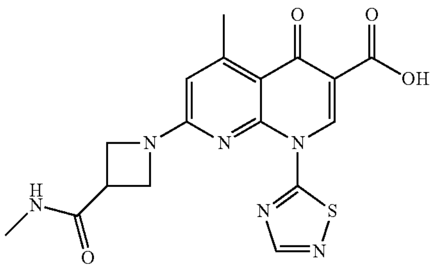

5-Methyl-7-[3-(methylcarbamoyl)azetidin-1-yl]-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-methylazetidine-3-carboxamide hydrochloride obtained from methylamine by the method described in Example 005-(1) and Example 001-(2) or a method equivalent thereto by the method described in Example 002-(3) or a method equivalent thereto.

1H-NMR (DMSO-d6): δ 2.08 (3H, s), 2.78 (3H, s), 3.06-3.76 (1H, m), 4.15-4.72 (4H, m), 6.61 (1H, s), 8.83 (1H, s), 9.76 (1H, s), 15.05 (1H, brs)

Example 235

Compound 235

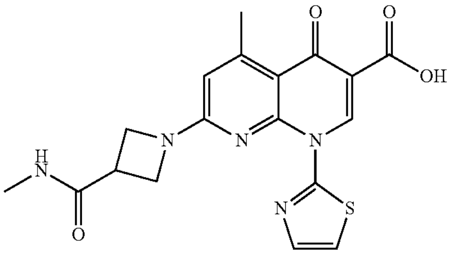

5-Methyl-7-[3-(methylcarbamoyl)azetidin-1-yl]-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-methylazetidine-3-carboxamide hydrochloride obtained in Example 234 by the method described in Example 002-(3) or a method equivalent thereto.

1H-NMR (DMSO-d6): δ 2.54 (3H, s), 2.78 (3H, s), 3.63-3.74 (1H, m), 4.26-4.59 (4H, m), 6.57 (1H, d, J=1.0 Hz), 7.76 (1H, d, J=3.5 Hz), 7.84 (1H, d, J=3.5 Hz), 9.85 (1H, s), 12.88 (1H, s), 15.37 (1H, brs)

Example 236

Compound 236

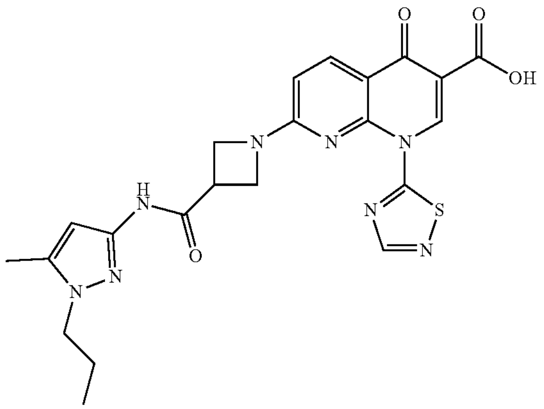

7-{3-[(5-Methyl-1-propyl-1H-pyrazol-3-yl)carbamoyl]azetidin-1-yl}-4-oxo-1-(1,2,4-thiadiazol-5-yl)-1,4-dihydro-1,8-naphthyridine-3-carboxylic acid The title compound was obtained using 7-chloro-4-oxo-1-(1,2,4-thiadiazol-5-yl)-1,4-dihydro-1,8-naphthyridine-3-carboxylic acid obtained in Reference Example 006-(2) and N-(5-methyl-1-propyl-1H-pyrazol-3-yl)azetidine-3-carboxamide hydrochloride obtained in Example 201 by the method described in Example 008 or a method equivalent thereto.

1H-NMR (DMSO-d6): δ 0.82 (3H, t, J=7.5 Hz), 1.66-1.76 (2H, m), 2.22 (3H, s), 3.77-3.84 (1H, m), 3.87 (2H, t, J=6.5 Hz), 4.29-4.68 (4H, m), 6.32 (1H, s), 6.67 (1H, d, J=9.5 Hz), 8.25 (1H, d, J=9.5 Hz), 8.76 (1H, s), 9.55 (1H, s), 10.60 (1H, s)

Example 237

Compound 237

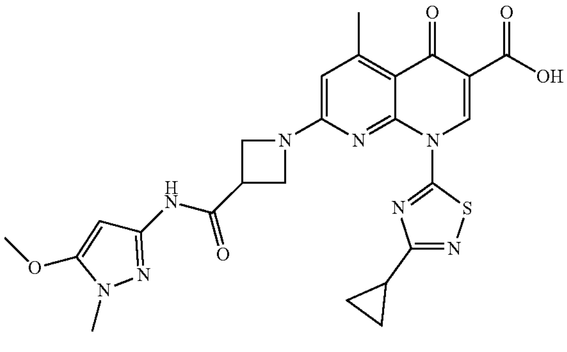

1-(3-Cyclopropyl-1,2,4-thiadiazol-5-yl)-7-{3-[(5-methoxy-1-methyl-1H-pyrazol-3-yl)carbamoyl]azetidin-1-yl}-5-methyl-4-oxo-1,4-dihydro-1,8-naphthyridine-3-carboxylic acid The title compound was obtained using 7-chloro-1-(3-cyclopropyl-1,2,4-thiadiazol-5-yl)-5-methyl-4-oxo-1,4-dihydro-1,8-naphthyridine-3-carboxylic acid obtained in Reference Example 031-(2) and N-(5-methoxy-1-methyl-1H-pyrazol-3-yl)azetidine-3-carboxamide hydrochloride obtained in Example 169 by the method described in Example 008 or a method equivalent thereto.

1H-NMR (DMSO-d6): δ 1.01-1.14 (4H, m), 2.29-2.38 (1H, m), 2.76 (3H, brs), 3.45 (3H, s), 3.75-3.87 (1H, m), 3.84 (3H, s), 4.27-4.62 (4H, m), 6.01 (1H, s), 6.60 (1H, brs), 9.63-9.67 (1H, m), 10.57 (1H, brs), 15.12 (1H, brs)

Example 238

Compound 238

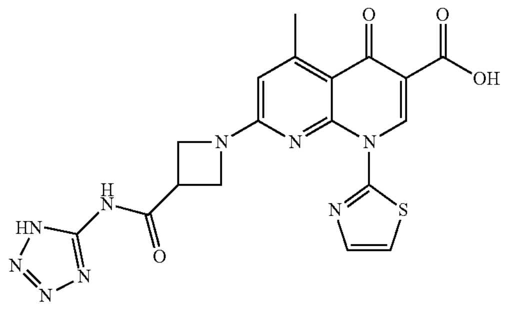

5-Methyl-4-oxo-7-{3-[(1H-1,2,3,4-tetrazol-5-yl)carbamoyl]azetidin-1-yl}-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-(1H-1,2,3,4-tetrazol-5-yl)azetidine-3-carboxamide trifluoroacetate obtained from 1H-1,2,3,4-tetrazol-5-amine by the method described in Example 005-(1) and Example 001-(2) or a method equivalent thereto by the method described in Example 002-(3) or a method equivalent thereto.

Property: orange solid;

Melting point: 222-225° C.

Example 239

Compound 239

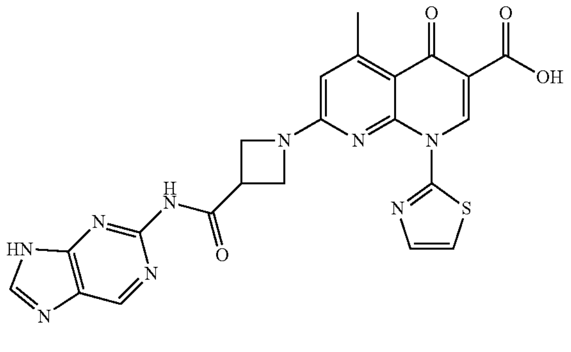

5-Methyl-4-oxo-7-{3-[(9H-purin-2-yl)carbamoyl]azetidin-1-yl}-1-(1,3-thiazol-2-yl)-1,4-dihydro-1,8-naphthyridine-3-carboxylic acid The title compound was obtained by the method described in Example 002-(3) or a method equivalent thereto using N-(9H-purin-2-yl)azetidine-3-carboxamide trifluoroacetate obtained from 9H-purin-2-amine by the methods described in Examples 005-(1) and 001-(2) or methods equivalent thereto, and 7-chloro-5-methyl-4-oxo-1-(1,3-thiazol-2-yl)-1,4-dihydro-1,8-naphthyridine-3-carboxylic acid obtained in Reference Example 001-(2).

Property: pale orange solid;

Melting point: 198-201° C.

Example 240

Compound 240

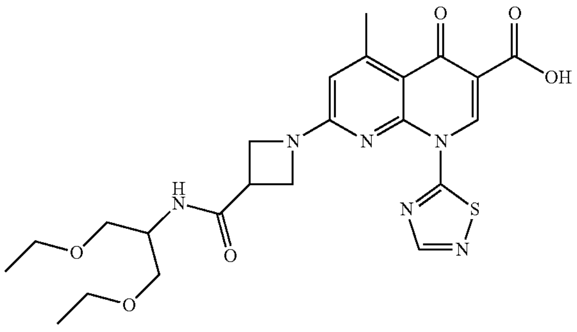

7-{3-[(1,3-Diethoxypropan-2-yl)carbamoyl]azetidin-1-yl}-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-(1,3-diethoxypropan-2-yl)azetidine-3-carboxamide hydrochloride obtained in Example 006-(3) by the method described in Example 001-(3) or a method equivalent thereto.

1H-NMR (DMSO-d6): δ 1.11 (6H, t, J=7.0 Hz), 2.77 (3H, d, J=0.9 Hz), 3.39-3.48 (8H, m), 3.63-3.70 (1H, m), 4.02-4.10 (1H, m), 4.24-4.63 (4H, m), 6.59 (1H, d, J=0.9 Hz), 8.13 (1H, d, J=8.3 Hz), 8.81 (1H, s), 9.74 (1H, s), 15.07 (1H, brs)

Example 241

Compound 241

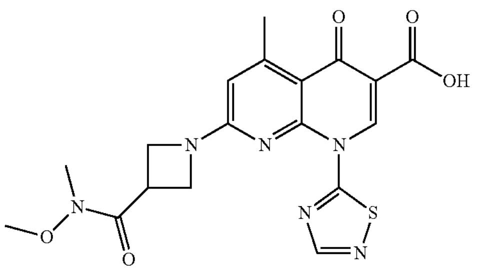

7-{3-[Methoxy(methyl)carbamoyl]azetidin-1-yl}-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-methoxy-N-methylazetidine-3-carboxamide hydrochloride obtained from methoxy(methyl)amine by the method described in Example 005-(1) and Example 001-(2) or a method equivalent thereto by the method described in Example 001-(3) or a method equivalent thereto.

1H-NMR (DMSO-d6): δ 2.74 (3H, s), 3.19 (3H, s), 3.75 (3H, s), 4.02-4.10 (1H, m), 4.32-4.64 (4H, m), 6.57 (1H, s), 8.81 (1H, s), 9.69 (1H, s), 15.02 (1H, brs)

Example 242

Compound 242

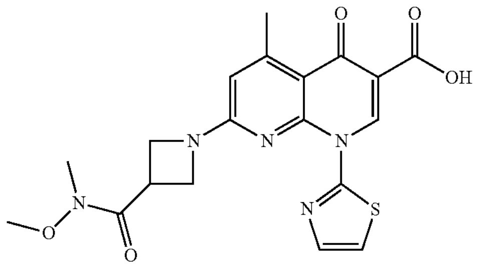

7-{3-[Methoxy(methyl)carbamoyl]azetidin-1-yl}-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-methoxy-N-methylazetidine-3-carboxamide hydrochloride obtained in Example 241 by the method described in Example 001-(3) or a method equivalent thereto.

1H-NMR (DMSO-d6): δ 2.76 (3H, s), 3.17 (3H, s), 3.73 (3H, s), 3.98-4.08 (1H, m), 4.27-4.54 (4H, m), 6.54 (1H, s), 7.77 (1H, d, J=3.5 Hz), 7.83 (1H, d, J=3.5 Hz), 9.83 (1H, s), 15.37 (1H, brs)

Example 243

Compound 243

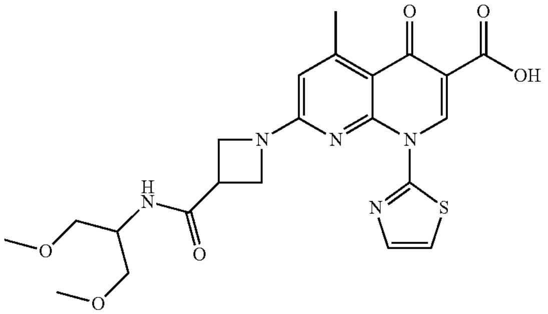

7-{3-[(1,3-Dimethoxypropan-2-yl)carbamoyl]azetidin-1-yl}-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-(1,3-dimethoxypropan-2-yl)azetidine-3-carboxamide hydrochloride obtained from 2-aminopropane-1,3-diol by the method described in Example 005-(1), Example 006-(2) and Example 001-(2) or a method equivalent thereto by the method described in Example 001-(3) or a method equivalent thereto.

1H-NMR (DMSO-d6): δ 2.77 (3H, s), 3.26 (6H, s), 3.33-3.39 (4H, m), 3.60-3.66 (1H, m), 4.06-4.12 (1H, m), 4.18-4.49 (4H, m), 6.53 (1H, d, J=0.9 Hz), 7.75 (1H, d, J=3.5 Hz), 7.84 (1H, d, J=3.5 Hz), 8.16 (1H, d, J=8.3 Hz), 9.83 (1H, s), 15.39 (1H, brs)

Example 244

Compound 244

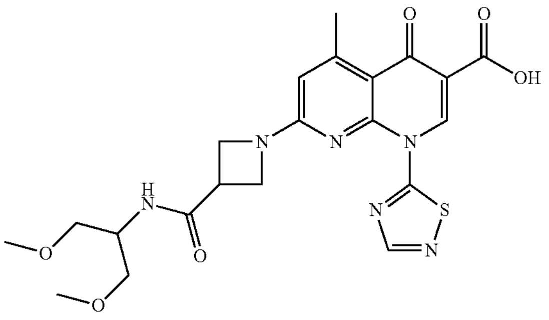

7-{3-[(1,3-Dimethoxypropan-2-yl)carbamoyl]azetidin-1-yl}-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-(1,3-dimethoxypropan-2-yl)azetidine-3-carboxamide hydrochloride obtained in Example 243 by the method described in Example 001-(3) or a method equivalent thereto.

1H-NMR (DMSO-d6): δ 2.74 (3H, s), 3.26 (6H, s), 3.34-3.41 (4H, m), 3.62-3.70 (1H, m), 4.07-4.14 (1H, m), 4.23-4.59 (4H, m), 6.55 (1H, s), 8.19 (1H, d, J=8.3 Hz), 8.80 (1H, s), 9.68 (1H, s), 15.03 (1H, brs)

Example 245

Compound 245

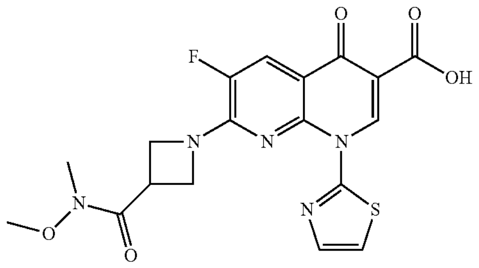

6-Fluoro-7-{3-[methoxy(methyl)carbamoyl]azetidin-1-yl}-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-methoxy-N-methylazetidine-3-carboxamide hydrochloride obtained in Example 241 by the method described in Example 001-(3) or a method equivalent thereto.

1H-NMR (DMSO-d6): δ 3.18 (3H, s), 3.72 (3H, s), 3.03-4.11 (1H, m), 4.41-4.82 (4H, m), 7.81 (1H, d, J=3.5 Hz), 7.85 (1H, d, J=3.5 Hz), 8.09 (1H, d, J=11.4 Hz), 9.80 (1H, s), 14.75 (1H, brs)

Example 246

Compound 246

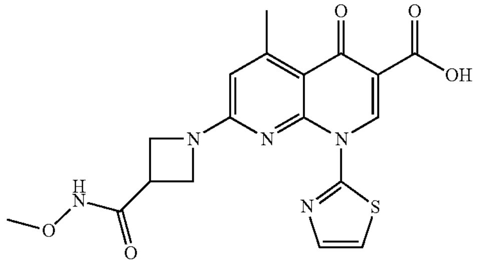

7-[3-(Methoxycarbamoyl)azetidin-1-yl]-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-methoxyazetidine-3-carboxamide hydrochloride obtained from O-methylhydroxylamine by the method described in Example 005-(1) and Example 001-(2) or a method equivalent thereto by the method described in Example 001-(3) or a method equivalent thereto.

1H-NMR (DMSO-d6): δ 2.78 (3H, s), 3.72 (3H, s), 3.76-3.83 (1H, m), 4.28-4.60 (4H, m), 6.57 (1H, s), 7.76 (1H, d, J=3.5 Hz), 7.84 (1H, d, J=3.5 Hz), 9.84 (1H, s), 15.34 (1H, brs)

Example 247

Compound 247

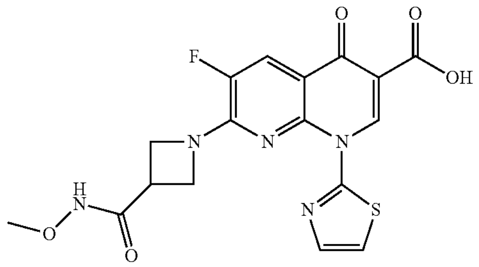

6-Fluoro-7-[3-(methoxycarbamoyl)azetidin-1-yl]-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-methoxyazetidine-3-carboxamide hydrochloride obtained in Example 246 by the method described in Example 001-(3) or a method equivalent thereto.

1H-NMR (DMSO-d6): δ 3.73 (3H, s), 3.79-3.87 (1H, m), 4.42-4.80 (4H, m), 7.79 (1H, d, J=3.5 Hz), 7.85 (1H, d, J=3.5 Hz), 8.11 (1H, d, J=11.4 Hz), 9.81 (1H, s), 14.73 (1H, brs)

Example 248

Compound 248

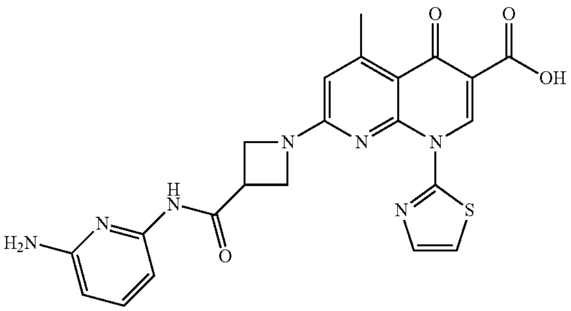

7-{3-[(6-Aminopyridin-2-yl)carbamoyl]azetidin-1-yl}-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-(6-aminopyridin-2-yl)azetidine-3-carboxamide trifluoroacetate obtained from pyridine-2,6-diamine by the method described in Example 005-(1) and Example 001-(2) or a method equivalent thereto by the method described in Example 002-(3) or a method equivalent thereto.

1H-NMR (DMSO-d6): δ 2.77 (3H, s), 3.92-4.00 (1H, m), 4.34-4.60 (4H, m), 6.53-6.58 (1H, m), 6.58 (1H, s), 6.64-6.71 (1H, m), 7.76 (1H, d, J=3.5 Hz), 7.84 (1H, d, J=3.5 Hz), 7.77-7.82 (1H, m), 9.82 (1H, s), 11.87 (1H, brs)

Example 249

Compound 249

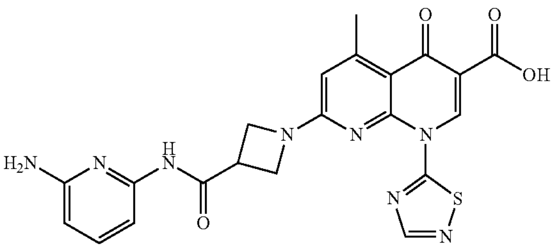

7-{3-[(6-Aminopyridin-2-yl)carbamoyl]azetidin-1-yl}-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-(6-aminopyridin-2-yl)azetidine-3-carboxamide trifluoroacetate obtained in Example 248 by the method described in Example 002-(3) or a method equivalent thereto.

1H-NMR (DMSO-d6): δ 2.79 (3H, s), 3.89-3.99 (1H, m), 4.29-4.72 (4H, s), 6.37-6.53 (2H, m), 6.65 (1H, s), 6.82 (1H, brs), 7.67 (1H, brs), 8.82 (1H, s), 9.75 (1H, s), 14.98 (1H, brs)

Example 250

Compound 250

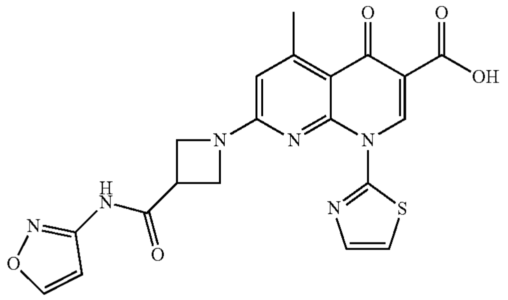

5-Methyl-7-{3-[(1,2-oxazol-3-yl)carbamoyl]azetidin-1-yl}-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-(1,2-oxazol-3-yl)azetidine-3-carboxamide trifluoroacetate obtained from 1,2-oxazol-3-amine by the method described in Example 005-(1) and Example 001-(2) or a method equivalent thereto by the method described in Example 002-(3) or a method equivalent thereto.

1H-NMR (DMSO-d6): δ 2.77 (3H, s), 3.82-3.91 (1H, m), 4.21-4.58 (4H, m), 6.56 (1H, s), 6.98 (1H, d, J=2.0 Hz), 7.75 (1H, d, J=3.5 Hz), 7.83 (1H, d, J=3.5 Hz), 8.82 (1H, d, J=2.0 Hz), 9.84 (1H, s), 11.32 (1H, brs), 15.37 (1H, brs)

Example 251

Compound 251

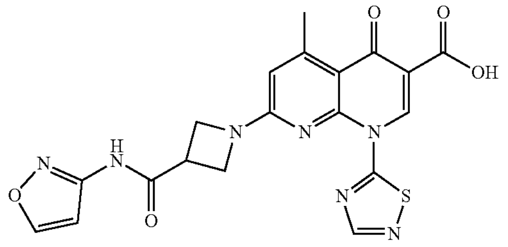

5-Methyl-7-{3-[(1,2-oxazol-3-yl)carbamoyl]azetidin-1-yl}-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-(1,2-oxazol-3-yl)azetidine-3-carboxamide trifluoroacetate obtained in Example 250 by the method described in Example 002-(3) or a method equivalent thereto.

1H-NMR (DMSO-d6): δ 2.77 (3H, s), 3.86-3.95 (1H, m), 4.26-4.71 (4H, m), 6.61 (1H, s), 6.98 (1H, s), 8.81-8.83 (2H, m), 9.74 (1H, s), 11.34 (1H, s), 15.06 (1H, brs)

Example 252

Compound 252

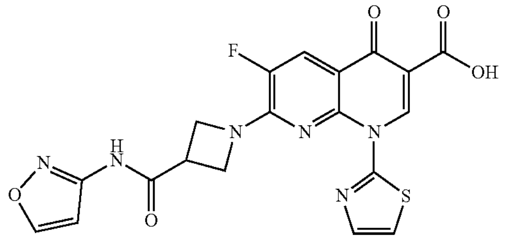

6-Fluoro-7-{3-[(1,2-oxazol-3-yl)carbamoyl]azetidin-1-yl}-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-(1,2-oxazol-3-yl)azetidine-3-carboxamide trifluoroacetate obtained in Example 250 by the method described in Example 002-(3) or a method equivalent thereto.

1H-NMR (DMSO-d6): δ 3.86-3.96 (1H, m), 4.44-4.90 (4H, m), 6.99 (1H, d, J=1.5 Hz), 7.80 (1H, d, J=3.5 Hz), 7.86 (1H, d, J=3.5 Hz), 8.12 (1H, d, J=11.5 Hz), 8.82 (1H, d, J=1.5 Hz), 9.82 (1H, s), 11.31 (1H, s), 14.77 (1H, brs)

Example 253

Compound 253

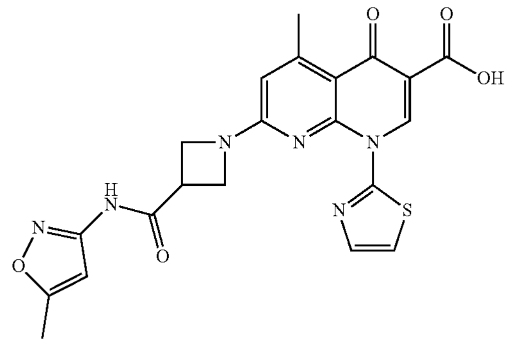

5-Methyl-7-{3-[(5-methyl-1,2-oxazol-3-yl)carbamoyl]azetidin-1-yl}-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-(5-methyl-1,2-oxazol-3-yl)azetidine-3-carboxamide trifluoroacetate obtained from 5-methyl-1,2-oxazol-3-amine by the method described in Example 005-(1) and Example 001-(2) or a method equivalent thereto by the method described in Example 002-(3) or a method equivalent thereto.

1H-NMR (DMSO-d6): δ 2.38 (3H, s), 2.78 (3H, s), 3.80-3.89 (1H, m), 4.28-4.56 (4H, m), 6.56 (1H, s), 6.67 (1H, s), 7.75 (1H, d, J=3.5 Hz), 7.83 (1H, d, J=3.5 Hz), 9.84 (1H, s), 11.17 (1H, brs), 15.37 (1H, brs)

Example 254

Compound 254

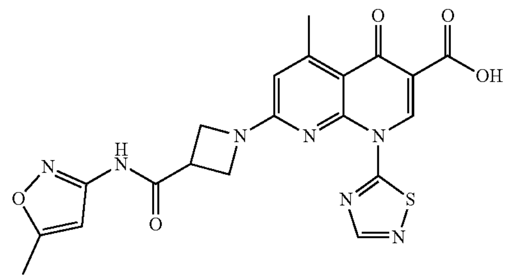

5-Methyl-7-{3-[(5-methyl-1,2-oxazol-3-yl)carbamoyl]azetidin-1-yl}-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-(5-methyl-1,2-oxazol-3-yl)azetidine-3-carboxamide trifluoroacetate obtained in Example 253 by the method described in Example 002-(3) or a method equivalent thereto.

1H-NMR (DMSO-d6): δ 2.39 (3H, s), 2.79 (3H, s), 3.83-3.93 (1H, m), 4.27-4.70 (4H, m), 6.62 (1H, s), 6.68 (1H, s), 8.82 (1H, s), 9.76 (1H, s), 11.19 (1H, s), 15.05 (1H, brs)

Example 255

Compound 255

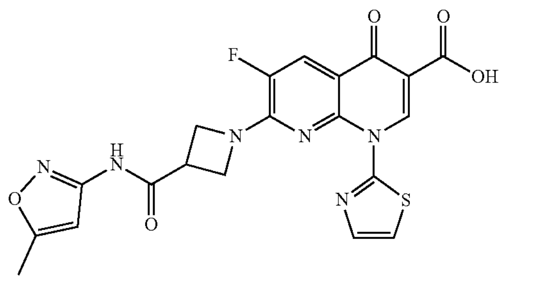

6-Fluoro-7-{3-[(5-methyl-1,2-oxazol-3-yl)carbamoyl]azetidin-1-yl}-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-(5-methyl-1,2-oxazol-3-yl)azetidine-3-carboxamide trifluoroacetate obtained in Example 253 by the method described in Example 002-(3) or a method equivalent thereto.

1H-NMR (DMSO-d6): δ 2.39 (3H, s), 3.85-3.94 (1H, m), 4.43-4.93 (4H, m), 6.68 (1H, s), 7.78-7.81 (1H, m), 7.85-7.87 (1H, m), 8.12 (1H, d, J=11.5 Hz), 9.82 (1H, s), 11.16 (1H, s)

Example 256

Compound 256

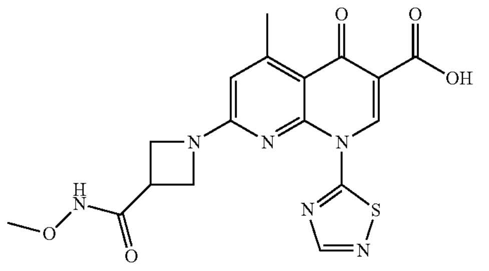

7-[3-(Methoxycarbamoyl)azetidin-1-yl]-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-methoxyazetidine-3-carboxamide hydrochloride obtained in Example 246 by the method described in Example 001-(3) or a method equivalent thereto.

Property: pale orange solid;

Melting point: 236-240° C. (decomposition)

Example 257

Compound 257

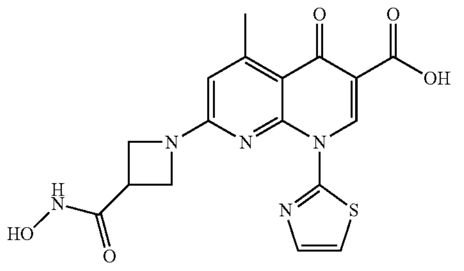

7-[3-(Hydroxycarbamoyl)azetidin-1-yl]-5-methyl-4-oxo-1-(1,3-thiazol-2-yl)-1,4-dihydro-1,8-naphthyridine-3-carboxylic acid (1) A suspension of tert-butyl 3-[(benzyloxy)carbamoyl]azetidine-1-carboxylate (200 mg) obtained from O-benzylhydroxylamine by the method described in Example 005-(1) or a method equivalent thereto, and palladium carbon (10 mg) in methanol (6 mL) was hydrogenated at room temperature for 2 days. The catalyst was filtered off, and the filtrate was then concentrated to obtain crude tert-butyl 3-(hydroxycarbamoyl)azetidine-1-carboxylate.

(2) The title compound was obtained by the method described in Example 001-(3) or a method equivalent thereto using N-hydroxyazetidine-3-carboxamide hydrochloride obtained by the method described in Example 001-(2) or a method equivalent thereto from crude tert-butyl 3-(hydroxycarbamoyl)azetidine-1-carboxylate obtained in the preceding section, and 7-chloro-5-methyl-4-oxo-1-(1,3-thiazol-2-yl)-1,4-dihydro-1,8-naphthyridine-3-carboxylic acid obtained in Reference Example 001-(2).

1H-NMR (DMSO-d6): δ 2.73 (3H, s), 3.38-3.79 (1H, m), 4.27-4.49 (4H, m), 6.17 (1H, d, J=8.4 Hz), 6.35 (1H, s), 7.57 (1H, d, J=3.5 Hz), 7.71 (1H, d, J=3.5 Hz), 8.94 (1H, d, J=8.4 Hz), 9.86 (1H, s), 15.35 (1H, brs)

Example 258

Compound 258

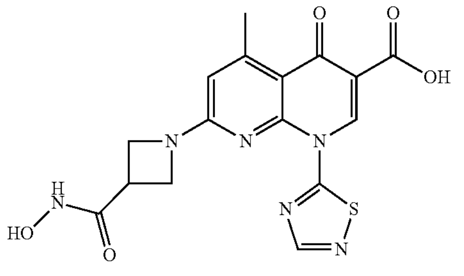

7-[3-(Hydroxycarbamoyl)azetidin-1-yl]-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-hydroxyazetidine-3-carboxamide hydrochloride obtained in Example 257-(2) by the method described in Example 001-(3) or a method equivalent thereto.

Property: pale yellow solid;

Melting point: 145-148° C.

Example 259

Compound 259

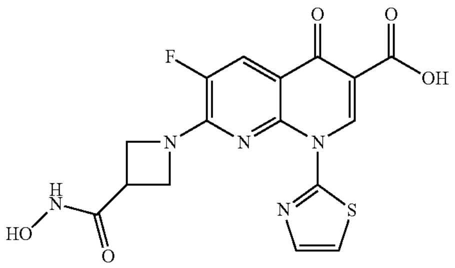

6-Fluoro-7-[3-(hydroxycarbamoyl)azetidin-1-yl]-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-hydroxyazetidine-3-carboxamide hydrochloride obtained in Example 257-(2) by the method described in Example 001-(3) or a method equivalent thereto.

1H-NMR (DMSO-d6): δ 3.78-3.87 (1H, m), 4.45-4.80 (4H, m), 7.80 (1H, d, J=3.5 Hz), 7.85 (1H, d, J=3.5 Hz), 8.10 (1H, d, J=11.4 Hz), 9.80 (1H, s), 14.73 (1H, brs)

Example 260

Compound 260

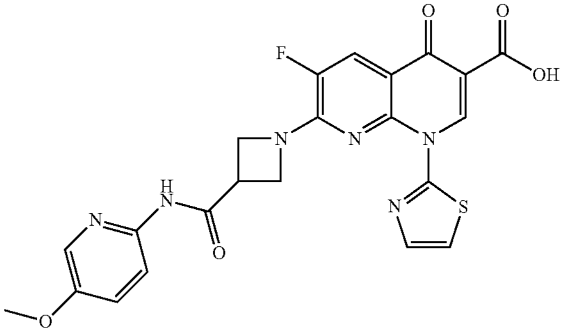

6-Fluoro-7-{3-[(5-methoxypyridin-2-yl)carbamoyl]azetidin-1-yl}-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-(5-methoxypyridin-2-yl)azetidine-3-carboxamide hydrochloride obtained in Example 017 by the method described in Example 001-(3) or a method equivalent thereto.

1H-NMR (DMSO-d6): δ 3.81 (3H, s), 3.91-3.99 (1H, m), 4.43-4.84 (4H, m), 7.45 (1H, dd, J=9.1, 3.1 Hz), 7.77 (1H, d, J=3.5 Hz), 7.85 (1H, d, J=3.5 Hz), 8.05-8.10 (3H, m), 9.79 (1H, s), 10.63 (1H, s), 14.73 (1H, brs)

Example 261

Compound 261

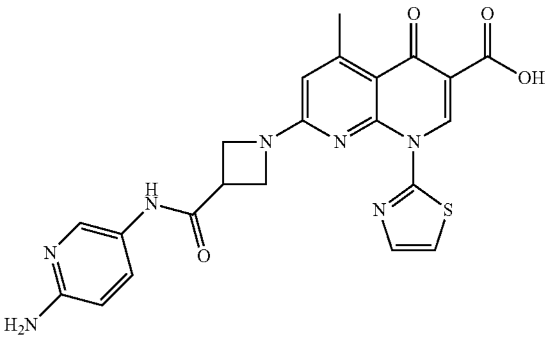

7-{3-[(6-Aminopyridin-3-yl)carbamoyl]azetidin-1-yl}-5-methyl-4-oxo-1-(1,3-thiazol-2-yl)-1,4-dihydro-1,8-naphthyridine-3-carboxylic acid The title compound was obtained by the method described in Example 002-(3) or a method equivalent thereto using N-(6-aminopyridin-3-yl)azetidine-3-carboxamide trifluoroacetate obtained from pyridine-2,5-diamine by the methods described in Examples 005-(1) and 001-(2) or methods equivalent thereto, and 7-chloro-5-methyl-4-oxo-1-(1,3-thiazol-2-yl)-1,4-dihydro-1,8-naphthyridine-3-carboxylic acid obtained in Reference Example 001-(2).

1H-NMR (DMSO-d6): δ 2.79 (3H, s), 3.79-3.87 (1H, m), 4.30-4.59 (4H, m), 6.58 (1H, s), 7.03 (1H, d, J=9.5 Hz), 7.76 (1H, d, J=3.5 Hz), 7.79 (2H, brs), 7.85 (1H, d, J=3.5 Hz), 7.94 (1H, dd, J=9.5, 2.5 Hz), 8.45 (1H, d, J=2.5 Hz), 9.86 (1H, s), 10.66 (1H, brs), 15.33 (1H, brs)

Example 262

Compound 262

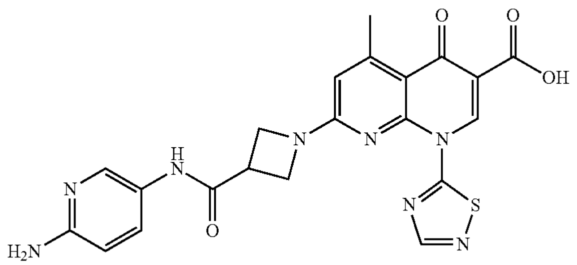

7-{3-[(6-Aminopyridin-3-yl)carbamoyl]azetidin-1-yl}-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-(6-aminopyridin-3-yl)azetidine-3-carboxamide trifluoroacetate obtained in Example 261 by the method described in Example 002-(3) or a method equivalent thereto.

1H-NMR (DMSO-d6): δ 2.79 (3H, s), 3.74-3.90 (1H, m), 4.17-4.74 (4H, m), 6.63 (1H, d, J=1.0 Hz), 8.46 (1H, dd, J=9.5, 2.0 Hz), 7.92-7.96 (1H, m), 8.46 (1H, d, J=2.5 Hz), 9.76 (1H, s), 10.60 (1H, s), 13.35 (1H, brs)

Example 263

Compound 263

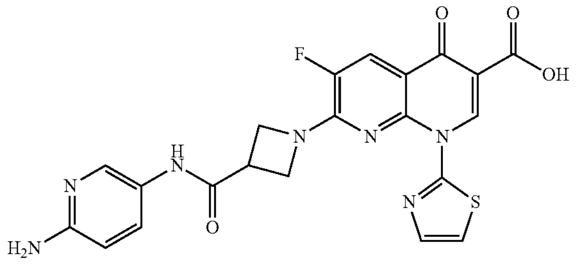

7-{3-[(6-Aminopyridin-3-yl)carbamoyl]azetidin-1-yl}-6-fluoro-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-(6-aminopyridin-3-yl)azetidine-3-carboxamide trifluoroacetate obtained in Example 261 by the method described in Example 002-(3) or a method equivalent thereto.

1H-NMR (DMSO-d6): δ 3.83-3.90 (1H, m), 4.45-4.87 (4H, m), 7.01 (1H, d, J=9.5 Hz), 7.77-7.81 (3H, m), 7.87 (1H, d, J=3.5 Hz), 7.93 (1H, dd, J=9.5, 2.5 Hz), 8.14 (1H, d, J=11.5 Hz), 8.44 (1H, d, J=2.0 Hz), 9.83 (1H, s), 10.61 (1H, s), 13.41 (1H, brs)

Example 264

Compound 264

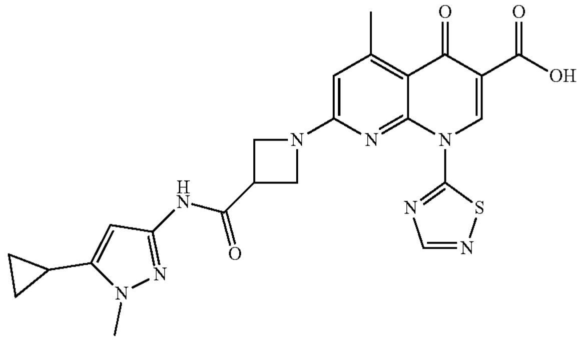

7-{3-[(5-Cyclopropyl-1-methyl-1H-pyrazol-3-yl)carbamoyl]azetidin-1-yl}-5-methyl-4-oxo-1-(1,2,4-thiadiazol-5-yl)-1,4-dihydro-1,8-naphthyridine-3-carboxylic acid The title compound was obtained by the method described in Example 008 or a method equivalent thereto using N-(5-cyclopropyl-1-methyl-1H-pyrazol-3-yl)azetidine-3-carboxamide hydrochloride obtained from 5-cyclopropyl-1-methyl-1H-pyrazol-3-amine by the methods described in Examples 007-(1) and 001-(2) or methods equivalent thereto, and 7-chloro-5-methyl-4-oxo-1-(1,2,4-thiadiazol-5-yl)-1,4-dihydro-1,8-naphthyridine-3-carboxylic acid obtained in Reference Example 002-(2).

1H-NMR (DMSO-d6): δ 0.55-0.60 (2H, m), 0.91-0.96 (2H, m), 1.81-1.89 (1H, m), 2.77 (3H, s), 3.73 (3H, s), 3.76-3.84 (1H, m), 4.27-4.69 (4H, m), 6.14 (1H, s), 6.61 (1H, a), 8.81 (1H, s), 9.76 (1H, s), 10.57 (1H, s), 15.08 (1H, brs)

Example 265

Compound 265

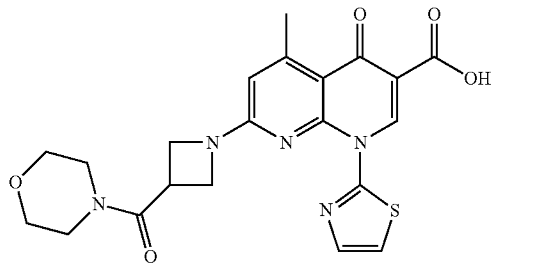

5-Methyl-7-[3-(morpholine-4-carbonyl)azetidin-1-yl]-4-oxo-1-(1,3-thiazol-2-yl)-1,4-dihydro-1,8-naphthyridine-3-carboxylic acid The title compound was obtained by the method described in Example 001-(3) or a method equivalent thereto using 4-(azetidine-3-carbonyl)morpholine hydrochloride obtained from morpholine by the method described in Examples 005-(1) and 001-(2) or methods equivalent thereto, and 7-chloro-5-methyl-4-oxo-1-(1,3-thiazol-2-yl)-1,4-dihydro-1,8-naphthyridine-3-carboxylic acid obtained in Reference Example 001-(2).

1H-NMR (DMSO-d6): δ 2.75 (3H, s), 3.35-3.65 (8H, m), 3.94-4.03 (1H, m), 4.30-4.55 (4H, m), 6.51 (1H, s), 7.76 (1H, d, J=3.5 Hz), 7.83 (1H, d, J=3.5 Hz), 9.81 (1H, s)

Example 266

Compound 266

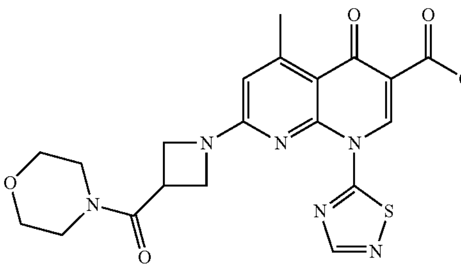

5-Methyl-7-[3-(morpholine-4-carbonyl)azetidin-1-yl]-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and 4-(azetidine-3-carbonyl)morpholine hydrochloride obtained in Example 265 by the method described in Example 001-(3) or a method equivalent thereto.

1H-NMR (DMSO-d6): δ 2.77 (3H, s), 3.39-3.67 (8H, m), 3.97-4.06 (1H, m), 4.37-4.73 (4H, m), 6.60 (1H, s), 8.82 (1H, s), 9.74 (1H, s)

Example 267

Compound 267

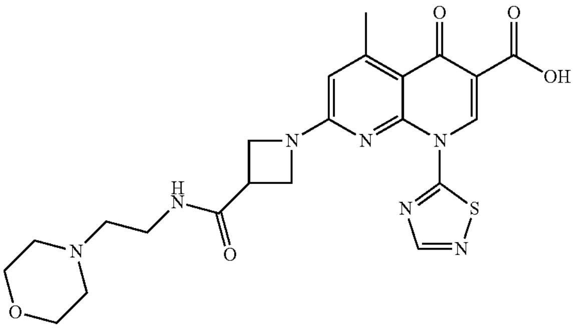

5-Methyl-7-(3-{[2-(morpholin-4-yl)ethyl]carbamoyl}azetidin-1-yl)-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-[2-(morpholin-4-yl)ethyl]azetidine-3-carboxamide hydrochloride obtained from 2-(morpholin-4-yl)ethan-1-amine by the method described in Example 007-(1) and Example 001-(2) or a method equivalent thereto by the method described in Example 008 or a method equivalent thereto.

1H-NMR (DMSO-d6): δ 2.32-2.43 (6H, m), 2.77 (3H, s), 3.21-3.27 (2H, m), 3.52-3.58 (4H, m), 3.59-3.66 (1H, m), 4.22-4.63 (4H, m), 6.58 (1H, brs), 8.08-8.14 (1H, m), 8.81 (1H, s), 9.73 (1H, s), 15.07 (1H, brs)

Example 268

Compound 268

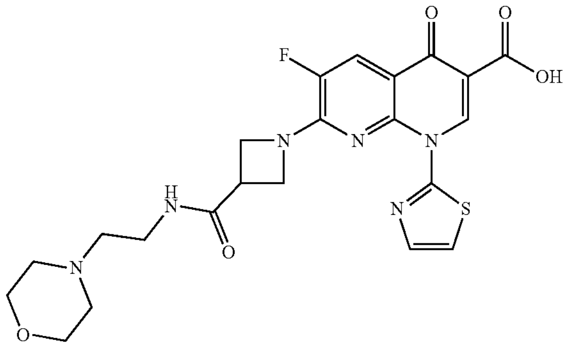

6-Fluoro-7-(3-{[2-(morpholin-4-yl)ethyl]carbamoyl}azetidin-1-yl)-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-[2-(morpholin-4-yl)ethyl]azetidine-3-carboxamide hydrochloride obtained in Example 267 by the method described in Example 008 or a method equivalent thereto.

1H-NMR (DMSO-d6): δ 2.32-2.41 (6H, m), 3.21-3.27 (2H, m), 3.52-3.58 (4H, m), 3.59-3.66 (1H, m), 4.40-4.84 (4H, m), 7.79 (1H, d, J=3.5 Hz), 7.86 (1H, d, J=3.5 Hz), 8.06-8.10 (1H, m), 8.11 (1H, d, J=11.5 Hz), 9.83 (1H, s), 14.80 (1H, brs)

Example 269

Compound 269

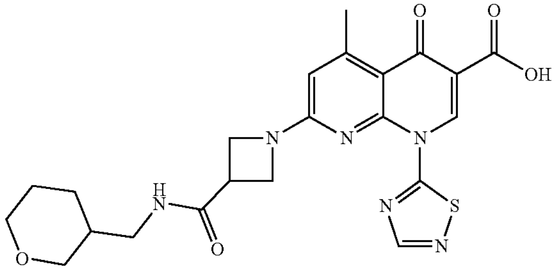

5-Methyl-7-{3-[(oxan-3-ylmethyl)carbamoyl]azetidin-1-yl}-4-oxo-1-(1,2,4-thiadiazol-5-yl)-1,4-dihydro-1,8-naphthyridine-3-carboxylic acid The title compound was obtained by the method described in Example 008 or a method equivalent thereto using N-(oxan-3-ylmethyl)azetidine-3-carboxamide hydrochloride obtained from oxan-3-ylmethylamine by the methods described in Examples 007-(1) and 001-(2) or methods equivalent thereto, and 7-chloro-5-methyl-4-oxo-1-(1,2,4-thiadiazol-5-yl)-1,4-dihydro-1,8-naphthyridine-3-carboxylic acid obtained in Reference Example 002-(2).

1H-NMR (DMSO-d6): δ 1.16-1.25 (1H, m), 1.39-1.50 (1H, m), 1.51-1.59 (1H, m), 1.63-1.71 (1H, m), 1.71-1.78 (1H, m), 2.77 (3H, s), 2.96-3.04 (2H, m), 3.05-3.10 (1H, m), 3.56-3.65 (1H, m), 3.67-3.78 (2H, m), 4.19-4.65 (4H, m), 6.58 (1H, brs), 8.16 (1H, t, J=5.5 Hz), 8.81 (1H, s), 9.74 (1H, s), 15.07 (1H, brs)

Example 270

Compound 270

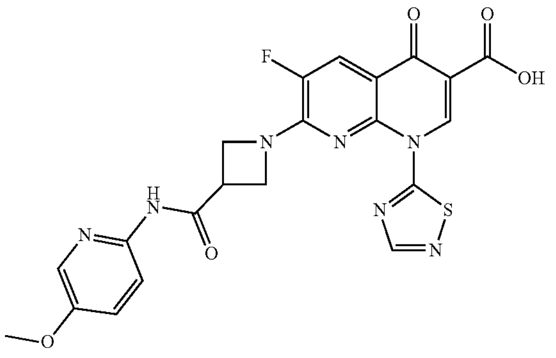

6-Fluoro-7-{3-[(5-methoxypyridin-2-yl)carbamoyl]azetidin-1-yl}-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and N-(5-methoxypyridin-2-yl)azetidine-3-carboxamide hydrochloride obtained in Example 017 by the method described in Example 001-(3) or a method equivalent thereto.

1H-NMR (DMSO-d6): δ 3.81 (3H, s), 3.93-4.01 (1H, m), 4.57-4.90 (4H, m), 7.46 (1H, dd, J=9.0, 3.1 Hz), 8.06 (1H, d, J=3.1 Hz), 8.10 (1H, d, J=9.0 Hz), 8.15 (1H, d, J=11.4 Hz), 8.85 (1H, s), 9.74 (1H, s), 10.65 (1H, a), 14.46 (1H, brs)

Example 271

Compound 271

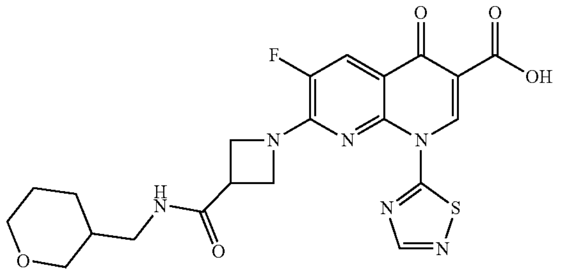

6-Fluoro-7-{3-[(oxan-3-ylmethyl)carbamoyl]azetidin-1-yl}-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) N-(oxan-3-ylmethyl)azetidine-3-carboxamide hydrochloride obtained in Example 269 by the method described in Example 008 or a method equivalent thereto.

1H-NMR (DMSO-d6): δ 1.16-1.26 (1H, m), 1.39-1.49 (1H, m), 1.53-1.60 (1H, m), 1.63-1.72 (1H, m), 1.72-1.79 (1H, m), 2.95-3.05 (2H, m), 3.05-3.11 (1H, m), 3.60-3.67 (1H, m), 3.67-3.78 (2H, m), 4.46-4.81 (4H, m), 8.14 (1H, d, J=11.5 Hz), 8.15 (1H, t, J=5.5 Hz), 8.84 (1H, s), 9.74 (1H, s), 14.47 (1H, brs)

Example 272

Compound 272

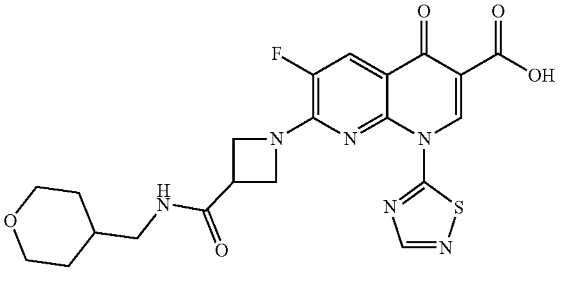

6-Fluoro-7-{3-[(oxan-4-ylmethyl)carbamoyl]azetidin-1-yl}-4-oxo-1-(1,2,4-thiadiazol-5-yl)-1,4-dihydro-1,8-naphthyridine-3-carboxylic acid The title compound was obtained by the method described in Example 008 or a method equivalent thereto using N-(oxan-4-ylmethyl)azetidine-3-carboxamide hydrochloride obtained from oxan-4-ylmethylamine by the methods described in Examples 007-(1) and 001-(2) or methods equivalent thereto, and 7-chloro-6-fluoro-4-oxo-1-(1,2,4-thiadiazol-5-yl)-1,4-dihydro-1,8-naphthyridine-3-carboxylic acid obtained in Reference Example 004-(2).

1H-NMR (DMSO-d6): δ 1.10-1.21 (2H, m), 1.50-1.60 (2H, m), 1.62-1.71 (1H, m), 3.03 (2H, t, J=6.0 Hz), 3.25 (2H, dt, J=12.0, 2.0 Hz), 3.61-3.71 (1H, m), 3.80-3.89 (2H, m), 4.47-4.81 (4H, m), 8.14 (1H, d, J=11.5 Hz), 8.15 (1H, t, J=5.5 Hz), 8.85 (1H, s), 9.75 (1H, s), 14.48 (1H, brs)

Example 273

Compound 273

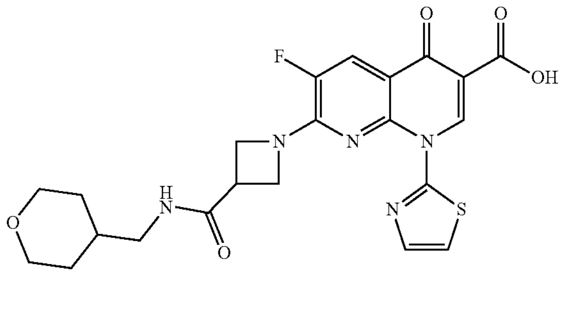

6-Fluoro-7-{3-[(oxan-4-ylmethyl)carbamoyl]azetidin-1-yl}-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) N-(oxan-4-ylmethyl)azetidine-3-carboxamide hydrochloride obtained in Example 272 by the method described in Example 008 or a method equivalent thereto.

1H-NMR (DMSO-d6): δ 1.09-1.23 (2H, m), 1.50-1.60 (2H, m), 1.60-1.71 (1H, m), 2.99-3.06 (2H, m), 3.25 (2H, dt, J=12.0, 2.0 Hz), 3.58-3.69 (1H, m), 3.80-3.89 (2H, m), 4.40-4.81 (4H, m), 7.79 (1H, d, J=3.5 Hz), 7.86 (1H, J=3.5 Hz), 8.10 (1H, d, J=11.5 Hz), 8.14 (1H, t, J=5.5 Hz), 9.83 (1H, s), 14.79 (1H, s)

Example 274

Compound 274

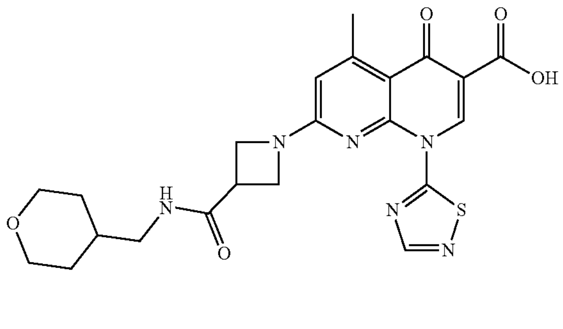

5-Methyl-7-{3-[(oxan-4-ylmethyl)carbamoyl]azetidin-1-yl}-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) N-(oxan-4-ylmethyl)azetidine-3-carboxamide hydrochloride obtained in Example 272 by the method described in Example 008 or a method equivalent thereto.

1H-NMR (DMSO-d6): δ 1.11-1.22 (2H, m), 1.51-1.61 (2H, m), 1.61-1.73 (1H, m), 2.75 (3H, s), 2.96-3.06 (2H, m), 3.25 (2H, dt, J=12.0, 2.0 Hz), 3.58-3.67 (1H, m), 3.79-3.88 (2H, m), 4.21-4.61 (4H, m), 6.56 (1H, s), 8.17 (1H, d, J=5.5 Hz), 8.80 (1H, s), 9.71 (1H, s), 15.06 (1H, s)

Example 275

Compound 275

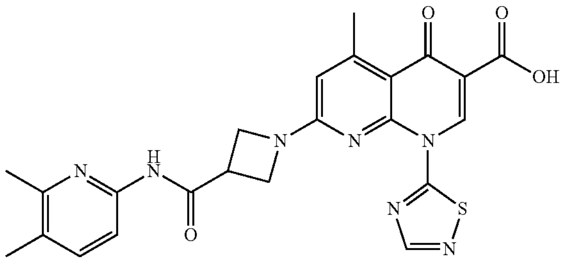

7-{3-[(5,6-Dimethylpyridin-2-yl)carbamoyl]azetidin-1-yl}-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-(5,6-dimethylpyridin-2-yl)azetidine-3-carboxamide hydrochloride obtained in Example 007-(2) by the method described in Example 001-(3) or a method equivalent thereto.

1H-NMR (DMSO-d6): δ 2.21 (3H, s), 2.38 (3H, s), 2.78 (3H, s), 3.89-3.98 (4H, m), 4.36-4.72 (4H, m), 6.62 (1H, s), 7.52 (1H, d, J=8.0 Hz), 7.87 (1H, d, J=7.5 Hz), 8.82 (1H, d, J=2.0 Hz), 9.75 (1H, s), 10.62 (1H, s), 15.07 (1H, brs)

Example 276

Compound 276

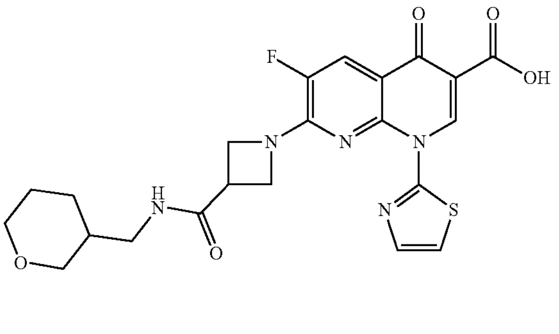

6-Fluoro-7-{3-[(oxan-3-ylmethyl)carbamoyl]azetidin-1-yl}-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) N-(oxan-3-ylmethyl)azetidine-3-carboxamide hydrochloride obtained in Example 269 by the method described in Example 008 or a method equivalent thereto.

1H-NMR (DMSO-d6): δ 1.15-1.25 (1H, m), 1.39-1.49 (1H, m), 1.53-1.60 (1H, m), 1.62-1.70 (1H, m), 1.70-1.79 (1H, m), 2.92-3.05 (2H, m), 3.05-3.11 (1H, m), 3.56-3.67 (1H, m), 3.67-3.79 (2H, m), 4.37-4.80 (4H, m), 7.78 (1H, d, J=3.5 Hz), 7.85 (1H, d, J=3.5 Hz), 8.09 (1H, d, J=11.5 Hz), 8.14 (1H, t, J=5.5 Hz), 9.81 (1H, s), 14.79 (1H, s)

Example 277

Compound 277

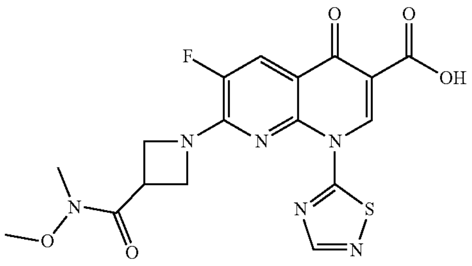

6-Fluoro-7-{3-[methoxy(methyl)carbamoyl]azetidin-1-yl}-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and N-methoxy-N-methylazetidine-3-carboxamide hydrochloride obtained in Example 241 by the method described in Example 001-(3) or a method equivalent thereto.

1H-NMR (DMSO-d6): δ 3.19 (3H, s), 3.74 (3H, S), 4.05-4.14 (1H, m), 4.59-4.86 (4H, m), 8.15 (1H, d, J=11.4 Hz), 8.85 (1H, s), 9.74 (1H, s), 14.45 (1H, brs)

Example 278

Compound 278

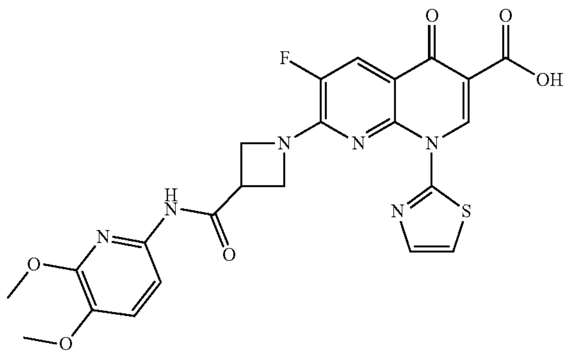

7-{3-[(5,6-Dimethoxypyridin-2-yl)carbamoyl]azetidin-1-yl}-6-fluoro-4-oxo-1-(1,3-thiazol-2-yl)-1,4-dihydro-1,8-naphthyridine-3-carboxylic acid The title compound was obtained by the method described in Example 001-(3) or a method equivalent thereto using N-(5,6-dimethoxypyridin-2-yl)azetidine-3-carboxamide hydrochloride obtained from 5,6-dimethoxypyridin-2-amine by the methods described in Examples 007-(1) and 001-(2) or methods equivalent thereto, and 7-chloro-6-fluoro-4-oxo-1-(1,3-thiazol-2-yl)-1,4-dihydro-1,8-naphthyridine-3-carboxylic acid obtained in Reference Example 003-(2).

1H-NMR (DMSO-d6): δ 3.75 (3H, s), 3.88 (3H, s), 3.92-4.00 (1H, m), 4.40-4.85 (4H, m), 7.34 (1H, d, J=8.5 Hz), 7.66 (1H, d, J=8.5 Hz), 7.79 (1H, d, J=3.5 Hz), 7.86 (1H, d, J=3.5 Hz), 8.12 (1H, d, J=11.0 Hz), 9.82 (1H, s), 10.34 (1H, s), 14.79 (1H, brs)

Example 279

Compound 279

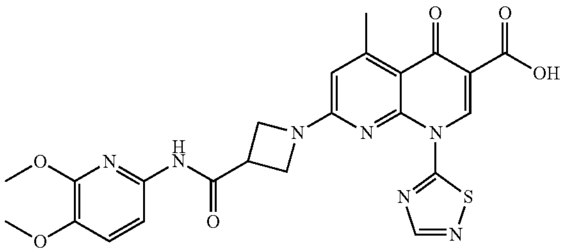

7-{3-[(5,6-Dimethoxypyridin-2-yl)carbamoyl]azetidin-1-yl}-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-(5,6-dimethoxypyridin-2-yl)azetidine-3-carboxamide hydrochloride obtained in Example 278 by the method described in Example 001-(3) or a method equivalent thereto.

1H-NMR (DMSO-d6): δ 2.77 (3H, s), 3.75 (3H, s), 3.91-3.99 (4H, m), 4.36-4.70 (4H, m), 6.60 (1H, s), 7.33 (1H, d, J=8.5 Hz), 7.66 (1H, d, J=8.5 Hz), 8.81 (1H, s), 9.72 (1H, s), 10.37 (1H, s), 15.02 (1H, brs)

Example 280

Compound 280

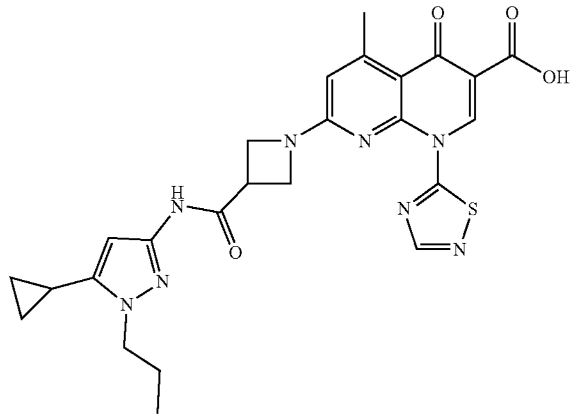

7-{3-[(5-Cyclopropyl-1-propyl-1H-pyrazol-3-yl) carbamoyl]azetidin-1-yl}-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-(5-cyclopropyl-1-propyl-1H-pyrazol-3-yl)azetidine-3-carboxamide hydrochloride obtained from 5-cyclopropyl-1-propyl-1H-pyrazol-3-amine by the method described in Example 007-(1) and Example 001-(2) or a method equivalent thereto by the method described in Example 008 or a method equivalent thereto.

1H-NMR (DMSO-d6): δ 0.56-0.61 (2H, m), 0.85 (3H, t, J=7.5 Hz), 0.91-0.97 (2H, m), 1.72-1.81 (2H, m), 1.84-1.91 (1H, m), 2.78 (3H, s), 3.75-3.84 (1H, m), 4.02 (2H, t, J=6.5 Hz), 4.21-4.69 (4H, m), 6.14 (1H, s), 6.59 (1H, brs), 8.80 (1H, s), 9.71 (1H, brs), 10.62 (1H, s), 15.07 (1H, brs)

Example 281

Compound 281

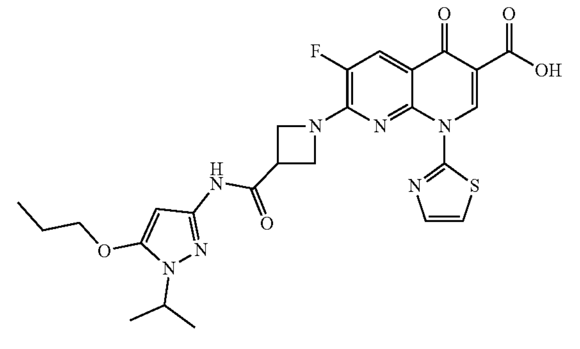

6-Fluoro-4-oxo-7-(3-{[1-(propan-2-yl)-5-propoxy-1H-pyrazol-3-yl]carbamoyl}azetidin-1-yl)-1-(1,3-thiazol-2-yl)-1,4-dihydro-1,8-naphthyridine-3-carboxylic acid The title compound was obtained by the method described in Example 008 or a method equivalent thereto using N-[1-(propan-2-yl)-5-propoxy-1H-pyrazol-3-yl]azetidine-3-carboxamide trifluoroacetate obtained by the methods described in Examples 007-(1) and 001-(2) or methods equivalent thereto using 1-(propan-2-yl)-5-propoxy-1H-pyrazol-3-amine obtained by the methods described in Examples 009-(1) to 009-(3) or methods equivalent thereto, and 7-chloro-6-fluoro-4-oxo-1-(1,3-thiazol-2-yl)-1,4-dihydro-1,8-naphthyridine-3-carboxylic acid obtained in Reference Example 003-(2).

1H-NMR (DMSO-d6): δ 0.96 (3H, t, J=7.5 Hz), 1.28 (6H, d, J=6.5 Hz), 1.68-1.76 (2H, m), 3.76-3.85 (1H, m), 4.01 (2H, t, J=6.5 Hz), 4.39 (1H, q, J=6.5 Hz), 4.43-4.79 (4H, m), 7.78 (1H, d, J=3.5 Hz), 7.86 (1H, d, J=3.5 Hz), 8.12 (1H, d, J=11.5 Hz), 9.83 (1H, s), 10.64 (1H, s), 14.80 (1H, s)

Example 282

Compound 282

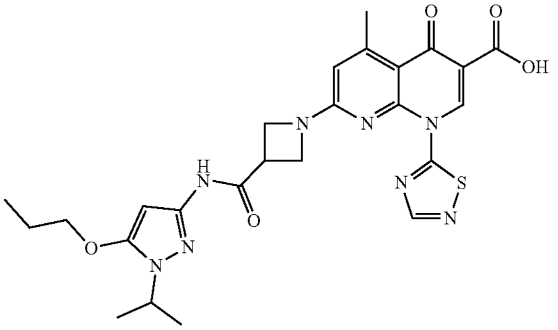

5-Methyl-4-oxo-7-(3-{[1-(propan-2-yl)-5-propoxy-H-pyrazol-3-yl]carbamoyl}azetidin-1-yl)-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-[1-(propan-2-yl)-5-propoxy-1H-pyrazol-3-yl]azetidine-3-carboxamide trifluoroacetate obtained in Example 281 by the method described in Example 008 or a method equivalent thereto.

1H-NMR (DMSO-d6): δ 0.95 (3H, t, J=7.5 Hz), 1.29 (6H, d, J=6.5 Hz), 1.66-1.77 (2H, m), 2.78 (3H, s), 3.75-3.84 (1H, m), 4.01 (2H, t, J=6.5 Hz), 4.29-4.69 (5H, m), 5.98 (1H, s), 6.61 (1H, brs), 8.81 (1H, s), 9.75 (1H, s), 10.66 (1H, s), 15.09 (1H, brs)

Example 283

Compound 283

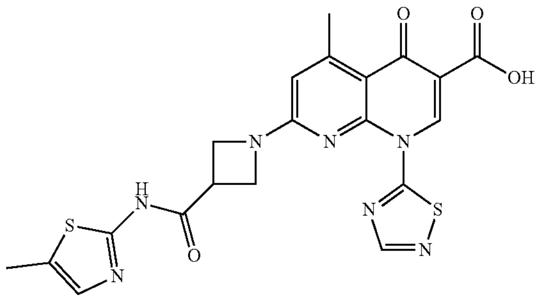

5-Methyl-7-{3-[(5-methyl-1,3-thiazol-2-yl)carbamoyl]azetidin-1-yl}-4-oxo-1-(1,2,4-thiadiazol-5-yl)-1,4-dihydro-1,8-naphthyridine-3-carboxylic acid The title compound was obtained by the method described in Example 008 or a method equivalent thereto using N-(5-methyl-1,3-thiazol-2-yl)azetidine-3-carboxamide hydrochloride obtained from 5-methyl-1,3-thiazol-2-amine by the methods described in Examples 007-(1) and 001-(2) or methods equivalent thereto, and 7-chloro-5-methyl-4-oxo-1-(1,2,4-thiadiazol-5-yl)-1,4-dihydro-1,8-naphthyridine-3-carboxylic acid obtained in Reference Example 002-(2).

1H-NMR (DMSO-d6): δ 2.35 (3H, s), 2.78 (3H, s), 3.89-3.98 (1H, m), 4.29-4.75 (4H, m), 6.63 (1H, s), 7.16 (1H, s), 8.82 (1H, s), 9.75 (1H, s), 12.19 (1H, s), 15.06 (1H, brs)

Example 284

Compound 284

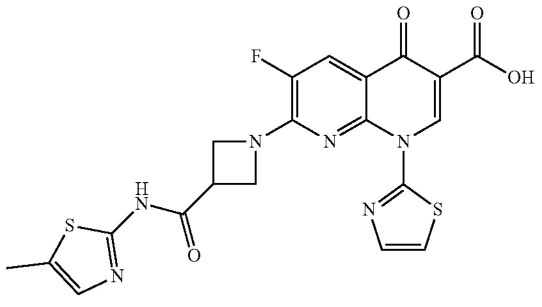

6-Fluoro-7-{3-[(5-methyl-1,3-thiazol-2-yl)carbamoyl]azetidin-1-yl}-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-(5-methyl-1,3-thiazol-2-yl)azetidine-3-carboxamide hydrochloride obtained in Example 283 by the method described in Example 008 or a method equivalent thereto.

1H-NMR (DMSO-d6): δ 2.36 (3H, s), 3.85-4.04 (1H, m), 4.43-4.89 (4H, m), 7.15 (1H, s), 7.78 (1H, d, J=3.5 Hz), 7.86 (1H, d, J=3.5 Hz), 8.13 (1H, d, J=11.5 Hz), 9.83 (1H, s), 10.16 (1H, brs), 14.77 (1H, brs)

Example 285

Compound 285

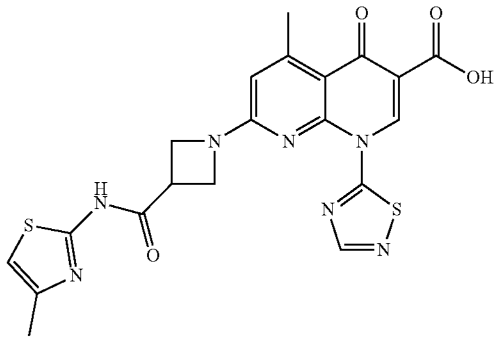

5-Methyl-7-{3-[(4-methyl-1,3-thiazol-2-yl)carbamoyl]azetidin-1-yl}-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-(4-methyl-1,3-thiazol-2-yl)azetidine-3-carboxamide hydrochloride obtained from 4-methyl-1,3-thiazol-2-amine by the method described in Example 007-(1) and Example 001-(2) or a method equivalent thereto by the method described in Example 008 or a method equivalent thereto.

1H-NMR (DMSO-d6): δ 2.27 (3H, s), 2.78 (3H, s), 3.87-3.98 (1H, m), 4.35-4.72 (4H, m), 6.62 (1H, s), 6.79 (1H, s), 8.82 (1H, s), 9.76 (1H, s), 12.31 (1H, s), 15.06 (1H, brs)

Example 286

Compound 286

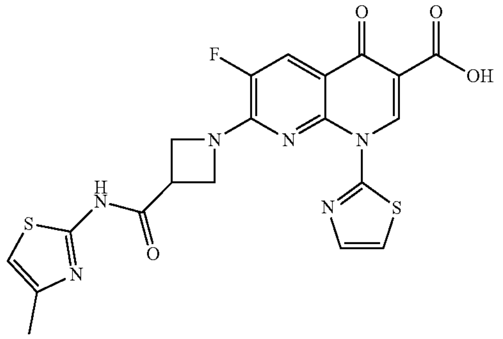

6-Fluoro-7-{3-[(4-methyl-1,3-thiazol-2-yl)carbamoyl]azetidin-1-yl}-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-(4-methyl-1,3-thiazol-2-yl)azetidine-3-carboxamide hydrochloride obtained in Example 285 by the method described in Example 008 or a method equivalent thereto.

1H-NMR (DMSO-d6): δ 2.26 (3H, s), 3.86-4.02 (1H, m), 4.37-4.96 (4H, m), 6.79 (1H, s), 7.78 (1H, brs), 7.85 (1H, brs), 8.12 (1H, d, J=11.5 Hz), 9.81 (1H, s), 10.28 (1H, brs), 14.77 (1H, brs)

Example 287

Compound 287

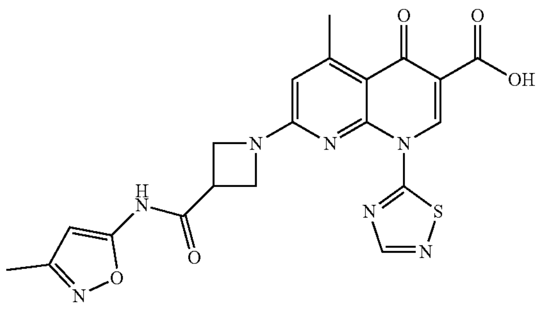

5-Methyl-7-{3-[(3-methyl-1,2-oxazol-5-yl)carbamoyl]azetidin-1-yl}-4-oxo-1-(1,2,4-thiadiazol-5-yl)-1,4-dihydro-1,8-naphthyridine-3-carboxylic acid The title compound was obtained by the method described in Example 001-(3) or a method equivalent thereto using N-(3-methyl-1,2-oxazol-5-yl)azetidine-3-carboxamide hydrochloride obtained from 3-methyl-1,2-oxazol-5-amine by the methods described in Examples 007-(1) and 001-(2) or methods equivalent thereto, and 7-chloro-5-methyl-4-oxo-1-(1,2,4-thiadiazol-5-yl)-1,4-dihydro-1,8-naphthyridine-3-carboxylic acid obtained in Reference Example 002-(2).

1H-NMR (DMSO-d6): δ 2.19 (3H, s), 2.76 (3H, s), 3.84-3.93 (1H, m), 4.31-4.70 (4H, m), 6.19 (1H, s), 6.60 (1H, s), 8.81 (1H, s), 9.72 (1H, s)

Example 288

Compound 288

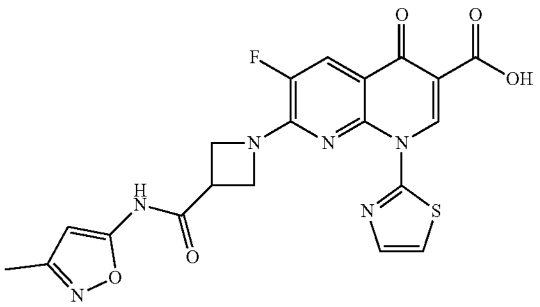

6-Fluoro-7-{3-[(3-methyl-1,2-oxazol-5-yl)carbamoyl]azetidin-1-yl}-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-(3-methyl-1,2-oxazol-5-yl)azetidine-3-carboxamide hydrochloride obtained in Example 287 by the method described in Example 001-(3) or a method equivalent thereto.

1H-NMR (DMSO-d6): δ 2.19 (3H, s), 3.85-3.93 (1H, m), 4.42-4.95 (4H, m), 6.20 (1H, brs), 7.79 (1H, d, J=3.5 Hz), 7.86 (1H, d, J=3.5 Hz), 8.12 (1H, d, J=11.5 Hz), 9.81 (1H, s), 11.79 (1H, brs), 14.76 (1H, brs)

Example 289

Compound 289

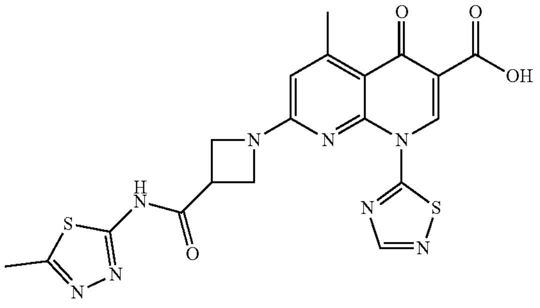

5-Methyl-7-{3-[(5-methyl-1,3,4-thiadiazol-2-yl)carbamoyl]azetidin-1-yl}-4-oxo-1-(1,2,4-thiadiazol-5-yl)-1,4-dihydro-1,8-naphthyridine-3-carboxylic acid The title compound was obtained by the method described in Example 001-(3) or a method equivalent thereto using N-(5-methyl-1,3,4-thiadiazol-2-yl)azetidine-3-carboxamide hydrochloride obtained from 5-methyl-1,3,4-thiadiazol-2-amine by the methods described in Examples 007-(1) and 001-(2) or methods equivalent thereto, and 7-chloro-5-methyl-4-oxo-1-(1,2,4-thiadiazol-5-yl)-1,4-dihydro-1,8-naphthyridine-3-carboxylic acid obtained in Reference Example 002-(2).

1H-NMR (DMSO-d6): δ 2.62 (3H, s), 2.70 (3H, s), 3.92-4.05 (1H, m), 4.30-4.66 (4H, m), 6.53 (1H, brs), 8.78 (1H, s), 9.61 (1H, s), 12.65 (1H, brs), 14.93 (1H, brs)

Example 290

Compound 290

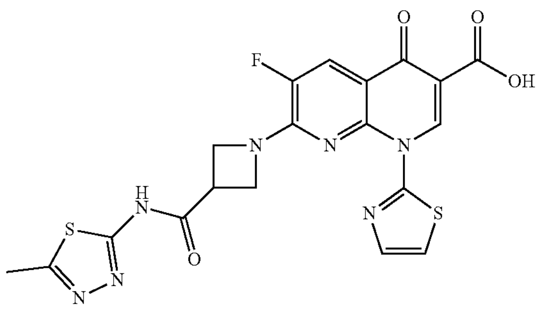

6-Fluoro-7-{3-[(5-methyl-1,3,4-thiadiazol-2-yl)carbamoyl]azetidin-1-yl}-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-(5-methyl-1,3,4-thiadiazol-2-yl)azetidine-3-carboxamide hydrochloride obtained in Example 289 by the method described in Example 001-(3) or a method equivalent thereto.

1H-NMR (DMSO-d6): δ 2.62 (3H, s), 3.95-4.05 (1H, m), 4.50-4.90 (4H, m), 7.79 (1H, d, J=3.5 Hz), 7.87 (1H, d, J=3.5 Hz), 8.14 (1H, d, J=11.5 Hz), 9.83 (1H, s), 12.63 (1H, brs), 14.89 (1H, brs)

Example 291

Compound 291

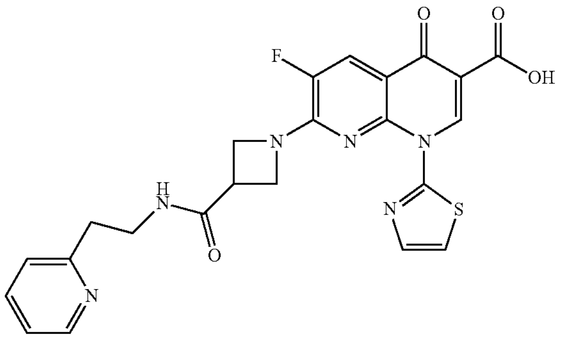

6-Fluoro-4-oxo-7-(3-{[2-(pyridin-2-yl)ethyl]carbamoyl}azetidin-1-yl)-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-[2-(pyridin-2-yl)ethyl]azetidine-3-carboxamide hydrochloride obtained from 2-(pyridin-2-yl)ethan-1-amine by the method described in Example 007-(1) and Example 001-(2) or a method equivalent thereto by the method described in Example 001-(3) or a method equivalent thereto.

1H-NMR (DMSO-d6): δ 2.95 (2H, t, J=7.0 Hz), 3.47-3.53 (2H, m), 3.54-3.60 (1H, m), 4.30-4.78 (4H, m), 7.28-7.44 (2H, m), 7.81 (1H, d, J=3.5 Hz), 7.87 (1H, d, J=3.5 Hz), 8.11 (1H, d, J=11.5 Hz), 8.22-8.27 (1H, m), 8.53-8.58 (1H, m), 9.82 (1H, s), 14.80 (1H, brs)

Example 292

Compound 292

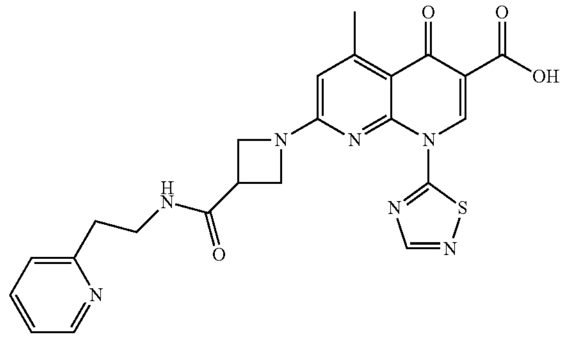

5-Methyl-4-oxo-7-(3-{[2-(pyridin-2-yl)ethyl]carbamoyl}azetidin-1-yl)-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-[2-(pyridin-2-yl)ethyl]azetidine-3-carboxamide hydrochloride obtained in Example 291 by the method described in Example 001-(3) or a method equivalent thereto.

1H-NMR (DMSO-d6): δ 2.71 (3H, s), 2.98 (2H, t, J=7.0 Hz), 3.48-3.61 (3H, m), 4.17-4.53 (4H, m), 6.50 (1H, s), 7.32-7.48 (2H, m), 7.83-7.93 (1H, m), 8.24-8.33 (1H, m), 8.54-8.60 (1H, m), 8.80 (1H, s), 9.63 (1H, s), 15.00 (1H, brs)

Example 293

Compound 293

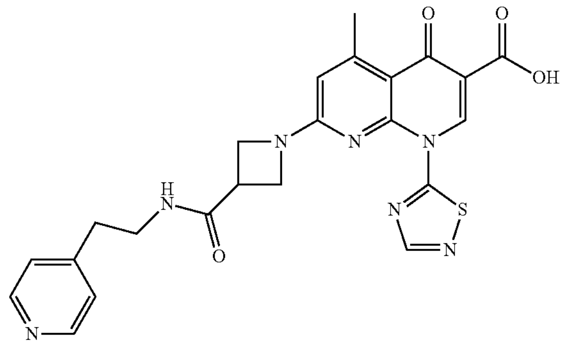

5-Methyl-4-oxo-7-(3-{[2-(pyridin-4-yl)ethyl]carbamoyl}azetidin-1-yl)-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-[2-(pyridin-4-yl)ethyl]azetidine-3-carboxamide hydrochloride obtained from 2-(pyridin-4-yl)ethan-1-amine by the method described in Example 007-(1) and Example 001-(2) or a method equivalent thereto by the method described in Example 001-(3) or a method equivalent thereto.

1H-NMR (DMSO-d6): δ 2.76 (3H, s), 2.92 (2H, t, J=7.0 Hz), 3.44-3.49 (2H, m), 3.52-3.60 (1H, m), 4.19-4.59 (4H, m), 6.56 (1H, s), 7.58 (2H, d, J=5.0 Hz), 8.28-8.33 (1H, m), 8.63 (2H, d, J=5.0 Hz), 8.82 (1H, s), 9.72 (1H, s), 15.06 (1H, brs)

Example 294

Compound 294

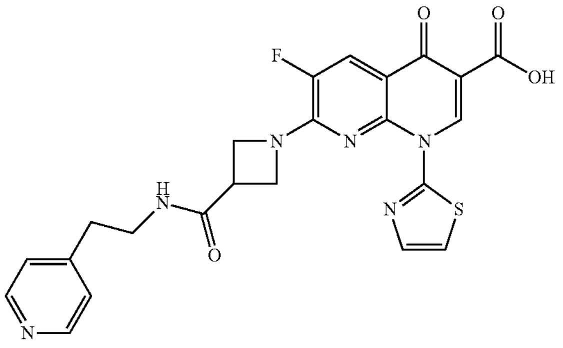

6-Fluoro-4-oxo-7-(3-{[2-(pyridin-4-yl)ethyl]carbamoyl}azetidin-1-yl)-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-[2-(pyridin-4-yl)ethyl]azetidine-3-carboxamide hydrochloride obtained in Example 293 by the method described in Example 001-(3) or a method equivalent thereto.

1H-NMR (DMSO-d6): δ 2.93 (2H, t, J=7.0 Hz), 3.43-3.49 (2H, m), 3.52-3.66 (1H, m), 4.27-4.78 (4H, m), 7.63 (2H, d, J=5.5 Hz), 7.81 (1H, d, J=3.5 Hz), 7.87 (1H, d, J=3.5 Hz), 8.11 (1H, d, J=11.5 Hz), 8.28 (1H, brt, J=5.5 Hz), 8.66 (2H, d, J=5.5 Hz), 9.52 (1H, s), 14.78 (1H, brs)

Example 295

Compound 295

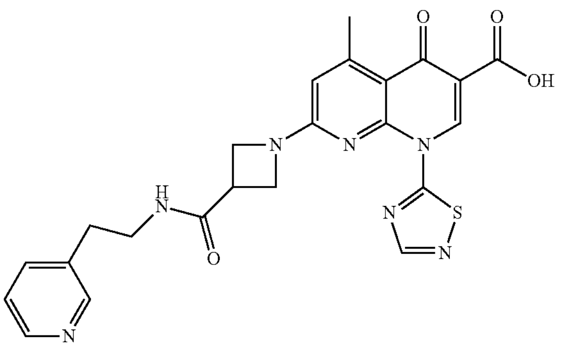

5-Methyl-4-oxo-7-(3-{[2-(pyridin-3-yl)ethyl]carbamoyl}azetidin-1-yl)-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-[2-(pyridin-3-yl)ethyl]azetidine-3-carboxamide hydrochloride obtained from 2-(pyridin-3-yl)ethan-1-amine by the method described in Example 007-(1) and Example 001-(2) or a method equivalent thereto by the method described in Example 001-(3) or a method equivalent thereto.

1H-NMR (DMSO-d6): δ 2.77 (3H, s), 2.84 (2H, t, J=7.0 Hz), 3.40-3.46 (2H, m), 3.52-3.60 (1H, m), 4.17-4.60 (4H, m), 6.57 (1H, s), 7.48-7.55 (1H, m), 7.86-7.93 (1H, m), 8.24-8.31 (1H, m), 8.49-8.55 (1H, m), 8.57 (1H, brs), 8.83 (1H, s), 9.75 (1H, s), 15.08 (1H, brs)

Example 296

Compound 296

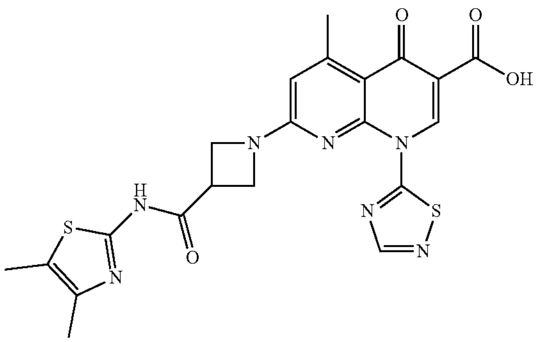

7-{3-[(Dimethyl-1,3-thiazol-2-yl)carbamoyl]azetidin-1-yl}-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-(dimethyl-1,3-thiazol-2-yl)azetidine-3-carboxamide hydrochloride obtained from dimethyl-1,3-thiazol-2-amine by the method described in Example 007-(1) and Example 001-(2) or a method equivalent thereto by the method described in Example 001-(3) or a method equivalent thereto.

1H-NMR (DMSO-d6): δ 2.16 (3H, s), 2.24 (3H, s), 2.75 (3H, s), 3.87-3.95 (1H, m), 4.34-4.67 (4H, m), 6.59 (1H, s), 8.80 (1H, s), 9.70 (1H, s), 12.14 (1H, brs), 15.03 (1H, s)

Example 297

Compound 297

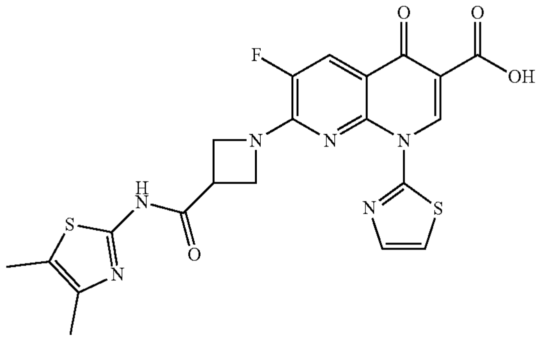

7-{3-[(Dimethyl-1,3-thiazol-2-yl)carbamoyl]azetidin-1-yl}-6-fluoro-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-(dimethyl-1,3-thiazol-2-yl)azetidine-3-carboxamide hydrochloride obtained in Example 296 by the method described in Example 001-(3) or a method equivalent thereto.

1H-NMR (DMSO-d6): δ 2.16 (3H, s), 2.24 (3H, s), 3.87-3.96 (1H, m), 4.46-4.83 (4H, m), 7.76 (1H, d, J=3.5 Hz), 7.85 (1H, d, J=3.5 Hz), 8.10 (1H, d, J=11.5 Hz), 9.82 (1H, s), 12.12 (1H, brs), 14.77 (1H, brs)

Example 298

Compound 298

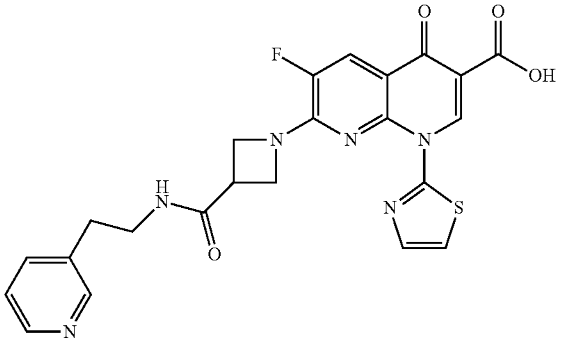

6-Fluoro-4-oxo-7-(3-{[2-(pyridin-3-yl)ethyl]carbamoyl}azetidin-1-yl)-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-[2-(pyridin-3-yl)ethyl]azetidine-3-carboxamide hydrochloride obtained in Example 295 by the method described in Example 001-(3) or a method equivalent thereto.

1H-NMR (DMSO-d6): δ 2.83 (2H, t, J=7.0 Hz), 3.53-3.60 (1H, m), 4.29-4.79 (4H, m), 7.46-7.51 (1H, m), 7.81 (1H, d, J=3.5 Hz), 7.87 (1H, d, J=3.5 Hz), 8.11 (1H, d, J=11.5 Hz), 8.22-8.27 (1H, m), 8.49-8.53 (1H, m), 8.54 (1H, brs), 9.82 (1H, s)

Example 299

Compound 299

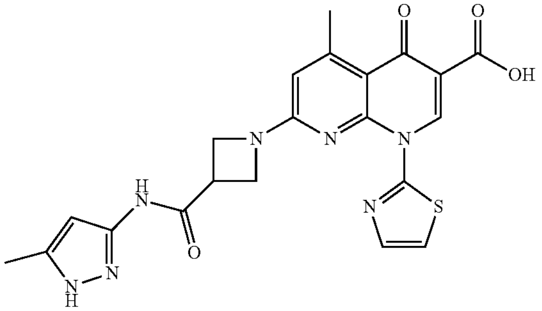

5-Methyl-7-{3-[(5-methyl-1H-pyrazol-3-yl)carbamoyl]azetidin-1-yl}-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-(5-methyl-1H-pyrazol-3-yl)azetidine-3-carboxamide hydrochloride obtained from tert-butyl amino-5-methyl-1H-pyrazole-1-carboxylate by the method described in Example 007-(1) and Example 001-(2) or a method equivalent thereto by the method described in Example 008 or a method equivalent thereto.

1H-NMR (DMSO-d6): δ 2.19 (3H, s), 2.76 (3H, s), 3.74-3.84 (1H, m), 4.16-4.53 (4H, m), 6.31 (1H, brs), 6.53 (1H, brs), 7.69-7.74 (1H, m), 7.81-7.84 (1H, m), 9.82 (1H, s), 10.54 (1H, brs), 12.02 (1H, brs), 15.32 (1H, brs)

Example 300

Compound 300

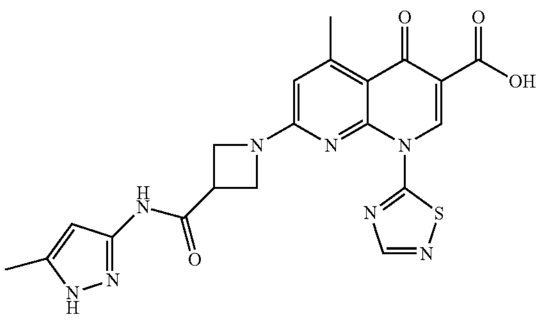

5-Methyl-7-{3-[(5-methyl-1H-pyrazol-3-yl)carbamoyl]azetidin-1-yl}-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-(5-methyl-1H-pyrazol-3-yl)azetidine-3-carboxamide hydrochloride obtained in Example 299 by the method described in Example 008 or a method equivalent thereto.

1H-NMR (DMSO-d6): δ 2.20 (3H, s), 2.76 (3H, s), 3.75-3.91 (1H, m), 4.26-4.71 (4H, m), 6.31 (1H, brs), 6.58 (1H, brs), 8.81 (1H, brs), 9.71 (1H, s), 10.57 (1H, brs), 12.04 (1H, brs), 15.00 (1H, brs)

Example 301

Compound 301

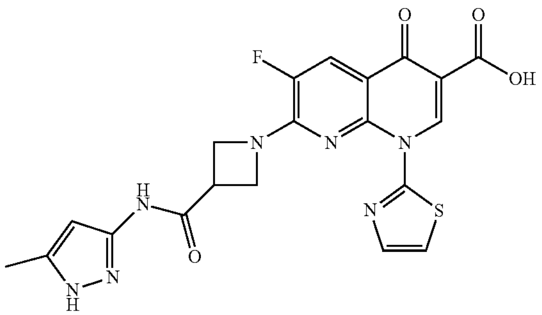

6-Fluoro-7-{3-[(5-methyl-1H-pyrazol-3-yl)carbamoyl]azetidin-1-yl}-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-(5-methyl-1H-pyrazol-3-yl)azetidine-3-carboxamide hydrochloride obtained in Example 299 by the method described in Example 008 or a method equivalent thereto.

1H-NMR (DMSO-d6): δ 2.19 (3H, s), 3.76-3.87 (1H, m), 4.46-4.71 (4H, m), 6.32 (1H, brs), 7.64-7.74 (1H, m), 7.78-7.82 (1H, m), 8.04 (1H, d, J=11.5 Hz), 9.80 (1H, brs), 10.51 (1H, brs), 12.02 (1H, brs)

Example 302

Compound 302

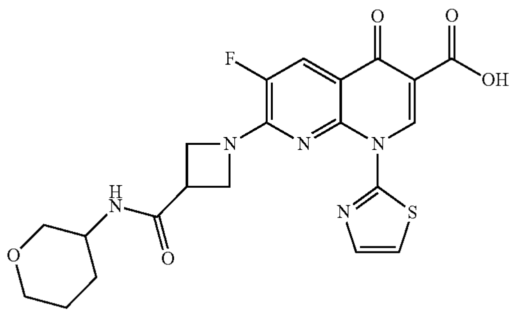

6-Fluoro-7-{3-[(oxan-3-yl)carbamoyl]azetidin-1-yl}-4-oxo-1-(1,3-thiazol-2-yl)-1,4-dihydro-1,8-naphthyridine-3-carboxylic acid The title compound was obtained by the method described in Example 002-(3) or a method equivalent thereto using N-(oxan-3-yl)azetidine-3-carboxamide trifluoroacetate obtained from oxan-3-amine by the methods described in Examples 007-(1) and 001-(2) or methods equivalent thereto, and 7-chloro-6-fluoro-4-oxo-1-(1,3-thiazol-2-yl)-1,4-dihydro-1,8-naphthyridine-3-carboxylic acid obtained in Reference Example 003-(2).

1H-NMR (DMSO-d6): δ 1.42-1.56 (1H, m), 1.64-1.74 (1H, m), 1.82-1.90 (1H, m), 3.13 (1H, dd, J=12.0, 9.0 Hz), 3.34-3.40 (1H, m), 3.61-3.67 (2H, m), 3.67-3.78 (2H, m), 4.33-4.81 (5H, m), 7.79 (1H, d, J=3.5 Hz), 7.86 (1H, d, J=3.5 Hz), 8.10 (1H, d, J=11.5 Hz), 8.14 (1H, d, J=7.5 Hz), 9.81 (1H, s)

Example 303

Compound 303

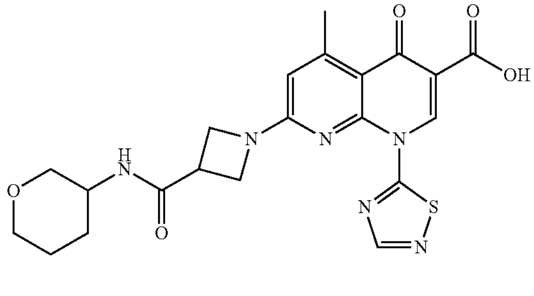

5-Methyl-7-{3-[(oxan-3-yl)carbamoyl]azetidin-1-yl}-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8- naphthyridine-3-carboxylic acid obtained in Reference Example 002-(2) and N-(oxan-3-yl)azetidine-3-carboxamide trifluoroacetate obtained in Example 302 by the method described in Example 002-(3) or a method equivalent thereto.

1H-NMR (DMSO-d6): δ 1.42-1.56 (2H, m), 1.64-1.74 (1H, m), 1.82-1.92 (1H, m), 2.77 (3H, s), 3.11-3.18 (1H, m), 3.34-3.41 (1H, m), 3.60-3.70 (1H, m), 3.70-3.78 (2H, m), 4.22-4.63 (5H, m), 6.58 (1H, s), 8.27 (1H, d, J=7.5 Hz), 8.82 (1H, s), 9.74 (1H, s)

Example 304

Compound 304

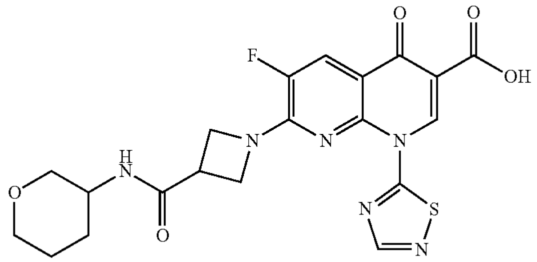

6-Fluoro-7-{3-[(oxan-3-yl)carbamoyl]azetidin-1-yl}-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and N-(oxan-3-yl)azetidine-3-carboxamide trifluoroacetate obtained in Example 302 by the method described in Example 002-(3) or a method equivalent thereto.

1H-NMR (DMSO-d6): δ 1.44-1.57 (2H, m), 1.61-1.75 (1H, m), 1.81-1.92 (1H, m), 3.10-3.18 (1H, m), 3.42-3.47 (1H, m), 3.62-3.79 (4H, m), 4.46-4.83 (4H, m), 8.15 (2H, d, J=11.0 Hz), 8.85 (1H, s), 9.75 (1H, s), 14.47 (1H, brs)

Example 305

Compound 305

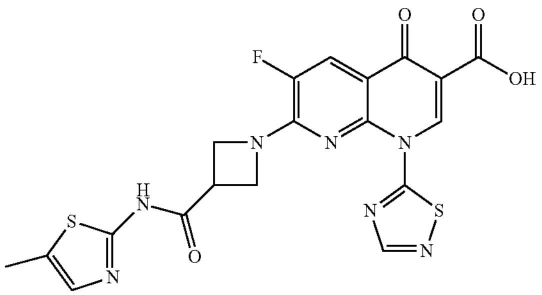

6-Fluoro-7-{3-[(5-methyl-1,3-thiazol-2-yl)carbamoyl]azetidin-1-yl}-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and N-(5-methyl-1,3-thiazol-2-yl)azetidine-3-carboxamide hydrochloride obtained in Example 283 by the method described in Example 008 or a method equivalent thereto.

1H-NMR (DMSO-d6): δ 2.33-2.36 (3H, m), 3.90-4.05 (1H, m), 4.55-4.94 (4H, m), 7.16 (1H, s), 8.16 (1H, d, J=11.5 Hz), 8.85 (1H, s), 9.74 (1H, s), 12.17 (1H, brs), 14.39 (1H, brs)

Example 306

Compound 306

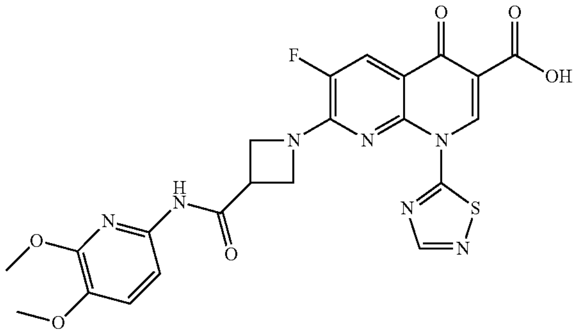

7-{3-[(5,6-Dimethoxypyridin-2-yl)carbamoyl]azetidin-1-yl}-6-fluoro-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and N-(5,6-dimethoxypyridin-2-yl)azetidine-3-carboxamide hydrochloride obtained in Example 278 by the method described in Example 008 or a method equivalent thereto.

1H-NMR (DMSO-d6): δ 3.74 (3H, s), 3.87 (3H, s), 3.92-4.02 (1H, m), 4.52-4.97 (4H, m), 7.33 (1H, d, J=8.5 Hz), 7.66 (1H, d, J=8.5 Hz), 8.14 (1H, d, J=11.5 Hz), 8.84 (1H, s), 9.73 (1H, s), 10.36 (1H, s), 14.47 (1H, brs)

Example 307

Compound 307

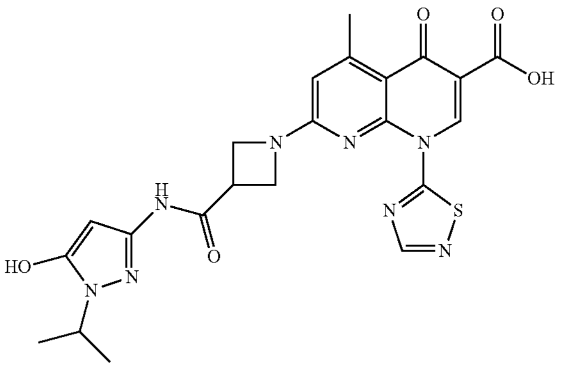

7-(3-({[5-Hydroxy-1-(propan-2-yl)-1H-pyrazol-3-yl] carbamoyl}azetidin-1-yl)-5-methyl-4-oxo-1-(1,2,4-thiadiazol-5-yl)-1,4-dihydro-1,8-naphthyridine-3-carboxylic acid (1) To a solution of tert-butyl 3-{[5-(benzyloxy)-1-(propan-2-yl)-1H-pyrazol-3-yl]carbamoyl}azetidine-1-carboxylate (104 mg) in methanol obtained by the method described in Example 007-(1) or a method equivalent thereto using 5-(benzyloxy)-1-(propan-2-yl)-1H-pyrazol-3-amine obtained by the methods described in Examples 009-(1) to 009-(3) or methods equivalent thereto was added 10% palladium carbon (20 mg), and the mixture was hydrogenated at 40° C. for 3 hours. The catalyst was filtered off, and the filtrate was then concentrated to obtain 80 mg of tert-butyl 3-{[5-hydroxy-1-(propan-2-yl)-1H-pyrazol-3-yl] carbamoyl}azetidine-1-carboxylate.

1H-NMR (DMSO-d6): δ 1.24 (6H, d, J=6.5 Hz), 1.37 (9H, s), 3.36-3.45 (1H, m), 3.79-4.00 (4H, m), 4.36 (1H, q, J=6.5 Hz), 5.71 (1H, s), 10.36 (1H, s), 10.91 (1H, brs)

(2) The title compound was obtained by the method described in Example 008 or a method equivalent thereto using N-[5-hydroxy-1-(propan-2-yl)-1H-pyrazol-3-yl]azetidine-3-carboxamide hydrochloride obtained by the method described in Example 001-(2) or a method equivalent thereto from tert-butyl 3-{[5-hydroxy-1-(propan-2-yl)-1H-pyrazol-3-yl]carbamoyl}azetidine-1-carboxylate obtained in the preceding section, and 7-chloro-5-methyl-4-oxo-1-(1,2,4-thiadiazol-5-yl)-1,4-dihydro-1,8-naphthyridine-3-carboxylic acid obtained in Reference Example 002-(2).

1H-NMR (DMSO-d6): δ 1.27 (6H, d, J=6.5 Hz), 2.76 (3H, s), 3.70-3.87 (1H, m), 4.21-4.68 (5H, m), 5.74 (1H, a), 6.58 (1H, s), 8.81 (1H, s), 9.73 (1H, s), 10.56 (1H, a), 10.91 (1H, brs), 15.07 (1H, brs)

Example 308

Compound 308

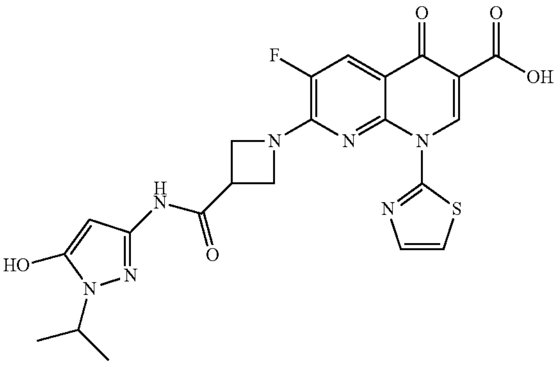

6-Fluoro-7-(3-{[5-hydroxy-1-(propan-2-yl)-1H-pyrazol-3-yl]carbamoyl}azetidin-1-yl)-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-[5-hydroxy-1-(propan-2-yl)-1H-pyrazol-3-yl]azetidine-3-carboxamide hydrochloride obtained in Example 307 by the method described in Example 008 or a method equivalent thereto.

1H-NMR (DMSO-d6): δ 1.26 (6H, d, J=6.5 Hz), 3.72-3.87 (1H, m), 4.26-4.88 (5H, m), 5.74 (1H, s), 7.68-7.96 (2H, m), 8.00-8.22 (1H, m), 9.82 (1H, s), 10.54 (1H, s), 10.92 (1H, s), 14.80 (1H, brs)

Example 309

Compound 309

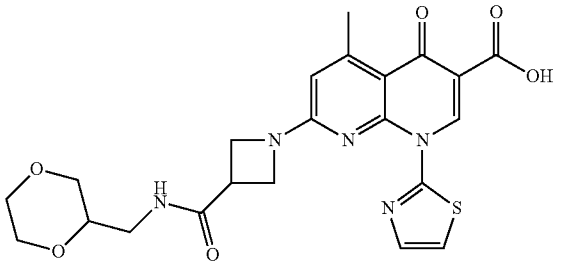

7-{3-[(1,4-Dioxan-2-ylmethyl)carbamoyl]azetidin-1-yl}-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-(1,4-dioxan-2-ylmethyl)azetidine-3-carboxamide trifluoroacetate obtained from 1,4-dioxan-2-ylmethylamine by the method described in Example 005-(1) and Example 001-(2) or a method equivalent thereto by the method described in Example 001-(3) or a method equivalent thereto.

1H-NMR (DMSO-d6): δ 2.77 (3H, d, J=0.9 Hz), 3.12-3.23 (3H, m), 3.45 (1H, td, J=11.0, 2.7 Hz), 3.52-3.65 (4H, m), 3.68-3.75 (2H, m), 4.19-4.49 (4H, m), 6.54 (1H, d, J=0.9 Hz), 7.75 (1H, d, J=3.5 Hz), 7.84 (1H, d, J=3.5 Hz), 8.27 (1H, t, J=5.9 Hz), 9.84 (1H, s), 15.41 (1H, brs)

Example 310

Compound 310

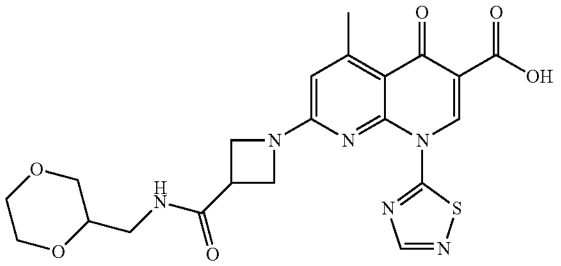

7-{3-[(1,4-Dioxan-2-ylmethyl)carbamoyl]azetidin-1-yl}-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8- naphthyridine-3-carboxylic acid obtained in Reference Example 002-(2) and N-(1,4-dioxan-2-ylmethyl)azetidine-3-carboxamide trifluoroacetate obtained in Example 309 by the method described in Example 001-(3) or a method equivalent thereto.

1H-NMR (DMSO-d6): δ 2.76 (3H, d, J=0.9 Hz), 3.12-3.23 (3H, m), 3.45 (1H, td, J=11.1, 2.6 Hz), 3.53-3.76 (6H, m), 4.25-4.62 (4H, m), 6.58 (1H, d, J=0.9 Hz), 8.30 (1H, t, J=5.8 Hz), 8.82 (1H, s), 9.73 (1H, s), 15.08 (1H, brs)

Example 311

Compound 311

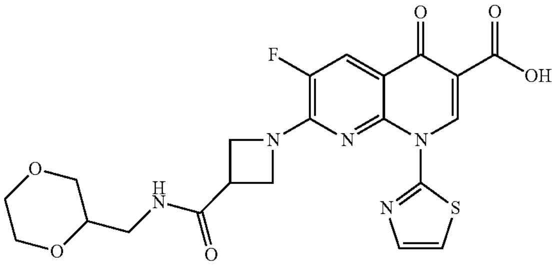

7-{3-[(1,4-Dioxan-2-ylmethyl)carbamoyl]azetidin-1-yl}-6-fluoro-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-(1,4-dioxan-2-ylmethyl)azetidine-3-carboxamide trifluoroacetate obtained in Example 309 by the method described in Example 001-(3) or a method equivalent thereto.

1H-NMR (DMSO-d6): δ 3.10-3.23 (3H, m), 3.45 (1H, td, J=11.2, 2.7 Hz), 3.52-3.75 (6H, m), 4.37-4.80 (4H, m), 7.79 (1H, d, J=3.5 Hz), 7.86 (1H, d, J=3.5 Hz), 8.09 (1H, d, J=11.4 Hz), 8.29 (1H, t, J=5.8 Hz), 9.80 (1H, s), 14.79 (1H, brs)

Example 312

Compound 312

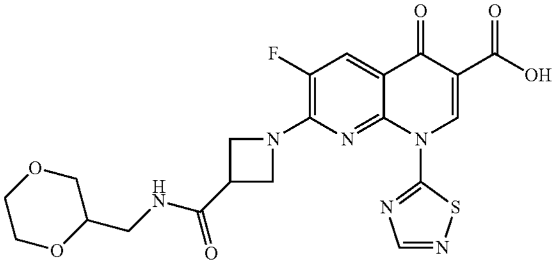

7-{3-[(1,4-Dioxan-2-ylmethyl)carbamoyl]azetidin-1-yl}-6-fluoro-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) N-(1,4-dioxan-2-ylmethyl)azetidine-3-carboxamide trifluoroacetate obtained in Example 309 by the method described in Example 001-(3) or a method equivalent thereto.

1H-NMR (DMSO-d6): δ 3.11-3.23 (3H, m), 3.45 (1H, td, J=11.2, 2.6 Hz), 3.53-3.76 (6H, m), 4.48-4.82 (4H, m), 8.15 (1H, d, J=11.4 Hz), 8.29 (1H, t, J=5.8 Hz), 8.85 (1H, s), 9.75 (1H, s), 14.50 (1H, brs)

Example 313

Compound 313

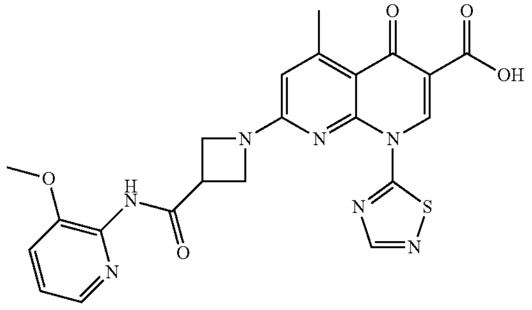

7-{3-[(3-Methoxypyridin-2-yl)carbamoyl]azetidin-1-yl}-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-(3-methoxypyridin-2-yl)azetidine-3-carboxamide hydrochloride obtained from 3-methoxy-pyridin-2-amine by the method described in Example 007-(1) and Example 001-(2) or a method equivalent thereto by the method described in Example 001-(3) or a method equivalent thereto.

1H-NMR (DMSO-d6): δ 2.76 (3H, s), 3.83 (3H, s), 3.91-4.00 (1H, m), 4.28-4.68 (4H, m), 6.62 (1H, s), 7.26 (1H, dd, J=8.5, 5.0 Hz), 7.50 (1H, dd, J=8.5, 1.5 Hz), 7.98 (1H, dd, J=5.0, 1.5 Hz), 8.81 (1H, s), 9.72 (1H, s), 9.96 (1H, brs), 15.05 (1H, brs)

Example 314

Compound 314

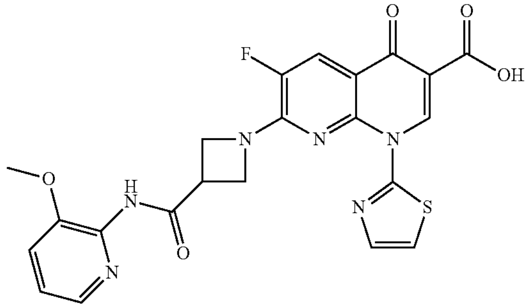

6-Fluoro-7-{3-[(3-methoxypyridin-2-yl)carbamoyl]azetidin-1-yl}-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-(3-methoxypyridin-2-yl)azetidine-3-carboxamide hydrochloride obtained in Example 313 by the method described in Example 001-(3) or a method equivalent thereto.

1H-NMR (DMSO-d6): δ 3.83 (3H, s), 3.90-3.99 (1H, m), 4.47-4.92 (4H, m), 7.26 (1H, dd, J=8.0, 5.0 Hz), 7.51 (1H, dd, J=8.0, 1.5 Hz), 7.82 (1H, d, J=3.5 Hz), 7.87 (1H, d, J=3.5 Hz), 7.97 (1H, dd, J=5.0, 1.5 Hz), 8.13 (1H, d, J=12.0 Hz), 9.83 (1H, s), 9.95 (1H, brs)

Example 315

Compound 315

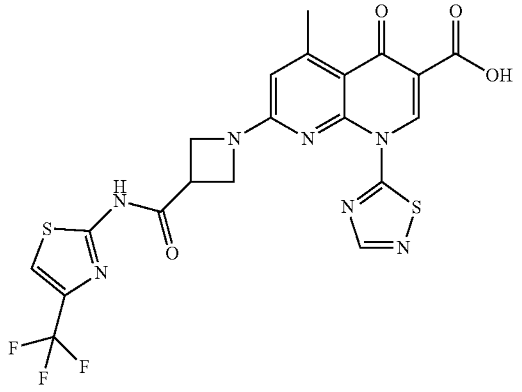

5-Methyl-4-oxo-1-(1,2,4-thiadiazol-5-yl)-7-(3-{[4-(trifluoromethyl)-1,3-thiazol-2-yl]carbamoyl}azetidin-1-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-[4-(trifluoromethyl)-1,3-thiazol-2-yl]azetidine-3-carboxamide hydrochloride obtained from 4-(trifluoromethyl)-1,3-thiazol-2-amine by the method described in Example 007-(1) and Example 001-(2) or a method equivalent thereto by the method described in Example 008 or a method equivalent thereto.

1H-NMR (DMSO-d6): δ 2.79 (3H, s), 3.92-4.02 (1H, m), 4.41-4.73 (4H, m), 6.63 (1H, s), 7.99 (1H, s), 8.82 (1H, s), 9.76 (1H, s), 12.83 (1H, brs), 15.06 (1H, brs)

Example 316

Compound 316

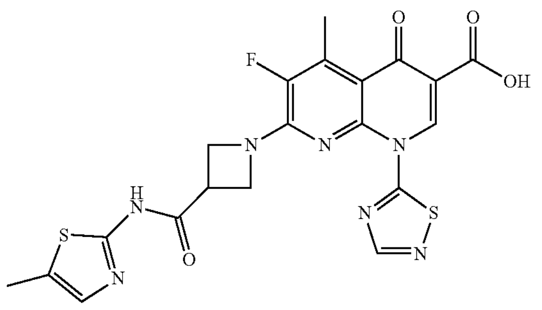

6-Fluoro-5-methyl-7-{3-[(5-methyl-1,3-thiazol-2-yl)carbamoyl]azetidin-1-yl}-4-oxo-1-(1,2,4-thiadiazol-5-yl)-1,4-dihydro-1,8-naphthyridine-3-carboxylic acid The title compound was obtained using 7-chloro-6-fluoro-5-methyl-4-oxo-1-(1,2,4-thiadiazol-5-yl)-1,4-dihydro-1,8-naphthyridine-3-carboxylic acid obtained in Reference Example 008-(2) and N-(5-methyl-1,3-thiazol-2-yl)azetidine-3-carboxamide hydrochloride obtained in Example 283 by the method described in Example 008 or a method equivalent thereto.

1H-NMR (DMSO-d6): δ 2.35 (3H, d, J=1.5 Hz), 2.70 (3H, d, J=2.5 Hz), 3.91-4.00 (1H, m), 4.60-4.86 (4H, m), 7.16 (1H, d, J=1.5 Hz), 8.84 (1H, s), 9.77 (1H, s), 12.17 (1H, brs), 14.81 (1H, brs)

Example 317

Compound 317

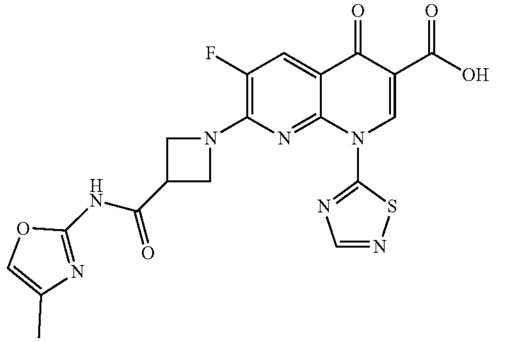

6-Fluoro-7-{3-[(4-methyl-1,3-oxazol-2-yl)carbamoyl]azetidin-1-yl}-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and N-(4-methyl-1,3-oxazol-2-yl)azetidine-3-carboxamide trifluoroacetate obtained from 4-methyl-1,3-oxazol-2-amine by the method described in Example 005-(1) and Example 001-(2) or a method equivalent thereto by the method described in Example 001-(3) or a method equivalent thereto.

1H-NMR (DMSO-d6): δ 2.06 (3H, d, J=1.2 Hz), 3.83-4.00 (1H, m), 4.55-4.87 (4H, m), 7.58 (1H, d, J=1.2 Hz), 8.17 (1H, d, J=11.4 Hz), 8.86 (1H, s), 9.75 (1H, s), 11.40 (1H, s), 14.47 (1H, brs)

Example 318

Compound 318

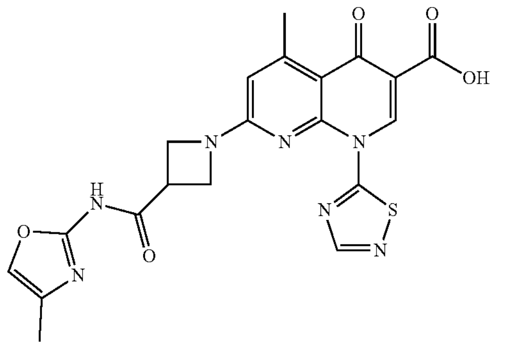

5-Methyl-7-{3-[(4-methyl-1,3-oxazol-2-yl)carbamoyl]azetidin-1-yl}-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-(4-methyl-1,3-oxazol-2-yl)azetidine-3-carboxamide trifluoroacetate obtained in Example 317 by the method described in Example 001-(3) or a method equivalent thereto.

1H-NMR (DMSO-d6): δ 2.05 (3H, d, J=1.3 Hz), 2.79 (3H, d, J=1.0 Hz), 3.83-3.93 (1H, m), 4.36-4.70 (4H, m), 6.64 (1H, d, J=1.0 Hz), 7.57-7.58 (1H, m), 8.83 (1H, s), 9.77 (1H, S), 11.41 (1H, s), 15.08 (1H, brs)

Example 319

Compound 319

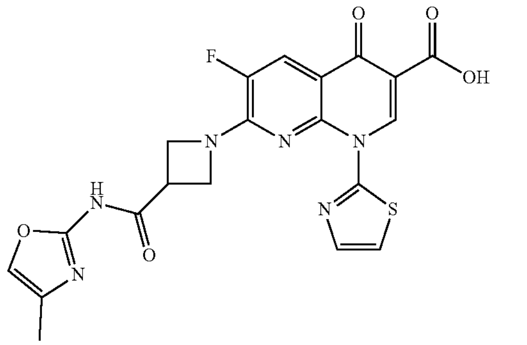

6-Fluoro-7-{3-[(4-methyl-1,3-oxazol-2-yl)carbamoyl]azetidin-1-yl}-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) N-(4-methyl-1,3-oxazol-2-yl)azetidine-3-carboxamide trifluoroacetate obtained in Example 317 by the method described in Example 001-(3) or a method equivalent thereto.

1H-NMR (DMSO-d6): δ 2.05 (3H, d, J=1.2 Hz), 3.81-3.97 (1H, m), 4.45-4.88 (4H, m), 7.57 (1H, d, J=1.2 Hz), 7.80 (1H, d, J=3.5 Hz), 7.86 (1H, d, J=3.5 Hz), 8.12 (1H, d, J=11.4 Hz), 9.82 (1H, s), 11.38 (1H, s), 14.78 (1H, brs)

Example 320

Compound 320

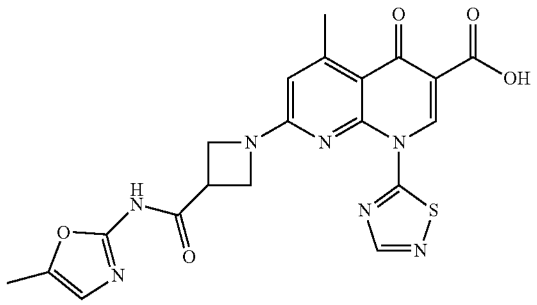

5-Methyl-7-{3-[(5-methyl-1,3-oxazol-2-yl)carbamoyl]azetidin-1-yl}-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) N-(5-methyl-1,3-oxazol-2-yl)azetidine-3-carboxamide trifluoroacetate obtained from 5-methyl-1,3-oxazol-2-amine by the method described in Example 005-(1) and Example 001-(2) or a method equivalent thereto by the method described in Example 001-(3) or a method equivalent thereto.

1H-NMR (DMSO-d6): δ 2.26 (3H, d, J=1.2 Hz), 2.78 (3H, d, J=0.9 Hz), 3.80-3.93 (1H, m), 4.34-4.68 (4H, m), 6.62 (1H, d, J=0.9 Hz), 6.73 (1H, d, J=1.2 Hz), 8.82 (1H, s), 9.74 (1H, s), 11.33 (1H, s), 15.06 (1H, brs)

Example 321

Compound 321

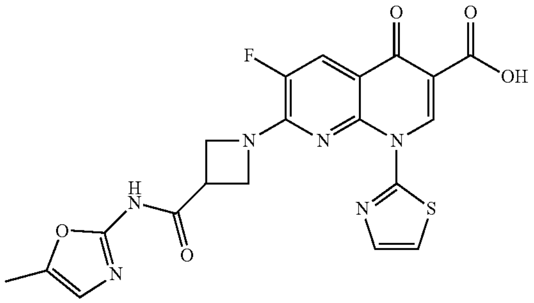

6-Fluoro-7-{3-[(5-methyl-1,3-oxazol-2-yl)carbamoyl]azetidin-1-yl}-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-(5-methyl-1,3-oxazol-2-yl)azetidine-3-carboxamide trifluoroacetate obtained in Example 320 by the method described in Example 001-(3) or a method equivalent thereto.

1H-NMR (DMSO-d6): δ 2.26 (3H, d, J=1.0 Hz), 3.79-3.97 (1H, m), 4.42-4.87 (4H, m), 6.73 (1H, d, J=1.0 Hz), 7.80 (1H, d, J=3.5 Hz), 7.85 (1H, d, J=3.5 Hz), 8.09 (1H, d, J=11.4 Hz), 9.82 (1H, s), 11.38 (1H, s), 14.78 (1H, brs)

Example 322

Compound 322

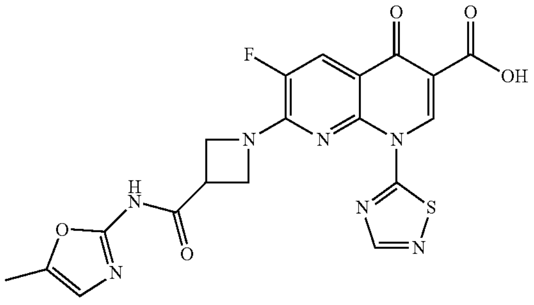

6-Fluoro-7-{3-[(5-methyl-1,3-oxazol-2-yl)carbamoyl]azetidin-1-yl}-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-carboxylic acid obtained in Reference Example 004-(2) and N-(5-methyl-1,3-oxazol-2-yl)azetidine-3-carboxamide trifluoroacetate obtained in Example 320 by the method described in Example 001-(3) or a method equivalent thereto.

1H-NMR (DMSO-d6): δ 2.26 (3H, d, J=1.0 Hz), 3.83-3.97 (1H, m), 4.57-4.87 (4H, m), 6.73-6.74 (1H, m), 8.16 (1H, d, J=11.4 Hz), 8.85 (1H, s), 9.74 (1H, s), 11.33 (1H, s), 14.43 (1H, brs)

Example 323

Compound 323

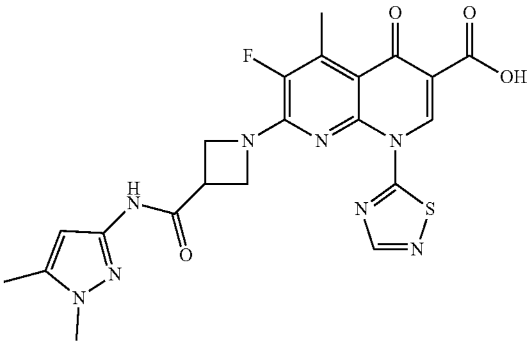

7-{3-[(1,5-Dimethyl-1H-pyrazol-3-yl)carbamoyl]azetidin-1-yl}-6-fluoro-5-methyl-4-oxo-1-(1,2,4-thiadiazol-5-yl)-1,4-dihydro-1,8-naphthyridine-3-carboxylic acid The title compound was obtained using 7-chloro-6-fluoro-5-methyl-4-oxo-1-(1,2,4-thiadiazol-5-yl)-1,4-dihydro-1,8-naphthyridine-carboxylic acid obtained in Reference Example 008-(2) and N-(1,5-dimethyl-1H-pyrazol-3-yl)azetidine-3-carboxamide hydrochloride obtained in Example 219 by the method described in Example 008 or a method equivalent thereto.

1H-NMR (DMSO-d6): δ 2.21 (3H, s), 2.70 (3H, d, J=2.5 Hz), 3.61 (3H, s), 3.77-3.85 (1H, m), 4.54-4.84 (4H, m), 6.33 (1H, s), 8.84 (1H, s), 9.77 (1H, s), 10.55 (1H, s), 14.84 (1H, brs)

Example 324

Compound 324

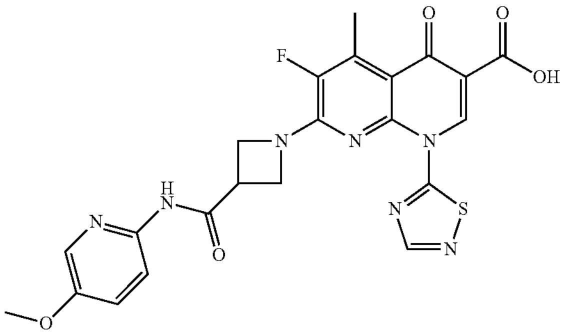

6-Fluoro-7-{3-[(5-methoxypyridin-2-yl)carbamoyl]azetidin-1-yl}-5-methyl-4-oxo-1-(1,2,4-thiadiazol-5-yl)-1,4-dihydro-1,8-naphthyridine-3-carboxylic acid The title compound was obtained using 7-chloro-6-fluoro-5-methyl-4-oxo-1-(1,2,4-thiadiazol-5-yl)-1,4-dihydro-1,8-naphthyridine-3-carboxylic acid obtained in Reference Example 008-(2) and N-(5-methoxypyridin-2-yl) azetidine-3-carboxamide hydrochloride obtained in Example 017 by the method described in Example 008 or a method equivalent thereto.

1H-NMR (DMSO-d6): δ 2.71 (3H, d, J=2.5 Hz), 3.81 (3H, s), 3.89-4.00 (1H, m), 4.62-4.89 (4H, m), 7.46 (1H, dd, J=9.0, 3.0 Hz), 8.06 (1H, d, J=3.0 Hz), 8.10 (1H, d, J=9.0 Hz), 8.84 (1H, s), 9.77 (1H, s), 10.65 (1H, s), 14.87 (1H, s)

Example 325

Compound 325

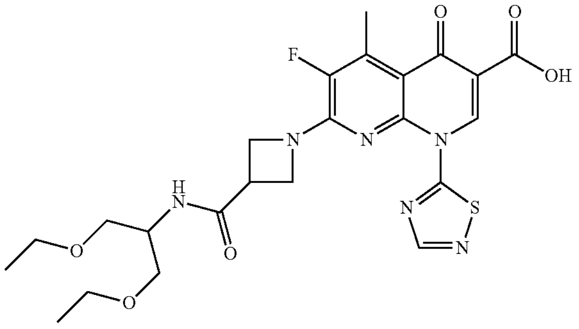

7-{3-[(1,3-Diethoxypropan-2-yl)carbamoyl]azetidin-1-yl}-6-fluoro-5-methyl-4-oxo-1-(1,2,4-thiadiazol-5-yl)-1,4-dihydro-1,8-naphthyridine-3-carboxylic acid The title compound was obtained using 7-chloro-6-fluoro-5-methyl-4-oxo-1-(1,2,4-thiadiazol-5-yl)-1,4-dihydro-1,8-naphthyridine-3-carboxylic acid obtained in Reference Example 008-(2) and N-(1,3-diethoxypropan-2-yl) azetidine-3-carboxamide hydrochloride obtained in Example 006-(3) by the method described in Example 008 or a method equivalent thereto.

1H-NMR (DMSO-d6): δ 1.10 (6H, t, J=7.0 Hz), 2.69 (3H, d, J=2.5 Hz), 3.37-3.40 (4H, m), 3.40-3.47 (4H, m), 3.62-3.71 (1H, m), 4.00-4.11 (1H, m), 4.42-4.86 (4H, m), 8.11 (1H, d, J=8.0 Hz), 8.84 (1H, s), 9.76 (1H, s), 14.85 (1H, s)

Example 326

Compound 326

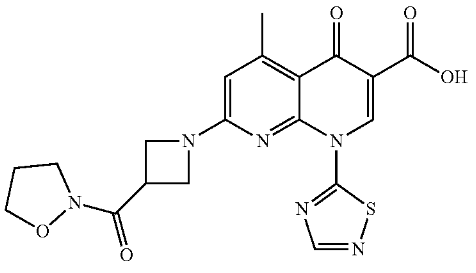

5-Methyl-7-[3-(1,2-oxazolidine-2-carbonyl)azetidin-1-yl]-4-oxo-1-(1,2,4-thiadiazol-5-yl)-1,4-dihydro-1,8-naphthyridine-3-carboxylic acid The title compound was obtained by the method described in Example 001-(3) or a method equivalent thereto using 2-(azetidine-3-carbonyl)-1,2-oxazolidine trifluoroacetate obtained from 1,2-oxazolidine by the methods described in Examples 005-(1) and 001-(2) or methods equivalent thereto, and 7-chloro-5-methyl-4-oxo-1-(1,2,4-thiadiazol-5-yl)-1,4-dihydro-1,8-naphthyridine-3-carboxylic acid obtained in Reference Example 002-(2).

1H-NMR (DMSO-d6): δ 2.23-2.34 (2H, m), 2.78 (3H, s), 3.58-3.77 (2H, m), 3.91-4.06 (3H, m), 4.37-4.64 (4H, m), 6.62 (1H, s), 8.82 (1H, s), 9.76 (1H, s), 15.07 (1H, brs)

Example 327

Compound 327

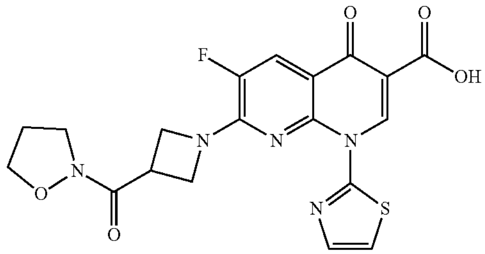

6-Fluoro-7-[3-(1,2-oxazolidine-2-carbonyl)azetidin-1-yl]-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and 2-(azetidine-3-carbonyl)-1,2-oxazolidine trifluoroacetate obtained in Example 326 by the method described in Example 001-(3) or a method equivalent thereto.

1H-NMR (DMSO-d6): δ 2.22-2.34 (2H, m), 3.55-3.80 (2H, m), 4.00 (3H, t, J=6.7 Hz), 4.37-4.88 (4H, m), 7.80 (1H, d, J=3.5 Hz), 7.84 (1H, d, J=3.5 Hz), 8.05 (1H, d, J=11.3 Hz), 9.77 (1H, s), 14.73 (1H, brs)

Example 328

Compound 328

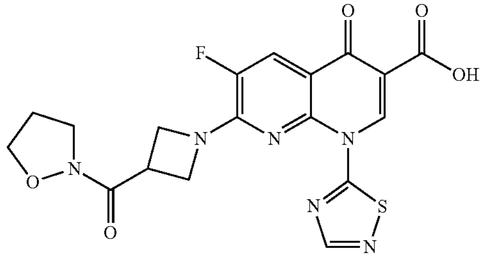

6-Fluoro-7-[3-(1,2-oxazolidine-2-carbonyl)azetidin-1-yl]-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and 2-(azetidine-3-carbonyl)-1,2-oxazolidine trifluoroacetate obtained in Example 326 by the method described in Example 001-(3) or a method equivalent thereto.

1H-NMR (DMSO-d6): δ 2.24-2.34 (2H, m), 3.56-3.71 (2H, m), 3.90-4.10 (3H, m), 4.52-4.92 (4H, m), 8.16 (1H, d, J=11.4 Hz), 8.86 (1H, s), 9.75 (1H, s), 14.58 (1H, brs)

Example 329

Compound 329

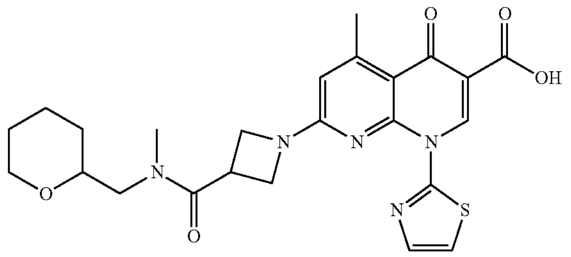

5-Methyl-7-{3-[methyl(oxan-2-ylmethyl)carbamoyl]azetidin-1-yl}-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-methyl-N-(oxan-2-ylmethyl)azetidine-3-carboxamide trifluoroacetate obtained in Example 010-(2) by the method described in Example 002-(3) or a method equivalent thereto.

1H-NMR (DMSO-d6): δ 1.15-1.22 (1H, m), 1.38-1.59 (4H, m), 1.73-1.86 (1H, m), 2.78 (3H, s), 2.89 (2H, s), 2.90 (1H, s), 3.43-3.52 (1H, m), 3.82-3.95 (1H, m), 3.96-4.11 (1H, m), 4.20-4.57 (4H, m), 6.57 (1H, d, J=7.0 Hz), 7.77 (1H, dd, J=13.0, 3.5 Hz), 7.85 (1H, d, J=3.5 Hz), 9.86 (1H, d, J=4.5 Hz), 15.40 (1H, brs)

Example 330

Compound 330

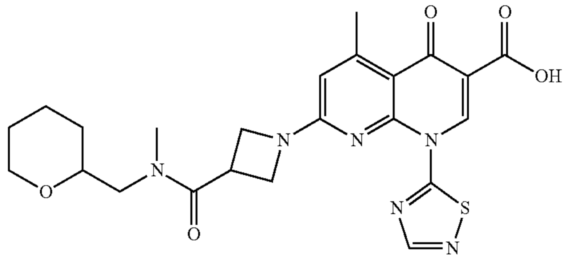

5-Methyl-7-{3-[methyl(oxan-2-ylmethyl)carbamoyl]azetidin-1-yl}-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-methyl-N-(oxan-2-ylmethyl)azetidine-3-carboxamide trifluoroacetate obtained in Example 010-(2) by the method described in Example 002-(3) or a method equivalent thereto.

1H-NMR (DMSO-d6): δ 1.15 (1H, s), 1.40-1.62 (4H, m), 1.73-1.87 (1H, m), 2.77-2.80 (3H, m), 2.90 (2H, brs), 3.00 (1H, s), 3.45-3.53 (1H, m), 3.83-3.97 (1H, m), 3.99-4.13 (1H, m), 4.30-4.73 (4H, m), 6.61-6.64 (1H, m), 8.81-8.83 (1H, m), 9.76-9.78 (1H, m), 15.03-15.16 (1H, m)

Example 331

Compound 331

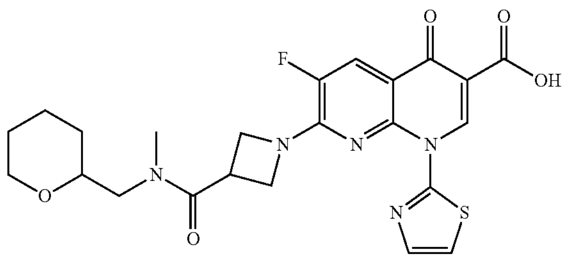

6-Fluoro-7-{3-[methyl(oxan-2-ylmethyl)carbamoyl]azetidin-1-yl}-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-methyl-N-(oxan-2-ylmethyl)azetidine-3-carboxamide trifluoroacetate obtained in Example 010-(2) by the method described in Example 002-(3) or a method equivalent thereto.

1H-NMR (DMSO-d6): δ 1.10-1.28 (1H, m), 1.38-1.60 (4H, m), 1.72-1.85 (1H, m), 2.89 (2H, s), 2.97 (1H, s), 3.43-3.52 (1H, m), 3.82-3.92 (1H, m), 4.00-4.15 (1H, m), 4.37-4.93 (4H, m), 7.81 (1H, dd, J=12.5, 3.5 Hz), 7.87 (1H, dd, J=3.5, 0.5 Hz), 8.12 (1H, dd, J=11.5, 4.0 Hz), 9.83 (1H, d, J=5.5 Hz), 14.80 (1H, brs)

Example 332

Compound 332

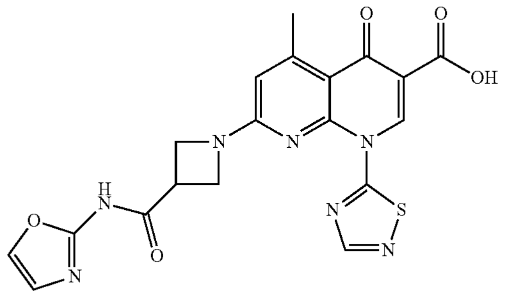

5-Methyl-7-{3-[(1,3-oxazol-2-yl)carbamoyl]azetidin-1-yl}-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-(1,3-oxazol-2-yl)azetidine-3-carboxamide trifluoroacetate obtained from 1,3-oxazol-2-amine by the method described in Example 005-(1) and Example 001-(2) or a method equivalent thereto by the method described in Example 001-(3) or a method equivalent thereto.

1H-NMR (DMSO-d6): δ 2.77 (3H, s), 3.80-3.99 (1H, m), 4.36-4.68 (4H, m), 6.61 (1H, d, J=1.1 Hz), 7.13 (1H, d, J=0.8 Hz), 7.90 (1H, d, J=0.8 Hz), 8.81 (1H, s), 9.73 (1H, s), 11.52 (1H, s), 15.04 (1H, brs)

Example 333

Compound 333

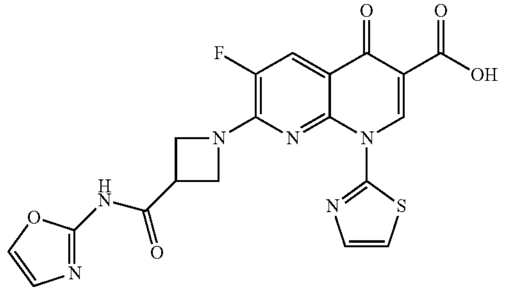

6-Fluoro-7-{3-[(1,3-oxazol-2-yl)carbamoyl]azetidin-1-yl}-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-(1,3-oxazol-2-yl)azetidine-3-carboxamide trifluoroacetate obtained in Example 332 by the method described in Example 001-(3) or a method equivalent thereto.

1H-NMR (DMSO-d6): δ 3.81-3.99 (1H, m), 4.46-4.90 (4H, m), 7.13 (1H, d, J=0.8 Hz), 7.79 (1H, d, J=3.5 Hz), 7.85 (1H, d, J=3.5 Hz), 7.90 (1H, d, J=0.8 Hz), 8.09 (1H, d, J=11.4 Hz), 9.79 (1H, s), 11.49 (1H, s), 14.75 (1H, brs)

Example 334

Compound 334

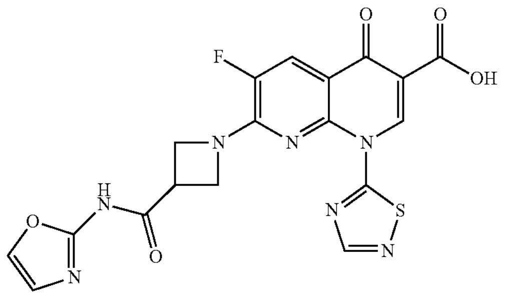

6-Fluoro-7-{3-[(1,3-oxazol-2-yl)carbamoyl]azetidin-1-yl}-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and N-(1,3-oxazol-2-yl)azetidine-3-carboxamide trifluoroacetate obtained in Example 332 by the method described in Example 001-(3) or a method equivalent thereto.

1H-NMR (DMSO-d6): δ 3.81-4.02 (1H, m), 4.58-4.88 (4H, m), 7.13 (1H, d, J=0.9 Hz), 7.89 (1H, d, J=0.9 Hz), 8.15 (1H, d, J=11.5 Hz), 8.85 (1H, s), 9.74 (1H, s), 11.51 (1H, s), 14.44 (1H, brs)

Example 335

Compound 335

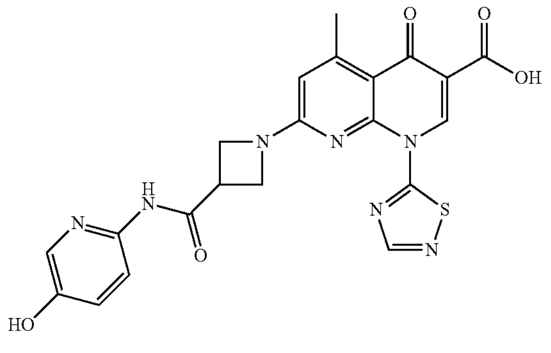

7-{3-[(5-Hydroxypyridin-2-yl)carbamoyl]azetidin-1-yl}-5-methyl-4-oxo-1-(1,2,4-thiadiazol-5-yl)-1,4-dihydro-1,8-naphthyridine-3-carboxylic acid (1) To a solution of 3-(6-{1-[(tert-butoxy) carbonyl]azetidin-3-amido}pyridin-3-yl)-1-tert-butyl azetidine-1,3-dicarboxylate (555 mg) in THF (4.7 mL) obtained from 6-aminopyridin-3-ol by the method described in Example 007-(1) or a method equivalent thereto was added a 1 mol/L aqueous sodium hydroxide solution (1.2 mL) under ice cooling, and the mixture was stirred overnight at the same temperature. To the reaction solution was added chloroform, and the mixture was washed with an aqueous ammonium chloride solution and brine. The organic layer was dried over sodium sulfate and concentrated. The residue was subjected to silica gel column chromatography (eluent: methanol/methylene chloride) to obtain crude tert-butyl 3-[(5-hydroxypyridin-2-yl)carbamoyl]azetidine-1-carboxylate.

(2) The title compound was obtained by the method described in Example 002-(3) or a method equivalent thereto using N-(5-hydroxypyridin-2-yl)azetidine-3-carboxamide trifluoroacetate obtained by the method described in Example 001-(2) or a method equivalent thereto from crude tert-butyl 3-[(5-hydroxypyridin-2-yl)carbamoyl]azetidine-1-carboxylate obtained in the preceding section, and 7-chloro-5-methyl-4-oxo-1-(1,2,4-thiadiazol-5-yl)-1,4-dihydro-1,8-naphthyridine-3-carboxylic acid obtained in Reference Example 002-(2).

1H-NMR (DMSO-d6): δ 2.79 (3H, s), 3.86-3.96 (1H, m), 4.32-4.71 (4H, m), 6.62 (1H, d, J=1.0 Hz), 7.22 (1H, d, J=9.0, 3.0 Hz), 7.88 (1H, d, J=3.0 Hz), 7.97 (1H, d, J=9.0 Hz), 8.82 (1H, s), 9.69 (1H, brs), 9.76 (1H, s), 10.53 (1H, s), 15.09 (1H, brs)

Example 336

Compound 336

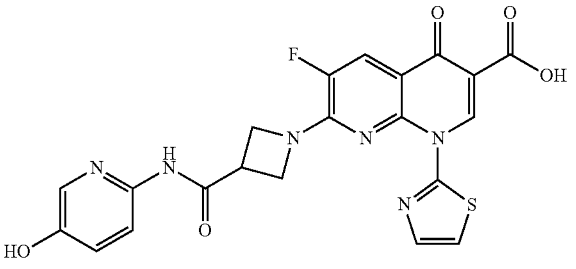

6-Fluoro-7-{3-[(5-hydroxypyridin-2-yl)carbamoyl]azetidin-1-yl}-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-(5-hydroxypyridin-2-yl)azetidine-3-carboxamide trifluoroacetate obtained in Example 335-(2) by the method described in Example 002-(3) or a method equivalent thereto.

1H-NMR (DMSO-d6): δ 3.88-3.98 (1H, m), 4.37-4.95 (4H, m), 7.22 (1H, d, J=9.0, 3.0 Hz), 7.78 (1H, d, J=3.5 Hz), 7.85 (1H, d, J=3.5 Hz), 7.87 (1H, d, J=2.5 Hz), 7.98 (1H, d, J=9.0 Hz), 8.10 (1H, d, J=11.5 Hz), 9.69 (1H, s), 9.81 (1H, s), 10.50 (1H, s), 14.78 (1H, brs)

Example 337

Compound 337

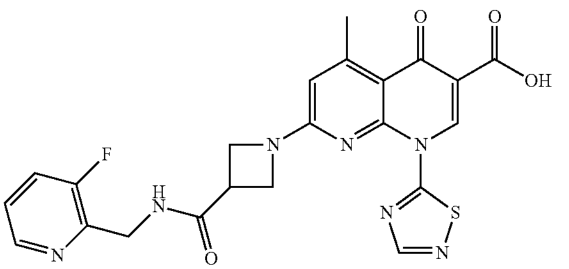

7-(3-{[(3-Fluoropyridin-2-yl)methyl]carbamoyl}azetidin-1-yl)-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-[(3-fluoropyridin-2-yl)methyl]azetidine-3-carboxamide hydrochloride obtained from (3-fluoropyridin-2-yl)methylamine by the method described in Example 007-(1) and Example 001-(2) or a method equivalent thereto by the method described in Example 008 or a method equivalent thereto.

1H-NMR (DMSO-d6): δ 2.73 (3H, s), 3.65-3.75 (1H, m), 4.15-4.61 (4H, m), 4.52 (2H, dd, J=5.5, 1.5 Hz), 6.40 (1H, s), 7.41 (1H, ddd, J=8.5, 4.5, 4.5 Hz), 7.70 (1H, ddd, J=10.0, 8.5, 1.5 Hz), 8.39 (1H, ddd, J=4.5, 1.5, 1.5 Hz), 8.68-8.73 (2H, m), 9.61 (1H, s)

Example 338

Compound 338

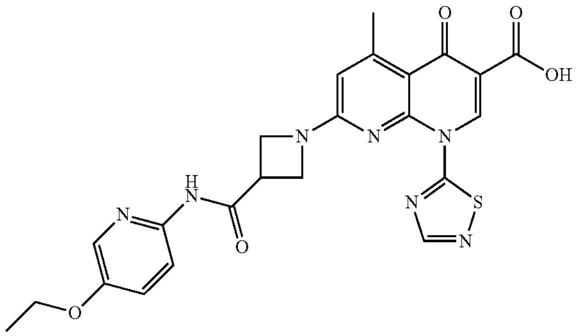

7-{3-[(5-Ethoxypyridin-2-yl)carbamoyl]azetidin-1-yl}-5-methyl-4-oxo-1-(1,2,4-thiadiazol-5-yl)-1,4-dihydro-1,8-naphthyridine-3-carboxylic acid The title compound was obtained by the method described in Example 002-(3) or a method equivalent thereto using N-(5-ethoxypyridin-2-yl)azetidine-3-carboxamide trifluoroacetate obtained by the methods described in Examples 009-(1) and 001-(2) or methods equivalent thereto from crude tert-butyl 3-[(5-hydroxypyridin-2-yl)carbamoyl]azetidine-1-carboxylate obtained in Example 335-(1), and 7-chloro-5-methyl-4-oxo-1-(1,2,4-thiadiazol-5-yl)-1,4-dihydro-1,8-naphthyridine-3-carboxylic acid obtained in Reference Example 002-(2).

1H-NMR (DMSO-d6): δ 1.33 (3H, t, J=7.0 Hz), 2.70 (3H, s), 3.89-3.97 (1H, m), 4.08 (2H, q, J=7.0 Hz), 4.36-4.76 (4H, m), 6.63 (1H, s), 7.44 (1H, dd, J=9.0, 3.0 Hz), 8.04 (1H, d, J=3.0 Hz), 8.07 (1H, d, J=9.0 Hz), 8.82 (1H, s), 9.77 (1H, s), 10.64 (1H, s), 15.10 (1H, brs)

Example 339

Compound 339

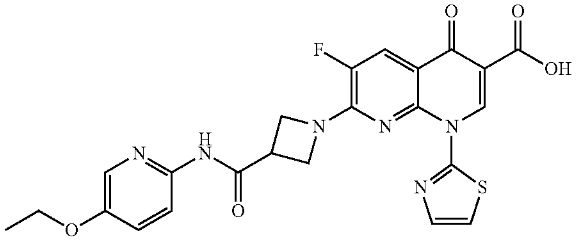

7-{3-[(5-Ethoxypyridin-2-yl)carbamoyl]azetidin-1-yl}-6-fluoro-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-(5-ethoxypyridin-2-yl)azetidine-3-carboxamide trifluoroacetate obtained in Example 338 by the method described in Example 002-(3) or a method equivalent thereto.

1H-NMR (DMSO-d6): δ 1.33 (3H, t, J=7.0 Hz), 3.89-3.99 (1H, m), 4.08 (2H, d, J=7.0 Hz), 4.48-4.89 (4H, m), 7.44 (1H, dd, J=9.0, 7.5 Hz), 7.78 (1H, d, J=3.5 Hz), 7.86 (1H, d, J=3.5 Hz), 8.04 (1H, d, J=3.0 Hz), 8.07 (1H, d, J=9.0 Hz), 8.12 (1H, d, J=11.5 Hz), 9.83 (1H, s), 10.61 (1H, s), 14.79 (1H, brs)

Example 340

Compound 340

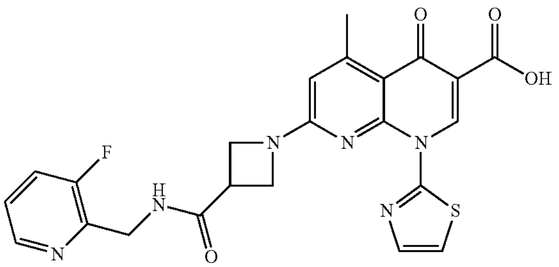

7-(3-{[(3-Fluoropyridin-2-yl)methyl]carbamoyl}azetidin-1-yl)-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-[(3-fluoropyridin-2-yl)methyl]azetidine-3-carboxamide hydrochloride obtained in Example 337 by the method described in Example 008 or a method equivalent thereto.

1H-NMR (DMSO-d6): δ 2.76 (3H, s), 3.63-3.72 (1H, m), 4.15-4.48 (4H, m), 4.51 (2H, dd, J=5.5, 1.5 Hz), 6.47 (1H, brs), 7.41 (1H, ddd, J=8.5, 4.5, 4.5 Hz), 7.66-7.71 (1H, m), 7.70 (1H, ddd, J=10.0, 8.5, 1.5 Hz), 7.80 (1H, d, J=3.5 Hz), 8.39 (1H, ddd, J=4.5, 1.5, 1.5 Hz), 8.68 (1H, t, J=5.5 Hz), 9.79 (1H, s), 15.42 (1H, brs)

Example 341

Compound 341

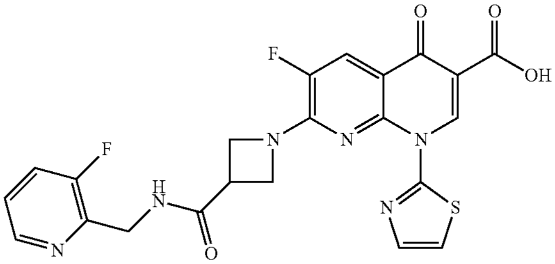

6-Fluoro-7-(3-{[(3-fluoropyridin-2-yl)methyl]carbamoyl}azetidin-1-yl)-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-[(3-fluoropyridin-2-yl)methyl]azetidine-3-carboxamide hydrochloride obtained in Example 337 by the method described in Example 008 or a method equivalent thereto.

1H-NMR (DMSO-d6): δ 3.66-3.75 (1H, m), 4.44-4.50 (2H, m), 4.52 (2H, dd, J=5.5, 1.5 Hz), 4.55-4.64 (2H, m), 7.41 (1H, ddd, J=8.5, 4.5, 4.5 Hz), 7.68 (1H, d, J=3.5 Hz), 7.70 (1H, ddd, J=10.0, 8.5, 1.5 Hz), 7.80 (1H, d, J=3.5 Hz), 8.02 (1H, d, J=11.5 Hz), 8.39 (1H, ddd, J=4.5, 1.5, 1.5 Hz), 8.67 (1H, t, J=5.5 Hz), 9.79 (1H, s)

Example 342

Compound 342

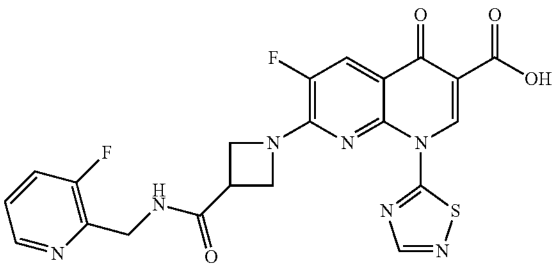

6-Fluoro-7-(3-{[(3-fluoropyridin-2-yl)methyl]carbamoyl}azetidin-1-yl)-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and N-[(3-fluoropyridin-2-yl)methyl]azetidine-3-carboxamide hydrochloride obtained in Example 337 by the method described in Example 008 or a method equivalent thereto.

1H-NMR (DMSO-d6): δ 3.66-3.78 (1H, m), 4.48-4.58 (4H, m), 4.63-4.71 (2H, m), 7.41 (1H, ddd, J=8.5, 4.5, 4.5 Hz), 7.70 (1H, ddd, J=10.0, 8.5, 1.5 Hz), 8.02 (1H, d, J=11.5 Hz), 8.39 (1H, ddd, J=4.5, 1.5, 1.5 Hz), 8.69 (1H, t, J=5.5 Hz), 8.74 (1H, s), 9.66 (1H, s)

Example 343

Compound 343

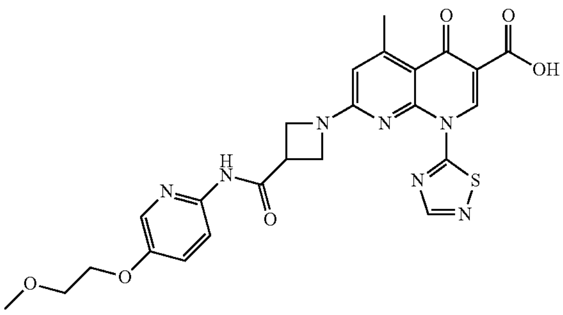

7-(3-{[5-(2-Methoxyethoxy)pyridin-2-yl]carbamoyl}azetidin-1-yl)-5-methyl-4-oxo-1-(1,2,4-thiadiazol-5-yl)-1,4-dihydro-1,8-naphthyridine-3-carboxylic acid The title compound was obtained by the method described in Example 002-(3) or a method equivalent thereto using N-[5-(2-methoxyethoxy)pyridin-2-yl]azetidine-3-carboxamide trifluoroacetate obtained by the methods described in Examples 009-(1) and 001-(2) or methods equivalent thereto from crude tert-butyl 3-[(5-hydroxypyridin-2-yl)carbamoyl]azetidine-1-carboxylate obtained in Example 335-(1), and 7-chloro-5-methyl-4-oxo-1-(1,2,4-thiadiazol-5-yl)-1,4-dihydro-1,8-naphthyridine-3-carboxylic acid obtained in Reference Example 002-(2).

1H-NMR (DMSO-d6): δ 2.79 (3H, s), 3.64-3.67 (2H, m), 3.88-3.98 (1H, m), 4.13-4.17 (2H, m), 4.34-4.71 (4H, m), 6.63 (1H, d, J=1.0 Hz), 7.47 (1H, dd, J=9.0, 3.0 Hz), 8.05-8.10 (2H, m), 8.82 (1H, s), 9.77 (1H, s), 10.65 (1H, s), 15.10 (1H, s)

Example 344

Compound 344

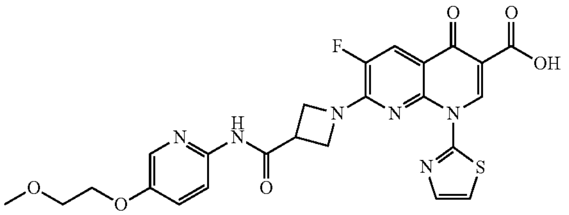

6-Fluoro-7-(3-{[5-(2-methoxyethoxy)pyridin-2-yl]carbamoyl}azetidin-1-yl)-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-[5-(2-methoxyethoxy)pyridin-2-yl]azetidine-3-carboxamide trifluoroacetate obtained in Example 343 by the method described in Example 002-(3) or a method equivalent thereto.

1H-NMR (DMSO-d6): δ 3.64-3.67 (2H, m), 3.92-3.98 (1H, m), 4.13-4.17 (2H, m), 4.45-4.94 (4H, m), 7.47 (1H, dd, J=9.0, 3.0 Hz), 7.79 (1H, d, J=3.5 Hz), 7.86 (1H, d, J=3.5 Hz), 8.05-8.10 (2H, m), 8.12 (1H, d, J=11.5 Hz), 9.83 (1H, s), 10.62 (1H, s), 14.80 (1H, s)

Example 345

Compound 345

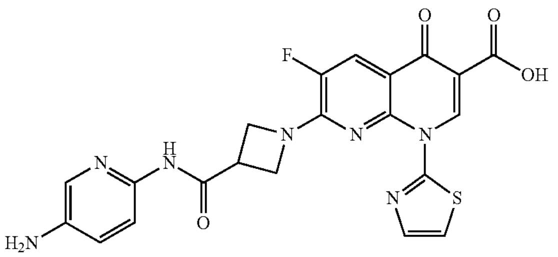

7-{3-[(5-Aminopyridin-2-yl)carbamoyl]azetidin-1-yl}-6-fluoro-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-(5-aminopyridin-2-yl)azetidine-3-carboxamide trifluoroacetate obtained in Example 012-(2) by the method described in Example 002-(3) or a method equivalent thereto.

1H-NMR (DMSO-d6): δ 3.86-3.94 (1H, m), 4.41-4.85 (4H, m), 5.11 (2H, s), 6.98 (1H, dd, J=8.0, 3.0 Hz), 7.69 (1H, d, J=2.5 Hz), 7.76-7.80 (1H, m), 7.82 (1H, d, J=9.0 Hz), 7.85-7.87 (1H, m), 8.07-8.14 (1H, m), 9.82 (1H, s), 10.31 (1H, s), 14.77 (1H, brs)

Example 346

Compound 346

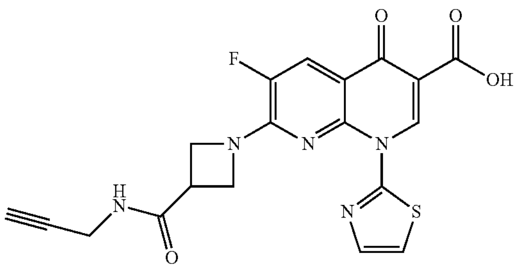

6-Fluoro-4-oxo-7-{3-[(prop-2-yn-1-yl)carbamoyl]azetidin-1-yl}-1-(1,3-thiazol-2-yl)-1,4-dihydro-1,8-naphthyridine-3-carboxylic acid The title compound was obtained by the method described in Example 001-(3) or a method equivalent thereto using N-(prop-2-yn-1-yl)azetidine-3-carboxamide trifluoroacetate obtained from prop-2-yn-1-amine by the methods described in Examples 005-(1) and 001-(2) or methods equivalent thereto, and 7-chloro-6-fluoro-4-oxo-1-(1,3-thiazol-2-yl)-1,4-dihydro-1,8-naphthyridine-3-carboxylic acid obtained in Reference Example 003-(2).

1H-NMR (DMSO-d6): δ 3.17 (1H, t, J=2.5 Hz), 3.61-3.68 (1H, m), 3.94 (2H, dd, J=5.5, 2.5 Hz), 4.38-4.80 (4H, m), 7.79 (1H, d, J=3.5 Hz), 7.86 (1H, d, J=3.5 Hz), 8.11 (1H, d, J=11.5 Hz), 8.63 (1H, t, J=5.5 Hz), 9.82 (1H, s), 14.79 (1H, brs)

Example 347

Compound 347

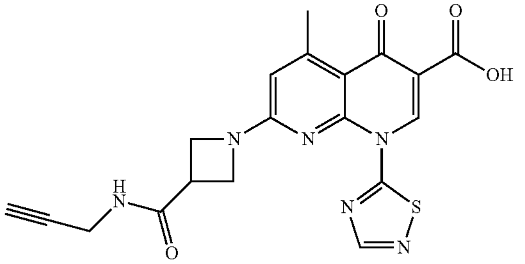

5-Methyl-4-oxo-7-{3-[(prop-2-yn-1-yl)carbamoyl]azetidin-1-yl}-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-(prop-2-yn-1-yl)azetidine-3-carboxamide trifluoroacetate obtained in Example 346 by the method described in Example 001-(3) or a method equivalent thereto.

1H-NMR (DMSO-d6): δ 2.77 (3H, d, J=1.0 Hz), 3.17 (1H, t, J=2.6 Hz), 3.60-3.67 (1H, m), 3.93-3.96 (2H, m), 4.23-4.64 (4H, m), 6.60 (1H, d, J=1.0 Hz), 8.66 (1H, t, J=5.5 Hz), 8.82 (1H, s), 9.75 (1H, s), 15.08 (1H, brs)

Example 348

Compound 348

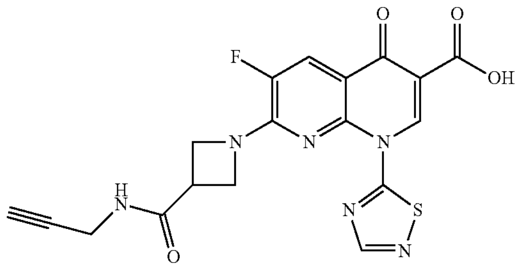

6-Fluoro-4-oxo-7-{3-[(prop-2-yn-1-yl)carbamoyl]azetidin-1-yl}-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and N-(prop-2-yn-1-yl)azetidine-3-carboxamide trifluoroacetate obtained in Example 346 by the method described in Example 001-(3) or a method equivalent thereto.

1H-NMR (DMSO-d6): δ 3.17 (1H, t, J=2.5 Hz), 3.64-3.71 (1H, m), 3.96 (2H, dd, J=5.5, 2.5 Hz), 4.48-4.82 (4H, m), 8.15 (1H, d, J=11.4 Hz), 8.65 (1H, t, J=5.5 Hz), 8.85 (1H, s), 9.74 (1H, s), 14.48 (1H, brs)

Example 349

Compound 349

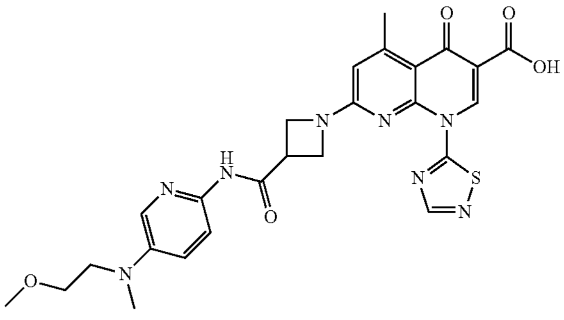

7-[3-({5-[(2-Methoxyethyl) (methyl)amino]pyridin-2-yl}carbamoyl)azetidin-1-yl]-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-{5-[(2-methoxyethyl)(methyl)amino]pyridin-2-yl}azetidine-3-carboxamide trifluoroacetate obtained from N5-(2-methoxyethyl)-N5-methylpyridine-2,5-diamine by the method described in Example 007-(1) and Example 001-(2) or a method equivalent thereto by the method described in Example 002-(3) or a method equivalent thereto.

1H-NMR (DMSO-d6): δ 2.79 (3H, s), 2.91 (3H, s), 3.24 (3H, s), 3.43-3.51 (4H, m), 3.86-3.95 (1H, m), 4.34-4.71 (4H, m), 6.63 (1H, d, J=1.0 Hz), 7.19 (1H, dd, J=9.0, 3.0 Hz), 7.83 (1H, d, J=3.0 Hz), 7.93 (1H, d, J=9.0 Hz), 8.82 (1H, s), 9.76 (1H, s), 10.44 (1H, s), 15.10 (1H, s)

Example 350

Compound 350

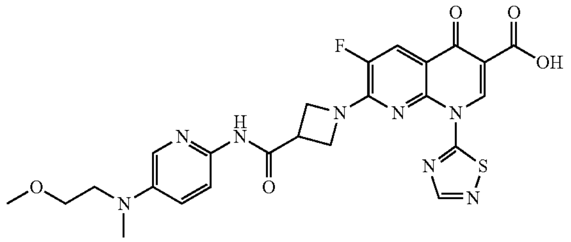

6-Fluoro-7-[3-({5-[(2-methoxyethyl) (methyl)amino]pyridin-2-yl}carbamoyl)azetidin-1-yl]-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and N-{5-[(2-methoxyethyl)(methyl)amino]pyridin-2-yl}azetidine-3-carboxamide trifluoroacetate obtained in Example 349 by the method described in Example 002-(3) or a method equivalent thereto.

1H-NMR (DMSO-d6): δ 2.91 (3H, s), 3.24 (3H, s), 3.43-3.53 (4H, m), 3.86-3.99 (1H, m), 4.53-4.88 (4H, m), 7.19 (1H, dd, J=9.0, 3.0 Hz), 7.83 (1H, d, J=3.0 Hz), 7.95 (1H, d, J=9.0 Hz), 8.15 (1H, d, J=11.5 Hz), 8.85 (1H, s), 9.75 (1H, s), 10.43 (1H, brs), 14.49 (1H, brs)

Example 351

Compound 351

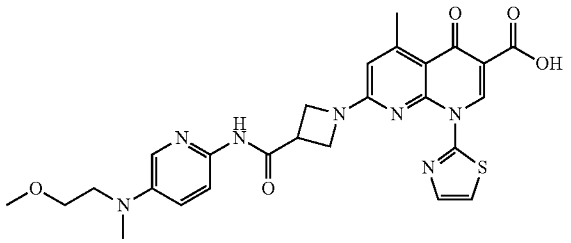

7-[3-({5-[(2-Methoxyethyl) (methyl)amino]pyridin-2-yl}carbamoyl)azetidin-1-yl]-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-{5-[(2-methoxyethyl) (methyl)amino]pyridin-2-yl}azetidine-3-carboxamide trifluoroacetate obtained in Example 349 by the method described in Example 002-(3) or a method equivalent thereto.

1H-NMR (DMSO-d6): δ 2.79 (3H, s), 2.91 (3H, s), 3.24 (3H, s), 3.45-3.50 (4H, m), 3.85-3.92 (1H, m), 4.30-4.57 (4H, m), 6.58 (1H, d, J=1.0 Hz), 7.18 (1H, dd, J=9.0, 3.0 Hz), 7.75 (1H, d, J=3.5 Hz), 7.82 (1H, d, J=3.0 Hz), 7.84 (1H, d, J=3.5 Hz), 7.93 (1H, d, J=9.0 Hz), 9.86 (1H, s), 10.42 (1H, s), 15.41 (1H, s)

Example 352

Compound 352

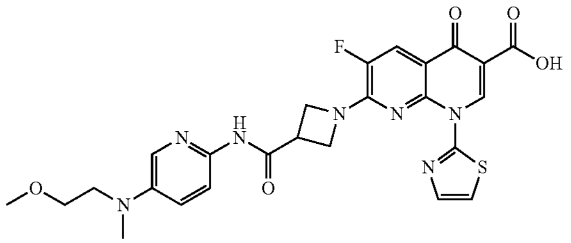

6-Fluoro-7-[3-({5-[(2-methoxyethyl) (methyl)amino]pyridin-2-yl}carbamoyl)azetidin-1-yl]-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-{5-[(2-methoxyethyl) (methyl)amino]pyridin-2-yl}azetidine-3-carboxamide trifluoroacetate obtained in Example 349 by the method described in Example 002-(3) or a method equivalent thereto.

1H-NMR (DMSO-d6): δ 2.95 (3H, s), 3.27 (3H, s), 3.49-3.55 (4H, m), 3.90-3.99 (1H, m), 4.51-4.86 (4H, m), 7.22 (1H, dd, J=9.0, 3.0 Hz), 7.82 (1H, d, J=3.5 Hz), 7.86 (1H, d, J=3.0 Hz), 7.90 (1H, d, J=3.5 Hz), 7.97 (1H, d, J=9.0 Hz), 8.16 (1H, d, J=11.5 Hz), 9.87 (1H, s), 10.45 (1H, s), 14.85 (1H, s)

Example 353

Compound 353

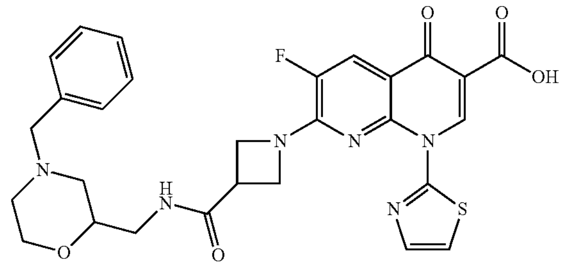

7-(3-{[(4-Benzylmorpholin-2-yl)methyl]carbamoyl}azetidin-1-yl)-6-fluoro-4-oxo-1-(1,3-thiazol-2-yl)-1,4-dihydro-1,8-naphthyridine-3-carboxylic acid The title compound was obtained by the method described in Example 001-(3) or a method equivalent thereto using N-[(4-benzylmorpholin-2-yl)methyl]azetidine-3-carboxamide hydrochloride obtained from (4-benzylmorpholin-2-yl)methylamine by the methods described in Examples 005-(1) and 001-(2) or methods equivalent thereto, and 7-chloro-6-fluoro-4-oxo-1-(1,3-thiazol-2-yl)-1,4-dihydro-1,8-naphthyridine-3-carboxylic acid obtained in Reference Example 003-(2).

1H-NMR (DMSO-d6): δ 4.62-4.64 (2H, m), 4.64-4.71 (8H, m), 4.71-4.74 (1H, m), 4.75-4.77 (1H, m), 4.33-4.80 (4H, m), 7.20-7.34 (5H, m), 7.72-7.77 (1H, m), 7.84 (1H, d, J=3.5 Hz), 8.06 (1H, brs), 8.26 (1H, t, J=6.0 Hz), 9.79 (1H, s)

Example 354

Compound 354

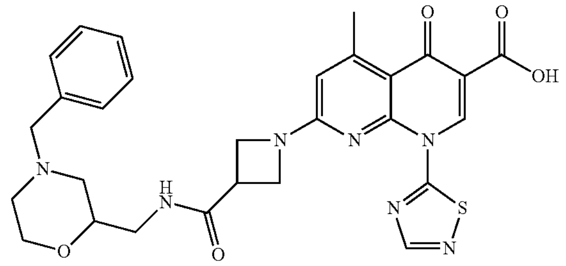

7-(3-{[(4-Benzylmorpholin-2-yl)methyl]carbamoyl}azetidin-1-yl)-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-[(4-benzylmorpholin-2-yl)methyl]azetidine-3-carboxamide hydrochloride obtained in Example 353 by the method described in Example 001-(3) or a method equivalent thereto.

1H-NMR (DMSO-d6): δ 2.63-2.78 (5H, m), 3.10-3.41 (2H, m), 3.45-3.66 (4H, m), 3.83 (1H, brs), 4.12-4.61 (4H, m), 6.55 (1H, s), 7.21-7.41 (5H, m), 8.32 (1H, brs), 8.81 (1H, a), 9.72 (1H, s)

Example 355

Compound 355

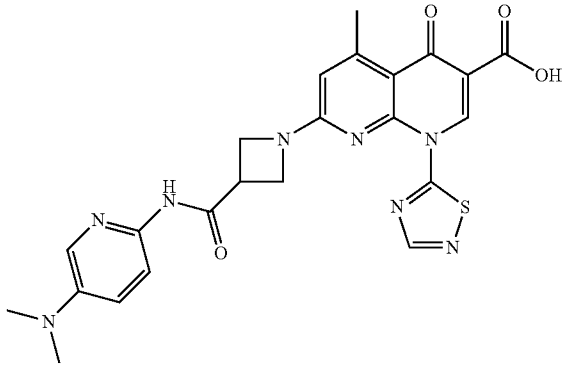

7-(3-{[5-(Dimethylamino)pyridin-2-yl]carbamoyl}azetidin-1-yl)-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-[5-(dimethylamino)pyridin-2-yl]azetidine-3-carboxamide trifluoroacetate obtained from N5,N5-dimethylpyridine-2,5-diamine by the method described in Example 007-(1) and Example 001-(2) or a method equivalent thereto by the method described in Example 002-(3) or a method equivalent thereto.

1H-NMR (DMSO-d6): δ 2.78 (3H, s), 2.89 (6H, s), 3.87-3.95 (1H, m), 4.36-4.71 (4H, m), 6.62 (1H, d, J=1.0 Hz), 7.23 (1H, d, J=9.0, 3.0 Hz), 7.85 (1H, d, J=3.0 Hz), 7.96 (1H, d, J=9.0 Hz), 8.82 (1H, d, J=2.0 Hz), 9.75 (1H, s), 10.50 (1H, s), 15.10 (1H, brs)

Example 356

Compound 356

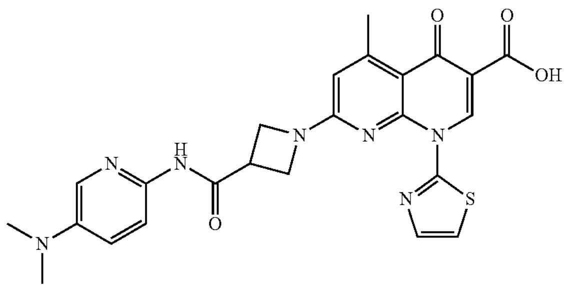

7-(3-{[5-(Dimethylamino)pyridin-2-yl]carbamoyl}azetidin-1-yl)-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-[5-(dimethylamino)pyridin-2-yl]azetidine-3-carboxamide trifluoroacetate obtained in Example 355 by the method described in Example 002-(3) or a method equivalent thereto.

1H-NMR (DMSO-d6): δ 2.79 (3H, d, J=1.0 Hz), 2.89 (6H, s), 3.85-3.92 (1H, m), 4.23-4.61 (4H, m), 6.58 (1H, d, J=1.0 Hz), 7.22 (1H, dd, J=9.0, 3.0 Hz), 7.75 (1H, d, J=3.5 Hz), 7.83-7.86 (2H, m), 7.96 (1H, d, J=9.0 Hz), 9.86 (1H, s), 10.46 (1H, s), 15.42 (1H, brs)

Example 357

Compound 357

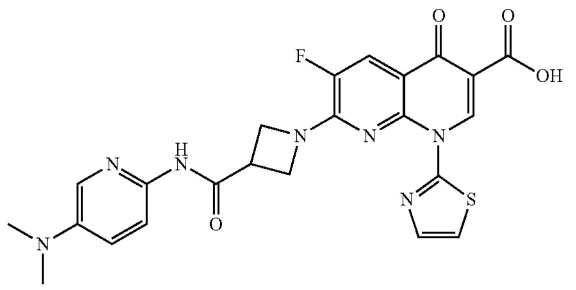

7-(3-{[5-(Dimethylamino)pyridin-2-yl]carbamoyl}azetidin-1-yl)-6-fluoro-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-[5-(dimethylamino)pyridin-2-yl]azetidine-3-carboxamide trifluoroacetate obtained in Example 355 by the method described in Example 002-(3) or a method equivalent thereto.

1H-NMR (DMSO-d6): δ 2.89 (6H, s), 3.87-3.97 (1H, m), 4.46-4.90 (4H, m), 7.22 (1H, dd, J=9.0, 3.0 Hz), 7.78 (1H, d, J=3.5 Hz), 7.84 (1H, d, J=3.0 Hz), 7.86 (1H, d, J=3.5 Hz), 7.97 (1H, d, J=9.0 Hz), 8.12 (1H, d, J=11.5 Hz), 9.83 (1H, s), 10.45 (1H, s), 14.81 (1H, brs)

Example 358

Compound 358

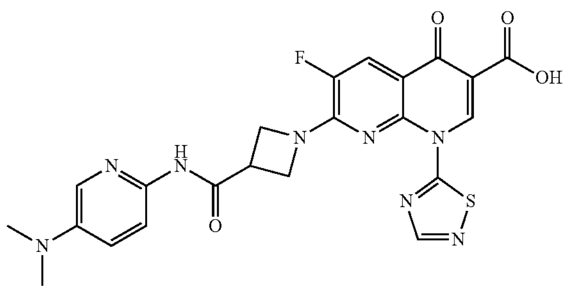

7-(3-{[5-(Dimethylamino)pyridin-2-yl]carbamoyl}azetidin-1-yl)-6-fluoro-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and N-[5-(dimethylamino)pyridin-2-yl]azetidine-3-carboxamide trifluoroacetate obtained in Example 355 by the method described in Example 002-(3) or a method equivalent thereto.

1H-NMR (DMSO-d6): δ 2.89 (6H, s), 3.89-3.99 (1H, m), 4.57-4.91 (4H, m), 7.22 (1H, dd, J=9.0, 3.0 Hz), 7.85 (1H, d, J=3.0 Hz), 7.98 (1H, d, J=2.5 Hz), 8.16 (1H, d, J=11.5 Hz), 8.71 (1H, s), 9.78 (1H, s), 10.47 (1H, s), 14.50 (1H, brs)

Example 359

Compound 359

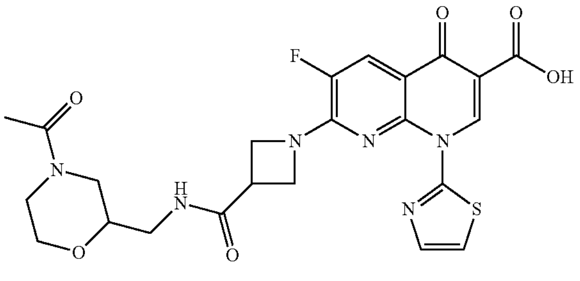

7-(3-{[(4-Acetylmorpholin-2-yl)methyl]carbamoyl}azetidin-1-yl)-6-fluoro-4-oxo-1-(1,3-thiazol-2-yl)-1,4-dihydro-1,8-naphthyridine-3-carboxylic acid (1) To a solution of tert-butyl 3-{[(4-benzylmorpholin-2-yl)methyl]carbamoyl)}azetidine-1-carboxylate (775 mg) in methanol obtained from (4-benzylmorpholin-2-yl)methylamine by the method described in Example 005-(1) or a method equivalent thereto was added 101 palladium carbon (155 mg), and the mixture was hydrogenated at room temperature for 2 days. The catalyst was filtered off, and the filtrate was then concentrated. The residue was subjected to silica gel column chromatography (eluent: methanol/chloroform) to obtain crude tert-butyl 3-{[(morpholin-2-yl)methyl]carbamoyl}azetidine-1-carboxylate.

(2) To a solution of crude tert-butyl 3-{[(morpholin-2-yl)methyl]carbamoyl}azetidine-1-carboxylate (100 mg) obtained in the preceding section, and triethylamine (152 μL) in methylene chloride was added acetyl chloride (74 μL) under ice cooling, and the mixture was stirred at room temperature for 18 hours. To the reaction solution was added an aqueous sodium bicarbonate solution, and the mixture was extracted with methylene chloride. The organic layer was dried over sodium sulfate and concentrated. The residue was purified by silica gel column chromatography (eluent: methanol/chloroform) to obtain tert-butyl 3-{[(4-acetylmorpholin-2-yl)methyl]carbamoyl}azetidine-1-carboxylate.

ESI-MS (m/z): 364 [M+Na]+

(3) The title compound was obtained by the method described in Example 001-(3) or a method equivalent thereto using N-[(4-acetylmorpholin-2-yl)methyl]azetidine-3-carboxamide hydrochloride obtained by the method described in Example 001-(2) or a method equivalent thereto from tert-butyl 3-{[(4-acetylmorpholin-2-yl)methyl]carbamoyl}azetidine-1-carboxylate obtained in the preceding section, and 7-chloro-6-fluoro-4-oxo-1-(1,3-thiazol-2-yl)-1,4-dihydro-1,8-naphthyridine-3-carboxylic acid obtained in Reference Example 003-(2).

1H-NMR (DMSO-d6): δ 1.99 (3H, s), 2.35-2.43 (1H, m), 2.60-2.72 (1H, m), 3.09-3.17 (1H, m), 3.19-3.48 (2H, m), 3.44 (1H, td, J=11.5, 2.5 Hz), 3.60-3.76 (2H, m), 3.80-3.90 (1H, m), 4.08-4.79 (5H, m), 7.77 (1H, J=3.5 Hz), 7.79-7.85 (2H, m), 8.06 (1H, d, J=11.5 Hz), 8.30-8.38 (1H, m), 9.77 (1H, s)

Example 360

Compound 360

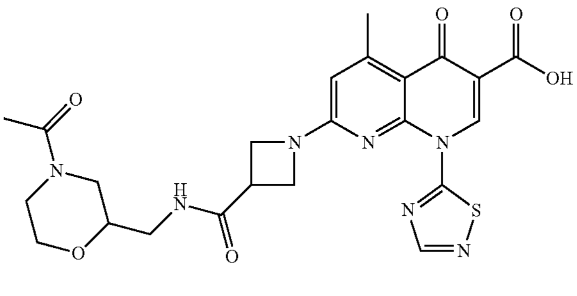

7-(3-{[(4-Acetylmorpholin-2-yl)methyl]carbamoyl}azetidin-1-yl)-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-[(4-acetylmorpholin-2-yl)methyl]azetidine-3-carboxamide hydrochloride obtained in Example 359-(3) by the method described in Example 001-(3) or a method equivalent thereto.

1H-NMR (DMSO-d6): δ 1.99 (3H, s), 2.35-2.43 (1H, m), 2.60-2.71 (1H, m), 2.74 (3H, s), 3.13 (1H, td, J=13.0, 3.0 Hz), 3.19-3.48 (2H, m), 3.44 (1H, td, J=11.5, 2.5 Hz), 3.60-3.76 (2H, m), 3.80-3.90 (1H, m), 4.12-4.63 (5H, m), 6.55 (1H, s), 8.31-8.40 (1H, m), 8.80 (1H, s), 9.69 (1H, s)

Example 361

Compound 361

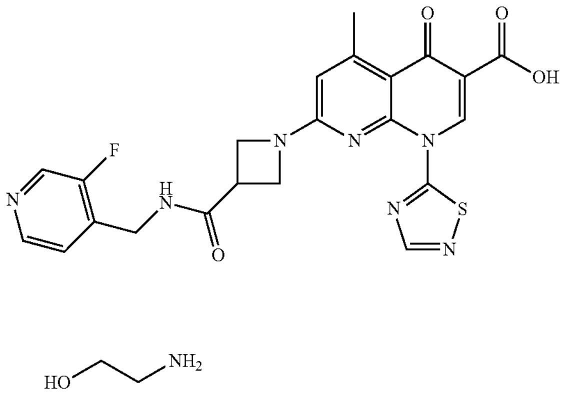

7-(3-{[(3-Fluoropyridin-4-yl)methyl]carbamoyl}azetidin-1-yl)-5-methyl-4-oxo-1-(1,2,4-thiadiazol-5-yl)-1,4-dihydro-1,8-naphthyridine-3-carboxylic acid 2-aminoethan-1-ol salt (1) Crude 7-(3-{[(3-fluoropyridin-4-yl)methyl]carbamoyl}azetidin-1-yl)-5-methyl-4-oxo-1-(1,2,4-thiadiazol-5-yl)-1,4-dihydro-1,8-naphthyridine-3-carboxylic acid was obtained by the method described in Example 008 or a method equivalent thereto using N-[(3-fluoropyridin-4-yl)methyl]azetidine-3-carboxamide hydrochloride obtained from (3-fluoropyridin-4-yl)methylamine by the methods described in Examples 007-(1) and 001-(2) or methods equivalent thereto, and 7-chloro-5-methyl-4-oxo-1-(1,2,4-thiadiazol-5-yl)-1,4-dihydro-1,8-naphthyridine-3-carboxylic acid obtained in Reference Example 002-(2).

(2) To a solution of crude 7-(3-{[(3-fluoropyridin-4-yl)methyl]carbamoyl}azetidin-1-yl)-5-methyl-4-oxo-1-(1,2,4-thiadiazol-5-yl)-1,4-dihydro-1,8-naphthyridine-3-carboxylic acid (40 mg) obtained in the preceding section in methanol (800 μL) were added 2-aminoethan-1-ol (60 μL) and water (5 mL), and the mixture was stirred at 60° C. for 10 minutes. Insoluble material was filtered off, and the filtrate was then concentrated to obtain 31 mg of the title compound.

1H-NMR (DMSO-d6): δ 2.54-2.58 (2H, m), 2.73 (3H, s), 3.62-3.79 (1H, m), 4.16-4.64 (6H, m), 6.41 (1H, brs), 7.34-7.45 (1H, m), 8.40 (1H, d, J=5.0 Hz), 8.51 (1H, d, J=1.5 Hz), 8.71 (1H, s), 8.79-8.90 (1H, m), 9.60 (1H, s)

Example 362

Compound 362

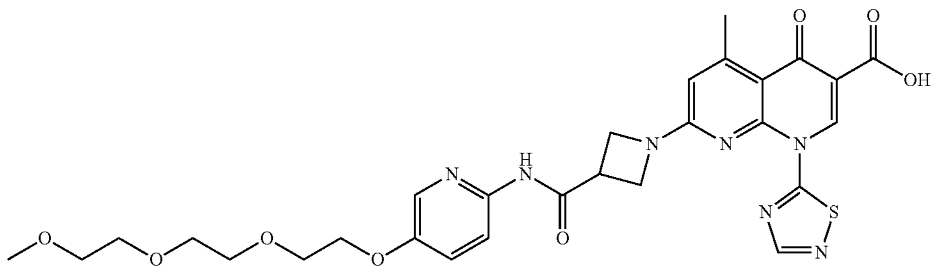

7-{3-[(5-{2-[2-(2-Methoxyethoxy)ethoxy]ethoxy}pyridin-2-yl)carbamoyl]azetidin-1-yl}-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-(5-{2-[2-(2-methoxyethoxy)ethoxy]ethoxy}pyridin-2-yl)azetidine-3-carboxamide trifluoroacetate obtained from crude tert-butyl 3-[(5-hydroxypyridin-2-yl)carbamoyl]azetidine-3-carboxylate obtained in Example 335-(1) by the method described in Example 009-(1) and Example 001-(2) or a method equivalent thereto by the method described in Example 002-(3) or a method equivalent thereto.

1H-NMR (DMSO-d6): δ 2.77 (3H, s), 3.23 (3H, s), 3.40-3.44 (2H, m), 3.49-3.56 (4H, m), 3.56-3.61 (2H, m), 3.70-3.76 (2H, m), 3.88-3.98 (1H, m), 4.12-4.17 (2H, m), 4.35-4.69 (4H, m), 6.61 (1H, s), 7.47 (1H, dd, J=9.0, 3.0 Hz), 8.00-8.11 (2H, m), 8.81 (1H, s), 9.73 (1H, s), 10.67 (1H, s), 15.08 (1H, s)

Example 363

Compound 363

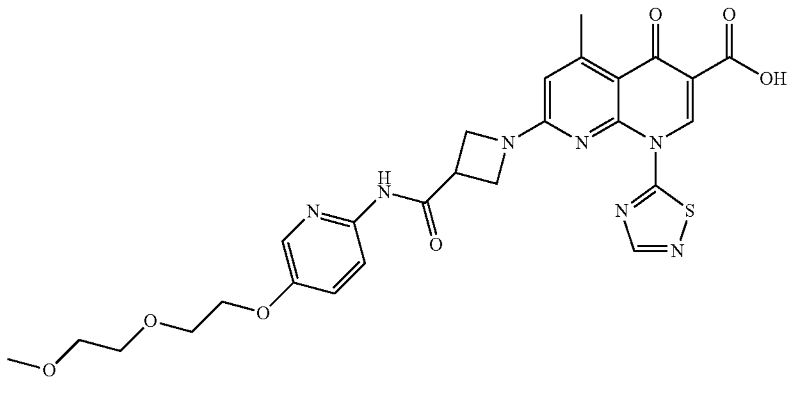

7-[3-({5-[2-(2-Methoxyethoxy)ethoxy]pyridin-2-yl}carbamoyl)azetidin-1-yl]-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-{5-[2-(2-methoxyethoxy)ethoxy]pyridin-2-yl}azetidine-3-carboxamide trifluoroacetate obtained from crude tert-butyl 3-[(5-hydroxypyridin-2-yl)carbamoyl]azetidine-3-carboxylate obtained in Example 335-(1) by the method described in Example 009-(1) and Example 001-(2) or a method equivalent thereto by the method described in Example 002-(3) or a method equivalent thereto.

1H-NMR (DMSO-d6): δ 2.79 (3H, s), 3.24 (3H, s), 3.44-3.48 (2H, m), 3.56-3.61 (2H, m), 3.71-3.76 (2H, m), 3.88-3.98 (1H, m), 4.12-4.17 (2H, m), 4.35-4.71 (4H, m), 6.63 (1H, d, J=1.0 Hz), 7.47 (1H, dd, J=9.0, 3.0 Hz), 8.05-8.10 (2H, m), 8.82 (1H, s), 9.76 (1H, s), 10.67 (1H, s), 15.09 (1H, s)

Example 364

Compound 364

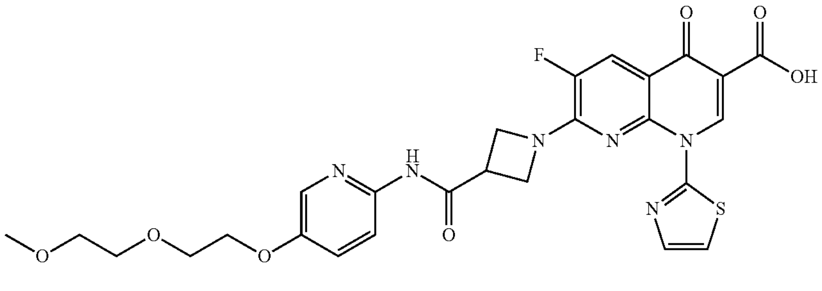

6-Fluoro-7-[3-({5-[2-(2-methoxyethoxy)ethoxy]pyridin-2-yl}carbamoyl)azetidin-1-yl]-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-{5-[2-(2-methoxyethoxy)ethoxy]pyridin-2-yl}azetidine-3-carboxamide trifluoroacetate obtained in Example 363 by the method described in Example 002-(3) or a method equivalent thereto.

1H-NMR (DMSO-d6): δ 3.24 (3H, s), 3.44-3.48 (2H, m), 3.56-3.60 (2H, m), 3.71-3.76 (2H, m), 3.90-3.98 (1H, m), 4.13-4.17 (2H, m), 4.45-4.91 (4H, m), 7.47 (1H, dd, J=9.0, 3.0 Hz), 7.79 (1H, d, J=3.5 Hz), 7.86 (1H, d, J=3.5 Hz), 8.06-8.10 (2H, m), 8.13 (1H, d, J=11.5 Hz), 9.84 (1H, s), 10.64 (1H, s), 14.81 (1H, s)

Example 365

Compound 365

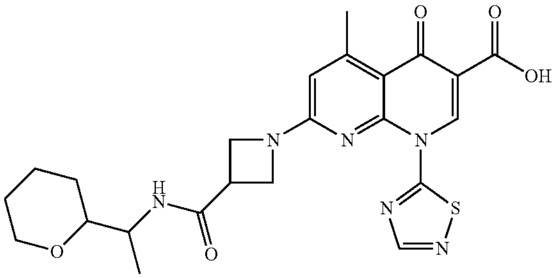

5-Methyl-7-(3-{[1-(oxan-2-yl)ethyl]carbamoyl}azetidin-1-yl)-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-[1-(oxan-2-yl)ethyl]azetidine-3-carboxamide trifluoroacetate obtained from 1-(oxan-2-yl)ethan-1-amine by the method described in Example 005-(1) and Example 001-(2) or a method equivalent thereto by the method described in Example 001-(3) or a method equivalent thereto.

1H-NMR (DMSO-d6): δ 1.06 (3H, d, J=6.9 Hz), 1.14-1.62 (5H, m), 1.71-1.83 (1H, m), 2.77 (3H, s), 3.11-3.17 (1H, m), 3.56-3.96 (3H, m), 4.12-4.69 (5H, m), 6.64 (1H, s), 8.01-8.09 (1H, m), 9.75 (1H, s), 15.14 (1H, brs)

Example 366

Compound 366

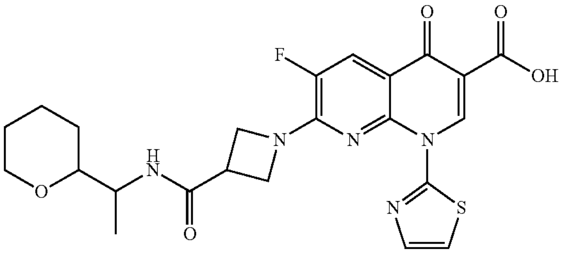

6-Fluoro-7-(3-{[1-(oxan-2-yl)ethyl]carbamoyl}azetidin-1-yl)-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-[1-(oxan-2-yl)ethyl]azetidine-3-carboxamide trifluoroacetate obtained in Example 365 by the method described in Example 001-(3) or a method equivalent thereto.

1H-NMR (DMSO-d6): δ 1.05 (3H, d, J=6.8 Hz), 1.12-1.27 (2H, m), 1.53-0.60 (3H, m), 1.73-1.83 (1H, m), 3.11-3.18 (1H, m), 3.59-3.96 (3H, m), 4.10-4.85 (5H, m), 7.79 (1H, d, J=3.4 Hz), 7.86 (1H, d, J=3.4 Hz), 7.98 (0.3H, d, J=8.6 Hz), 8.06 (0.7H, d, J=8.6 Hz), 8.11 (1H, d, J=11.6 Hz), 9.82 (1H, s), 14.82 (1H, brs)

Example 367

Compound 367

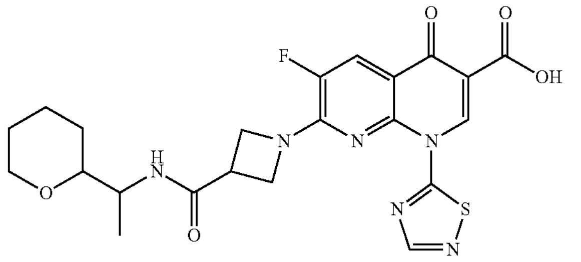

6-Fluoro-7-(3-{[1-(oxan-2-yl)ethyl]carbamoyl}azetidin-1-yl)-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and N-[1-(oxan-2-yl)ethyl]azetidine-3-carboxamide trifluoroacetate obtained in Example 365 by the method described in Example 001-(3) or a method equivalent thereto.

1H-NMR (DMSO-d6): δ 1.06 (3H, d, J=6.8 Hz), 1.37-1.61 (5H, m), 1.71-1.86 (1H, m), 3.12-3.19 (1H, m), 3.61-3.96 (3H, m), 4.40-4.94 (5H, m), 8.00 (0.3H, d, J=8.8 Hz), 8.08 (0.7H, d, J=8.8 Hz), 8.14 (1H, d, J=11.4 Hz), 8.85 (1H, s), 9.74 (1H, s), 14.51 (1H, brs)

Example 368

Compound 368

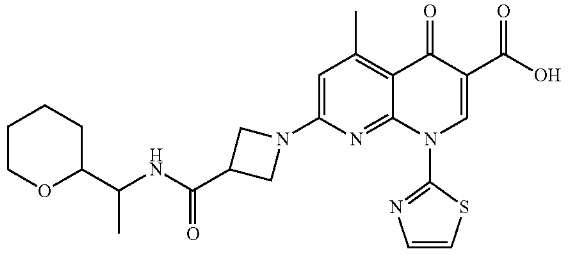

5-Methyl-7-(3-{[1-(oxan-2-yl)ethyl]carbamoyl}azetidin-1-yl)-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-[1-(oxan-2-yl)ethyl]azetidine-3-carboxamide trifluoroacetate obtained in Example 365 by the method described in Example 001-(3) or a method equivalent thereto.

1H-NMR (DMSO-d6): δ 1.05 (3H, d, J=6.8 Hz), 1.13-1.62 (5H, m), 1.73-1.84 (1H, m), 2.77 (3H, s), 3.10-3.18 (1H, m), 3.54-3.95 (3H, m), 4.10-4.85 (5H, m), 6.53 (1H, s), 7.75 (1H, d, J=3.6 Hz), 7.84 (1H, d, J=3.6 Hz), 7.98 (0.3H, d, J=8.7 Hz), 8.06 (0.7H, d, J=8.7 Hz), 9.84 (1H, s), 15.42 (1H, brs)

Example 369

Compound 369

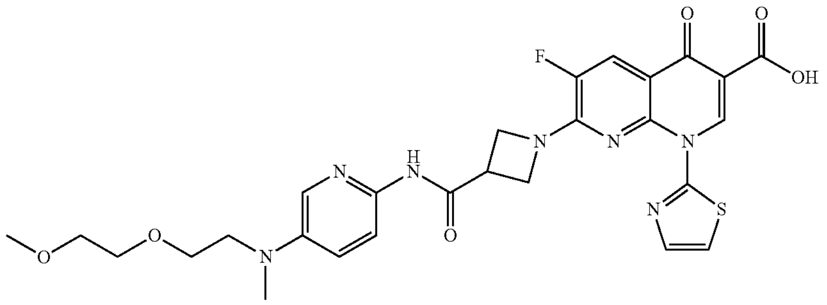

6-Fluoro-7-{3-[(5-{[2-(2-methoxyethoxy)ethyl](methyl)amino}pyridin-2-yl)carbamoyl]azetidin-1-yl}-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-(5-{[2-(2-methoxyethoxy)ethyl](methyl)amino}pyridin-2-yl)azetidine-3-carboxamide trifluoroacetate obtained in Example 013-(2) by the method described in Example 002-(3) or a method equivalent thereto.

1H-NMR (DMSO-d6): δ 2.92 (3H, s), 3.22 (3H, s), 3.39-3.43 (2H, m), 3.46-3.52 (4H, m), 3.53-3.58 (2H, m), 3.86-3.96 (1H, m), 4.41-4.87 (4H, m), 7.19 (1H, dd, J=9.0, 3.0 Hz), 7.78 (1H, d, J=3.5 Hz), 7.83 (1H, d, J=3.0 Hz), 7.86 (1H, d, J=3.5 Hz), 7.97 (1H, d, J=9.0 Hz), 8.10 (1H, d, J=11.5 Hz), 9.82 (1H, s), 10.42 (1H, s), 14.80 (1H, s)

Example 370

Compound 370

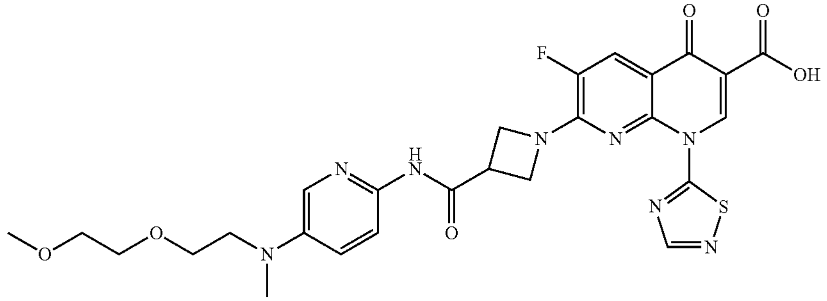

6-Fluoro-7-{3-[(5-{[2-(2-methoxyethoxy)ethyl](methyl)amino}pyridin-2-yl)carbamoyl]azetidin-1-yl}-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and N-(5-{[2-(2-methoxyethoxy)ethyl](methyl)amino}pyridin-2-yl)azetidine-3-carboxamide trifluoroacetate obtained in Example 013-(2) by the method described in Example 002-(3) or a method equivalent thereto.

1H-NMR (DMSO-d6): δ 2.92 (3H, s), 3.22 (3H, s), 3.39-3.42 (2H, m), 3.46-3.52 (4H, m), 3.53-3.56 (2H, m), 3.89-3.98 (1H, m), 4.60-4.90 (4H, m), 7.20 (1H, dd, J=9.0, 3.0 Hz), 7.83 (1H, d, J=3.0 Hz), 7.95 (1H, d, J=9.0 Hz), 8.16 (1H, d, J=11.5 Hz), 8.85 (1H, s), 9.75 (1H, s), 10.44 (1H, brs), 14.50 (1H, s)

Example 371

Compound 371

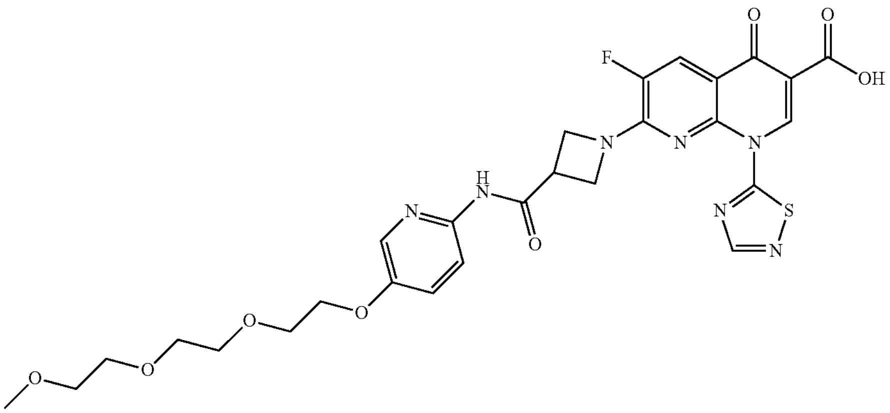

6-Fluoro-7-{3-[(5-{2-[2-(2-methoxyethoxy)ethoxy] ethoxy}pyridin-2-yl)carbamoyl]azetidin-1-yl}-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and N-(5-{2-[2-(2-methoxyethoxy) ethoxy]ethoxy}pyridin-2-yl)azetidine-3-carboxamide trifluoroacetate obtained in Example 362 by the method described in Example 002-(3) or a method equivalent thereto.

1H-NMR (DMSO-d6): δ 3.23 (3H, s), 3.40-3.44 (2H, m), 3.49-3.56 (4H, m), 3.56-3.60 (2H, m), 3.72-3.77 (2H, m), 3.93-4.00 (1H, m), 4.13-4.17 (2H, m), 4.58-4.90 (4H, m), 7.48 (1H, dd, J=9.0, 3.0 Hz), 8.06-8.11 (2H, m), 8.16 (1H, d, J=11.5 Hz), 8.85 (1H, s), 9.74 (1H, s), 10.66 (1H, s), 14.48 (1H, brs)

Example 372

Compound 372

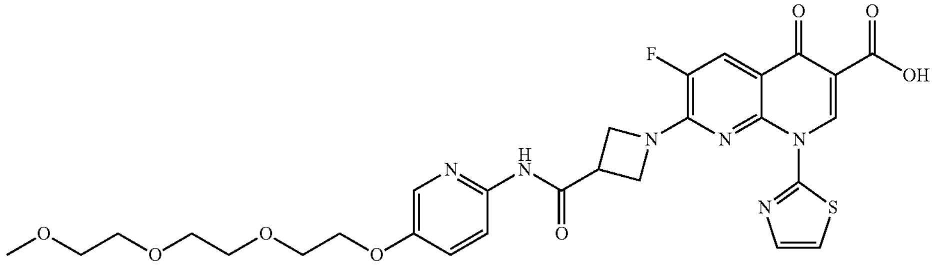

6-Fluoro-7-{3-[(5-{2-[2-(2-methoxyethoxy)ethoxy] ethoxy}pyridin-2-yl)carbamoyl]azetidin-1-yl}-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1-1,8-naphthyridine-3-carboxylic acid obtained in Reference Example 003-(2) N-(5-{2-[2-(2-methoxyethoxy)ethoxy] ethoxy}pyridin-2-yl)azetidine-3-carboxamide trifluoroacetate obtained in Example 362 by the method described in Example 002-(3) or a method equivalent thereto.

1H-NMR (DMSO-d6): δ 3.23 (3H, s), 3.40-3.44 (2H, m), 3.49-3.56 (4H, m), 3.56-3.61 (2H, m), 3.71-3.76 (2H, m), 3.91-3.99 (1H, m), 4.12-4.17 (2H, m), 4.44-4.87 (4H, m), 7.48 (1H, dd, J=9.0, 3.0 Hz), 7.79 (1H, d, J=3.5 Hz), 7.86 (1H, d, J=3.5 Hz), 8.06-8.14 (3H, m), 9.83 (1H, s), 10.64 (1H, s), 14.80 (1H, s)

Example 373

Compound 373

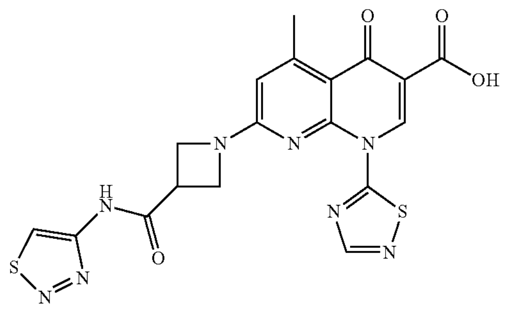

5-Methyl-4-oxo-7-{3-[(1,2,3-thiadiazol-4-yl)carbamoyl]azetidin-1-yl}-1-(1,2,4-thiadiazol-5-yl)-1,4-dihydro-1,8-naphthyridine-3-carboxylic acid The title compound was obtained by the method described in Example 001-(3) or a method equivalent thereto using N-(1,2,3-thiadiazol-4-yl)azetidine-3-carboxamide trifluoroacetate obtained from 1,2,3-thiadiazol-4-amine by the methods described in Examples 005-(1) and 001-(2) or methods equivalent thereto, and 7-chloro-5-methyl-4-oxo-1-(1,2,4-thiadiazol-5-yl)-1,4-dihydro-1,8-naphthyridine-3-carboxylic acid obtained in Reference Example 002-(2).

1H-NMR (DMSO-d6): δ 2.78 (3H, d, J=1.0 Hz), 3.97-4.04 (1H, m), 4.42-4.75 (4H, m), 6.64 (1H, d, J=1.0 Hz), 8.82 (1H, s), 9.08 (1H, s), 9.75 (1H, s), 12.11 (1H, s), 15.07 (1H, brs)

Example 374

Compound 374

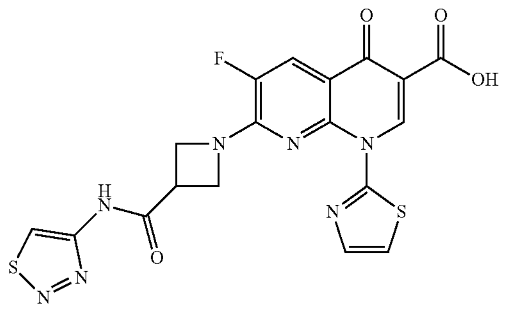

6-Fluoro-4-oxo-7-{3-[(1,2,3-thiadiazol-4-yl)carbamoyl]azetidin-1-yl}-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-(1,2,3-thiadiazol-4-yl)azetidine-3-carboxamide trifluoroacetate obtained in Example 373 by the method described in Example 001-(3) or a method equivalent thereto.

1H-NMR (DMSO-d6): δ 3.98-4.05 (1H, m), 4.46-4.92 (4H, m), 7.79 (1H, d, J=3.5 Hz), 7.86 (1H, d, J=3.5 Hz), 8.13 (1H, d, J=11.4 Hz), 9.08 (1H, s), 9.82 (1H, s), 12.09 (1H, s), 14.78 (1H, brs)

Example 375

Compound 375

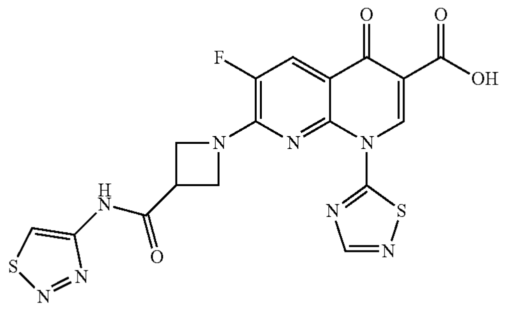

6-Fluoro-4-oxo-7-{3-[(1,2,3-thiadiazol-4-yl)carbamoyl]azetidin-1-yl}-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and N-(1,2,3-thiadiazol-4-yl)azetidine-3-carboxamide trifluoroacetate obtained in Example 373 by the method described in Example 001-(3) or a method equivalent thereto.

1H-NMR (DMSO-d6): δ 4.00-4.07 (1H, m), 4.70-4.91 (4H, m), 8.18 (1H, d, J=11.4 Hz), 8.86 (1H, s), 9.09 (1H, s), 9.76 (1H, s), 12.10 (1H, s), 14.48 (1H, brs)

Example 376

Compound 376

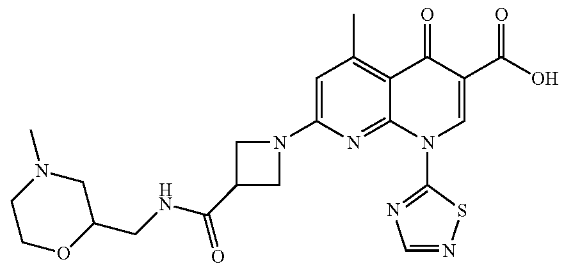

5-Methyl-7-(3-{[(4-methylmorpholin-2-yl)methyl]carbamoyl}azetidin-1-yl)-4-oxo-1-(1,2,4-thiadiazol-5-yl)-1,4-dihydro-1,8-naphthyridine-3-carboxylic acid (1) A mixture of crude tert-butyl 3-{[(morpholin-2-yl)methyl]carbamoyl}azetidine-1-carboxylate (100 mg) obtained in Example 359-(1), 36% aqueous formaldehyde solution (73 μL), sodium triacetoxyborohydride (262 mg), acetic acid (57 μL), and methanol (2.8 mL) was stirred at room temperature for 2 hours. The reaction solution was concentrated, and the residue was then purified by silica gel column chromatography (eluent: methanol/chloroform) to obtain 99 mg of tert-butyl 3-{[(4-methylmorpholin-2-yl)methyl]carbamoyl}azetidine-1-carboxylate.

1H-NMR (CDCl3): δ 1.45 (9H, s), 1.89 (1H, t, J=10.5 Hz), 2.15 (1H, td, J=12.0, 3.5 Hz), 2.31 (3H, s), 2.71 (1H, d, J=11.5 Hz), 2.76 (1H, d, J=11.5 Hz), 3.16-3.22 (2H, m), 3.56-3.60 (1H, m), 3.63-3.68 (1H, m), 3.67-3.72 (1H, m), 3.87-3.89 (1H, m), 4.02-4.17 (4H, m), 5.89 (1H, brs)

(2) The title compound was obtained by the method described in Example 001-(3) or a method equivalent thereto using N-[(4-methylmorpholin-2-yl)methyl]azetidine-3-carboxamide hydrochloride obtained by the method described in Example 001-(2) or a method equivalent thereto from tert-butyl 3-{([(4-methylmorpholin-2-yl)methyl]carbamoyl}azetidine-1-carboxylate obtained in the preceding section, and 7-chloro-5-methyl-4-oxo-1-(1,2,4-thiadiazol-5-yl)-1,4-dihydro-1,8-naphthyridine-3-carboxylic acid obtained in Reference Example 002-(2).

1H-NMR (DMSO-d6): δ 1.67 (1H, t, J=10.5 Hz), 1.94 (1H, td, J=11.0, 3.0 Hz), 2.15 (3H, s), 2.42-2.56 (1H, m), 2.66-2.68 (1H, m), 2.74 (3H, s), 3.14-3.20 (2H, m), 3.44-3.52 (2H, m), 3.59-3.68 (1H, m), 3.74-3.81 (1H, m), 4.12-4.66 (4H, m), 6.49 (1H, s), 8.29 (1H, t, J=5.5 Hz), 8.76 (1H, s), 9.68 (1H, s)

Example 377

Compound 377

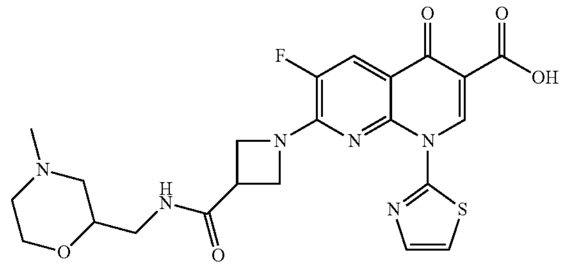

6-Fluoro-7-(3-{[(4-methylmorpholin-2-yl)methyl] carbamoyl}azetidin-1-yl)-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-[(4-methylmorpholin-2-yl)methyl]azetidine-3-carboxamide hydrochloride obtained in Example 376-(2) by the method described in Example 001-(3) or a method equivalent thereto.

1H-NMR (DMSO-d6): δ 1.67 (1H, t, J=11.0 Hz), 1.94 (1H, td, J=11.5, 3.0 Hz), 2.15 (3H, S), 2.42-2.57 (1H, m), 2.65-2.68 (1H, m), 3.13-3.20 (2H, m), 3.44-3.51 (2H, m), 3.60-3.69 (1H, m), 3.74-3.80 (1H, m), 4.31-4.76 (4H, m), 7.71 (1H, d, J=3.5 Hz), 7.81 (1H, d, J=3.5 Hz), 8.03 (1H, d, J=11.5 Hz), 8.27 (1H, t, J=6.0 Hz), 9.82 (1H, s)

Example 378

Compound 378

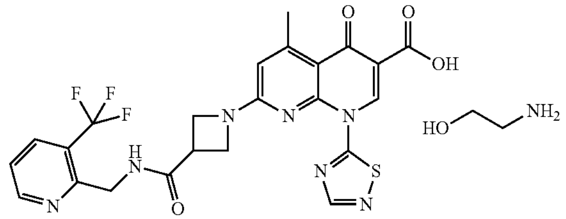

5-Methyl-4-oxo-1-(1,2,4-thiadiazol-5-yl)-7-[3-({[3-(trifluoromethyl)pyridin-2-yl]methyl}carbamoyl) azetidin-1-yl]-1,4-dihydro-1,8-naphthyridine-3-carboxylic acid 2-aminoethan-1-ol salt (1) Crude 5-methyl-4-oxo-1-(1,2,4-thiadiazol-5-yl)-7-[3-({[3-(trifluoromethyl)pyridin-2-yl]methyl}carbamoyl)azetidin-1-yl]-1,4-dihydro-1,8-naphthyridine-3-carboxylic acid was obtained by the method described in Example 008 or a method equivalent thereto using N-{([3-(trifluoromethyl) pyridin-2-yl]methyl}azetidine-3-carboxamide hydrochloride obtained from [3-(trifluoromethyl)pyridin-2-yl]methylamine by the methods described in Examples 007-(1) and 001-(2) or methods equivalent thereto, and 7-chloro-5-methyl-4-oxo-1-(1,2,4-thiadiazol-5-yl)-1,4-dihydro-1,8-naphthyridine-3-carboxylic acid obtained in Reference Example 002-(2).

(2) The title compound was obtained by the method described in Example 361-(2) or a method equivalent thereto from crude 5-methyl-4-oxo-1-(1,2,4-thiadiazol-5-yl)-7-[3-({[3-(trifluoromethyl)pyridin-2-yl]methyl}carbamoyl)azetidin-1-yl]-1,4-dihydro-1,8-naphthyridine-3-carboxylic acid obtained in the preceding section.

1H-NMR (DMSO-d6): δ 2.60-2.67 (2H, m), 2.75 (3H, brs), 3.37-3.43 (2H, m), 3.69-3.82 (1H, m), 4.16-4.73 (6H, m), 6.52 (1H, brs), 7.52-7.59 (1H, m), 8.18 (1H, d, J=8.0 Hz), 8.77 (1H, brs), 8.78 (1H, s), 8.79-8.85 (1H, m), 9.53 (1H, 8)

Example 379

Compound 379

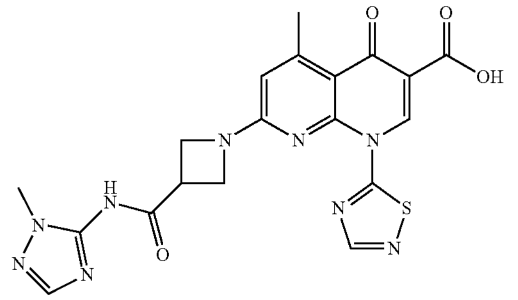

5-Methyl-7-{3-[(1-methyl-1H-1,2,4-triazol-5-yl) carbamoyl]azetidin-1-yl}-4-oxo-1-(1,2,4-thiadiazol-5-yl)-1,4-dihydro-1,8-naphthyridine-3-carboxylic acid The title compound was obtained by the method described in Example 001-(3) or a method equivalent thereto using N-(1-methyl-1H-1,2,4-triazol-5-yl)azetidine-3-carboxamide trifluoroacetate obtained from 1-methyl-1H-1,2,4-triazol-5-amine by the methods described in Examples 005-(1) and 001-(2) or methods equivalent thereto, and 7-chloro-5-methyl-4-oxo-1-(1,2,4-thiadiazol-5-yl)-1,4-dihydro-1,8-naphthyridine-3-carboxylic acid obtained in Reference Example 002-(2).

1H-NMR (DMSO-d6): δ 2.74 (3H, d, J=0.9 Hz), 3.70 (3H, s), 3.90-4.00 (1H, m), 4.34-4.70 (4H, m), 6.59 (1H, d, J=0.9 Hz), 7.87 (1H, s), 8.81 (1H, s), 9.68 (1H, s), 10.92 (1H, brs), 15.01 (1H, brs)

Example 380

Compound 380

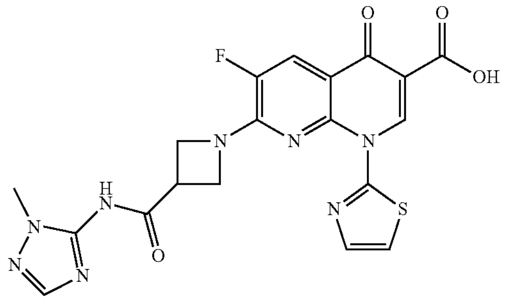

6-Fluoro-7-{3-[(1-methyl-1H-1,2,4-triazol-5-yl)carbamoyl]azetidin-1-yl}-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-(1-methyl-1H-1,2,4-triazol-5-yl)azetidine-3-carboxamide trifluoroacetate obtained in Example 379 by the method described in Example 001-(3) or a method equivalent thereto.

1H-NMR (DMSO-d6): δ 3.70 (3H, s), 3.90-4.00 (1H, m), 4.46-4.90 (4H, m), 7.81 (1H, d; J=3.5 Hz), 7.86-7.87 (2H, m), 8.21 (1H, d, J=11.3 Hz), 9.81 (1H, s), 10.89 (1H, brs), 14.77 (1H, brs)

Example 381

Compound 381

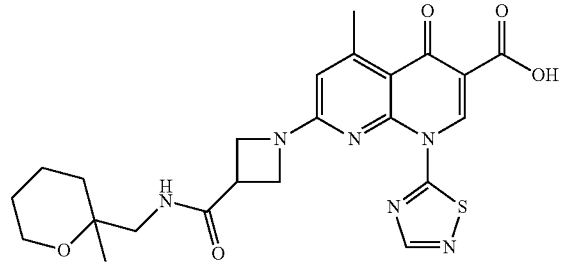

5-Methyl-7-(3-{[(2-methyloxan-2-yl)methyl]carbamoyl}azetidin-1-yl)-4-oxo-1-(1,2,4-thiadiazol-5-yl)-1,4-dihydro-1,8-naphthyridine-3-carboxylic acid The title compound was obtained by the method described in Example 001-(3) or a method equivalent thereto using N-[(2-methyloxan-2-yl)methyl]azetidine-3-carboxamide hydrochloride obtained from (2-methyloxan-2-yl)methylamine hydrochloride by the methods described in Examples 005-(1) and 001-(2) or methods equivalent thereto, and 7-chloro-5-methyl-4-oxo-1-(1,2,4-thiadiazol-5-yl)-1,4-dihydro-1,8-naphthyridine-3-carboxylic acid obtained in Reference Example 002-(2).

1H-NMR (DMSO-d6): δ 1.09 (3H, s), 1.29-1.47 (4H, m), 1.54-1.68 (2H, m), 2.76 (3H, d, J=1.0 Hz), 3.14-3.27 (2H, m), 3.51-3.65 (2H, m), 3.68-3.76 (1H, m), 4.22-4.63 (4H, m), 6.59 (1H, d, J=1.0 Hz), 8.09 (1H, brt, J=6.0 Hz), 8.81 (1H, s), 9.73 (1H, s), 15.09 (1H, s)

Example 382

Compound 382

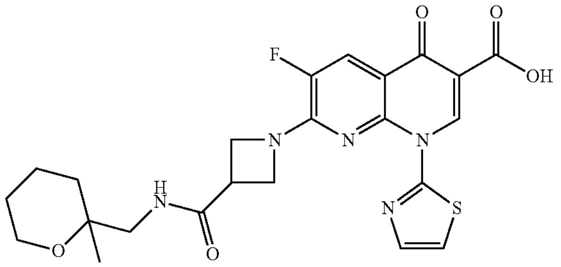

6-Fluoro-7-(3-{[(2-methyloxan-2-yl)methyl]carbamoyl}azetidin-1-yl)-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-[(2-methyloxan-2-yl)methyl]azetidine-3-carboxamide hydrochloride obtained in Example 381 by the method described in Example 001-(3) or a method equivalent thereto.

1H-NMR (DMSO-d6): δ 1.08 (3H, s), 1.29-1.47 (4H, m), 1.53-1.65 (2H, m), 3.16-3.25 (2H, m), 3.51-3.64 (2H, m), 3.69-3.78 (1H, m), 4.39-4.79 (4H, m), 7.79 (1H, d, J=3.5 Hz), 7.86 (1H, d, J=3.5 Hz), 8.06 (1H, brt, J=6.0 Hz), 8.10 (1H, d, J=11.5 Hz), 9.82 (1H, s), 14.80 (1H, brs)

Example 383

Compound 383

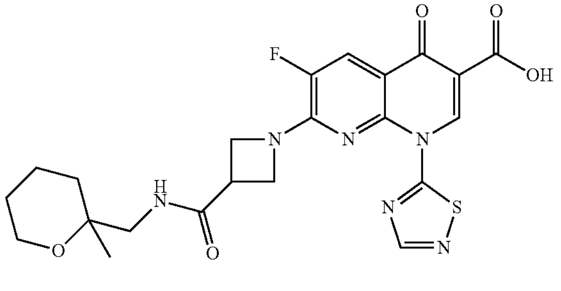

6-Fluoro-7-(3-{[(2-methyloxan-2-yl)methyl]carbamoyl}azetidin-1-yl)-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and N-[(2-methyloxan-2-yl)methyl]azetidine-3-carboxamide hydrochloride obtained in Example 381 by the method described in Example 001-(3) or a method equivalent thereto.

1H-NMR (DMSO-d6): δ 1.09 (3H, s), 1.28-1.47 (4H, m), 1.53-1.65 (2H, m), 3.22 (2H, d, J=6.0 Hz), 3.51-3.65 (2H, m), 3.70-3.79 (1H, m), 4.45-4.84 (4H, m), 8.08 (1H, brt, J=6.0 Hz), 8.15 (1H, d, J=11.5 Hz), 8.85 (1H, s), 9.74 (1H, s), 14.49 (1H, s)

Example 384

Compound 384

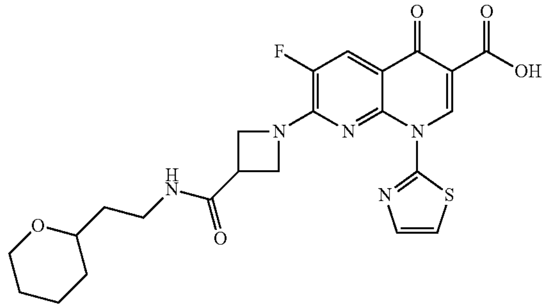

6-Fluoro-7-(3-{[2-(oxan-2-yl)ethyl]carbamoyl}azetidin-1-yl)-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) N-[2-(oxan-2-yl)ethyl]azetidine-3-carboxamide hydrochloride obtained from 2-(oxan-2-yl)ethan-1-amine by the method described in Example 005-(1) and Example 001-(2) or a method equivalent thereto by the method described in Example 001-(3) or a method equivalent thereto.

1H-NMR (DMSO-d6): δ 1.12-1.20 (1H, m), 1.37-1.59 (6H, m), 1.71-1.78 (1H, m), 3.09-3.15 (1H, m), 3.19-3.36 (3H, m), 3.56-3.62 (1H, m), 3.82-3.87 (1H, m), 4.31-4.82 (4H, m), 7.78 (1H, d, J=3.5 Hz), 7.86 (1H, d, J=3.5 Hz), 8.08-8.14 (2H, m), 9.82 (1H, s)

Example 385

Compound 385

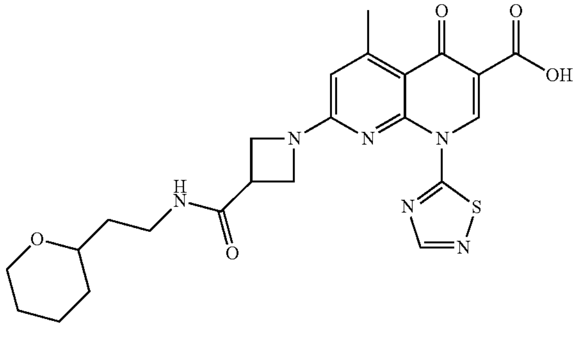

5-Methyl-7-(3-{[2-(oxan-2-yl)ethyl]carbamoyl}azetidin-1-yl)-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-[2-(oxan-2-yl)ethyl]azetidine-3-carboxamide hydrochloride obtained in Example 384 by the method described in Example 001-(3) or a method equivalent thereto.

1H-NMR (DMSO-d6): δ 1.12-1.20 (1H, m), 1.37-1.60 (6H, m), 1.69-1.79 (1H, m), 2.75 (3H, s), 3.10-3.16 (1H, m), 3.19-3.36 (3H, m), 3.56-3.61 (1H, m), 3.82-3.88 (1H, m), 4.20-4.61 (4H, m), 6.56 (1H, s), 8.15 (1H, t, J=5.5 Hz), 8.81 (1H, s), 9.71 (1H, s)

Example 386

Compound 386

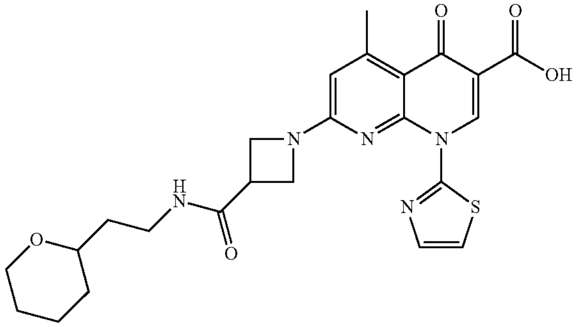

5-Methyl-7-(3-{([2-(oxan-2-yl)ethyl]carbamoyl}azetidin-1-yl)-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-[2-(oxan-2-yl)ethyl]azetidine-3-carboxamide hydrochloride obtained in Example 384 by the method described in Example 001-(3) or a method equivalent thereto.

1H-NMR (DMSO-d6): δ 1.10-1.21 (1H, m), 1.36-1.48 (3H, m), 1.49-1.59 (3H, m), 1.69-1.81 (1H, m), 2.75 (3H, s), 3.07-3.30 (4H, m), 3.51-3.60 (1H, m), 3.82-3.88 (1H, m), 4.14-4.48 (4H, m), 6.50 (1H, s), 7.73 (1H, d, J=3.5 Hz), 7.82 (1H, d, J=3.5 Hz), 8.13 (1H, t, J=5.5 Hz), 9.81 (1H, s), 15.38 (1H, brs)

Example 387

Compound 387

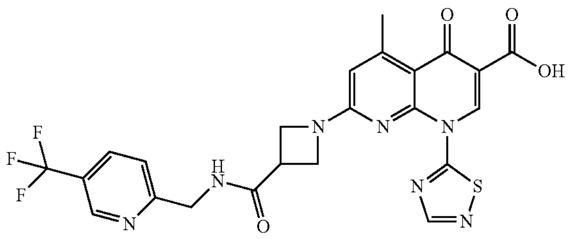

5-Methyl-4-oxo-1-(1,2,4-thiadiazol-5-yl)-7-[3-({[5-(trifluoromethyl)pyridin-2-yl]methyl}carbamoyl) azetidin-1-yl]-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-{([5-(trifluoromethyl)pyridin-2-yl] methyl}azetidine-3-carboxamide hydrochloride obtained from [5-(trifluoromethyl)pyridin-2-yl]methylamine by the method described in Example 005-(1) and Example 0.001-(2) or a method equivalent thereto by the method described in Example 008 or a method equivalent thereto.

1H-NMR (DMSO d6): δ 2.72 (3H, brs), 3.71-3.83 (1H, m), 4.19-4.66 (6H, m), 6.37 (1H, brs), 7.50-7.67 (1H, m), 8.18 (1H, d, J=7.5 Hz), 8.70 (1H, s), 8.90 (1H, s), 8.93-9.04 (1H, m), 9.61 (1H, s)

Example 388

Compound 388

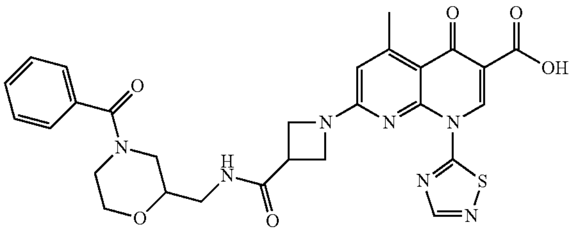

7-(3-{[(4-Benzoylmorpholin-2-yl)methyl] carbamoyl}azetidin-1-yl)-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-[(4-benzoylmorpholin-2-yl)methyl] azetidine-3-carboxamide hydrochloride obtained from crude tert-butyl 3-{[(morpholin-2-yl)methyl] carbamoyl}azetidine-1-carboxylate obtained in Example 359 and benzoyl chloride by the method described in Example 359-(2) and Example 001-(2) or a method equivalent thereto by the method described in Example 001-(3) or a method equivalent thereto.

1H-NMR (DMSO-d6): δ 2.78 (3H, s), 3.06-4.68 (14H, m), 6.58 (1H, brs), 7.35-7.48 (5H, m), 8.23-8.49 (1H, m), 8.83 (1H, s), 9.75 (1H, s), 15.06 (1H, brs)

Example 389

Compound 389

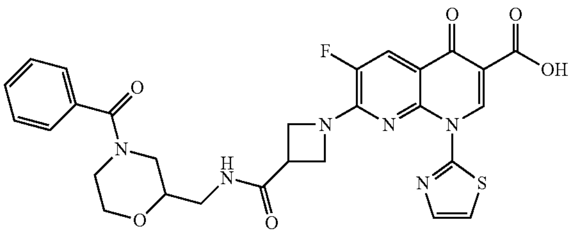

7-(3-{[(4-Benzoylmorpholin-2-yl)methyl] carbamoyl}azetidin-1-yl)-6-fluoro-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-[(4-benzoylmorpholin-2-yl)methyl]azetidine-3-carboxamide hydrochloride obtained in Example 388 by the method described in Example 001-(3) or a method equivalent thereto.

1H-NMR (DMSO-d6): δ 2.73-4.02 (10H, m), 4.1-4.89 (4H, m), 7.32-7.49 (5H, m), 7.79 (1H, d, J=3.0 Hz), 7.86 (1H, d, J=3.0 Hz), 8.12 (1H, d, J=11.5 Hz), 8.23-8.46 (1H, m), 9.82 (1H, s), 14.77 (1H, brs)

Example 390

Compound 390

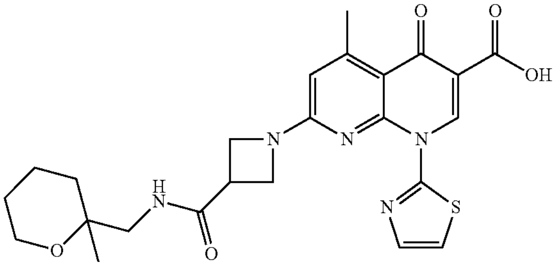

5-Methyl-7-(3-{[(2-methyloxan-2-yl)methyl] carbamoyl}azetidin-1-yl)-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-[(2-methyloxan-2-yl)methyl]azetidine-3-carboxamide hydrochloride obtained in Example 381 by the method described in Example 001-(3) or a method equivalent thereto.

1H-NMR (DMSO-d6): δ 1.08 (3H, s), 1.28-1.65 (6H, m), 2.75 (3H, d, J=1.0 Hz), 3.14-3.25 (2H, m), 3.52-3.63 (2H, m), 3.65-3.74 (1H, m), 4.18-4.49 (4H, m), 6.52 (1H, d, J=1.0 Hz), 7.74 (1H, d, J=3.5 Hz), 7.83 (1H, d, J=3.5 Hz), 8.07 (1H, t, J=6.0 Hz), 9.82 (1H, s), 15.41 (1H, s)

Example 391

Compound 391

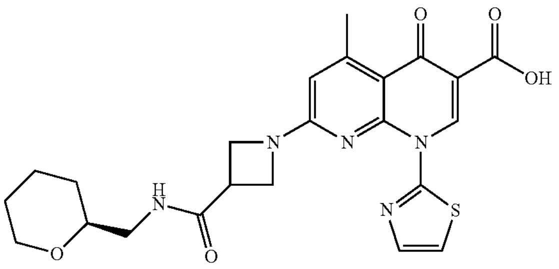

5-Methyl-7-(3-{[(2S)-oxan-2-ylmethyl] carbamoyl}azetidin-1-yl)-4-oxo-1-(1,3-thiazol-2-yl)-1,4-dihydro-1,8-naphthyridine-3-carboxylic acid The title compound was obtained by the method described in Example 008 or a method equivalent thereto using N-[(2S)-oxan-2-ylmethyl]azetidine-3-carboxamide hydrochloride obtained from (2S)-oxan-2-ylmethylamine by the methods described in Examples 005-(1) and 001-(2) or methods equivalent thereto, and 7-chloro-5-methyl-4-oxo-1-(1,3-thiazol-2-yl)-1,4-dihydro-1,8-naphthyridine-3-carboxylic acid obtained in Reference Example 001-(2).

1H-NMR (DMSO-d6): δ 1.10-1.20 (1H, m), 1.39-1.49 (3H, m), 1.52-1.59 (1H, m), 1.72-1.81 (1H, m), 2.75 (3H, s), 3.00-3.24 (4H, m), 3.58-3.66 (1H, m), 3.84-3.90 (1H, m), 4.16-4.48 (4H, m), 6.51 (1H, s), 7.73 (1H, d, J=3.5 Hz), 7.82 (1H, d, J=3.5 Hz), 8.22 (1H, t, J=5.5 Hz), 9.82 (1H, s)

Example 392

Compound 392

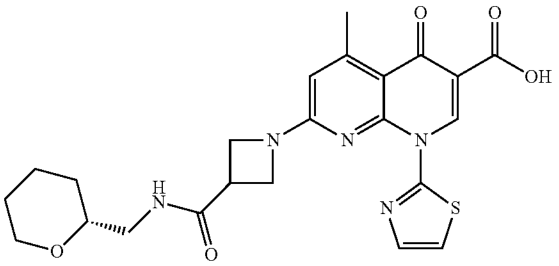

5-Methyl-7-(3-{[(2R)-oxan-2-ylmethyl] carbamoyl}azetidin-1-yl)-4-oxo-1-(1,3-thiazol-2-yl)-1,4-dihydro-1,8-naphthyridine-3-carboxylic acid The title compound was obtained by the method described in Example 008 or a method equivalent thereto using N-[(2S)-oxan-2-ylmethyl]azetidine-3-carboxamide hydrochloride obtained from (2R)-oxan-2-ylmethylamine by the methods described in Examples 005-(1) and 001-(2) or methods equivalent thereto, and 7-chloro-5-methyl-4-oxo-1-(1,3-thiazol-2-yl)-1,4-dihydro-1,8-naphthyridine-3-carboxylic acid obtained in Reference Example 001-(2).

1H-NMR (DMSO-d6): δ 1.10-1.20 (1H, m), 1.39-1.49 (3H, m), 1.52-1.59 (1H, m), 1.72-1.81 (1H, m), 2.75 (3H, s), 3.00-3.24 (4H, m), 3.58-3.66 (1H, m), 3.84-3.90 (1H, m), 4.16-4.48 (4H, m), 6.51 (1H, s), 7.73 (1H, d, J=3.5 Hz), 7.82 (1H, d, J=3.5 Hz), 8.22 (1H, t, J=5.5 Hz), 9.82 (1H, s)

Example 393

Compound 393

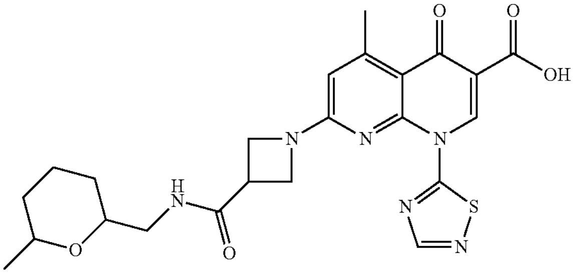

5-Methyl-7-(3-{[(6-methyloxan-2-yl)methyl] carbamoyl}azetidin-1-yl)-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-[(6-methyloxan-2-yl)methyl]azetidine-3-carboxamide hydrochloride obtained from (6-methyloxan-2-yl)methylamine by the method described in Example 005-(1) and Example 001-(2) or a method equivalent thereto by the method described in Example 001-(3) or a method equivalent thereto.

1H-NMR (DMSO-d6): δ 1.01-1.13 (4H, m), 1.17-1.34 (1H, m), 1.39-1.64 (3H, m), 1.71-1.80 (1H, m), 2.75 (3H, s), 3.08-3.23 (2H, m), 3.26-3.44 (2H, m), 3.61-3.70 (0.7H, m), 3.83-3.91 (0.3H, m), 4.21-4.62 (4H, m), 6.55-6.61 (1H, m), 8.18 (0.3H, t, J=5.5 Hz), 8.24 (0.7H, t, J=5.5 Hz), 8.81 (0.7H, s), 8.82 (0.3H, s), 9.70 (0.7H, s), 9.71 (0.3H, s), 15.07 (1H, brs)

Example 394

Compound 394

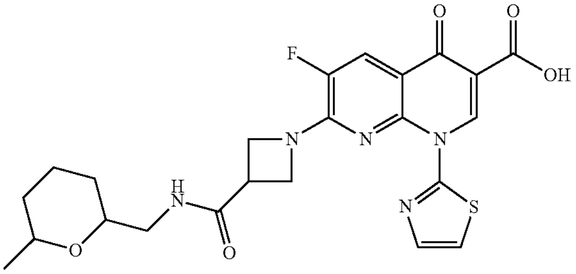

6-Fluoro-7-(3-{([6-methyloxan-2-yl)methyl]carbamoyl}azetidin-1-yl)-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-[(6-methyloxan-2-yl)methyl]azetidine-3-carboxamide hydrochloride obtained in Example 393 by the method described in Example 001-(3) or a method equivalent thereto.

1H-NMR (DMSO-d6): δ 1.00-1.14 (4H, m), 1.16-1.34 (1H, m), 1.39-1.80 (4H, m), 3.05-3.23 (2H, m), 3.28-3.43 (2H, m), 3.61-3.76 (0.7H, m), 3.82-3.89 (0.3H, m), 4.35-4.88 (4H, m), 7.75-7.79 (1H, m), 7.85 (1H, d, J=3.5 Hz), 8.08 (1H, d, J=11.5 Hz), 8.16 (0.3H, t, J=6.0 Hz), 8.22 (0.7H, t, J=6.0 Hz), 9.79 (0.7H, s), 9.80 (0.3H, s), 14.79 (1H, brs)

Example 395

Compound 395

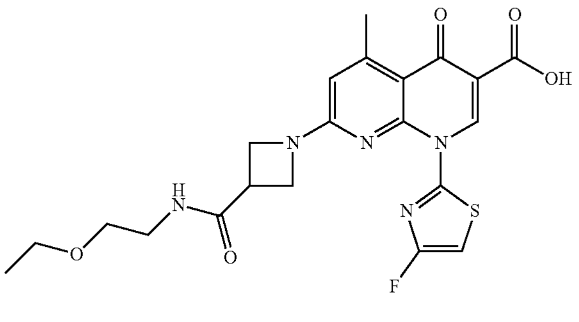

7-{3-[(2-Ethoxyethyl)carbamoyl]azetidin-1-yl}-1-(4-fluoro-1,3-thiazol-2-yl)-5-methyl-4-oxo-1,4-dihydro-1,8-naphthyridine-3-carboxylic acid The title compound was obtained using 7-chloro-1-(4-fluoro-1,3-thiazol-2-yl)-5-methyl-4-oxo-1,4-dihydro-1,8-naphthyridine-3-carboxylic acid obtained in Reference Example 009-(2) and N-(2-ethoxyethyl)azetidine-3-carboxamide hydrochloride obtained in Example 018-(1) by the method described in Example 001-(3) or a method equivalent thereto.

1H-NMR (DMSO-d6): δ 1.11 (3H, t, J=7.0 Hz), 2.74 (3H, s), 3.21-3.38 (2H, m), 3.41 (2H, t, J=5.5 Hz), 3.44 (2H, q, J=7.0 Hz), 3.57-3.64 (1H, m), 4.19-4.52 (4H, m), 6.50 (1H, s), 7.72 (1H, d, J=3.0 Hz), 8.24 (1H, t, J=5.5 Hz), 9.65 (1H, s)

Example 396

Compound 396

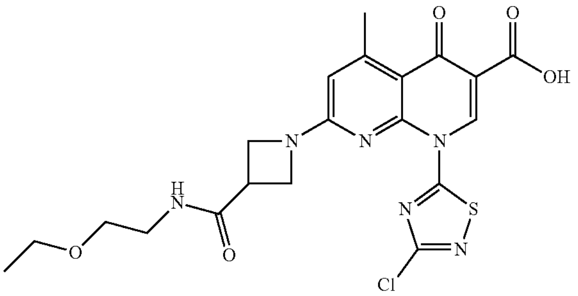

1-(3-Chloro-1,2,4-thiadiazol-5-yl)-7-{3-[(2-ethoxyethyl)carbamoyl]azetidin-1-yl}-5-methyl-4-oxo-1,4-dihydro-1,8-naphthyridine-3-carboxylic acid The title compound was obtained using 7-chloro-1-(3-chloro-1,2,4-thiadiazol-5-yl)-5-methyl-4-oxo-1,4-dihydro-1,8-naphthyridine-3-carboxylic acid obtained in Reference Example 013-(2) and N-(2-ethoxyethyl)azetidine-3-carboxamide hydrochloride obtained in Example 018-(1) by the method described in Example 001-(3) or a method equivalent thereto.

1H-NMR (DMSO-d6): δ 1.12 (3H, t, J=7.0 Hz), 2.77 (3H, s), 3.19-3.46 (6H, m), 3.58-3.67 (1H, m), 4.16-4.63 (4H, m), 6.59 (1H, s), 8.26 (1H, t, J=5.0 Hz), 9.51 (1H, s)

Example 397

Compound 397

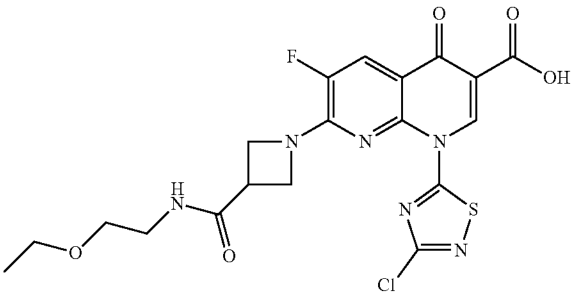

1-(3-Chloro-1,2,4-thiadiazol-5-yl)-7-{3-[(2-ethoxyethyl)carbamoyl]azetidin-1-yl}-6-fluoro-4-oxo-1,4-dihydro-1,8-naphthyridine-3-carboxylic acid The title compound was obtained using 7-chloro-1-(3-chloro-1,2,4-thiadiazol-5-yl)-6-fluoro-4-oxo-1,4-dihydro-1,8-naphthyridine-3-carboxylic acid obtained in Reference Example 014-(2) and N-(2-ethoxyethyl)azetidine-3-carboxamide hydrochloride obtained in Example 018-(1) by the method described in Example 001-(3) or a method equivalent thereto.

1H-NMR (DMSO-d6): δ 1.11 (3H, t, J=7.0 Hz), 3.18-3.36 (2H, m), 3.40 (2H, t, J=5.5 Hz), 3.43 (2H, q, J=7.0 Hz), 3.52-3.60 (1H, m), 4.24-4.77 (4H, m), 7.95 (1H, d, J=12.0 Hz), 8.17 (1H, t, J=5.5 Hz), 8.43 (1H, s), 13.30 (1H, brs)

Example 398

Compound 398

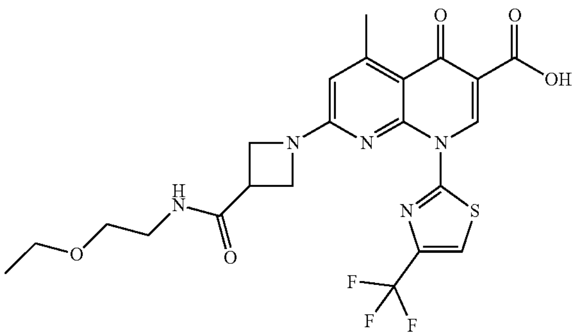

7-{3-[(2-Ethoxyethyl)carbamoyl]azetidin-1-yl}-5-methyl-4-oxo-1-[4-(trifluoromethyl)-1,3-thiazol-2-yl]-1,4-dihydro-1,8-naphthyridine-3-carboxylic acid The title compound was obtained using 7-chloro-5-methyl-4-oxo-1-[4-(trifluoromethyl)-1,3-thiazol-2-yl]-1,4-dihydro-1,8-naphthyridine-3-carboxylic acid obtained in Reference Example 017-(2) and N-(2-ethoxyethyl)azetidine-3-carboxamide hydrochloride obtained in Example 018-(1) by the method described in Example 001-(3) or a method equivalent thereto.

1H-NMR (DMSO-d6): δ 1.11 (3H, t, J=7.0 Hz), 2.78 (3H, s), 3.21-3.39 (2H, m), 3.41 (2H, t, J=5.5 Hz), 3.44 (2H, q, J=7.0 Hz), 3.58-3.66 (1H, m), 4.15-4.52 (4H, m), 6.57 (1H, s), 8.24 (1H, t, J=5.5 Hz), 8.41 (1H, s), 9.73 (1H, s)

Example 399

Compound 399

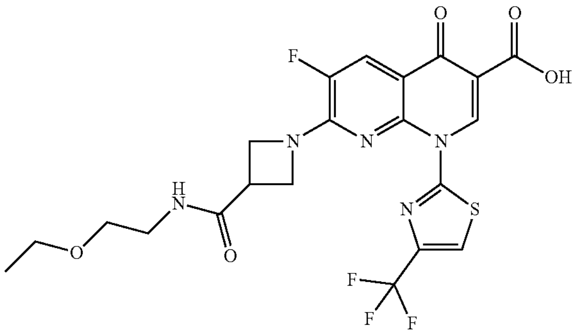

7-{3-[(2-Ethoxyethyl)carbamoyl]azetidin-1-yl}-6-fluoro-4-oxo-1-[4-(trifluoromethyl)-1,3-thiazol-2-yl]-1,4-dihydro-1,8-naphthyridine-3-carboxylic acid The title compound was obtained using 7-chloro-6-fluoro-4-oxo-1-[4-(trifluoromethyl)-1,3-thiazol-2-yl]-1,4-dihydro-1,8-naphthyridine-3-carboxylic acid obtained in Reference Example 018-(2) and N-(2-ethoxyethyl)azetidine-3-carboxamide hydrochloride obtained in Example 018-(1) by the method described in Example 001-(3) or a method equivalent thereto.

1H-NMR (DMSO-d6): δ 1.11 (3H, t, J=7.0 Hz), 3.18-3.38 (2H, m), 3.41 (2H, t, J=5.5 Hz), 3.44 (2H, q, J=7.0 Hz), 3.61-3.70 (1H, m), 4.40-4.84 (4H, m), 8.12 (1H, d, J=11.5 Hz), 8.24 (1H, t, J=5.5 Hz), 8.44 (1H, s), 9.69 (1H, s)

Example 400

Compound 400

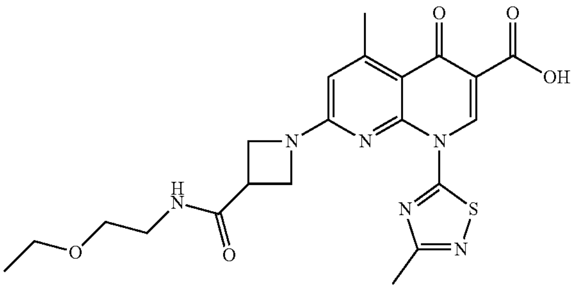

7-{3-[(2-Ethoxyethyl)carbamoyl]azetidin-1-yl}-5-methyl-1-(3-methyl-1,2,4-thiadiazol-5-yl)-4-oxo-1,4-dihydro-1,8-naphthyridine-3-carboxylic acid The title compound was obtained using 7-chloro-5-methyl-1-(3-methyl-1,2,4-thiadiazol-5-yl)-4-oxo-1,4-dihydro-1,8-naphthyridine-3-carboxylic acid obtained in Reference Example 019-(2) and N-(2-ethoxyethyl)azetidine-3-carboxamide hydrochloride obtained in Example 018-(1) by the method described in Example 001-(3) or a method equivalent thereto.

1H-NMR (DMSO-d6): δ 1.11 (3H, t, J=7.0 Hz), 2.60 (3H, s), 2.74 (3H, s), 3.12-3.51 (4H, m), 3.57-3.68 (1H, m), 4.27-4.52 (4H, m), 6.55 (1H, s), 8.25 (1H, t, J=5.0 Hz), 9.66 (1H, s)

Example 401

Compound 401

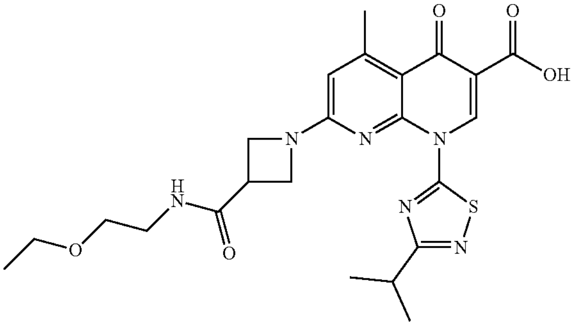

7-{3-[(2-Ethoxyethyl)carbamoyl]azetidin-1-yl}-5-methyl-4-oxo-1-[3-(propan-2-yl)-1,2,4-thiadiazol-5-yl]-1,4-dihydro-1,8-naphthyridine-3-carboxylic acid The title compound was obtained using 7-chloro-5-methyl-4-oxo-1-[3-(propan-2-yl)-1,2,4-thiadiazol-5-yl]-1,4-dihydro-1,8-naphthyridine-3-carboxylic acid obtained in Reference Example 020-(2) and N-(2-ethoxyethyl)azetidine-3-carboxamide hydrochloride obtained in Example 018-(1) by the method described in Example 001-(3) or a method equivalent thereto.

1H-NMR (DMSO-d6): δ 1.12 (3H, t, J=7.5 Hz), 1.36 (6H, d, J=6.5 Hz), 2.75 (3H, s), 3.25-3.30 (3H, m), 3.42 (2H, t, J=5.5 Hz), 3.44 (2H, q, J=7.5 Hz), 4.21-4.61 (4H, m), 6.55 (1H, s), 8.25 (1H, t, J=5.5 Hz), 9.70 (1H, s)

Example 402

Compound 402

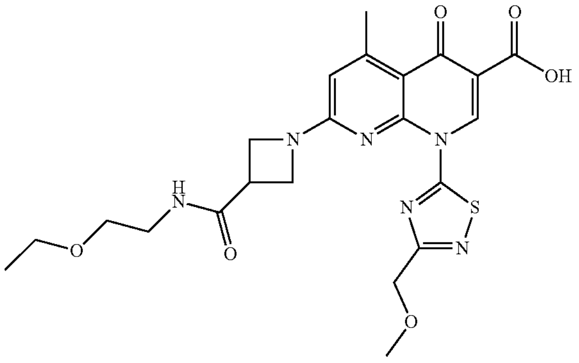

7-{3-[(2-Ethoxyethyl)carbamoyl]azetidin-1-yl}-1-[3-(methoxymethyl)-1,2,4-thiadiazol-5-yl]-5-methyl-4-oxo-1,4-dihydro-1,8-naphthyridine-3-carboxylic acid (1) A mixture of N-(2-ethoxyethyl)azetidine-3-carboxamide hydrochloride (48 mg) obtained in Example 018-(1), ethyl 7-chloro-1-[4-(methoxymethyl)-1,2,4-thiadiazol-5-yl]-5-methyl-4-oxo-1,4-dihydro-1,8-naphthyridine-3-carboxylate (13 mg) obtained in Reference Example 021-(1), diazabicycloundecene (80 μL), and N,N-dimethylformamide (600 μL) was stirred at room temperature for 4 days. The resulting solid was collected by filtration to obtain 11 mg of ethyl 7-{3-[(2-ethoxyethyl)carbamoyl]azetidin-1-yl}-1-[3-(methoxymethyl)-1,2,4-thiadiazol-5-yl]-5-methyl-4-oxo-1,4-dihydro-1,8-naphthyridine-3-carboxylate.

1H-NMR (DMSO-d6): δ 1.11 (3H, t, J=7.0 Hz), 1.30 (3H, t, J=7.5 Hz), 2.71 (3H, s), 3.27 (2H, q, J=5.0 Hz), 3.39 (3H, s), 3.39-3.42 (2H, m), 3.44 (2H, q, J=7.5 Hz), 3.56-3.63 (1H, m), 4.28 (2H, q, J=7.0 Hz), 4.29-4.59 (4H, m), 4.62 (2H, s), 6.42 (1H, s), 8.23 (1H, t, J=5.5 Hz), 9.39 (1H, s)

(2) The title compound was obtained by the method described in Example 028-(2) or a method equivalent thereto from ethyl 7-{3-[(2-ethoxyethyl)carbamoyl]azetidin-1-yl}-1-[3-(methoxymethyl)-1,2,4-thiadiazol-5-yl]-5-methyl-4-oxo-1,4-dihydro-1,8-naphthyridine-3-carboxylate obtained in the preceding section.

1H-NMR (DMSO-d6): δ 1.12 (3H, t, J=7.0 Hz), 2.76 (3H, s), 3.28 (2H, q, J=5.5 Hz), 3.39-3.49 (7H, m), 3.59-3.67 (1H, m), 4.27-4.57 (4H, m), 4.66 (2H, s), 6.57 (1H, s), 8.27 (1H, t, J=5.5 Hz), 9.68 (1H, s)

Example 403

Compound 403

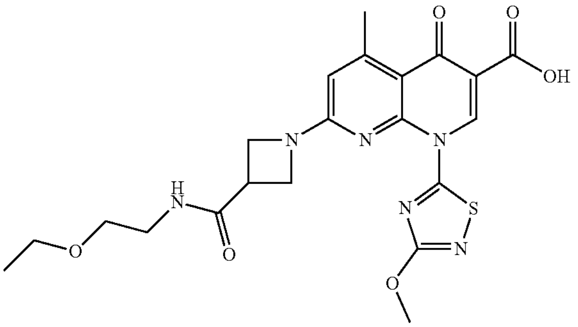

7-{3-[(2-Ethoxyethyl)carbamoyl]azetidin-1-yl}-1-(3-methoxy-1,2,4-thiadiazol-5-yl)-5-methyl-4-oxo-1,4-dihydro-1,8-naphthyridine-3-carboxylic acid The title compound was obtained using 7-chloro-1-(3-methoxy-1,2,4-thiadiazol-5-yl)-5-methyl-4-oxo-1,4-dihydro-1,8-naphthyridine-3-carboxylic acid obtained in Reference Example 023-(2) and N-(2-ethoxyethyl)azetidine-3-carboxamide hydrochloride obtained in Example 018-(1) by the method described in Example 018-(2) or a method equivalent thereto.

1H-NMR (DMSO-d6): δ 1.12 (3H, t, J=7.0 Hz), 2.74 (3H, s), 3.28 (2H, q, J=5.5 Hz), 3.41 (2H, t, J=5.5 Hz), 3.44 (2H, q, J=7.0 Hz), 3.58-3.68 (1H, m), 4.02 (3H, s), 4.26-4.51 (4H, m), 6.54 (1H, s), 8.26 (1H, t, J=5.5 Hz), 9.50 (1H, s)

Example 404

Compound 404

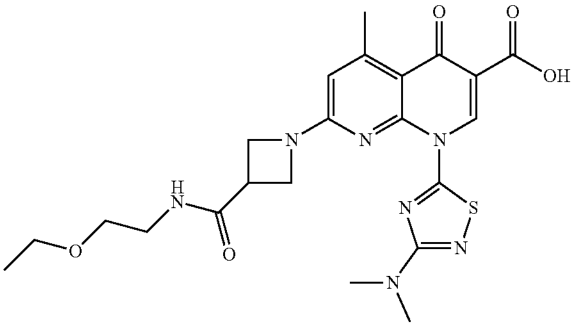

1-[3-(Dimethylamino)-1,2,4-thiadiazol-5-yl]-7-{3-[(2-ethoxyethyl)carbamoyl]azetidin-1-yl}-5-methyl-4-oxo-1,4-dihydro-1,8-naphthyridine-3-carboxylic acid The title compound was obtained using 7-chloro-1-[3-(dimethylamino)-1,2,4-thiadiazol-5-yl]-5-methyl-4-oxo-1, 4-dihydro-1,8-naphthyridine-3-carboxylic acid obtained in Reference Example 026-(2) and N-(2-ethoxyethyl)azetidine-3-carboxamide hydrochloride obtained in Example 018-(1) by the method described in Example 001-(3) or a method equivalent thereto.

1H-NMR (DMSO-d6): δ 1.12 (3H, t, J=7.0 Hz), 2.68 (3H, s), 3.09 (6H, s), 3.28 (2H, q, J=5.5 Hz), 3.42 (2H, t, J=5.5 Hz), 3.44 (2H, q, J=7.0 Hz), 3.54-3.65 (1H, m), 4.20-4.42 (4H, m), 6.42 (1H, s), 8.26 (1H, t, J=5.5 Hz), 9.42 (1H, s)

Example 405

Compound 405

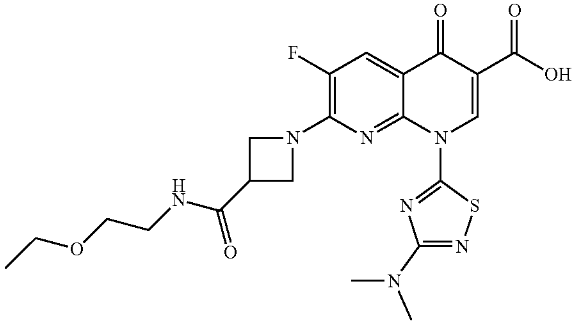

1-[3-(Dimethylamino)-1,2,4-thiadiazol-5-yl]-7-{3-[(2-ethoxyethyl)carbamoyl]azetidin-1-yl}-6-fluoro-4-oxo-1,4-dihydro-1,8-naphthyridine-3-carboxylic acid The title compound was obtained using 7-chloro-6-fluoro-1-[3-(dimethylamino)-1,2,4-thiadiazol-5-yl]-4-oxo-1,4-dihydro-1,8-naphthyridine-3-carboxylic acid obtained in Reference Example 027-(2) and N-(2-ethoxyethyl)azetidine-3-carboxamide hydrochloride and obtained in Example 018-(1) by the method described in Example 001-(3) or a method equivalent thereto.

1H-NMR (DMSO-d6): δ 1.11 (3H, t, J=7.0 Hz), 3.13 (6H, s), 3.20-3.46 (6H, m), 3.60-3.70 (1H, m), 4.34-4.4.79 (4H, m), 8.10 (1H, d, J=11.0 Hz), 8.25 (1H, t, J=6.0 Hz), 9.63 (1H, s)

Example 406

Compound 406

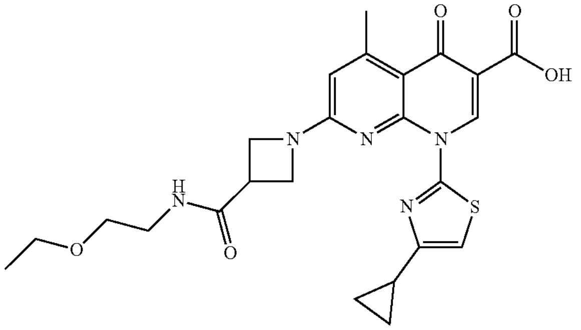

1-(4-Cyclopropyl-1,3-thiazol-2-yl)-7-{3-[(2-ethoxyethyl)carbamoyl]azetidin-1-yl}-5-methyl-4-oxo-1,4-dihydro-1,8-naphthyridine-3-carboxylic acid The title compound was obtained using 7-chloro-1-(4-cyclopropyl-1,3-thiazol-2-yl)-5-methyl-4-oxo-1,4-dihydro-1,8-naphthyridine-3-carboxylic acid obtained in Reference Example 030-(2) and N-(2-ethoxyethyl)azetidine-3-carboxamide hydrochloride obtained in Example 018-(1) by the method described in Example 001-(3) or a method equivalent thereto.

1H-NMR (DMSO-d6): δ 0.82-0.87 (2H, m), 0.94-0.99 (2H, m), 1.11 (3H, t, J=7.0 Hz), 2.10-2.17 (1H, m), 2.76 (3H, s), 3.22-3.37 (2H, m), 3.40 (2H, t, J=5.5 Hz), 3.43 (2H, q, J=7.0 Hz), 3.55-3.63 (1H, m), 4.15-4.48 (4H, m), 6.52 (1H, s), 7.28 (1H, s), 8.22 (1H, t, J=5.5 Hz), 9.75 (1H, s)

Example 407

Compound 407

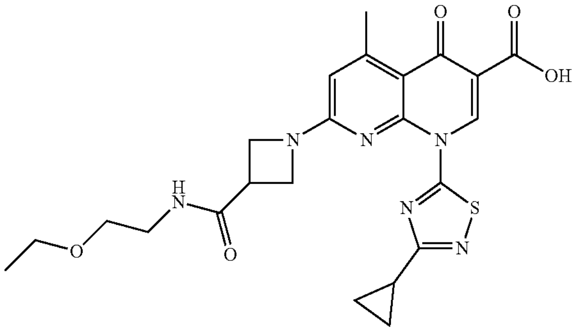

1-(3-Cyclopropyl-1,2,4-thiadiazol-5-yl)-7-{3-[(2-ethoxyethyl)carbamoyl]azetidin-1-yl}-5-methyl-4-oxo-1,4-dihydro-1,8-naphthyridine-3-carboxylic acid The title compound was obtained using 7-chloro-1-(3-cyclopropyl-1,2,4-thiadiazol-5-yl)-5-methyl-4-oxo-1,4-dihydro-1,8-naphthyridine-3-carboxylic acid obtained in Reference Example 031-(2) and N-(2-ethoxyethyl)azetidine-3-carboxamide hydrochloride obtained in Example 018-(1) by the method described in Example 001-(3) or a method equivalent thereto.

1H-NMR (DMSO-d6): δ 0.89-0.96 (2H, m), 0.97-1.03 (2H, m), 1.05 (3H, t, J=7.0 Hz), 1.98-2.06 (1H, m), 2.35 (3H, s), 3.33 (2H, t, J=5.5 Hz), 3.44-3.55 (5H, m), 3.82-3.99 (4H, m), 5.65 (1H, s), 8.86 (1H, s)

Example 408

Compound 408

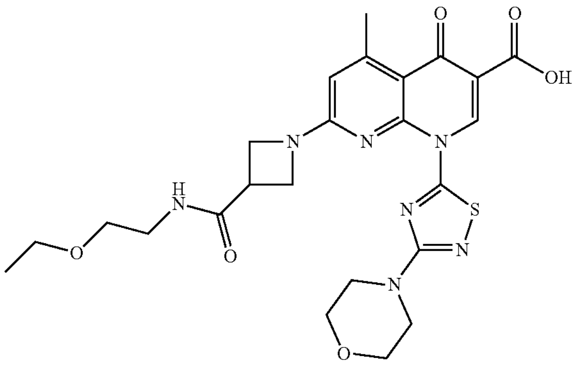

7-{3-[(2-Ethoxyethyl)carbamoyl]azetidin-1-yl}-5-methyl-1-[3-(morpholin-4-yl)-1,2,4-thiadiazol-5-yl]-4-oxo-1,4-dihydro-1,8-naphthyridine-3-carboxylic acid The title compound was obtained using 7-chloro-5-methyl-1-[3-(morpholin-4-yl)-1,2,4-thiadiazol-5-yl]-4-oxo-1,4-dihydro-1,8-naphthyridine-3-carboxylic acid obtained in Reference Example 033-(2) and N-(2-ethoxyethyl)azetidine-3-carboxamide hydrochloride obtained in Example 018-(1) by the method described in Example 001-(3) or a method equivalent thereto.

1H-NMR (DMSO-d6): δ 1.12 (3H, t, J=7.0 Hz), 2.73 (3H, s), 3.24-3.37 (2H, m), 3.41 (2H, t, J=5.5 Hz), 3.44 (2H, q, J=7.0 Hz), 3.57 (4H, t, J=5.0 Hz), 3.59-3.66 (1H, m), 3.72 (4H, t, J=5.0 Hz), 4.08-4.56 (4H, m), 6.52 (1H, s), 8.25 (1H, t, J=5.5 Hz), 9.57 (1H, s)

Example 409

Compound 409

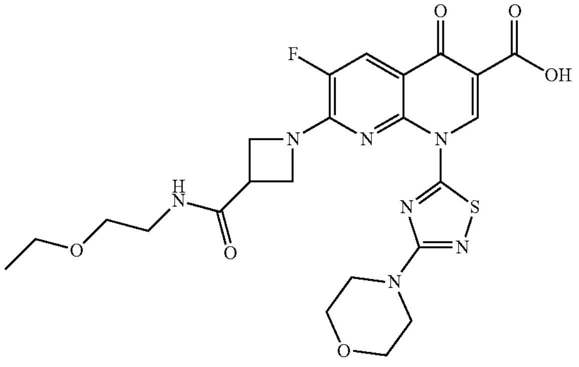

7-{3-[(2-Ethoxyethyl)carbamoyl]azetidin-1-yl}-6-fluoro-1-[3-(morpholin-4-yl)-1,2,4-thiadiazol-5-yl]-4-oxo-1,4-dihydro-1,8-naphthyridine-3-carboxylic acid The title compound was obtained using 7-chloro-6-fluoro-1-[3-(morpholin-4-yl)-1,2,4-thiadiazol-5-yl]-4-oxo-1,4-dihydro-1,8-naphthyridine-3-carboxylic acid obtained in Reference Example 034-(2) and N-(2-ethoxyethyl)azetidine-3-carboxamide hydrochloride obtained in Example 018-(1) by the method described in Example 001-(3) or a method equivalent thereto.

1H-NMR (DMSO-d6): δ 1.11 (3H, t, J=7.0 Hz), 3.21-3.37 (2H, m), 3.41 (2H, t, J=5.5 Hz), 3.44 (2H, q, J=7.0 Hz), 3.59 (4H, t, J=4.5 Hz), 3.62-3.67 (1H, m), 3.72 (4H, t, J=4.5 Hz), 4.35-4.88 (4H, m), 8.12 (1H, d, J=11.0 Hz), 8.24 (1H, t, J=5.5 Hz), 9.64 (1H, s)

Example 410

Compound 410

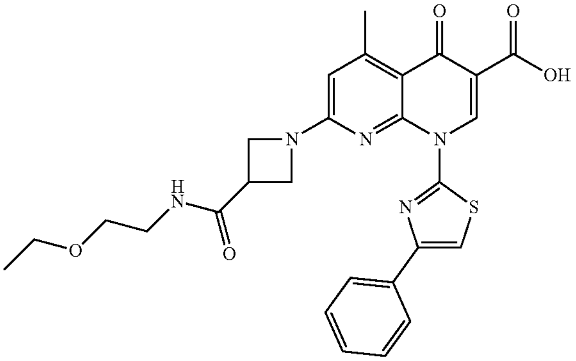

7-{3-[(2-Ethoxyethyl)carbamoyl]azetidin-1-yl}-5-methyl-4-oxo-1-(4-phenyl-1,3-thiazol-2-yl)-1,4-dihydro-1,8-naphthyridine-3-carboxylic acid The title compound was obtained using 7-chloro-5-methyl-4-oxo-1-(4-phenyl-1,3-thiazol-2-yl)-1,4-dihydro-1,8-naphthyridine-3-carboxylic acid obtained in Reference Example 035-(2) and N-(2-ethoxyethyl)azetidine-3-carboxamide hydrochloride obtained in Example 018-(1) by the method described in Example 018-(2) or a method equivalent thereto.

1H-NMR (DMSO-d6): δ 1.12 (3H, t, J=7.0 Hz), 2.78 (3H, s), 3.28 (2H, t, J=5.5 Hz), 3.41 (2H, t, J=5.5 Hz), 3.44 (2H, q, J=7.5 Hz), 3.57-3.65 (1H, m), 4.25-4.49 (4H, m), 6.55 (1H, s), 7.40 (1H, t, J=7.5 Hz), 7.51 (1H, t, J=7.5 Hz), 8.00 (1H, d, J=7.0 Hz), 8.10 (1H, s), 8.25 (1H, t, J=6.0 Hz), 9.97 (1H, s)

Example 411

Compound 411

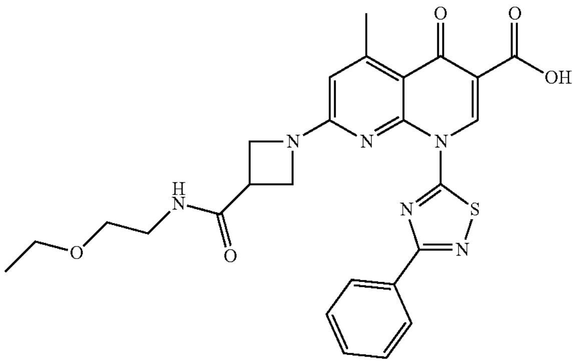

7-{3-[(2-Ethoxyethyl)carbamoyl]azetidin-1-yl}-5-methyl-4-oxo-1-(3-phenyl-1,2,4-thiadiazol-5-yl)-1,4-dihydro-1,8-naphthyridine-3-carboxylic acid The title compound was obtained using 7-chloro-5-methyl-4-oxo-1-(3-phenyl-1,2,4-thiadiazol-5-yl)-1,4-dihydro-1,8-naphthyridine-3-carboxylic acid obtained in Reference Example 036-(2) and N-(2-ethoxyethyl)azetidine-3-carboxamide hydrochloride obtained in Example 018-(1) by the method described in Example 018-(2) or a method equivalent thereto.

1H-NMR (DMSO-d6): δ 1.12 (3H, t, J=7.0 Hz), 2.78 (3H, s), 3.25-3.40 (2H, m), 3.43 (2H, t, J=5.5 Hz), 3.45 (2H, q, J=7.0 Hz), 3.62-3.68 (1H, m), 4.30-4.63 (4H, m), 6.60 (1H, s), 7.53-7.63 (3H, m), 8.27 (2H, d, J=6.5 Hz), 9.86 (1H, s)

Example 412

Compound 412

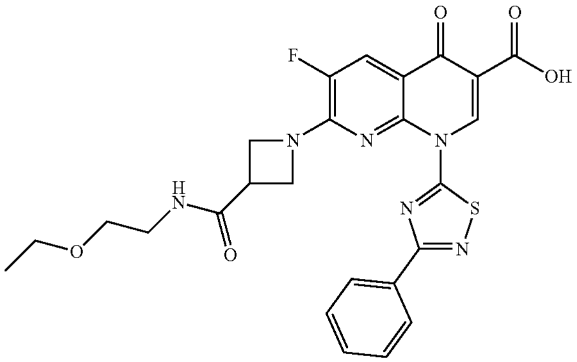

7-{3-[(2-Ethoxyethyl)carbamoyl]azetidin-1-yl}-6-fluoro-4-oxo-1-(3-phenyl-1,2,4-thiadiazol-5-yl)-1,4-dihydro-1,8-naphthyridine-3-carboxylic acid The title compound was obtained using 7-chloro-6-fluoro-4-oxo-1-(3-phenyl-1,2,4-thiadiazol-5-yl)-1,4-dihydro-1,8-naphthyridine-3-carboxylic acid obtained in Reference Example 037-(2) and N-(2-ethoxyethyl)azetidine-3-carboxamide hydrochloride obtained in Example 018-(1) by the method described in Example 025-(2) or a method equivalent thereto.

Property: pale yellow solid;

ESI-MS (m/z): 539 [M+H]+

Example 413

Compound 413

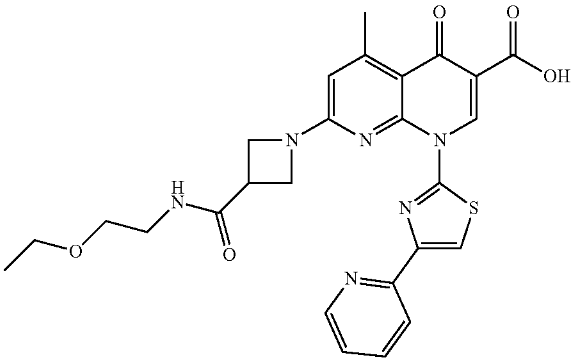

7-{3-[(2-Ethoxyethyl)carbamoyl]azetidin-1-yl}-5-methyl-4-oxo-1-[4-(pyridin-2-yl)-1,3-thiazol-2-yl]-1,4-dihydro-1,8-naphthyridine-3-carboxylic acid The title compound was obtained using 7-chloro-5-methyl-4-oxo-1-[4-(pyridin-2-yl)-1,3-thiazol-2-yl]-1,4-dihydro-1,8-naphthyridine-3-carboxylic acid obtained in Reference Example 038-(2) and N-(2-ethoxyethyl)azetidine-3-carboxamide hydrochloride obtained in Example 018-(1) by the method described in Example 018-(2) or a method equivalent thereto.

1H-NMR (D2O+NaOD): δ 1.04 (3H, t, J=7.0 Hz), 2.16 (3H, s), 3.27-3.41 (3H, m), 3.45 (2H, q, J=7.5 Hz), 3.49 (2H, t, J=5.5 Hz), 3.66-3.82 (4H, m), 5.26 (1H, s), 6.85 (2H, s), 7.37 (2H, s), 7.77 (1H, s), 8.91 (1H, s)

Example 414

Compound 414

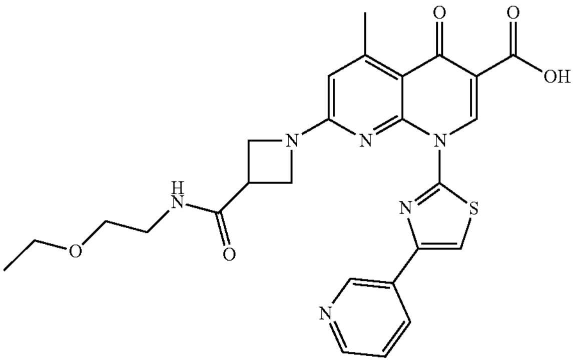

7-{3-[(2-Ethoxyethyl)carbamoyl]azetidin-1-yl}-5-methyl-4-oxo-1-[4-(pyridin-3-yl)-1,3-thiazol-2-yl]-1,4-dihydro-1,8-naphthyridine-3-carboxylic acid The title compound was obtained using 7-chloro-5-methyl-4-oxo-1-[4-(pyridin-3-yl)-1,3-thiazol-2-yl]-1,4-dihydro-1,8-naphthyridine-3-carboxylic acid obtained in Reference Example 039-(2) and N-(2-ethoxyethyl)azetidine-3-carboxamide hydrochloride obtained in Example 018-(1) by the method described in Example 002-(3) or a method equivalent thereto.

1H-NMR (DMSO-d6): δ 1.04-1.18 (3H, m), 2.71 (3H, brs), 3.42-3.64 (7H, m), 4.03-4.50 (4H, m), 6.29 (1H, brs), 7.50 (1H, brs), 8.08 (1H, brs), 8.31 (2H, brs), 8.56 (1H, brs), 9.17 (1H, brs), 9.85 (1H, brs)

Example 415

Compound 415

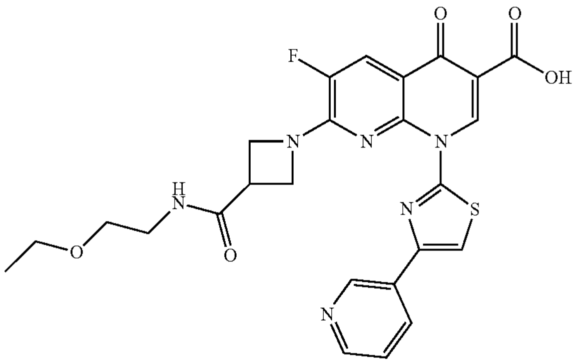

7-{3-[(2-Ethoxyethyl)carbamoyl]azetidin-1-yl}-6-fluoro-4-oxo-1-[4-(pyridin-3-yl)-1,3-thiazol-2-yl]-1,4-dihydro-1,8-naphthyridine-3-carboxylic acid The title compound was obtained using 7-chloro-6-fluoro-4-oxo-1-[4-(pyridin-3-yl)-1,3-thiazol-2-yl]-1,4-dihydro-1,8-naphthyridine-3-carboxylic acid obtained in Reference Example 040-(2) and N-(2-ethoxyethyl)azetidine-3-carboxamide hydrochloride obtained in Example 018-(1) by the method described in Example 001-(3) or a method equivalent thereto.

1H-NMR (CD3OD): δ 1.19 (3H, t, J=7.0 Hz), 3.24-3.82 (7H, m), 4.39-5.09 (4H, m), 7.45 (1H, brs), 7.80 (1H, brs), 7.86-7.95 (1H, m), 8.31-8.40 (1H, m), 8.44 (1H, brs), 9.05 (1H, brs), 9.88 (1H, brs)

Example 416

Compound 416

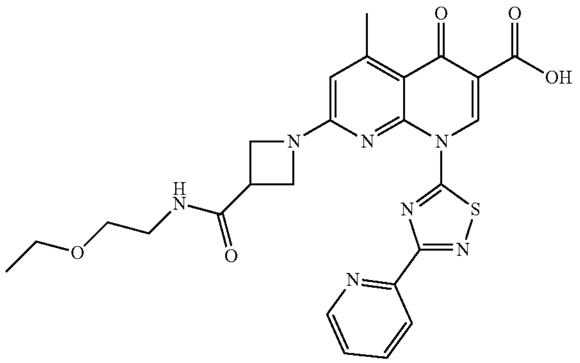

7-{3-[(2-Ethoxyethyl)carbamoyl]azetidin-1-yl}-5-methyl-4-oxo-1-[3-(pyridin-2-yl)-1,2,4-thiadiazol-5-yl]-1,4-dihydro-1,8-naphthyridine-3-carboxylic acid The title compound was obtained using 7-chloro-5-methyl-4-oxo-1-[3-(pyridin-2-yl)-1,2,4-thiadiazol-5-yl]-1,4-dihydro-1,8-naphthyridine-3-carboxylic acid obtained in Reference Example 041-(2) and N-(2-ethoxyethyl)azetidine-3-carboxamide hydrochloride obtained in Example 018-(1) by the method described in Example 018-(2) or a method equivalent thereto.

1H-NMR (DMSO-d6): δ 1.12 (3H, t, J=7.0 Hz), 2.78 (3H, S), 3.30 (2H, t, J=5.5 Hz), 3.43 (2H, t, J=5.5 Hz), 3.44 (2H, q, J=7.0 Hz), 3.60-3.69 (1H, m), 4.29-4.63 (4H, m), 6.60 (1H, s), 7.57 (1H, ddd, J=7.5, 5.5, 1.5 Hz), 8.03 (1H, td, J=7.5, 1.5 Hz), 8.28 (1H, t, J=5.5 Hz), 8.31 (1H, d, J=7.5 Hz), 8.80 (1H, d, J=4.0 Hz), 9.86 (1H, s)

Example 417

Compound 417

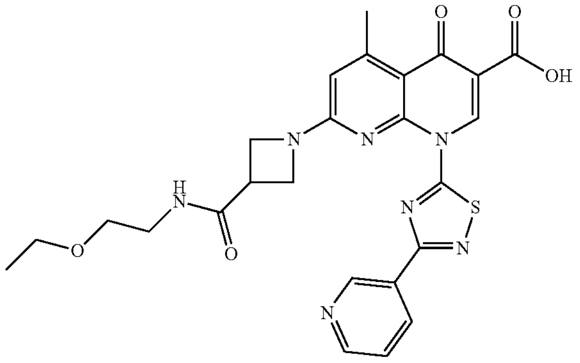

7-{3-[(2-Ethoxyethyl)carbamoyl]azetidin-1-yl}-5-methyl-4-oxo-1-[3-(pyridin-3-yl)-1,2,4-thiadiazol-5-yl]-1,4-dihydro-1,8-naphthyridine-3-carboxylic acid The title compound was obtained using 7-chloro-5-methyl-4-oxo-1-[3-(pyridin-3-yl)-1,2,4-thiadiazol-5-yl]-1, 4-dihydro-1,8-naphthyridine-3-carboxylic acid obtained in Reference Example 042-(2) and N-(2-ethoxyethyl)azetidine-3-carboxamide hydrochloride obtained in Example 018-(1) by the method described in Example 001-(3) or a method equivalent thereto.

1H-NMR (DMSO-d6): δ 1.12 (3H, t, J=7.0 Hz), 2.72 (3H, s), 3.13-3.54 (6H, m), 3.57-3.74 (1H, m), 4.20-4.60 (4H, m), 6.44 (1H, s), 7.58 (1H, dd, J=8.0, 4.5 Hz), 8.31 (1H, t, J=5.5 Hz), 8.50 (1H, d, J=8.0 Hz), 8.72 (1H, d, J=4.5 Hz), 9.33 (1H, s), 9.54 (1H, s)

Example 418

Compound 418

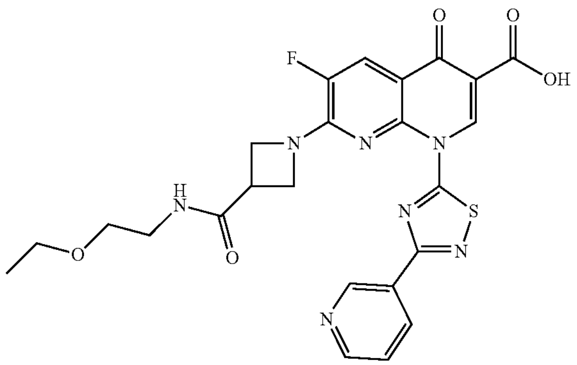

7-{3-[(2-Ethoxyethyl)carbamoyl]azetidin-1-yl}-6-fluoro-4-oxo-1-[3-(pyridin-3-yl)-1,2,4-thiadiazol-5-yl]-1,4-dihydro-1,8-naphthyridine-3-carboxylic acid The title compound was obtained using 7-chloro-6-fluoro-4-oxo-1-[3-(pyridin-3-yl)-1,2,4-thiadiazol-5-yl]-1,4-dihydro-1,8-naphthyridine-3-carboxylic acid obtained in Reference Example 043-(2) and N-(2-ethoxyethyl)azetidine-3-carboxamide hydrochloride obtained in Example 018-(1) by the method described in Example 001-(3) or a method equivalent thereto.

1H-NMR (DMSO-d6): δ 1.13 (3H, t, J=7.0 Hz), 2.89 (3H, s), 3.23-3.38 (2H, m), 3.42-3.47 (4H, m), 3.65-3.73 (1H, m), 4.53-4.84 (4H, m), 7.64 (1H, dd, J=7.5, 4.5 Hz), 8.14 (1H, d, J=11.0 Hz), 8.27 (1H, t, J=5.5 Hz), 8.57 (1H, d, J=7.5 Hz), 8.76 (1H, dd, J=4.5, 1.5 Hz), 9.41 (1H, s), 9.82 (1H, s)

Example 419

Compound 419

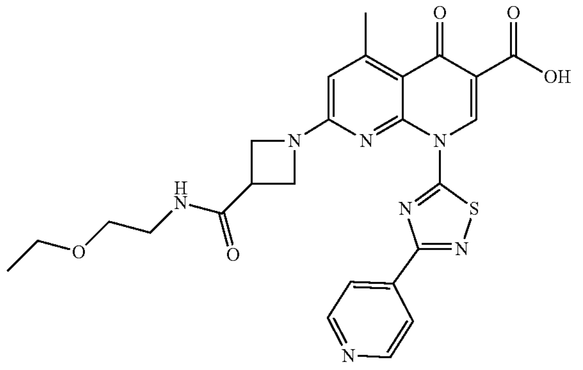

7-{3-[(2-Ethoxyethyl)carbamoyl]azetidin-1-yl}-5-methyl-4-oxo-1-[3-(pyridin-4-yl)-1,2,4-thiadiazol-5-yl]-1,4-dihydro-1,8-naphthyridine-3-carboxylic acid The title compound was obtained using 7-chloro-5-methyl-4-oxo-1-[3-(pyridin-4-yl)-1,2,4-thiadiazol-5-yl]-1,4-dihydro-1,8-naphthyridine-3-carboxylic acid obtained in Reference Example 044-(2) and N-(2-ethoxyethyl)azetidine-3-carboxamide hydrochloride obtained in Example 018-(1) by the method described in Example 001-(3) or a method equivalent thereto.

1H-NMR (DMSO-d6): δ 1.13 (3H, t, J=7.0 Hz), 2.74 (3H, s), 3.43-3.48 (6H, m), 3.59-3.71 (1H, m), 4.29-4.59 (4H, m), 6.54 (1H, s), 8.09 (2H, d, J=5.5 Hz), 8.29 (1H, t, J=5.0 Hz), 8.79 (2H, d, J=5.5 Hz), 9.74 (1H, s)

Example 420

Compound 420

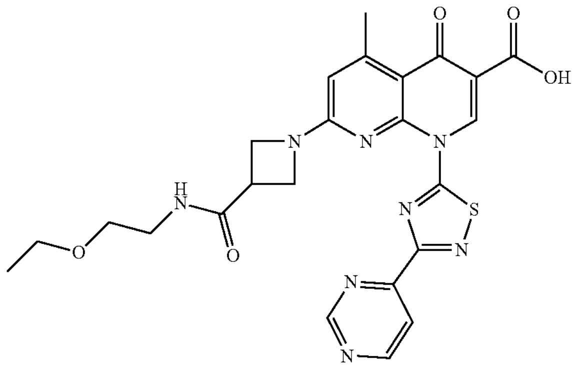

7-{3-[(2-Ethoxyethyl)carbamoyl]azetidin-1-yl}-5-methyl-4-oxo-1-[3-(pyrimidin-4-yl)-1,2,4-thiadiazol-5-yl]-1,4-dihydro-1,8-naphthyridine-3-carboxylic acid The title compound was obtained using 7-chloro-5-methyl-4-oxo-1-[3-(pyrimidin-4-yl)-1,2,4-thiadiazol-5-yl]-1,4-dihydro-1,8-naphthyridine-3-carboxylic acid obtained in Reference Example 045-(2) and N-(2-ethoxyethyl)azetidine-3-carboxamide hydrochloride obtained in Example 018-(1) by the method described in Example 001-(3) or a method equivalent thereto.

1H-NMR (DMSO-d6): δ 1.13 (3H, t, J=7.0 Hz), 2.74 (3H, s), 3.26-3.30 (2H, m), 3.44 (2H, t, J=6.0 Hz), 3.46 (2H, q, J=7.0 Hz), 3.62-3.70 (1H, m), 4.24-4.64 (4H, m), 6.55 (1H, s), 8.27 (1H, dd, J=5.0, 1.5 Hz), 8.29 (1H, t, J=6.0 Hz), 9.06 (1H, d, J=5.0 Hz), 9.40 (1H, d, J=1.5 Hz), 9.72 (1H, s)

Example 421

Compound 421

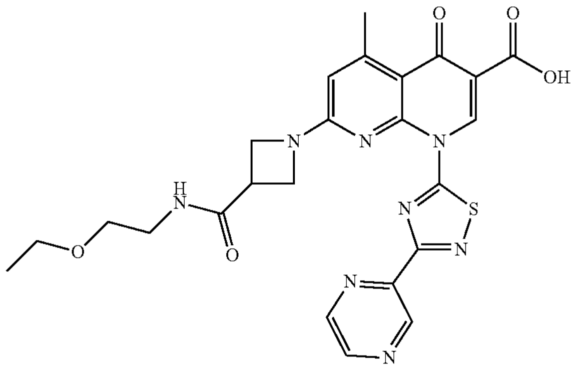

7-{3-[(2-Ethoxyethyl)carbamoyl]azetidin-1-yl}-5-methyl-4-oxo-1-[3-(pyrazin-2-yl)-1,2,4-thiadiazol-5-yl]-1,4-dihydro-1,8-naphthyridine-3-carboxylic acid The title compound was obtained using 7-chloro-5-methyl-4-oxo-1-[3-(pyrazin-2-yl)-1,2,4-thiadiazol-5-yl]-1,4-dihydro-1,8-naphthyridine-3-carboxylic acid obtained in Reference Example 046-(2) and N-(2-ethoxyethyl)azetidine-3-carboxamide hydrochloride obtained in Example 018-(1) by the method described in Example 001-(3) or a method equivalent thereto.

1H-NMR (DMSO-d6): δ 1.13 (3H, t, J=7.0 Hz), 2.77 (3H, s), 3.22-3.37 (2H, m), 3.43 (2H, t, J=5.5 Hz), 3.46 (2H, q, J=7.0 Hz), 3.62-3.70 (1H, m), 4.27-4.66 (4H, m), 6.59 (1H, s), 8.28 (1H, t, J=5.5 Hz), 8.83 (1H, d, J=2.0 Hz), 8.87 (1H, s), 9.47 (1H, s), 9.80 (1H, s)

Example 422

Compound 422

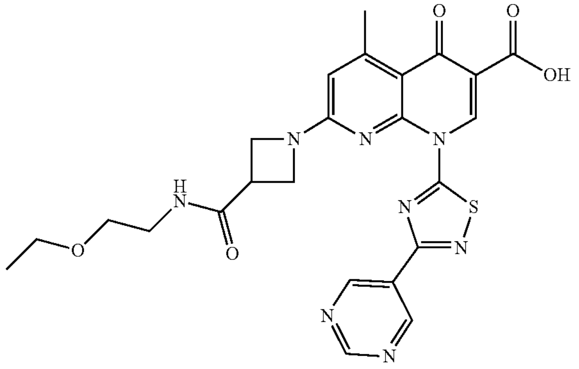

7-{3-[(2-Ethoxyethyl)carbamoyl]azetidin-1-yl}-5-methyl-4-oxo-1-[3-(pyrimidin-5-yl)-1,2,4-thiadiazol-5-yl]-1,4-dihydro-1,8-naphthyridine-3-carboxylic acid The title compound was obtained using 7-chloro-5-methyl-4-oxo-1-[3-(pyrimidin-5-yl)-1,2,4-thiadiazol-5-yl]-1,4-dihydro-1,8-naphthyridine-3-carboxylic acid obtained in Reference Example 047-(2) and N-(2-ethoxyethyl)azetidine-3-carboxamide hydrochloride obtained in Example 018-(1) by the method described in Example 001-(3) or a method equivalent thereto.

1H-NMR (DMSO-d6): δ 1.12 (3H, t, J=7.0 Hz), 2.75 (3H, s), 3.09-3.57 (6H, m), 3.58-3.72 (1H, m), 4.23-4.67 (4H, m), 6.57 (1H, brs), 8.28 (1H, brs), 9.36 (1H, s), 9.51 (1H, s), 9.76 (1H, s)

Example 423

Compound 423

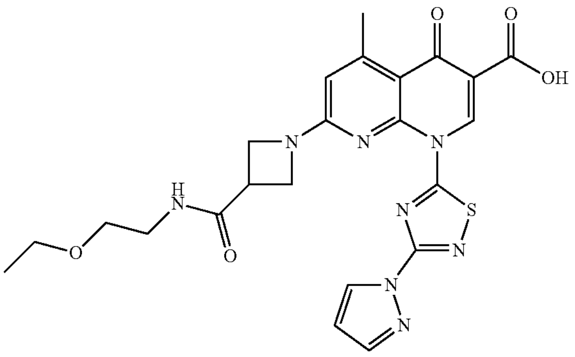

7-{3-[(2-Ethoxyethyl)carbamoyl]azetidin-1-yl}-5-methyl-4-oxo-1-[3-(1H-pyrazol-1-yl)-1,2,4-thiadiazol-5-yl]-1,4-dihydro-1,8-naphthyridine-3-carboxylic acid The title compound was obtained using 7-chloro-5-methyl-4-oxo-1-[3-(1H-pyrazol-1-yl)-1,2,4-thiadiazol-5-yl]-1,4-dihydro-1,8-naphthyridine-3-carboxylic acid obtained in Reference Example 048-(2) and N-(2-ethoxyethyl)azetidine-3-carboxamide hydrochloride obtained in Example 018-(1) by the method described in Example 001-(3) or a method equivalent thereto.

1H-NMR (DMSO-d6): δ 1.12 (3H, t, J=7.0 Hz), 2.77 (3H, s), 3.23-3.51 (6H, m), 3.61-3.69 (1H, m), 4.22-4.65 (4H, m), 6.59 (1H, s), 6.65 (1H, t, J=2.0 Hz), 7.90 (1H, s), 8.27 (1H, t, J=5.5 Hz), 8.61 (1H, d, J=2.0 Hz), 9.70 (1H, s)

Example 424

Compound 424

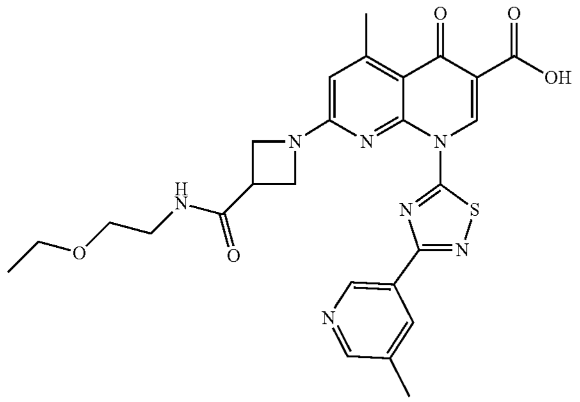

7-{3-[(2-Ethoxyethyl)carbamoyl]azetidin-1-yl}-5-methyl-1-[3-(5-methylpyridin-3-yl)-1,2,4-thiadiazol-5-yl]-4-oxo-1,4-dihydro-1,8-naphthyridine-3-carboxylic acid The title compound was obtained using 7-chloro-5-methyl-1-[3-(5-methylpyridin-3-yl)-1,2,4-thiadiazol-5-yl]-4-oxo-1,4-dihydro-1,8-naphthyridine-3-carboxylic acid obtained in Reference Example 050-(3) and N-(2-ethoxyethyl)azetidine-3-carboxamide hydrochloride obtained in Example 018-(1) by the method described in Example 001-(3) or a method equivalent thereto.

1H-NMR (DMSO-d6): δ 1.13 (3H, t, J=7.0 Hz), 2.42 (3H, s), 2.74 (3H, s), 3.27-3.31 (2H, m), 3.42-3.48 (4H, m), 3.61-3.69 (1H, m), 4.29-4.57 (4H, m), 6.55 (1H, s), 7.79 (1H, brs), 8.26 (1H, s), 8.29 (1H, t, J=6.0 Hz), 8.56 (1H, s), 9.13 (1H, s), 9.72 (1H, s)

Example 425

Compound 425

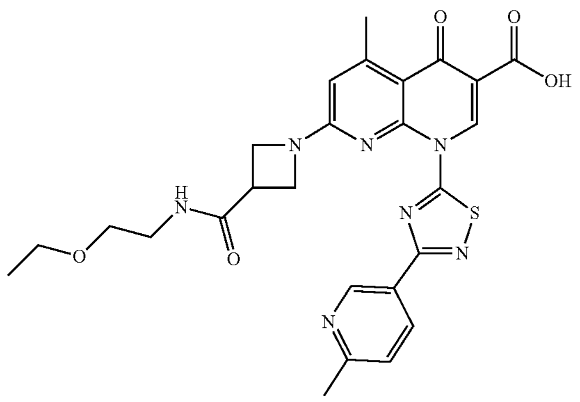

7-{3-[(2-Ethoxyethyl)carbamoyl]azetidin-1-yl}-5-methyl-1-[3-(6-methylpyridin-3-yl)-1,2,4-thiadiazol-5-yl]-4-oxo-1,4-dihydro-1,8-naphthyridine-3-carboxylic acid The title compound was obtained using 7-chloro-5-methyl-1-[3-(6-methylpyridin-3-yl)-1,2,4-thiadiazol-5-yl]-4-oxo-1,4-dihydro-1,8-naphthyridine-3-carboxylic acid obtained in Reference Example 051-(2) and N-(2-ethoxyethyl)azetidine-3-carboxamide hydrochloride obtained in Example 018-(1) by the method described in Example 001-(3) or a method equivalent thereto.

1H-NMR (DMSO-d6): δ 1.13 (3H, t, J=7.0 Hz), 2.56 (3H, s), 2.76 (3H, s), 3.21-3.39 (2H, m), 3.42-3.47 (4H, m), 3.59-3.70 (1H, m), 4.26-4.62 (4H, m), 6.57 (1H, s), 7.45 (1H, d, J=8.5 Hz), 8.27 (1H, t, J=5.5 Hz), 8.40 (1H, dd, J=8.0, 2.0 Hz), 9.23 (1H, d, J=2.0 Hz), 9.78 (1H, s)

Example 426

Compound 426

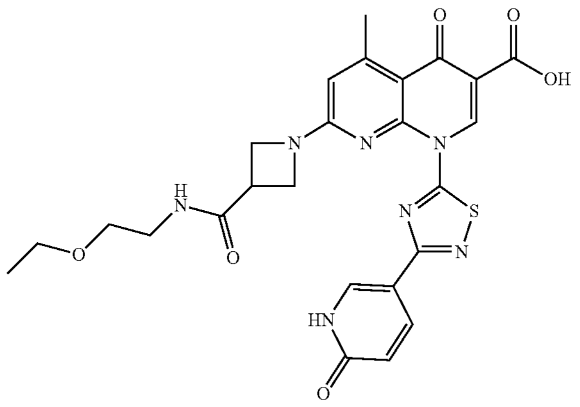

7-{3-[(2-Ethoxyethyl)carbamoyl]azetidin-1-yl}-5-methyl-4-oxo-1-[3-(6-oxo-1,6-dihydropyridin-3-yl)-1,2,4-thiadiazol-5-yl]-1,4-dihydro-1,8-naphthyridine-3-carboxylic acid The title compound was obtained using 7-chloro-5-methyl-4-oxo-1-[3-(6-methoxypyridin-3-yl)-1,2,4-thiadiazol-5-yl]-1,4-dihydro-1,8-naphthyridine-3-carboxylic acid obtained in Reference Example 052-(2) and N-(2-ethoxyethyl)azetidine-3-carboxamide hydrochloride obtained in Example 018-(1) by the method described in Example 001-(3) or a method equivalent thereto.

1H-NMR (DMSO-d6): δ 1.12 (3H, t, J=7.0 Hz), 2.69 (3H, s), 3.23-3.38 (2H, m), 3.40-3.50 (4H, m), 3.59-3.69 (1H, m), 4.24-4.55 (4H, m), 6.45 (1H, d, J=9.5 Hz), 6.48 (1H, s), 8.01 (1H, dd, J=9.5, 2.5 Hz), 8.10 (1H, brs), 8.28 (1H, t, J=5.5 Hz), 9.57 (1H, s), 11.94 (1H, brs)

Example 427

Compound 427

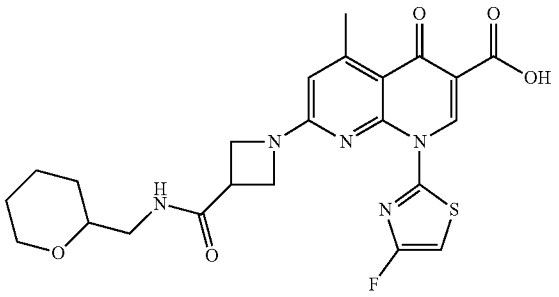

1-(4-Fluoro-1,3-thiazol-2-yl)-5-methyl-7-{3-[(oxan-2-ylmethyl)carbamoyl]azetidin-1-yl}-4-oxo-1,4-dihydro-1,8-naphthyridine-3-carboxylic acid The title compound was obtained using 7-chloro-1-(4-fluoro-1,3-thiazol-2-yl)-5-methyl-4-oxo-1,4-dihydro-1,8-naphthyridine-3-carboxylic acid obtained in Reference Example 009-(2) N-(oxan-2-ylmethyl)azetidine-3-carboxamide hydrochloride obtained in Example 078-(1) by the method described in Example 001-(3) or a method equivalent thereto.

1H-NMR (DMSO-d6): δ 1.06-1.22 (1H, m), 1.39-1.50 (3H, m), 1.52-1.59 (1H, m), 1.73-1.81 (1H, m), 2.75 (3H, s), 3.04-3.23 (4H, m), 3.57-3.67 (1H, m), 3.83-3.92 (1H, m), 4.16-4.51 (4H, m), 6.51 (1H, s), 7.72 (1H, d, J=3.0 Hz), 8.22 (1H, t, J=5.5 Hz), 9.67 (1H, s)

Example 428

Compound 428

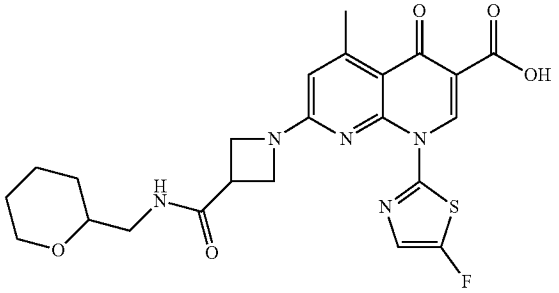

1-(5-Fluoro-1,3-thiazol-2-yl)-5-methyl-7-{3-[(oxan-2-ylmethyl)carbamoyl]azetidin-1-yl}-4-oxo-1,4-dihydro-1,8-naphthyridine-3-carboxylic acid The title compound was obtained using 7-chloro-1-(5-fluoro-1,3-thiazol-2-yl)-5-methyl-4-oxo-1,4-dihydro-1,8-naphthyridine-3-carboxylic acid obtained in Reference Example 010-(2) and N-(oxan-2-ylmethyl)azetidine-3-carboxamide hydrochloride obtained in Example 078-(1) by the method described in Example 001-(3) or a method equivalent thereto.

1H-NMR (DMSO-d6): δ 1.10-1.20 (1H, m), 1.38-1.50 (3H, m), 1.51-1.59 (1H, m), 1.72-1.82 (1H, m), 2.76 (3H, s), 3.03-3.25 (4H, m), 3.57-3.68 (1H, m), 3.84-3.91 (1H, m), 4.10-4.57 (4H, m), 6.55 (1H, s), 7.74 (1H, d, J=2.5 Hz), 8.25 (1H, t, J=5.5 Hz), 9.68 (1H, s), 15.34 (1H, brs)

Example 429

Compound 429

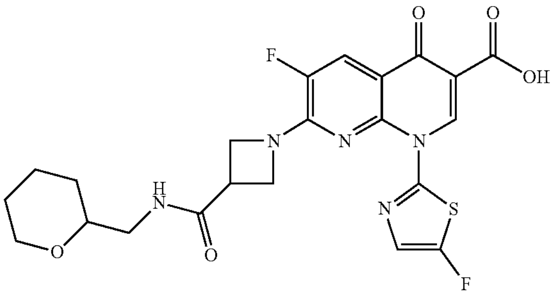

6-Fluoro-1-(5-fluoro-1,3-thiazol-2-yl)-7-{3-[(oxan-2-ylmethyl)carbamoyl]azetidin-1-yl}-4-oxo-1,4-dihydro-1,8-naphthyridine-3-carboxylic acid The title compound was obtained using 7-chloro-6-fluoro-1-(5-fluoro-1,3-thiazol-2-yl)-4-oxo-1,4-dihydro-1,8-naphthyridine-3-carboxylic acid obtained in Reference Example 011-(2) and N-(oxan-2-ylmethyl)azetidine-3-carboxamide hydrochloride obtained in Example 078-(1) by the method described in Example 001-(3) or a method equivalent thereto.

1H-NMR (DMSO-d6): δ 1.10-1.20 (1H, m), 1.38-1.50 (3H, m), 1.53-1.60 (1H, m), 1.72-1.82 (1H, m), 3.01-3.25 (4H, m), 3.61-3.71 (1H, m), 3.84-3.91 (1H, m), 4.22-4.96 (4H, m), 7.77 (1H, d, J=2.5 Hz), 8.10 (1H, d, J=11.5 Hz), 8.24 (1H, t, J=5.5 Hz), 9.66 (1H, s), 14.74 (1H, brs)

Example 430

Compound 430

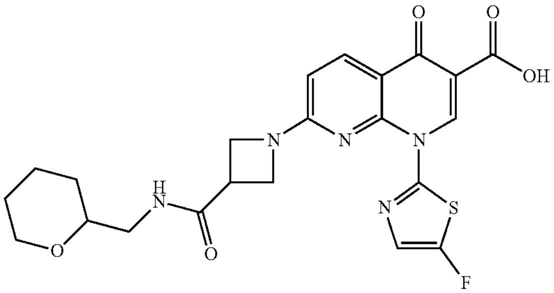

1-(5-Fluoro-1,3-thiazol-2-yl)-7-{3-[(oxan-2-ylmethyl)carbamoyl]azetidin-1-yl}-4-oxo-1,4-dihydro-1,8-naphthyridine-3-carboxylic acid The title compound was obtained using 7-chloro-1-(5-fluoro-1,3-thiazol-2-yl)-4-oxo-1,4-dihydro-1,8-naphthyridine-3-carboxylic acid obtained in Reference Example 012-(2) and N-(oxan-2-ylmethyl)azetidine-3-carboxamide hydrochloride obtained in Example 078 by the method described in Example 001-(3) or a method equivalent thereto.

1H-NMR (DMSO-d6): δ 1.11-1.21 (1H, m), 1.39-1.50 (3H, m), 1.52-1.59 (1H, m), 1.72-1.82 (1H, m), 3.01-3.25 (4H, m), 3.59-3.69 (1H, m), 3.83-3.91 (1H, m), 4.19-4.57 (4H, m), 6.76 (1H, d, J=9.0 Hz), 7.76 (1H, d, J=3.0 Hz), 8.26 (1H, t, J=5.5 Hz), 8.32 (1H, d, J=9.0 Hz), 9.69 (1H, s), 14.95 (1H, brs)

Example 431

Compound 431

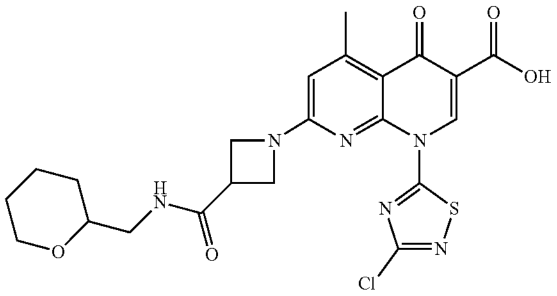

1-(3-Chloro-1,2,4-thiadiazol-5-yl)-5-methyl-7-{3-[(oxan-2-ylmethyl)carbamoyl]azetidin-1-yl}-4-oxo-1,4-dihydro-1,8-naphthyridine-3-carboxylic acid The title compound was obtained using 7-chloro-1-(3-chloro-1,2,4-thiadiazol-5-yl)-5-methyl-4-oxo-1,4-dihydro-1,8-naphthyridine-3-carboxylic acid obtained in Reference Example 013-(2) and N-(oxan-2-ylmethyl)azetidine-3-carboxamide hydrochloride obtained in Example 078 by the method described in Example 001-(3) or a method equivalent thereto.

1H-NMR (DMSO-d6): δ 1.06-1.22 (1H, m), 1.35-1.50 (3H, m), 1.50-1.62 (1H, m), 1.70-1.83 (1H, m), 2.76 (3H, s), 3.04-3.23 (4H, m), 3.59-3.70 (1H, m), 3.80-3.91 (1H, m), 4.08-4.60 (4H, m), 6.58 (1H, s), 8.24 (1H, t, J=5.5 Hz), 9.50 (1H, s)

Example 432

Compound 432

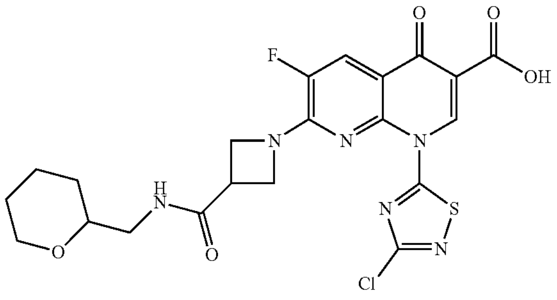

1-(3-Chloro-1,2,4-thiadiazol-5-yl)-6-fluoro-7-{3-[(oxan-2-ylmethyl)carbamoyl]azetidin-1-yl}-4-oxo-1,4-dihydro-1,8-naphthyridine-3-carboxylic acid The title compound was obtained using 7-chloro-1-(3-chloro-1,2,4-thiadiazol-5-yl)-6-fluoro-4-oxo-1,4-dihydro-1,8-naphthyridine-3-carboxylic acid obtained in Reference Example 014-(2) and N-(oxan-2-ylmethyl)azetidine-3-carboxamide hydrochloride obtained in Example 078 by the method described in Example 001-(3) or a method equivalent thereto.

1H-NMR (DMSO-d6): δ 1.09-1.21 (1H, m), 1.36-1.50 (3H, m), 1.50-1.60 (1H, m), 1.71-1.81 (1H, m), 3.04-3.23 (4H, m), 3.63-3.74 (1H, m), 3.81-3.92 (1H, m), 4.18-4.87 (4H, m), 7.96 (1H, d, J=12.0 Hz), 8.23 (1H, t, J=6.0 Hz), 9.51 (1H, s)

Example 433

Compound 433

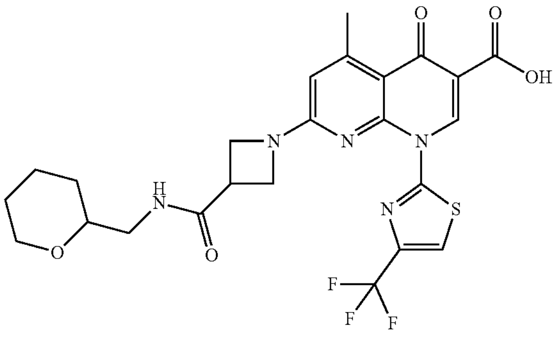

5-Methyl-7-{3-[(oxan-2-ylmethyl)carbamoyl]azetidin-1-yl}-4-oxo-1-[4-(trifluoromethyl)-1,3-thiazol-2-yl]-1,4-dihydro-1,8-naphthyridine-3-carboxylic acid The title compound was obtained using 7-chloro-5-methyl-4-oxo-1-[4-(trifluoromethyl)-1,3-thiazol-2-yl]-1,4-dihydro-1,8-naphthyridine-3-carboxylic acid obtained in Reference Example 017-(2) and N-(oxan-2-ylmethyl)azetidine-3-carboxamide hydrochloride obtained in Example 078 by the method described in Example 001-(3) or a method equivalent thereto.

1H-NMR (DMSO-d6): δ 1.09-1.22 (1H, m), 1.36-1.50 (3H, m), 1.51-1.60 (1H, m), 1.71-1.82 (1H, m), 2.77 (3H, s), 3.03-3.23 (4H, m), 3.60-3.69 (1H, m), 3.84-3.92 (1H, m), 4.18-4.51 (4H, m), 6.55 (1H, s), 8.23 (1H, t, J=6.0 Hz), 8.40 (1H, s), 9.72 (1H, s)

Example 434

Compound 434

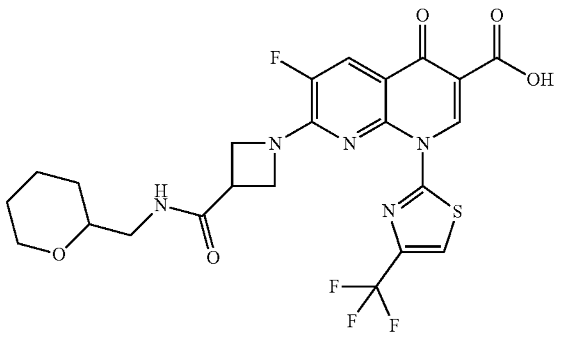

6-Fluoro-7-{3-[(oxan-2-ylmethyl)carbamoyl]azetidin-1-yl}-4-oxo-1-[4-(trifluoromethyl)-1,3-thiazol-2-yl]-1,4-dihydro-1,8-naphthyridine-3-carboxylic acid The title compound was obtained using 7-chloro-6-fluoro-4-oxo-1-[4-(trifluoromethyl)-1,3-thiazol-2-yl]-1,4-dihydro-1,8-naphthyridine-3-carboxylic acid obtained in Reference Example 018-(2) and N-(oxan-2-ylmethyl)azetidine-3-carboxamide hydrochloride obtained in Example 078 by the method described in Example 001-(3) or a method equivalent thereto.

1H-NMR (DMSO-d6): δ 1.09-1.21 (1H, m), 1.37-1.51 (3H, m), 1.51-1.60 (1H, m), 1.71-1.81 (1H, m), 3.04-3.24 (4H, m), 3.63-3.72 (1H, m), 3.83-3.92 (1H, m), 4.40-4.84 (4H, m), 8.11 (1H, d, J=11.5 Hz), 8.22 (1H, t, J=5.5 Hz), 8.44 (1H, s), 9.70 (1H, s)

Example 435

Compound 435

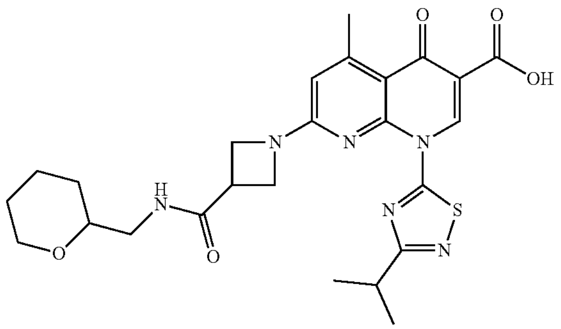

5-Methyl-7-{3-[(oxan-2-ylmethyl)carbamoyl]azetidin-1-yl}-4-oxo-1-[3-(propan-2-yl)-1,2,4-thiadiazol-5-yl]-1,4-dihydro-1,8-naphthyridine-3-carboxylic acid The title compound was obtained using 7-chloro-5-methyl-4-oxo-1-[3-(propan-2-yl)-1,2,4-thiadiazol-5-yl]-1,4-dihydro-1,8-naphthyridine-3-carboxylic acid obtained in Reference Example 020-(2) and N-(oxan-2-ylmethyl)azetidine-3-carboxamide hydrochloride obtained in Example 078 by the method described in Example 001-(3) or a method equivalent thereto.

1H-NMR (DMSO-d6): δ 1.11-1.22 (1H, m), 1.36 (6H, d, J=6.5 Hz), 1.39-1.50 (3H, m), 1.52-1.60 (1H, m), 1.72-1.81 (1H, m), 2.75 (3H, s), 3.05-3.15 (1H, m), 3.15-3.23 (1H, m), 3.27-3.36 (3H, m), 3.60-3.70 (1H, m), 3.84-3.91 (1H, m), 4.19-4.59 (4H, m), 6.55 (1H, s), 8.23 (1H, t, J=5.5 Hz), 9.70 (1H, s)

Example 436

Compound 436

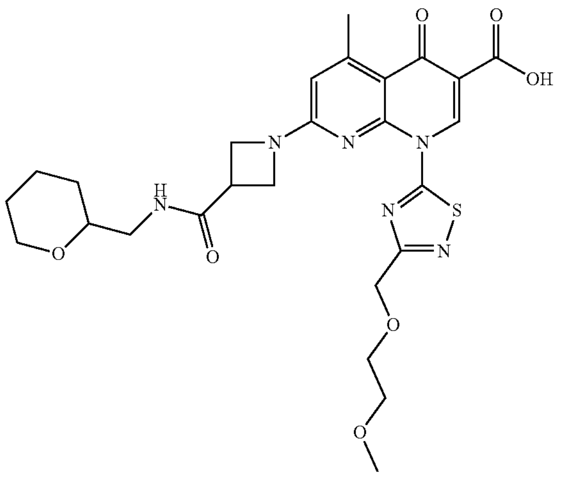

1-{3-[(2-Methoxyethoxy)methyl]-1,2,4-thiadiazol-5-yl}-5-methyl-7-{3-[(oxan-2-ylmethyl)carbamoyl]azetidin-1-yl}-4-oxo-1,4-dihydro-1,8-naphthyridine-3-carboxylic acid (1) Ethyl 1-{3-[(2-methoxyethoxy)methyl]-1,2,4-thiadiazol-5-yl}-5-methyl-7-{3-[(oxan-2-ylmethyl)carbamoyl]azetidin-1-yl}-4-oxo-1,4-dihydro-1,8-naphthyridine-3-carboxylate was obtained using ethyl 7-chloro-1-{3-[(2-methoxyethoxy)methyl]-1,2,4-thiadiazol-5-yl}-5-methyl-4-oxo-1,4-dihydro-1,8-naphthyridine-3-carboxylate obtained in Reference Example 022-(3) and N-(oxan-2-ylmethyl)azetidine-3-carboxamide hydrochloride obtained in Example 078 by the method described in Example 001-(3) or a method equivalent thereto.

1H-NMR (DMSO-d6): δ 1.10-1.19 (1H, m), 1.30 (3H, t, J=7.0 Hz), 1.39-1.48 (3H, brm), 1.55 (1H, d, J=13.0 Hz), 1.76 (1H, brs), 2.71 (3H, s), 3.04-3.13 (2H, m), 3.14-3.22 (1H, m), 3.26 (3H, s), 3.50 (2H, t, J=5.0 Hz), 3.57-3.67 (1H, m), 3.69 (2H, t, J=5.0 Hz), 3.87 (1H, d, J=9.5 Hz), 4.14-4.55 (4H, m), 4.28 (2H, q, J=7.0 Hz), 4.69 (2H, s), 6.41 (1H, s), 8.21 (1H, t, J=5.5 Hz), 9.39 (1H, s)

(2) The title compound was obtained from ethyl 1-{3-[(2-methoxyethoxy)methyl]-1,2,4-thiadiazol-5-yl}-5-methyl-7-{3-[(oxan-2-ylmethyl)carbamoyl]azetidin-1-yl}-4-oxo-1,4-dihydro-1,8-naphthyridine-3-carboxylate obtained in the preceding section by the method described in Example 028-(2) or a method equivalent thereto.

1H-NMR (D2O+NaOD): δ 1.10-1.24 (1H, m), 1.35-1.48 (3H, m), 1.51-1.60 (1H, m), 1.67-1.77 (1H, m), 2.34 (3H, s), 3.10-3.26 (2H, m), 3.29 (3H, s), 3.34-3.41 (1H, m), 3.42-

3.49 (1H, m), 3.49-3.56 (1H, m), 3.56-3.62 (2H, m), 3.71-3.77 (2H, m), 3.82-3.89 (1H, m), 3.89-4.03 (4H, m), 5.68 (1H, s), 8.92 (1H, s)

Example 437

Compound 437

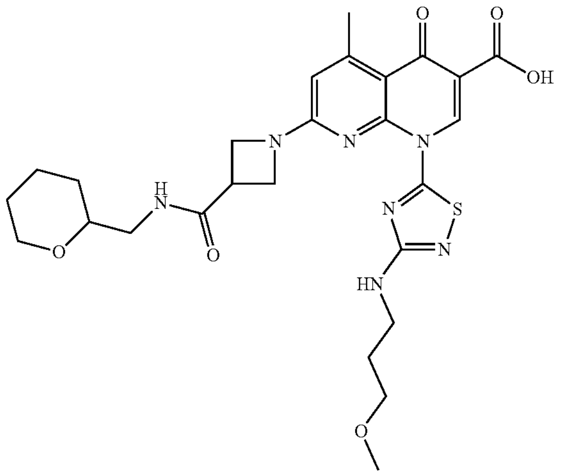

1-{3-[(3-Methoxypropyl)amino]-1,2,4-thiadiazol-5-yl}-5-methyl-7-{3-[(oxan-2-ylmethyl)carbamoyl]azetidin-1-yl}-4-oxo-1,4-dihydro-1,8-naphthyridine-3-carboxylic acid (1) A crude ethyl 1-{3-[(3-methoxypropyl)amino]-1,2,4-thiadiazol-5-yl}-5-methyl-7-{3-[(oxan-2-ylmethyl)carbamoyl]azetidin-1-yl}-4-oxo-1,4-dihydro-1,8-naphthyridine-3-carboxylate was obtained using ethyl 7-chloro-1-{3-[(3-methoxypropyl)amino]-1,2,4-thiadiazol-5-yl}-5-methyl-4-oxo-1,4-dihydro-1,8-naphthyridine-3-carboxylate obtained in Reference Example 028-(2) and N-(oxan-2-ylmethyl)azetidine-3-carboxamide hydrochloride obtained in Example 078 by the method described in Example 001-(3) or a method equivalent thereto.

(2) The title compound was obtained from crude ethyl 1-{3-[(3-methoxypropyl)amino]-1,2,4-thiadiazol-5-yl}-5-methyl-7-{3-[(oxan-2-ylmethyl)carbamoyl]azetidin-1-yl}-4-oxo-1,4-dihydro-1,8-naphthyridine-3-carboxylate obtained in the preceding section by the method described in Example 028-(2) or a method equivalent thereto.

Property: yellow solid;

ESI-MS (m/z): 572 [M+H]+

Example 438

Compound 438

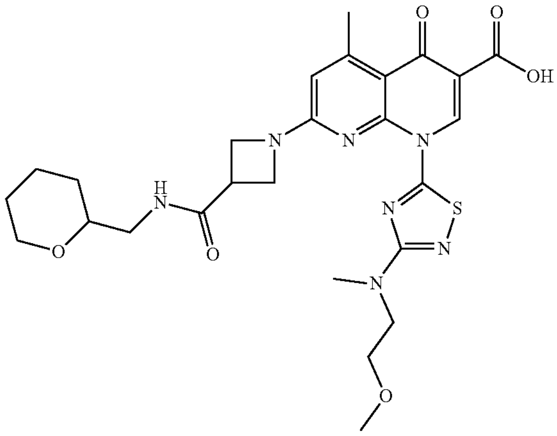

1-{3-[(2-Methoxyethyl) (methyl)amino]-1,2,4-thiadiazol-5-yl}-5-methyl-7-{3-[(oxan-2-ylmethyl)carbamoyl]azetidin-1-yl}-4-oxo-1,4-dihydro-1,8-naphthyridine-3-carboxylic acid (1) A crude ethyl 1-{3-[(2-methoxyethyl) (methyl)amino]-1,2,4-thiadiazol-5-yl}-5-methyl-7-{3-[(oxan-2-ylmethyl)carbamoyl]azetidin-1-yl}-4-oxo-1,4-dihydro-1,8-naphthyridine-3-carboxylate was obtained using ethyl 7-chloro-1-{3-[(2-methoxyethyl)(methyl)amino]-1,2,4-thiadiazol-5-yl}-5-methyl-4-oxo-1,4-dihydro-1,8-naphthyridine-3-carboxylate obtained in Reference Example 029 and N-(oxan-2-ylmethyl)azetidine-3-carboxamide hydrochloride obtained in Example 078 by the method described in Example 001-(3) or a method equivalent thereto.

(2) A title compound was obtained from crude ethyl 1-{3-[(2-methoxyethyl) (methyl)amino]-1,2,4-thiadiazol-5-yl}-5-methyl-7-{3-[(oxan-2-ylmethyl)carbamoyl]azetidin-1-yl}-4-oxo-1,4-dihydro-1,8-naphthyridine-3-carboxylate obtained in the preceding section by the method described in Example 028-(2) or a method equivalent thereto.

Property: pale yellow solid;

ESI-MS (m/z): 586 [M+H]+

Example 439

Compound 439

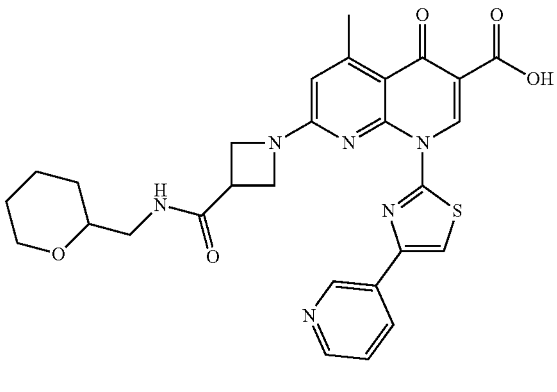

5-Methyl-7-{3-[(oxan-2-ylmethyl)carbamoyl]azetidin-1-yl}-4-oxo-1-[4-(pyridin-3-yl)-1,3-thiazol-2-yl]-1,4-dihydro-1,8-naphthyridine-3-carboxylic acid The title compound was obtained using 7-chloro-5-methyl-4-oxo-1-[4-(pyridin-3-yl)-1,3-thiazol-2-yl]-1,4-dihydro-1,8-naphthyridine-3-carboxylic acid obtained in Reference Example 039-(2) and N-(oxan-2-ylmethyl)azetidine-3-carboxamide hydrochloride obtained in Example 078 by the method described in Example 001-(3) or a method equivalent thereto.

Property: dark brown solid;

ESI-MS (m/z): 561 [M+H]+

Example 440

Compound 440

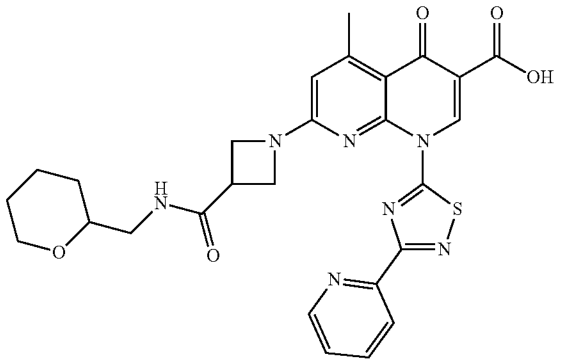

5-Methyl-7-{3-[(oxan-2-ylmethyl)carbamoyl]azetidin-1-yl}-4-oxo-1-[3-(pyridin-2-yl)-1,2,4-thiadiazol-5-yl]-1,4-dihydro-1,8-naphthyridine-3-carboxylic acid The title compound was obtained using 7-chloro-5-methyl-4-oxo-1-[3-(pyridin-2-yl)-1,2,4-thiadiazol-5-yl]-1,4-dihydro-1,8-naphthyridine-3-carboxylic acid obtained in Reference Example 041-(2) and N-(oxan-2-ylmethyl)azetidine-3-carboxamide hydrochloride obtained in Example 078 by the method described in Example 001-(3) or a method equivalent thereto.

1H-NMR (DMSO-d6): δ 1.10-1.23 (1H, m), 1.40-1.51 (3H, m), 1.53-1.60 (1H, m), 1.72-1.82 (1H, m), 2.78 (3H, s), 3.05-3.16 (1H, m), 3.17-3.24 (1H, m), 3.25-3.39 (2H, m), 3.62-3.71 (1H, m), 3.85-3.92 (1H, m), 4.25-4.65 (4H, m), 6.60 (1H, s), 7.57 (1H, ddd, J=7.5, 4.5, 1.5 Hz), 8.03 (1H, td, J=7.5, 1.5 Hz), 8.26 (1H, t, J=5.5 Hz), 8.31 (1H, d, J=7.5 Hz), 8.80 (1H, d, J=4.5 Hz), 9.85 (1H, s)

Example 441

Compound 441

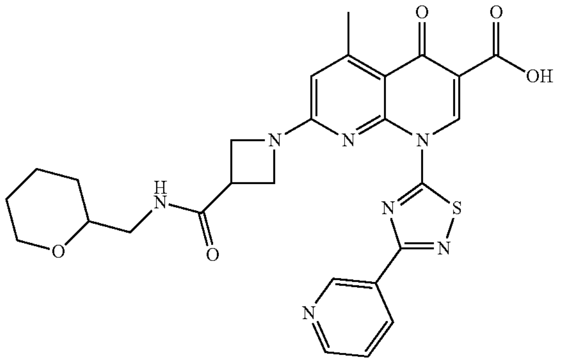

5-Methyl-7-{3-[(oxan-2-ylmethyl)carbamoyl]azetidin-1-yl}-4-oxo-1-[3-(pyridin-3-yl)-1,2,4-thiadiazol-5-yl]-1,4-dihydro-1,8-naphthyridine-3-carboxylic acid The title compound was obtained using 7-chloro-5-methyl-4-oxo-1-[3-(pyridin-3-yl)-1,2,4-thiadiazol-5-yl]-1,4-dihydro-1,8-naphthyridine-3-carboxylic acid obtained in Reference Example 042-(2) and N-(oxan-2-ylmethyl)azetidine-3-carboxamide hydrochloride obtained in Example 078 by the method described in Example 001-(3) or a method equivalent thereto.

1H-NMR (DMSO-d6): δ 1.09-1.21 (1H, m), 1.37-1.50 (3H, m), 1.54-1.60 (1H, m), 1.71-1.81 (1H, m), 2.75 (3H, s), 3.07-3.26 (4H, m), 3.62-3.73 (1H, m), 3.85-3.92 (1H, m), 4.25-4.63 (4H, m), 6.57 (1H, s), 7.61 (1H, dd, J=7.5, 4.5 Hz), 8.27 (1H, t, J=5.5 Hz), 8.53 (1H, dt, J=8.0, 1.5 Hz), 8.74 (1H, dd, J=4.5, 1.5 Hz), 9.37 (1H, s), 9.78 (1H, s)

Example 442

Compound 442

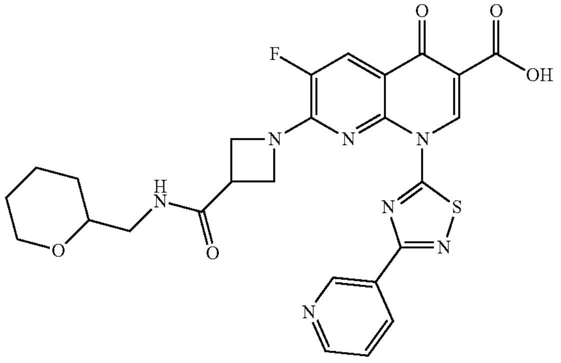

6-Fluoro-7-{3-[(oxan-2-ylmethyl)carbamoyl]azetidin-1-yl}-4-oxo-1-[3-(pyridin-3-yl)-1,2,4-thiadiazol-5-yl]-1,4-dihydro-1,8-naphthyridine-3-carboxylic acid The title compound was obtained using 7-chloro-6-fluoro-4-oxo-1-[3-(pyridin-3-yl)-1,2,4-thiadiazol-5-yl]-1,4- dihydro-1,8-naphthyridine-3-carboxylic acid obtained in Reference Example 043-(2) and N-(oxan-2-ylmethyl)azetidine-3-carboxamide hydrochloride obtained in Example 078 by the method described in Example 008 or a method equivalent thereto.

1H-NMR (DMSO-d6): δ 1.10-1.20 (1H, m), 1.37-1.49 (3H, m), 1.52-1.59 (1H, m), 1.71-1.80 (1H, m), 3.05-3.14 (1H, m), 3.15-3.22 (1H, m), 3.65-3.77 (1H, m), 3.82-3.91 (1H, m), 4.52-4.64 (2H, m), 4.66-4.82 (2H, m), 7.61-7.67 (1H, m), 8.16 (1H, d, J=12.0 Hz), 8.23-8.28 (1H, m), 8.57-8.62 (1H, m), 8.75-8.79 (1H, m), 9.41-9.44 (1H, m), 9.83 (1H, brs), 14.47 (1H, brs)

Example 443

Compound 443

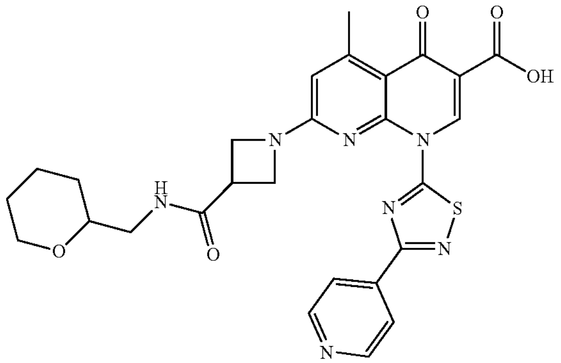

5-Methyl-7-{3-[(oxan-2-ylmethyl)carbamoyl]azetidin-1-yl}-4-oxo-1-[3-(pyridin-4-yl)-1,2,4-thiadiazol-5-yl]-1,4-dihydro-1,8-naphthyridine-3-carboxylic acid The title compound was obtained using 7-chloro-5-methyl-4-oxo-1-[3-(pyridin-4-yl)-1,2,4-thiadiazol-5-yl]-1,4-dihydro-1,8-naphthyridine-3-carboxylic acid obtained in Reference Example 044-(2) and N-(oxan-2-ylmethyl)azetidine-3-carboxamide hydrochloride obtained in Example 078 by the method described in Example 001-(3) or a method equivalent thereto.

1H-NMR (DMSO-d6): δ 1.12-1.25 (1H, m), 1.40-1.51 (3H, m), 1.54-1.62 (1H, m), 1.74-1.82 (1H, m), 2.70 (3H, s), 3.06-3.25 (2H, m), 3.26-3.40 (2H, m), 3.61-3.71 (1H, m), 3.85-3.94 (1H, m), 4.21-4.57 (4H, m), 6.49 (1H, s), 8.03 (2H, dd, J=4.5, 1.5 Hz), 8.27 (1H, t, J=6.0 Hz), 8.77 (2H, dd, J=4.5, 1.5 Hz), 9.65 (1H, s)

Example 444

Compound 444

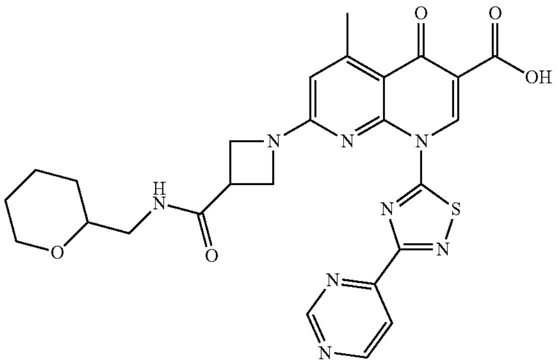

5-Methyl-7-{3-[(oxan-2-ylmethyl)carbamoyl]azetidin-1-yl}-4-oxo-1-[3-(pyrimidin-4-yl)-1,2,4-thiadiazol-5-yl]-1,4-dihydro-1,8-naphthyridine-3-carboxylic acid The title compound was obtained using 7-chloro-5-methyl-4-oxo-1-[3-(pyrimidin-4-yl)-1,2,4-thiadiazol-5-yl]-1,4-dihydro-1,8-naphthyridine-3-carboxylic acid obtained in Reference Example 045-(2) and N-(oxan-2-ylmethyl) azetidine-3-carboxamide hydrochloride obtained in Example 078 by the method described in Example 001-(3) or a method equivalent thereto.

1H-NMR (DMSO-d6): δ 1.12-1.22 (1H, m), 1.40-1.51 (3H, m), 1.54-1.60 (1H, m), 1.74-1.81 (1H, m), 2.74 (3H, s), 3.06-3.25 (2H, m), 3.26-3.39 (2H, m), 3.63-3.71 (1H, m), 3.86-3.92 (1H, m), 4.23-4.62 (4H, m), 6.56 (1H, s), 8.24-8.30 (2H, m), 9.06 (1H, d, J=5.0 Hz), 9.40 (1H, s), 9.73 (1H, s)

Example 445

Compound 445

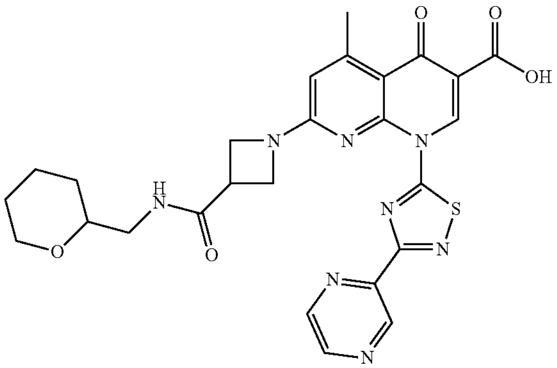

5-Methyl-7-{3-[(oxan-2-ylmethyl)carbamoyl]azetidin-1-yl}-4-oxo-1-[3-(pyrazin-2-yl)-1,2,4-thiadiazol-5-yl]-1,4-dihydro-1,8-naphthyridine-3-carboxylic acid The title compound was obtained using 7-chloro-5-methyl-4-oxo-1-[3-(pyrazin-2-yl)-1,2,4-thiadiazol-5-yl]-1, 4-dihydro-1,8-naphthyridine-3-carboxylic acid obtained in Reference Example 046-(2) and N-(oxan-2-ylmethyl)azetidine-3-carboxamide hydrochloride obtained in Example 078 by the method described in Example 001-(3) or a method equivalent thereto.

1H-NMR (DMSO-d6): δ 1.11-1.21 (1H, m), 1.37-1.52 (3H, m), 1.53-1.61 (1H, m), 1.72-1.83 (1H, m), 2.75 (3H, s), 3.06-3.25 (2H, m), 3.25-3.40 (2H, m), 3.63-3.71 (1H, m), 3.84-3.93 (1H, m), 4.24-4.64 (4H, m), 6.57 (1H, s), 8.26 (1H, t, J=5.5 Hz), 8.81-8.86 (2H, m), 9.45 (1H, s), 9.77 (1H, s)

Example 446

Compound 446

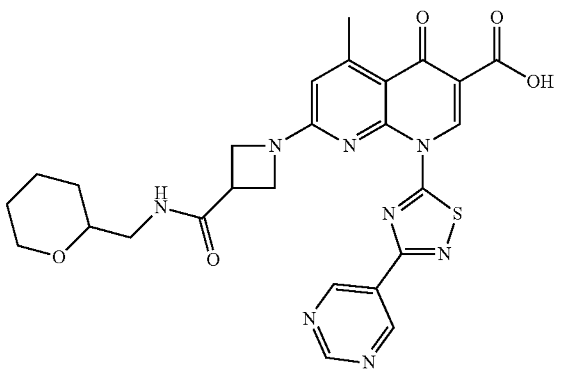

5-Methyl-7-{3-[(oxan-2-ylmethyl)carbamoyl]azetidin-1-yl}-4-oxo-1-[3-(pyrimidin-5-yl)-1,2,4-thiadiazol-5-yl]-1,4-dihydro-1,8-naphthyridine-3-carboxylic acid The title compound was obtained using 7-chloro-5-methyl-4-oxo-1-[3-(pyrimidin-5-yl)-1,2,4-thiadiazol-5-yl]-1,4-dihydro-1,8-naphthyridine-3-carboxylic acid obtained in Reference Example 047-(2) and N-(oxan-2-ylmethyl) azetidine-3-carboxamide hydrochloride obtained in Example 078 by the method described in Example 001-(3) or a method equivalent thereto.

1H-NMR (DMSO-d6): δ 1.07-1.21 (1H, m), 1.32-1.62 (4H, m), 1.71-1.84 (1H, m), 2.75 (3H, s), 2.87-3.45 (4H, m), 3.56-3.77 (1H, m), 3.79-3.93 (1H, m), 4.07-4.68 (4H, m), 6.57 (1H, s), 8.26 (1H, brs), 9.36 (1H, s), 9.51 (2H, s), 9.77 (1H, s)

Example 447

Compound 447

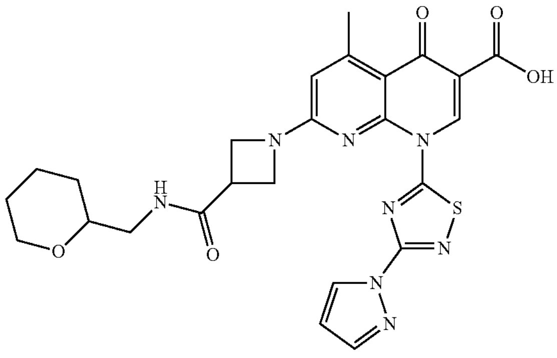

5-Methyl-7-{3-[(oxan-2-ylmethyl)carbamoyl]azetidin-1-yl}-4-oxo-1-[3-(1H-pyrazol-1-yl)-1,2,4-thiadiazol-5-yl]-1,4-dihydro-1,8-naphthyridine-3-carboxylic acid The title compound was obtained using 7-chloro-5-methyl-4-oxo-1-[3-(1H-pyrazol-1-yl)-1,2,4-thiadiazol-5-yl]-1,4-dihydro-1,8-naphthyridine-3-carboxylic acid obtained in Reference Example 048-(2) and N-(oxan-2-ylmethyl)azetidine-3-carboxamide hydrochloride obtained in Example 078 by the method described in Example 001-(3) or a method equivalent thereto.

1H-NMR (DMSO-d6): δ 1.06-1.22 (1H, m), 1.37-1.51 (3H, m), 1.52-1.61 (1H, m), 1.72-1.82 (1H, m), 2.78 (3H, s), 3.07-3.23 (2H, m), 3.24-3.43 (2H, m), 3.61-3.70 (1H, m), 3.84-3.92 (1H, m), 4.23-4.66 (4H, m), 6.61 (1H, s), 6.65 (1H, s), 7.90 (1H, s), 8.24 (1H, t, J=5.5 Hz), 8.59-8.64 (1H, m), 9.72 (1H, s)

Example 448

Compound 448

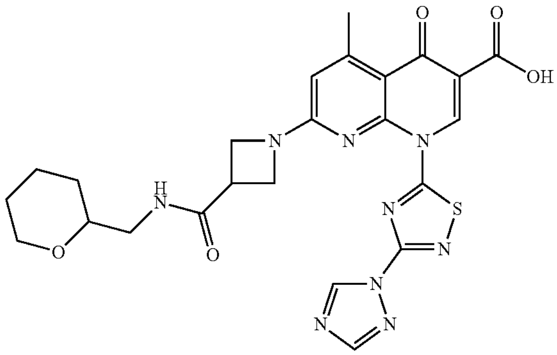

5-Methyl-7-{3-[(oxan-2-ylmethyl)carbamoyl]azetidin-1-yl}-4-oxo-1-[3-(1H-1,2,4-triazol-1-yl)-1,2,4-thiadiazol-5-yl]-1,4-dihydro-1,8-naphthyridine-3-carboxylic acid The title compound was obtained using 7-chloro-5-methyl-4-oxo-1-[3-(1H-1,2,4-triazol-1-yl)-1,2,4-thiadiazol- 5-yl]-1,4-dihydro-1,8-naphthyridine-3-carboxylic acid obtained in Reference Example 049-(2) and N-(oxan-2-ylmethyl)azetidine-3-carboxamide hydrochloride obtained in Example 078 by the method described in Example 001-(3) or a method equivalent thereto.

1H-NMR (DMSO-d6): δ 1.10-1.22 (1H, m), 1.37-1.50 (3H, m), 1.53-1.60 (1H, m), 1.72-1.82 (1H, m), 2.73 (3H, s), 3.03-3.25 (2H, m), 3.25-3.40 (2H, m), 3.62-3.71 (1H, m), 3.84-3.92 (1H, m), 4.16-4.64 (4H, m), 6.56 (1H, s), 8.26 (1H, t, J=5.5 Hz), 8.36 (1H, s), 9.51 (1H, s), 9.63 (1H, 8)

Example 449

Compound 449

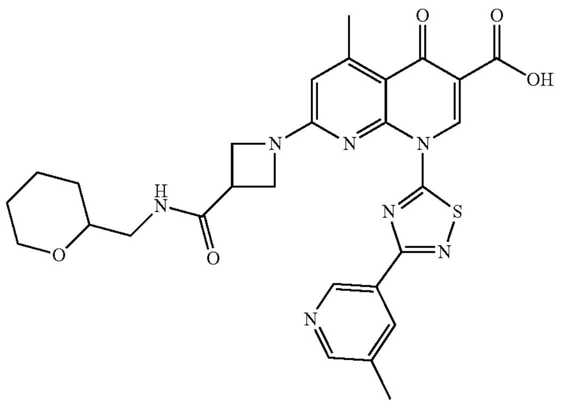

5-Methyl-1-[3-(5-methylpyridin-3-yl)-1,2,4-thiadiazol-5-yl]-7-{3-[(oxan-2-ylmethyl)carbamoyl]azetidin-1-yl}-4-oxo-1,4-dihydro-1,8-naphthyridine-3-carboxylic acid The title compound was obtained using 7-chloro-5-methyl-1-[3-(5-methylpyridin-3-yl)-1,2,4-thiadiazol-5-yl]-4-oxo-1,4-dihydro-1,8-naphthyridine-3-carboxylic acid obtained in Reference Example 050-(3) and N-(oxan-2-ylmethyl)azetidine-3-carboxamide hydrochloride obtained in Example 078 by the method described in Example 001-(3) or a method equivalent thereto.

1H-NMR (DMSO-d6): δ 1.11-1.26 (1H, m), 1.39-1.53 (3H, m), 1.53-1.62 (1H, m), 1.73-1.83 (1H, m), 2.40 (3H, s), 2.71 (3H, s), 3.07-3.25 (2H, m), 3.26-3.41 (2H, m), 3.61-3.72 (1H, m), 3.86-3.93 (1H, m), 4.22-4.57 (4H, m), 6.51 (1H, s), 8.21 (1H, s), 8.27 (1H, t, J=5.5 Hz), 8.54 (1H, d, J=1.5 Hz), 9.09 (1H, d, J=1.5 Hz), 9.65 (1H, s)

Example 450

Compound 450

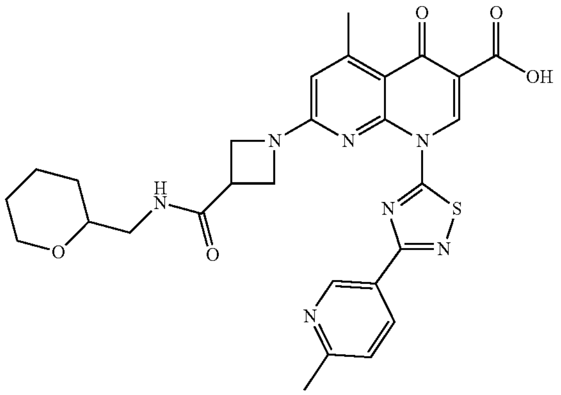

5-Methyl-1-[3-(6-methylpyridin-3-yl)-1,2,4-thiadiazol-5-yl]-7-{3-[(oxan-2-ylmethyl)carbamoyl]azetidin-1-yl}-4-oxo-1,4-dihydro-1,8-naphthyridine-3-carboxylic acid The title compound was obtained using 7-chloro-5-methyl-1-[3-(6-methylpyridin-3-yl)-1,2,4-thiadiazol-5-yl]-4-oxo-1,4-dihydro-1,8-naphthyridine-3-carboxylic acid obtained in Reference Example 051-(2) and N-(oxan-2-ylmethyl)azetidine-3-carboxamide hydrochloride obtained in Example 078 by the method described in Example 001-(3) or a method equivalent thereto.

Property: orange solid;

ESI-MS (m/z): 576 [M+H]+

Example 451

Compound 451

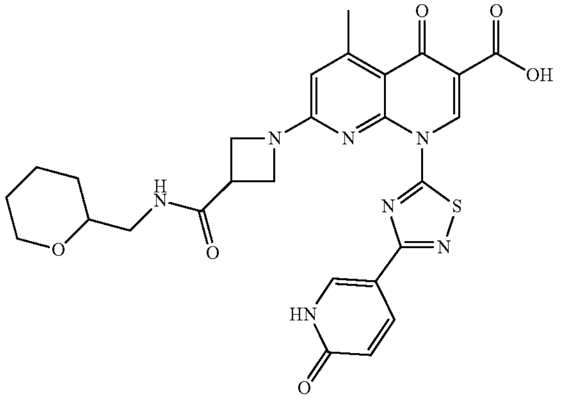

5-Methyl-7-{3-[(oxan-2-ylmethyl)carbamoyl]azetidin-1-yl}-4-oxo-1-[3-(6-oxo-1,6-dihydropyridin-3-yl)-1,2,4-thiadiazol-5-yl]-1,4-dihydro-1,8-naphthyridine-3-carboxylic acid The title compound was obtained using 7-chloro-1-[3-(6-methoxypyridin-3-yl)-1,2,4-thiadiazol-5-yl]-5-methyl-4- oxo-1,4-dihydro-1,8-naphthyridine-3-carboxylic acid obtained in Reference Example 052-(2) and N-(oxan-2-ylmethyl)azetidine-carboxamide hydrochloride obtained in Example 078 by the method described in Example 001-(3) or a method equivalent thereto.

1H-NMR (DMSO-d6): δ 1.11-1.22 (1H, m), 1.39-1.52 (3H, m), 1.53-1.61 (1H, m), 1.73-0.82 (1H, m), 2.72 (3H, s), 3.07-3.24 (4H, m), 3.61-3.70 (1H, m), 3.85-3.91 (1H, m), 4.23-4.57 (4H, m), 6.48 (1H, d, J=9.5 Hz), 6.52 (1H, s), 8.06 (1H, dd, J=9.5, 2.0 Hz), 8.16 (1H, brs), 8.26 (1H, t, J=5.0 Hz), 9.65 (1H, s), 11.96 (1H, s)

Example 452

Compound 452

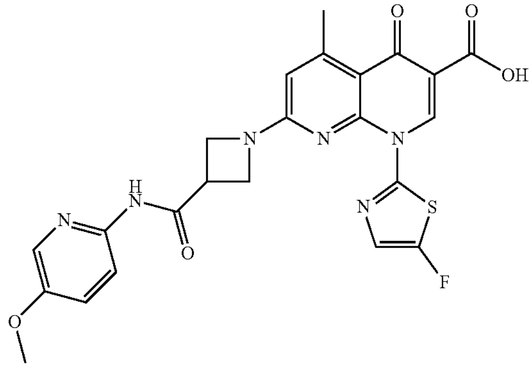

1-(5-Fluoro-1,3-thiazol-2-yl)-7-{3-[(5-methoxypyridin-2-yl)carbamoyl]azetidin-1-yl}-5-methyl-4-oxo-1,4-dihydro-1,8-naphthyridine-3-carboxylic acid The title compound was obtained using 7-chloro-1-(5-fluoro-1,3-thiazol-2-yl)-5-methyl-4-oxo-1,4-dihydro-1,8-naphthyridine-3-carboxylic acid obtained in Reference Example 010-(2) and N-(5-methoxypyridin-2-yl)azetidine-3-carboxamide hydrochloride obtained in Example 017 by the method described in Example 001-(3) or a method equivalent thereto.

1H-NMR (DMSO-d6): δ 2.76 (3H, s), 3.81 (3H, s), 3.86-3.93 (1H, m), 4.30-4.60 (4H, m), 6.57 (1H, s), 7.45 (1H, dd, J=9.0, 3.0 Hz), 7.74 (1H, d, J=2.5 Hz), 8.05 (1H, d, J=3.0 Hz), 8.08 (1H, d, J=9.0 Hz), 9.67 (1H, s), 10.66 (1H, s), 15.32 (1H, brs)

Example 453

Compound 453

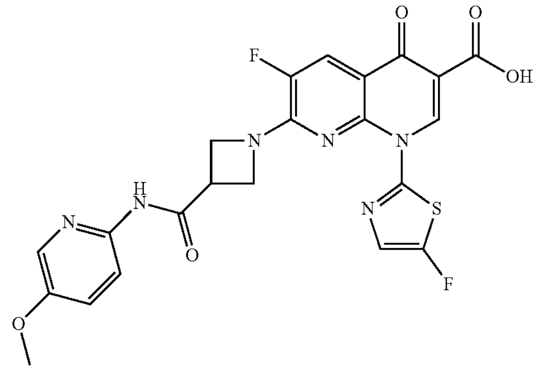

6-Fluoro-1-(5-fluoro-1,3-thiazol-2-yl)-7-{3-[(5-methoxypyridin-2-yl)carbamoyl]azetidin-1-yl}-4-oxo-1,4-dihydro-1,8-naphthyridine-3-carboxylic acid The title compound was obtained using 7-chloro-6-fluoro-1-(5-fluoro-1,3-thiazol-2-yl)-4-oxo-1,4-dihydro-1,8-naphthyridine-3-carboxylic acid obtained in Reference Example 011-(2) and N-(5-methoxypyridin-2-yl)azetidine-3-carboxamide hydrochloride obtained in Example 017 by the method described in Example 001-(3) or a method equivalent thereto.

1H-NMR (DMSO-d6): δ 3.81 (3H, s), 3.89-3.97 (1H, m), 4.48-4.94 (4H, m), 7.46 (1H, dd, J=9.0, 3.0 Hz), 7.75 (1H, d, J=3.0 Hz), 8.05 (1H, d, J=2.5 Hz), 8.07-8.13 (2H, m), 9.65 (1H, s), 10.65 (1H, s), 14.66 (1H, brs)

Example 454

Compound 454

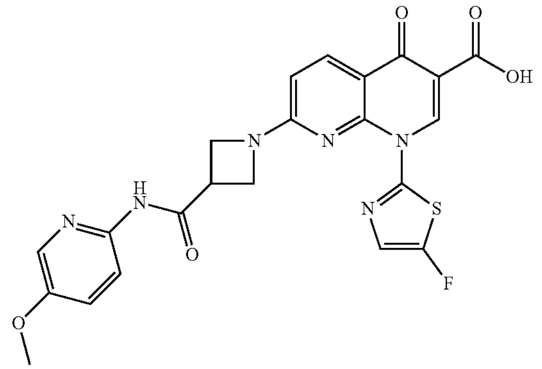

1-(5-Fluoro-1,3-thiazol-2-yl)-7-{3-[(5-methoxypyridin-2-yl)carbamoyl]azetidin-1-yl}-4-oxo-1,4-dihydro-1,8-naphthyridine-3-carboxylic acid The title compound was obtained using 7-chloro-1-(5-fluoro-1,3-thiazol-2-yl)-4-oxo-1,4-dihydro-1,8-naphthyridine-3-carboxylic acid obtained in Reference Example 012-(2) and N-(5-methoxypyridin-2-yl)azetidine-3-carboxamide hydrochloride obtained in Example 017 by the method described in Example 001-(3) or a method equivalent thereto.

1H-NMR (DMSO-d6): δ 3.81 (3H, s), 3.89-3.96 (1H, m), 4.36-4.61 (4H, m), 6.79 (1H, d, J=9.0 Hz), 7.46 (1H, dd, J=9.0, 3.5 Hz), 7.76 (1H, d, J=2.5 Hz), 8.06 (1H, d, J=2.5 Hz), 8.09 (1H, d, J=9.0 Hz), 8.34 (1H, d, J=9.0 Hz), 9.69 (1H, s), 10.67 (1H, s), 14.94 (1H, brs)

Example 455

Compound 455

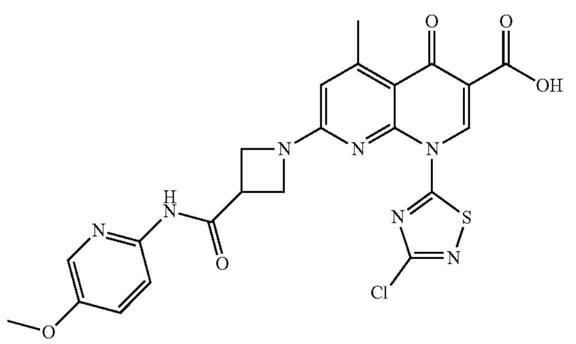

1-(3-Chloro-1,2,4-thiadiazol-5-yl)-7-{3-[(5-methoxypyridin-2-yl)carbamoyl]azetidin-1-yl}-5-methyl-4-oxo-1,4-dihydro-1,8-naphthyridine-3-carboxylic acid The title compound was obtained using 7-chloro-1-(3-chloro-1,2,4-thiadiazol-5-yl)-5-methyl-4-oxo-1,4-dihydro-1,8-naphthyridine-3-carboxylic acid obtained in Reference Example 013-(2) and N-(5-methoxypyridin-2-yl)azetidine-3-carboxamide hydrochloride obtained in Example 017 by the method described in Example 017-(2) or a method equivalent thereto.

1H-NMR (DMSO-d6): δ 2.75 (3H, s), 3.81 (3H, s), 3.88-3.97 (1H, m), 4.35-4.67 (4H, m), 6.60 (1H, s), 7.44 (1H, dd, J=9.0, 2.5 Hz), 8.05 (1H, d, J=2.5 Hz), 8.07 (1H, d, J=9.0 Hz), 9.47 (1H, s), 10.66 (1H, s)

Example 456

Compound 456

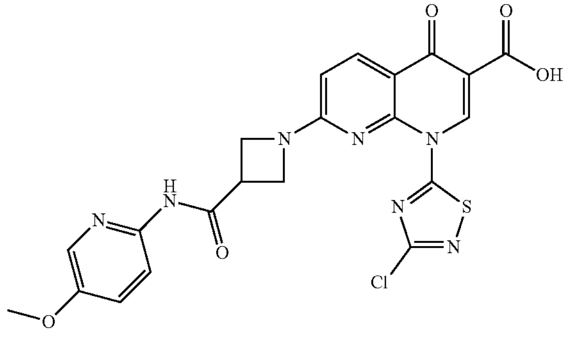

1-(3-Chloro-1,2,4-thiadiazol-5-yl)-7-{3-[(5-methoxypyridin-2-yl)carbamoyl]azetidin-1-yl}-4-oxo-1,4-dihydro-1,8-naphthyridine-3-carboxylic acid The title compound was obtained using 7-chloro-1-(3-chloro-1,2,4-thiadiazol-5-yl)-4-oxo-1,4-dihydro-1,8-naphthyridine-3-carboxylic acid obtained in Reference Example 015-(2) and N-(5-methoxypyridin-2-yl)azetidine-3-carboxamide hydrochloride obtained in Example 017 by the method described in Example 017-(2) or a method equivalent thereto.

1H-NMR (DMSO-d6): δ 3.81 (3H, s), 3.89-4.00 (1H, m), 4.39-4.66 (4H, m), 6.80 (1H, d, J=9.0 Hz), 7.44 (1H, dd, J=9.0, 3.0 Hz), 8.05 (1H, d, J=2.5 Hz), 8.08 (1H, d, J=9.0 Hz), 8.32 (1H, d, J=9.0 Hz), 9.48 (1H, s), 10.67 (1H, s)

Example 457

Compound 457

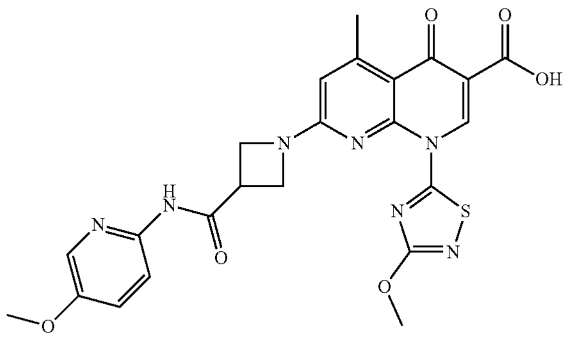

1-(3-Methoxy-1,2,4-thiadiazol-5-yl)-7-{3-[(5-methoxypyridin-2-yl)carbamoyl]azetidin-1-yl}-5-methyl-4-oxo-1,4-dihydro-1,8-naphthyridine-3-carboxylic acid The title compound was obtained using 7-chloro-1-(3-methoxy-1,2,4-thiadiazol-5-yl)-5-methyl-4-oxo-1,4-dihydro-1,8-naphthyridine-3-carboxylic acid obtained in Reference Example 023-(2) and N-(5-methoxypyridin-2-yl)azetidine-3-carboxamide hydrochloride obtained in Example 017 by the method described in Example 001-(3) or a method equivalent thereto.

1H-NMR (DMSO-d6): δ 2.71 (3H, s), 3.81 (3H, s), 3.88-3.96 (1H, m), 4.01 (3H, s), 4.31-4.57 (4H, m), 6.51 (1H, s), 7.43 (1H, dd, J=9.0, 3.0 Hz), 8.05 (1H, d, J=3.0 Hz), 8.07 (1H, d, J=9.0 Hz), 9.41 (1H, s), 10.66 (1H, s)

Example 458

Compound 458

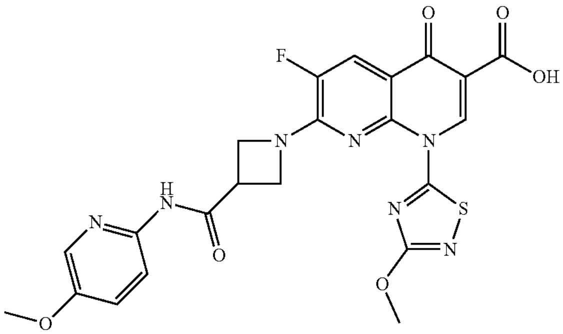

6-Fluoro-1-(3-methoxy-1,2,4-thiadiazol-5-yl)-7-{3-[(5-methoxypyridin-2-yl)carbamoyl]azetidin-1-yl}-4-oxo-1,4-dihydro-1,8-naphthyridine-3-carboxylic acid The title compound was obtained using 7-chloro-6-fluoro-1-(3-methoxy-1,2,4-thiadiazol-5-yl)-4-oxo-1,4-dihydro-1,8-naphthyridine-3-carboxylic acid obtained in Reference Example 024-(2) and N-(5-methoxypyridin-2-yl) azetidine-3-carboxamide hydrochloride obtained in Example 017 by the method described in Example 001-(3) or a method equivalent thereto.

1H-NMR (DMSO-d6): δ 3.81 (3H, s), 3.91-4.00 (1H, m), 4.01 (3H, s), 4.33-4.57 (4H, m), 7.44 (1H, dd, J=9.0, 3.0 Hz), 8.05 (1H, d, J=3.0 Hz), 8.08 (1H, d, J=9.0 Hz), 8.10 (1H, d, J=11.5 Hz), 9.49 (1H, s), 10.64 (1H, a)

Example 459

Compound 459

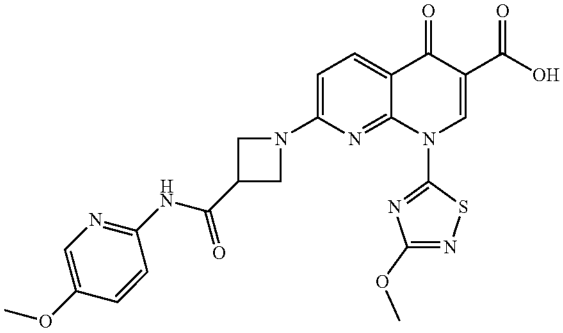

1-(3-Methoxy-1,2,4-thiadiazol-5-yl)-7-{3-[(5-methoxypyridin-2-yl)carbamoyl]azetidin-1-yl}-4-oxo-1,4-dihydro-1,8-naphthyridine-3-carboxylic acid The title compound was obtained using 7-chloro-1-(3-methoxy-1,2,4-thiadiazol-5-yl)-4-oxo-1,4-dihydro-1,8-naphthyridine-3-carboxylic acid obtained in Reference Example 025-(2) and N-(5-methoxypyridin-2-yl)azetidine-3-carboxamide hydrochloride obtained in Example 017 by the method described in Example 001-(3) or a method equivalent thereto.

1H-NMR (DMSO-d6): δ 3.81 (3H, s), 3.89-3.98 (1H, m), 4.02 (3H, s), 4.37-4.60 (4H, m), 6.76 (1H, d, J=8.5 Hz), 7.44 (1H, dd, J=9.0, 3.0 Hz), 8.05 (1H, d, J=3.0 Hz), 8.08 (1H, d, J=9.0 Hz), 8.28 (1H, d, J=9.0 Hz), 9.47 (1H, s), 10.66 (1H, s)

Example 460

Compound 460

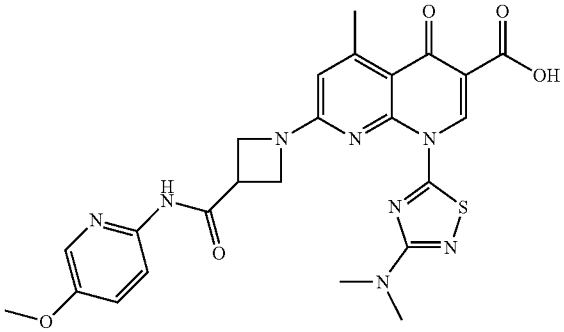

1-[3-(Dimethylamino)-1,2,4-thiadiazol-5-yl]-7-{3-[(5-methoxypyridin-2-yl)carbamoyl]azetidin-1-yl}-5-methyl-4-oxo-1,4-dihydro-1,8-naphthyridine-3-carboxylic acid The title compound was obtained using 7-chloro-1-[3-(dimethylamino)-1,2,4-thiadiazol-5-yl]-5-methyl-4-oxo-1,4-dihydro-1,8-naphthyridine-3-carboxylic acid obtained in Reference Example 026-(2) and N-(5-methoxypyridin-2-yl) azetidine-3-carboxamide hydrochloride obtained in Example 017 by the method described in Example 001-(3) or a method equivalent thereto.

1H-NMR (DMSO-d6): δ 2.73 (3H, s), 3.11 (6H, s), 3.81 (3H, s), 3.86-3.94 (1H, m), 4.32-4.56 (4H, m), 6.51 (1H, s), 7.45 (1H, dd, J=9.0, 3.0 Hz), 7.78 (1H, brs), 8.05 (1H, d, J=3.0 Hz), 8.07 (1H, d, J=9.0 Hz), 9.55 (1H, s), 10.66 (1H, s)

Example 461

Compound 461

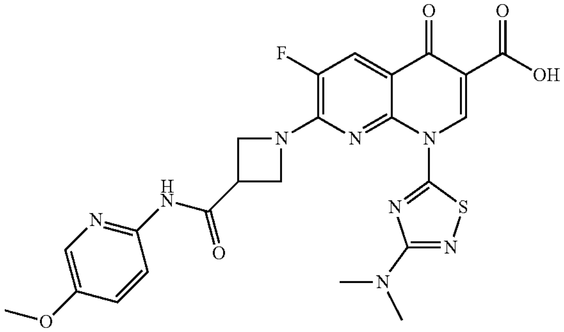

1-[3-(Dimethylamino)-1,2,4-thiadiazol-5-yl]-6-fluoro-7-{3-[(5-methoxypyridin-2-yl)carbamoyl]azetidin-1-yl}-4-oxo-1,4-dihydro-1,8-naphthyridine-3-carboxylic acid The title compound was obtained using 7-chloro-6-fluoro-1-[3-(dimethylamino)-1,2,4-thiadiazol-5-yl]-4-oxo-1,4-dihydro-1,8-naphthyridine-3-carboxylic acid obtained in Reference Example 027-(2) and N-(5-methoxypyridin-2-yl)azetidine-3-carboxamide hydrochloride obtained in Example 017 by the method described in Example 001-(3) or a method equivalent thereto.

1H-NMR (DMSO-d6): δ 3.13 (6H, s), 3.81 (3H, s), 3.90-3.99 (1H, m), 4.50-4.86 (4H, m), 7.45 (1H, dd, J=9.0, 3.0 Hz), 7.78 (1H, brs), 8.05 (1H, d, J=3.0 Hz), 8.08 (1H, d, J=9.0 Hz), 8.10 (1H, d, J=11.5 Hz), 9.63 (1H, s), 10.64 (1H, s)

Example 462

Compound 462

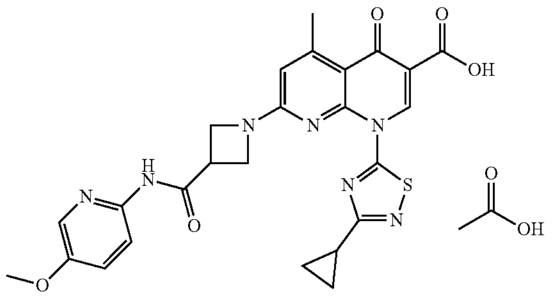

1-(3-Cyclopropyl-1,2,4-thiadiazol-5-yl)-7-{3-[(5-methoxypyridin-2-yl)carbamoyl]azetidin-1-yl}-5-methyl-4-oxo-1,4-dihydro-1,8-naphthyridine-3-carboxylic acid acetate The title compound was obtained using 7-chloro-1-(3-cyclopropyl-1,2,4-thiadiazol-5-yl)-5-methyl-4-oxo-1,4-dihydro-1,8-naphthyridine-3-carboxylic acid obtained in Reference Example 031-(2) and N-(5-methoxypyridin-2-yl)azetidine-3-carboxamide hydrochloride obtained in Example 017 by the method described in Example 019 or a method equivalent thereto.

1H-NMR (DMSO-d6): δ 1.04-1.13 (4H, m), 1.91 (3H, s), 2.33-2.37 (1H, m), 2.77 (3H, s), 3.81 (3H, s), 3.89-3.96 (1H, m), 4.36-4.64 (4H, m), 6.59 (1H, d, J=1.0 Hz), 7.45 (1H, dd, J=9.1, 3.1 Hz), 8.05-8.10 (2H, m), 9.65 (1H, s), 10.66 (1H, brs), 11.95 (1H, brs), 15.09 (1H, brs)

Example 463

Compound 463

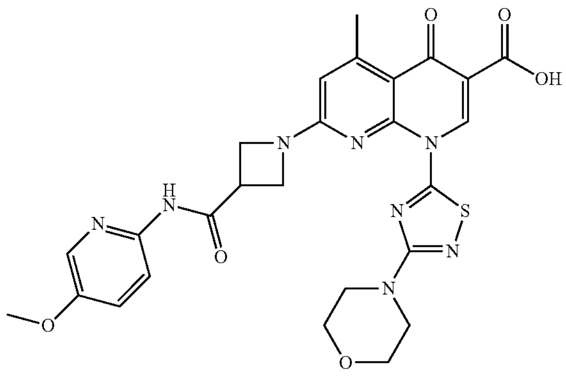

7-{3-[(5-Methoxypyridin-2-yl)carbamoyl]azetidin-1-yl}-5-methyl-1-[3-(morpholin-4-yl)-1,2,4-thiadiazol-5-yl]-4-oxo-1,4-dihydro-1,8-naphthyridine-3-carboxylic acid The title compound was obtained using 7-chloro-5-methyl-1-[3-(morpholin-4-yl)-1,2,4-thiadiazol-5-yl]-4-oxo-1,4-dihydro-1,8-naphthyridine-3-carboxylic acid obtained in Reference Example 033-(2) and N-(5-methoxypyridin-2-yl)azetidine-3-carboxamide hydrochloride obtained in Example 017 by the method described in Example 001-(3) or a method equivalent thereto.

1H-NMR (DMSO-d6): δ 2.73 (3H, s), 3.56 (4H, t, J=5.0 Hz), 3.72 (4H, t, J=5.0 Hz), 3.80 (3H, s), 3.85-3.95 (1H, m), 4.31-4.59 (4H, m), 6.53 (1H, s), 7.44 (1H, dd, J=9.0, 3.0 Hz), 8.05 (1H, d, J=3.0 Hz), 8.07 (1H, d, J=9.0 Hz), 9.55 (1H, s), 10.65 (1H, s)

Example 464

Compound 464

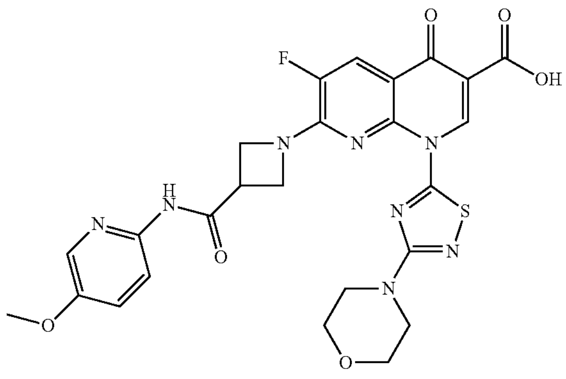

6-Fluoro-7-{3-[(5-methoxypyridin-2-yl)carbamoyl]azetidin-1-yl}-1-[3-(morpholin-4-yl)-1,2,4-thiadiazol-5-yl]-4-oxo-1,4-dihydro-1,8-naphthyridine-3-carboxylic acid The title compound was obtained using 7-chloro-6-fluoro-1-[3-(morpholin-4-yl)-1,2,4-thiadiazol-5-yl]-4-oxo- 1,4-dihydro-1,8-naphthyridine-3-carboxylic acid obtained in Reference Example 034-(2) and N-(5-methoxypyridin-2-yl)azetidine-3-carboxamide hydrochloride obtained in Example 017 by the method described in Example 001-(3) or a method equivalent thereto.

1H-NMR (DMSO-d6): δ 3.59 (4H, t, J=5.0 Hz), 3.72 (4H, t, J=5.0 Hz), 3.81 (3H, s), 3.85-4.00 (1H, m), 4.51-4.87 (4H, m), 7.45 (1H, dd, J=9.0, 3.0 Hz), 8.05 (1H, d, J=3.0 Hz), 8.07 (1H, d, J=9.0 Hz), 8.12 (1H, d, J=11.5 Hz), 9.66 (1H, s)

Example 465

Compound 465

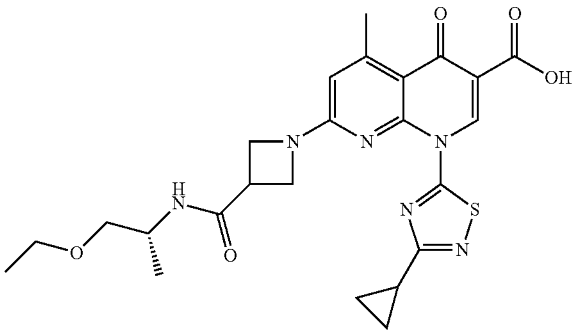

1-(3-Cyclopropyl-1,2,4-thiadiazol-5-yl)-7-(3-{[(2R)-1-ethoxypropan-2-yl]carbamoyl}azetidin-1-yl)-5-methyl-4-oxo-1,4-dihydro-1,8-naphthyridine-3-carboxylic acid The title compound was obtained using 7-chloro-1-(3-cyclopropyl-1,2,4-thiadiazol-5-yl)-5-methyl-4-oxo-1,4-dihydro-1,8-naphthyridine-3-carboxylic acid obtained in Reference Example 031-(2) and N-[(2R)-1-ethoxypropan-2-yl]azetidine-3-carboxamide hydrochloride obtained in Example 192 by the method described in Example 019 or a method equivalent thereto.

1H-NMR (DMSO-d6): δ 1.02-1.13 (10H, m), 2.30-2.36 (1H, m), 2.76 (3H, s), 3.25 (1H, dd, J=9.6, 5.9 Hz), 3.40-3.49 (2H, m), 3.56-3.63 (1H, m), 3.93-4.01 (1H, m), 4.22-4.57 (4H, m), 6.56 (1H, s), 8.06 (1H, d, J=8.0 Hz), 9.65 (1H, s), 15.13 (1H, brs)

Example 466

Compound 466

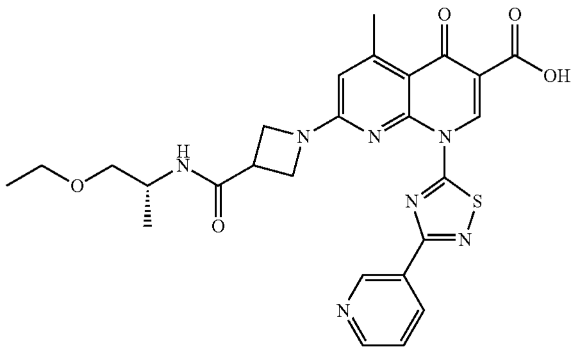

7-(3-{[(2R)-1-Ethoxypropan-2-yl]carbamoyl}azetidin-1-yl)-5-methyl-4-oxo-1-[3-(pyridin-3-yl)-1,2,4-thiadiazol-5-yl]-1,4-dihydro-1,8-naphthyridine-3-carboxylic acid The title compound was obtained using 7-chloro-5-methyl-4-oxo-1-[3-(pyridin-3-yl)-1,2,4-thiadiazol-5-yl]-1,4-dihydro-1,8-naphthyridine-3-carboxylic acid obtained in Reference Example 042-(2) and N-[(2R)-1-ethoxypropan-2-yl]azetidine-3-carboxamide hydrochloride obtained in Example 192 by the method described in Example 002-(3) or a method equivalent thereto.

1H-NMR (DMSO-d6): δ 1.07-1.14 (6H, m), 2.78 (3H, s), 3.42-3.49 (1H, m), 3.59-3.67 (1H, m), 3.96-4.02 (1H, m), 4.25-4.66 (4H, m), 7.64-7.68 (1H, m), 8.09 (1H, d, J=8.0 Hz), 8.58-8.61 (1H, m), 8.76-8.78 (1H, m), 9.41 (1H, s), 9.83 (1H, s), 15.06 (1H, brs)

Example 467

Compound 467

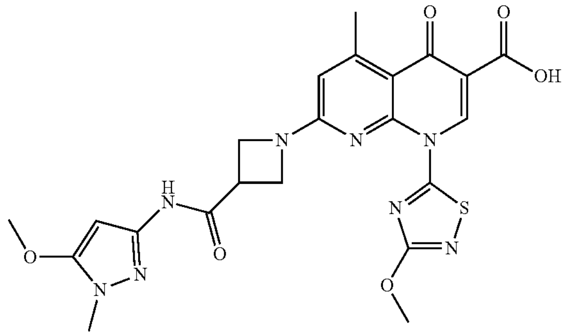

1-(3-Methoxy-1,2,4-thiadiazol-5-yl)-7-{3-[(5-methoxy-1-methyl-1H-pyrazol-3-yl)carbamoyl]azetidin-1-yl}-5-methyl-4-oxo-1,4-dihydro-1,8-naphthyridine-3-carboxylic acid The title compound was obtained using 7-chloro-1-(3-methoxy-1,2,4-thiadiazol-yl)-5-methyl-4-oxo-1,4-dihydro-1,8-naphthyridine-3-carboxylic acid obtained in Reference Example 023-(2) and N-(5-methoxy-1-methyl-1H-pyrazol-3-yl)azetidine-3-carboxamide hydrochloride obtained in Example 169 by the method described in Example 018-(2) or a method equivalent thereto.

1H-NMR (DMSO-d6): δ 2.68 (3H, s), 3.45 (3H, s), 3.66-3.90 (4H, m), 3.96 (3H, s), 4.12-4.61 (4H, m), 6.00 (1H, s), 6.20 (1H, d, J=7.5 Hz), 6.33 (1H, s), 8.68 (1H, d, J=7.5 Hz), 10.53 (1H, s)

Example 468

Compound 468

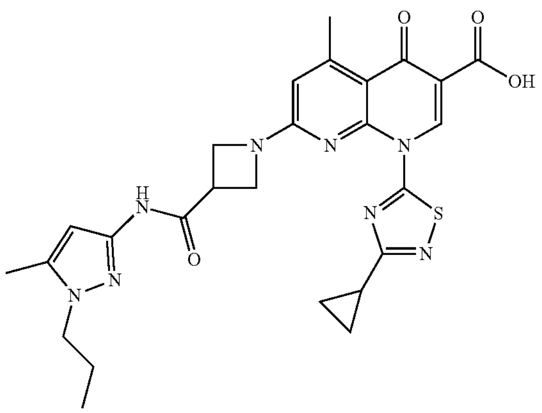

1-(3-Cyclopropyl-1,2,4-thiadiazol-5-yl)-5-methyl-7-{3-[(5-methyl-1-propyl-1H-pyrazol-3-yl)carbamoyl]azetidin-1-yl}-4-oxo-1,4-dihydro-1,8-naphthyridine-3-carboxylic acid The title compound was obtained using 7-chloro-1-(3-cyclopropyl-1,2,4-thiadiazol-5-yl)-5-methyl-4-oxo-1,4-dihydro-1,8-naphthyridine-3-carboxylic acid obtained in Reference Example 031-(2) and N-(5-methyl-1-propyl-1H-pyrazol-3-yl)azetidine-3-carboxamide hydrochloride obtained in Example 201 by the method described in Example 008 or a method equivalent thereto.

1H-NMR (DMSO-d6): δ 0.82 (3H, t, J=7.5 Hz), 1.02-1.13 (4H, m), 1.66-1.76 (2H, m), 2.22 (3H, s), 2.29-2.38 (1H, m), 2.77 (3H, s), 3.75-3.83 (1H, m), 3.87 (2H, t, J=6.5 Hz), 4.29-4.61 (4H, m), 6.32 (1H, s), 6.58 (1H, s), 9.65-9.67 (1H, m), 10.60 (1H, s), 15.13 (1H, s)

Example 469

Compound 469

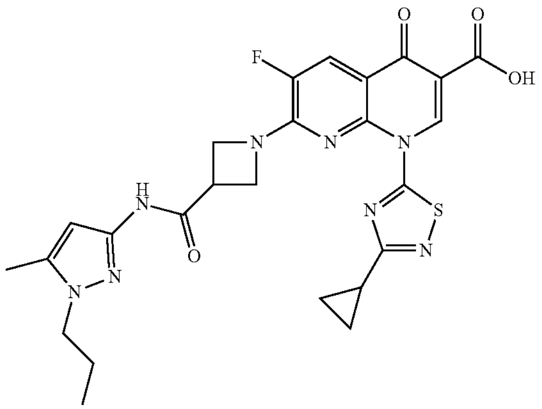

1-(3-Cyclopropyl-1,2,4-thiadiazol-5-yl)-6-fluoro-7-{3-[(5-methyl-1-propyl-1H-pyrazol-3-yl)carbamoyl]azetidin-1-yl}-4-oxo-1,4-dihydro-1,8-naphthyridine-3-carboxylic acid The title compound was obtained using 7-chloro-1-(3-cyclopropyl-1,2,4-thiadiazol-5-yl)-6-fluoro-4-oxo-1,4-dihydro-1,8-naphthyridine-3-carboxylic acid obtained in Reference Example 032-(2) and N-(5-methyl-1-propyl-1H-pyrazol-3-yl)azetidine-3-carboxamide hydrochloride obtained in Example 201 by the method described in Example 001-(3) or a method equivalent thereto.

1H-NMR (DMSO-d6): δ 0.82 (3H, t, J=7.0 Hz), 1.03-1.08 (2H, m), 1.08-1.15 (2H, m), 1.71 (2H, sext, J=7.0 Hz), 2.22 (3H, s), 2.31-2.38 (1H, m), 3.80-3.85 (1H, m), 3.87 (2H, t, J=7.0 Hz), 4.50-4.80 (4H, m), 6.33 (1H, s), 8.12 (1H, d, J=11.0 Hz), 9.65 (1H, s), 10.59 (1H, s)

Example 470

Compound 470

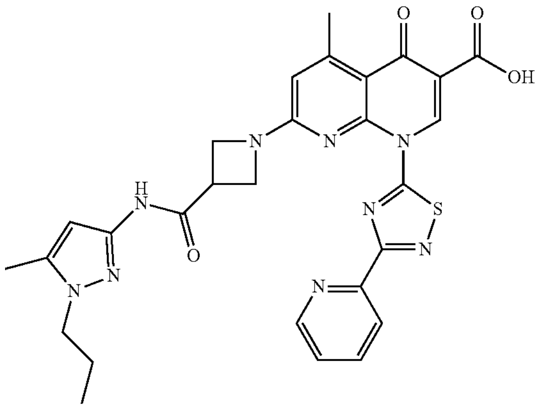

5-Methyl-7-{3-[(5-methyl-1-propyl-1H-pyrazol-3-yl)carbamoyl]azetidin-1-yl}-4-oxo-1-[3-(pyridin-2-yl)-1,2,4-thiadiazol-5-yl]-1,4-dihydro-1,8-naphthyridine-3-carboxylic acid The title compound was obtained using 7-chloro-5-methyl-4-oxo-1-[3-(pyridin-2-yl)-1,2,4-thiadiazol-5-yl]-1,4-dihydro-1,8-naphthyridine-3-carboxylic acid obtained in Reference Example 041-(2) and N-(5-methyl-1-propyl-1H-pyrazol-3-yl)azetidine-3-carboxamide hydrochloride obtained in Example 201 by the method described in Example 008 or a method equivalent thereto.

1H-NMR (DMSO-d6): δ 0.83 (3H, t, J=7.5 Hz), 1.66-1.76 (2H, m), 2.22 (3H, s), 2.79 (3H, s), 3.75-3.90 (1H, m), 3.87 (2H, t, J=6.5 Hz), 4.31-4.74 (4H, m), 6.34 (1H, s), 6.61 (1H, brs), 7.57 (1H, dd, J=7.5, 5.0 Hz), 8.03 (1H, dd, J=7.5, 7.5 Hz), 8.32 (1H, d, J=7.5 Hz), 8.80 (1H, d, J=5.0 Hz), 9.84 (1H, s), 10.64 (1H, s), 15.05 (1H, brs)

Example 471

Compound 471

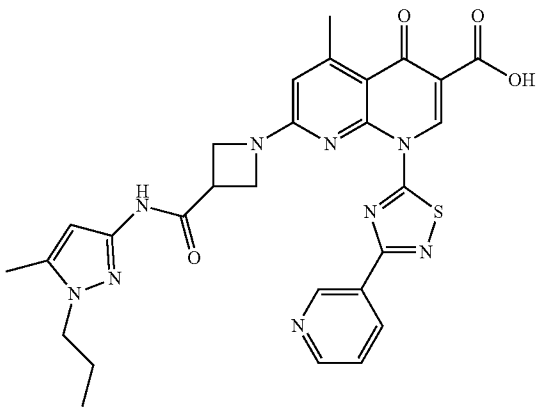

5-Methyl-7-{3-[(5-methyl-1-propyl-1H-pyrazol-3-yl)carbamoyl]azetidin-1-yl}-4-oxo-1-[3-(pyridin-3-yl)-1,2,4-thiadiazol-5-yl]-1,4-dihydro-1,8-naphthyridine-3-carboxylic acid The title compound was obtained using 7-chloro-5-methyl-4-oxo-1-[3-(pyridin-3-yl)-1,2,4-thiadiazol-5-yl]-1,4-dihydro-1,8-naphthyridine-3-carboxylic acid obtained in Reference Example 042-(2) and N-(5-methyl-1-propyl-1H-pyrazol-3-yl)azetidine-3-carboxamide hydrochloride obtained in Example 201 by the method described in Example 008 or a method equivalent thereto.

1H-NMR (DMSO-d6): δ 0.83 (3H, t, J=7.5 Hz), 1.66-1.76 (2H, m), 2.22 (3H, s), 2.78 (3H, s), 3.78-3.85 (1H, m), 3.87 (2H, t, J=6.5 Hz), 4.16-4.71 (4H, m), 6.34 (1H, a), 6.55 (1H, brs), 7.62 (1H, dd, J=7.5, 4.5 Hz), 8.57 (1H, ddd, J=7.5, 2.0, 2.0 Hz), 8.74 (1H, dd, J=4.5, 2.0 Hz), 9.41 (1H, d, J=2.0 Hz), 9.71 (1H, brs), 10.62 (1H, s)

Example 472

Compound 472

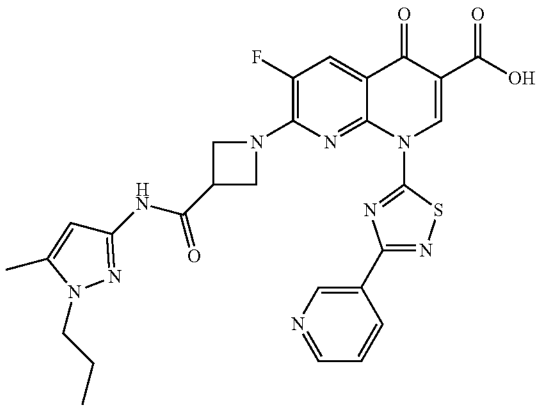

6-Fluoro-7-{3-[(5-methyl-1-propyl-1H-pyrazol-3-yl)carbamoyl]azetidin-1-yl}-4-oxo-1-[3-(pyridin-3-yl)-1,2,4-thiadiazol-5-yl]-1,4-dihydro-1,8-naphthyridine-3-carboxylic acid The title compound was obtained using 7-chloro-6-fluoro-4-oxo-1-[3-(pyridin-3-yl)-1,2,4-thiadiazol-5-yl]-1,4-dihydro-1,8-naphthyridine-3-carboxylic acid obtained in Reference Example 043-(2) and N-(5-methyl-1-propyl-1H-pyrazol-3-yl)azetidine-3-carboxamide hydrochloride obtained in Example 201 by the method described in Example 008 or a method equivalent thereto.

1H-NMR (DMSO-d6): δ 0.83 (3H, t, J=7.5 Hz), 1.66-1.76 (2H, m), 2.23 (3H, s), 3.75-3.90 (1H, m), 3.87 (2H, t, J=6.5 Hz), 4.57-4.77 (4H, m), 6.34 (1H, s), 7.59-7.65 (1H, m), 8.05 (1H, d, J=12.0 Hz), 8.54-8.60 (1H, m), 8.72-8.76 (1H, m), 9.39-9.42 (1H, m), 9.50-9.64 (1H, m), 10.59 (1H, s)

Example 473

Compound 473

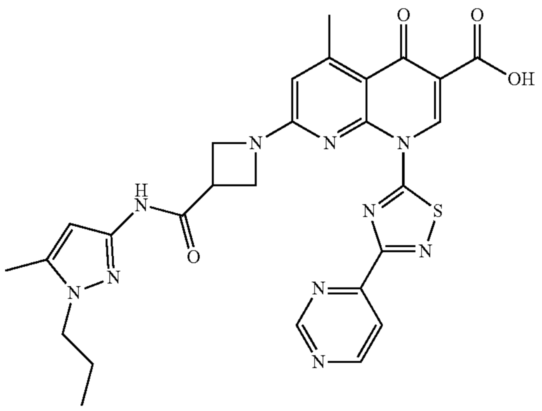

5-Methyl-7-{3-[(5-methyl-1-propyl-1H-pyrazol-3-yl)carbamoyl]azetidin-1-yl}-4-oxo-1-[3-(pyrimidin-4-yl)-1,2,4-thiadiazol-5-yl]-1,4-dihydro-1,8-naphthyridine-3-carboxylic acid The title compound was obtained using 7-chloro-5-methyl-4-oxo-1-[3-(pyrimidine-4-yl)-1,2,4-thiadiazol-5-yl]-1,4-dihydro-1,8-naphthyridine-3-carboxylic acid obtained in Reference Example 045-(2) and N-(5-methyl-1-propyl-1H-pyrazol-3-yl)azetidine-3-carboxamide hydrochloride obtained in Example 201 by the method described in Example 001-(3) or a method equivalent thereto.

1H-NMR (DMSO-d6): δ 0.83 (3H, t, J=7.5 Hz), 1.72 (2H, sext, J=7.5 Hz), 2.22 (3H, s), 2.77 (3H, s), 3.79-3.85 (1H, m), 3.87 (2H, t, J=7.5 Hz), 4.31-4.69 (4H, m), 6.34 (1H, s), 6.60 (1H, s), 8.30 (1H, dd, J=5.0, 1.5 Hz), 9.06 (1H, d, J=5.0 Hz), 9.41 (1H, d, J=1.5 Hz), 9.78 (1H, s), 10.63 (1H, s)

Example 474

Compound 474

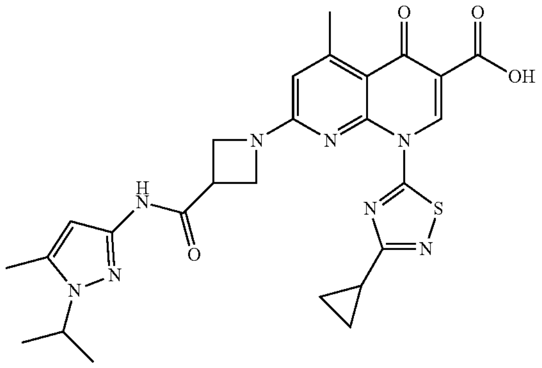

1-(3-Cyclopropyl-1,2,4-thiadiazol-5-yl)-5-methyl-7-(3-{[5-methyl-1-(propan-2-yl)-1H-pyrazol-3-yl]carbamoyl}azetidin-1-yl)-4-oxo-1,4-dihydro-1,8-naphthyridine-3-carboxylic acid The title compound was obtained using 7-chloro-1-(3-cyclopropyl-1,2,4-thiadiazol-5-yl)-5-methyl-4-oxo-1,4-dihydro-1,8-naphthyridine-3-carboxylic acid obtained in Reference Example 031-(2) and N-[5-methyl-1-(propan-2-yl)-1H-pyrazol-3-yl]azetidine-3-carboxamide hydrochloride obtained in Example 222 by the method described in Example 008 or a method equivalent thereto.

1H-NMR (DMSO-d6): δ 0.98-1.16 (4H, m), 1.32 (6H, d, J=6.0 Hz), 2.22 (3H, s), 2.27-2.39 (1H, m), 2.89 (3H, s), 3.66-3.77 (1H, m), 4.20-4.63 (4H, m), 6.32 (1H, s), 7.77 (1H, brs), 9.65 (1H, s), 10.65 (1H, brs)

Example 475

Compound 475

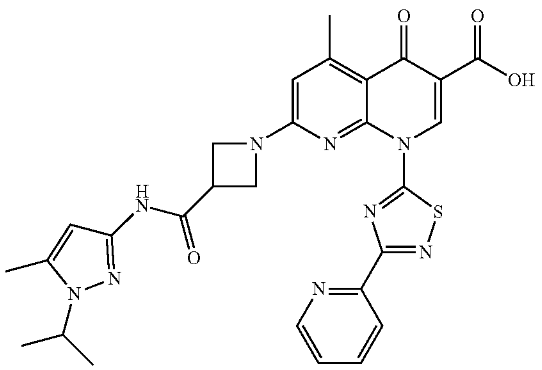

5-Methyl-7-(3-{[5-methyl-1-(propan-2-yl)-H-pyrazol-3-yl]carbamoyl}azetidin-1-yl)-4-oxo-1-[3-(pyridin-2-yl)-1,2,4-thiadiazol-5-yl]-1,4-dihydro-1,8-naphthyridine-3-carboxylic acid The title compound was obtained using 7-chloro-5-methyl-4-oxo-1-[3-(pyridin-2-yl)-1,2,4-thiadiazol-5-yl]-1,4-dihydro-1,8-naphthyridine-3-carboxylic acid obtained in Reference Example 041-(2) and N-[5-methyl-1-(propan-2-yl)-1H-pyrazol-3-yl]azetidine-3-carboxamide hydrochloride obtained in Example 222 by the method described in Example 008 or a method equivalent thereto.

1H-NMR (DMSO-d6): δ 1.33 (6H, d, J=6.0 Hz), 2.23 (3H, s), 2.81 (3H, brs), 3.69-3.77 (1H, m), 4.21-4.75 (4H, m), 6.32 (1H, s), 6.67 (1H, brs), 7.53-7.62 (1H, m), 7.97-8.09 (1H, m), 8.27-8.38 (1H, m), 8.75-8.86 (1H, m), 9.88 (1H, s), 10.69 (1H, brs), 15.13 (1H, brs)

Example 476

Compound 476

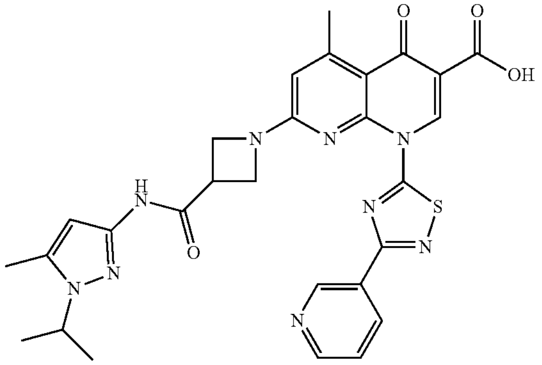

5-Methyl-7-(3-{[5-methyl-1-(propan-2-yl)-1H-pyrazol-3-yl]carbamoyl}azetidin-1-yl)-4-oxo-1-[3-(pyridin-3-yl)-1,2,4-thiadiazol-5-yl]-1,4-dihydro-1,8-naphthyridine-3-carboxylic acid The title compound was obtained using 7-chloro-5-methyl-4-oxo-1-[3-(pyridin-3-yl)-1,2,4-thiadiazol-5-yl]-1,4-dihydro-1,8-naphthyridine-3-carboxylic acid obtained in Reference Example 042-(2) and N-[5-methyl-1-(propan-2-yl)-1H-pyrazol-3-yl]azetidine-3-carboxamide hydrochloride obtained in Example 222 by the method described in Example 008 or a method equivalent thereto.

1H-NMR (DMSO-d6): δ 1.33 (6H, d, J=6.0 Hz), 2.23 (3H, s), 2.79 (3H, brs), 3.69-3.77 (1H, m), 4.21-4.75 (4H, m), 6.32 (1H, s), 6.65 (1H, brs), 7.56-7.69 (1H, m), 8.50-8.62 (1H, m), 8.72-8.80 (1H, m), 9.34-9.46 (1H, m), 9.85 (1H, s), 10.69 (1H, brs), 15.06 (1H, brs)

Example 477

Compound 477

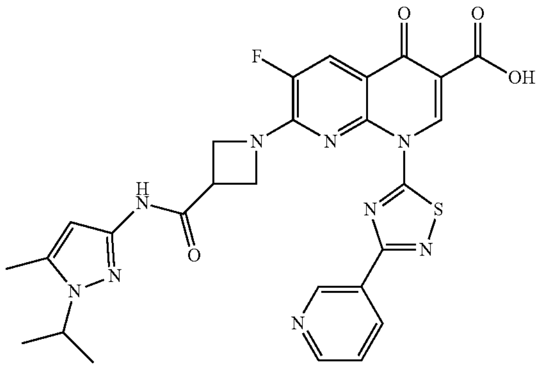

6-Fluoro-7-(3-{[5-methyl-1-(propan-2-yl)-1H-pyrazol-3-yl]carbamoyl}azetidin-1-yl)-4-oxo-1-[3-(pyridin-3-yl)-1,2,4-thiadiazol-5-yl]-1,4-dihydro-1,8-naphthyridine-3-carboxylic acid The title compound was obtained using 7-chloro-6-fluoro-4-oxo-1-[3-(pyridin-3-yl)-1,2,4-thiadiazol-5-yl]-1,4-dihydro-1,8-naphthyridine-3-carboxylic acid obtained in Reference Example 043-(2) and N-[5-methyl-1-(propan-2-yl)-1H-pyrazol-3-yl]azetidine-3-carboxamide hydrochloride obtained in Example 222 by the method described in Example 016 or a method equivalent thereto.

1H-NMR (DMSO-d6): δ 1.33 (6H, d, J=6.0 Hz), 2.24 (3H, s), 3.80-3.89 (1H, m), 4.38-4.47 (1H, m), 4.54-4.62 (2H, m), 4.63-4.72 (2H, m), 6.32 (1H, s), 7.55-7.64 (1H, m), 7.97 (1H, d, J=12.0 Hz), 8.53-8.59 (1H, m), 8.70-8.75 (1H, m), 9.15 (1H, brs), 9.39 (1H, brs), 10.63 (1H, brs)

Example 478

Compound 478

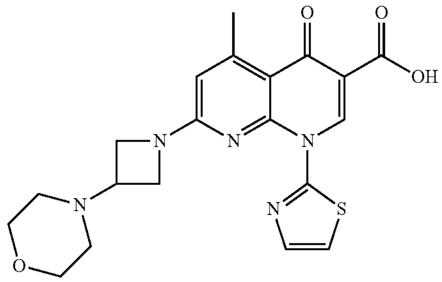

5-Methyl-7-[3-(morpholin-4-yl)azetidin-1-yl]-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and 4-(azetidin-3-yl)morpholine hydrochloride by the method described in Example 001-(3) or a method equivalent thereto.

1H-NMR (DMSO-d6): δ 2.78 (3H, s), 2.84-3.12 (2H, m), 3.20-3.48 (2H, m), 3.54-3.84 (4H, m), 4.02-4.78 (5H, m), 6.55 (1H, s), 7.74 (1H, d, J=4.0 Hz), 7.85 (1H, d, J=4.0 Hz), 9.85 (1H, s)

Example 479

Compound 479

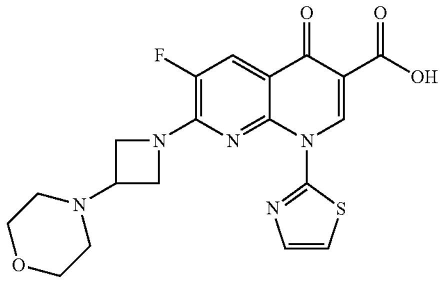

6-Fluoro-7-[3-(morpholin-4-yl)azetidin-1-yl]-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and 4-(azetidin-3-yl)morpholine hydrochloride by the method described in Example 001-(3) or a method equivalent thereto.

1H-NMR (DMSO-d6): δ 2.81-3.12 (4H, m), 3.53-3.78 (4H, m), 4.07-4.93 (5H, m), 7.78 (1H, d, J=3.5 Hz), 7.86 (1H, d, J=3.5 Hz), 8.12 (1H, d, J=10.5 Hz), 9.83 (1H, s)

Example 480

Compound 480

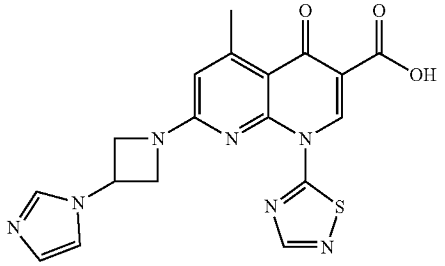

7-[3-(1H-Imidazol-1-yl)azetidin-1-yl]-5-methyl-4-oxo-1-(1,2,4-thiadiazol-5-yl)-1,4-dihydro-1,8-naphthyridine-3-carboxylic acid (1) A solution of 1H-imidazole (3.4 g), 1-(diphenylmethyl)azetidin-3-yl methanesulfonate (6.4 g), and triethylamine (3 g) in acetonitrile (30 mL) was stirred at 80° C. for 1 day. The reaction solution was concentrated. Then, chloroform was added to the residue, and the mixture was washed with an aqueous sodium carbonate solution and brine. The organic layer was dried and concentrated, and the residue was subjected to silica gel column chromatography (eluent: ethyl acetate/chloroform) to obtain 5.0 g of crude 1-[1-(diphenylmethyl)azetidin-3-yl]-1H-imidazole.

(2) To a solution of crude 1-[1-(diphenylmethyl)azetidin-3-yl]-1H-imidazole (5.0 g) obtained in the preceding section in diethyl ether (50 mL), a 4 mol/L solution of hydrochloric acid in 1,4-dioxane (12 mL) was added under ice cooling. Diethyl ether (300 mL) was further added thereto, and precipitates were collected by filtration. The obtained solid was dissolved in acetic acid (20 mL) and methanol (110 mL). To the solution was added 10% palladium carbon (700 mg), and the mixture was hydrogenated at 50° C. for 3 days. The catalyst was filtered off, and the filtrate was then concentrated. Ethanol was added to the residue, and the solid was collected by filtration to obtain 2.1 g of crude 1-(azetidin-3-yl)-1H-imidazole hydrochloride.

(3) The title compound was obtained by the method described in Example 001-(3) or a method equivalent thereto using 1-(azetidin-3-yl)-1H-imidazole hydrochloride obtained in the preceding section, and 7-chloro-5-methyl-4-oxo-1-(1,2,4-thiadiazol-5 yl)-1,4-dihydro-1,8-naphthyridine-3-carboxylic acid obtained in Reference Example 002-(2).

1H-NMR (DMSO-d6): δ 2.77 (3H, d, J=0.9 Hz), 4.47-5.02 (4H, m), 5.45-5.51 (1H, m), 6.64 (1H, d, J=0.9 Hz), 7.02-7.03 (1H, m), 7.62-7.63 (1H, m), 7.96-7.97 (1H, m), 8.80 (1H, s), 9.71 (1H, s), 14.99 (1H, brs)

Example 481

Compound 481

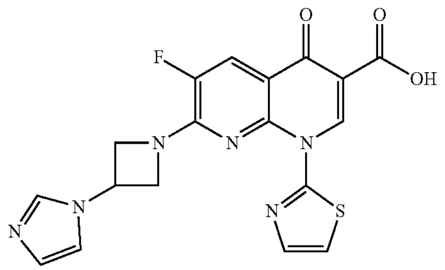

6-Fluoro-7-[3-(1H-imidazol-1-yl)azetidin-1-yl]-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and 1-(azetidin-3-yl)-1H-imidazole hydrochloride obtained in Example 480-(2) by the method described in Example 001-(3) or a method equivalent thereto.

1H-NMR (DMSO-d6): δ 4.50-5.10 (4H, m), 5.47-5.53 (1H, m), 7.02-7.03 (1H, m), 7.66-7.67 (1H, m), 7.74 (1H, d, J=3.5 Hz), 7.85 (1H, d, J=3.5 Hz), 7.97-7.98 (1H, m), 8.17 (1H, d, J=11.2 Hz), 9.84 (1H, s), 14.73 (1H, brs)

Example 482

Compound 482

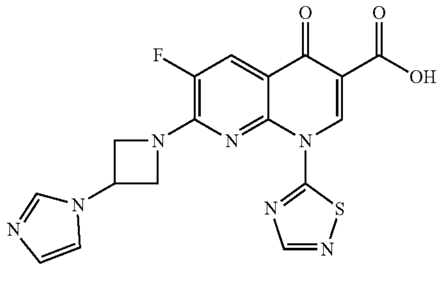

6-Fluoro-7-[3-(1H-imidazol-1-yl)azetidin-1-yl]-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and 1-(azetidin-3-yl)-1H-imidazole hydrochloride obtained in Example 480-(2) by the method described in Example 001-(3) or a method equivalent thereto.

1H-NMR (DMSO-d6): δ 4.66-5.12 (4H, m), 5.47-5.53 (1H, m), 7.02-7.03 (1H, m), 7.66-7.67 (1H, m), 7.98-7.99 (1H, m), 8.20 (1H, d, J=11.3 Hz), 8.84 (1H, s), 9.75 (1H, s), 14.41 (1H, brs)

Example 483

Compound 483

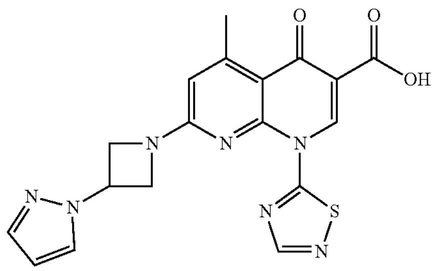

5-Methyl-4-oxo-7-[3-(1H-pyrazol-1-yl)azetidin-1-yl]-1-(1,2,4-thiadiazol-5-yl)-1,4-dihydro-1,8-naphthyridine-3-carboxylic acid (1) To a solution of 1H-pyrazole (129 mg) in N,N-dimethylformamide (5 mL) was added 55% sodium hydride (95 mg) under ice cooling, and the mixture was stirred at room temperature for 2 hours. 1-(Diphenylmethyl)azetidin-3-yl methanesulfonate (500 mg) was added thereto, and the mixture was stirred at 80° C. for 4 hours. To the reaction solution was added water, and the mixture was extracted with ethyl acetate. The organic layer was dried and concentrated to obtain 124 mg of crude 1-[1-(diphenylmethyl)azetidin-3-yl]-1H-pyrazole.

(2) The title compound was obtained by the method described in Example 001-(3) or a method equivalent thereto using 1-(azetidin-3-yl)-1H-pyrazole hydrochloride obtained by the method described in Example 002-(2) or a method equivalent thereto from crude 1-[1-(diphenylmethyl)azetidin-3-yl]-1H-pyrazole obtained in the preceding section, and 7-chloro-5-methyl-4-oxo-1-(1,2,4-thiadiazol-5-yl)-1,4-dihydro-1,8-naphthyridine-3-carboxylic acid obtained in Reference Example 002-(2).

1H-NMR (DMSO-d6): δ 2.77 (3H, d, J=0.8 Hz), 4.52-4.99 (4H, m), 5.54-5.62 (1H, m), 6.35-6.36 (1H, m), 6.65 (1H, d, J=0.8 Hz), 7.61-7.62 (1H, m), 8.00-8.01 (1H, m), 8.80 (1H, s), 9.71 (1H, s), 15.00 (1H, brs)

Example 484

Compound 484

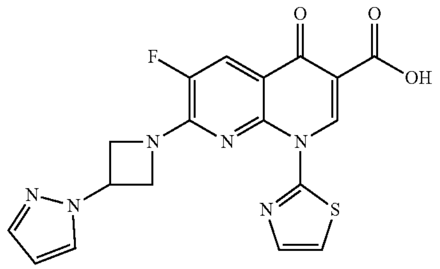

6-Fluoro-4-oxo-7-[3-(1H-pyrazol-1-yl)azetidin-1-yl]-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and 1-(azetidin-3-yl)-1H-pyrazole hydrochloride obtained in Example 483-(2) by the method described in Example 001-(3) or a method equivalent thereto.

1H-NMR (DMSO-d6): δ 4.66-5.12 (4H, m), 5.55-5.61 (1H, m), 6.34-6.35 (1H, m), 7.61-7.62 (1H, m), 7.73 (1H, d, J=3.5 Hz), 7.84 (1H, d, J=3.5 Hz), 8.00-8.01 (1H, m), 8.16 (1H, d, J=11.4 Hz), 9.83 (1H, s), 14.74 (1H, brs)

Example 485

Compound 485

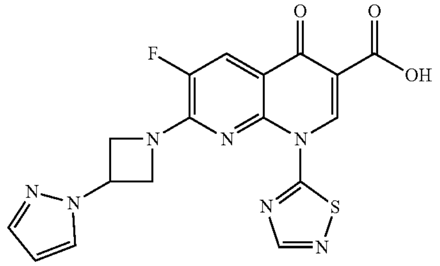

6-Fluoro-4-oxo-7-[3-(1H-pyrazol-1-yl)azetidin-1-yl]-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and 1-(azetidin-3-yl)-1H-pyrazole hydrochloride obtained in Example 483-(2) by the method described in Example 001-(3) or a method equivalent thereto.

1H-NMR (DMSO-d6): δ 4.78-5.14 (4H, m), 5.56-5.62 (1H, m), 6.35-6.36 (1H, m), 7.61-7.62 (1H, m), 8.01-8.02 (1H, m), 8.22 (1H, d, J=11.3 Hz), 8.84 (1H, s), 9.77 (1H, s), 14.44 (1H, brs)

Example 486

Compound 486

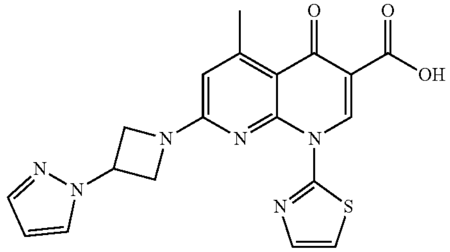

5-Methyl-4-oxo-7-[3-(1H-pyrazol-1-yl)azetidin-1-yl]-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and 1-(azetidin-3-yl)-1H-pyrazole hydrochloride obtained in Example 483-(2) by the method described in Example 001-(3) or a method equivalent thereto.

1H-NMR (DMSO-d6): δ 2.77 (3H, s), 4.49-4.66 (2H, m), 4.67-4.92 (2H, m), 5.51-5.62 (1H, m), 6.34 (1H, t, J=2.0 Hz), 6.61 (1H, s), 7.61 (1H, d, J=2.0 Hz), 7.69 (1H, d, J=3.5 Hz), 7.82 (1H, d, J=3.5 Hz), 7.99 (1H, d, J=2.0 Hz), 9.83 (1H, s), 15.36 (1H, brs)

Example 487

Compound 487

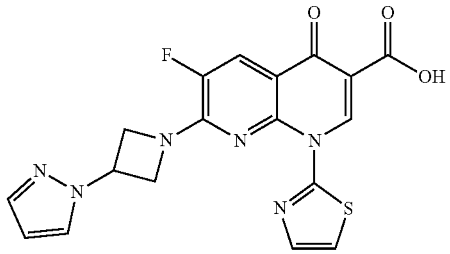

6-Fluoro-5-methyl-4-oxo-7-[3-(1H-pyrazol-1-yl) azetidin-1-yl]-1-(1,3-thiazol-2-yl)-1,4-dihydro-1,8-naphthyridine-3-carboxylic acid The title compound was obtained using 7-chloro-6-fluoro-5-methyl-4-oxo-1-(1,3-thiazol-2-yl)-1,4-dihydro-1,8-naphthyridine-3-carboxylic acid obtained in Reference Example 007-(2) and 1-(azetidin-3-yl)-1H-pyrazole hydrochloride obtained in Example 483-(2) by the method described in Example 001-(3) or a method equivalent thereto.

1H-NMR (DMSO-d6): δ 2.70 (3H, d, J=2.9 Hz), 4.62-0.85 (2H, m), 4.86-5.11 (2H, m), 5.50-5.63 (2H, m), 6.35 (1H, t, J=2.0 Hz), 7.61 (1H, d, J=2.0 Hz), 7.71 (1H, d, J=3.5 Hz), 7.83 (1H, d, J=3.5 Hz), 8.00 (1H, d, J=2.0 Hz), 9.81 (1H, s), 15.14 (1H, brs)

Example 488

Compound 488

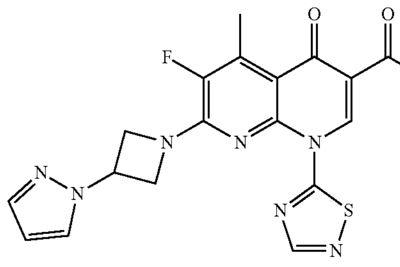

6-Fluoro-5-methyl-4-oxo-7-[3-(1H-pyrazol-1-yl) azetidin-1-yl]-1-(1,2,4-thiadiazol-5-yl)-1,4-dihydro-1,8-naphthyridine-3-carboxylic acid The title compound was obtained using 7-chloro-6-fluoro-5-methyl-4-oxo-1-(1,2,4-thiadiazol-5-yl)-1,4-dihydro-1,8-naphthyridine-3-carboxylic acid obtained in Reference Example 008-(2) and 1-(azetidin-3-yl)-1H-pyrazole hydrochloride obtained in Example 483-(2) by the method described in Example 001-(3) or a method equivalent thereto.

1H-NMR (DMSO-d6): δ 2.72 (3H, d, J=2.8 Hz), 4.73-4.93 (2H, m), 4.99-5.18 (2H, m), 5.48-5.65 (1H, m), 6.35 (1H, t, J=2.0 Hz), 7.62 (1H, d, J=2.0 Hz), 8.02 (1H, d, J=2.0 Hz), 8.84 (1H, s), 9.77 (1H, s), 14.82 (1H, brs)

Example 489

Compound 489

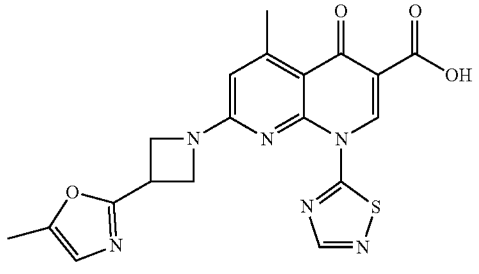

5-Methyl-7-[3-(5-methyl-1,3-oxazol-2-yl)azetidin-1-yl]-4-oxo-1-(1,2,4-thiadiazol-5-yl)-1,4-dihydro-1,8-naphthyridine-3-carboxylic acid (1) To a suspension of tert-butyl 3-[(prop-2-yn-1-yl)carbamoyl]azetidine-1-carboxylate (240 mg) in acetonitrile (4 mL) obtained from prop-2-yn-1-amine by the method described in Example 005-(1) or a method equivalent thereto was added gold trichloride (15 mg), and the mixture was stirred at 45° C. for 1 day. The reaction solution was concentrated. Then, to the residue was added methylene chloride, and the mixture was washed with water. The organic layer was dried over sodium sulfate and concentrated, and the residue was purified by silica gel column chromatography (eluent: ethyl acetate/n-hexane) to obtain 80 mg of tert-butyl 3-[(5-methyl-1,3-oxazol-2-yl)carbamoyl]azetidine-1-carboxylate.

1H-NMR (CDCl3): δ 1.45 (9H, s), 2.31 (3H, d, J=1.3 Hz), 3.79-3.86 (1H, m), 4.16-4.27 (4H, m), 6.66-6.67 (1H, m)

(2) The title compound was obtained by the method described in Example 001-(3) or a method equivalent thereto using 2-(azetidin-3-yl)-5-methyl-1,3-oxazole trifluoroacetate obtained by the method described in Example 001-(2) or a method equivalent thereto from tert-butyl 3-[(5-methyl-1,3-oxazol-2-yl)carbamoyl]azetidine-1-carboxylate obtained in the preceding section, and 7-chloro-5-methyl-4-oxo-1-(1,2,4-thiadiazol-5-yl)-1,4-dihydro-1,8-naphthyridine-3-carboxylic acid obtained in Reference Example 002-(2).

1H-NMR (DMSO-d6): δ 2.21 (3H, d, J=1.3 Hz), 2.78 (3H, d, J=1.0 Hz), 4.23-4.30 (1H, m), 4.42-4.90 (4H, m), 6.64 (1H, d, J=1.0 Hz), 6.85-6.86 (1H, m), 8.82 (1H, s), 9.75 (1H, s), 15.03 (1H, brs)

Example 490

Compound 490

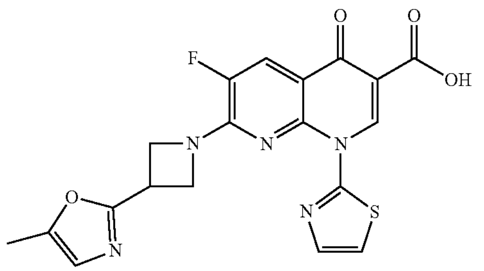

6-Fluoro-7-[3-(5-methyl-1,3-oxazol-2-yl)azetidin-1-yl]-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and 2-(azetidin-3-yl)-5-methyl-1,3-oxazole trifluoroacetate obtained in Example 489-(2) by the method described in Example 001-(3) or a method equivalent thereto.

1H-NMR (DMSO-d6): δ 2.31 (3H, d, J=1.5 Hz), 4.25-4.32 (1H, m), 4.58-4.96 (4H, m), 6.85-6.86 (1H, m), 7.78

(1H, d, J=3.5 Hz), 7.86 (1H, d, J=3.5 Hz), 8.15 (1H, d, J=11.4 Hz), 9.84 (1H, s), 14.75 (1H, brs)

Example 491

Compound 491

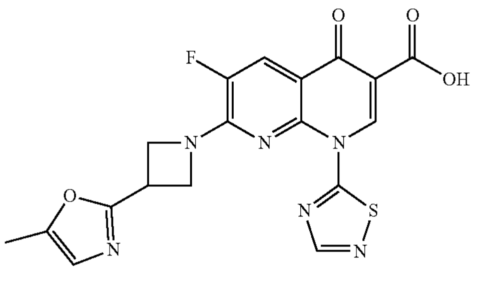

6-Fluoro-7-[3-(5-methyl-1,3-oxazol-2-yl)azetidin-1-yl]-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and 2-(azetidin-3-yl)-5-methyl-1,3-oxazole trifluoroacetate obtained in Example 489-(2) by the method described in Example 001-(3) or a method equivalent thereto.

1H-NMR (DMSO-d6): δ 2.31 (3H, d, J=1.3 Hz), 4.26-4.33 (1H, m), 4.68-5.05 (4H, m), 6.85-6.87 (1H, m), 8.18 (1H, d, J=11.5 Hz), 8.85 (1H, s), 9.75 (1H, s), 14.43 (1H, brs)

Example 492

Compound 492

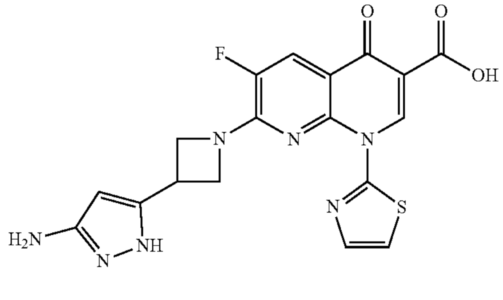

7-[3-(3-Amino-1H-pyrazol-5-yl)azetidin-1-yl]-6-fluoro-4-oxo-1-(1,3-thiazol-2-yl)-1,4-dihydro-1,8-naphthyridine-3-carboxylic acid (1) To a solution of 1-tert-butyl 3-methyl azetidine-1,3-dicarboxylate (2.0 g) in THF (50 mL) were added acetonitrile (720 μL) and potassium tert-butoxide (1.6 g), and the mixture was stirred for 210 minutes. To the reaction solution was added an aqueous ammonium chloride solution, and the mixture was extracted with ethyl acetate. The organic layer was washed with brine, dried over sodium sulfate, and concentrated. The residue was purified by silica gel column chromatography (eluent: ethyl acetate/n-hexane) to obtain 540 mg of tert-butyl 3-(2-cyanoacetyl)azetidine-1-carboxylate.

1H-NMR (CDCl3): δ 1.44 (9H, s), 3.50 (2H, s), 3.66-3.72 (1H, m), 4.10-4.16 (4H, m)

(2) To a solution of tert-butyl 3-(2-cyanoacetyl)azetidine-1-carboxylate (130 mg) obtained in the preceding section in 2-propanol (2.5 mL) was added hydrazine monohydrate (500 μL), and the mixture was stirred overnight at 80° C. The reaction solution was concentrated. Then, to the residue was added methylene chloride, and the mixture was washed with water and brine. The organic layer was dried over sodium sulfate and concentrated, and the residue was purified by silica gel column chromatography (eluent: methanol/ethyl acetate) to obtain 42 mg of tert-butyl 3-[(3-amino-1H-pyrazol-5-yl)carbamoyl]azetidine-1-carboxylate.

1H-NMR (CDCl3): δ 1.38 (9H, s), 3.53-3.66 (1H, m), 3.74-3.84 (2H, m), 4.05-4.15 (2H, m), 4.31 (1H, brs), 4.90 (1H, brs), 5.12-5.44 (1H, m), 11.10-11.40 (1H, m)

(3) The title compound was obtained by the method described in Example 001-(3) or a method equivalent thereto using N-(3-amino-1H-pyrazol-5-yl)azetidine-3-carboxamide trifluoroacetate obtained by the method described in Example 001-(2) or a method equivalent thereto from tert-butyl 3-[(3-amino-1H-pyrazol-5-yl)carbamoyl]azetidine-1-carboxylate obtained in the preceding section, and 7-chloro-6-fluoro-4-oxo-1-(1,3-thiazol-2-yl)-1,4-dihydro-1,8-naphthyridine-3-carboxylic acid obtained in Reference Example 003-(2).

1H-NMR (DMSO-d6): δ 4.02-4.10 (1H, m), 4.36-4.99 (4H, m), 5.62 (1H, brs), 7.76 (1H, d, J=3.5 Hz), 7.86 (1H, d, J=3.5 Hz), 8.13 (1H, d, J=11.4 Hz), 9.83 (1H, s), 14.79 (1H, brs)

Example 493

Compound 493

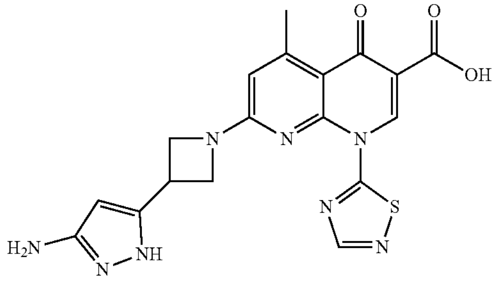

7-[3-(3-Amino-1H-pyrazol-5-yl)azetidin-1-yl]-5-methyl-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and 2-(azetidin-3-yl)-5-methyl-1,3-oxazole trifluoroacetate obtained in Example 489-(2) by the method described in Example 001-(3) or a method equivalent thereto.

1H-NMR (DMSO-d6): δ 2.78 (3H, d, J=1.0 Hz), 4.16-4.23 (1H, m), 4.31-4.90 (4H, m), 6.04 (1H, brs), 6.61 (1H, d, J=1.0 Hz), 8.82 (1H, s), 9.73 (1H, s), 15.02 (1H, brs)

Example 494

Compound 494

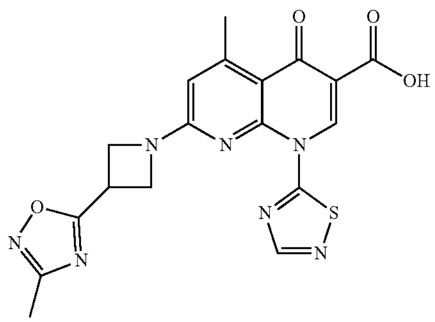

5-Methyl-7-[3-(3-methyl-1,2,4-oxadiazol-5-yl)azetidin-1-yl]-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and 5-(azetidin-3-yl)-3-methyl-1,2,4-oxadiazole hydrochloride by the method described in Example 001-(3) or a method equivalent thereto.

1H-NMR (DMSO-d6): δ 2.37 (3H, s), 2.77 (3H, d, J=1.0 Hz), 4.44-4.93 (5H, m), 6.65 (1H, d, J=1.0 Hz), 8.81 (1H, s), 9.73 (1H, s), 14.97 (1H, brs)

Example 495

Compound 495

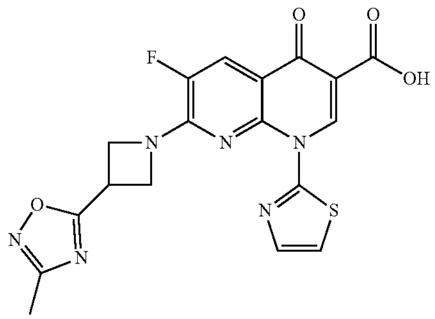

6-Fluoro-7-[3-(3-methyl-1,2,4-oxadiazol-5-yl)azetidin-1-yl]-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and 5-(azetidin-3-yl)-3-methyl-1,2,4-oxadiazole hydrochloride by the method described in Example 001-(3) or a method equivalent thereto.

1H-NMR (DMSO-d6): δ 2.37 (3H, s), 4.46-4.53 (1H, m), 4.66-5.02 (4H, m), 7.79 (1H, d, J=3.5 Hz), 7.87 (1H, d, J=3.5 Hz), 8.18 (1H, d, J=11.3 Hz), 9.84 (1H, s), 14.73 (1H, brs)

Example 496

Compound 496

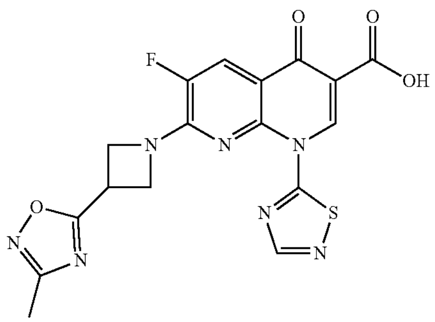

6-Fluoro-7-[3-(3-methyl-1,2,4-oxadiazol-5-yl)azetidin-1-yl]-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and 5-(azetidin-3-yl)-3-methyl-1,2,4-oxadiazole hydrochloride by the method described in Example 001-(3) or a method equivalent thereto.

1H-NMR (DMSO-d6): δ 2.37 (3H, s), 4.47-4.55 (1H, m), 4.75-5.09 (4H, m), 8.20 (1H, d, J=11.3 Hz), 8.85 (1H, s), 9.76 (1H, s), 14.40 (1H, brs)

Example 497

Compound 497

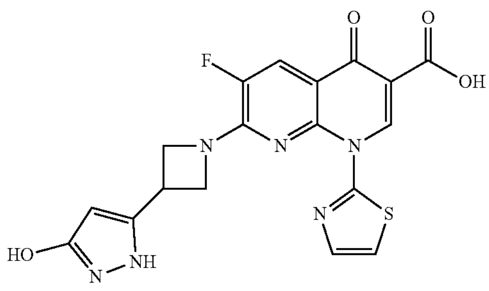

6-Fluoro-7-[3-(3-hydroxy-1H-pyrazol-5-yl)azetidin-1-yl]-4-oxo-1-(1,3-thiazol-2-yl)-1,4-dihydro-1,8-naphthyridine-3-carboxylic acid (1) To a solution of 1-[(tert-butoxy)carbonyl]azetidine-3-carboxylic acid in THF (5 mL) was added carbonyldiimidazole (454 mg), and the mixture was stirred overnight at room temperature. To a solution of potassium ethyl malonate (408 mg) and magnesium chloride (270 mg) in acetonitrile (5 mL) was added triethylamine (550 μL) under ice cooling, and the mixture was stirred overnight at room temperature. To the reaction solution was added the THF solution described above, and the mixture was stirred at room temperature for 7 hours. To the reaction solution was added 1 mol/L hydrochloric acid under ice cooling, and the mixture was extracted with ethyl acetate. The organic layer was dried over sodium sulfate and concentrated, and the residue was purified by silica gel column chromatography (eluent: ethyl acetate/n-hexane) to obtain 430 mg of tert-butyl 3-(3-ethoxy-3-oxopropanoyl)azetidine-1-carboxylate.

1H-NMR (CDCl3): δ 1.29 (3H, t, J=7.1 Hz), 1.43 (9H, s), 3.47 (2H, s), 3.58-3.64 (1H, m), 4.02-4.11 (4H, m), 4.20 (2H, q, J=7.1 Hz)

(2) A solution of tert-butyl 3-(3-ethoxy-3-oxopropanoyl) azetidine-1-carboxylate (280 mg) obtained in the preceding section, and hydrazine monohydrate (59 μL) in methanol (4 mL) was stirred at room temperature for 2 days. The reaction solution was concentrated, and the residue was dispersed in ethyl acetate. Then, the solid was collected by filtration to obtain 210 mg of tert-butyl 3-(3-hydroxy-1H-pyrazol-5-yl) azetidine-1-carboxylate.

1H-NMR (CDCl3): δ 1.45 (9H, s), 3.47-3.54 (1H, m), 3.94-3.98 (2H, m), 4.29 (2H, t, J=8.8 Hz), 5.65 (1H, s), 8.38 (1H, s)

(3) The title compound was obtained by the method described in Example 001-(3) or a method equivalent thereto using 5-(azetidin-3-yl)-1H-pyrazol-3-ol trifluoroacetate obtained by the method described in Example 001-(2) or a method equivalent thereto from tert-butyl 3-(3-hydroxy-1H-pyrazol-5-yl)azetidine-1-carboxylate obtained in the preceding section, and 7-chloro-6-fluoro-4-oxo-1-(1,3-thiazol-2-yl)-1,4-dihydro-1,8-naphthyridine-3-carboxylic acid obtained in Reference Example 003-(2).

1H-NMR (DMSO-d6): δ 4.34-4.96 (5H, m), 5.58 (1H, brs), 7.75 (1H, d, J=3.4 Hz), 7.85 (1H, d, J=3.4 Hz), 8.11 (1H, d, J=11.4 Hz), 9.49 (1H, brs), 9.82 (1H, s), 11.64 (1H, brs), 14.79 (1H, brs)

Example 498

Compound 498

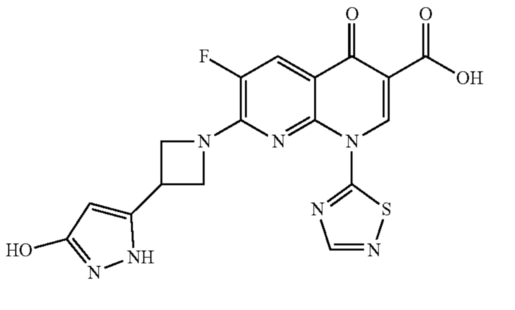

6-Fluoro-7-[3-(3-hydroxy-1H-pyrazol-5-yl)azetidin-1-yl]-4-oxo-1-(1,2,4-thiadiazol-1-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and 5-(azetidin-3-yl)-1H-pyrazol-3-ol trifluoroacetate obtained in Example 497-(3) by the method described in Example 001-(3) or a method equivalent thereto.

Property: orange solid;

ESI-MS (m/z): 430 [M+H]+

Example 499

Compound 499

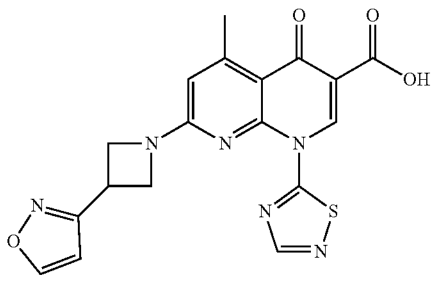

5-Methyl-7-[3-(1,2-oxazol-3-yl)azetidin-1-yl]-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and 3-(azetidin-3-yl)-1,2-oxazole hydrochloride by the method described in Example 001-(3) or a method equivalent thereto.

1H-NMR (DMSO-d6): δ 2.73 (3H, d, J=0.9 Hz), 4.28-4.35 (1H, m), 4.37-4.90 (4H, m), 6.58 (1H, d, J=0.9 Hz), 6.89 (1H, d, J=1.7 Hz), 8.80 (1H, s), 8.97 (1H, d, J=1.7 Hz), 9.65 (1H, s), 15.00 (1H, brs)

Example 500

Compound 500

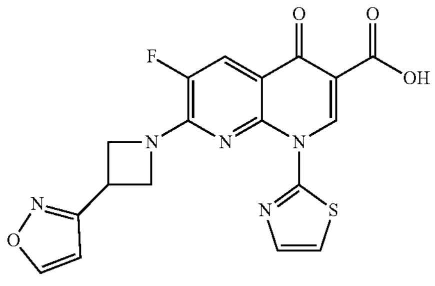

6-Fluoro-7-[3-(1,2-oxazol-3-yl)azetidin-1-yl]-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and 3-(azetidin-3-yl)-1,2-oxazole hydrochloride by the method described in Example 001-(3) or a method equivalent thereto.

1H-NMR (DMSO-d6): δ 4.30-4.37 (1H, m), 4.44-5.04 (4H, m), 6.89 (1H, d, J=1.7 Hz), 7.77 (1H, d, J=3.5 Hz), 7.85 (1H, d, J=3.5 Hz), 8.14 (1H, d, J=11.4 Hz), 8.96 (1H, d, J=1.7 Hz), 9.82 (1H, s), 14.77 (1H, brs)

Example 501

Compound 501

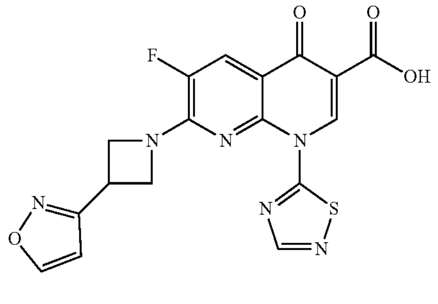

6-Fluoro-7-[3-(1,2-oxazol-3-yl)azetidin-1-yl]-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and 3-(azetidin-3-yl)-1,2-oxazole hydrochloride by the method described in Example 001-(3) or a method equivalent thereto.

1H-NMR (DMSO-d6): δ 4.32-4.39 (1H, m), 4.56-5.10 (4H, m), 6.91 (1H, d, J=1.7 Hz), 8.18 (1H, d, J=11.4 Hz), 8.85 (1H, s), 8.96 (1H, d, J=1.7 Hz), 9.75 (1H, s), 14.46 (1H, brs)

Example 502

Compound 502

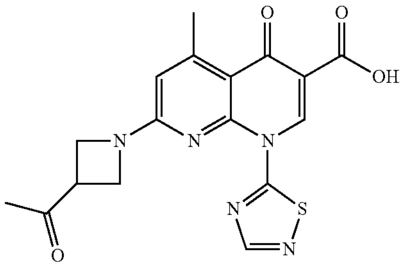

7-(3-Acetylazetidin-1-yl)-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and 1-(azetidin-3-yl)ethan-1-one hydrochloride obtained in Example 020-(2) by the method described in Example 001-(3) or a method equivalent thereto.

1H-NMR (DMSO-d6): δ 2.26 (3H, s), 2.75 (3H, s), 3.85-3.94 (1H, m), 4.29-4.70 (4H, m), 6.57 (1H, s), 8.81 (1H, s), 9.71 (1H, s), 15.03 (1H, brs)

Example 503

Compound 503

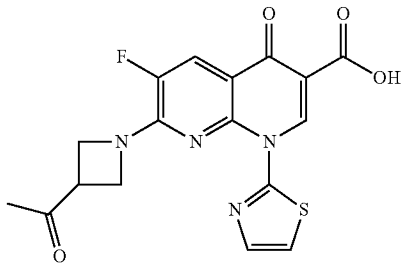

7-(3-Acetylazetidin-1-yl)-6-fluoro-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and 1-(azetidin-3-yl)ethan-1-one hydrochloride obtained in Example 020-(2) by the method described in Example 001-(3) or a method equivalent thereto.

1H-NMR (DMSO-d6): δ 2.24 (3H, s), 3.86-3.94 (1H, m), 4.46-4.76 (4H, m), 7.81 (1H, d, J=3.5 Hz), 7.86 (1H, d, J=3.5 Hz), 8.10 (1H, d, J=11.4 Hz), 9.81 (1H, s), 14.74 (1H, brs)

Example 504

Compound 504

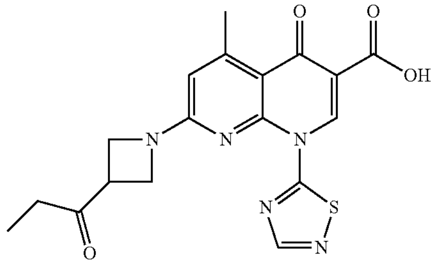

5-Methyl-4-oxo-7-(3-propanoylazetidin-1-yl)-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and 1-(azetidin-3-yl)propan-1-one hydrochloride obtained from tert-butyl 3-[methoxy(methyl)carbamoyl]azetidine-1-carboxylate and ethyl magnesium bromide by the method described in Example 020-(1) and Example 001-(2) or a method equivalent thereto by the method described in Example 001-(3) or a method equivalent thereto.

1H-NMR (DMSO-d6): δ 1.00 (3H, t, J=7.2 Hz), 2.57-2.68 (2H, m), 2.77 (3H, s), 3.88-3.95 (1H, m), 4.32-4.65 (4H, m), 6.58 (1H, s), 8.81 (1H, s), 9.73 (1H, s), 15.05 (1H, brs)

Example 505

Compound 505

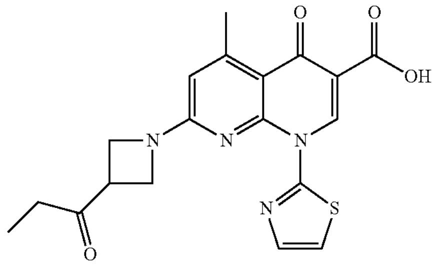

5-Methyl-4-oxo-7-(3-propanoylazetidin-1-yl)-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and 1-(azetidin-3-yl)propan-1-one hydrochloride obtained in Example 504 by the method described in Example 001-(3) or a method equivalent thereto.

1H-NMR (DMSO-d6): δ 1.00 (3H, t, J=7.3 Hz), 2.59 (2H, q, J=7.3 Hz), 2.76 (3H, s), 3.85-3.93 (1H, m), 4.22-4.50 (4H, m), 6.52 (1H, s), 7.76 (1H, d, J=3.5 Hz), 7.83 (1H, d, J=3.5 Hz), 9.82 (1H, s), 15.36 (1H, brs)

Example 506

Compound 506

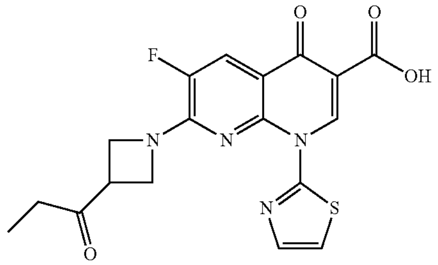

6-Fluoro-4-oxo-7-(3-propanoylazetidin-1-yl)-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and 1-(azetidin-3-yl)propan-1-one hydrochloride obtained in Example 504 by the method described in Example 001-(3) or a method equivalent thereto.

1H-NMR (DMSO-d6): δ 1.00 (3H, t, J=7.2 Hz), 2.60 (2H, q, J=7.2 Hz), 3.88-3.95 (1H, m), 4.40-4.80 (4H, m), 7.80 (1H, d, J=3.5 Hz), 7.86 (1H, d, J=3.5 Hz), 8.09 (1H, d, J=11.4 Hz), 9.80 (1H, s), 14.75 (1H, brs)

Example 507

Compound 507

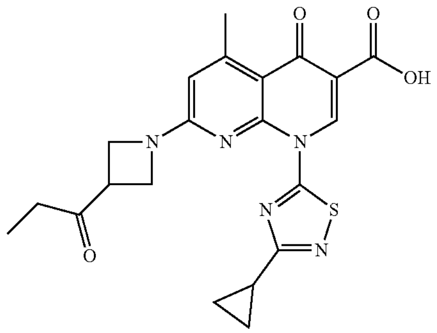

1-(3-Cyclopropyl-1,2,4-thiadiazol-5-yl)-5-methyl-4-oxo-7-(3-propanoylazetidin-1-yl)-1,4-dihydro-1,8-naphthyridine-3-carboxylic acid The title compound was obtained using 7-chloro-1-(3-cyclopropyl-1,2,4-thiadiazol-5-yl)-5-methyl-4-oxo-1,4-dihydro-1,8-naphthyridine-3-carboxylic acid obtained in Reference Example 031-(2) and 1-(azetidin-3-yl)propan-1-one hydrochloride obtained in Example 504 by the method described in Example 001-(3) or a method equivalent thereto.

1H-NMR (DMSO-d6): δ 1.00 (3H, t, J=7.2 Hz), 1.03-1.13 (4H, m), 2.30-2.37 (1H, m), 2.56-2.66 (2H, m), 2.75 (3H, s), 3.86-3.94 (1H, m), 4.29-4.61 (4H, m), 6.55 (1H, s), 9.63 (1H, s), 15.03 (1H, brs)

Example 508

Compound 508

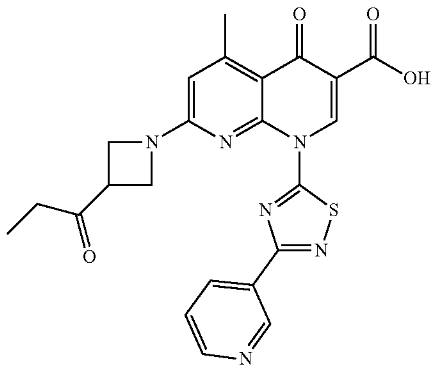

5-Methyl-4-oxo-7-(3-propanoylazetidin-1-yl)-1-[3-(pyridin-3-yl)-1,2,4-thiadiazol-5-yl]-1,4-dihydro-1,8-naphthyridine-3-carboxylic acid The title compound was obtained using 7-chloro-5-methyl-4-oxo-1-[3-(pyridin-2-yl)-1,2,4-thiadiazol-5-yl]-1,4-dihydro-1,8-naphthyridine-3-carboxylic acid obtained in Reference Example 042-(2) and 1-(azetidin-3-yl)propan-1- one hydrochloride obtained in Example 504 by the method described in Example 001-(3) or a method equivalent thereto.

1H-NMR (DMSO-d6): δ 1.02 (3H, t, J=7.2 Hz), 2.78 (3H, s), 3.89-3.97 (1H, m), 4.35-4.69 (4H, m), 6.60 (1H, s), 7.63 (1H, dd, J=7.8, 4.7 Hz), 8.55-8.58 (1H, m), 8.74-8.78 (1H, m), 9.40 (1H, s), 9.83 (1H, s), 15.04 (1H, brs)

Example 509

Compound 509

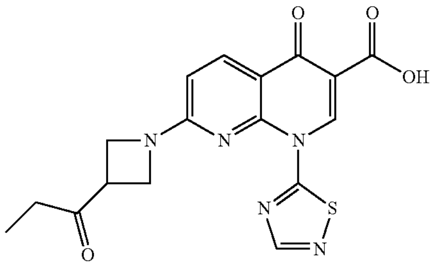

4-Oxo-7-(3-propanoylazetidin-1-yl)-1-(1,2,4-thiadiazol-5-yl)-1,4-dihydro-1,8-naphthyridine-3-carboxylic acid The title compound was obtained using 7-chloro-4-oxo-1-(1,2,4-thiadiazol-5-yl)-1,4-dihydro-1,8-naphthyridine-3-carboxylic acid obtained in Reference Example 006-(2) and 1-(azetidin-3-yl)propan-1-one hydrochloride obtained in Example 504 by the method described in Example 001-(3) or a method equivalent thereto.

1H-NMR (DMSO-d6): δ 1.01 (3H, t, J=7.2 Hz), 2.57-2.70 (2H, m), 3.89-3.97 (1H, m), 4.30-4.68 (4H, m), 6.79 (1H, d, J=9.0 Hz), 8.35 (1H, d, J=9.0 Hz), 8.83 (1H, s), 9.74 (1H, s), 14.68 (1H, brs)

Example 510

Compound 510

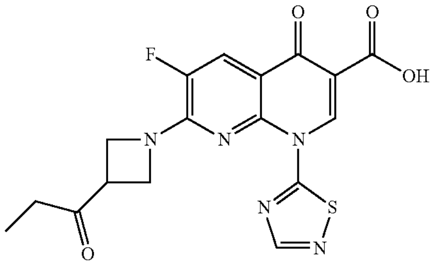

6-Fluoro-4-oxo-7-(3-propanoylazetidin-1-yl)-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and 1-(azetidin-3-yl)propan-1-one hydrochloride obtained in Example 504 by the method described in Example 001-(3) or a method equivalent thereto.

1H-NMR (DMSO-d6): δ 1.00 (3H, t, J=7.2 Hz), 2.60-2.66 (2H, m), 3.90-3.97 (1H, m), 4.56-4.81 (4H, m), 8.14 (1H, d, J=11.5 Hz), 8.85 (1H, s), 9.73 (1H, s), 14.45 (1H, brs)

Example 511

Compound 511

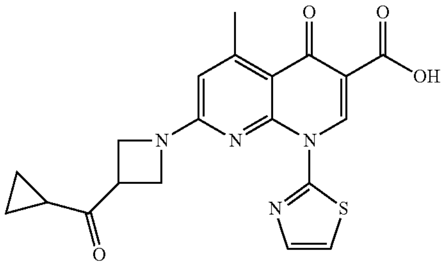

7-(3-Cyclopropanecarbonylazetidin-1-yl)-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and 3-cyclopropanecarbonylazetidine trifluoroacetate obtained from tert-butyl 3-[methoxy(methyl)carbamoyl]azetidine-1-carboxylate and cyclopropyl magnesium bromide by the method described in Example 020-(1) and Example 001-(2) or a method equivalent thereto by the method described in Example 001-(3) or a method equivalent thereto.

1H-NMR (DMSO-d6): δ 0.95-1.03 (4H, m), 2.11-2.16 (1H, m), 2.76 (3H, s), 4.00-4.07 (1H, m), 4.31-4.60 (4H, m), 6.54 (1H, s), 7.76 (1H, d, J=3.5 Hz), 7.83 (1H, d, J=3.5 Hz), 9.82 (1H, s), 15.35 (1H, brs)

Example 512

Compound 512

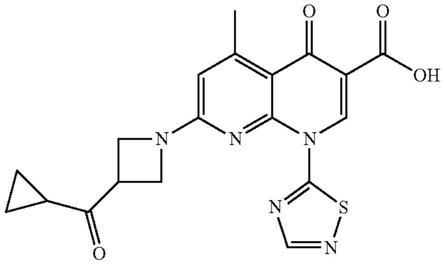

7-(3-Cyclopropanecarbonylazetidin-1-yl)-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8- naphthyridine-3-carboxylic acid obtained in Reference Example 002-(2) and 3-cyclopropanecarbonylazetidine trifluoroacetate obtained in Example 511 by the method described in Example 001-(3) or a method equivalent thereto.

1H-NMR (DMSO-d6): δ 0.95-1.04 (4H, m), 2.14-2.20 (1H, m), 2.77 (3H, s), 4.03-4.10 (1H, m), 4.34-4.74 (4H, m), 6.61 (1H, s), 8.82 (1H, s), 9.75 (1H, s), 15.04 (1H, brs)

Example 513

Compound 513

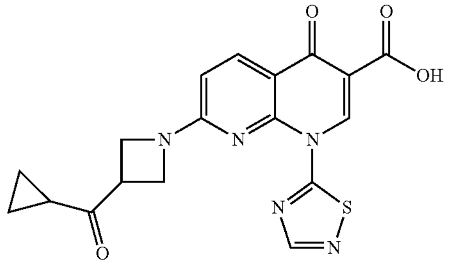

7-(3-Cyclopropanecarbonylazetidin-1-yl)-4-oxo-1-(1,2,4-thiadiazol-5-yl)-1,4-dihydro-1,8-naphthyridine-3-carboxylic acid The title compound was obtained using 7-chloro-4-oxo-1-(1,2,4-thiadiazol-5-yl)-1,4-dihydro-1,8-naphthyridine-3-carboxylic acid obtained in Reference Example 006-(2) and 3-cyclopropanecarbonylazetidine trifluoroacetate obtained in Example 511 by the method described in Example 001-(3) or a method equivalent thereto.

1H-NMR (DMSO-d6): δ 0.95-1.04 (4H, m), 2.14-2.21 (1H, m), 4.02-4.12 (1H, m), 4.33-4.62 (4H, m), 6.80 (1H, d, J=8.9 Hz), 8.35 (1H, d, J=8.9 Hz), 8.83 (1H, s), 9.74 (1H, s), 14.65 (1H, brs)

Example 514

Compound 514

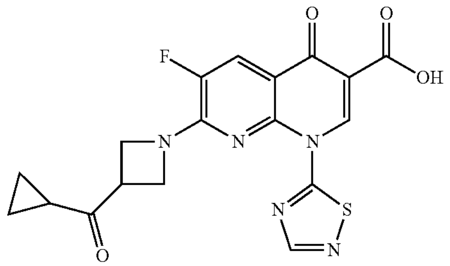

7-(3-Cyclopropanecarbonylazetidin-1-yl)-6-fluoro-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and 3-cyclopropanecarbonylazetidine trifluoroacetate obtained in Example 511 by the method described in Example 001-(3) or a method equivalent thereto.

1H-NMR (DMSO-d6): δ 0.96-1.04 (4H, m), 2.16-2.21 (1H, m), 4.04-4.12 (1H, m), 4.59-4.85 (4H, m), 8.15 (1H, d, J=11.5 Hz), 8.85 (1H, s), 9.75 (1H, s), 14.44 (1H, brs)

Example 515

Compound 515

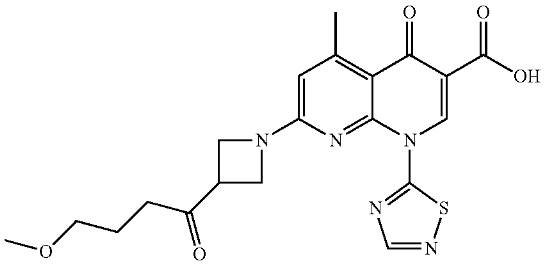

7-[3-(4-Methoxybutanoyl)azetidin-1-yl]-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and 1-(azetidin-3-yl)-4-methoxybutan-1-one hydrochloride obtained from tert-butyl 3-[methoxy(methyl)carbamoyl]azetidine-1-carboxylate and cyclopropyl magnesium bromide by the method described in Example 020-(1) and Example 001-(2) or a method equivalent thereto by the method described in Example 001-(3) or a method equivalent thereto.

1H-NMR (DMSO-d6): δ 0.97-1.02 (2H, m), 1.96-2.02 (2H, m), 2.77 (3H, s), 3.67 (2H, t, J=6.6 Hz), 3.88-3.98 (1H, m), 4.32-4.72 (4H, m), 6.60 (1H, s), 8.82 (1H, s), 9.74 (1H, s), 15.03 (1H, brs)

Example 516

Compound 516

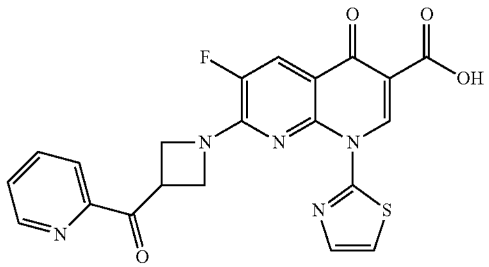

6-Fluoro-4-oxo-7-[3-(pyridine-2-carbonyl)azetidin-1-yl]-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and 2-(azetidine-3-carbonyl)pyridine hydrochloride obtained from tert-butyl 3-[methoxy(methyl)carbamoyl] azetidine-1-carboxylate and (2-pyridyl)magnesium chloride by the method described in Example 020-(1) and Example 001-(2) or a method equivalent thereto by the method described in Example 001-(3) or a method equivalent thereto.

1H-NMR (DMSO-d6): δ 4.57-4.91 (5H, m), 7.71-7.74 (1H, m), 7.81 (1H, d, J=3.4 Hz), 7.85 (1H, d, J=3.4 Hz), 8.05-8.11 (3H, m), 8.77-8.79 (1H, m), 9.81 (1H, s), 14.76 (1H, brs)

Example 517

Compound 517

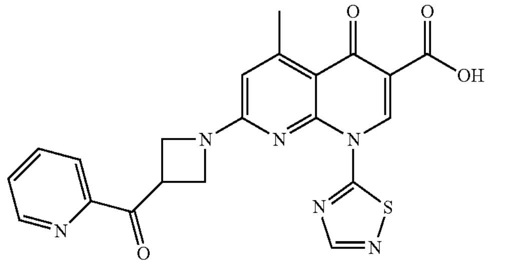

5-Methyl-4-oxo-7-[3-(pyridine-2-carbonyl)azetidin-1-yl]-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and 2-(azetidine-3-carbonyl)pyridine hydrochloride obtained in Example 516 by the method described in Example 001-(3) or a method equivalent thereto.

1H-NMR (DMSO-d6): δ 2.77 (3H, s), 4.45-4.80 (4H, m), 4.83-4.91 (1H, m), 6.65 (1H, s), 7.72-7.75 (1H, m), 8.07-8.09 (2H, m), 8.80 (1H, d, J=4.8 Hz), 8.81 (1H, s), 9.76 (1H, s), 15.06 (1H, brs)

Example 518

Compound 518

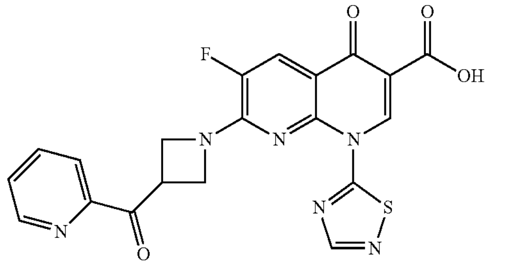

6-Fluoro-4-oxo-7-[3-(pyridine-2-carbonyl)azetidin-1-yl]-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and 2-(azetidine-3-carbonyl)pyridine hydrochloride obtained in Example 516 by the method described in Example 001-(3) or a method equivalent thereto.

1H-NMR (DMSO-d6): δ 4.69-5.01 (5H, m), 7.71-7.75 (1H, m), 8.05-8.11 (2H, m), 8.15 (1H, d, J=11.4 Hz), 8.78-8.81 (1H, m), 8.85 (1H, s), 9.74 (1H, s), 14.41 (1H, brs)

Example 519

Compound 519

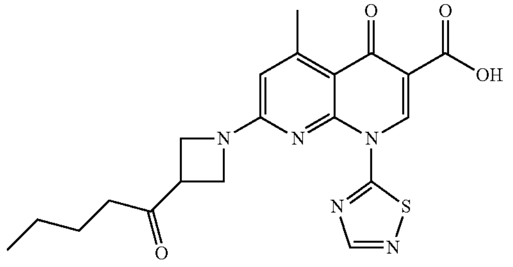

5-Methyl-4-oxo-7-(3-pentanoylazetidin-1-yl)-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and 1-(azetidin-3-yl)pentan-1-one hydrochloride obtained from tert-butyl 3-[methoxy(methyl)carbamoyl]azetidine-1-carboxylate and n-butyllithium by the method described in Example 020-(1) and Example 001-(2) or a method equivalent thereto by the method described in Example 001-(3) or a method equivalent thereto.

1H-NMR (DMSO-d6): δ 0.89 (3H, t, J=7.4 Hz), 1.26-1.34 (2H, m), 1.48-1.55 (2H, m), 2.55-2.64 (2H, m), 2.76 (3H, s), 3.88-3.95 (1H, m), 4.32-4.65 (4H, m), 6.58 (1H, s), 8.82 (1H, s), 9.73 (1H, s), 15.05 (1H, brs)

Example 520

Compound 520

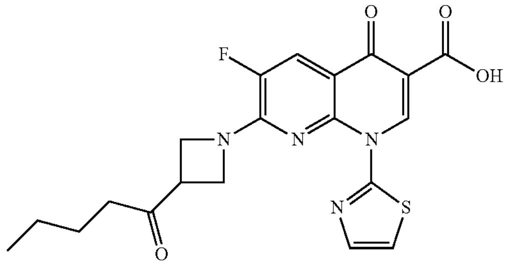

6-Fluoro-4-oxo-7-(3-pentanoylazetidin-1-yl)-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and 1-(azetidin-3-yl)pentan-1-one hydrochloride obtained in Example 519 by the method described in Example 001-(3) or a method equivalent thereto.

1H-NMR (DMSO-d6): δ 0.89 (3H, t, J=7.4 Hz), 1.26-1.34 (2H, m), 1.45-1.54 (2H, m), 2.58 (2H, t, J=7.4 Hz), 3.88-3.95 (1H, m), 4.36-4.80 (4H, m), 7.80 (1H, d, J=3.5 Hz), 7.85 (1H, d, J=3.5 Hz), 8.08 (1H, d, J=11.4 Hz), 9.79 (1H, s), 14.75 (1H, brs)

Example 521

Compound 521

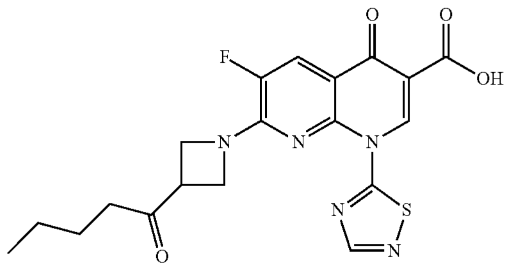

6-Fluoro-4-oxo-7-(3-pentanoylazetidin-1-yl)-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and 1-(azetidin-3-yl)pentan-1-one hydrochloride obtained in Example 519 by the method described in Example 001-(3) or a method equivalent thereto.

1H-NMR (DMSO-d6): δ 0.89 (3H, t, J=7.4 Hz), 1.26-0.34 (2H, m), 1.48-1.55 (2H, m), 2.61 (2H, t, J=7.4 Hz), 3.90-3.97 (1H, m), 4.52-4.81 (4H, m), 8.15 (1H, d, J=11.5 Hz), 8.85 (1H, s), 9.74 (1H, s), 14.46 (1H, brs)

Example 522

Compound 522

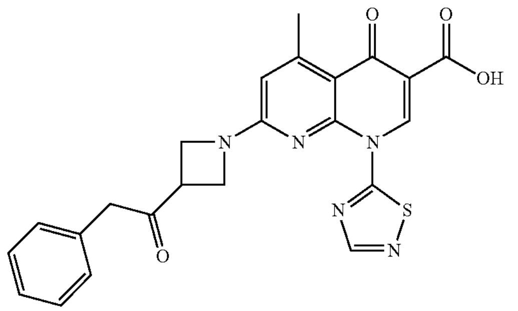

5-Methyl-4-oxo-7-[3-(2-phenylacetyl)azetidin-1-yl]-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and 1-(azetidin-3-yl)-2-phenylethan-1-one hydrochloride obtained from tert-butyl 3-[methoxy(methyl)carbamoyl]azetidine-1-carboxylate and benzyl magnesium bromide by the method described in Example 020-(1) and Example 001-(2) or a method equivalent thereto by the method described in Example 001-(3) or a method equivalent thereto.

1H-NMR (DMSO-d6): δ 2.74 (3H, s), 3.88-3.95 (3H, m), 4.30-4.58 (4H, m), 6.57 (1H, s), 7.26-7.37 (5H, m), 8.81 (1H, s), 9.71 (1H, s), 15.01 (1H, brs)

Example 523

Compound 523

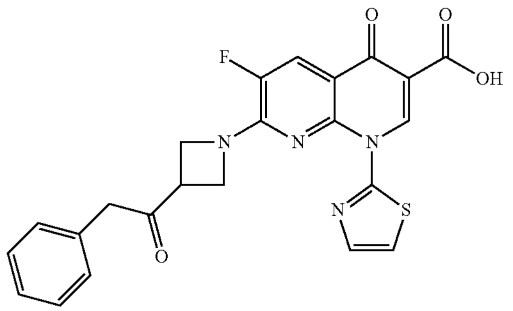

6-Fluoro-4-oxo-7-[3-(2-phenylacetyl)azetidin-1-yl]-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and 1-(azetidin-3-yl)-2-phenylethan-1-one hydrochloride obtained in Example 522 by the method described in Example 001-(3) or a method equivalent thereto.

1H-NMR (DMSO-d6): δ 3.95 (2H, s), 3.98-4.06 (1H, m), 4.32-4.76 (4H, m), 7.25-7.37 (5H, m), 7.83 (1H, d, J=3.5 Hz), 7.87 (1H, d, J=3.5 Hz), 8.10 (1H, d, J=11.5 Hz), 9.80 (1H, s), 14.76 (1H, brs)

Example 524

Compound 524

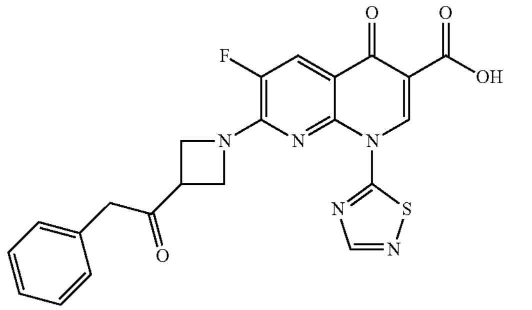

6-Fluoro-4-oxo-7-[3-(2-phenylacetyl)azetidin-1-yl]-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and 1-(azetidin-3-yl)-2-phenylethan-1-one hydrochloride obtained in Example 522 by the method described in Example 001-(3) or a method equivalent thereto.

1H-NMR (DMSO-d6): δ 3.98 (2H, s), 4.01-4.08 (1H, m), 4.46-4.75 (4H, m), 7.25-7.37 (5H, m), 8.13 (1H, d, J=11.5 Hz), 8.85 (1H, s), 9.73 (1H, s), 14.40 (1H, brs)

Example 525

Compound 525

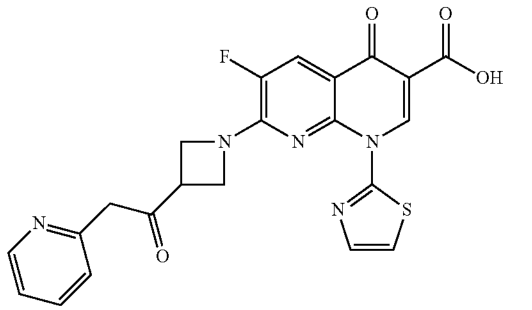

6-Fluoro-4-oxo-7-{3-[2-(pyridin-2-yl)acetyl]azetidin-1-yl}-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and 1-(azetidin-3-yl)-2-(pyridin-2-yl)ethan-1-one hydrochloride obtained from tert-butyl 3-[methoxy(methyl)carbamoyl]azetidine-1-carboxylate and pyridin-2-ylmethyl lithium by the method described in Example 020-(1) and Example 001-(2) or a method equivalent thereto by the method described in Example 001-(3) or a method equivalent thereto.

1H-NMR (DMSO-d6): δ 3.99-4.06 (1H, m), 4.11 (2H, s), 4.46-4.80 (4H, m), 7.30-7.33 (1H, m), 7.37-7.40 (1H, m), 7.78-7.82 (1H, m), 7.84 (1H, d, J=3.5 Hz), 7.87 (1H, d, J=3.5 Hz), 8.12 (1H, d, J=11.4 Hz), 8.52-8.54 (1H, m), 9.82 (1H, s), 14.76 (1H, brs)

Example 526

Compound 526

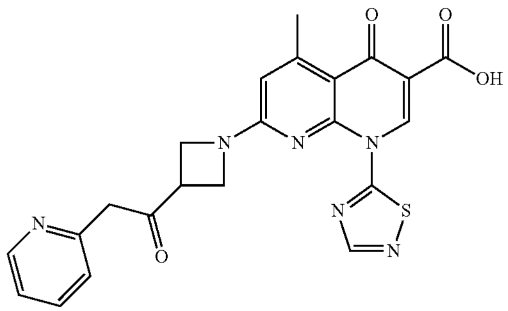

5-Methyl-4-oxo-7-{3-[2-(pyridin-2-yl)acetyl]azetidin-1-yl}-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and 1-(azetidin-3-yl)-2-(pyridin-2-yl)ethan-1-one hydrochloride obtained in Example 525 by the method described in Example 001-(3) or a method equivalent thereto.

1H-NMR (DMSO-d6): δ 2.76 (3H, d, J=0.9 Hz), 4.00-4.06 (1H, m), 4.13 (2H, s), 4.33-4.70 (4H, m), 6.60 (1H, d, J=0.9 Hz), 7.29-7.33 (1H, m), 7.38-7.41 (1H, m), 7.78-7.82 (1H, m), 8.52-8.54 (1H, m), 8.82 (1H, s), 9.73 (1H, s), 15.04 (1H, brs)

Example 527

Compound 527

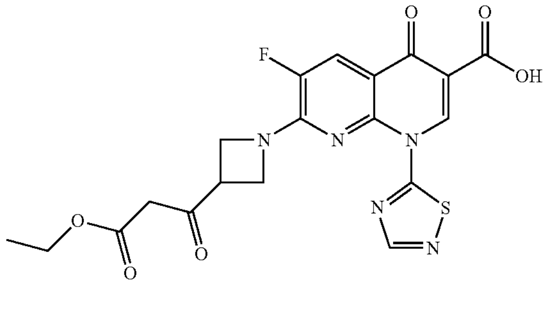

7-[3-(3-Ethoxy-3-oxopropanoyl)azetidin-1-yl]-6-fluoro-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8- naphthyridine-3-carboxylic acid obtained in Reference Example 004-(2) and ethyl 3-(azetidin-3-yl)-3-oxopropanoate trifluoroacetate obtained from tert-butyl 3-(3-ethoxy-3-oxopropanoyl)azetidine-1-carboxylate obtained in Example 497-(1) by the method described in Example 001-(2) or a method equivalent thereto by the method described in Example 001-(3) or a method equivalent thereto.

1H-NMR (DMSO-d6): δ 1.22 (3H, t, J=7.2 Hz), 3.83 (2H, s), 4.02-4.08 (1H, m), 4.14 (2H, q, J=7.2 Hz), 4.54-4.79 (4H, m), 8.16 (1H, d, J=11.5 Hz), 8.85 (1H, s), 9.75 (1H, s), 14.43 (1H, brs)

Example 528

Compound 528

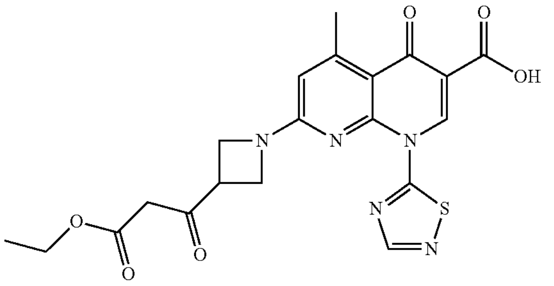

7-[3-(3-Ethoxy-3-oxopropanoyl)azetidin-1-yl]-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and ethyl 3-(azetidin-3-yl)-3-oxopropanoate trifluoroacetate obtained in Example 527 by the method described in Example 001-(3) or a method equivalent thereto.

1H-NMR (DMSO-d6): δ 1.22 (3H, t, J=7.2 Hz), 2.77 (3H, s), 3.82 (2H, s), 3.99-4.07 (1H, m), 4.14 (2H, q, J=7.2 Hz), 4.33-4.67 (4H, m), 6.61 (1H, s), 8.82 (1H, s), 9.73 (1H, s), 14.95 (1H, brs)

Example 529

Compound 529

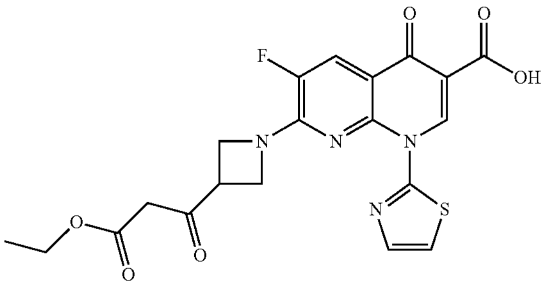

7-[3-(3-Ethoxy-3-oxopropanoyl)azetidin-1-yl]-6-fluoro-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and ethyl 3-(azetidin-3-yl)-3-oxopropanoate trifluoroacetate obtained in Example 527 by the method described in Example 001-(3) or a method equivalent thereto.

1H-NMR (DMSO-d6): δ 1.21 (3H, t, J=7.2 Hz), 3.80 (2H, s), 3.99-4.07 (1H, m), 4.13 (2H, q, J=7.2 Hz), 4.44-4.75 (4H, m), 7.80 (1H, d, J=3.5 Hz), 7.86 (1H, d, J=3.5 Hz), 8.10 (1H, d, J=11.5 Hz), 9.80 (1H, s), 14.64 (1H, brs)

Example 530

Compound 530

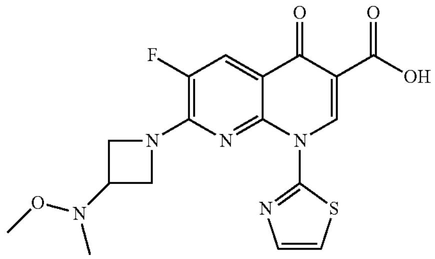

6-Fluoro-7-{3-[methoxy(methyl)amino]azetidin-1-yl}-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-methoxy-N-methylazetidine-3-amine trifluoroacetate obtained in Example 021-(2) by the method described in Example 001-(3) or a method equivalent thereto.

1H-NMR (DMSO-d6): δ 2.56 (3H, s), 3.53 (3H, s), 3.85-3.91 (1H, m), 4.28-4.86 (4H, m), 7.80 (1H, d, J=3.5 Hz), 7.86 (1H, d, J=3.5 Hz), 8.10 (1H, d, J=11.4 Hz), 9.82 (1H, s), 14.81 (1H, brs)

Example 531

Compound 531

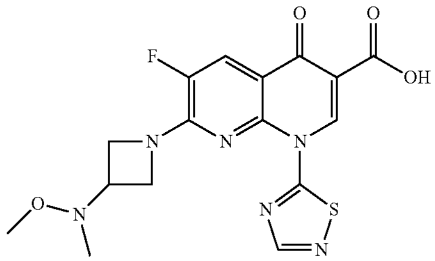

6-Fluoro-7-{3-[methoxy(methyl)amino]azetidin-1-yl}-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and N-methoxy-N-methylazetidine-3-amine trifluoroacetate obtained in Example 021-(2) by the method described in Example 001-(3) or a method equivalent thereto.

1H-NMR (DMSO-d6): δ 2.58 (3H, s), 3.54 (3H, s), 3.87-3.93 (1H, m), 4.41-4.77 (4H, m), 8.15 (1H, d, J=11.4 Hz), 8.85 (1H, s), 9.76 (1H, s), 14.51 (1H, brs)

Example 532

Compound 532

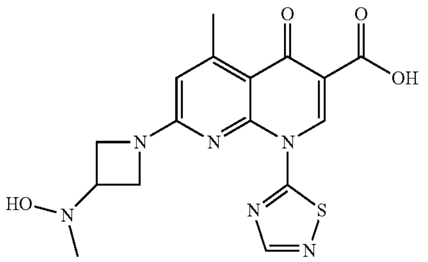

7-{3-[Hydroxy(methyl)amino]azetidin-1-yl}-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-(azetidin-3-yl)-N-methylhydroxylamine trifluoroacetate obtained from N-methylhydroxylamine hydrochloride and tert-butyl 3-oxoazetidine-1-carboxylate by the method described in Example 021-(1) and Example 001-(2) or a method equivalent thereto by the method described in Example 001-(3) or a method equivalent thereto.

1H-NMR (DMSO-d6): δ 2.53 (3H, s), 2.75 (3H, d, J=1.0 Hz), 3.77-3.83 (1H, m), 4.19-4.50 (4H, m), 6.55 (1H, d, J=1.0 Hz), 8.30 (1H, brs), 8.82 (1H, s), 9.72 (1H, s), 15.10 (1H, brs)

Example 533

Compound 533

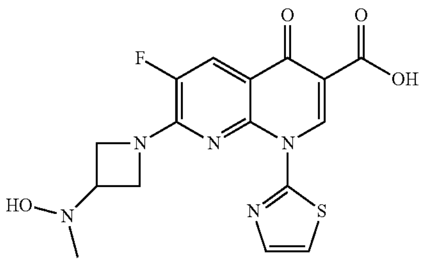

6-Fluoro-7-{3-[hydroxy(methyl)amino]azetidin-1-yl}-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-(azetidin-3-yl)-N-methylhydroxylamine trifluoroacetate obtained in Example 532 by the method described in Example 001-(3) or a method equivalent thereto.

1H-NMR (DMSO-d6): δ 3.75-3.80 (1H, m), 4.32-4.70 (4H, m), 7.82 (1H, d, J=3.5 Hz), 7.86 (1H, d, J=3.5 Hz), 8.08 (1H, d, J=11.6 Hz), 8.30 (1H, s), 9.81 (1H, s), 14.82 (1H, brs)

Example 534

Compound 534

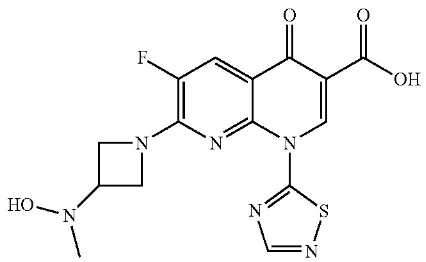

6-Fluoro-7-{3-[hydroxy(methyl)amino]azetidin-1-yl}-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and N-(azetidin-3-yl)-N-methyl hydroxylamine trifluoroacetate obtained in Example 532 by the method described in Example 001-(3) or a method equivalent thereto.

1H-NMR (DMSO-d6): δ 2.53 (3H, s), 3.77-3.83 (1H, m), 4.47-4.73 (4H, m), 8.14 (1H, d, J=11.5 Hz), 8.32 (1H, s), 8.86 (1H, s), 9.75 (1H, s), 14.51 (1H, brs)

Example 535

Compound 535

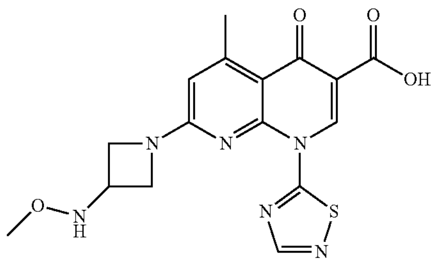

7-[3-(Methoxyamino) azetidin-1-yl]-5-methyl-4-oxo-1-(1,2,4-thiadiazol-5-yl)-1,4-dihydro-1,8-naphthyridine-3-carboxylic acid The title compound was obtained by the method described in Example 001-(3) or a method equivalent thereto using N-methoxyazetidin-3-amine trifluoroacetate obtained by the methods described in Examples 021-(1) and 001-(2) or methods equivalent thereto from O-methylhydroxylamine hydrochloride and tert-butyl 3-oxoazetidine-1-carboxylate, and 7-chloro-5-methyl-4-oxo-1-(1,2,4-thiadiazol-5-yl)-1,4-dihydro-1,8-naphthyridine-3-carboxylic acid obtained in Reference Example 002-(2).

1H-NMR (DMSO-d6): δ 2.76 (3H, d, J=0.9 Hz), 3.50 (3H, s), 4.06-4.58 (5H, m), 6.57 (1H, d, J=0.9 Hz), 7.18 (1H, d, J=6.3 Hz), 8.82 (1H, s), 9.73 (1H, s), 15.03 (1H, brs)

Example 536

Compound 536

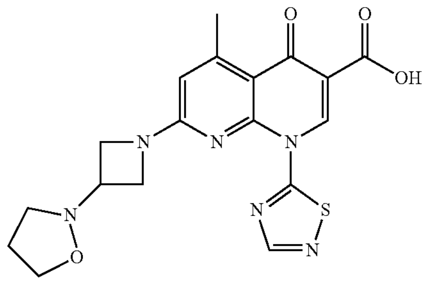

5-Methyl-7-[3-(1,2-oxazolidin-2-yl)azetidin-1-yl]-4-oxo-1-(1,2,4-thiadiazol-5-yl)-1,4-dihydro-1,8-naphthyridine-3-carboxylic acid The title compound was obtained by the method described in Example 001-(3) or a method equivalent thereto using 2-(azetidin-3-yl)-1,2-oxazolidine trifluoroacetate obtained by the methods described in Examples 021-(1) and 001-(2) or methods equivalent thereto from 1,2-oxazolidine hydrochloride and tert-butyl 3-oxoazetidine-1-carboxylate, and 7-chloro-5-methyl-4-oxo-1-(1,2,4-thiadiazol-5-yl)-1,4-dihydro-1,8-naphthyridine-3-carboxylic acid obtained in Reference Example 002-(2).

1H-NMR (DMSO-d6): δ 2.18-2.27 (2H, m), 2.78 (3H, s), 2.86-3.05 (2H, m), 3.79-3.93 (3H, m), 4.20-4.59 (4H, m), 6.59 (1H, s), 8.82 (1H, s), 9.76 (1H, s), 15.10 (1H, brs)

Example 537

Compound 537

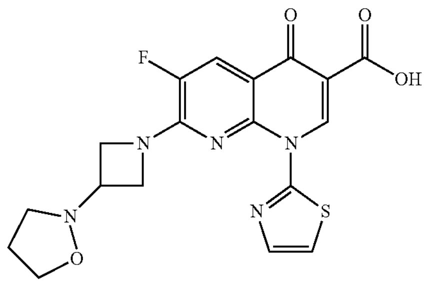

6-Fluoro-7-[3-(1,2-oxazolidin-2-yl)azetidin-1-yl]-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and 2-(azetidin-3-yl)-1,2-oxazolidine trifluoroacetate obtained in Example 536 by the method described in Example 001-(3) or a method equivalent thereto.

1H-NMR (DMSO-d6): δ 2.18-2.27 (2H, m), 2.79-3.07 (2H, m), 3.78-3.95 (3H, m), 4.18-4.77 (4H, m), 7.79 (1H, d, J=3.5 Hz), 7.85 (1H, d, J=3.5 Hz), 8.07 (1H, d, J=11.5 Hz), 9.80 (1H, s), 14.78 (1H, brs)

Example 538

Compound 538

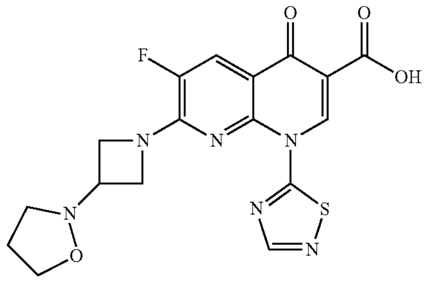

6-Fluoro-7-[3-(1,2-oxazolidin-2-yl)azetidin-1-yl]-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and 2-(azetidin-3-yl)-1,2-oxazolidine trifluoroacetate obtained in Example 536 by the method described in Example 001-(3) or a method equivalent thereto.

1H-NMR (DMSO-d6): δ 2.19-2.27 (2H, m), 2.85-3.10 (2H, m), 3.78-3.90 (2H, m), 3.92-3.96 (1H, m), 4.27-4.78 (4H, m), 8.12 (1H, d, J=11.4 Hz), 8.84 (1H, s), 9.73 (1H, s), 14.47 (1H, brs)

Example 539

Compound 539

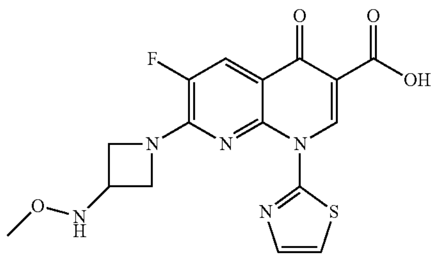

6-Fluoro-7-[3-(methoxyamino)azetidin-1-yl]-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-methoxyazetidin-3-amine trifluoroacetate obtained in Example 535 by the method described in Example 001-(3) or a method equivalent thereto.

1H-NMR (DMSO-d6): δ 3.49 (3H, s), 4.11-4.18 (1H, m), 4.20-4.75 (4H, m), 7.16 (1H, d, J=6.9 Hz), 7.81 (1H, d, J=3.5 Hz), 7.86 (1H, d, J=3.5 Hz), 8.09 (1H, d, J=11.5 Hz), 9.81 (1H, s), 14.81 (1H, brs)

Example 540

Compound 540

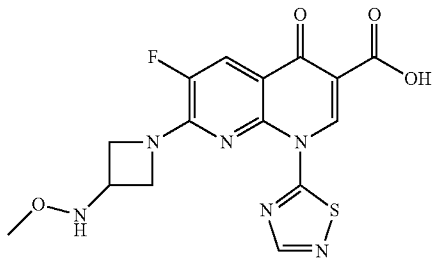

6-Fluoro-7-[3-(methoxyamino)azetidin-1-yl]-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and N-methoxyazetidin-3-amine trifluoroacetate obtained in Example 535 by the method described in Example 001-(3) or a method equivalent thereto.

1H-NMR (DMSO-d6): δ 3.51 (3H, s), 4.13-4.20 (1H, m), 4.26-4.79 (4H, m), 7.17 (1H, d, J=6.3 Hz), 8.14 (1H, d, J=11.5 Hz), 8.85 (1H, s), 9.73 (1H, s), 14.49 (1H, brs)

Example 541

Compound 541

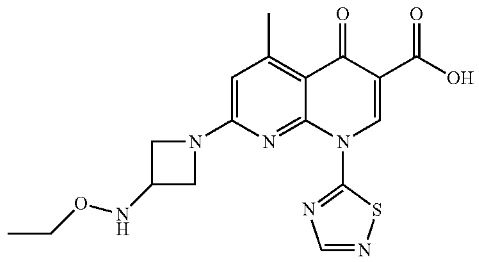

7-[3-(Ethoxyamino)azetidin-1-yl]-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-ethoxyazetidin-3-amine trifluoroacetate obtained from O-ethylhydroxylamine hydrochloride and tert-butyl 3-oxoazetidine-1-carboxylate by the method described in Example 021-(1) and Example 001-(2) or a method equivalent thereto by the method described in Example 001-(3) or a method equivalent thereto.

1H-NMR (DMSO-d6): δ 1.12 (3H, t, J=7.0 Hz), 2.74 (3H, d, J=0.8 Hz), 3.71 (2H, q, J=7.0 Hz), 4.03-4.57 (5H, m), 6.56 (1H, d, J=0.8 Hz), 7.04 (1H, d, J=6.5 Hz), 8.81 (1H, s), 9.71 (1H, s), 14.93 (1H, brs)

Example 542

Compound 542

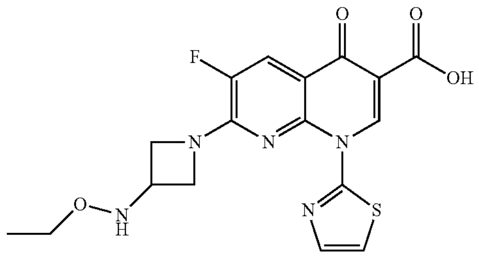

7-[3-(Ethoxyamino) azetidin-1-yl]-6-fluoro-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-ethoxyazetidin-3-amine trifluoroacetate obtained in Example 541 by the method described in Example 001-(3) or a method equivalent thereto.

1H-NMR (DMSO-d6): δ 1.11 (3H, t, J=7.0 Hz), 3.70 (2H, q, J=7.0 Hz), 4.10-4.16 (1H, m), 4.19-4.75 (4H, m), 7.02 (1H, d, J=6.9 Hz), 7.81 (1H, d, J=3.5 Hz), 7.86 (1H, d, J=3.5 Hz), 8.09 (1H, d, J=11.5 Hz), 9.81 (1H, a), 14.82 (1H, brs)

Example 543

Compound 543

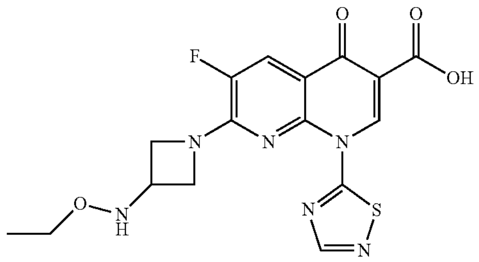

7-[3-(Ethoxyamino) azetidin-1-yl]-6-fluoro-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and N-ethoxyazetidin-3-amine trifluoroacetate obtained in Example 541 by the method described in Example 001-(3) or a method equivalent thereto.

1H-NMR (DMSO-d6): δ 1.13 (3H, t, J=7.0 Hz), 3.73 (2H, q, J=7.0 Hz), 4.12-4.20 (1H, m), 4.22-4.80 (4H, m), 7.03 (1H, d, J=6.9 Hz), 8.12 (1H, d, J=11.5 Hz), 8.85 (1H, s), 9.71 (1H, s), 14.47 (1H, brs)

Example 544

Compound 544

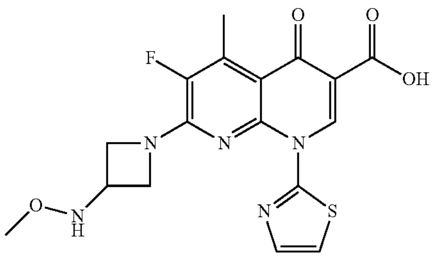

6-Fluoro-7-[3-(methoxyamino) azetidin-1-yl]-5-methyl-4-oxo-1-(1,3-thiazol-2-yl)-1,4-dihydro-1,8-naphthyridine-3-carboxylic acid The title compound was obtained using 7-chloro-6-fluoro-5-methyl-4-oxo-1-(1,3-thiazol-2-yl)-1,4-dihydro-1,8-naphthyridine-3-carboxylic acid obtained in Reference Example 007-(2) and N-methoxyazetidin-3-amine trifluoroacetate obtained in Example 535 by the method described in Example 001-(3) or a method equivalent thereto.

1H-NMR (DMSO-d6): δ 2.68 (3H, d, J=3.0 Hz), 3.49 (3H, s), 4.09-4.72 (5H, m), 7.15 (1H, d, J=6.9 Hz), 7.78 (1H, d, J=3.5 Hz), 7.85 (1H, d, J=3.5 Hz), 9.80 (1H, s), 15.05 (1H, brs)

Example 545

Compound 545

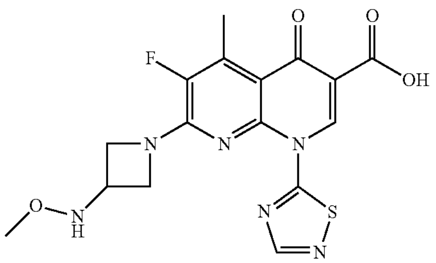

6-Fluoro-7-[3-(methoxyamino)azetidin-1-yl]-5-methyl-4-oxo-1-(1,2,4-thiadiazol-5-yl)-1,4-dihydro-1,8-naphthyridine-3-carboxylic acid The title compound was obtained using 7-chloro-6-fluoro-5-methyl-4-oxo-1-(1,2,4-thiadiazol-5-yl)-1,4-dihydro-1,8-naphthyridine-3-carboxylic acid obtained in Reference Example 008-(2) and N-methoxyazetidin-3-amine trifluoroacetate obtained in Example 535 by the method described in Example 001-(3) or a method equivalent thereto.

1H-NMR (DMSO-d6): δ 2.65 (3H, d, J=2.9 Hz), 3.51 (3H, s), 4.11-4.19 (1H, m), 4.26-4.78 (4H, m), 7.16 (1H, d, J=6.0 Hz), 8.83 (1H, s), 9.68 (1H, s), 14.34 (1H, brs)

Example 546

Compound 546

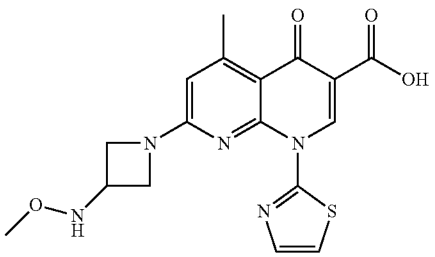

7-[3-(Methoxyamino)azetidin-1-yl]-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-methoxyazetidin-3-amine trifluoroacetate obtained in Example 535 by the method described in Example 001-(3) or a method equivalent thereto.

1H-NMR (DMSO-d6): δ 2.71 (3H, d, J=0.9 Hz), 3.49 (3H, s), 3.98-4.42 (5H, m), 6.46 (1H, d, J=0.9 Hz), 7.16 (1H, d, J=6.5 Hz), 7.74 (1H, d, J=3.5 Hz), 7.81 (1H, d, J=3.5 Hz), 9.78 (1H, s), 15.05 (1H, brs)

Example 547

Compound 547

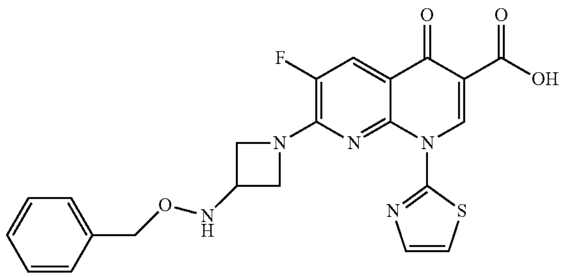

7-{3-[(Benzyloxy)amino]azetidin-1-yl}-6-fluoro-4-oxo-1-(1,3-thiazol-2-yl)-1,4-dihydro-1,8-naphthyridine-3-carboxylic acid The title compound was obtained by the method described in Example 001-(3) or a method equivalent thereto using N-(benzyloxy)azetidin-3-amine trifluoroacetate obtained by the methods described in Examples 021-(1) and 001-(2) or methods equivalent thereto from O-benzylhydroxylamine hydrochloride and tert-butyl 3-oxoazetidine-1-carboxylate, and 7-chloro-6-fluoro-4-oxo-1-(1,3-thiazol-2-yl)-1,4-dihydro-1,8-naphthyridine-3-carboxylic acid obtained in Reference Example 003-(2).

1H-NMR (DMSO-d6): δ 4.10-4.36 (3H, m), 4.42-4.70 (2H, m), 4.70 (2H, s), 7.20 (1H, d, J=6.6 Hz), 7.27-7.37 (5H, m), 7.81 (1H, d, J=3.5 Hz), 7.86 (1H, d, J=3.5 Hz), 8.08 (1H, d, J=11.5 Hz), 9.81 (1H, s), 14.81 (1H, brs)

Example 548

Compound 548

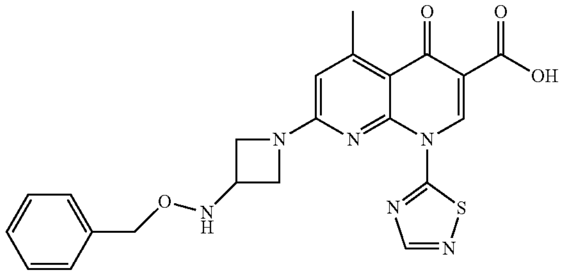

7-{3-[(Benzyloxy)amino]azetidin-1-yl}-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-(benzyloxy)azetidin-3-amine trifluoroacetate obtained in Example 547 by the method described in Example 001-(3) or a method equivalent thereto.

1H-NMR (DMSO-d6): δ 2.74 (3H, d, J=1.0 Hz), 4.04-4.21 (3H, m), 4.31-4.38 (1H, m), 4.44-4.51 (1H, m), 4.72 (2H, s), 6.53 (1H, d, J=1.0 Hz), 7.22 (1H, d, J=5.7 Hz), 7.26-7.37 (5H, m), 8.81 (1H, s), 9.70 (1H, s), 15.09 (1H, brs)

Example 549

Compound 549

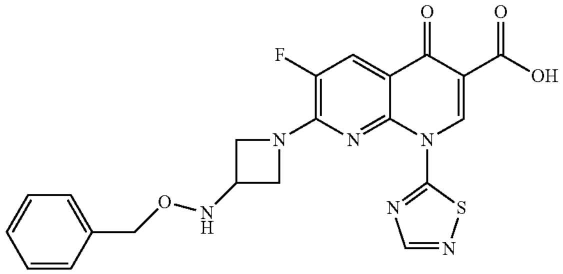

7-{3-[(Benzyloxy)amino]azetidin-1-yl}-6-fluoro-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and N-(benzyloxy) azetidin-3-amine trifluoroacetate obtained in Example 547 by the method described in Example 001-(3) or a method equivalent thereto.

1H-NMR (DMSO-d6): δ 4.03-4.64 (5H, m), 4.69 (2H, s), 7.15 (1H, d, J=6.5 Hz), 7.26-7.37 (5H, m), 7.95 (1H, d, J=11.7 Hz), 8.44 (1H, s), 15.52 (1H, brs)

Example 550

Compound 550

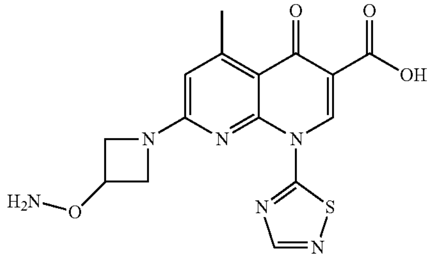

7-[3-(Aminooxy) azetidin-1-yl]-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and O-(azetidin-3-yl)hydroxylamine hydrochloride by the method described in Example 001-(3) or a method equivalent thereto.

1H-NMR (DMSO-d6): δ 2.71 (3H, s), 4.06-4.73 (5H, m), 6.51 (1H, s), 8.79 (1H, s), 9.65 (1H, s), 15.02 (1H, brs)

Example 551

Compound 551

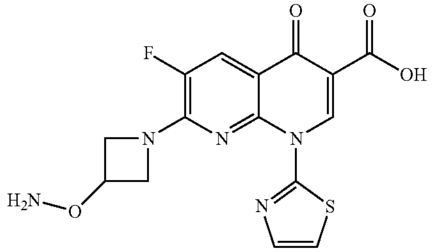

7-[3-(Aminooxy)azetidin-1-yl]-6-fluoro-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and O-(azetidin-3-yl)hydroxylamine hydrochloride by the method described in Example 001-(3) or a method equivalent thereto.

1H-NMR (DMSO-d6): δ 4.20-4.82 (5H, m), 6.44 (2H, brs), 7.80 (1H, d, J=3.5 Hz), 7.85 (1H, d, J=3.5 Hz), 8.06 (1H, d, J=11.5 Hz), 9.78 (1H, s), 14.78 (1H, brs)

Example 552

Compound 552

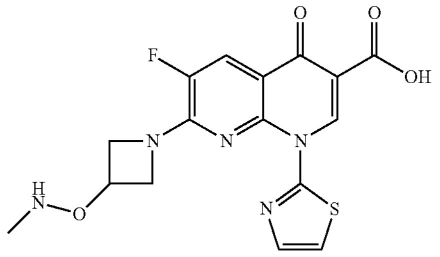

6-Fluoro-7-{3-[(methylamino)oxy]azetidin-1-yl}-4-oxo-1-(1,3-thiazol-2-yl)-1,4-dihydro-1,8-naphthyridine-3-carboxylic acid (1) To a solution of tert-butyl 3-hydroxyazetidine-1-carboxylate (2.0 g) in THF (150 mL) were added triphenylphosphine (6.0 g), 2-hydroxy-2H-isoindole-1,3-dione (3.8 g), and 1,1'-(azodicarbonyl)dipiperidine (6.4 g), and the mixture was stirred at room temperature for 5 days. The reaction solution was concentrated, and the residue was subjected to silica gel column chromatography (eluent: ethyl acetate/n-hexane) to obtain crude tert-butyl 3-[(1,3-dioxo-2,3-dihydro-1H-isoindol-2-yl)oxy]azetidine-1-carboxylate.

(2) To a solution of crude tert-butyl 3-[(1,3-dioxo-2,3-dihydro-1H-isoindol-2-yl)oxy]azetidine-1-carboxylate (2.8 g) obtained in the preceding section in methylene chloride was added hydrazine monohydrate (1.28 mL), and the mixture was stirred at room temperature for 2 days. Insoluble material was filtered off, and the filtrate was concentrated to obtain 1.4 g of tert-butyl 3-(aminooxy) azetidine-1-carboxylate.

1H-NMR (CDCl3): δ 1.43 (9H, s), 3.83-3.88 (2H, m), 4.01-4.06 (2H, m), 4.42-4.47 (1H, m), 5.45 (2H, brs)

(3) To a suspension of tert-butyl 3-(aminooxy)azetidine-1-carboxylate (585 mg) obtained in the preceding section in methylene chloride (25 mL) was added di-tert-butyl dicarbonate (4.1 g), and the mixture was stirred at room temperature for 3 days. The reaction solution was concentrated, and the residue was subjected to silica gel column chromatography (eluent: ethyl acetate/n-hexane) to obtain crude tert-butyl 3-({[(tert-butoxy) carbonyl]amino}oxy) azetidine-1-carboxylate.

(4) The title compound was obtained by the method described in Example 001-(3) or a method equivalent thereto using (azetidin-3-yloxy) (methyl)amine hydrochloride obtained by the methods described in Examples 010-(1) and 001-(2) or methods equivalent thereto from crude tert-butyl 3-({[(tert-butoxy)carbonyl]amino}oxy)azetidine-1-carboxylate obtained in the preceding section, and 7-chloro-6-fluoro-4-oxo-1-(1,3-thiazol-2-yl)-1,4-dihydro-1,8-naphthyridine-3-carboxylic acid obtained in Reference Example 003-(2).

1H-NMR (DMSO-d6): δ 2.61 (3H, s), 4.17-4.77 (5H, m), 7.78 (1H, d, J=3.5 Hz), 7.83 (1H, d, J=3.5 Hz), 8.03 (1H, d, J=11.5 Hz), 9.76 (1H, s), 14.75 (1H, brs)

Example 553

Compound 553

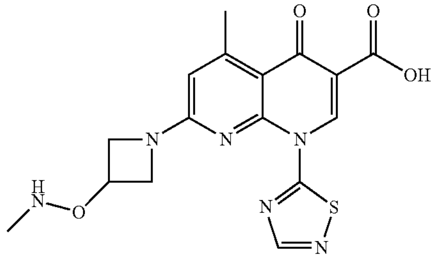

5-Methyl-7-{3-[(methylamino)oxy]azetidin-1-yl}-4-oxo-1-(1,2,4-thiadiazol-5-yl)-1,4-dihydro-1,8-naphthyridine-3-carboxylic acid The title compound was obtained by the method described in Example 001-(3) or a method equivalent thereto using (azetidin-3-yloxy) (methyl)amine hydrochloride obtained in Example 552-(4), and 7-chloro-5-methyl-4-oxo-1-(1,2,4-thiadiazol-5-yl)-1,4-dihydro-1,8-naphthyridine-3-carboxylic acid obtained in Reference Example 002-(2).

1H-NMR (DMSO-d6): δ 2.63 (3H, s), 2.69 (3H, s), 4.14-4.55 (4H, m), 4.72-4.77 (1H, m), 6.48 (1H, s), 8.79 (1H, s), 9.61 (1H, s), 14.99 (1H, brs)

Example 554

Compound 554

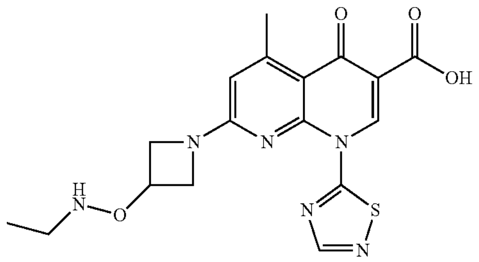

7-{3-[(Ethylamino)oxy]azetidin-1-yl}-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and (azetidin-3-yloxy) (ethyl)amine hydrochloride obtained from crude tert-butyl 3-({[(tert-butoxy) carbonyl]amino})oxy) azetidine-1-carboxylate obtained in Example 552-(3) by the method described in Example 010-(1) and Example 001-(2) or a method equivalent thereto by the method described in Example 001-(3) or a method equivalent thereto.

1H-NMR (DMSO-d6): δ 1.03 (3H, t, J=7.0 Hz), 2.74 (3H, s), 2.89 (2H, q, J=7.0 Hz), 4.07-4.62 (4H, m), 4.70-4.78 (1H, m), 6.54 (1H, s), 6.87 (1H, brs), 8.80 (1H, s), 9.69 (1H, s), 15.05 (1H, brs)

Example 555

Compound 555

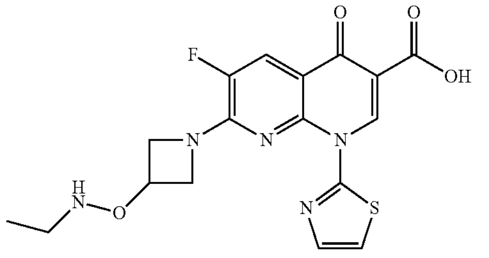

7-{3-[(Ethylamino)oxy]azetidin-1-yl}-6-fluoro-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and (azetidin-3-yloxy) (ethyl)amine hydrochloride obtained in Example 554 by the method described in Example 001-(3) or a method equivalent thereto.

1H-NMR (DMSO-d6): δ 1.02 (3H, t, J=7.0 Hz), 2.88 (2H, q, J=7.0 Hz), 4.20-4.76 (5H, m), 7.80 (1H, d, J=3.5 Hz), 7.85 (1H, d, J=3.5 Hz), 8.07 (1H, d, J=11.5 Hz), 9.79 (1H, s), 14.78 (1H, brs)

Example 556

Compound 556

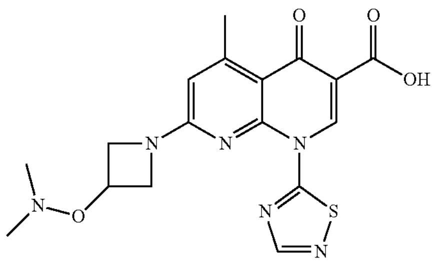

7-{3-[(Dimethylamino)oxy]azetidin-1-yl}-5-methyl-4-oxo-1-(1,2,4-thiadiazol-5-yl)-1,4-dihydro-1,8-naphthyridine-3-carboxylic acid (1) To a solution of tert-butyl 3-(aminooxy)azetidine-1-carboxylate (188 mg) obtained in Example 552-(2) in N,N-dimethylformamide (5 mL) were added potassium carbonate (415 mg) and methyl iodide (160 μL), and the mixture was stirred at room temperature for 16 hours. To the reaction solution was added water, and the mixture was extracted with a mixed solution of n-hexane and ethyl acetate. The organic layer was washed with brine, dried over sodium sulfate, and concentrated. The residue was subjected to silica gel column chromatography (eluent: ethyl acetate/n-hexane) to obtain crude tert-butyl 3-[(dimethylamino)oxy]azetidine-1-carboxylate.

(2) The title compound was obtained by the method described in Example 001-(3) or a method equivalent thereto using (azetidin-3-yloxy)dimethylamine hydrochloride obtained by the method described in Example 001-(2) or a method equivalent thereto from crude tert-butyl 3-[(dimethylamino)oxy]azetidine-1-carboxylate obtained in the preceding section, and 7-chloro-5-methyl-4-oxo-1-(1,2,4-thiadiazol-5-yl)-1,4-dihydro-1,8-naphthyridine-3-carboxylic acid obtained in Reference Example 002-(2).

1H-NMR (DMSO-d6): δ 2.61 (6H, s), 2.75 (3H, s), 4.05-4.69 (4H, m), 4.76-4.86 (1H, m), 6.56 (1H, s), 8.81 (1H, s), 9.72 (1H, s), 15.06 (1H, s)

Example 557

Compound 557

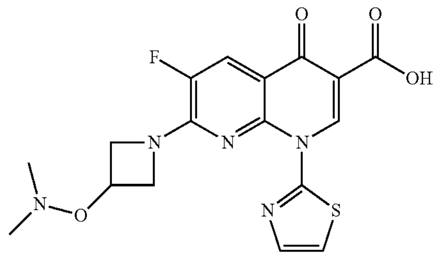

7-{3-[(Dimethylamino)oxy]azetidin-1-yl}-6-fluoro-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and (azetidin-3-yloxy)dimethylamine hydrochloride obtained in Example 556-(2) by the method described in Example 001-(3) or a method equivalent thereto.

1H-NMR (DMSO-d6): δ 2.60 (6H, s), 4.15-4.76 (4H, m), 4.78-4.84 (1H, m), 7.79 (1H, d, J=3.5 Hz), 7.85 (1H, d, J=3.5 Hz), 8.10 (1H, d, J=11.5 Hz), 9.81 (1H, S), 14.78 (1H, s)

Example 558

Compound 558

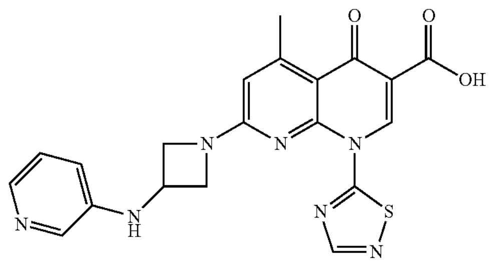

5-Methyl-4-oxo-7-{3-[(pyridin-3-yl)amino]azetidin-1-yl}-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-2-yl)-1,4-dihydro-1,8-naphthyridine-3-carboxylic acid obtained in Reference Example 002-(2) and N-(azetidin-3-yl)pyridin-3-amine hydrochloride obtained from 3-bromopyridine and 1-(diphenylmethyl)azetidin-3-amine by the method described in Example 022-(1) and Example 002-(2) or a method equivalent thereto by the method described in Example 001-(3) or a method equivalent thereto.

1H-NMR (DMSO-d6): δ 2.80 (3H, s), 4.33-4.96 (5H, m), 6.63 (1H, s), 7.63-7.89 (1H, brs), 8.10-8.18 (2H, m), 8.83 (1H, s), 9.74 (1H, s)

Example 559

Compound 559

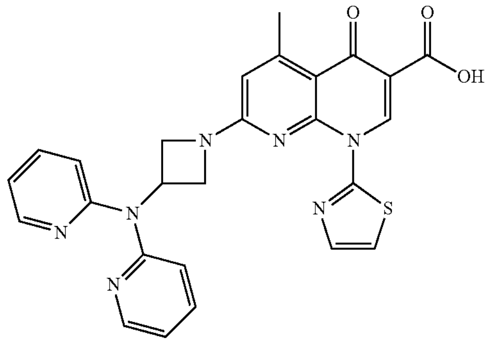

7-{3-[Bis(pyridin-2-yl)amino]azetidin-1-yl}-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-(azetidin-3-yl)-N-(pyridin-2-yl)pyridin-2-amine hydrochloride obtained from 2-bromopyridine and tert-butyl 3-aminoazetidine-1-carboxylate by the method described in Example 022-(1) and Example 001-(2) or a method equivalent thereto by the method described in Example 022-(2) or a method equivalent thereto.

Property: brown solid;

ESI-MS (m/z): 512 [M+H]+

Example 560

Compound 560

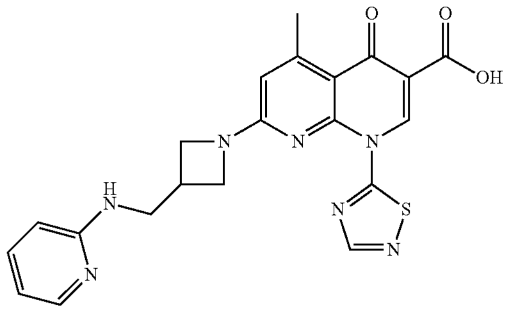

5-Methyl-4-oxo-7-(3-{([(pyridin-2-yl)amino] methyl}azetidin-1-yl)-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-(azetidin-3-ylmethyl)pyridin-2-amine hydrochloride obtained from 2-bromopyridine and tert-butyl 3-(aminomethyl)azetidine-1-carboxylate by the method described in Example 022-(1) and Example 001-(2) or a method equivalent thereto by the method described in Example 001-(3) or a method equivalent thereto.

1H-NMR (DMSO-d6): δ 2.76 (3H, s), 3.09-3.18 (1H, m), 3.54-4.60 (7H, m), 6.49-6.67 (2H, m), 6.56 (1H, s), 7.39-7.56 (1H, m), 7.94-8.00 (1H, m), 8.82 (1H, s), 9.74 (1H, s), 15.13 (1H, brs)

Example 561

Compound 561

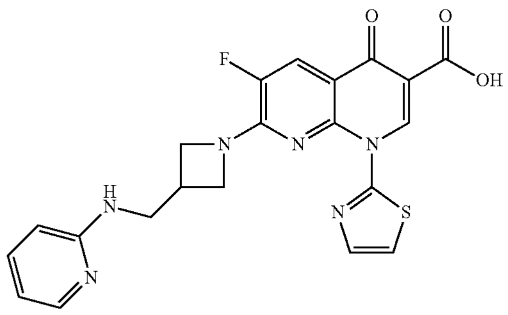

6-Fluoro-4-oxo-7-(3-{[(pyridin-2-yl)amino] methyl}azetidin-1-yl)-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-(azetidin-3-ylmethyl)pyridin-2-amine hydrochloride obtained in Example 560 by the method described in Example 001-(3) or a method equivalent thereto.

1H-NMR (DMSO-d6): δ 3.10-3.21 (1H, m), 3.61-3.69 (2H, m), 3.69-3.76 (1H, m), 4.11-4.78 (4H, m), 6.53-6.79 (2H, m), 7.48-7.64 (1H, m), 7.82 (1H, d, J=3.5 Hz), 7.87 (1H, d, J=3.5 Hz), 7.93-7.98 (1H, m), 8.09 (1H, d, J=11.5 Hz), 9.80 (1H, s), 14.81 (1H, brs)

Example 562

Compound 562

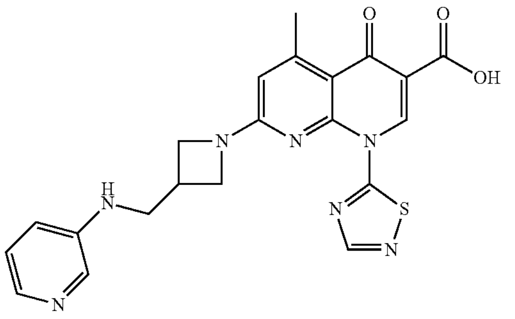

5-Methyl-4-oxo-7-(3-{[(pyridin-3-yl)amino] methyl}azetidin-1-yl)-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) N-(azetidin-3-ylmethyl)pyridin-3-amine hydrochloride obtained from 3-bromopyridine and tert-butyl 3-(aminomethyl)azetidine-1-carboxylate by the method described in Example 022-(1) and Example 001-(2) or a method equivalent thereto by the method described in Example 001-(3) or a method equivalent thereto.

1H-NMR (DMSO-d6): δ 2.77 (3H, s), 3.09-3.19 (1H, m), 3.40-3.47 (2H, m), 3.98-4.05 (1H, m), 4.19-4.26 (1H, m), 4.35-4.42 (1H, m), 4.51-4.60 (1H, m), 6.28 (1H, brs), 6.57 (1H, s), 7.05-7.11 (1H, m), 7.15-7.21 (1H, m), 7.79-7.83 (1H, m), 8.02-8.05 (1H, m), 8.82 (1H, s), 9.74 (1H, a), 15.13 (1H, s)

Example 563

Compound 563

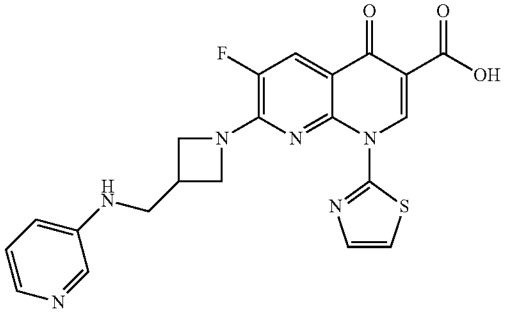

6-Fluoro-4-oxo-7-(3-{[(pyridin-3-yl)amino] methyl}azetidin-1-yl)-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-(azetidin-3-ylmethyl)pyridin-3-amine hydrochloride obtained in Example 562 by the method described in Example 001-(3) or a method equivalent thereto.

1H-NMR (DMSO-d6): δ 3.10-3.19 (1H, m), 3.42-3.49 (2H, m), 4.10-4.39 (2H, m), 4.42-4.77 (2H, m), 6.38 (1H, brs), 7.11-7.18 (1H, m), 7.21-7.28 (1H, m), 7.79-7.89 (3H, m), 8.01-8.04 (1H, m), 8.07 (1H, d, J=11.5 Hz), 9.79 (1H, s), 14.82 (1H, brs)

Example 564

Compound 564

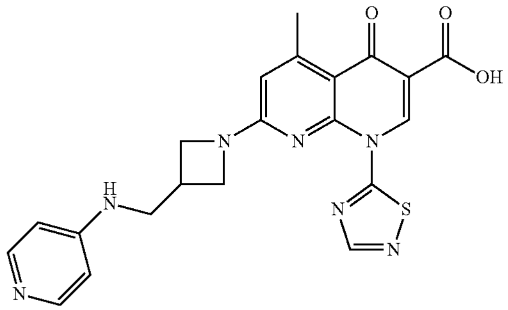

5-Methyl-4-oxo-7-(3-{[(pyridin-4-yl)amino] methyl}azetidin-1-yl)-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-(azetidin-3-ylmethyl)pyridin-4-amine hydrochloride obtained from 4-bromopyridine and tert-butyl 3-(aminomethyl)azetidine-1-carboxylate by the method described in Example 022-(l) and Example 001-(2) or a method equivalent thereto by the method described in Example 001-(3) or a method equivalent thereto.

1H-NMR (DMSO-d6): δ 2.73 (3H, s), 3.05-3.14 (1H, m), 3.41-3.53 (2H, m), 3.92-4.00 (1H, m), 4.14-4.22 (1H, m), 4.30-4.39 (1H, m), 4.47-4.56 (1H, m), 6.53 (1H, d, J=1.0 Hz), 6.61 (1H, dd, J=6.0, 2.0 Hz), 6.75 (1H, d, J=2.0 Hz), 7.12-7.19 (1H, m), 7.80 (1H, d, J=6.0 Hz), 8.80 (1H, s), 9.68 (1H, s), 15.08 (1H, brs)

Example 565

Compound 565

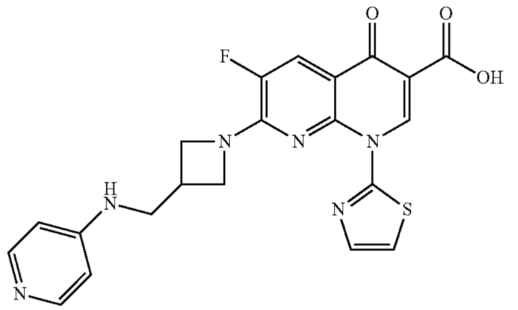

6-Fluoro-4-oxo-7-(3-{[(pyridin-4-yl)amino]methyl}azetidin-1-yl)-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-(azetidin-3-ylmethyl)pyridin-4-amine hydrochloride obtained in Example 564 by the method described in Example 001-(3) or a method equivalent thereto.

1H-NMR (DMSO-d6): δ 3.09-3.19 (1H, m), 3.57-3.65 (2H, m), 4.14-4.40 (2H, m), 4.46-4.78 (2H, m), 6.81 (2H, d, J=6.5 Hz), 7.83 (1H, d, J=3.5 Hz), 7.88 (1H, d, J=3.5 Hz), 8.11 (1H, d, J=11.5 Hz), 8.14 (2H, d, J=6.5 Hz), 9.81 (1H, s), 14.80 (1H, brs)

Example 566

Compound 566

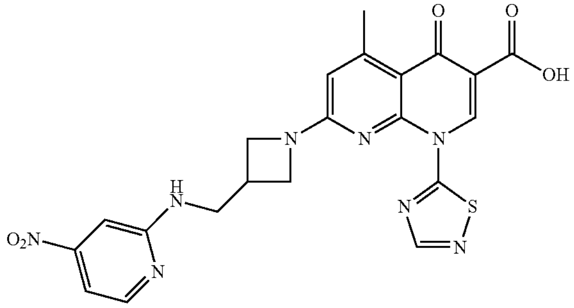

5-Methyl-7-(3-{[(4-nitropyridin-2-yl)amino]methyl}azetidin-1-yl)-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-(azetidin-3-ylmethyl)-4-nitropyridin-2-amine hydrochloride obtained from 2-bromo-4-nitropyridine and tert-butyl 3-(aminomethyl)azetidine-1-carboxylate by the method described in Example 022-(1) and Example 001-(2) or a method equivalent thereto by the method described in Example 001-(3) or a method equivalent thereto.

1H-NMR (DMSO-d6): δ 2.73 (3H, s), 3.05-3.14 (1H, m), 3.41-3.53 (2H, m), 3.92-4.00 (1H, m), 4.14-4.22 (1H, m), 4.30-4.39 (1H, m), 4.47-4.56 (1H, m), 6.53 (1H, d, J=1.0 Hz), 6.61 (1H, dd, J=6.0, 2.0 Hz), 6.75 (1H, d, J=2.0 Hz), 7.12-7.19 (1H, m), 7.80 (1H, d, J=6.0 Hz), 8.80 (1H, s), 9.68 (1H, s), 15.08 (1H, brs)

Example 567

Compound 567

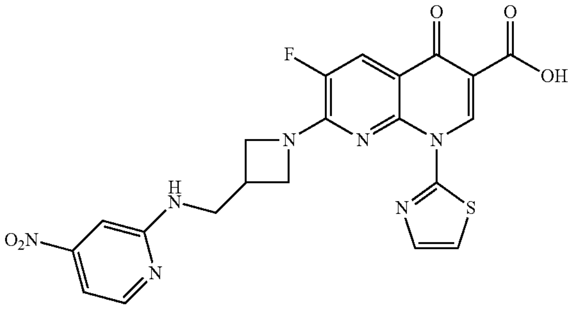

6-Fluoro-7-(3-{[(4-nitropyridin-2-yl)amino]methyl}azetidin-1-yl)-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-(azetidin-3-ylmethyl)-4-nitropyridin-2-amine hydrochloride obtained in Example 566 by the method described in Example 001-(3) or a method equivalent thereto.

1H-NMR (DMSO-d6): δ 3.05-3.16 (1H, m), 3.47-3.53 (2H, m), 4.04-4.38 (2H, m), 4.42-4.76 (2H, m), 6.60-6.66 (1H, m), 6.80 (1H, s), 7.39 (1H, brs), 7.82 (1H, d, J=3.5 Hz), 7.82-7.85 (1H, m), 7.86 (1H, d, J=3.5 Hz), 8.07 (1H, d, J=11.5 Hz), 9.79 (1H, s), 14.81 (1H, brs)

Example 568

Compound 568

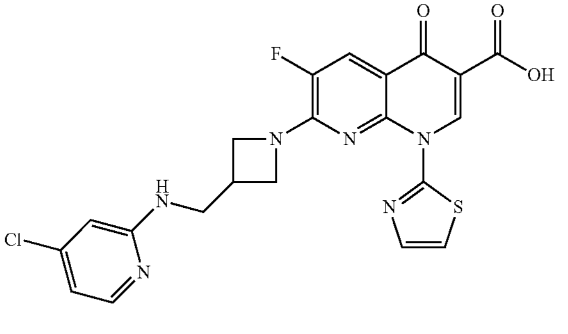

7-(3-{[(4-Chloropyridin-2-yl)amino]methyl}azetidin-1-yl)-6-fluoro-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-(azetidin-3-ylmethyl)-4-chloropyridin-2-amine hydrochloride obtained from 2-bromo-4-chloropyridin and tert-butyl 3-(aminomethyl)azetidine-1-carboxylate by the method described in Example 022-(1) and Example 001-(2) or a method equivalent thereto by the method described in Example 001-(3) or a method equivalent thereto.

1H-NMR (DMSO-d6): δ 3.06-3.17 (1H, m), 3.57-3.66 (2H, m), 4.08-4.39 (2H, m), 4.42-4.75 (2H, m), 6.53-6.61 (2H, m), 7.18 (1H, brs), 7.80 (1H, d, J=3.5 Hz), 7.85 (1H, d, J=3.5 Hz), 7.94 (1H, d, J=6.0 Hz), 8.05 (1H, d, J=11.5 Hz), 9.79 (1H, s), 14.80 (1H, brs)

Example 569

Compound 569

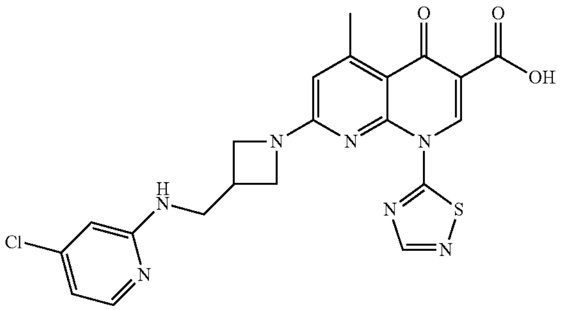

7-(3-{[(4-Chloropyridin-2-yl)amino]methyl}azetidin-1-yl)-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-(azetidin-3-ylmethyl)-4-chloropyridin-2-amine hydrochloride obtained in Example 568 by the method described in Example 001-(3) or a method equivalent thereto.

1H-NMR (DMSO-d6): δ 2.72 (3H, s), 3.06-3.16 (1H, m), 3.54-3.73 (2H, m), 3.93-4.05 (1H, m), 4.16-4.26 (1H, m), 4.29-4.38 (1H, m), 4.43-4.53 (1H, m), 6.50 (1H, d, J=1.0 Hz), 6.57-6.66 (2H, m), 7.29 (1H, brs), 7.95 (1H, d, J=5.5 Hz), 8.80 (1H, s), 9.67 (1H, s), 15.08 (1H, brs)

Example 570

Compound 570

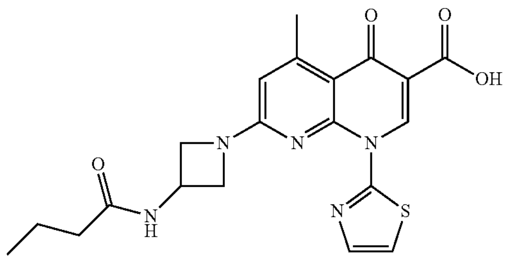

7-(3-Butanamidoazetidin-1-yl)-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-(azetidin-3-yl)butaneamide hydrochloride obtained from butanoyl chloride by the method described in Example 002-(1) and Example 001-(2) or a method equivalent thereto by the method described in Example 002-(3) or a method equivalent thereto.

Property: orange solid;

ESI-MS (m/z): 428 [M+H]+

Example 571

Compound 571

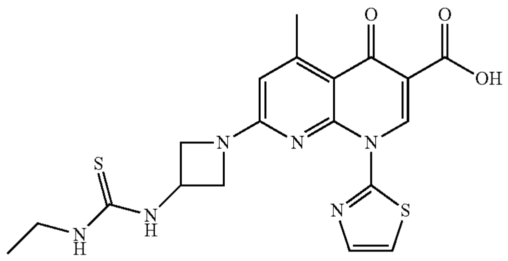

7-{3-[(Ethylcarbamothioyl)amino]azetidin-1-yl}-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and (azetidin-3-yl)thiourea hydrochloride obtained from ethyl isothiocyanate by the method described in Example 025-(1) and Example 001-(2) or a method equivalent thereto by the method described in Example 025-(2) or a method equivalent thereto.

Property: orange solid;

Melting point: 220-224° C.

Example 572

Compound 572

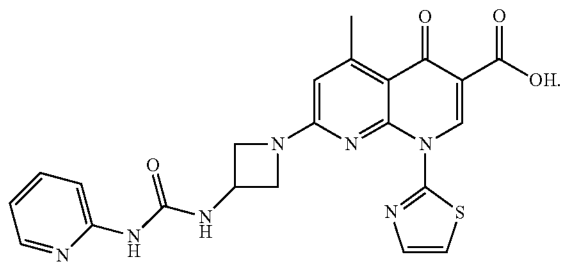

5-Methyl-4-oxo-7-(3-{[(pyridin-2-yl)carbamoyl]amino}azetidin-1-yl)-1-(1,3-thiazol-2-yl)-1,4-dihydro-1,8-naphthyridine-3-carboxylic acid (1) A solution of 1-[(tert-butoxy)carbonyl]azetidine-3-carboxylic acid (201 mg), diphenylphosphoryl azide (216 μL), and triethylamine (139 μL) in toluene (5 mL) was stirred at 100° C. for 1 hour. The reaction mixture was cooled down to room temperature. Pyridin-2-amine (94 mg) was added thereto, and the mixture was stirred at 60° C. for 18 hours. The reaction solution was concentrated, and the residue was purified by silica gel column chromatography (eluent: ethyl acetate/n-hexane) to obtain 117 mg of tert-butyl 3-{[(pyridin-2-yl)carbamoyl]amino}azetidine-1-carboxylate.

1H-NMR (CDCl3): δ 1.47 (9H, s), 3.93 (2H, dd, J=9.0, 5.5 Hz), 4.31 (2H, t, J=9.0 Hz), 4.64-4.74 (1H, m), 6.68-6.78 (1H, m), 6.89-6.97 (1H, m), 7.57-7.67 (1H, m), 8.02 (1H, brs), 8.19-8.26 (1H, m), 9.98 (1H, brs)

(2) The title compound was obtained by the method described in Example 014 or a method equivalent thereto using 3-(azetidin-3-yl)-1-(pyridin-2-yl)urea hydrochloride obtained by the method described in Example 001-(2) or a method equivalent thereto from tert-butyl 3-{[(pyridin-2-yl)carbamoyl]amino}azetidine-1-carboxylate obtained in the preceding section, and 7-chloro-5-methyl-4-oxo-1-(1,3-thiazol-2-yl)-1,4-dihydro-1,8-naphthyridine-3-carboxylic acid obtained in Reference Example 001-(2).

1H-NMR (DMSO-d6): δ 2.76 (3H, s), 4.10-4.35 (2H, m), 4.49-4.70 (2H, m), 4.74-4.82 (1H, m), 6.53 (1H, s), 6.94-6.98 (1H, m), 7.35 (1H, d, J=8.5 Hz), 7.68-7.73 (1H, m), 7.74 (1H, d, J=3.5 Hz), 7.82 (1H, d, J=3.5 Hz), 8.20-8.22 (1H, m), 8.88 (1H, brs), 9.44 (1H, brs), 9.82 (1H, s), 15.39 (1H, brs)

Example 573

Compound 573

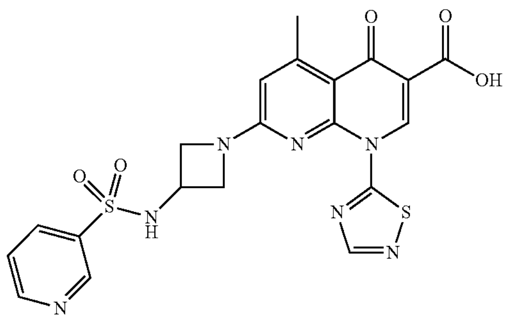

5-Methyl-4-oxo-7-[3-(pyridine-3-sulfonamido)azetidin-1-yl]-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-2-yl)-1,4-dihydro-1,8-naphthyridine-3-carboxylic acid obtained in Reference Example 002-(2) and N-(azetidin-3-yl)pyridine-3-sulfonamide hydrochloride obtained from pyridine-3-sulfonyl chloride by the method described in Example 023-(1) and Example 001-(2) or a method equivalent thereto by the method described in Example 019 or a method equivalent thereto.

1H-NMR (DMSO-d6): δ 2.75 (3H, s), 3.94-4.06 (2H, m), 4.37-4.63 (3H, m), 6.57 (1H, s), 7.70-7.74 (1H, m), 8.25-8.29 (1H, m), 8.82 (1H, s), 8.91 (1H, dd, J=1.6, 4.9 Hz), 9.03 (1H, d, J=1.8 Hz), 9.74 (1H, s), 15.31 (1H, brs)

Example 574

Compound 574

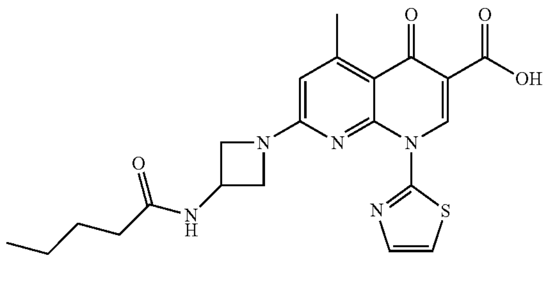

5-Methyl-4-oxo-7-(3-pentanamidoazetidin-1-yl)-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-(azetidin-3-yl)pentaneamide acetate obtained from pentanoyl chloride by the method described in Example 023-(1) and Example 002-(2) or a method equivalent thereto by the method described in Example 002-(3) or a method equivalent thereto.

1H-NMR (DMSO-d6): δ 0.87 (3H, t, J=7.5 Hz), 1.22-0.32 (2H, m), 1.46-1.54 (2H, m), 2.12 (2H, t, J=7.0 Hz), 2.79 (3H, s), 3.98-4.25 (2H, m), 4.46-4.65 (2H, m), 4.65-4.73 (1H, m), 6.57 (1H, s), 7.77 (1H, d, J=3.5 Hz), 7.84 (1H, d, J=3.5 Hz), 8.58 (1H, brd, J=6.5 Hz), 9.85 (1H, s)

Example 575

Compound 575

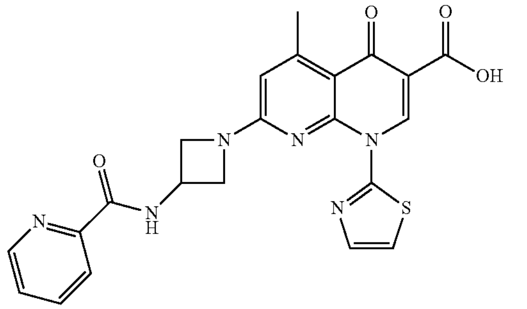

5-Methyl-4-oxo-7-[3-(pyridine-2-amido) azetidin-1-yl]-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-(azetidin-3-yl)pyridine-2-carboxamide acetate obtained from pyridine-2-carbonyl chloride by the method described in Example 023-(1) and Example 002-(2) or a method equivalent thereto by the method described in Example 014 or a method equivalent thereto.

1H-NMR (DMSO-d6): δ 2.79 (3H, s), 4.34-4.74 (4H, m), 4.96-5.08 (1H, m), 6.56-6.57 (1H, m), 7.63 (1H, ddd, J=7.5, 5.0, 1.5 Hz), 7.74 (1H, d, J=3.5 Hz), 7.83 (1H, d, J=3.5 Hz), 8.01 (1H, ddd, J=7.5, 7.5, 1.5 Hz), 8.06 (1H, ddd, J=7.5, 1.5, 1.0 Hz), 8.67 (1H, ddd, 5.0, 1.5, 1.0), 9.64 (1H, d, J=8.0 Hz), 9.85 (1H, s), 15.32 (1H, brs)

Example 576

Compound 576

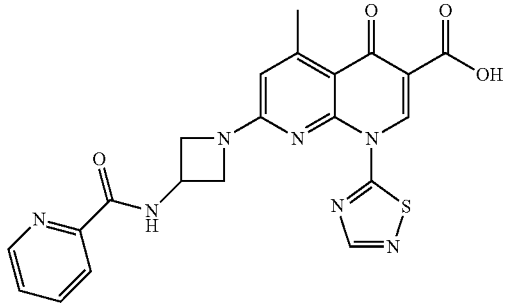

5-Methyl-4-oxo-7-[3-(pyridine-2-amido)azetidin-1-yl]-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-(azetidin-3-yl)pyridine-2-carboxamide hydrochloride obtained in Example 575 by the method described in Example 002-(3) or a method equivalent thereto.

1H-NMR (DMSO-d6): δ 2.74 (3H, s), 4.22-4.86 (4H, m), 4.98-5.06 (1H, m), 6.42 (1H, s), 7.63 (1H, ddd, J=7.5, 4.5, 1.5 Hz), 8.00-8.04 (1H, m), 8.05-8.09 (1H, m), 8.59 (1H, brs), 8.67 (1H, d, J=4.5 Hz), 8.71 (1H, s), 9.65 (1H, d, J=8.0 Hz)

Example 577

Compound 577

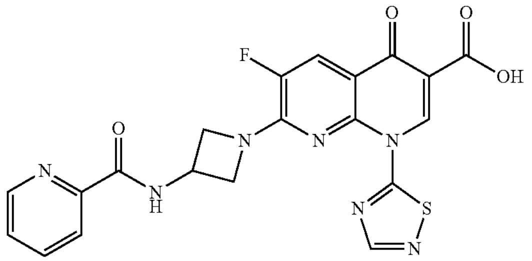

6-Fluoro-4-oxo-7-[3-(pyridine-2-amido)azetidin-1-yl]-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and N-(azetidin-3-yl)pyridine-2-carboxamide hydrochloride obtained in Example 575 by the method described in Example 002-(3) or a method equivalent thereto.

1H-NMR (DMSO-d6): δ 4.62-5.00 (4H, m), 5.02-5.11 (1H, m), 7.64 (1H, ddd, J=7.5, 4.5, 1.5 Hz), 8.01-8.05 (1H, m), 8.06-8.09 (1H, m), 8.17 (1H, d, J=11.5 Hz), 8.68 (1H, d, J=4.5 Hz), 8.85 (1H, s), 9.67 (1H, d, J=7.5 Hz), 9.75 (1H, s), 14.49 (1H, brs)

Example 578

Compound 578

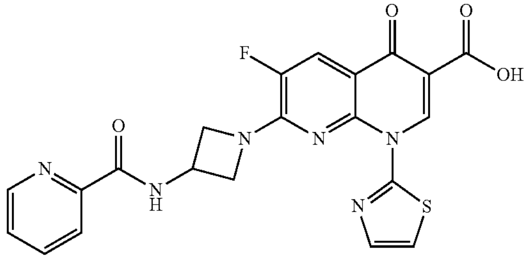

6-Fluoro-4-oxo-7-[3-(pyridine-2-amido)azetidin-1-yl]-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-(azetidin-3-yl)pyridine-2-carboxamide hydrochloride obtained in Example 575 by the method described in Example 002-(3) or a method equivalent thereto.

1H-NMR (DMSO-d6): δ 4.46-4.97 (4H, m), 5.03-5.12 (1H, m), 7.63 (1H, ddd, J=7.5, 5.0, 1.5 Hz), 7.78 (1H, d, J=3.5 Hz), 7.86 (1H, d, J=3.5 Hz), 8.00-8.05 (1H, m), 8.05-8.09 (1H, m), 8.14 (1H, d, J=11.5 Hz), 8.68 (1H, d, J=4.5 Hz), 9.66 (1H, d, J=8.0 Hz), 9.83 (1H, s), 14.74 (1H, brs)

Example 579

Compound 579

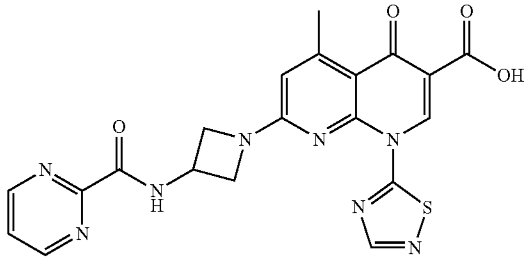

5-Methyl-4-oxo-7-[3-(pyrimidine-2-amido)azetidin-1-yl]-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-(azetidin-3-yl)pyrimidine-2-carboxamide hydrochloride obtained in Example 024-(2) by the method described in Example 002-(3) or a method equivalent thereto.

1H-NMR (DMSO-d6): δ 2.70 (3H, s), 4.33-4.43 (1H, m), 4.57-4.72 (2H, m), 4.75-4.84 (1H, m), 4.97-5.06 (1H, m), 6.62 (1H, s), 7.71 (1H, dd, J=5.0, 5.0 Hz), 8.82 (1H, s), 8.99 (2H, d, J=5.0 Hz), 9.74 (1H, s), 9.76 (1H, d, J=7.0 Hz), 15.10 (1H, s)

Example 580

Compound 580

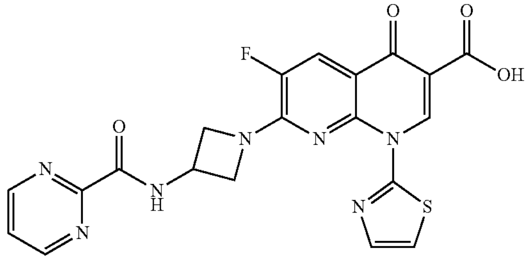

6-Fluoro-4-oxo-7-[3-(pyrimidine-2-amido)azetidin-1-yl]-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-(azetidin-3-yl)pyrimidine-2-carboxamide hydrochloride obtained in Example 024-(2) by the method described in Example 002-(3) or a method equivalent thereto.

1H-NMR (DMSO-d6): δ 4.43-4.98 (4H, m), 5.01-5.10 (1H, m), 7.71 (1H, dd, J=5.0, 5.0 Hz), 7.79 (1H, d, J=3.5 Hz), 7.86 (1H, d, J=3.5 Hz), 8.14 (1H, d, J=11.5 Hz), 8.99 (2H, d, J=5.0 Hz), 9.76 (1H, d, J=7.5 Hz), 9.83 (1H, s), 14.80 (1H, s)

Example 581

Compound 581

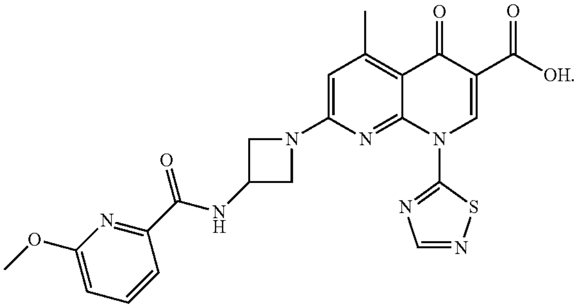

7-[3-(6-Methoxypyridine-2-amido)azetidin-1-yl]-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-(azetidin-3-yl)-6-methoxypyridine-2-carboxamide hydrochloride obtained from 6-methoxy-pyridine-2-carboxylic acid by the method described in Example 024-(1) and Example 001-(2) or a method equivalent thereto by the method described in Example 002-(3) or a method equivalent thereto.

1H-NMR (DMSO-d6): δ 2.76 (3H, s), 4.02 (3H, s), 4.27-4.85 (4H, m), 5.02-5.11 (1H, m), 6.59 (1H, brs), 7.04 (1H, d, J=8.5 Hz), 7.66 (1H, d, J=7.5 Hz), 7.89 (1H, dd, J=8.0, 7.5 Hz), 8.81 (1H, d, J=8.0 Hz), 9.23 (1H, d, J=8.0 Hz), 9.70 (1H, brs), 14.88 (1H, brs)

Example 582

Compound 582

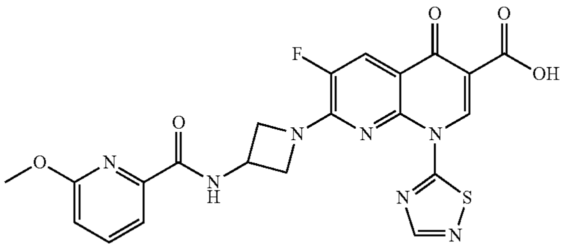

6-Fluoro-7-[3-(6-methoxypyridine-2-amido)azetidin-1-yl]-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and N-(azetidin-3-yl)-6-methoxypyridine-2-carboxamide hydrochloride obtained in Example 581 by the method described in Example 002-(3) or a method equivalent thereto.

1H-NMR (DMSO-d6): δ 4.02 (3H, s), 4.63-4.95 (4H, m), 5.03-5.12 (1H, m), 7.05 (1H, d, J=8.0 Hz), 7.66 (1H, d, J=7.5 Hz), 7.89 (1H, dd, J=8.0, 7.5 Hz), 7.99-8.15 (1H, m), 8.85 (1H, s), 9.21 (1H, d, J=7.0 Hz), 9.70 (1H, brs)

Example 583

Compound 583

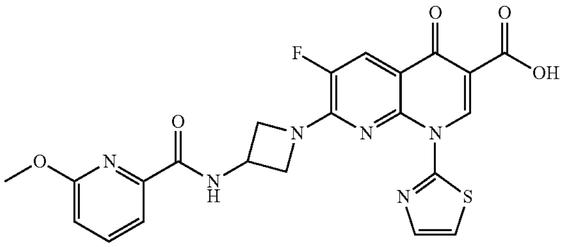

6-Fluoro-7-[3-(6-methoxypyridine-2-amido)azetidin-1-yl]-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-(azetidin-3-yl)-6-methoxypyridine-2-carboxamide hydrochloride obtained in Example 581 by the method described in Example 002-(3) or a method equivalent thereto.

1H-NMR (DMSO-d6): δ 4.01 (3H, s), 4.44-5.02 (4H, m), 5.05-5.12 (1H, m), 7.05 (1H, d, J=8.5 Hz), 7.65 (2H, d, J=7.0 Hz), 7.77 (1H, d, J=3.5 Hz), 8.05-8.20 (2H, m), 9.22 (1H, d, J=8.0 Hz), 9.83 (1H, s), 14.51 (1H, brs)

Example 584

Compound 584

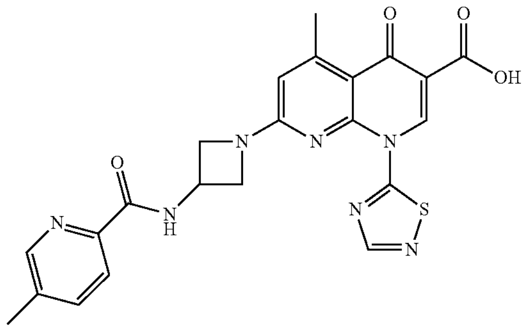

5-Methyl-7-[3-(5-methylpyridine-2-amido)azetidin-1-yl]-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-(azetidin-3-yl)-5-methylpyridine-2-carboxamide hydrochloride obtained from 5-methylpyridine-2-carboxylic acid by the method described in Example 024-(1) and Example 001-(2) or a method equivalent thereto by the method described in Example 002-(3) or a method equivalent thereto.

1H-NMR (DMSO-d6): δ 2.39 (3H, s), 2.77 (3H, s), 4.33-4.81 (4H, m), 4.98-5.06 (1H, m), 6.58 (1H, s), 7.82 (1H, d, J=8.0 Hz), 7.97 (1H, d, J=8.0 Hz), 8.51 (1H, a), 8.81 (1H, s), 9.58 (1H, d, J=7.5 Hz), 9.72 (1H, s), 15.10 (1H, brs)

Example 585

Compound 585

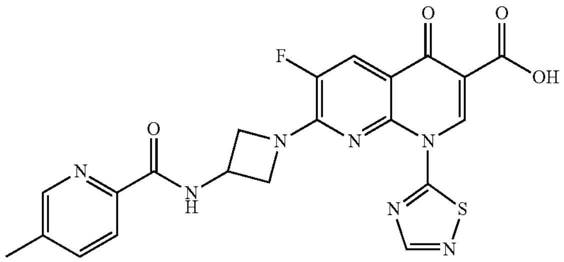

6-Fluoro-7-[3-(5-methylpyridine-2-amido)azetidin-1-yl]-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and N-(azetidin-3-yl)-5-methylpyridine-2-carboxamide hydrochloride obtained in Example 584 by the method described in Example 002-(3) or a method equivalent thereto.

1H-NMR (DMSO-d6): δ 2.39 (3H, s), 4.61-4.95 (4H, m), 4.98-5.08 (1H, m), 6.36 (1H, d, J=8.5 Hz), 7.82 (1H, d, J=8.0 Hz), 7.98 (1H, d, J=11.5 Hz), 8.51 (1H, s), 8.70 (1H, s), 8.98 (1H, d, J=8.5 Hz), 9.55 (1H, d, J=7.5 Hz), 14.50 (1H, brs)

Example 586

Compound 586

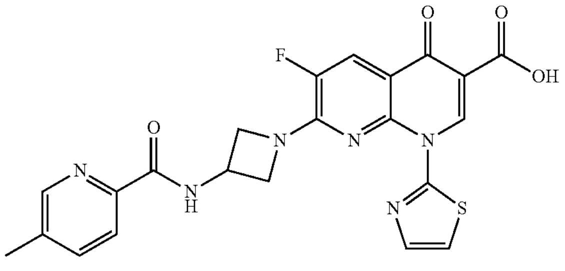

6-Fluoro-7-[3-(5-methylpyridine-2-amido) azetidin-1-yl]-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-(azetidin-3-yl)-5-methylpyridine-2-carboxamide hydrochloride obtained in Example 584 by the method described in Example 002-(3) or a method equivalent thereto.

1H-NMR (DMSO-d6): δ 2.39 (3H, s), 4.48-4.94 (4H, m), 5.01-5.10 (1H, m), 7.78 (1H, d, J=3.5 Hz), 7.82 (1H, dd, J=8.5, 2.0 Hz), 7.86 (1H, d, J=3.5 Hz), 7.96 (1H, d, J=8.0 Hz), 8.14 (1H, d, J=11.5 Hz), 8.51 (1H, s), 9.58 (1H, d, J=8.0 Hz), 9.84 (1H, s), 14.82 (1H, s)

Example 587

Compound 587

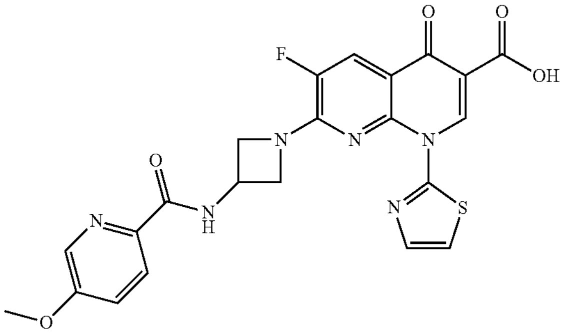

6-Fluoro-7-[3-(5-methoxypyridine-2-amido)azetidin-1-yl]-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-(azetidin-3-yl)-5-methoxypyridine-2-carboxamide hydrochloride obtained from 5-methoxypyridine-2-carboxylic acid by the method described in Example 024-(1) and Example 001-(2) or a method equivalent thereto by the method described in Example 002-(3) or a method equivalent thereto.

1H-NMR (DMSO-d6): δ 3.91 (3H, 8), 4.44-4.94 (4H, m), 5.00-5.09 (1H, m), 7.56 (1H, dd, J=8.5, 3.0 Hz), 7.78 (1H, d, J=3.5 Hz), 7.86 (1H, d, J=3.5 Hz), 8.03 (1H, d, J=8.5 Hz), 8.14 (1H, d, J=11.5 Hz), 8.32 (1H, d, J=3.0 Hz), 9.46 (1H, d, J=8.0 Hz), 9.84 (1H, s), 14.81 (1H, brs)

Example 588

Compound 588

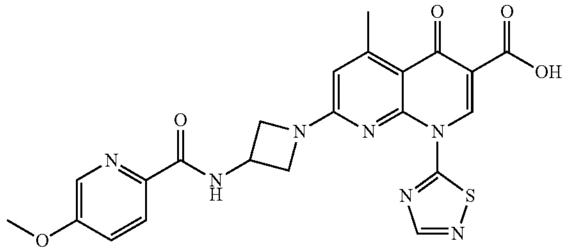

7-[3-(5-Methoxypyridine-2-amido)azetidin-1-yl]-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-(azetidin-3-yl)-5-methoxypyridine-2-carboxamide hydrochloride obtained in Example 587 by the method described in Example 002-(3) or a method equivalent thereto.

1H-NMR (DMSO-d6): δ 2.76 (3H, s), 3.91 (3H, s), 4.33-4.80 (4H, m), 4.96-5.06 (1H, m), 6.58 (1H, s), 7.57 (1H, dd, J=8.5, 3.0 Hz), 8.04 (1H, d, J=8.5 Hz), 8.32 (1H, d, J=3.0 Hz), 8.81 (1H, s), 9.46 (1H, d, J=7.5 Hz), 9.72 (1H, s), 15.09 (1H, brs)

Example 589

Compound 589

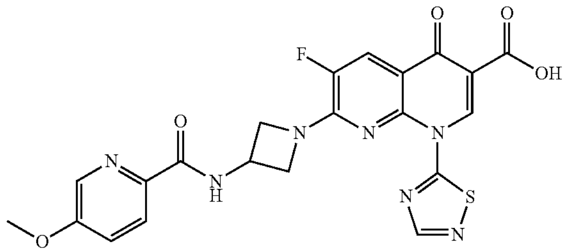

6-Fluoro-7-[3-(5-methoxypyridine-2-amido)azetidin-1-yl]-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8- naphthyridine-3-carboxylic acid obtained in Reference Example 004-(2) and N-(azetidin-3-yl)-5-methoxypyridine-2-carboxamide hydrochloride obtained in Example 587 by the method described in Example 002-(3) or a method equivalent thereto.

1H-NMR (DMSO-d6): δ 3.91 (3H, s), 4.60-4.99 (4H, m), 4.99-5.09 (1H, m), 7.57 (1H, dd, J=8.5, 3.0 Hz), 8.04 (1H, d, J=8.5 Hz), 8.17 (1H, d, J=11.5 Hz), 8.32 (1H, d, J=3.0 Hz), 8.85 (1H, s), 9.47 (1H, d, J=7.5 Hz), 9.75 (1H, s), 14.49 (1H, brs)

Example 590

Compound 590

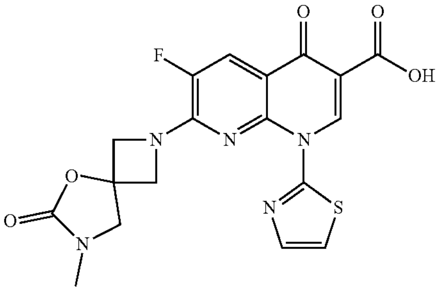

6-Fluoro-7-{7-methyl-6-oxo-5-oxa-2,7-diazaspiro[3.4]octan-2-yl}-4-oxo-1-(1,3-thiazol-2-yl)-1,4-dihydro-1,8-naphthyridine-3-carboxylic acid (1) To a solution of 3-(aminomethyl)-1-(diphenylmethyl)azetidin-3-ol (130 mg) obtained by the method described in WO 2016/42452 A or a method equivalent thereto in methylene chloride (4 mL) were added triethylamine (100 μL) and di-tert-butyl dicarbonate (160 mg), and the mixture was stirred at room temperature for 18 hours. To the reaction solution was added water, and the mixture was extracted with methylene chloride. The organic layer was washed with brine, dried over sodium sulfate, and concentrated. The residue was subjected to silica gel column chromatography (eluent: ethyl acetate/n-hexane) to obtain crude tert-butyl N-{[1-(diphenylmethyl)-3-hydroxyazetidin-3-yl]methyl}carbamate.

(2) To a solution of crude tert-butyl N-{[1-(diphenylmethyl)-3-hydroxyazetidin-3-yl]methyl}carbamate (150 mg) obtained in the preceding section in N,N-dimethylformamide (500 μL) was added 55% sodium hydride (40 mg), and the mixture was stirred at room temperature for 1.5 hours. To the reaction solution was added methyl iodide (100 μL) under ice cooling, and the mixture was stirred at room temperature for 1 day. The reaction solution was neutralized with an aqueous acetic acid solution, and the mixture was extracted with toluene. The organic layer was washed with brine, dried over sodium sulfate, and concentrated. The residue was purified by silica gel column chromatography (eluent: ethyl acetate/n-hexane) to obtain 76 mg of 2-(diphenylmethyl)-7-methyl-5-oxa-2,7-diazaspiro[3.4]octan-6-one.

1H-NMR (CDCl3): δ 2.87 (3H, s), 3.35 (4H, s), 3.75 (2H, s), 4.38 (1H, s), 7.16-7.41 (10H, m)

(3) The title compound was obtained by the method described in Example 001-(3) or a method equivalent thereto using 7-methyl-5-oxa-2,7-diazaspiro[3.4]octan-6-one hydrochloride obtained by the method described in Example 002-(2) or a method equivalent thereto from 2-(diphenylmethyl)-7-methyl-5-oxa-2,7-diazaspiro[3.4]octan-6-one obtained in the preceding section, and 7-chloro-6-fluoro-4-oxo-1-(1,3-thiazol-2-yl)-1,4-dihydro-1,8-naphthyridine-3-carboxylic acid obtained in Reference Example 003-(2).

1H-NMR (DMSO-d6): δ 2.78 (3H, s), 3.89 (2H, s), 4.58-4.88 (4H, m), 7.77-7.80 (1H, d, J=3.5 Hz), 7.85-7.88 (1H, d, J=3.5 Hz), 8.14-8.20 (1H, d, J=11.0 Hz), 9.83 (1H, s), 14.69 (1H, brs)

Example 591

Compound 591

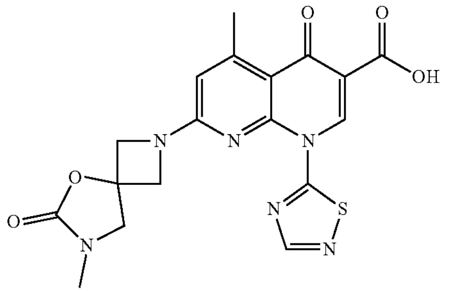

5-Methyl-7-{7-methyl-6-oxo-5-oxa-2,7-diazaspiro[3.4]octan-2-yl}-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and 7-methyl-5-oxa-2,7-diazaspiro[3.4]octan-6-one hydrochloride obtained in Example 590-(3) by the method described in Example 001-(3) or a method equivalent thereto.

1H-NMR (DMSO-d6): δ 2.78 (3H, s), 2.79 (3H, s), 3.91 (2H, brs), 4.33-4.85 (4H, m), 6.63 (1H, s), 8.81 (1H, s), 9.74 (1H, s), 14.96 (1H, brs)

Example 592

Compound 592

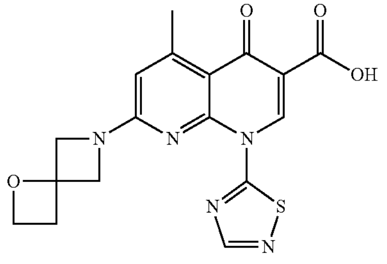

5-Methyl-7-{1-oxa-6-azaspiro[3.3]heptan-6-yl}-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8- naphthyridine-3-carboxylic acid obtained in Reference Example 002-(2) and 1-oxa-6-azaspiro[3.3]heptane trifluoroacetate by the method described in Example 001-(3) or a method equivalent thereto.

1H-NMR (DMSO-d6): δ 2.76 (3H, d, J=1.0 Hz), 2.93-3.02 (2H, m), 4.34-4.80 (6H, m), 6.55 (1H, d, J=1.0 Hz), 8.82 (1H, s), 9.72 (1H, s), 15.05 (1H, brs)

Example 593

Compound 593

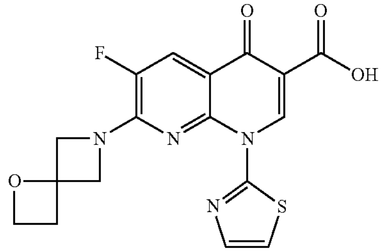

6-Fluoro-7-{1-oxa-6-azaspiro[3.3]heptan-6-yl}-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and 1-oxa-6-azaspiro[3.3]heptane trifluoroacetate by the method described in Example 001-(3) or a method equivalent thereto.

1H-NMR (DMSO-d6): δ 2.97 (2H, t, J=7.5 Hz), 4.48 (2H, t, J=7.5 Hz), 4.54-4.82 (4H, m), 7.80 (1H, d, J=3.5 Hz), 7.86 (1H, d, J=3.5 Hz), 8.09 (1H, d, J=11.3 Hz), 9.80 (1H, s), 14.78 (1H, brs)

Example 594

Compound 594

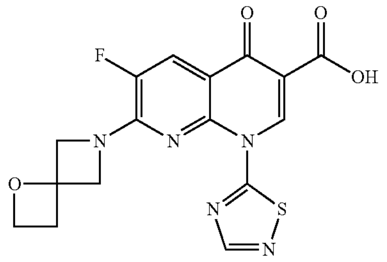

6-Fluoro-7-{1-oxa-6-azaspiro[3.3]heptan-6-yl}-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and 1-oxa-6-azaspiro[3.3]heptane trifluoroacetate by the method described in Example 001-(3) or a method equivalent thereto.

1H-NMR (DMSO-d6): δ 2.92 (2H, t, J=7.5 Hz), 4.45 (2H, t, J=7.5 Hz), 4.38-4.63 (4H, m), 7.96 (1H, d, J=11.6 Hz), 8.44 (1H, s), 13.35 (1H, brs)

Example 595

Compound 595

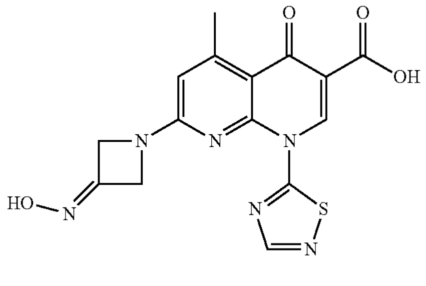

7-[3-(Hydroxyimino)azetidin-1-yl]-5-methyl-4-oxo-1-(1,2,4-thiadiazol-5-yl)-1,4-dihydro-1,8-naphthyridine-3-carboxylic acid (1) To a mixed solution of tert-butyl 3-oxoazetidine-1-carboxylate (510 mg), methanol (4.5 mL) and water (4.5 mL) were added hydroxylamine hydrochloride (250 mg) and sodium carbonate (320 mg), and the mixture was stirred at room temperature for 22 hours. To the reaction solution was added water, and the mixture was extracted with ethyl acetate. The organic layer was washed with water and brine, dried over sodium sulfate, and concentrated to obtain 420 mg of tert-butyl 3-(hydroxyimino)azetidine-1-carboxylate.

1H-NMR (CDCl3): δ 1.47 (9H, s), 4.59-4.64 (2H, m), 4.64-4.66 (2H, m), 7.03 (1H, s)

(2) The title compound was obtained by the method described in Example 008 or a method equivalent thereto using N-(azetidin-3-ylidene)hydroxylamine trifluoroacetate obtained by the method described in Example 001-(2) or a method equivalent thereto from tert-butyl 3-(hydroxyimino)azetidine-1-carboxylate obtained in the preceding section, and 7-chloro-5-methyl-4-oxo-1-(1,2,4-thiadiazol-5-yl)-1,4-dihydro-1,8-naphthyridine-3-carboxylic acid obtained in Reference Example 002-(2).

1H-NMR (DMSO-d6): δ 2.78 (3H, s), 4.81-5.30 (4H, m), 6.69 (1H, s), 8.82 (1H, s), 9.73 (1H, s), 11.26 (1H, s)

Example 596

Compound 596

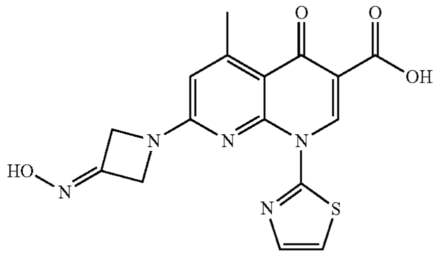

7-[3-(Hydroxyimino)azetidin-1-yl]-5-methyl-4-oxo-1-(1,3-thiazol-2-yl)-1,4-dihydro-1,8-naphthyridine-3-carboxylic acid The title compound was obtained by the method described in Example 008 or a method equivalent thereto using N-(azetidin-3-ylidene)hydroxylamine trifluoroacetate obtained in Example 595-(2), and 7-chloro-5-methyl-4-oxo-1-(1,3-thiazol-2-yl)-1,4-dihydro-1,8-naphthyridine-3-carboxylic acid obtained in Reference Example 001-(2).

1H-NMR (DMSO-d6): δ 2.80 (3H, s), 4.93-5.11 (4H, m), 6.69 (1H, s), 7.77 (1H, d, J=3.5 Hz), 7.84 (1H, d, J=3.5 Hz), 9.85 (1H, s), 11.22 (1H, s)

Example 597

Compound 597

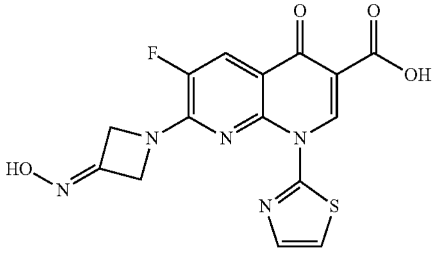

6-Fluoro-7-[3-(hydroxyimino)azetidin-1-yl]-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-(azetidin-3-ylidene)hydroxylamine trifluoroacetate obtained in Example 595-(2) by the method described in Example 008 or a method equivalent thereto.

1H-NMR (DMSO-d6): δ 5.05-5.27 (4H, m), 7.76 (1H, d, J=3.5 Hz), 7.83 (1H, d, J=3.5 Hz), 8.15 (1H, d, J=11.4), 9.84 (1H, s), 11.22 (1H, s)

Example 598

Compound 598

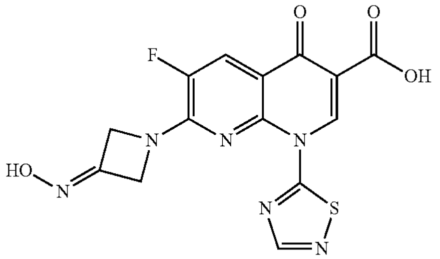

6-Fluoro-7-[3-(hydroxyimino)azetidin-1-yl]-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and N-(azetidin-3-ylidene)hydroxylamine trifluoroacetate obtained in Example 595-(2) by the method described in Example 008 or a method equivalent thereto.

1H-NMR (DMSO-d6): δ 4.81-5.30 (4H, m), 8.21 (1H, d, J=11.0 Hz), 8.82 (1H, s), 9.73 (1H, s), 11.26 (1H, s)

Example 599

Compound 599

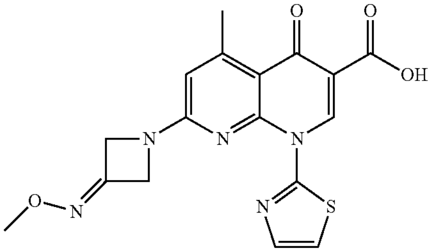

7-[3-(Methoxyimino)azetidin-1-yl]-5-methyl-4-oxo-1-(1,3-thiazol-2-yl)-1,4-dihydro-1,8-naphthyridine-3-carboxylic acid (1) tert-Butyl 3-(methoxyimino)azetidine-1-carboxylate was obtained by the method described in Example 595-(1) or a method equivalent thereto using tert-butyl 3-oxoazetidine-1-carboxylate and O-methylhydroxylamine hydrochloride.

1H-NMR (CDCl3): δ 1.47 (9H, s), 3.87 (3H, s), 4.57-4.62 (4H, m)

(2) The title compound was obtained by the method described in Example 008 or a method equivalent thereto using N-methoxyazetidin-3-imine trifluoroacetate obtained by the method described in Example 001-(2) or a method equivalent thereto from tert-butyl 3-(methoxyimino)azetidine-1-carboxylate obtained in the preceding section, and 7-chloro-5-methyl-4-oxo-1-(1,3-thiazol-2-yl)-1,4-dihydro-1,8-naphthyridine-3-carboxylic acid obtained in Reference Example 001-(2).

1H-NMR (DMSO-d6): δ 2.80 (3H, s), 3.87 (3H, s), 4.95-5.11 (4H, m), 6.69 (1H, s), 7.78 (1H, d, J=3.5 Hz), 7.84 (1H, d, J=3.5 Hz), 9.86 (1H, s), 15.27 (1H, brs)

Example 600

Compound 600

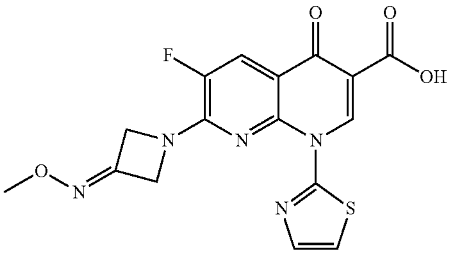

6-Fluoro-7-[3-(methoxyimino)azetidin-1-yl]-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-methoxyazetidin-3-imine trifluoroacetate obtained in Example 599-(2) by the method described in Example 008 or a method equivalent thereto.

1H-NMR (DMSO-d6): δ 3.87 (3H, s), 5.09-5.33 (4H, m), 7.82 (1H, d, J=3.5 Hz), 7.87 (1H, d, J=3.5 Hz), 8.20 (1H, d, J=11.0 Hz), 9.84 (1H, s), 14.6 (1H, brs)

Example 601

Compound 601

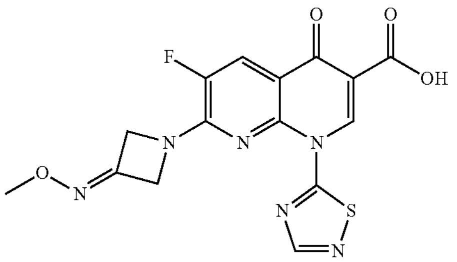

6-Fluoro-7-[3-(methoxyimino)azetidin-1-yl]-4-oxo-1-(1,2,4-thiadiazol-5-yl)-1,4-dihydro-1,8-naphthyridine-3-carboxylic acid The title compound was obtained using 7-chloro-6-fluoro4-oxo-1-(1,2,4-thiadiazol-5-yl)-1,4-dihydro-1,8-naphthyridine-3-carboxylic acid obtained in Reference Example 004-(2) and N-methoxyazetidin-3-imine trifluoroacetate obtained in Example 599-(2) by the method described in Example 008 or a method equivalent thereto.

1H-NMR (DMSO-d6): δ 3.88 (3H, s), 5.30-5.36 (4H, m), 8.26 (1H, d, J=11.0 Hz), 8.87 (1H, s), 9.78 (1H, s), 14.36 (1H, brs)

Example 602

Compound 602

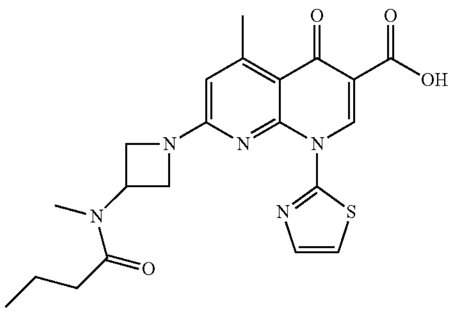

5-Methyl-7-[3-(N-methylbutanamido) azetidin-1-yl]-4-oxo-1-(1,3-thiazol-2-yl)-1,4-dihydro-1,8-naphthyridine-3-carboxylic acid (1) Ethyl 5-methyl-7-[3-(methylamino)azetidin-1-yl]-4-oxo-1-(1,3-thiazol-2-yl)-1,4-dihydro-1,8-naphthyridine-3-carboxylate was obtained by the method described in Example 026-(3) or a method equivalent thereto using ethyl 7-chloro-5-methyl-4-oxo-1-(1,3-thiazol-2-yl)-1,4-dihydro-1,8-naphthyridine-3-carboxylate obtained in Reference Example 001-(1), and N-methylazetidin-3-amine hydrochloride.

1H-NMR (CDCl3): δ 1.41 (3H, J=7.0 Hz), 2.50 (3H, s), 2.87 (3H, s), 3.78-3.85 (1H, m), 3.90-4.03 (2H, m), 4.37-4.49 (4H, m), 6.09 (1H, s), 7.23 (1H, J=3.5 Hz), 7.63 (1H, J=3.5 Hz), 9.78 (1H, s)

(2) To a solution of ethyl 5-methyl-7-[3-(methylamino) azetidin-1-yl]-4-oxo-1-(1,3-thiazol-2-yl)-1,4-dihydro-1,8-naphthyridine-3-carboxylate (15 mg) obtained in the preceding section in methylene chloride (376 μL) were added butanoyl chloride (5 L) and 1,1,3,3-tetramethylguanidine (5 L) under ice cooling, and the mixture was stirred at the same temperature to room temperature for 2 days. The reaction solution was concentrated, and the residue was dispersed in acetonitrile. Then, the solid was collected by filtration to obtain 11 mg of ethyl 5-methyl-7-[3-(N-methylbutanamido) azetidin-1-yl]-4-oxo-1-(1,3-thiazol-2-yl)-1,4-dihydro-1,8-naphthyridine-3-carboxylate.

1H-NMR (CDCl3): δ 1.00 (3H, t, J=7.5 Hz), 1.41 (3H, t, J=7.0 Hz), 1.65-1.74 (2H, m), 2.35 (2H, t, J=7.5 Hz), 2.89 (3H, s), 3.14 (3H, s), 4.18-4.30 (2H, m), 4.32-4.41 (1H, m), 4.41 (2H, q, J=7.0 Hz), 4.46-4.61 (2H, m), 6.11 (1H, s), 7.62-7.73 (1H, m), 9.78 (1H, s)

(3) The title compound was obtained by the method described in Example 028-(2) or a method equivalent thereto from ethyl 5-methyl-7-[3-(N-methylbutanamido) azetidin-1-yl]-4-oxo-1-(1,3-thiazol-2-yl)-1,4-dihydro-1,8-naphthyridine-3-carboxylate obtained in the preceding section.

1H-NMR (DMSO-d6): δ 0.91 (3H, t, J=7.5 Hz), 1.49-1.59 (2H, m), 2.31-2.41 (2H, m), 2.79 (3H, s), 3.07 (3H, s), 4.25-4.70 (4H, m), 5.13-5.43 (1H, m), 6.54-6.59 (1H, m), 7.74 (1H, d, J=3.5 Hz), 7.84 (1H, d, J=3.5 Hz), 9.86 (1H, s)

Example 603

Compound 603

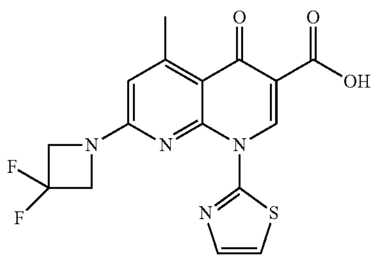

7-(3,3-Difluoroazetidin-1-yl)-5-methyl-4-oxo-1-(1,3-thiazol-2-yl)-1,4-dihydro-1,8-naphthyridine-3-carboxylic acid (1) To a suspension of 3,3-difluoroazetidine hydrochloride (130 mg) in acetonitrile (2 mL) were added N-methylpiperidine (100 μL) and ethyl 7-chloro-5-methyl-4-oxo-1-

(1,3-thiazol-2-yl)-1,4-dihydro-1,8-naphthyridine-3-carboxylate (35 mg) obtained in Reference Example 001-(1), and the mixture was stirred overnight at room temperature. The resulting solid was collected by filtration to obtain crude ethyl 7-(3,3-difluoroazetidin-1-yl)-5-methyl-4-oxo-1-(1,3-thiazol-2-yl)-1,4-dihydro-1,8-naphthyridine-3-carboxylate.

(2) The title compound was obtained by the method described in Example 027-(4) or a method equivalent thereto from crude ethyl 7-(3,3-difluoroazetidin-1-yl)-5-methyl-4-oxo-1-(1,3-thiazol-2-yl)-1,4-dihydro-1,8-naphthyridine-3-carboxylate obtained in the preceding section.

1H-NMR (DMSO-d6): δ 2.82 (3H, s), 4.78 (4H, t, J=12.1 Hz), 6.70 (1H, s), 7.75 (1H, d, J=3.5 Hz), 7.85 (1H, dd, J=3.5, 2.2 Hz), 9.87 (1H, s), 15.16 (, brs)

Example 604

Compound 604

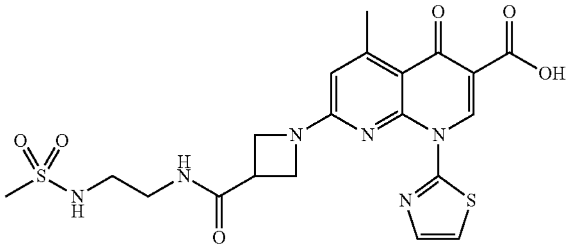

7-{3-[(2-Methanesulfonamidoethyl)carbamoyl]azetidin-1-yl}-5-methyl-4-oxo-1-(1,3-thiazol-2-yl)-1,4-dihydro-1,8-naphthyridine-3-carboxylic acid (1) A mixture of benzyl N-(2-aminoethyl)carbamate hydrochloride (460 mg), triethylamine (700 μL) and methylene chloride (5 mL) was stirred at room temperature for 30 minutes. To the reaction solution was added a solution of methanesulfonyl chloride (185 μL) in methylene chloride (5 mL) under ice cooling, and the mixture was stirred at room temperature for 2 hours. The reaction solution was washed with an aqueous ammonium chloride solution, water and brine and concentrated to obtain 492 mg of benzyl N-(2-methanesulfonamidoethyl)carbamate.

1H-NMR (CDCl3): δ 2.95 (3H, s), 3.21-3.34 (2H, m), 3.35-3.44 (2H, m), 4.68-4.80 (1H, m), 5.03-5.17 (3H, m), 7.29-7.43 (5H, m)

(2) To a solution of benzyl N-(2-methanesulfonamidoethyl)carbamate (492 mg) obtained in the preceding section in methanol (10 mL) were added 10% palladium carbon (50 mg) and a 4 mol/L solution of hydrochloric acid in ethyl acetate (1 mL), and the mixture was hydrogenated overnight at room temperature. The catalyst was filtered off, and the filtrate was concentrated to obtain crude N-(2-aminoethyl)methanesulfonamide.

(3) Crude tert-butyl 3-[(2-methanesulfonamidoethyl)carbamoyl]azetidine-carboxylate was obtained by the method described in Example 005-(1) or a method equivalent thereto from crude N-(2-aminoethyl)methanesulfonamide obtained in the preceding section.

(4) The title compound was obtained by the methods described in Examples 028-(1) and 028-(2) or methods equivalent thereto using crude N-(2-methanesulfonamidoethyl)azetidine-3-carboxamide hydrochloride obtained by the method described in Example 001-(2) or a method equivalent thereto from crude tert-butyl 3-[(2-methanesulfonamidoethyl)carbamoyl]azetidine-1-carboxylate obtained in the preceding section, and ethyl 7-chloro-5-methyl-4-oxo-1-(1,3-thiazol-2-yl)-1,4-dihydro-1,8-naphthyridine-3-carboxylate obtained in Reference Example 001-(1).

1H-NMR (DMSO-d6): δ 2.78 (3H, s), 3.01 (3H, s), 3.49-3.62 (4H, m), 4.22-4.51 (4H, m), 6.55 (1H, s), 7.76 (1H, d, J=4.4 Hz), 7.85 (1H, d, J=4.4 Hz), 8.43 (1H, t, J=5.9 Hz), 9.85 (1H, s), 15.39 (1H, brs)

Example 605

Compound 605

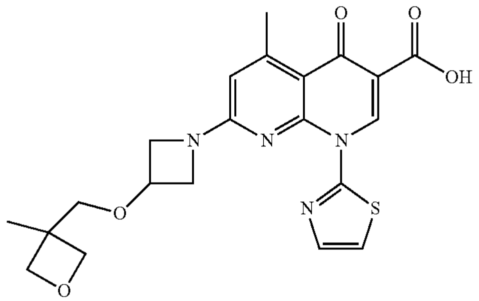

5-Methyl-7-{3-[(3-methyloxetan-3-yl)methoxy]azetidin-1-yl}-4-oxo-1-(1,3-thiazol-2-yl)-1,4-dihydro-1,8-naphthyridine-3-carboxylic acid The title compound (9 mg) was obtained using ethyl 7-chloro-5-methyl-4-oxo-1-(1,3-thiazol-2-yl)-1,4-dihydro-1,8-naphthyridine-3-carboxylate obtained in Example 001-(1) and 3-[(3-methyloxetan-3-yl)methoxy]azetidine hydrochloride obtained from (3-methyloxetan-3-yl)methanol by the method described in Example 003-(1) and Example 002-(2) or a method equivalent thereto by the method described in Example 028-(1) and Example 027-(4) or a method equivalent thereto.

1H-NMR (DMSO-d6): δ 0.88 (3H, s), 2.79 (3H, s), 3.70-3.82 (6H, m), 4.68 (1H, q, J=5.5 Hz), 6.69 (1H, s), 7.86 (1H, d, J=3.5 Hz), 7.89 (1H, d, J=3.5 Hz), 9.54 (1H, s), 15.18 (1H, brs)

Example 606

Compound 606

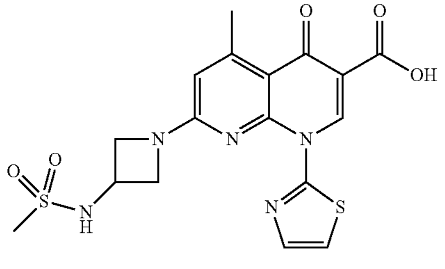

7-(3-Methanesulfonamidoazetidin-1-yl)-5-methyl-4-oxo-1-(1,3-thiazol-2-yl)-1,4-dihydro-1,8-naphthyridine-3-carboxylic acid (1) 36 mg of ethyl 7-(3-aminoazetidin-1-yl)-5-methyl-4-oxo-1-(1,3-thiazol-2-yl)-1,4-dihydro-1,8-naphthyridine-3-carboxylate was obtained by the method described in Example 026-(3) or a method equivalent thereto using ethyl 7-chloro-5-methyl-4-oxo-1-(1,3-thiazol-2-yl)-1,4-dihydro-1,8-naphthyridine-3-carboxylate obtained in Reference Example 001-(1), and azetidin-3-amine hydrochloride.

1H-NMR (DMSO-d6): δ 1.29 (3H, J=7.0 Hz), 2.72 (3H, s), 3.74-3.85 (1H, m), 3.95-4.12 (2H, m), 4.26 (2H, q, J=7.0 Hz), 4.36-4.52 (2H, m), 6.40 (1H, s), 7.67 (1H, J=3.5 Hz), 7.78 (1H, J=3.5 Hz), 9.55 (1H, s)

(2) To a solution of ethyl 7-(3-aminoazetidin-1-yl)-5-methyl-4-oxo-1-(1,3-thiazol-2-yl)-1,4-dihydro-1,8-naphthyridine-3-carboxylate (36 mg) obtained in the preceding section in methylene chloride (1 mL) were added methanesulfonyl chloride (36 μL) and triethylamine (210 μL) under ice cooling, and the mixture was stirred at the same temperature to room temperature for 4 days. To the reaction solution was added water, and the mixture was extracted with ethyl acetate. The organic layer was dried over sodium sulfate and concentrated, and the residue was purified by silica gel column chromatography (eluent: methanol/methylene chloride) to obtain 11 mg of ethyl 7-(3-methanesulfonamidoazetidin-1-yl)-5-methyl-4-oxo-1-(1,3-thiazol-2-yl)-1,4-dihydro-1,8-naphthyridine-3-carboxylate.

1H-NMR (DMSO-d6): δ 1.29 (3H, J=7.0 Hz), 2.73 (3H, a), 2.98 (3H, s), 4.03-4.16 (2H, m), 4.26 (2H, q, J=7.0 Hz), 4.38-4.50 (1H, m), 4.51-4.64 (2H, m), 6.41 (1H, s), 7.66 (1H, J=3.5 Hz), 7.77 (1H, J=3.5 Hz), 7.95-8.00 (1H, m), 9.57 (1H, s)

(3) The title compound was obtained by the method described in Example 027-(4) or a method equivalent thereto from ethyl 7-(3-methanesulfonamidoazetidin-1-yl)-5-methyl-4-oxo-1-(1,3-thiazol-2-yl)-1,4-dihydro-1,8-naphthyridine-3-carboxylate obtained in the preceding section.

1H-NMR (DMSO-d6): δ 2.74 (3H, s), 2.92 (3H, s), 3.57-3.66 (1H, m), 3.71-3.91 (4H, m), 6.66 (1H, s), 7.55 (1H, d, J=7.7 Hz), 7.80 (1H, d, J=3.5 Hz), 7.86 (1H, d, J=3.5 Hz), 9.71 (1H, 8)

Example 607

Compound 607

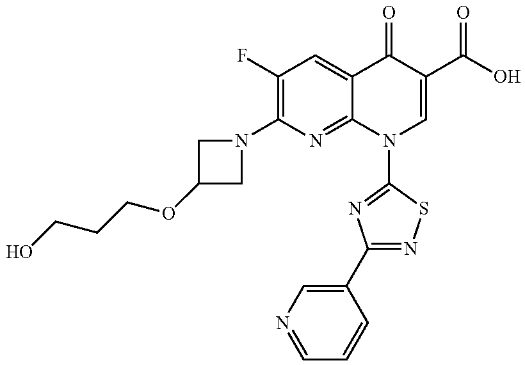

6-Fluoro-7-[3-(3-hydroxypropoxy)azetidin-1-yl]-4-oxo-1-[3-(pyridin-3-yl)-1,2,4-thiadiazol-5-yl]-1,4-dihydro-1,8-naphthyridine-3-carboxylic acid The title compound was obtained using 7-chloro-6-fluoro-4-oxo-1-[3-(pyridin-3-yl)-1,2,4-thiadiazol-5-yl]-1,4-dihydro-1,8-naphthyridine-3-carboxylic acid obtained in Reference Example 043-(2) and 3-(azetidin-3-yloxy)propan-1-ol hydrochloride obtained in Example 028-(1) by the method described in Example 008 or a method equivalent thereto.

1H-NMR (DMSO-d6): δ 1.69-1.75 (2H, m), 3.39-3.47 (2H, m), 3.53-3.58 (1H, m), 4.29-4.46 (4H, m), 4.51-4.59 (2H, m), 7.58-7.68 (1H, m), 8.07-8.16 (1H, m), 8.54-8.62 (1H, m), 8.72-8.80 (1H, m), 9.34-9.46 (1H, m), 9.80 (1H, brs)

Example 608

Compound 608

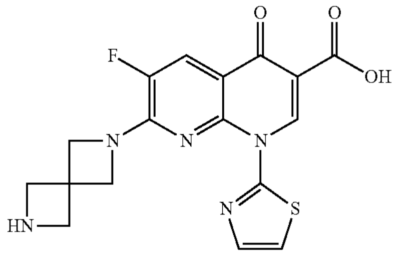

7-{2,6-Diazaspiro[3.3]heptan-2-yl}-6-fluoro-4-oxo-1-(1,3-thiazol-2-yl)-1,4-dihydro-1,8-naphthyridine-3-carboxylic acid (1) A suspension of ethyl 7-chloro-6-fluoro-4-oxo-1-(1,3-thiazol-2-yl)-1,4-dihydro-1,8-naphthyridine-3-carboxylate (21 mg) obtained in Reference Example 003-(1), tert-butyl 2,6-diazaspiro[3.3]heptane-2-carboxylate (29 mg), lithium chloride (20 mg) and 1,1,3,3-tetramethylguanidine (30 ML) in dimethyl sulfoxide (400 μL) was stirred at room temperature for 20 hours. To the reaction solution was added water, and the mixture was extracted with chloroform. The organic layer was dried over sodium sulfate and concentrated. The residue was purified by silica gel column chromatography (eluent: methanol/chloroform) to obtain 13 mg of ethyl 7-{6-[(tert-butoxy) carbonyl]-2,6-diazaspiro[3.3]heptan-2-yl}-6-fluoro-4-oxo-1-(1,3-thiazol-2-yl)-1,4-dihydro-1,8-naphthyridine-3-carboxylate.

1H-NMR (CDCl3): δ 1.43 (3H, t, J=7.0 Hz), 1.47 (9H, s), 4.19 (4H, s), 4.43 (2H, q, J=7.0 Hz), 4.61 (4H, brs), 7.29 (1H, d, J=3.0 Hz), 7.72 (1H, d, J=3.0 Hz), 8.14 (1H, d, J=11.0 Hz), 9.84 (1H, s)

(2) The title compound was obtained by the methods described in Examples 001-(2) and 028-(2) or methods equivalent thereto from ethyl 7-{6-[(tert-butoxy) carbonyl]-2,6-diazaspiro[3.3]heptan-2-yl}-6-fluoro-4-oxo-1-(1,3-thiazol-2-yl)-1,4-dihydro-1,8-naphthyridine-3-carboxylate obtained in the preceding section.

1H-NMR (DMSO-d6+TFA-d): δ 4.20-4.28 (4H, m), 4.48-4.90 (4H, m), 7.84 (1H, d, J=3.5 Hz), 7.88 (1H, d, J=3.5 Hz), 8.10 (1H, d, J=11.5 Hz), 8.56 (1H, brs), 9.77 (1H, s)

Example 609

Compound 609

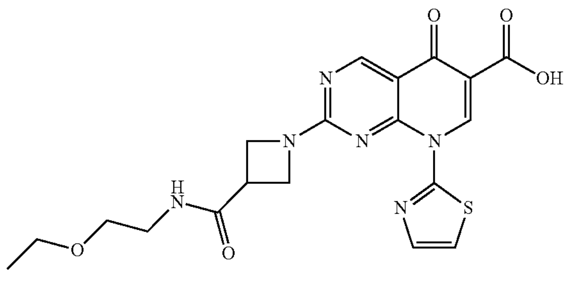

2-{3-[(2-Ethoxyethyl)carbamoyl]azetidin-1-yl}-5-oxo-8-(1,3-thiazol-2-yl)-5H,8H-pyrido[2,3-d]pyrimidine-6-carboxylic acid (1) Ethyl 2-{3-[(2-ethoxyethyl)carbamoyl]azetidin-1-yl}-5-oxo-8-(1,3-thiazol-2-yl)-5H,8H-pyrido[2,3-d]pyrimidine-6-carboxylate was obtained using ethyl 2-methanesulfonyl-5-oxo-8-(1,3-thiazol-2-yl)-5H,8H-pyrido[2,3-d]pyrimidine-6-carboxylate obtained by the method described in Journal of Medicinal Chemistry 45, 5564 (2002) or a method equivalent thereto and N-(2-ethoxyethyl)azetidine-3-carboxamide hydrochloride obtained in Example 018-(1) by the method described in Example 028-(1) or a method equivalent thereto.

1H-NMR (CDCl3): δ 1.22 (3H, t, J=7.0 Hz), 1.41 (3H, t, J=7.0 Hz), 3.48 (2H, q, J=7.0 Hz), 3.50-3.57 (6H, m), 4.41 (2H, q, J=7.0 Hz), 4.47-4.53 (2H, m), 4.60-4.66 (1H, m), 5.98 (1H, brs), 7.28 (1H, d, J=3.5 Hz), 7.69 (1H, d, J=3.5 Hz), 9.29 (1H, s), 9.81 (1H, s)

(2) The title compound was obtained from ethyl 2-{3-[(2-ethoxyethyl)carbamoyl]azetidin-1-yl}-5-oxo-8-(1,3-thiazol-2-yl)-5H, 8H-pyrido[2,3-d]pyrimidine-6-carboxylate obtained in the preceding section by the method described in Example 028-(2) or a method equivalent thereto.

1H-NMR (DMSO-d6): δ 1.11 (3H, t, J=7.0 Hz), 3.24-3.47 (6H, m), 3.57-3.65 (1H, m), 4.26-4.53 (4H, m), 7.80 (1H, d, J=3.5 Hz), 7.86 (1H, d, J=3.5 Hz), 8.25 (1H, brt, J=5.5 Hz), 9.25 (1H, s), 9.80 (1H, s), 14.18 (1H, brs)

Example 610

Compound 610

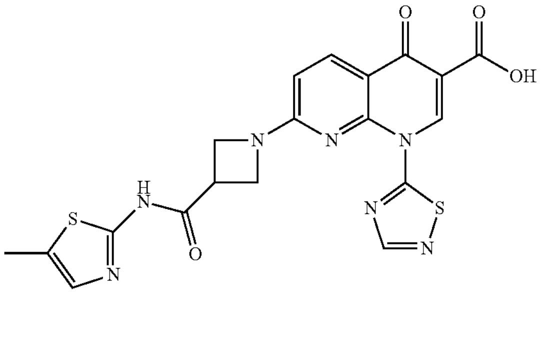

7-{3-[(5-Methyl-1,3-thiazol-2-yl)carbamoyl]azetidin-1-yl}-4-oxo-1-(1,2,4-thiadiazol-5-yl)-1,4-dihydro-1,8-naphthyridine-3-carboxylic acid (1) Ethyl 7-{3-[(5-methyl-1,3-thiazol-2-yl)carbamoyl]azetidin-1-yl}-4-oxo-1-(1,2,4-thiadiazol-5-yl)-1,4-dihydro-1,8-naphthyridine-3-carboxylate was obtained using ethyl 7-chloro-4-oxo-1-(1,2,4-thiadiazol-5-yl)-1,4-dihydro-1,8-naphthyridine-3-carboxylate obtained in Reference Example 006-(1) and N-(5-methyl-1,3-thiazol-2-yl)azetidine-3-carboxamide hydrochloride obtained in Example 283 by the method described in Example 018-(2) or a method equivalent thereto.

1H-NMR (DMSO-d6): δ 1.31 (3H, t, J=7.0 Hz), 2.35 (3H, brd, J=1.0 Hz), 3.88-3.98 (1H, m), 4.30 (2H, q, J=7.0 Hz), 4.35-4.72 (4H, m), 6.69 (1H, d, J=8.5 Hz), 7.16 (1H, brd, J=1.0 Hz), 8.27 (1H, d, J=8.5 Hz), 8.75 (1H, s), 9.55 (1H, s), 12.18 (1H, s)

(2) The title compound was obtained from ethyl 7-{3-[(5-methyl-1,3-thiazol-2-yl)carbamoyl]azetidin-1-yl}-4-oxo-1-(1,2,4-thiadiazol-5-yl)-1,4-dihydro-1,8-naphthyridine-3-carboxylate obtained in the preceding section by the method described in Example 028-(2) or a method equivalent thereto.

1H-NMR (DMSO-d6): δ 2.35 (3H, brd, J=1.0 Hz), 3.90-4.00 (1H, m), 4.33-4.73 (4H, m), 6.83 (1H, d, J=9.0 Hz), 7.16 (1H, brd, J=1.0 Hz), 8.38 (1H, d, J=9.0 Hz), 8.84 (1H, s), 9.76 (1H, s), 12.20 (1H, brs)

Example 611

Compound 611

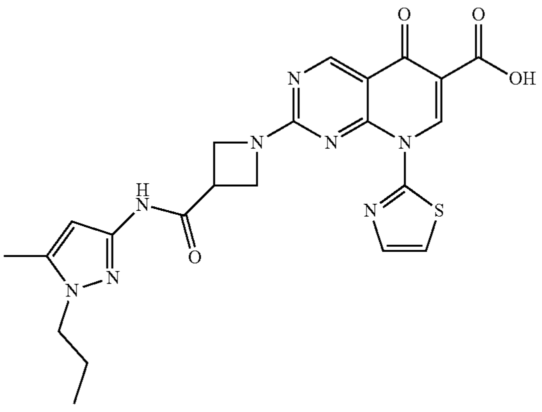

2-{3-[(5-Methyl-1-propyl-1H-pyrazol-3-yl)carbamoyl]azetidin-1-yl}-5-oxo-8-(1,3-thiazol-2-yl)-5H,8H-pyrido[2,3-d]pyrimidine-6-carboxylic acid (1) Ethyl 2-{3-[(5-methyl-1-propyl-1H-pyrazol-3-yl)carbamoyl]azetidin-1-yl}-5-oxo-8-(1,3-thiazol-2-yl)-5H,8H-pyrido[2,3-d]pyrimidine-carboxylate was obtained using ethyl 2-methanesulfonyl-5-oxo-8-(1,3-thiazol-2-yl)-5H, 8H-pyrido[2,3-d]pyrimidine-6-carboxylate obtained by the method described in Journal of Medicinal Chemistry 45, 5564 (2002) or a method equivalent thereto and N-(5-methyl-1-propyl-1H-pyrazol-3-yl)azetidine-3-carboxamide hydrochloride obtained in Example 201 by the method described in Example 027-(3) or a method equivalent thereto.

1H-NMR (CDCl3): δ 0.82 (3H, t, J=7.5 Hz), 1.30 (3H, t, J=7.0 Hz), 1.66-1.75 (2H, m), 2.22 (3H, s), 3.73-3.79 (1H, m), 3.86 (2H, t, J=6.5 Hz), 4.28 (2H, q, J=7.0 Hz), 4.38-4.52 (4H, m), 6.32 (1H, s), 7.71 (1H, d, J=3.5 Hz), 7.80 (1H, d, J=3.5 Hz), 9.07 (1H, s), 9.62 (1H, s), 10.59 (1H, s)

(2) The title compound was obtained from ethyl 2-{3-[(5-methyl-1-propyl-1H-pyrazol-3-yl)carbamoyl]azetidin-1-yl}-5-oxo-8-(1,3-thiazol-2-yl)-5H,8H-pyrido[2,3-d]pyrimidine-carboxylate obtained in the preceding section by the method described in Example 028-(2) or a method equivalent thereto.

1H-NMR (DMSO-d6): δ 0.82 (3H, t, J=7.5 Hz), 1.65-1.75 (2H, m), 2.22 (3H, d, J=0.5 Hz), 3.74-3.82 (1H, m), 3.86 (2H, t, J=7.0 Hz), 4.32-4.56 (4H, m), 6.32 (1H, d, J=0.5 Hz), 7.79 (1H, d, J=3.5 Hz), 7.85 (1H, d, J=3.5 Hz), 9.26 (1H, s), 9.81 (1H, s), 10.61 (1H, s), 14.19 (1H, brs)

Example 612

Compound 612

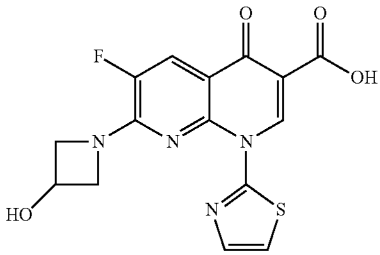

6-Fluoro-7-(3-hydroxyazetidin-1-yl)-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 003-(2) and azetidin-3-ol hydrochloride by the method described in Example 027-(3) or a method equivalent thereto.

1H-NMR (DMSO-d6): δ 4.17-4.30 (2H, m), 4.67-4.77 (3H, m), 5.97 (1H, brs), 7.80 (1H, d, J=3.5 Hz), 7.86 (1H, d, J=3.5 Hz), 8.10 (1H, d, J=11.5 Hz), 9.82 (1H, s)

Example 613

Compound 613

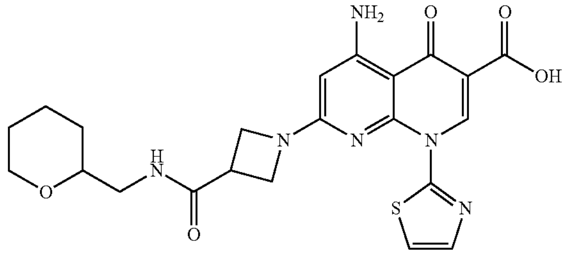

5-Amino-7-(3-{[(oxan-2-yl)methyl]carbamoyl}azetidin-1-yl)-4-oxo-1-(1,3-thiazol-2-yl)-1,4-dihydro-1,8-naphthyridine-3-carboxylic acid (1) To a mixture of ethyl 5,7-dichloro-4-oxo-1-(1,3-thiazol-2-yl)-1,4-dihydro-1,8-naphthyridine-3-carboxylate (100 mg) obtained by the method described in Journal of Medicinal Chemistry 47, 2097 (2004) or a method equivalent thereto, (2,4-dimethoxyphenyl)methanamine (86 mg) and toluene (3 mL) was added triethylamine (77 μL), and the mixture was refluxed for 2 hours. The reaction solution was concentrated, and the residue was then subjected to silica gel column chromatography (eluent: ethyl acetate/n-hexane) to obtain 129 mg of ethyl 7-chloro-5-{[(2,4-dimethoxyphenyl)methyl]amino}-4-oxo-1-(1,3-thiazol-2-yl)-1,4-dihydro-1,8-naphthyridine-3-carboxylate.

1H-NMR (DMSO-d6): δ 1.29 (3H, t, J=7.0 Hz), 3.76 (3H, s), 3.84 (3H, s), 4.27 (2H, q, J=7.0 Hz), 4.44 (2H, d, J=6.0 Hz), 6.52 (1H, dd, J=8.5, 2.5 Hz), 6.63 (1H, d, J=2.5 Hz), 6.85 (1H, s), 7.25 (1H, d, J=8.5 Hz), 7.73 (1H, d, J=3.5 Hz), 7.79 (1H, d, J=3.5 Hz), 9.60 (1H, s), 10.75 (1H, t, J=6.0 Hz)

(2) The title compound was obtained by the method described in Example 008 or a method equivalent thereto using 5-amino-7-chloro-4-oxo-1-(1,3-thiazol-2-yl)-1,4-dihydro-1,8-naphthyridine-3-carboxylic acid obtained by the method described in Reference Example 001-(2) or a method equivalent thereto from ethyl 7-chloro-5-{[(2,4-dimethoxyphenyl)methyl]amino}-4-oxo-1-(1,3-thiazol-2-yl)-1,4-dihydro-1,8-naphthyridine-3-carboxylate obtained in the preceding section, and N-(oxan-2-ylmethyl)azetidine-3-carboxamide hydrochloride obtained in Example 078-(1).

1H-NMR (DMSO-d6): δ 1.10-1.20 (1H, m), 1.37-1.49 (3H, m), 1.52-1.59 (1H, m), 1.71-1.80 (1H, m), 3.02-3.12 (1H, m), 3.14-3.22 (1H, m), 3.52-3.68 (3H, m), 3.84-3.91 (1H, m), 4.04-4.16 (2H, m), 4.18-4.30 (2H, m), 5.44 (1H, s), 7.31 (1H, brs), 7.60 (1H, d, J=3.5 Hz), 7.75 (1H, d, J=3.5 Hz), 8.16 (1H, t, J=5.5 Hz), 9.08 (1H, brs), 9.72 (1H, s)

Example 614

Compound 614

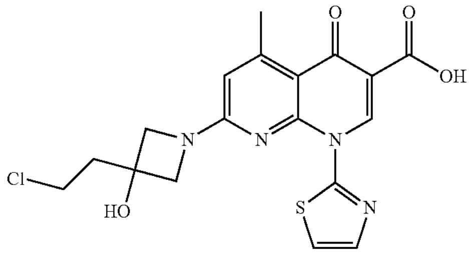

7-[3-(2-Chloroethyl)-3-hydroxyazetidin-1-yl]-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and 3-(2-chloroethyl)azetidin-3-ol by the method described in Example 001-(3) or a method equivalent thereto.

1H-NMR (DMSO-d6): δ 2.29 (2H, t, J=7.2 Hz), 2.76 (3H, s), 3.75-3.82 (2H, m), 4.02-4.44 (4H, m), 6.14 (1H, s), 6.52 (1H, s), 7.76 (1H, d, J=3.5 Hz), 7.84 (1H, d, J=3.5 Hz), 9.83 (1H, s), 15.40 (1H, brs)

Example 615

Compound 615

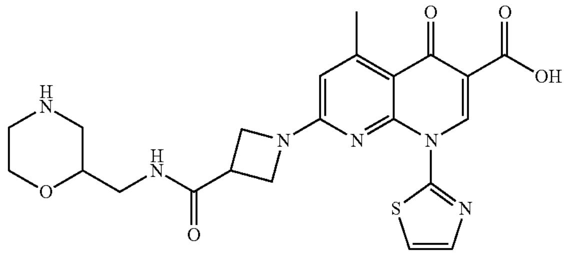

5-Methyl-7-{3-[(morpholin-2-ylmethyl)carbamoyl] azetidin-1-yl}-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-(morpholin-2-ylmethyl)azetidine-3-carboxamide hydrochloride obtained from (4-benzylmorpholin-2-yl)methanamine by the method described in Example 005-(1), Example 002-(2) and Example 001-(2) or a method equivalent thereto by the method described in Example 008 or a method equivalent thereto.

1H-NMR (DMSO-d6): δ 2.68-2.81 (4H, m), 2.90-3.01 (1H, m), 3.11-3.27 (3H, m), 3.54-3.79 (4H, m), 3.92-4.01 (1H, m), 4.16-4.52 (4H, m), 6.52 (1H, s), 7.75 (1H, d, J=3.5 Hz), 7.84 (1H, d, J=3.5 Hz), 8.40 (1H, t, J=6.0 Hz), 9.82 (1H, s), 15.36 (1H, brs)

Example 616

Compound 616

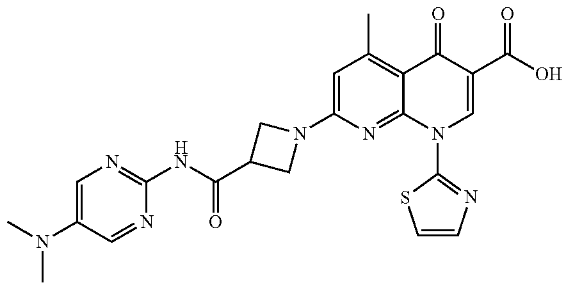

7-(3-{[5-(Dimethylamino)pyrimidin-2-yl] carbamoyl}azetidin-1-yl)-5-methyl-4-oxo-1-(1,3-thiazol-2-yl)-1,4-dihydro-1,8-naphthyridine-3-carboxylic acid The title compound was obtained by the method described in Example 002-(3) or a method equivalent thereto using N-[5-(dimethylamino)pyrimidin-2-yl]azetidine-3-carboxamide hydrochloride obtained from N5,N5-dimethylpyrimidine-2,5-diamine by the methods described in Examples 005-(1) and 001-(2) or methods equivalent thereto, and 7-chloro-5-methyl-4-oxo-1-(1,3-thiazol-2-yl)-1,4-dihydro-1,8-naphthyridine-3-carboxylic acid obtained in Reference Example 001-(2).

1H-NMR (DMSO-d6): δ 2.77 (3H, s), 2.93 (6H, s), 3.90-4.07 (1H, m), 4.28-4.54 (4H, m), 6.56 (1H, s), 7.76 (1H, d, J=3.5 Hz), 7.84 (1H, d, J=3.5 Hz), 8.23 (2H, s), 9.84 (1H, s), 10.51 (1H, s), 15.40 (1H, s)

Example 617

Compound 617

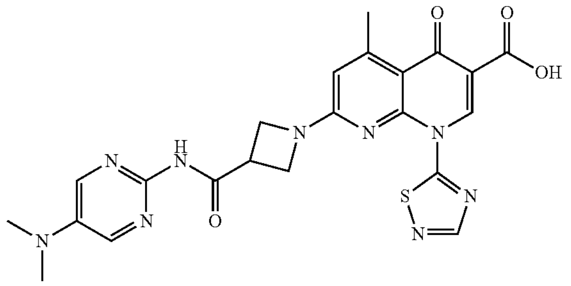

7-(3-{[5-(Dimethylamino)pyrimidin-2-yl] carbamoyl}azetidin-1-yl)-5-methyl-4-oxo-1-(1,2,4-thiadiazol-5-yl)-1,4-dihydro-1,8-naphthyridine-3-carboxylic acid The title compound was obtained by the method described in Example 002-(3) or a method equivalent thereto using N-[5-(dimethylamino)pyrimidin-2-yl]azetidine-3-carboxamide hydrochloride obtained in Example 616, and 7-chloro-5-methyl-4-oxo-1-(1,2,4-thiadiazol-5-yl)-1,4-dihydro-1,8-naphthyridine-3-carboxylic acid obtained in Reference Example 002-(2).

1H-NMR (DMSO-d6): δ '2.78 (3H, s), 2.93 (6H, s), 3.95-4.07 (1H, m), 4.31-4.72 (4H, m), 6.62 (1H, s), 8.23 (2H, s), 8.82 (1H, s), 9.75 (1H, s), 10.53 (1H, s), 15.08 (1H, brs)

Example 618

Compound 618

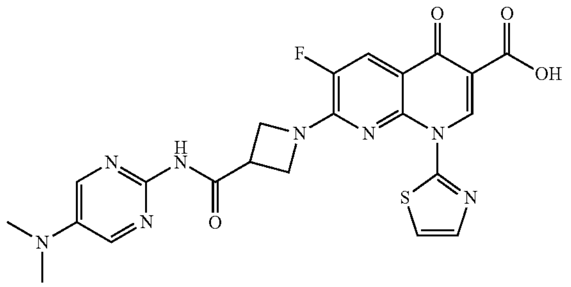

7-(3-{[5-(Dimethylamino)pyrimidin-2-yl]carbamoyl}azetidin-1-yl)-6-fluoro-4-oxo-1-(1,3-thiazol-2-yl)-1,4-dihydro-1,8-naphthyridine-3-carboxylic acid The title compound was obtained by the method described in Example 002-(3) or a method equivalent thereto using N-[5-(dimethylamino)pyrimidin-2-yl]azetidine-3-carboxamide hydrochloride obtained in Example 616, and 7-chloro-6-fluoro-4-oxo-1-(1,3-thiazol-2-yl)-1,4-dihydro-1,8-naphthyridine-3-carboxylic acid obtained in Reference Example 003-(2).

1H-NMR (DMSO-d6): δ 2.93 (6H, 8), 3.95-4.16 (1H, s), 4.47-4.88 (4H, m), 7.80 (1H, d, J=3.5 Hz), 7.87 (1H, d, J=3.5 Hz), 8.11 (1H, d, J=11.5 Hz), 8.23 (2H, s), 9.83 (1H, s), 10.51 (1H, s), 14.80 (1H, brs)

Example 619

Compound 619

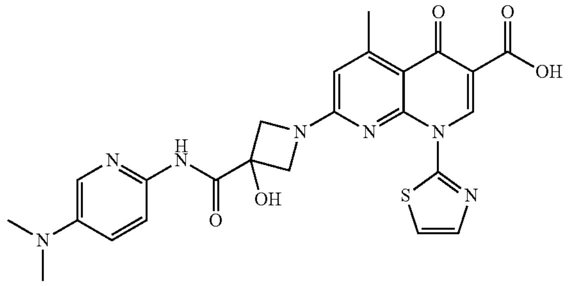

7-(3-{[5-(Dimethylamino)pyridin-2-yl]carbamoyl}-3-hydroxyazetidin-1-yl)-5-methyl-4-oxo-1-(1,3-thiazol-2-yl)-1,4-dihydro-1,8-naphthyridine-3-carboxylic acid The title compound was obtained by the method described in Example 002-(3) or a method equivalent thereto using N-[5-(dimethylamino)pyridin-2-yl]-3-hydroxyazetidine-3-carboxamide trifluoroacetate obtained by the methods described in Examples 005-(1) and 001-(2) or methods equivalent thereto from N5,N5-dimethylpyridine-2,5-diamine and 1-[(tert-butoxy)carbonyl]-3-hydroxyazetidine-3-carboxylic acid, and 7-chloro-5-methyl-4-oxo-1-(1,3-thiazol-2-yl)-1,4-dihydro-1,8-naphthyridine-3-carboxylic acid obtained in Reference Example 001-(2).

1H-NMR (DMSO-d6): δ 2.81 (3H, s), 2.90 (6H, s), 4.26 (1H, brd, J=9.5 Hz), 4.36 (1H, brd, J=9.5 Hz), 4.64 (1H, brd, J=10.0 Hz), 4.74 (1H, brd, J=10.0 Hz), 6.66 (1H, s), 7.24 (1H, dd, J=9.0, 3.0 Hz), 7.52 (1H, s), 7.72 (1H, d, J=3.5 Hz), 7.84 (1H, d, J=3.5 Hz), 7.86 (1H, d, J=3.0 Hz), 7.92 (1H, d, J=9.0 Hz), 9.38 (1H, s), 9.30 (1H, s), 15.38 (1H, brs)

Example 620

Compound 620

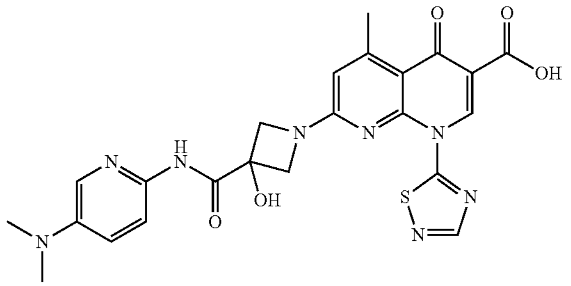

7-(3-{[5-(Dimethylamino)pyridin-2-yl]carbamoyl}-3-hydroxyazetidin-1-yl)-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-[5-(dimethylamino)pyridin-2-yl]-3-hydroxy azetidine-3-carboxamide trifluoroacetate obtained in Example 619 by the method described in Example 002-(3) or a method equivalent thereto.

1H-NMR (DMSO-d6): δ 2.81 (3H, s), 2.90 (6H, s), 4.28 (1H, d, J=9.5 Hz), 4.47 (1H, d, J=10.0 Hz), 4.68 (1H, d, J=9.5 Hz), 4.84 (1H, d, J=10.0 Hz), 6.70 (1H, s), 7.24 (1H, dd, J=9.0, 3.0 Hz), 7.52 (1H, s), 7.86 (1H, d, J=3.0 Hz), 7.93 (1H, d, J=9.0 Hz), 8.82 (1H, s), 9.35 (1H, s), 9.79 (1H, s), 15.06 (1H, brs)

Example 621

Compound 621

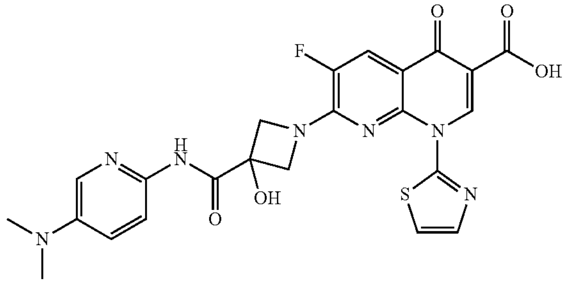

7-(3-{[5-(Dimethylamino)pyridin-2-yl]carbamoyl}-3-hydroxyazetidin-1-yl)-6-fluoro-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-[5-(dimethylamino)pyridin-2-yl]-3-hydroxy azetidine-3-carboxamide trifluoroacetate obtained in Example 619 by the method described in Example 002-(3) or a method equivalent thereto.

1H-NMR (DMSO-d6): δ 2.90 (6H, s), 4.34-4.47 (1H, m), 4.91-4.98 (1H, m), 4.52-4.61 (1H, m), 4.79-4.87 (1H, m), 7.24 (1H, dd, J=9.0, 3.0 Hz), 7.53 (1H, s), 7.76 (1H, d, J=3.5 Hz), 7.86 (2H, d, J=3.5 Hz), 7.94 (1H, d, J=9.0 Hz), 8.19 (1H, d, J=11.0 Hz), 9.33 (1H, s), 9.85 (1H, s), 14.76 (1H, brs)

Example 622

Compound 622

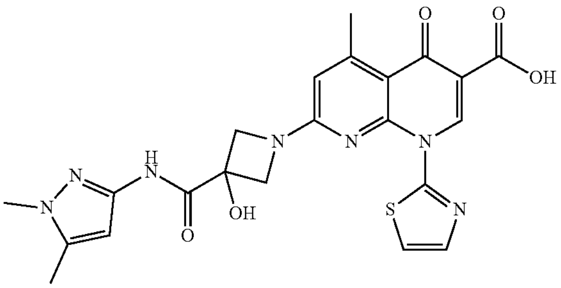

7-{3-[(1,5-Dimethyl-1H-pyrazol-3-yl)carbamoyl]-3-hydroxyazetidin-1-yl}-5-methyl-4-oxo-1-(1,3-thiazol-2-yl)-1,4-dihydro-1,8-naphthyridine-3-carboxylic acid The title compound was obtained by the method described in Example 002-(3) or a method equivalent thereto using N-(1,5-dimethyl-1H-pyrazol-3-yl)-3-hydroxyazetidine-3-carboxamide trifluoroacetate obtained by the methods described in Examples 005-(1) and 001-(2) or methods equivalent thereto from 1,5-dimethyl-1H-pyrazol-3-amine and 1-[(tert-butoxy) carbonyl]-3-hydroxyazetidine-3-carboxylic acid, and 7-chloro-5-methyl-4-oxo-1-(1,3-thiazol-2-yl)-1,4-dihydro-1,8-naphthyridine-3-carboxylic acid obtained in Reference Example 001-(2).

1H-NMR (DMSO-d6): δ 2.22 (3H, s), 2.80 (3H, s), 3.63 (3H, s), 4.22 (1H, d, J=9.0 Hz), 4.31 (1H, d, J=10.5 Hz), 4.59 (1H, d, J=10.0 Hz), 4.69 (1H, d, J=10.0 Hz), 6.31 (1H, s), 6.64 (1H, s), 7.28 (1H, s), 7.73 (1H, d, J=3.5 Hz), 7.84 (1H, d, J=3.5 Hz), 9.64 (1H, s), 9.87 (1H, s), 15.37 (1H, brs)

Example 623

Compound 623

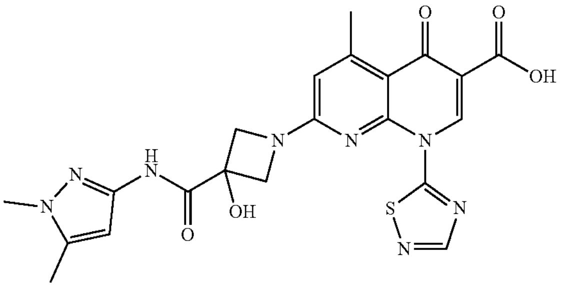

7-{3-[(1,5-Dimethyl-1H-pyrazol-3-yl)carbamoyl]-3-hydroxyazetidin-1-yl}-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-(1,5-dimethyl-1H-pyrazol-3-yl)-3-hydroxy azetidine-3-carboxamide trifluoroacetate obtained in Example 622 by the method described in Example 002-(3) or a method equivalent thereto.

1H-NMR (DMSO-d6): δ 2.22 (3H, s), 2.80 (3H, s), 3.63 (3H, s), 4.24 (1H, d, J=9.0 Hz), 4.43 (1H, d, J=10.5 Hz), 4.64 (1H, d, J=9.0 Hz), 4.79 (1H, d, J=10.0 Hz), 6.32 (1H, s), 6.69 (1H, s), 7.28 (1H, s), 8.82 (1H, s), 9.71 (1H, 8), 9.78 (1H, s), 15.06 (1H, s)

Example 624

Compound 624

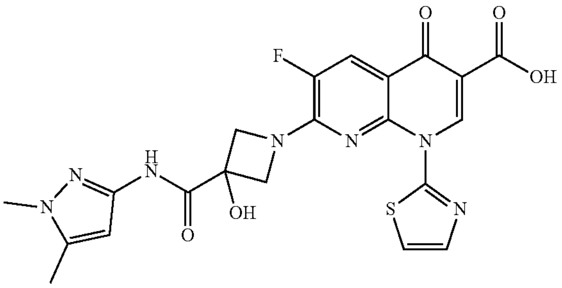

7-{3-[(1,5-Dimethyl-1H-pyrazol-3-yl)carbamoyl]-3-hydroxyazetidin-1-yl}-6-fluoro-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-(1,5-dimethyl-1H-pyrazol-3-yl)-3-hydroxy azetidine-3-carboxamide trifluoroacetate obtained in Example 622 by the method described in Example 002-(3) or a method equivalent thereto.

1H-NMR (DMSO-d6): δ 2.22 (3H, s), 3.63 (3H, s), 4.38 (1H, brs), 4.53 (1H, brs), 4.78 (1H, brs), 4.89 (1H, brs), 6.32 (1H, s), 7.27 (1H, s), 7.76 (1H, d, J=3.5 Hz), 7.86 (1H, d, J=3.5 Hz), 8.17 (1H, d, J=11.0 Hz), 9.70 (1H, s), 9.84 (1H, s), 14.75 (1H, brs)

Example 625

Compound 625

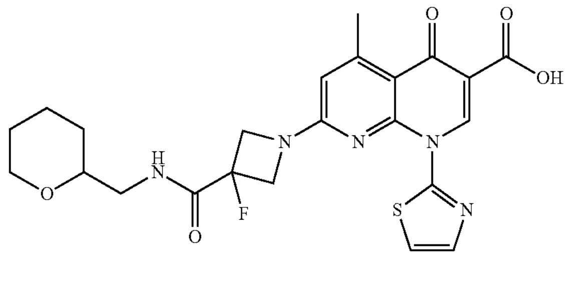

7-{3-Fluoro-3-[(oxan-2-ylmethyl)carbamoyl]azetidin-1-yl}-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and 3-fluoro-N-(oxan-2-ylmethyl)azetidine-3-carboxamide trifluoroacetate obtained from oxan-2-ylmethanamine and 1-[(tert-butoxy) carbonyl]-3-fluoroazetidine-3-carboxylic acid by the method described in Example 005-(1) and Example 001-(2) or a method equivalent thereto by the method described in Example 002-(3) or a method equivalent thereto.

1H-NMR (DMSO-d6): δ 1.08-1.19 (1H, m), 1.37-1.49 (3H, m), 1.54-1.60 (1H, m), 1.73-1.83 (1H, m), 2.81 (3H, d, J=1.0 Hz), 3.15-3.21 (2H, m), 3.36-3.43 (1H, m), 3.84-3.90 (1H, m), 4.47-4.86 (4H, m), 6.66 (1H, d, J=1.0 Hz), 7.72 (1H, d, J=3.5 Hz), 7.84 (1H, d, J=3.5 Hz), 8.53 (1H, t, J=6.0 Hz), 9.87 (1H, s), 15.27 (1H, s)

Example 626

Compound 626

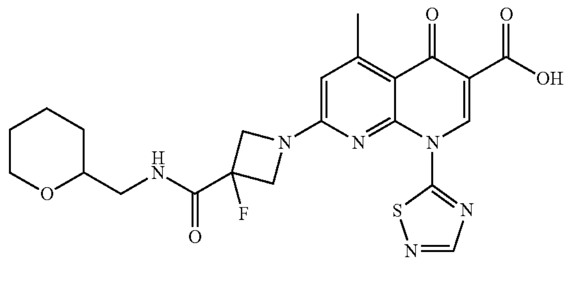

7-{3-Fluoro-3-[(oxan-2-ylmethyl)carbamoyl]azetidin-1-yl}-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and 3-fluoro-N-(oxan-2-ylmethyl)azetidine-3-carboxamide trifluoroacetate obtained in Example 625 by the method described in Example 002-(3) or a method equivalent thereto.

1H-NMR (DMSO-d6): δ 1.09-1.19 (1H, m), 1.37-1.50 (3H, m), 1.55-1.63 (1H, m), 1.72-1.83 (1H, m), 2.81 (3H, s), 3.14-3.22 (2H, m), 3.82-3.91 (1H, m), 4.35-4.93 (4H, m), 6.70 (1H, s), 8.54 (1H, t, J=5.5 Hz), 8.82 (1H, s), 9.79 (1H, s), 14.95 (1H, brs)

Example 627

Compound 627

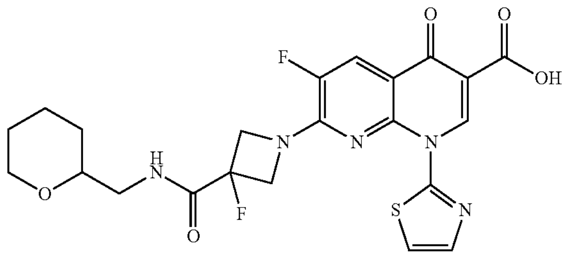

6-Fluoro-7-{3-fluoro-3-[(oxan-2-ylmethyl)carbamoyl]azetidin-1-yl}-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and 3-fluoro-N-(oxan-2-ylmethyl)azetidine-3-carboxamide trifluoroacetate obtained in Example 625 by the method described in Example 002-(3) or a method equivalent thereto.

1H-NMR (DMSO-d6): δ 1.09-1.19 (1H, m), 1.39-1.49 (3H, m), 1.55-1.62 (1H, m), 1.73-1.81 (1H, m), 3.16-3.21 (2H, m), 3.37-3.42 (1H, m), 3.83-3.90 (1H, m), 4.56-4.99 (4H, m), 7.76 (1H, d, J=3.5 Hz), 7.86 (1H, d, J=3.5 Hz), 8.21 (1H, d, J=11.0 Hz), 8.54 (1H, t, J=6.0 Hz), 9.85 (1H, s), 14.67 (1H, brs)

Example 628

Compound 628

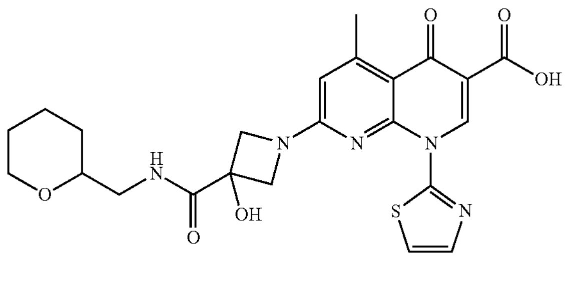

7-{3-Hydroxy-3-[(oxan-2-ylmethyl)carbamoyl]azetidin-1-yl}-5-methyl-4-oxo-1-(1,3-thiazol-2-yl)-1,4-dihydro-1,8-naphthyridine-3-carboxylic acid The title compound was obtained by the method described in Example 002-(3) or a method equivalent thereto using 3-hydroxy-N-(oxan-2-ylmethyl)azetidine-3-carboxamide trifluoroacetate obtained by the methods described in Examples 005-(1) and 001-(2) or methods equivalent thereto from oxan-2-ylmethanamine and 1-[(tert-butoxy)carbonyl]-3-hydroxyazetidine-3-carboxylic acid, and 7-chloro-5-methyl-4-oxo-1-(1,3-thiazol-2-yl)-1,4-dihydro-1,8-naphthyridine-3-carboxylic acid obtained in Reference Example 001-(2).

1H-NMR (DMSO-d6): δ 1.10-1.20 (1H, m), 1.38-1.49 (3H, m), 1.52-1.59 (1H, m), 1.72-1.82 (1H, m), 2.80 (3H, s), 3.18-3.25 (1H, m), 3.34-3.40 (1H, m), 3.84-3.91 (1H, m), 4.12 (1H, d, J=9.0 Hz), 4.26 (1H, d, J=10.0 Hz), 4.50 (1H, d, J=8.5 Hz), 4.61 (1H, d, J=10.0 Hz), 6.62 (1H, s), 7.14 (1H, s), 7.73 (1H, d, J=3.5 Hz), 7.80-7.85 (2H, m), 9.87 (1H, s), 15.38 (1H, s)

Example 629

Compound 629

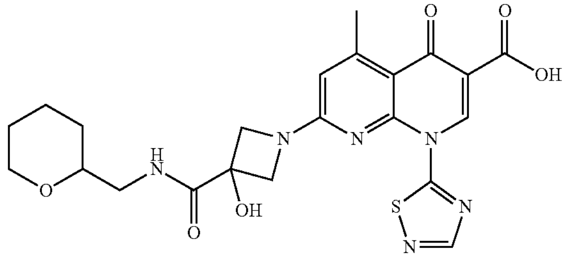

7-{3-Hydroxy-3-[(oxan-2-ylmethyl)carbamoyl]azetidin-1-yl}-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and 3-hydroxy-N-(oxan-2-ylmethyl)azetidine-3-carboxamide trifluoroacetate obtained in Example 628 by the method described in Example 002-(3) or a method equivalent thereto.

1H-NMR (DMSO-d6): δ 1.10-1.21 (1H, m), 1.39-1.49 (3H, m), 1.54-1.59 (1H, m), 1.71-1.81 (1H, m), 2.80 (3H, s), 3.09-3.16 (1H, m), 3.19-3.26 (1H, m), 3.34-3.41 (2H, m), 3.84-3.91 (1H, m), 4.19 (1H, d, J=9.5 Hz), 4.34 (1H, d, J=9.5 Hz), 4.54 (1H, d, J=9.5 Hz), 4.70 (1H, d, J=10.0 Hz), 6.66 (1H, s), 7.16 (1H, s), 7.83 (1H, t, J 5.5 Hz), 8.82 (1H, s), 9.78 (1H, s), 15.06 (1H, s)

Example 630

Compound 630

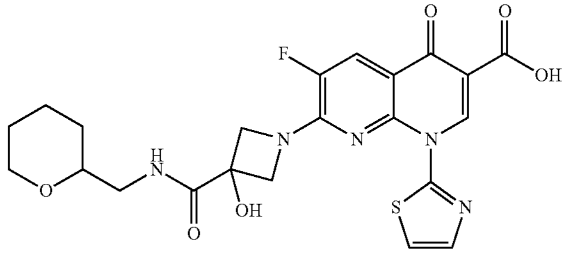

6-Fluoro-7-{3-hydroxy-3-[(oxan-2-ylmethyl)carbamoyl]azetidin-1-yl}-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and 3-hydroxy-N-(oxan-2-ylmethyl)azetidine-3-carboxamide trifluoroacetate obtained in Example 628 by the method described in Example 002-(3) or a method equivalent thereto.

1H-NMR (DMSO-d6): δ 1.10-1.21 (1H, m), 1.37-1.49 (3H, m), 1.53-1.60 (1H, m), 1.72-1.81 (1H, m), 3.08-3.16 (1H, m), 3.19-3.26 (1H, m), 3.34-3.41 (2H, m), 3.89-3.91 (1H, m), 4.28-4.56 (2H, m), 4.62-4.87 (2H, m), 7.16 (1H, s), 7.77 (1H, d, J=3.5 Hz), 7.82-7.87 (2H, m), 8.16 (1H, d, J=11.5 Hz), 9.84 (1H, s), 14.78 (1H, s)

Example 631

Compound 631

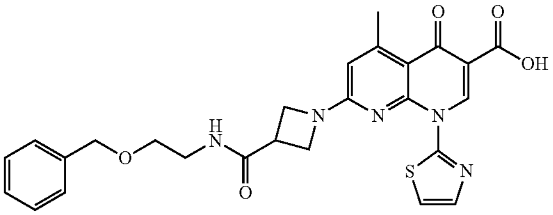

7-(3-{[2-(Benzyloxy)ethyl]carbamoyl}azetidin-1-yl)-5-methyl-4-oxo-1-(1,3-thiazol-2-yl)-1,4-dihydro-1,8-naphthyridine-3-carboxylic acid The title compound was obtained by the method described in Example 001-(3) or a method equivalent thereto using N-[2-(benzyloxy)ethyl]azetidine-3-carboxamide hydrochloride obtained from 2-(benzyloxy)ethan-1-amine by the methods described in Examples 005-(1) and 001-(2) or methods equivalent thereto, and 7-chloro-5-methyl-4-oxo-1-(1,3-thiazol-2-yl)-1,4-dihydro-1,8-naphthyridine-3-carboxylic acid obtained in Reference Example 001-(2).

1H-NMR (DMSO-d6): δ 2.76 (3H, s), 3.25-3.38 (2H, m), 3.48 (2H, t, J=5.5 Hz), 3.56-3.64 (1H, m), 4.13-4.46 (4H, m), 4.49 (2H, s), 6.48 (1H, s), 7.24-7.30 (1H, m), 7.30-7.35 (4H, m), 7.70 (1H, d, J=3.5 Hz), 7.82 (1H, d, J=3.5 Hz), 8.29 (1H, t, J=5.5 Hz), 9.81 (1H, s)

Example 632

Compound 632

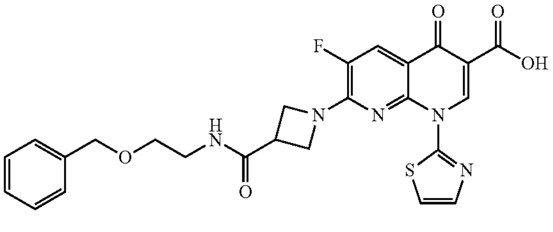

7-(3-{[2-(Benzyloxy)ethyl]carbamoyl}azetidin-1-yl)-6-fluoro-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-[2-(benzyloxy)ethyl]azetidine-3-carboxamide hydrochloride obtained in Example 631 by the method described in Example 001-(3) or a method equivalent thereto.

1H-NMR (DMSO-d6): δ 3.21-3.41 (2H, m), 3.48 (2H, t, J=5.5 Hz), 3.60-3.68 (1H, m), 4.39-4.92 (6H, m), 7.24-7.30 (1H, m), 7.30-7.36 (4H, m), 7.74 (1H, d, J=3.5 Hz), 7.83 (1H, d, J=3.5 Hz), 8.07 (1H, d, J=11.5 Hz), 8.29 (1H, t, J=5.5 Hz), 9.80 (1H, s)

Example 633

Compound 633

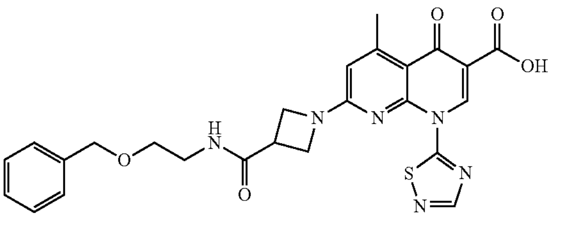

7-(3-{[2-(Benzyloxy)ethyl]carbamoyl}azetidin-1-yl)-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-[2-(benzyloxy)ethyl]azetidine-3-carboxamide hydrochloride obtained in Example 631 by the method described in Example 001-(3) or a method equivalent thereto.

1H-NMR (DMSO-d6): δ 2.76 (3H, s), 3.16-3.44 (2H, m), 3.49 (2H, t, J=5.5 Hz), 3.59-3.67 (1H, m), 4.14-4.61 (6H, m), 6.55 (1H, s), 7.23-7.29 (1H, m), 7.29-7.36 (4H, m), 8.31 (1H, t, J=5.5 Hz), 8.80 (1H, s), 9.71 (1H, s)

Example 634

Compound 634

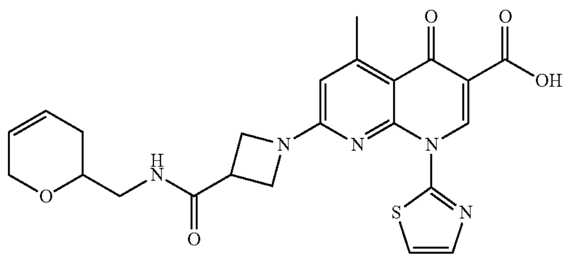

7-{3-[(3,6-Dihydro-2H-pyran-2-ylmethyl)carbamoyl]azetidin-1-yl}-5-methyl-4-oxo-1-(1,3-thiazol-2-yl)-1,4-dihydro-1,8-naphthyridine-3-carboxylic acid The title compound was obtained by the method described in Example 001-(3) or a method equivalent thereto using N-(3,6-dihydro-2H-pyran-2-ylmethyl)azetidine-3-carboxamide hydrochloride obtained from 3,6-dihydro-2H-pyran-2-ylmethanamine by the methods described in Examples 005-(1) and 001-(2) or methods equivalent thereto, and 7-chloro-5-methyl-4-oxo-1-(1,3-thiazol-2-yl)-1,4-dihydro-1,8-naphthyridine-3-carboxylic acid obtained in Reference Example 001-(2).

1H-NMR (DMSO-d6): δ 1.88-2.01 (2H, m), 2.77 (3H, s), 3.12-3.37 (2H, m), 3.51-3.58 (1H, m), 3.60-3.68 (1H, m), 4.04-4.15 (2H, m), 4.16-4.52 (4H, m), 5.72-5.83 (2H, m), 6.53 (1H, s), 7.74 (1H, d, J=3.5 Hz), 7.83 (1H, d, J=3.5 Hz), 8.29 (1H, t, J=6.0 Hz), 9.84 (1H, s), 15.40 (1H, s)

Example 635

Compound 635

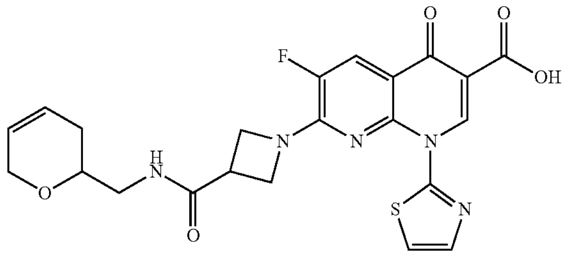

7-{3-[(3,6-Dihydro-2H-pyran-2-ylmethyl)carbamoyl]azetidin-1-yl}-6-fluoro-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-(3,6-dihydro-2H-pyran-2-ylmethyl)azetidine-3-carboxamide hydrochloride obtained in Example 634 by the method described in Example 001-(3) or a method equivalent thereto.

1H-NMR (DMSO-d6): δ 1.89-2.01 (2H, m), 3.14-3.37 (2H, m), 3.52-3.59 (1H, m), 3.63-3.73 (1H, m), 4.04-4.15 (2H, m), 4.37-4.82 (4H, m), 5.72-5.83 (2H, m), 7.78 (1H, d, J=3.5 Hz), 7.85 (1H, d, J=3.5 Hz), 8.09 (1H, d, J=11.5 Hz), 8.29 (1H, t, J=6.0 Hz), 9.81 (1H, s), 14.80 (1H, brs)

Example 636

Compound 636

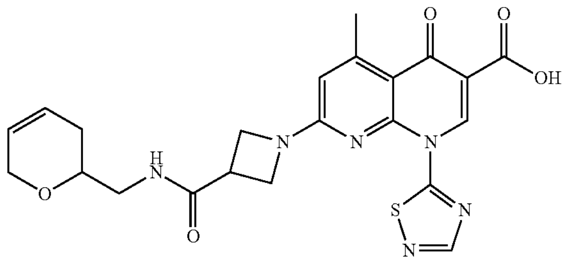

7-{3-[(3,6-Dihydro-2H-pyran-2-ylmethyl)carbamoyl]azetidin-1-yl}-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-(3,6-dihydro-2H-pyran-2-ylmethyl) azetidine-3-carboxamide hydrochloride obtained in Example 634 by the method described in Example 001-(3) or a method equivalent thereto.

1H-NMR (DMSO-d6): δ 1.88-2.01 (2H, m), 2.76 (3H, s), 3.14-3.42 (2H, m), 3.52-3.60 (1H, m), 3.61-3.72 (1H, m), 4.05-4.15 (2H, m), 4.21-4.65 (4H, m), 5.72-5.82 (2H, m), 6.59 (1H, s), 8.31 (1H, t, J=5.5 Hz), 8.81 (1H, s), 9.74 (1H, s), 15.07 (1H, brs)

Example 637

Compound 637

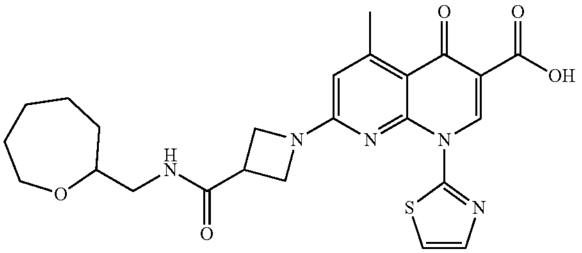

5-Methyl-7-{3-[(oxepan-2-ylmethyl)carbamoyl]azetidin-1-yl}-4-oxo-1-(1,3-thiazol-2-yl)-1,4-dihydro-1,8-naphthyridine-3-carboxylic acid The title compound was obtained by the method described in Example 001-(3) or a method equivalent thereto using N-(oxepan-2-ylmethyl)azetidine-3-carboxamide hydrochloride obtained from oxepan-2-ylmethanamine by the methods described in Examples 005-(1) and 001-(2) or methods equivalent thereto, and 7-chloro-5-methyl-4-oxo-1-(1,3-thiazol-2-yl)-1,4-dihydro-1,8-naphthyridine-3-carboxylic acid obtained in Reference Example 001-(2).

1H-NMR (DMSO-d6): δ 1.33-1.78 (8H, m), 2.74 (3H, s), 2.97-3.10 (1H, m), 3.12-3.23 (1H, m), 3.43-3.57 (2H, m), 3.58-3.67 (1H, m), 3.73-3.82 (1H, m), 4.14-4.50 (4H, m), 6.50 (1H, s), 7.73 (1H, d, J=3.5 Hz), 7.82 (1H, d, J=3.5 Hz), 8.20 (1H, t, J=5.5 Hz), 9.81 (1H, s), 15.39 (1H, brs)

Example 638

Compound 638

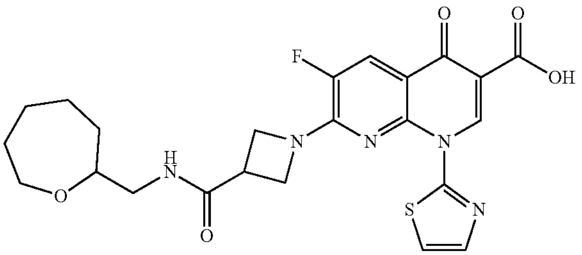

6-Fluoro-7-{3-[(oxepan-2-ylmethyl)carbamoyl]azetidin-1-yl}-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-(oxepan-2-ylmethyl)azetidine-3-carboxamide hydrochloride obtained in Example 637 by the method described in Example 001-(3) or a method equivalent thereto.

1H-NMR (DMSO-d6): δ 1.34-1.78 (8H, m), 2.99-3.09 (1H, m), 3.13-3.22 (1H, m), 3.43-3.56 (2H, m), 3.62-3.71 (1H, m), 3.74-3.81 (1H, m), 4.78-4.80 (4H, m), 7.79 (1H, d, J=3.5 Hz), 7.85 (1H, d, J=3.5 Hz), 8.10 (1H, d, J=11.5 Hz), 8.19 (1H, t, J=5.5 Hz), 9.82 (1H, s), 14.78 (1H, brs)

Example 639

Compound 639

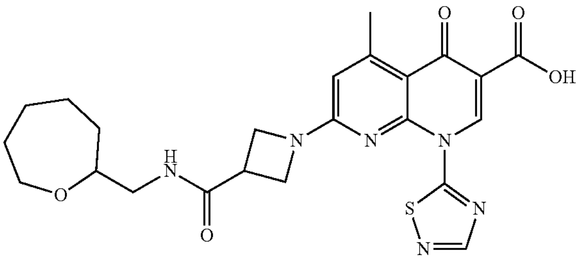

5-Methyl-7-{3-[(oxepan-2-ylmethyl)carbamoyl]azetidin-1-yl}-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-(oxepan-2-ylmethyl)azetidine-3-carboxamide hydrochloride obtained in Example 637 by the method described in Example 001-(3) or a method equivalent thereto.

1H-NMR (DMSO-d6): δ 1.34-1.78 (8H, m), 2.77 (3H, s), 3.00-3.10 (1H, m), 3.14-3.22 (1H, m), 3.44-3.58 (2H, m), 3.61-3.69 (1H, m), 3.74-3.82 (1H, m), 4.20-4.65 (4H, m), 6.59 (1H, s), 8.22 (1H, t, J=5.5 Hz), 8.81 (1H, s), 9.74 (1H, s), 15.08 (1H, brs)

Example 640

Compound 640

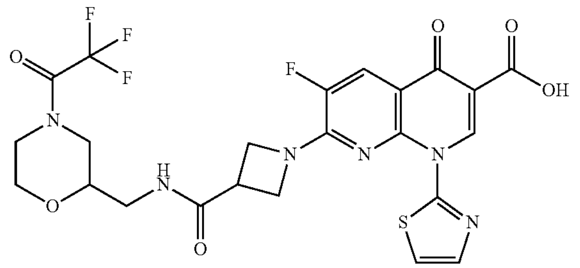

6-Fluoro-4-oxo-1-(1,3-thiazol-2-yl)-7-[3-({[4-(trifluoroacetyl)morpholin-2-yl]methyl}carbamoyl)azetidin-1-yl]-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-{[4-(trifluoroacetyl)morpholin-2-yl]methyl}azetidine-3-carboxamide trifluoroacetate obtained from 1-[2-(aminomethyl)morpholin-4-yl]-2,2,2-trifluoroethan-1-one by the method described in Example 005-(1) and Example 001-(2) or a method equivalent thereto by the method described in Example 001-(3) or a method equivalent thereto.

1H-NMR (DMSO-d6): δ 2.75-3.43 (4H, m), 3.47-3.56 (2H, m), 3.61-3.79 (2H, m), 3.90-3.98 (1H, m), 4.07-4.23 (1H, m), 4.34-4.84 (4H, m), 7.78 (1H, t, J=3.5 Hz), 7.85-7.90 (1H, m), 8.09-8.14 (1H, m), 8.37-8.44 (1H, m), 9.82 (1H, s), 14.82 (1H, brs)

Example 641

Compound 641

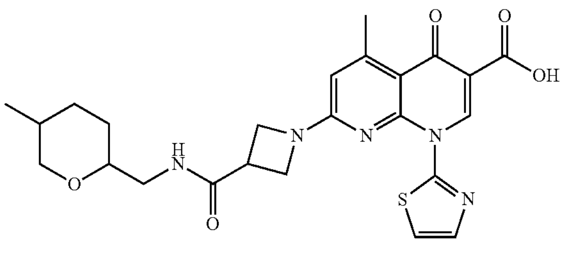

5-Methyl-7-(3-{[(5-methyloxan-2-yl)methyl]carbamoyl}azetidin-1-yl)-4-oxo-1-(1,3-thiazol-2-yl)-1,4-dihydro-1,8-naphthyridine-3-carboxylic acid The title compound was obtained by the method described in Example 001-(3) or a method equivalent thereto using N-[(5-methyloxan-2-yl)methyl]azetidine-3-carboxamide hydrochloride obtained from (5-methyloxan-2-yl)methanamine by the methods described in Examples 005-(1) and 001-(2) or methods equivalent thereto, and 7-chloro-5-methyl-4-oxo-1-(1,3-thiazol-2-yl)-1,4-dihydro-1,8-naphthyridine-3-carboxylic acid obtained in Reference Example 001-(2).

1H-NMR (DMSO-d6): δ 0.72-1.02 (3H, m), 1.03-1.80 (5H, m), 2.76 (3H, s), 3.02-3.82 (6H, m), 4.13-4.56 (4H, m), 6.52 (1H, s), 7.74 (1H, d, J=3.5 Hz), 7.83 (1H, d, J=3.5 Hz), 8.20-8.26 (1H, m), 9.83 (1H, s), 15.40 (1H, s)

Example 642

Compound 642

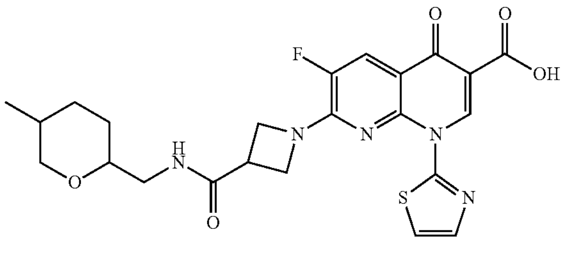

6-Fluoro-7-(3-{[(5-methyloxan-2-yl)methyl]carbamoyl}azetidin-1-yl)-4-oxo-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-[(5-methyloxan-2-yl)methyl]azetidine-3-carboxamide hydrochloride obtained in Example 641 by the method described in Example 001-(3) or a method equivalent thereto.

1H-NMR (DMSO-d6): δ 0.71-1.02 (3H, m), 1.02-1.81 (5H, m), 3.04-3.40 (3H, m), 3.46-3.81 (3H, m), 4.37-4.79 (4H, m), 7.78 (1H, d, J=3.5 Hz), 7.85 (1H, d, J=3.5 Hz), 8.09 (1H, d, J=11.0 Hz), 8.21-8.26 (1H, m), 9.81 (1H, a), 14.78 (1H, brs)

Example 643

Compound 643

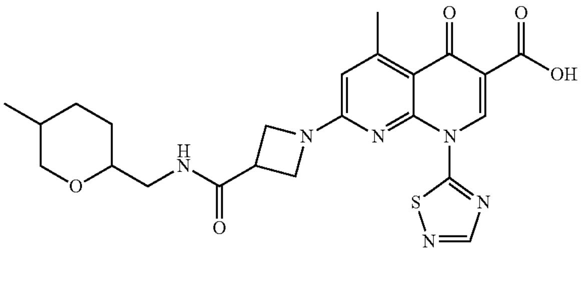

5-Methyl-7-(3-{[(5-methyloxan-2-yl)methyl]carbamoyl)}azetidin-1-yl)-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-[(5-methyloxan-2-yl)methyl]azetidine-3-carboxamide hydrochloride obtained in Example 641 by the method described in Example 001-(3) or a method equivalent thereto.

1H-NMR (DMSO-d6): δ 0.73-1.01 (3H, m), 1.03-1.81 (5H, m), 2.77 (3H, s), 3.05-3.41 (3H, m), 3.46-3.82 (3H, m), 4.19-4.65 (4H, m), 6.58 (1H, s), 8.23-8.29 (1H, m), 8.79-8.83 (1H, m), 9.72-9.75 (1H, m)

Example 644

Compound 644

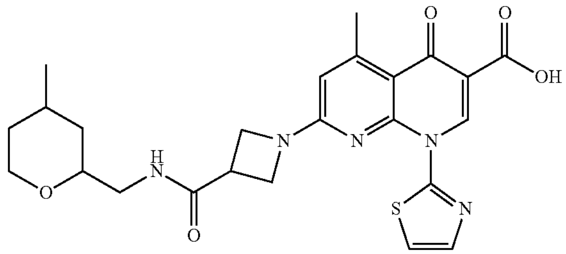

5-Methyl-7-(3-{[(4-methyloxan-2-yl)methyl]carbamoyl}azetidin-1-yl)-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-[(4-methyloxan-2-yl)methyl]azetidine-3-carboxamide hydrochloride obtained from (4-methyloxan-2-yl) methanamine by the method described in Example 005-(1) and Example 001-(2) or a method equivalent thereto by the method described in Example 001-(3) or a method equivalent thereto.

1H-NMR (DMSO-d6): δ 0.87-1.02 (3H, m), 1.02-1.71 (5H, m), 2.76 (3H, s), 3.03-3.92 (6H, m), 4.09-4.51 (4H, m), 6.52 (1H, s), 7.73-7.75 (1H, m), 7.83 (1H, d, J=3.0 Hz), 8.17-8.24 (1H, m), 9.83 (1H, s), 15.39 (1H, s)

Example 645

Compound 645

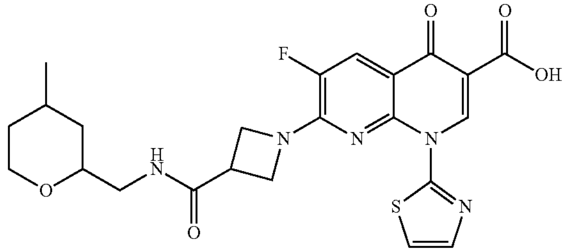

6-Fluoro-7-(3-{[(4-methyloxan-2-yl)methyl]carbamoyl}azetidin-1-yl)-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-[(4-methyloxan-2-yl)methyl]azetidine-3-carboxamide hydrochloride obtained in Example 644 by the method described in Example 001-(3) or a method equivalent thereto.

1H-NMR (DMSO-d6): δ 0.87-1.02 (3H, m), 1.04-1.69 (5H, m), 3.05-3.24 (3H, m), 3.52-3.72 (2H, m), 3.85-3.91 (1H, m), 4.38-4.81 (4H, m), 7.78-7.80 (1H, m), 7.86 (1H, d, J=3.5 Hz), 8.11 (1H, d, J=11.5 Hz), 8.17-8.24 (1H, m), 9.82 (1H, s), 14.80 (1H, s)

Example 646

Compound 646

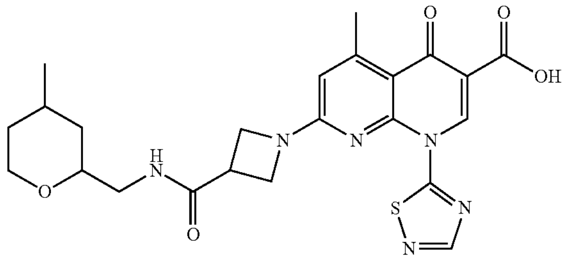

5-Methyl-7-(3-{[(4-methyloxan-2-yl)methyl]carbamoyl}azetidin-1-yl)-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-[(4-methyloxan-2-yl)methyl]azetidine-3-carboxamide hydrochloride obtained in Example 644 by the method described in Example 001-(3) or a method equivalent thereto.

1H-NMR (DMSO-d6): δ 0.88-1.02 (3H, m), 1.03-1.69 (5H, m), 2.77 (3H, s), 3.06-3.23 (3H, m), 3.07-3.54 (2H, m), 3.85-3.92 (1H, m), 4.09-4.65 (4H, m), 6.58 (1H, s), 8.20-8.27 (1H, m), 8.81 (1H, s), 9.74 (1H, s), 15.08 (1H, s)

Example 647

Compound 647

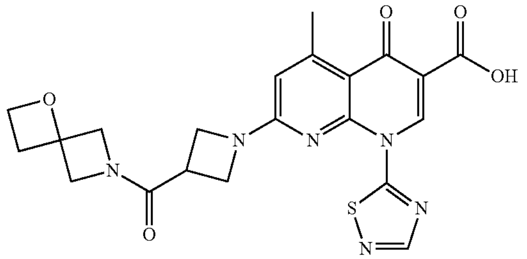

5-Methyl-7-(3-{1-oxa-6-azaspiro[3.3]heptane-6-carbonyl}azetidin-1-yl)-4-oxo-1-(1,2,4-thiadiazol-5-yl)}-1,4-dihydro-1,8-naphthyridine-3-carboxylic acid The title compound was obtained by the method described in Example 001-(3) or a method equivalent thereto using 6-(azetidine-3-carbonyl)-1-oxa-6-azaspiro[3.3]heptane hydrochloride obtained from 1-oxa-6-azaspiro[3.3]heptane by the methods described in Examples 005-(1) and 001-(2) or methods equivalent thereto, and 7-chloro-5-methyl-4- oxo-1-(1,2,4-thiadiazol-5-yl)-1,4-dihydro-1,8-naphthyridine-3-carboxylic acid obtained in Reference Example 002-(2).

1H-NMR (DMSO-d6): δ 2.18 (2H, t, J=7.4 Hz), 2.75 (3H, s), 3.64-3.78 (5H, m), 3.90-4.02 (2H, m), 4.24-4.65 (4H, m), 6.56 (1H, s), 8.81 (1H, s), 9.70 (1H, s), 15.03 (1H, brs)

Example 648

Compound 648

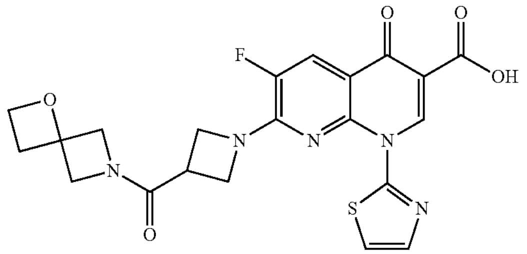

6-Fluoro-7-(3-{1-oxa-6-azaspiro[3.3]heptane-6-carbonyl}azetidin-1-yl)-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and 6-(azetidine-3-carbonyl)-1-oxa-6-azaspiro[3.3]heptane hydrochloride obtained in Example 647 by the method described in Example 001-(3) or a method equivalent thereto.

1H-NMR (DMSO-d6): δ 2.17 (2H, t, J=7.4 Hz), 3.65-3.75 (5H, m), 3.90-3.97 (2H, m), 4.38-4.82 (4H, m), 7.79 (1H, d, J=3.5 Hz), 7.86 (1H, d, J=3.5 Hz), 8.09 (1H, d, J=11.5 Hz), 9.80 (1H, s), 14.77 (1H, brs)

Example 649

Compound 649

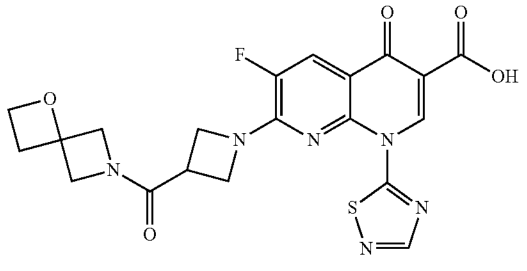

6-Fluoro-7-(3-{1-oxa-6-azaspiro[3.3]heptane-6-carbonyl}azetidin-1-yl)-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and 6-(azetidine-3-carbonyl)-1-oxa-6-azaspiro[3.3]heptane hydrochloride obtained in Example 647 by the method described in Example 001-(3) or a method equivalent thereto.

1H-NMR (DMSO-d6): δ 2.18 (2H, t, J=7.3 Hz), 3.62-3.69 (5H, m), 3.87-4.00 (2H, m), 4.44-4.82 (4H, m), 8.14 (1H, d, J=11.4 Hz), 8.85 (1H, s), 9.72 (1H, s), 14.41 (1H, brs)

Example 650

Compound 650

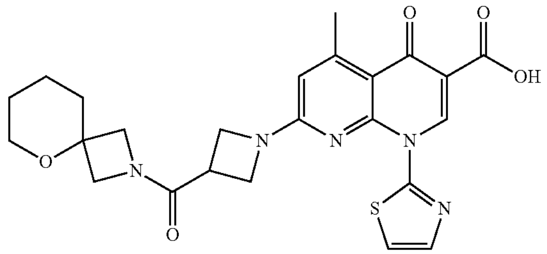

5-Methyl-7-(3-{5-oxa-2-azaspiro[3.5]nonane-2-carbonyl}azetidin-1-yl)-4-oxo-1-(1,3-thiazol-2-yl)-1,4-dihydro-1,8-naphthyridine-3-carboxylic acid The title compound was obtained by the method described in Example 001-(3) or a method equivalent thereto using 2-(azetidine-3-carbonyl)-5-oxa-2-azaspiro[3.5]nonane hydrochloride obtained from 5-oxa-2-azaspiro[3.5]nonane by the methods described in Examples 005-(1) and 001-(2) or methods equivalent thereto, and 7-chloro-5-methyl-4-oxo-1-(1,3-thiazol-2-yl)-1,4-dihydro-1,8-naphthyridine-3-carboxylic acid obtained in Reference Example 001-(2).

1H-NMR (DMSO-d6): δ 1.42-1.49 (2H, m), 1.53-1.64 (2H, m), 1.66-1.76 (2H, m), 2.76 (3H, s), 3.53-3.63 (2H, m), 3.67-3.79 (3H, m), 3.96-4.04 (2H, m), 4.21-4.51 (4H, m), 6.53 (1H, s), 7.75 (1H, d, J=3.5 Hz), 7.84 (1H, d, J=3.5 Hz), 9.84 (1H, s), 15.38 (1H, brs)

Example 651

Compound 651

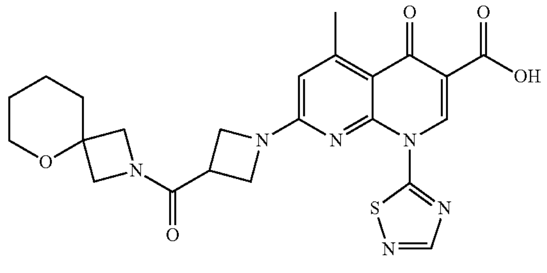

5-Methyl-7-(3-{5-oxa-2-azaspiro[3.5]nonane-2-carbonyl}azetidin-1-yl)-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and 2-(azetidine-3-carbonyl)-5-oxa-2-azaspiro[3.5]nonane hydrochloride obtained in Example 650 by the method described in Example 001-(3) or a method equivalent thereto.

1H-NMR (DMSO-d6): δ 1.42-1.50 (2H, m), 1.53-1.65 (2H, m), 1.66-1.78 (2H, m), 2.75 (3H, s), 3.53-3.64 (2H, m), 3.69-3.81 (3H, m), 3.96-4.00 (2H, m), 4.28-4.64 (4H, m), 6.57 (1H, s), 8.81 (1H, s), 9.74 (1H, s), 15.04 (1H, brs)

Example 652

Compound 652

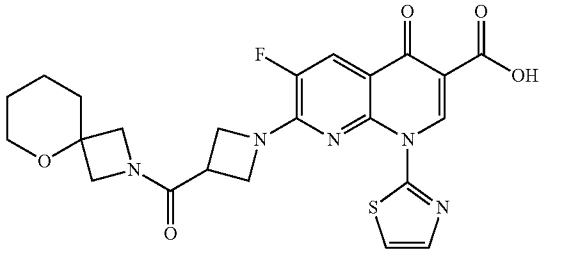

6-Fluoro-7-(3-{5-oxa-2-azaspiro[3.5]nonane-2-carbonyl}azetidin-1-yl)-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and 2-(azetidine-3-carbonyl)-5-oxa-2-azaspiro[3.5]nonane hydrochloride obtained in Example 650 by the method described in Example 001-(3) or a method equivalent thereto.

1H-NMR (DMSO-d6): δ 1.42-1.48 (2H, m), 1.52-1.64 (2H, m), 1.66-1.76 (2H, m), 3.53-3.63 (2H, m), 3.71-3.79 (3H, m), 4.01 (2H, brs), 4.39-4.78 (4H, m), 7.79 (1H, d, J=3.5 Hz), 7.86 (1H, d, J=3.5 Hz), 8.10 (1H, d, J=11.5 Hz), 9.81 (1H, s), 14.78 (1H, brs)

Example 653

Compound 653

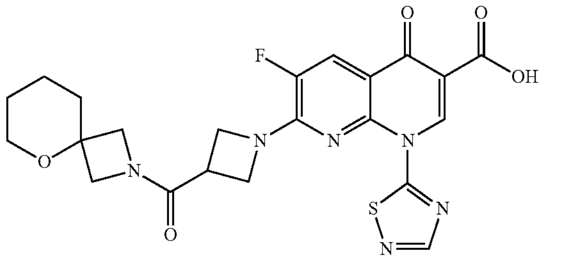

6-Fluoro-7-(3-{5-oxa-2-azaspiro[3.5]nonane-2-carbonyl}azetidin-1-yl)-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and 2-(azetidine-3-carbonyl)-5-oxa-2-azaspiro[3.5]nonane hydrochloride obtained in Example 650 by the method described in Example 001-(3) or a method equivalent thereto.

1H-NMR (DMSO-d6): δ 1.41-1.49 (2H, m), 1.54-1.64 (2H, m), 1.66-1.78 (2H, m), 3.53-3.64 (2H, m), 3.70-3.80 (3H, m), 4.03 (2H, brs), 4.48-4.82 (4H, m), 8.15 (1H, d, J=11.4 Hz), 8.85 (1H, s), 9.74 (1H, s), 14.47 (1H, brs)

Example 654

Compound 654

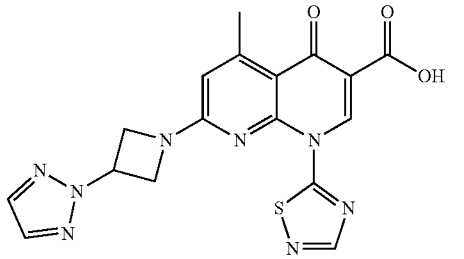

5-Methyl-4-oxo-1-(1,2,4-thiadiazol-5-yl)-7-[3-(2H-1,2,3-triazol-2-yl)azetidin-1-yl]-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and 2-(azetidin-3-yl)-2H-1,2,3-triazole hydrochloride by the method described in Example 001-(3) or a method equivalent thereto.

1H-NMR (DMSO-d6): δ 2.81 (3H, d, J=1.0 Hz), 4.58-5.15 (4H, m), 5.83-5.89 (1H, m), 6.72 (1H, d, J=1.0 Hz), 7.96 (2H, s), 8.82 (1H, s), 9.78 (1H, s), 15.01 (1H, brs)

Example 655

Compound 655

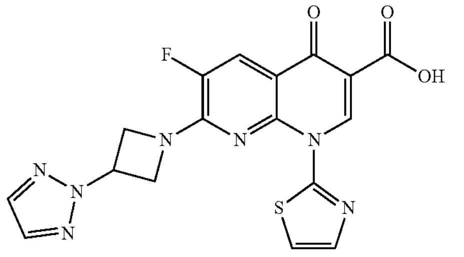

6-Fluoro-4-oxo-1-(1,3-thiazol-2-yl)-7-[3-(2H-1,2,3-triazol-2-yl)azetidin-1-yl]-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and 2-(azetidin-3-yl)-2H-1,2,3-triazole hydrochloride by the method described in Example 001-(3) or a method equivalent thereto.

1H-NMR (DMSO-d6): δ 4.72-5.20 (4H, m), 5.83-5.89 (1H, m), 7.74 (1H, d, J=3.5 Hz), 7.85 (1H, d, J=3.5 Hz), 7.97 (2H, s), 8.19 (1H, d, J=11.3 Hz), 9.84 (1H, s), 14.71 (1H, brs)

Example 656

Compound 656

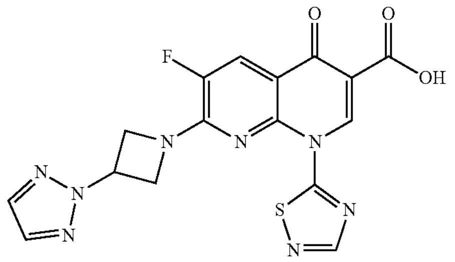

6-Fluoro-4-oxo-1-(1,2,4-thiadiazol-5-yl)-7-[3-(2H-1,2,3-triazol-2-yl)azetidin-1-yl]-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and 2-(azetidin-3-yl)-2H-1,2,3-triazole hydrochloride by the method described in Example 001-(3) or a method equivalent thereto.

1H-NMR (DMSO-d6): δ 4.89-4.95 (2H, m), 5.14-5.25 (2H, m), 5.84-5.90 (1H, m), 7.97 (2H, s), 8.23 (1H, d, J=11.3 Hz), 8.84 (1H, s), 9.77 (1H, s), 14.40 (1H, brs)

Example 657

Compound 657

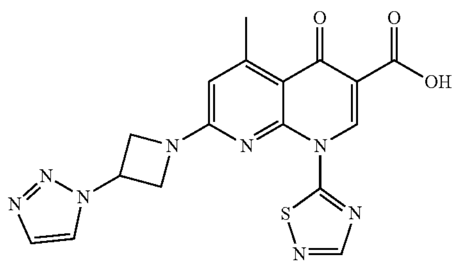

5-Methyl-4-oxo-1-(1,2,4-thiadiazol-5-yl)-7-[3-(1H-1,2,3-triazol-1-yl)azetidin-1-yl]-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and 1-(azetidin-3-yl)-1H-1,2,3-triazole hydrochloride by the method described in Example 001-(3) or a method equivalent thereto.

1H-NMR (DMSO-d6): δ 2.76 (3H, s), 4.61-5.09 (4H, m), 5.82-5.89 (1H, m), 6.67 (1H, s), 7.87 (1H, d, J=0.8 Hz), 8.51 (1H, d, J=0.8 Hz), 8.80 (1H, s), 9.69 (1H, s), 14.95 (1H, brs)

Example 658

Compound 658

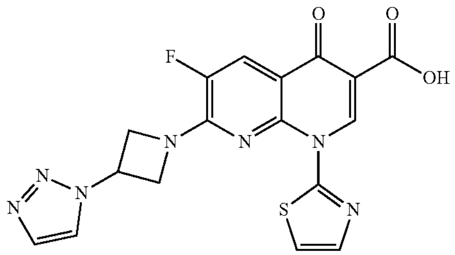

6-Fluoro-4-oxo-1-(1,3-thiazol-2-yl)-7-[3-(1H-1,2,3-triazol-1-yl)azetidin-1-yl]-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and 1-(azetidin-3-yl)-1H-1,2,3-triazole hydrochloride by the method described in Example 001-(3) or a method equivalent thereto.

1H-NMR (DMSO-d6): δ 4.74-5.20 (4H, m), 5.84-5.90 (1H, m), 7.75 (1H, d, J=3.5 Hz), 7.85 (1H, d, J=3.5 Hz), 7.86 (1H, d, J=1.0 Hz), 8.19 (1H, d, J=11.3 Hz), 8.53 (1H, d, J=1.0 Hz), 9.83 (1H, s), 14.71 (1H, brs)

Example 659

Compound 659

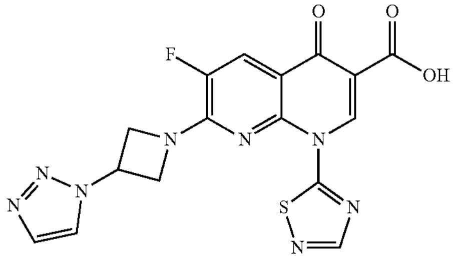

6-Fluoro-4-oxo-1-(1,2,4-thiadiazol-5-yl)-7-[3-(1H-1,2,3-triazol-1-yl)azetidin-1-yl]-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and 1-(azetidin-3-yl)-1H-1,2,3-triazole hydrochloride by the method described in Example 001-(3) or a method equivalent thereto.

1H-NMR (DMSO-d6): δ 4.88-5.01 (2H, m), 5.13-5.24 (2H, m), 5.84-5.90 (1H, m), 7.87 (1H, d, J=1.0 Hz), 8.24 (1H, d, J=11.3 Hz), 8.53 (1H, d, J=1.0 Hz), 8.85 (1H, s), 9.77 (1H, s), 14.41 (1H, brs)

Example 660

Compound 660

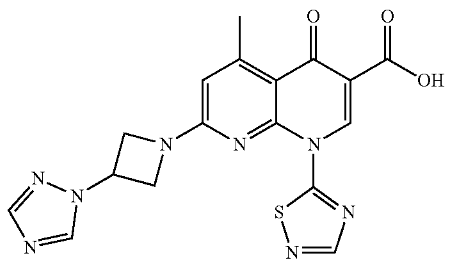

5-Methyl-4-oxo-1-(1,2,4-thiadiazol-5-yl)-7-[3-(1H-1,2,4-triazol-1-yl)azetidin-1-yl]-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and 1-(azetidin-3-yl)-1H-1,2,4-triazole hydrochloride by the method described in Example 001-(3) or a method equivalent thereto.

1H-NMR (DMSO-d6): δ 2.79 (3H, d, J=1.0 Hz), 4.52-5.03 (4H, m), 5.66-5.72 (1H, m), 6.68 (1H, d, J=1.0 Hz), 8.12 (1H, s), 8.76 (1H, s), 8.81 (1H, s), 9.76 (1H, s), 15.00 (1H, brs)

Example 661

Compound 661

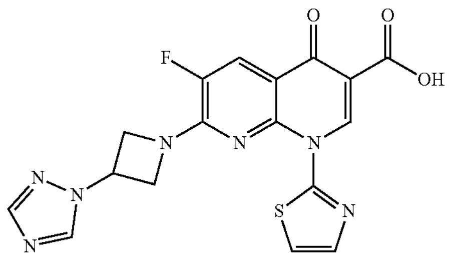

6-Fluoro-4-oxo-1-(1,3-thiazol-2-yl)-7-[3-(1H-1,2,4-triazol-1-yl)azetidin-1-yl]-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and 1-(azetidin-3-yl)-1H-1,2,4-triazole hydrochloride by the method described in Example 001-(3) or a method equivalent thereto.

1H-NMR (DMSO-d6): δ 4.64-5.14 (4H, m), 5.67-5.74 (1H, m), 7.74 (1H, d, J=3.5 Hz), 7.85 (1H, d, J=3.5 Hz), 8.14 (1H, s), 8.17 (1H, d, J=11.3 Hz), 8.77 (1H, s), 9.82 (1H, s), 14.71 (1H, brs)

Example 662

Compound 662

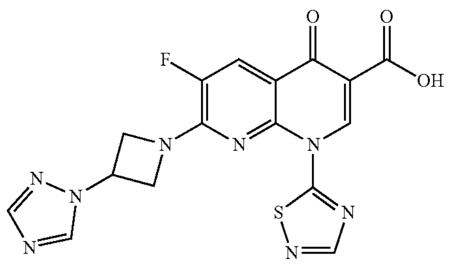

6-Fluoro-4-oxo-1-(1,2,4-thiadiazol-5-yl)-7-[3-(1H-1,2,4-triazol-1-yl)azetidin-1-yl]-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and 1-(azetidin-3-yl)-1H-1,2,4-triazole hydrochloride by the method described in Example 001-(3) or a method equivalent thereto.

1H-NMR (DMSO-d6): δ 4.80-5.17 (4H, m), 5.67-5.73 (1H, m), 8.14 (1H, s), 8.22 (1H, d, J=11.3 Hz), 8.78 (1H, s), 8.84 (1H, s), 9.76 (1H, s), 14.41 (1H, brs)

Example 663

Compound 663

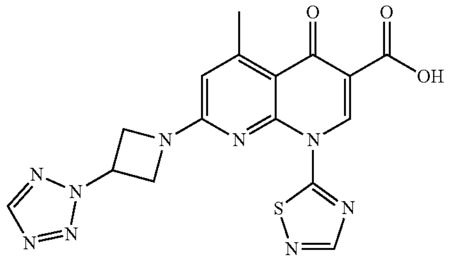

5-Methyl-4-oxo-7-[3-(2H-1,2,3,4-tetrazol-2-yl)azetidin-1-yl]-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and 2-(azetidin-3-yl)-2H-1,2,3,4-tetrazole hydrochloride obtained by the method described in Example 480-(1) and Example 480-(2) or a method equivalent thereto from 1H-tetrazole by the method described in Example 001-(3) or a method equivalent thereto.

1H-NMR (DMSO-d6): δ 2.82 (3H, d, J=1.0 Hz), 4.54-5.20 (4H, m), 6.15-6.21 (1H, m), 6.75 (1H, d, J=1.0 Hz), 8.82 (1H, s), 9.14 (1H, s), 9.79 (1H, s), 14.97 (1H, brs)

Example 664

Compound 664

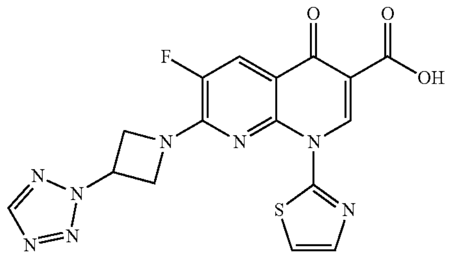

6-Fluoro-4-oxo-7-[3-(2H-1,2,3,4-tetrazol-2-yl)azetidin-1-yl]-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and 2-(azetidin-3-yl)-2H-1,2,3,4-tetrazole hydrochloride obtained in Example 663 by the method described in Example 001-(3) or a method equivalent thereto.

1H-NMR (DMSO-d6): δ 4.84-5.22 (4H, m), 6.15-6.21 (1H, m), 7.76 (1H, d, J=3.5 Hz), 7.86 (1H, d, J=3.5 Hz), 8.21 (1H, d, J=11.3 Hz), 9.15 (1H, s), 9.84 (1H, s), 14.67 (1H, brs)

Example 665

Compound 665

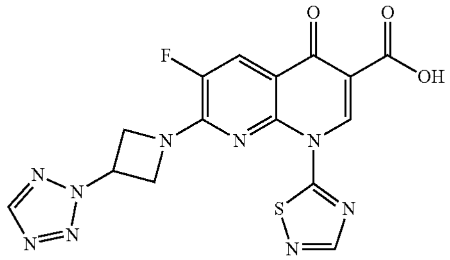

6-Fluoro-4-oxo-7-[3-(2H-1,2,3,4-tetrazol-2-yl)azetidin-1-yl]-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and 2-(azetidin-3-yl)-2H-1,2,3,4-tetrazole hydrochloride obtained in Example 663 by the method described in Example 001-(3) or a method equivalent thereto.

1H-NMR (DMSO-d6): δ 4.97-5.59 (4H, m), 6.16-6.22 (1H, m), 8.26 (1H, d, J=11.2 Hz), 8.85 (1H, s), 9.15 (1H, s), 9.78 (1H, s), 14.36 (1H, brs)

Example 666

Compound 666

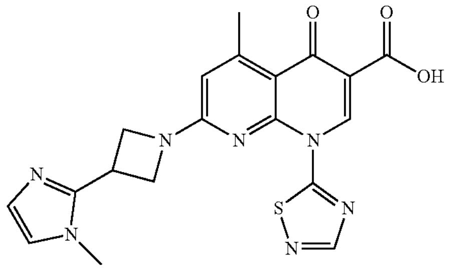

5-Methyl-7-[3-(1-methyl-1H-imidazol-2-yl)azetidin-1-yl]-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and 2-(azetidin-3-yl)-1-methyl-1H-imidazole trifluoroacetate by the method described in Example 001-(3) or a method equivalent thereto.

1H-NMR (DMSO-d6): δ 2.77 (3H, s), 3.62 (3H, s), 4.25-4.33 (1H, m), 4.48-4.89 (4H, m), 6.59 (1H, s), 6.86 (1H, s), 7.14 (1H, s), 8.80 (1H, s), 9.72 (1H, s), 15.07 (1H, brs)

Example 667

Compound 667

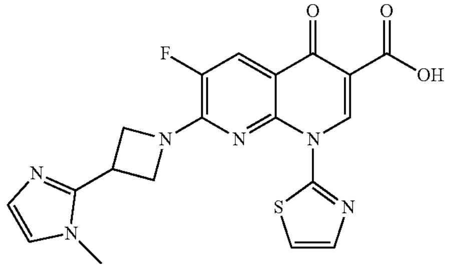

6-Fluoro-7-[3-(1-methyl-1H-imidazol-2-yl)azetidin-1-yl]-4-oxo-1-(1,3-thiazol-2-yl)-1,4-dihydro-1,8-naphthyridine-3-carboxylic acid The title compound was obtained using 7-chloro-6-fluoro4-oxo-1-(1,3-thiazol-2-yl)-1,4-dihydro-1,8-naphthyridine-3-carboxylic acid obtained in Reference Example 003-(2) and 2-(azetidin-3-yl)-1-methyl-1H-imidazole trifluoroacetate by the method described in Example 001-(3) or a method equivalent thereto.

1H-NMR (DMSO-d6): δ 3.68 (3H, s), 4.40-4.48 (1H, m), 4.56-5.06 (4H, m), 7.18 (1H, s), 7.34 (1H, s), 7.79 (1H, d, J=3.5 Hz), 7.87 (1H, d, J=3.5 Hz), 8.14 (1H, d, J=11.3 Hz), 9.81 (1H, s), 14.74 (1H, brs)

Example 668

Compound 668

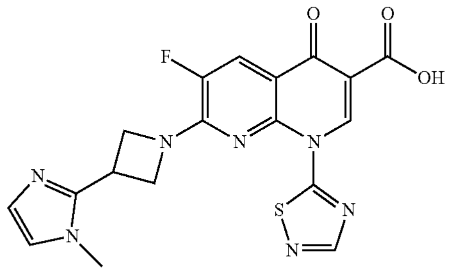

6-Fluoro-7-[3-(1-methyl-1H-imidazol-2-yl)azetidin-1-yl]-4-oxo-1-(1,2,4-thiadiazol-5-yl)-1,4-dihydro-1,8-naphthyridine-3-carboxylic acid The title compound was obtained using 7-chloro-6-fluoro4-oxo-1-(1,2,4-thiadiazol-5-yl)-1,4-dihydro-1,8-naphthyridine-3-carboxylic acid obtained in Reference Example 004-(2) and 2-(azetidin-3-yl)-1-methyl-1H-imidazole trifluoroacetate by the method described in Example 001-(3) or a method equivalent thereto.

1H-NMR (DMSO-d6): δ 3.64 (3H, s), 4.33-4.41 (1H, m), 4.68-5.06 (4H, m), 6.98 (1H, s), 7.22 (1H, sa), 8.18 (1H, d, J=11.3 Hz), 8.85 (1H, s), 9.76 (1H, s), 14.50 (1H, brs)

Example 669

Compound 669

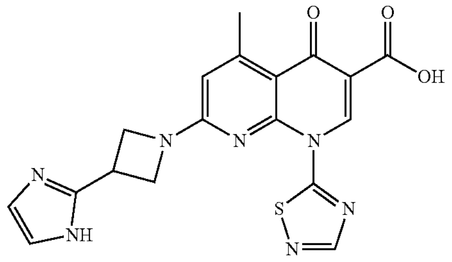

7-[3-(1H-Imidazol-2-yl)azetidin-1-yl]-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and 2-(azetidin-3-yl)-1H-imidazole trifluoroacetate by the method described in Example 001-(3) or a method equivalent thereto.

1H-NMR (DMSO-d6): δ 2.77 (3H, s), 4.19-4.26 (1H, m), 4.40-4.48 (1H, m), 4.56-4.71 (2H, m), 4.77-4.86 (1H, m), 6.62 (1H, d, J=1.0 Hz), 7.08 (2H, s), 8.82 (1H, s), 9.73 (1H, s), 12.48 (1H, brs), 15.10 (1H, brs)

Example 670

Compound 670

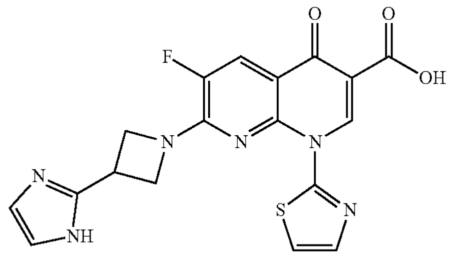

6-Fluoro-7-[3-(1H-imidazol-2-yl)azetidin-1-yl]-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and 2-(azetidin-3-yl)-1H-imidazole trifluoroacetate by the method described in Example 001-(3) or a method equivalent thereto.

1H-NMR (DMSO-d6): δ 4.24-4.31 (1H, m), 4.52-5.04 (4H, m), 7.17 (2H, s), 7.81 (1H, d, J=3.5 Hz), 7.86 (1H, d, J=3.5 Hz), 8.14 (1H, d, J=11.4 Hz), 9.82 (1H, s), 12.86 (1H, brs), 14.75 (1H, brs)

Example 671

Compound 671

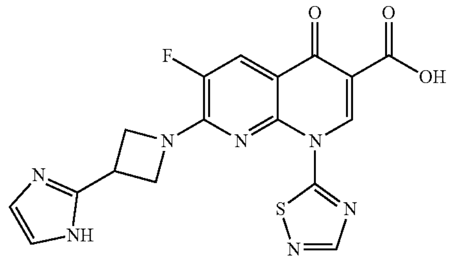

6-Fluoro-7-[3-(1H-imidazol-2-yl)azetidin-1-yl]-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and 2-(azetidin-3-yl)-1H-imidazole trifluoroacetate by the method described in Example 001-(3) or a method equivalent thereto.

1H-NMR (DMSO-d6): δ 4.43-4.51 (1H, m), 4.73-5.10 (4H, m), 7.54 (2H, s), 8.22 (1H, d, J=11.4 Hz), 8.86 (1H, s), 9.75 (1H, s), 14.27 (2H, brs)

Example 672

Compound 672

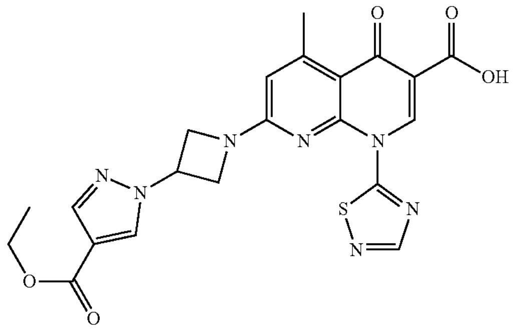

7-{3-[4-(Ethoxycarbonyl)-1H-pyrazol-1-yl]azetidin-1-yl}-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and ethyl 1-(azetidin-3-yl)-1H-pyrazole-4-carboxylate acetate obtained from ethyl 1H-pyrazole-4-carboxylate by the method described in Example 480-(1) and Example 480-(2) or a method equivalent thereto by the method described in Example 001-(3) or a method equivalent thereto.

1H-NMR (DMSO-d6): δ 1.27 (3H, t, J=7.3 Hz), 2.77 (3H, s), 4.50 (2H, q, J=7.3 Hz), 4.50-5.02 (4H, m), 5.54-5.65 (1H, m), 6.63 (1H, s), 8.01 (1H, s), 8.62 (1H, s), 8.79 (1H, s), 9.72 (1H, s)

Example 673

Compound 673

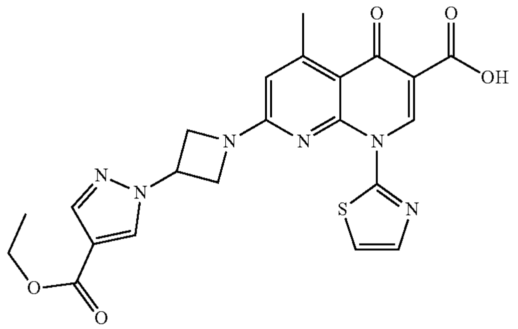

7-{3-[4-(Ethoxycarbonyl)-1H-pyrazol-1-yl]azetidin-1-yl}-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and ethyl 1-(azetidin-3-yl)-1H-pyrazole-4-carboxylate acetate obtained in Example 672 by the method described in Example 008 or a method equivalent thereto.

1H-NMR (DMSO-d6): δ 1.27 (3H, t, J=7.5 Hz), 2.79 (3H, s), 4.60 (2H, q, J=7.5 Hz), 4.50-5.02 (4H, m), 5.56-5.63 (1H, m), 6.62 (1H, s), 7.70 (1H, d, J=3.5 Hz), 7.83 (1H, d, J=3.5 Hz), 8.01 (1H, s), 8.60 (1H, s), 9.85 (1H, s)

Example 674

Compound 674

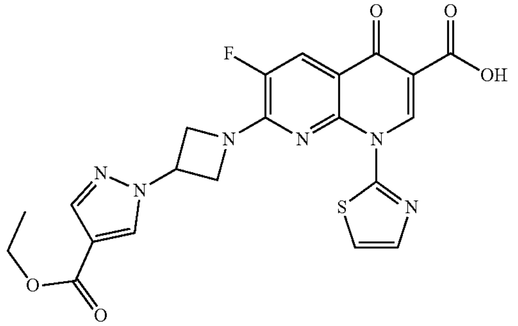

7-{3-[4-(Ethoxycarbonyl)-1H-pyrazol-1-yl]azetidin-1-yl}-6-fluoro-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and ethyl 1-(azetidin-3-yl)-1H-pyrazole-4-carboxylate acetate obtained in Example 672 by the method described in Example 008 or a method equivalent thereto.

1H-NMR (DMSO-d6): δ 1.27 (3H, t, J=7.3 Hz), 4.22 (2H, q, J=7.3 Hz), 4.70-5.07 (4H, m), 5.56-5.67 (1H, m), 7.71 (1H, d, J=3.5 Hz), 7.83 (1H, d, J=3.5 Hz), 8.01 (1H, s), 8.15 (1H, d, J=10.7 Hz), 8.56 (1H, s), 9.85 (1H, s)

Example 675

Compound 675

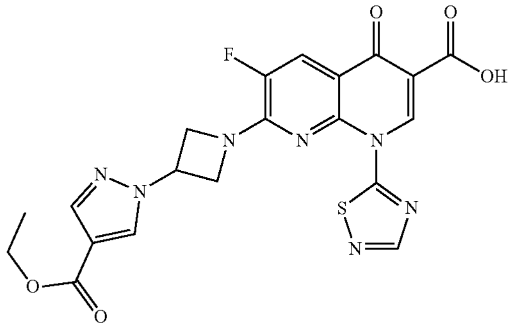

7-{3-[4-(Ethoxycarbonyl)-1H-pyrazol-1-yl]azetidin-1-yl}-6-fluoro-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8- naphthyridine-3-carboxylic acid obtained in Reference Example 004-(2) and ethyl 1-(azetidin-3-yl)-1H-pyrazole-4-carboxylate acetate obtained in Example 672 by the method described in Example 008 or a method equivalent thereto.

1H-NMR (DMSO-d6): δ 1.27 (3H, t, J=7.3 Hz), 4.23 (2H, q, J=7.3 Hz), 4.74-5.17 (4H, m), 5.54-5.68 (1H, m), 8.02 (1H, s), 8.19 (1H, d, J=12.0 Hz), 8.66 (1H, s), 8.84 (1H, s), 9.74 (1H, s)

Example 676

Compound 676

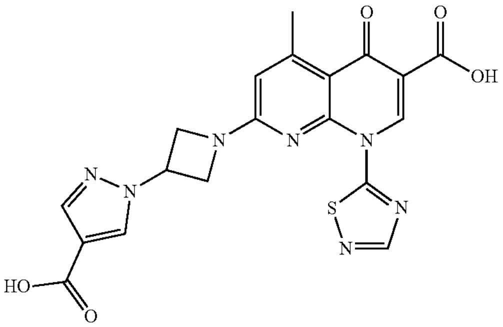

7-[3-(4-Carboxy-1H-pyrazol-1-yl)azetidin-1-yl]-5-methyl-4-oxo-1-(1,2,4-thiadiazol-5-yl)-1,4-dihydro-1,8-naphthyridine-3-carboxylic acid The title compound was obtained using 7-{3-[4-(ethoxycarbonyl)-1H-pyrazol-1-yl]azetidin-1-yl}-5-methyl-4-oxo-(1,2,4-thiadiazol-5-yl)-1,4-dihydro-1,8-naphthyridine-3-carboxylic acid obtained in Example 672 by the method described in Example 028-(2) or a method equivalent thereto.

1H-NMR (DMSO-d6): δ 2.79 (3H, s), 4.52-5.03 (4H, m), 5.54-5.65 (1H, m), 6.67 (1H, s), 7.96 (1H, s), 8.54 (1H, s), 8.81 (1H, s), 9.74 (1H, s)

Example 677

Compound 677

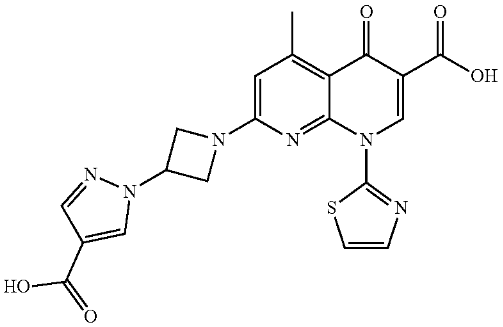

7-[3-(4-Carboxy-1H-pyrazol-1-yl)azetidin-1-yl]-5-methyl-4-oxo-1-(1,3-thiazol-2-yl)-1,4-dihydro-1,8-naphthyridine-3-carboxylic acid The title compound was obtained using 7-{3-[4-(ethoxycarbonyl)-1H-pyrazol-1-yl]azetidin-1-yl}-5-methyl-4-oxo-1-(1,3-thiazol-2-yl)-1,4-dihydro-1,8-naphthyridine-3-carboxylic acid obtained in Example 673 by the method described in Example 028-(2) or a method equivalent thereto.

1H-NMR (DMSO-d6): δ 2.81 (3H, s), 4.52-5.03 (4H, m), 5.53-5.62 (1H, m), 6.65 (1H, as), 7.71 (1H, d, J=3.5 Hz), 7.83 (1H, d, J=3.5 Hz), 7.93 (1H, s), 8.47 (1H, s), 9.87 (1H, s)

Example 678

Compound 678

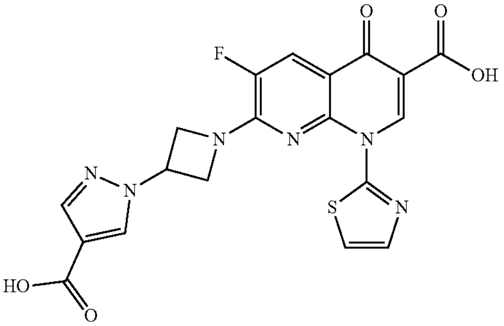

7-[3-(4-Carboxy-1H-pyrazol-1-yl)azetidin-1-yl]-6-fluoro-4-oxo-1-(1,3-thiazol-2-yl)-1,4-dihydro-1,8-naphthyridine-3-carboxylic acid The title compound was obtained using 7-{3-[4-(ethoxycarbonyl)-1H-pyrazol-1-yl]azetidin-1-yl}-6-fluoro-4-oxo-1-(1,3-thiazol-2-yl)-1,4-dihydro-1,8-naphthyridine-3-carboxylic acid obtained in Example 674 by the method described in Example 028-(2) or a method equivalent thereto.

1H-NMR (DMSO-d6): δ 4.63-5.11 (4H, m), 5.54-5.65 (1H, m), 7.74 (1H, d, J=3.8 Hz), 7.85 (1H, d, J=3.8 Hz), 7.95 (1H, s), 8.16 (1H, d, J=12.0 Hz), 8.53 (1H, s), 9.83 (1H, s)

Example 679

Compound 679

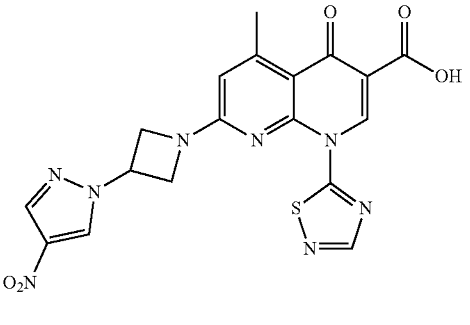

5-Methyl-7-[3-(4-nitro-1H-pyrazol-1-yl)azetidin-1-yl]-4-oxo-1-(1,2,4-thiadiazol-5-yl)-1,4-dihydro-1,8-naphthyridine-3-carboxylic acid (1) To a solution of 1-[1-(diphenylmethyl)azetidin-3-yl]-4-nitro-1H-pyrazole (170 mg) in methylene chloride obtained from 4-nitro-1H-pyrazole by the method described in Example 480-(1) or a method equivalent thereto was added 1-chloroethyl chloroformate (78 μL) under ice cooling, and the mixture was stirred at 50° C. for 30 minutes. After concentration, to the residue was added methanol (5 mL), and the mixture was stirred at 80° C. for 19 hours. To the reaction solution was added 1 mol/L hydrochloric acid, and the mixture was washed with methylene chloride. The aqueous layer was concentrated to obtain 69 mg of 1-(azetidin-3-yl)-4-nitro-1H-pyrazole hydrochloride.

1H-NMR (DMSO-d6): δ 4.28-4.48 (4H, m), 5.40-5.54 (1H, m), 8.49 (1H, s), 9.05 (1H, s), 9.08 (2H, brs)

(2) The title compound was obtained by the method described in Example 001-(3) or a method equivalent thereto using 1-(azetidin-3-yl)-4-nitro-1H-pyrazole hydrochloride obtained in the preceding section, and 7-chloro-5-methyl-4-oxo-1-(1,2,4-thiadiazol-5-yl)-1,4-dihydro-1,8-naphthyridine-3-carboxylic acid obtained in Reference Example 002-(2).

1H-NMR (DMSO-d6): δ 2.79 (3H, s), 4.51-5.06 (4H, m), 5.53-5.67 (1H, m), 6.69 (1H, s), 8.43 (1H, s), 8.82 (1H, s), 9.19 (1H, s), 9.76 (1H, s), 15.00 (1H, brs)

Example 680

Compound 680

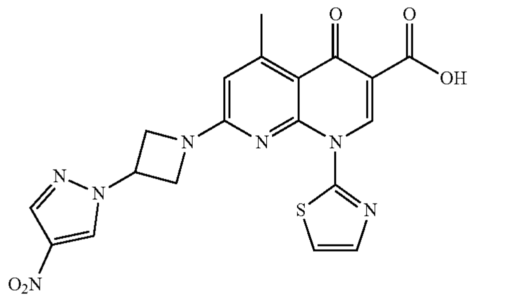

5-Methyl-7-[3-(4-nitro-1H-pyrazol-1-yl)azetidin-1-yl]-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and 1-(azetidin-3-yl)-4-nitro-1H-pyrazole hydrochloride obtained in Example 679-(1) by the method described in Example 008 or a method equivalent thereto.

1H-NMR (DMSO-d6): δ 2.78 (3H, s), 4.50-4.92 (4H, m), 5.56-5.63 (1H, m), 6.62 (1H, s), 7.70 (1H, d, J=3.5 Hz), 7.83 (1H, d, J=3.5 Hz), 8.43 (1H, s), 9.17 (1H, s), 9.83 (1H, s)

Example 681

Compound 681

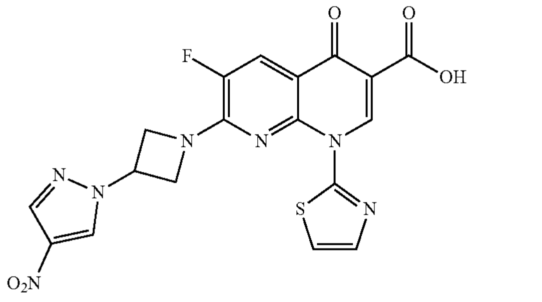

6-Fluoro-7-[3-(4-nitro-1H-pyrazol-1-yl)azetidin-1-yl]-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and 1-(azetidin-3-yl)-4-nitro-1H-pyrazole hydrochloride obtained in Example 679-(1) by the method described in Example 008 or a method equivalent thereto.

1H-NMR (DMSO-d6): δ 4.69-5.15 (4H, m), 5.55-5.68 (1H, m), 7.75 (1H, d, J=3.5 Hz), 7.85 (1H, d, J=3.5 Hz), 8.18 (1H, d, J=11.2 Hz), 8.44 (1H, s), 9.21 (1H, s), 9.84 (1H, s)

Example 682

Compound 682

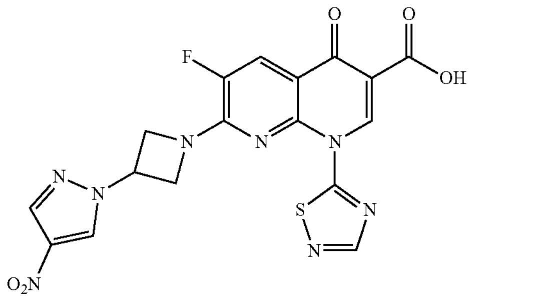

6-Fluoro-7-[3-(4-nitro-1H-pyrazol-1-yl)azetidin-1-yl]-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and 1-(azetidin-3-yl)-4-nitro-1H-pyrazole hydrochloride obtained in Example 679-(1) by the method described in Example 008 or a method equivalent thereto.

1H-NMR (DMSO-d6): δ 4.79-5.24 (4H, m), 5.54-5.70 (1H, m), 8.24 (1H, d, J=10.3 Hz), 8.44 (1H, s), 8.85 (1H, s), 9.23 (1H, s), 9.77 (1H, s), 14.39 (1H, brs)

Example 683

Compound 683

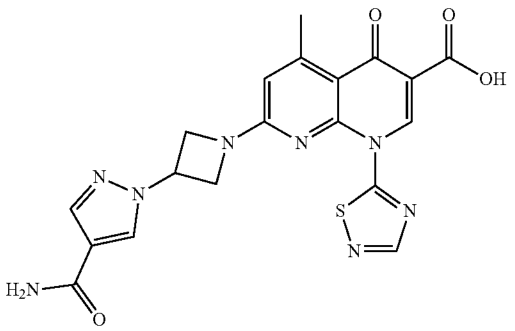

7-[3-(4-Carbamoyl-1H-pyrazol-1-yl)azetidin-1-yl]-5-methyl-4-oxo-1-(1,2,4-thiadiazol-5-yl)-1,4-dihydro-1,8-naphthyridine-3-carboxylic acid (1) To a solution of I-[1-(diphenylmethyl)azetidin-3-yl]-1H-pyrazole-4-carboxylic acid (230 mg) in DMF (2 mL) obtained from ethyl 1H-pyrazole-4-carboxylate by the methods described in Examples 480-(1) and 028-(2) or methods equivalent thereto was added CDI (170 mg) under ice cooling, and the mixture was stirred at room temperature for 30 minutes. To the reaction solution was added 28% ammonia water (2 mL) under ice cooling, and the mixture was stirred at room temperature for 1 week. To the reaction solution was added a saturated aqueous solution of ammonium chloride, and the mixture was extracted with ethyl acetate. The organic layer was washed with water and brine and then dried over sodium sulfate. After concentration, the residue was purified by silica gel column chromatography (eluent: ethyl acetate/n-hexane) to obtain 140 mg of 1-[1-(diphenylmethyl)azetidin-3-yl]-1H-pyrazole-4-carboxamide.

1H-NMR (CDCl3): δ 3.44-3.51 (2H, m), 3.64-3.74 (2H, m), 4.51 (1H, s), 4.93-5.02 (1H, m), 7.21 (2H, t, J=7.4 Hz), 7.29 (4H, t, J=7.2 Hz), 7.44 (4H, d, J=7.3 Hz), 7.77 (1H, s), 8.15 (1H, s)

(2) The title compound was obtained by the method described in Example 001-(3) or a method equivalent thereto using 1-(azetidin-3-yl)-1H-pyrazole-4-carboxamide acetate obtained by the method described in Example 480-(2) or a method equivalent thereto using 1-[l-(diphenylmethyl)azetidin-3-yl]-1H-pyrazole-4-carboxamide obtained in the preceding section, and 7-chloro-5-methyl-4-oxo-1-(1,2,4-thiadiazol-5-yl)-1,4-dihydro-1,8-naphthyridine-3-carboxylic acid obtained in Reference Example 002-(2).

1H-NMR (DMSO-d6): δ 2.78 (3H, s), 4.44-5.08 (4H, m), 5.48-5.64 (1H, m), 6.66 (1H, s), 7.99 (1H, s), 8.40 (1H, a), 8.80 (1H, s), 9.72 (1H, s), 14.98 (1H, brs)

Example 684

Compound 684

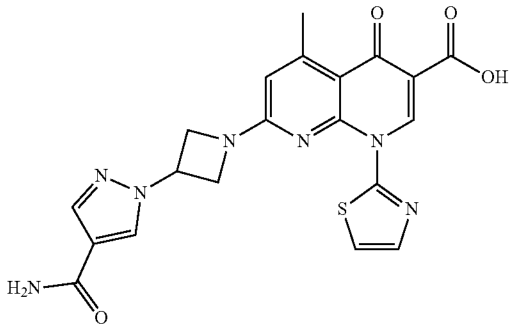

7-[3-(4-Carbamoyl-1H-pyrazol-1-yl)azetidin-1-yl]-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and 1-(azetidin-3-yl)-1H-pyrazole-4-carboxamide acetate obtained in Example 683 by the method described in Example 008 or a method equivalent thereto.

1H-NMR (DMSO-d6): δ 2.78 (3H, s), 4.46-4.91 (4H, m), 5.51-5.59 (1H, m), 6.64 (1H, s), 7.05 (2H, brs), 7.70 (1H, d, J=3.5 Hz), 7.83 (1H, d, J=3.5 Hz), 7.99 (1H, s), 8.38 (1H, s), 9.86 (1H, s), 15.35 (1H, brs)

Example 685

Compound 685

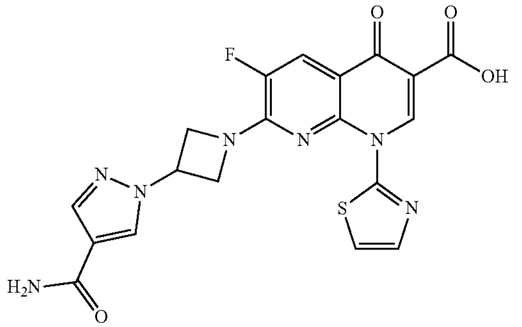

7-[3-(4-Carbamoyl-1H-pyrazol-1-yl)azetidin-1-yl]-6-fluoro-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and 1-(azetidin-3-yl)-1H-pyrazole-4-carboxamide acetate obtained in Example 683 by the method described in Example 008 or a method equivalent thereto.

1H-NMR (DMSO-d6): δ 4.61-5.14 (4H, m), 5.49-5.66 (1H, m), 7.74 (1H, d, J=3.5 Hz), 7.85 (1H, d, J=3.5 Hz), 8.01 (1H, s), 8.18 (1H, d, J=11.0 Hz), 8.40 (1H, s), 9.84 (1H, s), 14.71 (1H, brs)

Example 686

Compound 686

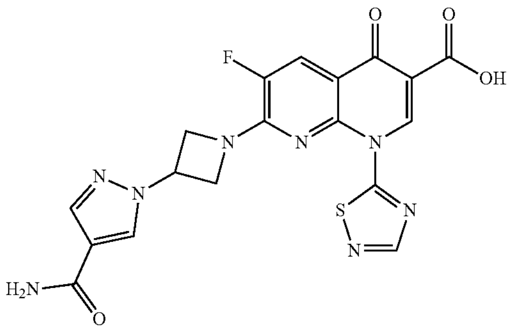

7-[3-(4-Carbamoyl-1H-pyrazol-1-yl)azetidin-1-yl]-6-fluoro-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and 1-(azetidin-3-yl)-1H-pyrazole-4-carboxamide acetate obtained in Example 683 by the method described in Example 008 or a method equivalent thereto.

1H-NMR (DMSO-d6): δ 4.74-5.16 (4H, m), 5.50-5.61 (1H, m), 8.01 (1H, s), 8.22 (1H, d, J=11.1 Hz), 8.43 (1H, s), 8.84 (1H, s), 9.76 (1H, s), 14.43 (1H, brs)

Example 687

Compound 687

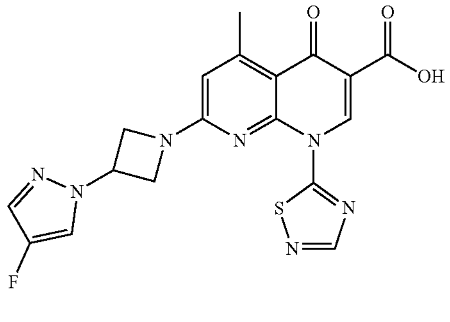

7-[3-(4-Fluoro-1H-pyrazol-1-yl)azetidin-1-yl]-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and 1-(azetidin-3-yl)-4-fluoro-1H-pyrazole hydrochloride obtained from 4-fluoro-1H-pyrazole by the method described in Example 480-(1) and Example 480-(2) or a method equivalent thereto by the method described in Example 001-(3) or a method equivalent thereto.

1H-NMR (DMSO-d6): δ 2.76 (3H, s), 4.43-4.99 (4H, m), 5.33-5.53 (1H, m), 6.62 (1H, s), 7.65 (1H, d, J=4.3 Hz), 8.19 (1H, d, J=4.3 Hz), 8.80 (1H, s), 9.69 (1H, s), 14.95 (1H, brs)

Example 688

Compound 688

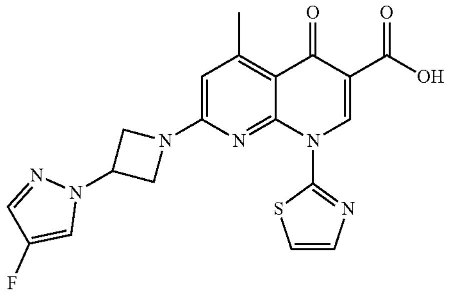

7-[3-(4-Fluoro-1H-pyrazol-1-yl)azetidin-1-yl]-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and 1-(azetidin-3-yl)-4-fluoro-1H-pyrazole hydrochloride obtained in Example 687 by the method described in Example 008 or a method equivalent thereto.

1H-NMR (DMSO-d6): δ 2.76 (3H, s), 4.46-4.88 (4H, m), 5.37-5.50 (1H, m), 6.58 (1H, s), 7.66 (1H, d, J=4.3 Hz), 7.68 (1H, d, J=3.5 Hz), 7.81 (1H, d, J=3.5 Hz), 8.19 (1H, d, J=4.3 Hz), 9.81 (1H, s), 15.30 (1H, brs)

Example 689

Compound 689

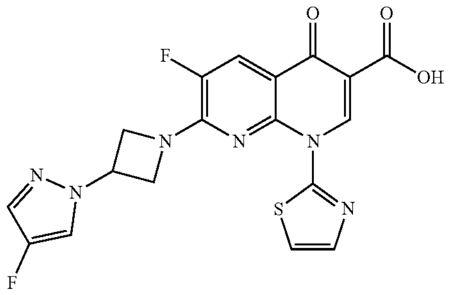

6-Fluoro-7-[3-(4-fluoro-1H-pyrazol-1-yl)azetidin-1-yl]-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and 1-(azetidin-3-yl)-4-fluoro-1H-pyrazole hydrochloride obtained in Example 687 by the method described in Example 008 or a method equivalent thereto.

1H-NMR (DMSO-d6): δ 4.69-5.15 (4H, m), 5.55-5.68 (1H, m), 7.66 (1H, d, J=4.6 Hz), 7.74 (1H, d, J=3.5 Hz), 7.85 (1H, d, J=3.5 Hz), 8.16 (1H, d, J=11.2 Hz), 8.20 (1H, d, J=4.6 Hz), 9.83 (1H, s), 14.71 (1H, brs)

Example 690

Compound 690

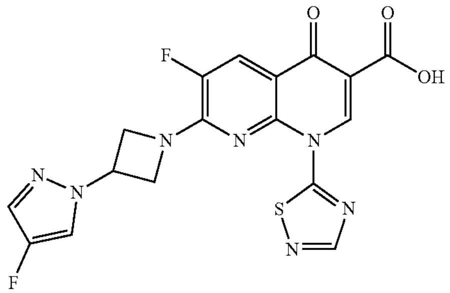

6-Fluoro-7-[3-(4-fluoro-1H-pyrazol-1-yl)azetidin-1-yl]-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and 1-(azetidin-3-yl)-4-fluoro-1H-pyrazole hydrochloride obtained in Example 687 by the method described in Example 008 or a method equivalent thereto.

1H-NMR (DMSO-d6): δ 4.75-5.15 (4H, m), 5.41-5.52 (1H, m), 7.67 (1H, d, J=4.3 Hz), 8.18-8.24 (2H, m), 8.85 (1H, s), 9.77 (1H, s), 14.36 (1H, brs)

Example 691

Compound 691

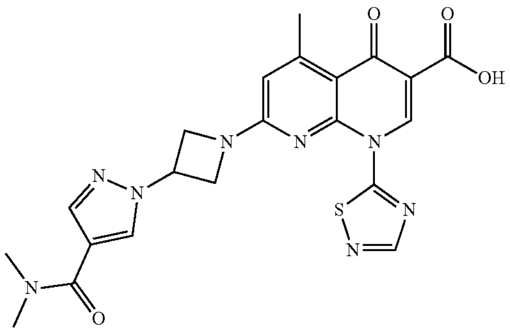

7-{3-[4-(Dimethylcarbamoyl)-1H-pyrazol-1-yl]azetidin-1-yl}-5-methyl-4-oxo-1-(1,2,4-thiadiazol-5-yl)-1,4-dihydro-1,8-naphthyridine-3-carboxylic acid The title compound was obtained by the method described in Example 001-(3) or a method equivalent thereto using 7-chloro-5-methyl-4-oxo-1-(1,2,4-thiadiazol-5-yl)-1,4-dihydro-1,8-naphthyridine-3-carboxylic acid obtained in Reference Example 002-(2) and 1-(azetidin-3-yl)-N,N-dimethyl-1H-pyrazole-4-carboxamide acetate obtained by the method described in Example 683-(1) and Example 480-(2) or a method equivalent thereto from 1-[1-(diphenylmethyl)azetidin-3-yl]-1H-pyrazole-4-carboxylic acid obtained by the method described in Example 480-(1) and Example 028-(2) or a method equivalent thereto from ethyl 1H-pyrazole-4-carboxylate.

1H-NMR (DMSO-d6): δ 2.78 (3H, s), 2.91-3.24 (6H, m), 4.54-5.03 (4H, m), 5.51-5.66 (1H, m), 6.65 (1H, s), 7.88 (1H, s), 8.40 (1H, s), 8.88 (1H, s), 9.73 (1H, 8)

Example 692

Compound 692

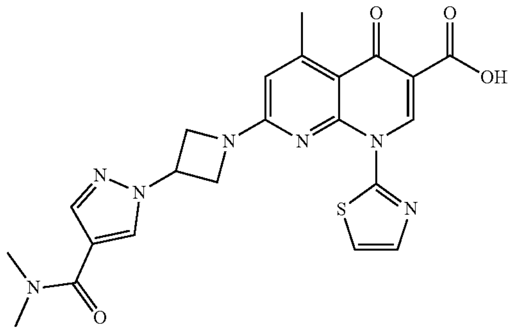

7-{3-[4-(Dimethylcarbamoyl)-1H-pyrazol-1-yl]azetidin-1-yl}-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and 1-(azetidin-3-yl)-N,N-dimethyl-1H-pyrazole-4-carboxamide acetate obtained in Example 691 by the method described in Example 008 or a method equivalent thereto.

1H-NMR (DMSO-d6): δ 2.77 (3H, s), 2.89-3.22 (6H, m), 4.48-4.89 (4H, m), 5.51-5.63 (1H, m), 6.61 (1H, s), 7.69 (1H, d, J=3.5 Hz), 7.81 (1H, d, J=3.5 Hz), 7.89 (1H, s), 8.38 (1H, s), 9.82 (1H, s), 15.32 (1H, brs)

Example 693

Compound 693

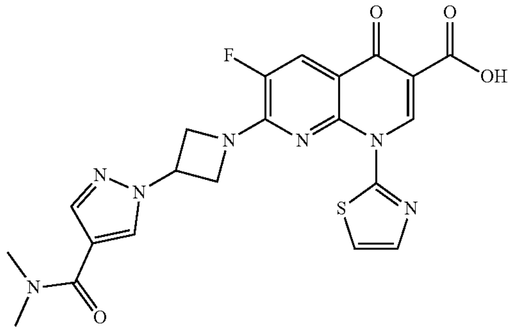

7-{3-[4-(Dimethylcarbamoyl)-1H-pyrazol-1-yl]azetidin-1-yl}-6-fluoro-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and 1-(azetidin-3-yl)-N,N-dimethyl-1H-pyrazole-4-carboxamide acetate obtained in Example 691 by the method described in Example 008 or a method equivalent thereto.

1H-NMR (DMSO-d6): δ 2.91-3.24 (6H, m), 4.54-5.03 (4H, m), 5.51-5.66 (1H, m), 7.74 (1H, d, J=3.5 Hz), 7.85 (1H, d, J=3.5 Hz), 7.89 (1H, s), 8.17 (1H, d, J=11.4 Hz), 8.40 (1H, s), 9.84 (1H, s), 14.75 (1H, brs)

Example 694

Compound 694

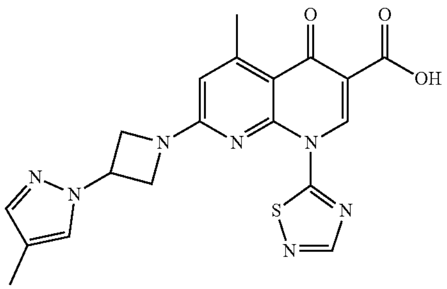

5-Methyl-7-[3-(4-methyl-1H-pyrazol-1-yl)azetidin-1-yl]-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and 1-(azetidin-3-yl)-4-methyl-1H-pyrazole hydrochloride by the method described in Example 001-(3) or a method equivalent thereto.

1H-NMR (DMSO-d6): δ 2.04 (3H, s), 2.80 (3H, s), 4.47-5.02 (4H, m), 5.33-5.51 (1H, m), 6.67 (1H, s), 7.41 (1H, s), 7.75 (1H, s), 8.21 (1H, s), 9.77 (1H, s), 15.04 (1H, brs)

Example 695

Compound 695

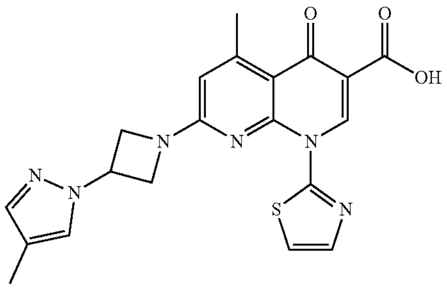

5-Methyl-7-[3-(4-methyl-1H-pyrazol-1-yl)azetidin-1-yl]-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and 1-(azetidin-3-yl)-4-methyl-1H-pyrazole hydrochloride by the method described in Example 008 or a method equivalent thereto.

1H-NMR (DMSO-d6): δ 2.03 (3H, s), 2.76 (3H, s), 4.44-4.83 (4H, m), 5.40-5.51 (1H, m), 6.59 (1H, s), 7.40 (1H, s), 7.69 (1H, d, J=3.5 Hz), 7.74 (1H, s), 7.81 (1H, d, J=3.5 Hz), 9.81 (1H, s), 15.33 (1H, brs)

Example 696

Compound 696

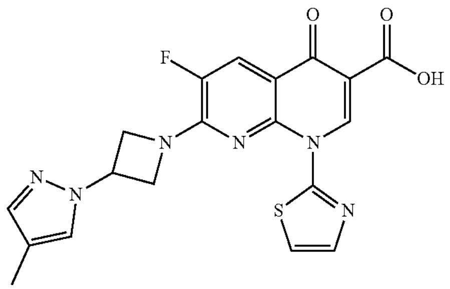

6-Fluoro-7-[3-(4-methyl-1H-pyrazol-1-yl)azetidin-1-yl]-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and 1-(azetidin-3-yl)-4-methyl-1H-pyrazole hydrochloride by the method described in Example 008 or a method equivalent thereto.

1H-NMR (DMSO-d6): δ 2.03 (3H, s), 4.60-5.10 (4H, m), 5.41-5.54 (1H, m), 7.41 (1H, s), 7.74 (1H, d, J=3.5 Hz), 7.77 (1H, s), 7.85 (1H, d, J=3.5 Hz), 8.17 (1H, d, J=11.2 Hz), 9.85 (1H, s), 14.76 (1H, brs)

Example 697

Compound 697

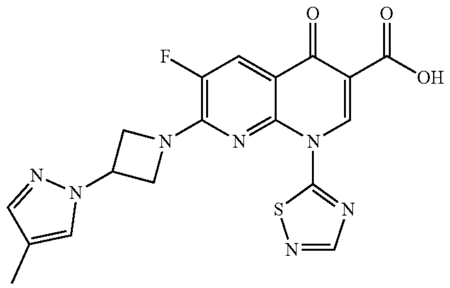

6-Fluoro-7-[3-(4-methyl-1H-pyrazol-1-yl)azetidin-1-yl]-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and 1-(azetidin-3-yl)-4-methyl-1H-pyrazole hydrochloride by the method described in Example 008 or a method equivalent thereto.

1H-NMR (DMSO-d6): δ 2.03 (3H, s), 4.69-5.17 (4H, m), 5.43-5.55 (1H, m), 7.41 (1H, s), 7.78 (1H, s), 8.18 (1H, d, J=11.3 Hz), 8.84 (1H, s), 9.75 (1H, s), 14.42 (1H, brs)

Example 698

Compound 698

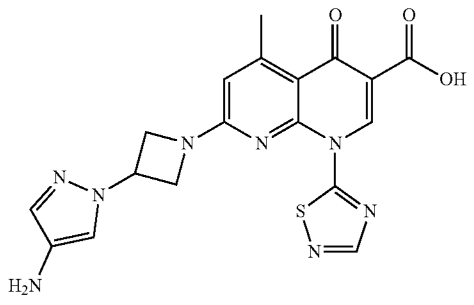

7-[3-(4-Amino-1H-pyrazol-1-yl)azetidin-1-yl]-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and 1-(azetidin-3-yl)-1H-pyrazol-4-amine hydrochloride by the method described in Example 001-(3) or a method equivalent thereto.

Property: brown solid;

ESI-MS (m/z): 425 [M+H]+

Example 699

Compound 699

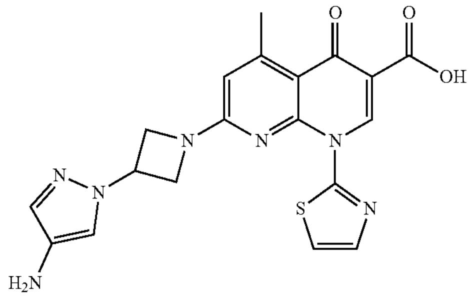

7-[3-(4-Amino-1H-pyrazol-1-yl)azetidin-1-yl]-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and 1-(azetidin-3-yl)-1H-pyrazol-4-amine hydrochloride by the method described in Example 008 or a method equivalent thereto.

1H-NMR (DMSO-d6): δ 2.76 (3H, s), 4.37-4.90 (4H, m), 5.26-5.37 (1H, m), 6.58 (1H, s), 7.08 (1H, s), 7.26 (1H, s), 7.68 (1H, d, J=3.5 Hz), 7.81 (1H, d, J=3.5 Hz), 9.83 (1H, s)

Example 700

Compound 700

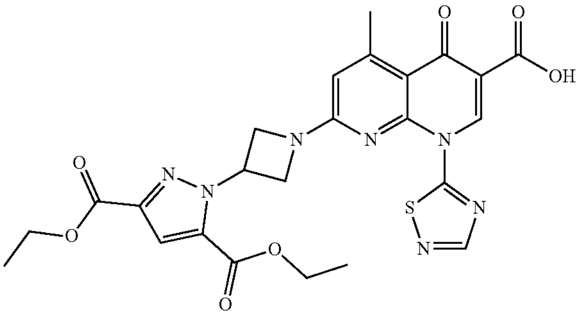

7-{3-[3,5-Bis(ethoxycarbonyl)-1H-pyrazol-1-yl]azetidin-1-yl}-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and 3,5-diethyl 1-(azetidin-3-yl)-H-pyrazole-3,5-dicarboxylate hydrochloride obtained from 3,5-diethyl 1H-pyrazole-3,5-dicarboxylate by the method described in Example 480-(1) and Example 480-(2) or a method equivalent thereto by the method described in Example 001-(3) or a method equivalent thereto.

1H-NMR (DMSO-d6): δ 1.28 (3H, t, J=7.0 Hz), 1.36 (3H, t, J=7.0 Hz), 2.77 (3H, sa), 4.30 (2H, q, J=7.0 Hz), 4.37 (2H, q, J=7.0 Hz), 4.63-5.02 (4H, m), 6.14-6.25 (1H, m), 6.67 (1H, s), 7.34 (1H, s), 8.80 (1H, s), 9.70 (1H, s)

Example 701

Compound 701

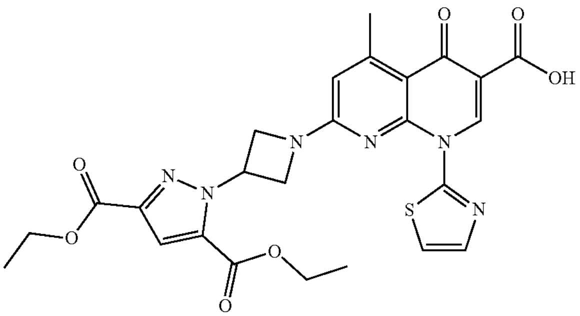

7-{3-[3,5-Bis(ethoxycarbonyl)-1H-pyrazol-1-yl]azetidin-1-yl}-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and 3,5-diethyl 1-(azetidin-3-yl)-1H-pyrazole-3,5-dicarboxylate hydrochloride obtained in Example 700 by the method described in Example 008 or a method equivalent thereto.

1H-NMR (DMSO-d6): δ 1.37 (3H, t, J=7.0 Hz), 1.45 (3H, t, J=7.0 Hz), 2.85 (3H, s), 4.40 (2H, q, J=7.0 Hz), 4.45 (2H, q, J=7.0 Hz), 4.67-4.99 (4H, m), 6.21-6.31 (1H, m), 6.70 (1H, s), 7.42 (1H, s), 7.81 (1H, d, J=3.5 Hz), 7.91 (1H, d, J=3.5 Hz), 9.91 (1H, s), 15.42 (1H, brs)

Example 702

Compound 702

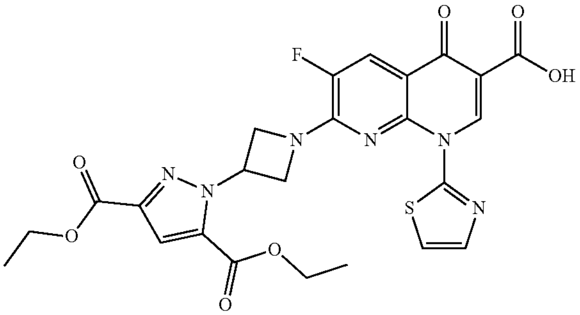

7-{3-[3,5-Bis(ethoxycarbonyl)-1H-pyrazol-1-yl]azetidin-1-yl}-6-fluoro-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and 3,5-diethyl 1-(azetidin-3-yl)-1H-pyrazole-3,5-dicarboxylate hydrochloride obtained in Example 700 by the method described in Example 008 or a method equivalent thereto.

1H-NMR (DMSO-d6): δ 1.29 (3H, t, J=7.0 Hz), 1.35 (3H, t, J=7.0 Hz), 4.31 (2H, q, J=7.0 Hz), 4.35 (2H, q, J=7.0 Hz), 4.81-5.15 (4H, m), 6.14-6.27 (1H, m), 7.34 (1H, s), 7.75 (1H, d, J=3.5 Hz), 7.77 (1H, d, J=3.5 Hz), 8.15 (1H, d, J=10.0 Hz), 9.81 (1H, s), 14.73 (1H, brs)

Example 703

Compound 703

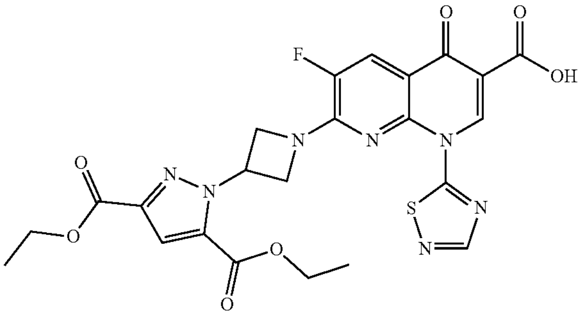

7-{3-[3,5-Bis(ethoxycarbonyl)-1H-pyrazol-1-yl]azetidin-1-yl}-6-fluoro-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and 3,5-diethyl 1-(azetidin-3-yl)-1H-pyrazole-3,5-dicarboxylate hydrochloride obtained in Example 700 by the method described in Example 008 or a method equivalent thereto.

1H-NMR (DMSO-d6): δ 1.29 (3H, t, J=7.0 Hz), 1.36 (3H, t, J=7.0 Hz), 4.31 (2H, q, J=7.0 Hz), 4.37 (2H, q, J=7.0 Hz), 4.89-5.24 (4H, m), 6.14-6.27 (1H, m), 7.36 (1H, s), 8.21 (1H, d, J=12.0 Hz), 8.84 (1H, s), 9.75 (1H, s), 14.42 (1H, brs)

Example 704

Compound 704

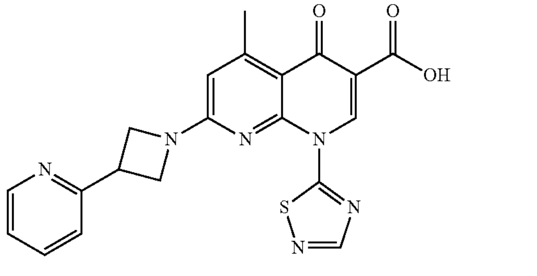

5-Methyl-4-oxo-7-[3-(pyridin-2-yl)azetidin-1-yl]-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and 2-(azetidin-3-yl)pyridine hydrochloride by the method described in Example 001-(3) or a method equivalent thereto.

1H-NMR (DMSO-d6): δ 2.79 (3H, s), 4.26-4.33 (1H, m), 4.42-4.90 (4H, m), 6.63 (1H, s), 7.31-7.34 (1H, m), 7.47 (1H, d, J=7.9 Hz), 7.79-7.83 (1H, m), 8.61-8.63 (1H, m), 8.82 (1H, s), 9.75 (1H, s), 15.12 (1H, brs)

Example 705

Compound 705

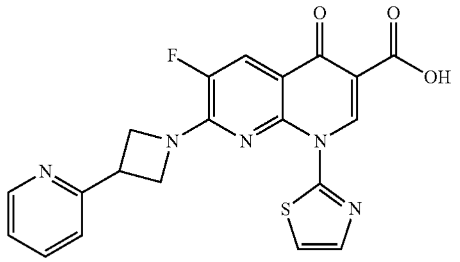

6-Fluoro-4-oxo-7-[3-(pyridin-2-yl)azetidin-1-yl]-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and 2-(azetidin-3-yl)pyridine hydrochloride by the method described in Example 001-(3) or a method equivalent thereto.

1H-NMR (DMSO-d6): δ 4.28-4.35 (1H, m), 4.54-5.06 (4H, m), 7.31-7.35 (1H, m), 7.46 (1H, d, J=7.9 Hz), 7.74 (1H, d, J=3.5 Hz), 7.81 (1H, td, J=7.7, 3.5 Hz), 7.84 (1H, d, J=3.5 Hz), 8.12 (1H, d, J=11.4 Hz), 8.63-8.65 (1H, m), 9.83 (1H, s), 14.83 (1H, brs)

Example 706

Compound 706

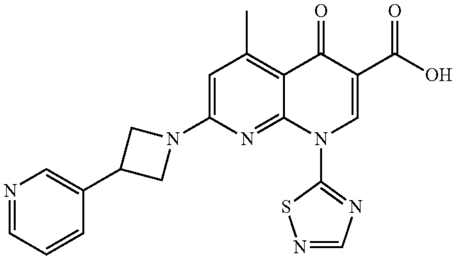

5-Methyl-4-oxo-7-[3-(pyridin-3-yl)azetidin-1-yl]-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and 3-(azetidin-3-yl)pyridine hydrochloride by the method described in Example 001-(3) or a method equivalent thereto.

1H-NMR (DMSO-d6): δ 2.80 (3H, s), 4.21-4.29 (1H, m), 4.36-4.98 (4H, m), 6.63 (1H, s), 7.44-7.48 (1H, m), 8.00-8.03 (1H, m), 7.52-7.54 (1H, m), 8.69-8.71 (1H, m), 8.81 (1H, s), 9.76 (1H, s), 15.08 (1H, brs)

Example 707

Compound 707

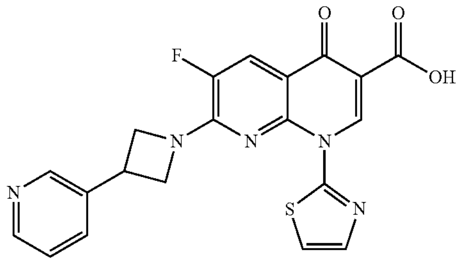

6-Fluoro-4-oxo-7-[3-(pyridin-3-yl)azetidin-1-yl]-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and 3-(azetidin-3-yl)pyridine hydrochloride by the method described in Example 001-(3) or a method equivalent thereto.

1H-NMR (DMSO-d6): δ 4.24-4.32 (1H, m), 4.40-5.05 (4H, m), 7.50-7.54 (1H, m), 7.74 (1H, d, J=3.5 Hz), 7.85 (1H, d, J=3.5 Hz), 8.11-8.16 (2H, m), 8.55-8.57 (1H, m), 8.74-8.76 (1H, m), 9.84 (1H, s), 14.80 (1H, brs)

Example 708

Compound 708

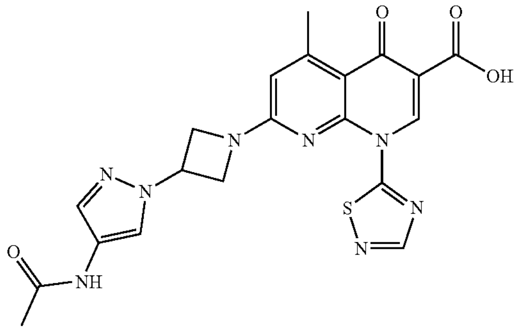

7-[3-(4-Acetamido-1H-pyrazol-1-yl)azetidin-1-yl]-5-methyl-4-oxo-1-(1,2,4-thiadiazol-5-yl)-1,4-dihydro-1,8-naphthyridine-3-carboxylic acid (1) To a solution of 1-[l-(diphenylmethyl)azetidin-3-yl]-1H-pyrazol-4-amine (300 mg) in methylene chloride (5 mL)

was added acetic anhydride (95 μL) under ice cooling, and the mixture was stirred at room temperature for 2 hours. To the reaction solution was added ice, and the mixture was extracted with ethyl acetate. The organic layer was washed with water and brine and dried, and the residue was then concentrated. The residue was purified by silica gel column chromatography (eluent: ethyl acetate/n-hexane) to obtain 250 mg of N-{1-[1-(diphenylmethyl)azetidin-3-yl]-H-pyrazol-4-yl}acetamide.

1H-NMR (DMSO-d6): δ 1.96 (3H, s), 3.26-3.58 (4H, m), 4.57 (1H, s), 4.95-5.02 (1H, m), 7.16-7.49 (11H, m), 8.02 (1H, s), 9.92 (1H, s)

(2) The title compound was obtained by the method described in Example 001-(3) or a method equivalent thereto using N-[1-(azetidin-3-yl)-1H-pyrazol-4-yl]acetamide hydrochloride obtained by the method described in Example 480-(2) or a method equivalent thereto using N-{1-[1-(diphenylmethyl)azetidin-3-yl]-1H-pyrazol-4-yl}acetamide obtained in the preceding section, and 7-chloro-5-methyl-4-oxo-1-(1,2,4-thiadiazol-5-yl)-1,4-dihydro-1,8-naphthyridine-3-carboxylic acid obtained in Reference Example 002-(2).

1H-NMR (DMSO-d6): δ 1.99 (3H, s), 2.80 (3H, s), 4.50-5.00 (4H, m), 5.46-5.57 (1H, m), 6.68 (1H, s), 7.54 (1H, s), 8.14 (1H, s), 8.82 (1H, s), 9.77 (1H, s), 10.00 (1H, s), 15.05 (1H, brs)

Example 709

Compound 709

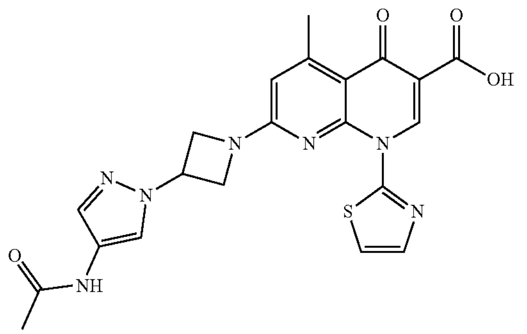

7-[3-(4-Acetamido-1H-pyrazol-1-yl)azetidin-1-yl]-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-[1-(azetidin-3-yl)-1H-pyrazol-4-yl]acetamide hydrochloride obtained in Example 708-(2) by the method described in Example 008 or a method equivalent thereto.

1H-NMR (DMSO-d6): δ 1.98 (3H, s), 2.80 (3H, s), 4.43-4.88 (4H, m), 5.43-5.55 (1H, m), 6.64 (1H, s), 7.81 (1H, d, J=3.5 Hz), 7.54 (1H, s), 7.83 (1H, d, J=3.5 Hz), 8.12 (1H, s), 9.87 (1H, s), 9.99 (1H, s), 15.38 (1H, brs)

Example 710

Compound 710

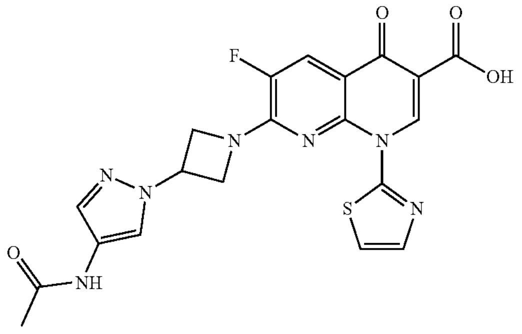

7-[3-(4-Acetamido-1H-pyrazol-1-yl)azetidin-1-yl]-6-fluoro-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-[1-(azetidin-3-yl)-1H-pyrazol-4-yl]acetamide hydrochloride obtained in Example 708-(2) by the method described in Example 008 or a method equivalent thereto.

1H-NMR (DMSO-d6): δ 1.99 (3H, s), 4.55-5.11 (4H, m), 5.48-5.60 (1H, m), 7.55 (1H, s), 7.73 (1H, d, J=3.5 Hz), 7.85 (1H, d, J=3.5 Hz), 8.15 (1H, d, J=12.0 Hz), 8.18 (1H, s), 9.85 (1H, s), 10.00 (1H, s), 14.76 (1H, brs)

Example 711

Compound 711

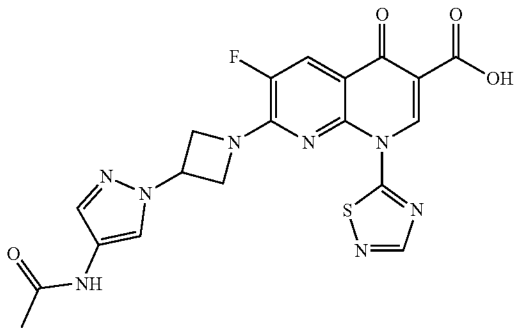

7-[3-(4-Acetamido-1H-pyrazol-1-yl)azetidin-1-yl]-6-fluoro-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and N-[1-(azetidin-3-yl)-1H-pyrazol-4-yl]acetamide hydrochloride obtained in Example 708-(2) by the method described in Example 008 or a method equivalent thereto.

1H-NMR (DMSO-d6): δ 1.99 (3H, s), 4.71-5.17 (4H, m), 5.47-5.59 (1H, m), 7.55 (1H, s), 8.16 (1H, s), 8.21 (1H, d, J=12.0 Hz), 8.85 (1H, s), 9.77 (1H, s), 10.00 (1H, 8)

Example 712

Compound 712

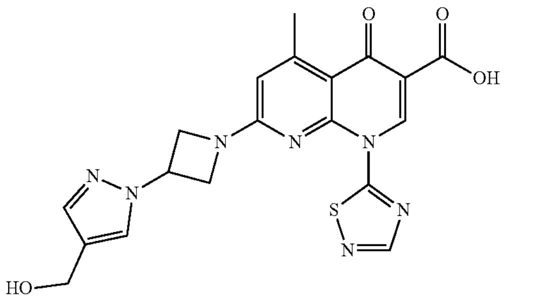

7-{3-[4-(Hydroxymethyl)-1H-pyrazol-1-yl]azetidin-1-yl}-5-methyl-4-oxo-1-(1,2,4-thiadiazol-5-yl)-1,4-dihydro-1,8-naphthyridine-3-carboxylic acid (1) To a solution of ethyl 1-[1-(diphenylmethyl)azetidin-3-yl]-1H-pyrazole-4-carboxylate (200 mg) in THF (1 mL) obtained from ethyl 1H-pyrazole-4-carboxylate by the method described in Example 480-(1) or a method equivalent thereto was added lithium borohydride (36 mg) under ice cooling, and the mixture was stirred at room temperature for 20 hours. To the reaction solution was added water, and the mixture was extracted with ethyl acetate. The organic layer was washed with water and brine and dried, and the residue was then concentrated. The residue was purified by silica gel column chromatography (eluent: ethyl acetate/n-hexane) to obtain 83 mg of {1-[1-(diphenylmethyl)azetidin-3-yl]-1H-pyrazol-4-yl}methanol.

1H-NMR (CDCl3): δ 3.42-3.51 (2H, m), 3.62-3.71 (2H, m), 4.51-4.62 (3H, m), 4.86-4.98 (1H, m), 7.19 (2H, t, J=7.5 Hz), 0.7.28 (4H, t, J=7.5 Hz), 7.43 (4H, d, J=7.5 Hz), 7.54 (1H, s), 7.62 (1H, s)

(2) The title compound was obtained by the method described in Example 001-(3) or a method equivalent thereto using [1-(azetidin-3-yl)-1H-pyrazol-4-yl]methanol hydrochloride obtained by the method described in Example 480-(2) or a method equivalent thereto using {1-[1-(diphenylmethyl)azetidin-3-yl]-1H-pyrazol-4-yl}methanol obtained in the preceding section, and 7-chloro-5-methyl-4-oxo-1-(1,2,4-thiadiazol-5-yl)-1,4-dihydro-1,8-naphthyridine-3-carboxylic acid obtained in Reference Example 002-(2).

1H-NMR (DMSO-d6): δ 2.71 (3H, s), 4.42 (2H, s), 4.45-5.03 (4H, m), 5.42-5.55 (1H, m), 6.48 (1H, s), 7.49 (1H, s), 7.75 (1H, s), 8.77 (1H, s), 9.65 (1H, s)

Example 713

Compound 713

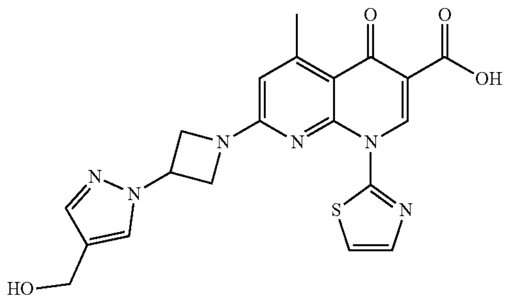

7-{3-[4-(Hydroxymethyl)-1H-pyrazol-1-yl]azetidin-1-yl}-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and [1-(azetidin-3-yl)-1H-pyrazol-4-yl]methanol hydrochloride obtained in Example 712-(2) by the method described in Example 008 or a method equivalent thereto.

1H-NMR (DMSO-d6): δ 2.70 (3H, s), 4.38 (2H, s), 4.45-4.90 (4H, m), 5.42-5.56 (1H, m), 6.51 (1H, s), 7.55 (1H, s), 7.66 (1H, d, J=3.5 Hz), 7.77 (1H, d, J=3.5 Hz), 8.00 (1H, s), 9.76 (1H, s)

Example 714

Compound 714

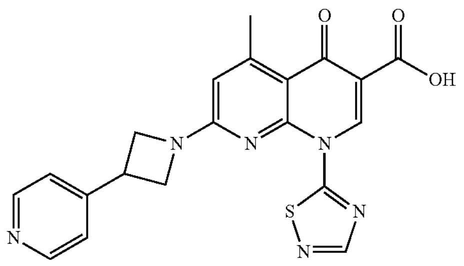

5-Methyl-4-oxo-7-[3-(pyridin-4-yl)azetidin-1-yl]-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and 4-(azetidin-3-yl)pyridine hydrochloride by the method described in Example 001-(3) or a method equivalent thereto.

1H-NMR (DMSO-d6): δ 2.75 (3H, s), 4.19-4.26 (1H, m), 4.32-4.92 (4H, m), 6.58 (1H, s), 8.55-8.57 (2H, m), 8.59-8.61 (2H, m), 8.79 (1H, s), 9.68 (1H, s), 15.02 (1H, brs)

Example 715

Compound 715

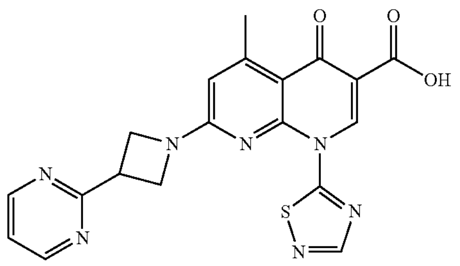

5-Methyl-4-oxo-7-[3-(pyrimidin-2-yl)azetidin-1-yl]-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and 2-(azetidin-3-yl)pyrimidine hydrochloride by the method described in Example 001-(3) or a method equivalent thereto.

1H-NMR (DMSO-d6): δ 2.78 (3H, s), 4.34-4.41 (1H, m), 4.48-4.94 (4H, m), 6.65 (1H, s), 7.46 (1H, t, J=4.9 Hz), 8.81 (1H, s), 8.86 (2H, d, J=4.9 Hz), 9.75 (1H, s), 15.09 (1H, brs)

Example 716

Compound 716

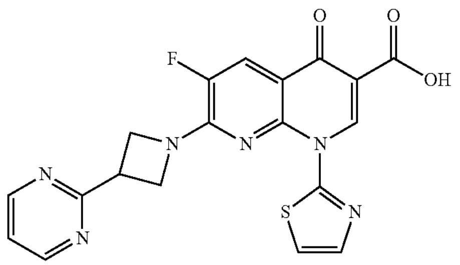

6-Fluoro-4-oxo-7-[3-(pyrimidin-2-yl)azetidin-1-yl]-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and 2-(azetidin-3-yl)pyrimidine hydrochloride by the method described in Example 001-(3) or a method equivalent thereto.

1H-NMR (DMSO-d6): δ 4.35-4.42 (1H, m), 4.66-5.08 (4H, m), 7.47 (1H, t, J=4.9 Hz), 7.78 (1H, d, J=3.5 Hz), 7.86 (1H, d, J=3.5 Hz), 8.14 (1H, d, J=11.3 Hz), 8.86 (2H, d, J=4.9 Hz), 9.84 (1H, s), 14.82 (1H, brs)

Example 717

Compound 717

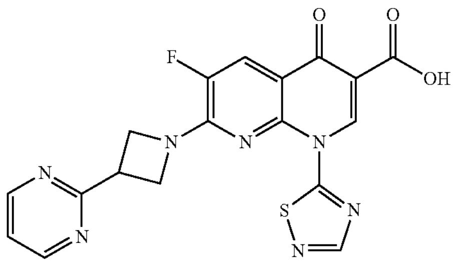

6-Fluoro-4-oxo-7-[3-(pyrimidin-2-yl)azetidin-1-yl]-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and 2-(azetidin-3-yl)pyrimidine hydrochloride by the method described in Example 001-(3) or a method equivalent thereto.

1H-NMR (DMSO-d6): δ 4.37-4.44 (1H, m), 4.74-5.12 (4H, m), 7.47 (1H, t, J=4.9 Hz), 8.18 (1H, d, J=11.5 Hz), 8.85 (1H, s), 8.87 (2H, d, J=4.9 Hz), 9.77 (1H, s), 14.50 (1H, brs)

Example 718

Compound 718

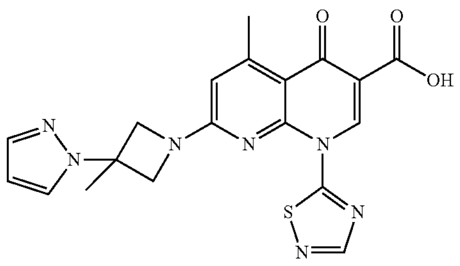

5-Methyl-7-[3-methyl-3-(1H-pyrazol-1-yl)azetidin-1-yl]-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and 1-(3-methylazetidin-3-yl)-1H-pyrazole hydrochloride obtained from 1H-pyrazole and 1-(diphenylmethyl)-3-methanesulfonyl-3-methylazetidine by the method described in Example 480-(1) and Example 480-(2) or a method equivalent thereto by the method described in Example 001-(3) or a method equivalent thereto.

1H-NMR (DMSO-d6): δ 1.97 (3H, s), 2.80 (3H, d, J=0.9 Hz), 4.47-4.92 (4H, m), 6.37-6.39 (1H, m), 6.68 (1H, d,

J=0.9 Hz), 7.60-7.61 (1H, m), 8.07-8.09 (1H, m), 8.82 (1H, s), 9.77 (1H, s), 15.04 (1H, brs)

Example 719

Compound 719

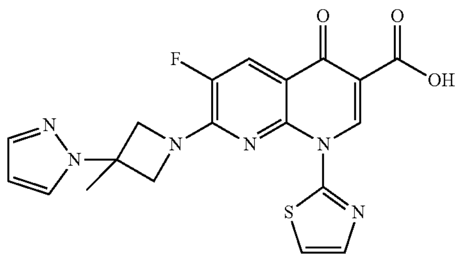

6-Fluoro-7-[3-methyl-3-(1H-pyrazol-1-yl)azetidin-1-yl]-4-oxo-1-(1,3-thiazol-2-yl)-1,4-dihydro-1,8-naphthyridine-3-carboxylic acid The title compound was obtained using 7-chloro-6-fluoro4-oxo-1-(1,3-thiazol-2-yl)-1,4-dihydro-1,8-naphthyridine-3-carboxylic acid obtained in Reference Example 003-(2) and 1-(3-methylazetidin-3-yl)-1H-pyrazole hydrochloride obtained in Example 718 by the method described in Example 001-(3) or a method equivalent thereto.

1H-NMR (DMSO-d6): δ 1.96 (3H, s), 4.46-5.10 (4H, m), 6.37-6.38 (1H, m), 7.60-7.61 (1H, m), 7.76 (1H, d, J=3.5 Hz), 7.85 (1H, d, J=3.5 Hz), 8.06-8.07 (1H, m), 8.15 (1H, d, J=11.2 Hz), 9.83 (1H, s), 14.74 (1H, brs)

Example 720

Compound 720

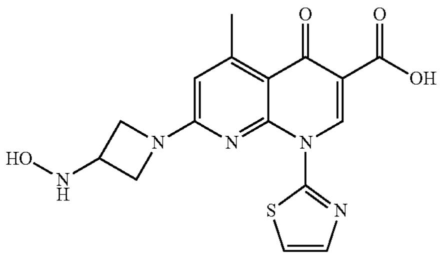

7-[3-(Hydroxyamino)azetidin-1-yl]-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-(azetidin-3-yl)hydroxylamine hydrochloride by the method described in Example 001-(3) or a method equivalent thereto.

1H-NMR (DMSO-d6): δ 2.96 (3H, s), 3.96-4.43 (5H, m), 6.23 (1H, brs), 7.56 (1H, s), 7.77 (1H, d, J=3.5 Hz), 7.83 (1H, d, J=3.5 Hz), 9.82 (1H, s)

Example 721

Compound 721

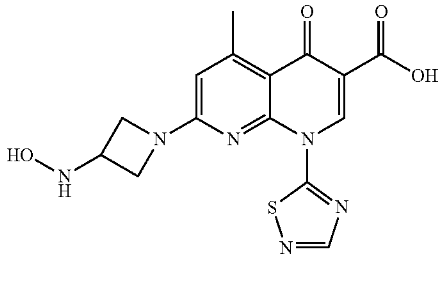

7-[3-(Hydroxyamino) azetidin-1-yl]-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-(azetidin-3-yl)hydroxylamine hydrochloride by the method described in Example 001-(3) or a method equivalent thereto.

1H-NMR (DMSO-d6): δ 2.87 (3H, s), 4.18-4.66 (5H, m), 6.64 (1H, s), 8.83 (1H, s), 9.74 (1H, s)

Example 722

Compound 722

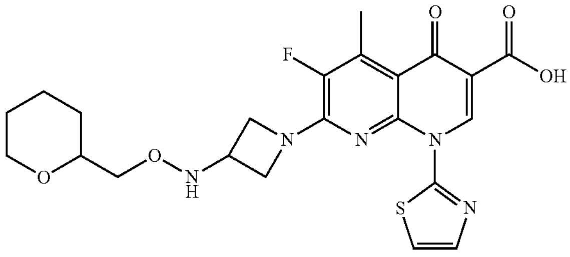

6-Fluoro-5-methyl-7-{3-[(oxan-2-ylmethoxy)amino]azetidin-1-yl}-4-oxo-1-(1,3-thiazol-2-yl)-1,4-dihydro-1,8-naphthyridine-3-carboxylic acid (1) To a solution of tert-butyl 3-[(oxan-2-ylmethoxy)imino]azetidine-1-carboxylate (63 mg) obtained in Example 735-(3) in methanol (1.1 mL) was added sodium borohydride (83 mg), and the mixture was stirred at 60° C. for 22 hours. Sodium borohydride (42 mg) was further added thereto, and the mixture was stirred at 60° C. for 17 hours. The reaction mixture was cooled down to room temperature, and a saturated aqueous solution of sodium bicarbonate (20 mL) was added thereto. After extraction with ethyl acetate, the organic layer was washed with water and brine, dried over sodium sulfate, and concentrated. The residue was purified by silica gel column chromatography (eluent: ethyl acetate/n-hexane) to obtain 26 mg of tert-butyl 3-{[(oxan-2-yl)methoxy]amino}azetidine-1-carboxylate.

1H-NMR (CDCl3): δ 1.23-1.33 (1H, m), 1.43 (9H, s), 1.46-1.62 (4H, m), 1.82-1.88 (1H, m), 3.40-3.47 (1H, m), 3.52-3.58 (1H, m), 3.66-3.74 (2H, m), 3.77-3.82 (2H, m), 3.87-3.93 (1H, m), 3.98-4.04 (3H, m)

(2) The title compound was obtained by the method described in Example 008 or a method equivalent thereto using N-[(oxan-2-yl)methoxy]azetidin-3-amine trifluoroacetate obtained by the method described in Example 001-(2) or a method equivalent thereto from tert-butyl 3-{[(oxan-2-yl)methoxy]amino}azetidine-1-carboxylate obtained in the preceding section, and 7-chloro-6-fluoro-5-methyl-4-oxo-1-(1,3-thiazol-2-yl)-1,4-dihydro-1,8-naphthyridine-3-carboxylic acid obtained in Reference Example 007-(2).

1H-NMR (DMSO-d6): δ 1.05-1.18 (1H, m), 1.33-1.56 (4H, m), 1.69-1.80 (1H, m), 2.66 (3H, d, J=3.0 Hz), 3.46-3.56 (2H, m), 3.58-3.64 (1H, m), 3.77-3.85 (1H, m), 4.04-4.14 (1H, m), 4.16-4.78 (5H, m), 7.11 (1H, d, J=6.5 Hz), 7.78 (1H, d, J=3.5 Hz), 7.84 (1H, d, J=3.5 Hz), 9.77 (1H, s), 15.18 (1H, brs)

Example 723

Compound 723

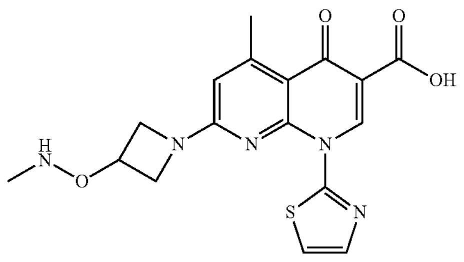

5-Methyl-7-{3-[(methylamino)oxy]azetidin-1-yl}-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and (azetidin-3-yloxy) (methyl)amine hydrochloride obtained in Example 552-(4) by the method described in Example 001-(3) or a method equivalent thereto.

1H-NMR (DMSO-d6): δ 2.60 (3H, s), 2.75 (3H, d, J=1.0 Hz), 4.07-4.26 (2H, m), 4.32-4.50 (2H, m), 4.70-4.76 (1H, m), 6.51 (1H, d, J=1.0 Hz), 7.75 (1H, d, J=3.5 Hz), 7.83 (1H, d, J=3.5 Hz), 9.82 (1H, s), 15.39 (1H, brs)

Example 724

Compound 724

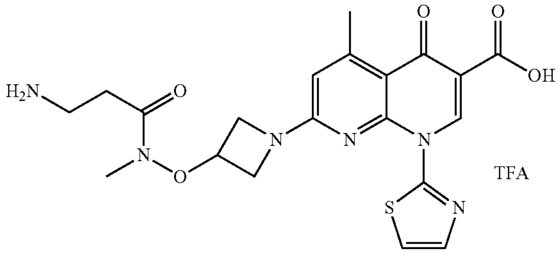

7-{3-[(3-Amino-N-methylpropanamido)oxy]azetidin-1-yl}-5-methyl-4-oxo-1-(1,3-thiazol-2-yl)-1,4-dihydro-1,8-naphthyridine-3-carboxylic acid trifluoroacetate (1) To a suspension of 3-{[(tert-butoxy)carbonyl]amino}propanoic acid (19 mg), 5-methyl-7-{3-[(methylamino)oxy]azetidin-1-yl}-4-oxo-1-(1,3-thiazol-2-yl)-1,4-dihydro-1,8-naphthyridine-3-carboxylic acid (39 mg) obtained in Example 723, and HATU (38 mg) in methylene chloride was added N,N-diisopropylethylamine (23 μL), and the mixture was stirred at room temperature for 1 hour. The reaction solution was subjected to silica gel column chromatography (eluent: methanol/chloroform) to obtain 30 mg of 7-{3-[(tert-butoxy) carbonyl]amino}-N-methylpropanamido)oxy]azetidin-1-yl}-5-methyl-4-oxo-1-(1,3-thiazol-2-yl)-1,4-dihydro-1,8-naphthyridine-3-carboxylic acid.

1H-NMR (CDCl3): δ 1.44 (9H, s), 2.66-2.78 (5H, m), 3.33 (3H, s), 3.43-3.49 (2H, m), 4.31-4.40 (2H, m), 4.54-4.68 (2H, m), 5.00-5.07 (1H, m), 5.16-5.24 (1H, m), 6.13 (1H, s), 7.31 (1H, d, J=3.5 Hz), 7.65 (1H, d, J=3.5 Hz), 9.91 (1H, s), 15.16 (1H, s)

(2) The title compound was obtained by the method described in Example 001-(2) or a method equivalent thereto using 7-{3-[(tert-butoxy) carbonyl]amino}-N-methylpropanamido)oxy]azetidin-1-yl}-5-methyl-4-oxo-1-(1,3-thiazol-2-yl)-1,4-dihydro-1,8-naphthyridine-3-carboxylic acid obtained in the preceding section.

1H-NMR (DMSO-d6): δ 2.73-2.86 (5H, m), 2.97-3.08 (2H, m), 3.25 (3H, s), 4.28-4.37 (2H, m), 4.52-4.74 (2H, m), 5.07-5.15 (1H, m), 6.58 (1H, s), 7.65 (3H, brs), 7.76 (1H, d, J=3.5 Hz), 7.85 (1H, d, J=3.5 Hz), 9.85 (1H, s), 15.29 (1H, s)

Example 725

Compound 725

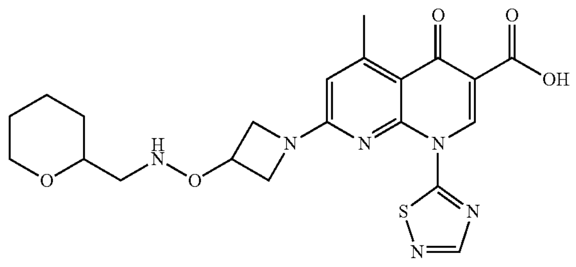

5-Methyl-7-[3-({[(oxan-2-yl)methyl]amino}oxy)azetidin-1-yl]-4-oxo-1-(1,2,4-thiadiazol-5-yl)-1,4-dihydro-1,8-naphthyridine-3-carboxylic acid (1) To a solution of tert-butyl 3-(aminooxy)azetidine-1-carboxylate (300 mg) in methylene chloride (13 mL) was added (Boc)2O (2.1 g), and the mixture was stirred at room temperature for 19 hours. The reaction solution was concentrated, and the residue was purified by silica gel column chromatography (eluent: ethyl acetate/n-hexane) to obtain 442 mg of tert-butyl 3-({[(tert-butoxy) carbonyl]amino}oxy) azetidine-1-carboxylate.

1H-NMR (CDCl3): δ 1.43 (9H, s), 1.48 (9H, s), 3.94-3.98 (2H, m), 4.04-4.09 (2H, m), 4.65-4.70 (1H, m), 7.19 (1H, brs)

(2) tert-Butyl 3-({[(tert-butoxy) carbonyl]oxan-2-ylmethyl)amino}oxy)azetidine-1-carboxylate was obtained by the method described in Example 483-001 or a method equivalent thereto using tert-butyl 3-({[(tert-butoxy) carbonyl]amino}oxy) azetidine-1-carboxylate obtained in the preceding section, and (tetrahydro-2H-pyran-2-yl)methyl 4-methylbenzenesulfonate.

1H-NMR (CDCl3): δ 1.18-1.29 (2H, m), 1.43 (9H, s), 1.48 (9H, s), 1.49-1.67 (4H, m), 3.33-3.44 (2H, m), 3.51-3.58 (2H, m), 3.93-4.10 (5H, m), 4.68-4.75 (1H, m)

(3) The title compound was obtained by the method described in Example 001-(3) or a method equivalent thereto using (azetidin-3-yloxy) (oxan-2-ylmethyl)amine hydrochloride obtained by the method described in Example 001-(2) or a method equivalent thereto from tert-butyl 3-(([(tert-butoxy) carbonyl](oxan-2-ylmethyl)amino)oxy) azetidine-1-carboxylate obtained in the preceding section, and 7-chloro-5-methyl-4-oxo-1-(1,2,4-thiadiazol-5-yl)-1,4-dihydro-1,8-naphthyridine-3-carboxylic acid obtained in Reference Example 002-(2).

1H-NMR (DMSO-d6): δ 1.09-1.21 (1H, m), 1.38-1.51 (3H, m), 1.55-1.63 (1H, m), 1.70-1.82 (1H, m), 2.75 (3H, d, J=1.0 Hz), 2.79-2.91 (2H, m), 3.46-3.50 (1H, m), 3.82-3.90 (1H, m), 4.14-4.23 (1H, m), 4.32-4.46 (2H, m), 4.50-4.61 (1H, m), 4.71-4.79 (1H, m), 6.54 (1H, d, J=1.0 Hz), 6.81-6.89 (1H, m), 8.81 (1H, s), 9.71 (1H, s), 15.08 (1H, s)

Example 726

Compound 726

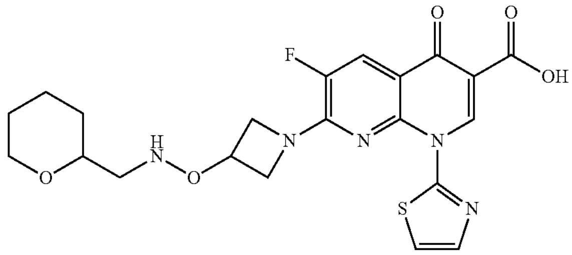

6-Fluoro-7-(3-{[(oxan-2-ylmethyl)amino] oxy}azetidin-1-yl)-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and (azetidin-3-yloxy)(oxan-2-ylmethyl)amine hydrochloride obtained in Example 725-(3) by the method described in Example 001-(3) or a method equivalent thereto.

1H-NMR (DMSO-d6): δ 1.08-1.19 (1H, m), 1.35-1.49 (3H, m), 1.55-1.62 (1H, m), 1.71-1.81 (1H, m), 2.78-2.89 (2H, m), 3.40-3.49 (1H, m), 3.82-3.88 (1H, m), 4.26-4.78 (5H, m), 6.80-6.86 (1H, m), 7.80 (1H, d, J=3.5 Hz), 7.86 (1H, d, J=3.5 Hz), 8.10 (1H, d, J=11.5 Hz), 9.82 (1H, s), 14.79 (1H, brs)

Example 727

Compound 727

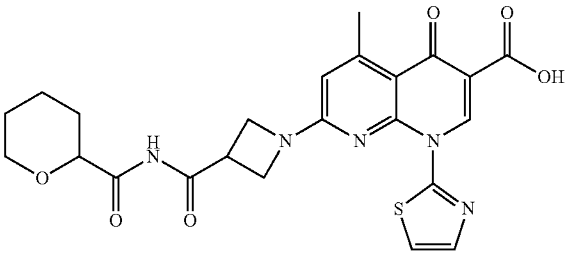

5-Methyl-7-(3-{[(oxan-2-yl)formamido] carbonyl}azetidin-1-yl)-4-oxo-1-(1,3-thiazol-2-yl)-1,4-dihydro-1,8-naphthyridine-3-carboxylic acid The title compound was obtained by the method described in Example 008 or a method equivalent thereto using N-(azetidine-3-carbonyl)oxane-2-carboxamide trifluoroacetate obtained by the methods described in Examples 002-(1) and 001-(2) or methods equivalent thereto from tert-butyl 3-carbamoylazetidine-1-carboxylate and oxane-2-carbonyl chloride, and 7-chloro-5-methyl-4-oxo-1-(1,3-thiazol-2-yl)-1,4-dihydro-1,8-naphthyridine-3-carboxylic acid obtained in Reference Example 001-(2).

1H-NMR (DMSO-d6): δ 1.19-1.31 (2H, m), 1.37-1.58 (3H, m), 1.77-1.87 (1H, m), 2.77 (3H, s), 3.92-4.16 (3H, m), 4.18-4.56 (5H, m), 6.56 (1H, s), 7.72-7.79 (1H, m), 7.82-7.85 (1H, m), 9.83 (1H, s)

Example 728

Compound 728

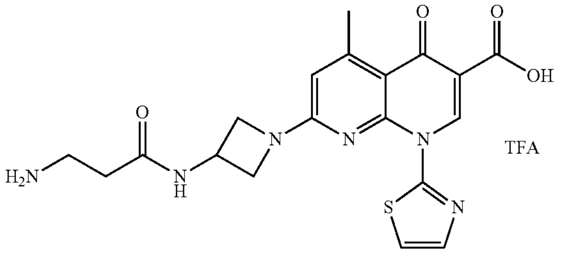

7-[3-(3-Aminopropanamido) azetidin-1-yl]-5-methyl-4-oxo-1-(1,3-thiazol-2-yl)-1,4-dihydro-1,8-naphthyridine-3-carboxylic acid trifluoroacetate The title compound was obtained using 7-[3-(3-{[(tert-butoxy)carbonyl]amino}propaneamide)azetidin-1-yl]-5-methyl-4-oxo-1-(1,3-thiazol-2-yl)-1,4-dihydro-1,8-naphthyridine-3-carboxylic acid obtained from 7-(3-aminoazetidin-1-yl)-5-methyl-4-oxo-1-(1,3-thiazol-2-yl)-1,4-dihydro-1,8-naphthyridine-3-carboxylic acid by the method described in Example 724-(1) or a method equivalent thereto by the method described in Example 001-(2) or a method equivalent thereto.

1H-NMR (DMSO-d6): δ 2.78 (3H, s), 2.98-3.07 (2H, m), 4.04-4.27 (2H, m), 4.48-4.66 (2H, m), 4.67-4.75 (1H, m), 6.57 (1H, s), 7.67 (3H, brs), 7.77 (1H, d, J=3.5 Hz), 7.85 (1H, d, J=3.5 Hz), 8.87 (1H, d, J=7.0 Hz), 9.85 (1H, s), 15.36 (1H, brs)

Example 729

Compound 729

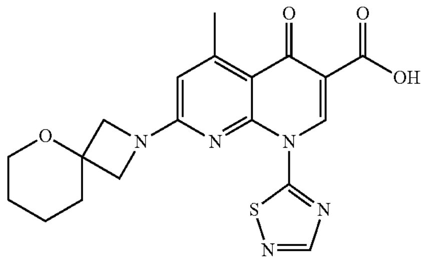

5-Methyl-7-{5-oxa-2-azaspiro[3.5]nonan-2-yl}-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and 5-oxa-2-azaspiro[3.5]nonane hydrochloride by the method described in Example 001-(3) or a method equivalent thereto.

1H-NMR (DMSO-d6): δ 1.44-1.55 (2H, m), 1.58-1.92 (4H, m), 2.75 (3H, d, J=0.9 Hz), 3.60-3.77 (2H, m), 4.08-4.38 (4H, m), 6.56 (1H, d, J=0.9 Hz), 8.81 (1H, s), 9.72 (1H, s), 15.06 (1H, brs)

Example 730

Compound 730

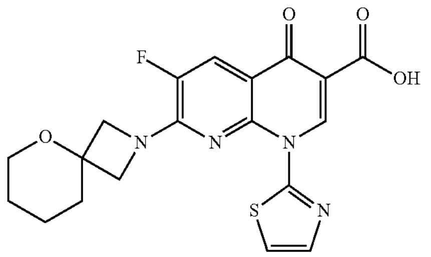

6-Fluoro-7-{5-oxa-2-azaspiro[3.5]nonan-2-yl}-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and 5-oxa-2-azaspiro[3.5]nonane hydrochloride by the method described in Example 001-(3) or a method equivalent thereto.

1H-NMR (DMSO-d6): δ 1.46-1.54 (2H, m), 1.60-1.70 (2H, m), 1.81-1.89 (2H, m), 3.61-3.74 (2H, m), 4.14-4.56 (4H, m), 7.78 (1H, d, J=3.5 Hz), 7.85 (1H, d, J=3.5 Hz), 8.08 (1H, d, J=11.5 Hz), 9.81 (1H, s), 14.78 (1H, brs)

Example 731

Compound 731

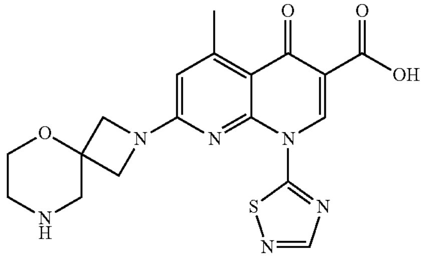

5-Methyl-7-{5-oxa-2,8-diazaspiro[3.5]nonan-2-yl}-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and 5-oxa-2,8-diazaspiro[3.5]nonane hydrochloride by the method described in Example 001-(3) or a method equivalent thereto.

1H-NMR (DMSO-d6): δ 2.75 (3H, s), 2.88-3.00 (2H, m), 3.70-4.57 (8H, m), 6.57 (1H, s), 8.81 (1H, s), 9.68 (1H, s)

Example 732

Compound 732

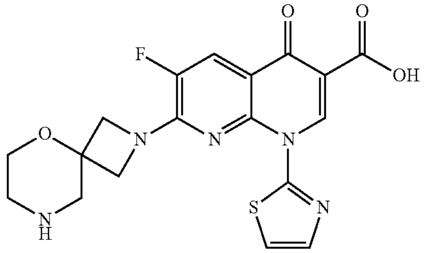

6-Fluoro-7-{5-oxa-2,8-diazaspiro[3.5]nonan-2-yl}-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and 5-oxa-2,8-diazaspiro[3.5]nonane hydrochloride by the method described in Example 001-(3) or a method equivalent thereto.

1H-NMR (DMSO-d6): δ 2.86-2.95 (2H, m), 3.67-3.83 (2H, m), 3.87-3.99 (2H, m), 4.19-4.72 (4H, m), 7.82 (1H, d, J=3.5 Hz), 7.87 (1H, d, J=3.5 Hz), 8.13 (1H, d, J=11.5 Hz), 9.81 (1H, s)

Example 733

Compound 733

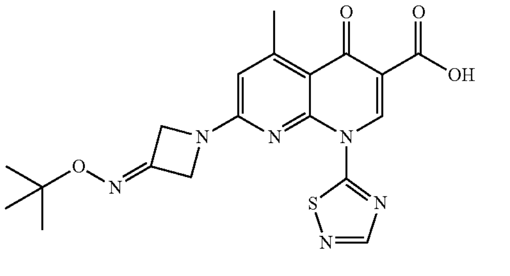

7-{3-[(tert-Butoxy)imino]azetidin-1-yl}-5-methyl-4-oxo-1-(1,2,4-thiadiazol-5-yl)-1,4-dihydro-1,8-naphthyridine-3-carboxylic acid (1) tert-Butyl 3-[(tert-butoxy)imino]azetidine-1-carboxylate was obtained using tert-butyl 3-oxoazetidine-1-carboxylate and O-(tert-butyl)hydroxylamine hydrochloride by the method described in Example 595-(1) or a method equivalent thereto.

1H-NMR (CDCl3): δ 1.26 (9H, s), 1.46 (9H, s), 4.54-4.62 (4H, m)

(2) The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-(tert-butoxy)azetidin-3-imine trifluoroacetate obtained from tert-butyl 3-[(tert-butoxy)imino]azetidine-1-carboxylate obtained in a preceding section by the method described in Example 001-(2) or a method equivalent thereto by the method described in Example 008 or a method equivalent thereto.

1H-NMR (DMSO-d6): δ 1.29 (9H, s), 2.78 (3H, s), 4.86-5.34 (4H, m), 6.69 (1H, s), 8.82 (1H, s), 9.76 (1H, s), 14.92 (1H, brs)

Example 734

Compound 734

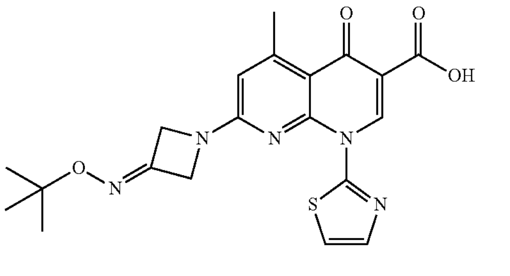

7-{3-[(tert-Butoxy)imino]azetidin-1-yl}-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-(tert-butoxy) azetidin-3-imine trifluoroacetate obtained in Example 733-(2) by the method described in Example 008 or a method equivalent thereto.

1H-NMR (DMSO-d6): δ 1.30 (9H, s), 2.73 (3H, s), 4.90-5.06 (4H, m), 6.58 (1H, s), 7.69-7.81 (2H, m), 9.77 (1H, s), 15.18 (1H, brs)

Example 735

Compound 736

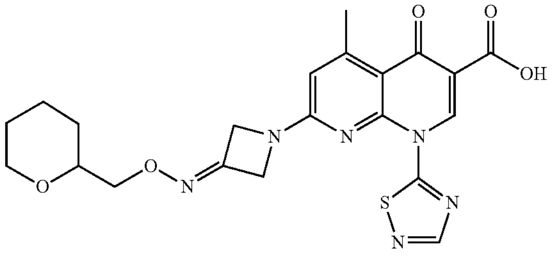

5-Methyl-7-(3-{[(oxan-2-yl)methoxy]imino}azetidin-1-yl)-4-oxo-1-(1,2,4-thiadiazol-5-yl)-1,4-dihydro-1,8-naphthyridine-3-carboxylic acid (1) To a solution of 2-hydroxy-2,3-dihydro-1H-isoindole-1,3-dione (390 mg), oxan-2-ylmethanol (230 mg), and triphenylphosphine (1.0 g) in THF (8 mL) was added diethyl azodicarboxylate (40% solution in toluene; 1.4 mL) under ice cooling, and the mixture was stirred at room temperature for 21 hours. To the reaction solution was added a saturated aqueous solution of sodium bicarbonate, and the mixture was extracted with ethyl acetate. The organic layer was washed with water and brine, dried, and concentrated. The residue was purified by silica gel column chromatography (eluent: ethyl acetate/n-hexane) to obtain 410 mg of 2-(oxan-2-ylmethyl)-2,3-dihydro-1H-isoindole-1,3-dione.

1H-NMR (CDCl3): δ 1.31-1.69 (5H, m), 1.83-1.92 (1H, m), 3.39-3.49 (1H, m), 3.76-3.84 (1H, m), 3.89-3.97 (1H, m), 4.05-4.10 (1H, m), 4.21-4.28 (1H, m), 7.71-7.76 (2H, m), 7.82-7.87 (2H, m)

(2) A solution of 2-(oxan-2-ylmethyl)-2,3-dihydro-1H-isoindole-1,3-dione (130 mg) obtained in the preceding section, and hydrazine monohydrate (45 μL) in methanol (2 mL) was stirred at 60° C. for 24 hours. Insoluble material was filtered off, and the filtrate was then concentrated to obtain 87 mg of O-(oxan-2-ylmethyl)hydroxylamine.

1H-NMR (CDCl3): δ 1.21-1.38 (1H, m), 1.43-1.74 (4H, m), 1.81-1.93 (1H, m), 3.40-3.53 (1H, m), 3.55-3.74 (3H, m), 3.98-4.13 (1H, m)

(3) tert-Butyl 3-[(oxan-2-ylmethoxy)imino]azetidine-1-carboxylate was obtained by the method described in Example 595-(1) or a method equivalent thereto using tert-butyl 3-oxoazetidine-1-carboxylate and O-(oxan-2-ylmethyl)hydroxylamine obtained in the preceding section.

1H-NMR (CDCl3): δ 1.22-1.35 (2H, m), 1.45 (9H, s), 1.47-1.52 (3H, m), 1.80-1.92 (1H, m), 3.37-3.65 (2H, s), 3.92-4.10 (3H, m), 4.56-4.65 (4H, m)

(4) The title compound was obtained by the method described in Example 008 or a method equivalent thereto using N-(oxan-2-ylmethoxy) azetidin-3-imine trifluoroacetate obtained by the method described in Example 001-(2) or a method equivalent thereto from tert-butyl 3-[(oxan-2-ylmethoxy)imino]azetidine-1-carboxylate obtained in the preceding section, and 7-chloro-5-methyl-4-oxo-1-(1,2,4-thiadiazol-5-yl)-1,4-dihydro-1,8-naphthyridine-3-carboxylic acid obtained in Reference Example 002-(2).

1H-NMR (DMSO-d6): δ 1.15-1.29 (1H, m), 1.40-1.65 (4H, m), 1.76-1.88 (1H, m), 2.80 (3H, s), 3.53-3.64 (1H, m), 3.83-4.09 (3H, m), 4.98-5.38 (5H, m), 6.60 (1H, s), 8.83 (1H, s), 9.76 (1H, s)

Example 736

Compound 736

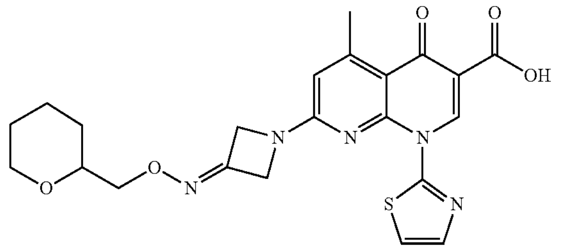

5-Methyl-7-{3-[(oxan-2-ylmethoxy)imino]azetidin-1-yl}-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-(oxan-2-ylmethoxy)azetidin-3-imine trifluoroacetate obtained in Example 735-(4) by the method described in Example 008 or a method equivalent thereto.

1H-NMR (DMSO-d6): δ 1.14-1.26 (1H, m), 1.40-1.62 (4H, m), 1.75-1.86 (1H, m), 2.80 (3H, s), 3.52-3.62 (1H, m), 3.78-4.09 (3H, m), 4.95-5.10 (4H, m), 6.67 (1H, s), 7.75 (1H, d, J=3.0 Hz), 7.83 (1H, d, J=3.0 Hz), 9.85 (1H, 8)

Example 737

Compound 737

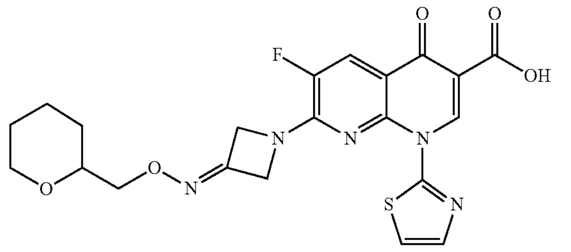

6-Fluoro-7-{3-[(oxan-2-ylmethoxy)imino]azetidin-1-yl}-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-(oxan-2-ylmethoxy)azetidin-3-imine trifluoroacetate obtained in Example 735-(4) by the method described in Example 008 or a method equivalent thereto.

1H-NMR (DMSO-d6): δ 1.13-1.26 (1H, m), 1.38-1.62 (4H, m), 1.74-1.86 (1H, m), 3.51-3.61 (1H, m), 3.83-3.90 (1H, m), 3.95 (1H, dd, J=11.5, 4.0 Hz), 4.02 (1H, dd, J=11.5, 6.5 Hz), 5.02-5.39 (4H, m), 7.81 (1H, d, J=3.5 Hz), 7.85 (1H, d, J=3.5 Hz), 8.18 (1H, d, J=11.5 Hz), 9.81 (1H, s), 14.63 (1H, brs)

Example 738

Compound 738

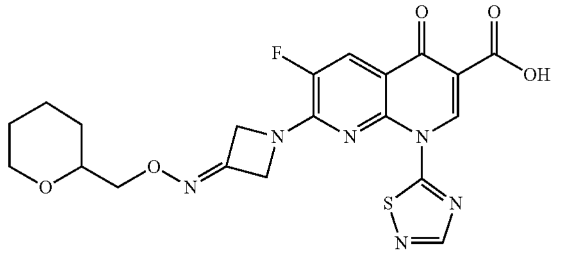

6-Fluoro-7-{3-[(oxan-2-ylmethoxy)imino]azetidin-1-yl}-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and N-(oxan-2-ylmethoxy) azetidin-3-imine trifluoroacetate obtained in Example 735-(4) by the method described in Example 008 or a method equivalent thereto.

1H-NMR (DMSO-d6): δ 1.15-1.27 (1H, m), 1.40-1.63 (4H, m), 1.74-1.84 (1H, m), 3.53-3.61 (1H, m), 3.83-3.90 (1H, m), 3.97 (1H, dd, J=11.5, 4.0 Hz), 4.04 (1H, dd, J=11.5, 6.5 Hz), 5.23-5.42 (4H, m), 8.25 (1H, d, J=11.5 Hz), 8.86 (1H, s), 9.76 (1H, s), 14.33 (1H, brs)

Example 739

Compound 739

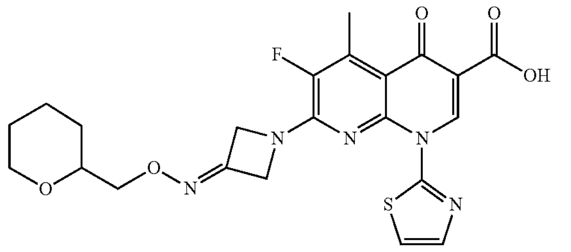

6-Fluoro-5-methyl-7-{3-[(oxan-2-ylmethoxy)imino]azetidin-1-yl}-4-oxo-1-(1,3-thiazol-2-yl)-1,4-dihydro-1,8-naphthyridine-3-carboxylic acid The title compound was obtained using 7-chloro-6-fluoro-5-methyl-4-oxo-1-(1,3-thiazol-2-yl)-1,4-dihydro-1,8-naphthyridine-3-carboxylic acid obtained in Reference Example 007-(2) and N-(oxan-2-ylmethoxy)azetidin-3- imine trifluoroacetate obtained in Example 735-(4) by the method described in Example 008 or a method equivalent thereto.

1H-NMR (DMSO-d6): δ 1.14-1.27 (1H, m), 1.40-1.64 (4H, m), 1.74-1.85 (1H, m), 2.69 (3H, d, J=2.5 Hz), 3.53-3.61 (1H, m), 3.83-3.90 (1H, m), 3.95 (1H, dd, J=11.5, 4.0 Hz), 4.02 (1H, dd, J=11.5, 6.5 Hz), 5.05-5.33 (4H, m), 7.79 (1H, d, J=3.5 Hz), 7.83 (1H, d, J=3.5 Hz), 9.77 (1H, s), 14.99 (1H, brs)

Example 740

Compound 741

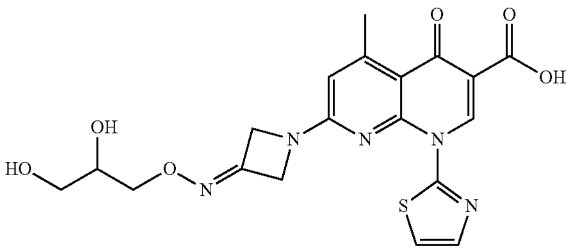

7-{3-[(2,3-Dihydroxypropoxy)imino]azetidin-1-yl}-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and 3-{[(azetidin-3-ylidene)amino]oxy}propane-1,2-diol hydrochloride obtained from (2,2-dimethyl-1,3-dioxolan-4-yl)methanol by the method described in Example 735-(1)~(3) and Example 001-(2) or a method equivalent thereto by the method described in Example 008 or a method equivalent thereto.

1H-NMR (DMSO-d6): δ 2.80 (3H, s), 3.69-3.77 (1H, m), 3.90-4.00 (1H, m), 4.07-4.15 (1H, m), 4.56-4.63 (1H, m), 4.76-4.80 (1H, m), 4.96-5.09 (4H, m), 6.68 (1H, s), 7.74-7.81 (1H, m), 7.84 (1H, d, J=3.5 Hz), 9.85 (1H, s), 15.21 (1H, brs)

Example 741

Compound 741

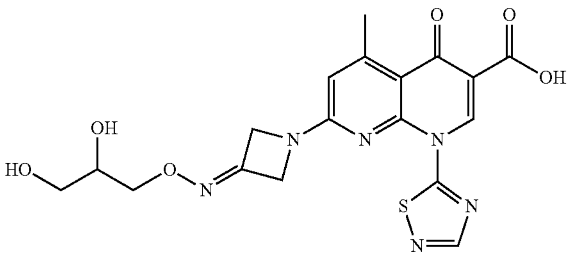

7-{3-[(2,3-Dihydroxypropoxy)imino]azetidin-1-yl}-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8- naphthyridine-3-carboxylic acid obtained in Reference Example 002-(2) and 3-{[(azetidin-3-ylidene)amino]oxy}propane-1,2-diol hydrochloride obtained in Example 740 by the method described in Example 008 or a method equivalent thereto.

1H-NMR (DMSO-d6): δ 2.80 (3H, s), 3.68-3.80 (1H, m), 3.91-4.01 (1H, m), 4.07-4.19 (1H, m), 4.56-4.65 (1H, m), 4.75-4.85 (1H, m), 4.97-5.36 (4H, m), 6.72 (1H, s), 8.83 (1H, s), 9.76 (1H, s), 14.92 (1H, brs)

Example 742

Compound 742

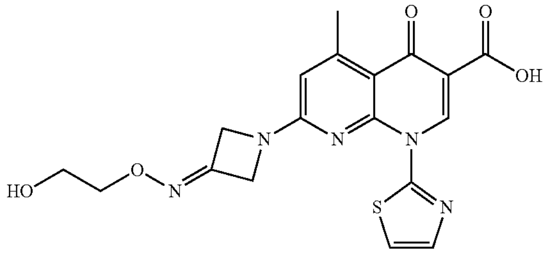

7-{3-[(2-Hydroxyethoxy)imino]azetidin-1-yl}-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and 2-{[(azetidin-3-ylidene)amino]oxy}ethan-1-ol trifluoroacetate obtained from 2-[(tert-butyldimethylsilyl)oxy]ethan-1-ol by the method described in Example 735-(1)~(3) and Example 001-(2) or a method equivalent thereto by the method described in Example 008 or a method equivalent thereto.

1H-NMR (DMSO-d6): δ 2.77 (3H, s), 3.61-3.67 (2H, m), 4.05-4.15 (2H, m), 4.97-5.01 (4H, m), 6.65 (1H, s), 7.75-7.80 (1H, m), 7.83 (1H, d, J=3.5 Hz), 9.82 (1H, s), 15.22 (1H, brs)

Example 743

Compound 743

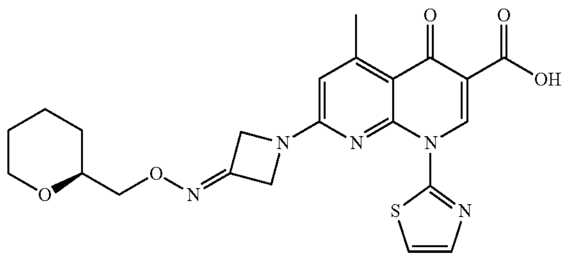

5-Methyl-7-(3-{[(2S)-oxan-2-ylmethoxy]imino}azetidin-1-yl)-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-{[(2S)-oxan-2-yl]methoxy}azetidin-3-imine trifluoroacetate obtained from [(2S)-oxan-2-yl]methanol by the method described in Example 735-(1)~(3) and Example 001-(2) or a method equivalent thereto by the method described in Example 001-(3) or a method equivalent thereto.

1H-NMR (DMSO-d6): δ 1.13-1.25 (1H, m), 1.40-1.51 (3H, m), 1.55-1.62 (31, m), 1.76-1.83 (1H, m), 2.80 (3H, s), 3.26-3.37 (1H, m), 3.53-3.60 (1H, m), 3.84-3.89 (1H, m), 3.96 (1H, dd, J=11.5, 4.0 Hz), 4.02 (1H, dd, J=11.5, 6.5 Hz), 4.96-5.10 (4H, m), 6.67 (1H, s), 7.77 (1H, brs), 7.84 (1H, d, J=3.5 Hz), 9.85 (1H, s), 15.22 (1H, brs)

Example 744

Compound 744

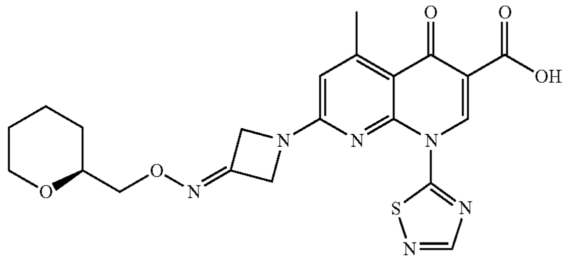

5-Methyl-7-(3-{[(2S)-oxan-2-ylmethoxy]imino}azetidin-1-yl)-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-{[(2S)-oxan-2-yl]methoxy}azetidin-3-imine trifluoroacetate obtained in Example 743 by the method described in Example 001-(3) or a method equivalent thereto.

1H-NMR (DMSO-d6): δ 1.16-1.27 (1H, m), 1.41-1.52 (3H, m), 1.56-1.64 (1H, m), 1.77-1.84 (1H, m), 2.79 (3H, s), 3.26-3.39 (1H, m), 3.54-3.62 (1H, m), 3.84-3.91 (1H, m), 3.98 (1H, dd, J=11.5, 3.5 Hz), 4.04 (1H, dd, J=11.5, 7.0 Hz), 4.85-5.31 (4H, m), 6.71 (1H, s), 8.82 (1H, s), 9.75 (1H, s), 14.92 (1H, brs)

Example 745

Compound 745

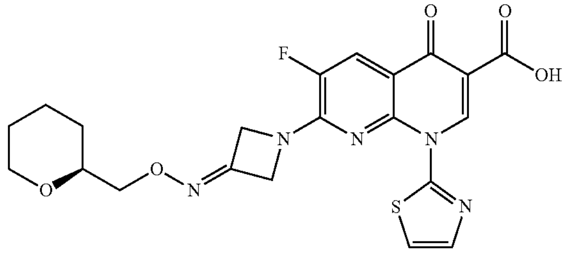

6-Fluoro-7-(3-{[(2S)-oxan-2-ylmethoxy]imino}azetidin-1-yl)-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-{[(2S)-oxan-2-yl]methoxy}azetidin-3-imine trifluoroacetate obtained in Example 743 by the method described in Example 001-(3) or a method equivalent thereto.

1H-NMR (DMSO-d6): δ 1.14-1.26 (1H, m), 1.40-1.51 (3H, m), 1.55-1.62 (1H, m), 1.76-1.83 (1H, m), 3.29-3.38 (1H, m), 3.53-3.60 (1H, m), 3.84-3.89 (1H, m), 3.95 (1H, dd, J=11.5, 4.0 Hz), 4.01 (1H, dd, J=11.5, 7.0 Hz), 5.14-5.26 (4H, m), 7.77 (1H, d, J=3.5 Hz), 7.83 (1H, d, J=3.5 Hz), 8.16 (1H, d, J=11.0 Hz), 9.84 (1H, s), 14.63 (1H, brs)

Example 746

Compound 746

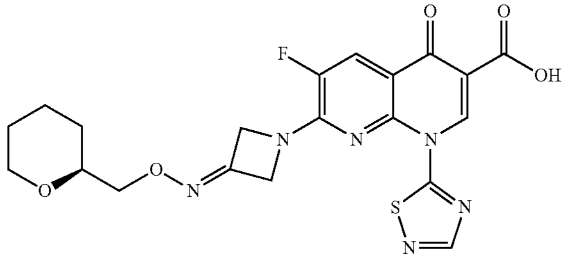

6-Fluoro-7-(3-{([(2S)-oxan-2-ylmethoxy]imino}azetidin-1-yl)-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and N-{[(2S)-oxan-2-yl]methoxy}azetidin-3-imine trifluoroacetate obtained in Example 743 by the method described in Example 001-(3) or a method equivalent thereto.

1H-NMR (DMSO-d6): δ 1.13-1.27 (1H, m), 1.41-1.52 (3H, m), 1.56-1.63 (1H, m), 1.76-1.84 (1H, m), 3.27-3.38 (1H, m), 3.54-3.61 (1H, m), 3.84-3.90 (1H, m), 3.97 (1H, dd, J=11.5, 4.0 Hz), 4.04 (1H, dd, J=11.5, 6.5 Hz), 5.29-5.39 (4H, m), 8.25 (1H, d, J=11.0 Hz), 8.86 (1H, s), 9.77 (1H, s), 14.32 (1H, s)

Example 747

Compound 747

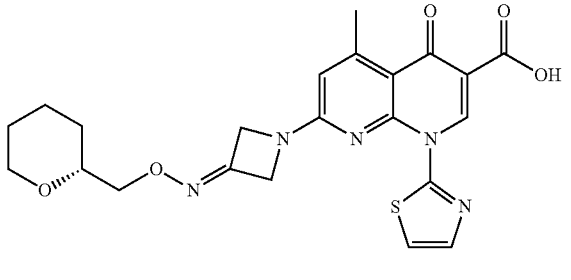

5-Methyl-7-(3-{[(2R)-oxan-2-ylmethoxy]imino}azetidin-1-yl)-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-{[(2R)-oxan-2-yl]methoxy}azetidin-3-imine trifluoroacetate obtained from [(2R)-oxan-2-yl]methanol by the method described in Example 735-(1)~(3) and Example 001-(2) or a method equivalent thereto by the method described in Example 008 or a method equivalent thereto.

1H-NMR (DMSO-d6): δ 1.13-1.30 (1H, m), 1.40-1.54 (3H, m), 1.56-1.62 (1H, m), 1.71-1.88 (1H, m), 2.75 (3H, s), 3.24-3.39 (1H, m), 3.52-3.62 (1H, m), 3.81-3.93 (1H, m), 4.00 (2H, dd, J=11.5, 6.5 Hz), 4.91-5.07 (4H, m), 6.62 (1H, s), 7.76 (1H, brs), 7.91 (1H, d, J=3.5 Hz), 9.80 (1H, s), 15.20 (1H, brs)

Example 748

Compound 748

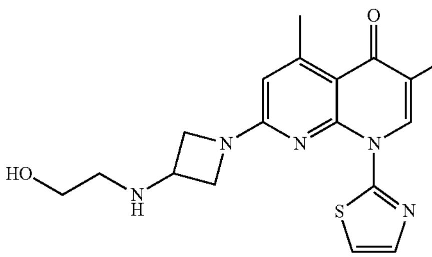

7-{3-[(2-Hydroxyethyl)amino]azetidin-1-yl}-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and 2-[(azetidin-3-yl)amino]ethan-1-ol hydrochloride obtained in Example 026-(2) by the method described in Example 001-(3) or a method equivalent thereto.

1H-NMR (DMSO-d6): δ 2.79 (3H, s), 2.94-3.07 (2H, m), 3.61-3.67 (2H, m), 4.18-4.63 (5H, m), 5.17-5.26 (1H, m), 6.62 (1H, s), 7.79 (1H, d, J=3.5 Hz), 7.86 (1H, d, J=3.5 Hz), 9.85 (1H, s)

Example 749

Compound 749

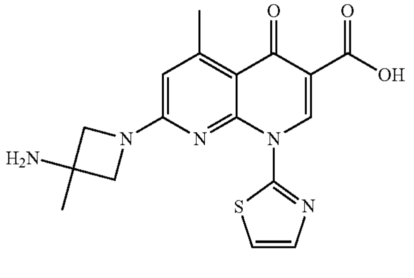

7-(3-Amino-3-methylazetidin-1-yl)-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and 3-methylazetidin-3-amine hydrochloride by the method described in Example 001-(3) or a method equivalent thereto.

1H-NMR (DMSO-d6): δ 1.55 (3H, s), 2.78 (3H, s), 4.10-4.36 (4H, m), 6.59 (1H, s), 7.79 (1H, d, J=3.5 Hz), 7.85 (1H, d, J=3.5 Hz), 9.84 (1H, s)

Example 750

Compound 750

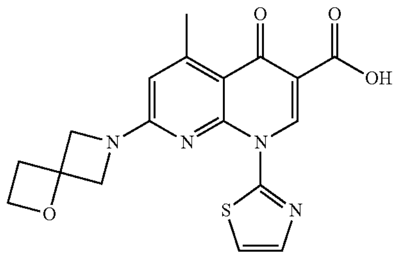

5-Methyl-7-{1-oxa-6-azaspiro[3.3]heptan-6-yl}-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and 1-oxa-6-azaspiro[3.3]heptane trifluoroacetate by the method described in Example 001-(3) or a method equivalent thereto.

1H-NMR (DMSO-d6): δ 2.76 (3H, s), 2.95 (2H, t, J=7.5 Hz), 4.35-4.46 (2H, m), 4.49 (2H, t, J=7.5 Hz), 4.52-4.60 (2H, m), 6.48 (1H, s), 7.73 (1H, d, J=3.5 Hz), 7.83 (1H, d, J=3.5 Hz), 9.79 (1H, s), 15.34 (1H, brs)

Example 751

Compound 751

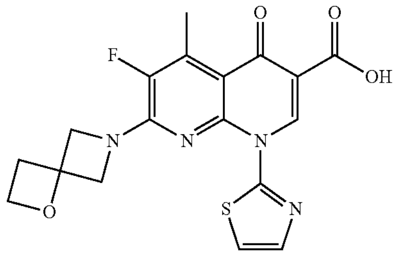

6-Fluoro-5-methyl-7-{1-oxa-6-azaspiro[3.3]heptan-6-yl}-4-oxo-1-(1,3-thiazol-2-yl)-1,4-dihydro-1,8-naphthyridine-3-carboxylic acid The title compound was obtained using 7-chloro-6-fluoro-5-methyl-4-oxo-1-(1,3-thiazol-2-yl)-1,4-dihydro-1, 8-naphthyridine-3-carboxylic acid obtained in Reference Example 007-(2) and 1-oxa-6-azaspiro[3.3]heptane trifluoroacetate by the method described in Example 001-(3) or a method equivalent thereto.

1H-NMR (DMSO-d6): δ 2.68 (3H, d, J=2.9 Hz), 2.96 (2H, t, J=7.5 Hz), 4.48 (2H, t, J=7.5 Hz), 4.52-4.79 (4H, m), 7.79 (1H, d, J=3.5 Hz), 7.85 (1H, d, J=3.5 Hz), 9.80 (1H, s), 15.14 (1H, brs)

Example 752

Compound 752

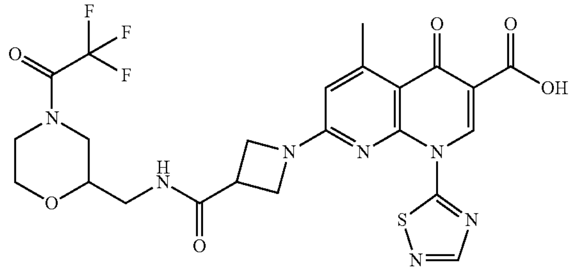

5-Methyl-4-oxo-1-(1,2,4-thiadiazol-5-yl)-7-[3-({[4-(trifluoroacetyl)morpholin-2-yl]methyl}carbamoyl)azetidin-1-yl]-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-{[4-(trifluoroacetyl)morpholin-2-yl]methyl}azetidine-3-carboxamide trifluoroacetate obtained in Example 640 by the method described in Example 001-(3) or a method equivalent thereto.

Property: Pale brown solid;

1H-NMR (DMSO-d6): δ 2.68-2.83 (4H, m), 2.98-3.08 (1H, m), 3.13-3.21 (1H, m), 3.22-3.44 (1H, m), 3.47-3.57 (2H, m), 3.59-3.80 (2H, m), 3.89-3.98 (1H, m), 4.05-4.67 (5H, m), 6.59 (1H, s), 8.39-8.47 (1H, m), 8.81 (1H, s), 9.73 (1H, s), 15.08 (1H, brs)

Example 753

Compound 753

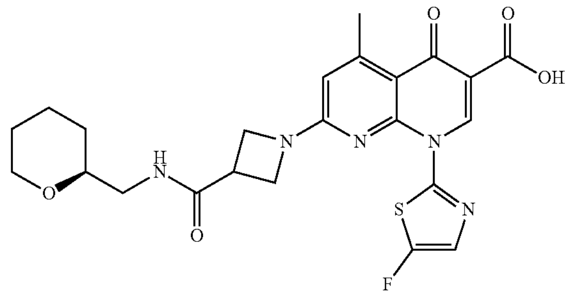

1-(5-Fluoro-1,3-thiazol-2-yl)-5-methyl-7-(3-{[(2S)-oxan-2-ylmethyl]carbamoyl}azetidin-1-yl)-4-oxo-1,4-dihydro-1,8-naphthyridine-3-carboxylic acid The title compound was obtained using 7-chloro-1-(5-fluoro-1,3-thiazol-2-yl)-5-methyl-4-oxo-1,4-dihydro-1,8-naphthyridine-3-carboxylic acid obtained in Reference Example 010-(2) and N-[(2S)-oxan-2-ylmethyl]azetidine-3-carboxamide hydrochloride obtained in Example 391 by the method described in Example 001-(3) or a method equivalent thereto.

1H-NMR (DMSO-d6): δ 1.09-1.20 (1H, m), 1.36-1.50 (3H, m), 1.50-1.60 (1H, m), 1.71-1.82 (1H, m), 2.74 (3H, s), 3.01-3.23 (4H, m), 3.57-3.67 (1H, m), 3.82-3.92 (1H, m), 4.14-4.54 (4H, m), 6.53 (1H, s), 7.73 (1H, d, J=2.5 Hz), 8.24 (1H, t, J=5.5 Hz), 9.67 (1H, s), 15.33 (1H, s)

Example 754

Compound 754

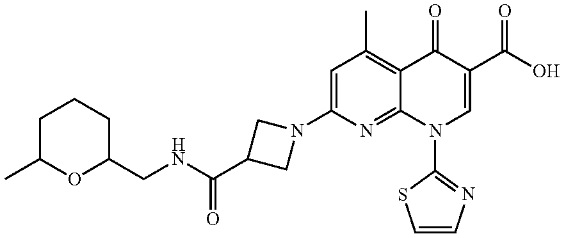

5-Methyl-7-(3-{([6-methyloxan-2-yl)methyl]carbamoyl}azetidin-1-yl)-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-[(6-methyloxan-2-yl)methyl]azetidine-3-carboxamide hydrochloride obtained in Example 393 by the method described in Example 001-(3) or a method equivalent thereto.

1H-NMR (DMSO-d6): δ 1.01-1.12 (4H, m), 1.16-1.36 (1H, m), 1.37-1.80 (4H, m), 2.76 (3H, s), 3.06-3.43 (4H, m), 3.56-3.90 (1H, m), 4.17-4.58 (4H, m), 6.51-6.56 (1H, m), 7.73-7.76 (1H, m), 7.82-7.84 (1H, m), 8.11-8.22 (1H, m), 9.83 (1H, d, J=0.5 Hz), 15.32-15.45 (1H, m)

Example 755

Compound 755

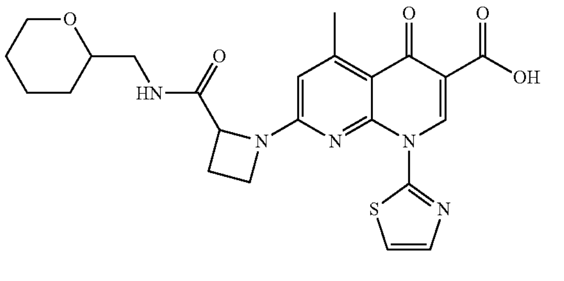

5-Methyl-7-{2-[(oxan-2-ylmethyl)carbamoyl]azetidin-1-yl}-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-(oxan-2-ylmethyl)azetidine-2-carboxamide hydrochloride obtained from oxan-2-ylmethanamine by the method described in Example 005-(1) and Example 001-(2) or a method equivalent thereto by the method described in Example 001-(3) or a method equivalent thereto.

1H-NMR (DMSO-d6): δ 0.90-1.84 (7H, m), 2.14-2.39 (1H, m), 2.42-3.44 (7H, m), 3.65-3.94 (1H, m), 4.04-4.40 (2H, m), 4.97-5.09 (1H, m), 6.24-6.64 (1H, m), 7.66-7.88 (2H, m), 8.17-8.50 (1H, m), 9.78-9.87 (1H, m), 15.27-15.48 (1H, m)

Example 756

Compound 756

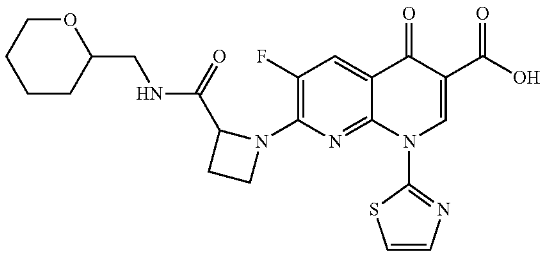

6-Fluoro-7-{2-[(oxan-2-ylmethyl)carbamoyl]azetidin-1-yl}-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-(oxan-2-ylmethyl)azetidine-2-carboxamide hydrochloride obtained in Example 755 by the method described in Example 001-(3) or a method equivalent thereto.

1H-NMR (DMSO-d6): δ 0.93-1.84 (7H, m), 2.18-2.28 (1H, m), 2.77-3.42 (4H, m), 3.68-3.95 (1H, m), 4.20-4.65 (2H, m), 5.04-5.34 (1H, m), 7.73-7.82 (1H, m), 7.83-7.90 (1H, m), 8.02-8.18 (1H, m), 8.24-8.36 (1H, m), 9.75-9.85 (1H, m), 14.70-14.81 (1H, m)

Example 757

Compound 757

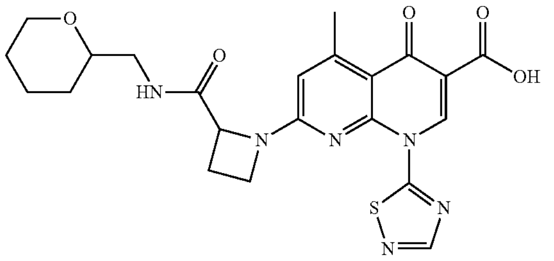

5-Methyl-7-{2-[(oxan-2-ylmethyl)carbamoyl]azetidin-1-yl}-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-(oxan-2-ylmethyl)azetidine-2-carboxamide hydrochloride obtained in Example 755 by the method described in Example 001-(3) or a method equivalent thereto.

ESI-MS (m/z): 485 [M+H]+;

1H-NMR (DMSO-d6): δ 0.97-1.84 (7H, m), 2.14-3.51 (8H, m), 3.62-3.94 (1H, m), 4.03-4.53 (2H, m), 4.94-5.24 (1H, m), 6.61-6.67 (1H, m), 8.39-8.54 (1H, m), 8.77-8.85 (1H, m), 9.76 (1H, brs), 15.03 (1H, s)

Example 758

Compound 758

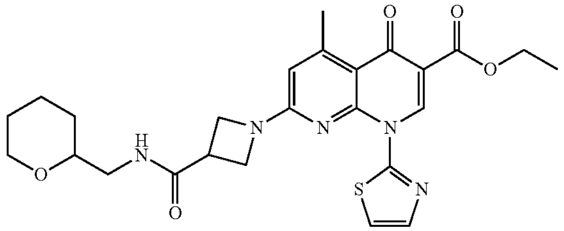

Ethyl 5-methyl-7-{3-[(oxan-2-ylmethyl)carbamoyl]azetidin-1-yl}-4-oxo-1-(1,3-thiazol-2-yl)-1,4-dihydro-1,8-naphthyridine-3-carboxylate The title compound was obtained using ethyl 7-chloro-5-methyl-4-oxo-1-(1,3-thiazol-2-yl)-1,4-dihydro-1,8-naphthyridine-3-carboxylate obtained in Reference Example 001-(1) and N-(oxan-2-ylmethyl)azetidine-3-carboxamide hydrochloride obtained in Example 078-(1) by the method described in Example 026-(3) or a method equivalent thereto.

1H-NMR (CDCl3): δ 1.25-1.36 (1H, m), 1.42 (3H, t, J=7.0 Hz), 1.48-1.64 (4H, m), 1.84-1.91 (1H, m), 2.88 (3H, s), 3.03-3.12 (1H, m), 3.39-3.54 (3H, m), 3.62-3.70 (1H, m), 3.97-4.03 (1H, m), 4.36-4.52 (6H, m), 5.99-6.03 (1H, m), 6.10 (1H, s), 7.22 (1H, d, J=3.5 Hz), 7.68 (1H, d, J=3.5 Hz), 9.78 (1H, s)

Example 759

Compound 759

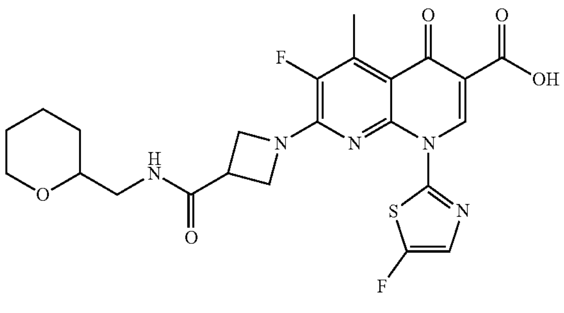

6-Fluoro-1-(5-fluoro-1,3-thiazol-2-yl)-5-methyl-7-{3-[(oxan-2-ylmethyl)carbamoyl]azetidin-1-yl}-4-oxo-1,4-dihydro-1,8-naphthyridine-3-carboxylic acid (1) Ethyl 7-chloro-6-fluoro-1-(5-fluoro-1,3-thiazol-2-yl)-5-methyl-4-oxo-1,4-dihydro-1,8-naphthyridine-3-carboxylate was obtained using ethyl 3-(2,6-dichloro-5-fluoro-4-methylpyridin-3-yl)-3-oxopropanoate obtained by the method described in JP-A-2-282384 or a method equivalent thereto and 5-fluoro-1,3-thiazol-2-amine hydrochloride by the method described in Reference Example 001-(1) or a method equivalent thereto.

1H-NMR (CDCl3): δ 1.43 (3H, t, J=7.0 Hz), 2.98 (3H, d, J=2.0 Hz), 4.44 (2H, q, J=7.0 Hz), 7.34 (1H, d, J=3.5 Hz), 9.76 (1H, s)

(2) 7-Chloro-6-fluoro-1-(5-fluoro-1,3-thiazol-2-yl)-5-methyl-4-oxo-1,4-dihydro-1,8-naphthyridine-3-carboxylic acid was obtained from ethyl 7-chloro-6-fluoro-1-(5-fluoro-1,3-thiazol-2-yl)-5-methyl-4-oxo-1,4-dihydro-1,8-naphthyridine-3-carboxylate obtained in a preceding section by the method described in Reference Example 001-(2) or a method equivalent thereto.

1H-NMR (DMSO-d6): δ 2.89 (3H, d, J=2.5 Hz), 7.81 (1H, d, J=2.5 Hz), 9.67 (1H, s), 13.72 (1H, s)

(3) The title compound was obtained using N-(oxan-2-ylmethyl)azetidine-3-carboxamide hydrochloride obtained in Example 078-(1) and 7-chloro-6-fluoro-1-(5-fluoro-1,3-thiazol-2-yl)-5-methyl-4-oxo-1,4-dihydro-1,8-naphthyridine-3-carboxylic acid obtained in a preceding section by the method described in Example 001-(3) or a method equivalent thereto.

1H-NMR (DMSO-d6): δ 1.08-1.20 (1H, m), 1.37-1.49 (3H, m), 1.51-1.60 (1H, m), 1.70-1.81 (1H, m), 2.67 (3H, d, J=3.0 Hz), 3.05-3.12 (1H, m), 3.15-3.23 (1H, m), 3.25-3.37 (2H, m), 3.60-3.68 (1H, m), 3.84-3.90 (1H, m), 4.31-4.77 (4H, m), 7.75 (1H, d, J=3.0 Hz), 8.22 (1H, t, J=5.5 Hz), 9.64 (1H, s), 15.10 (1H, brs)

Example 760

Compound 760

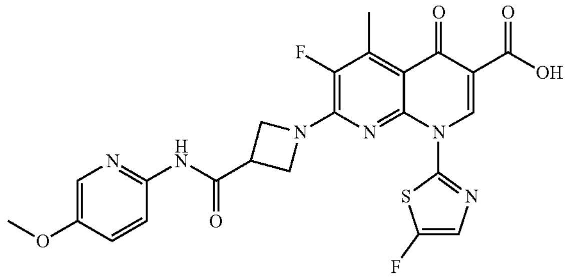

6-Fluoro-1-(5-fluoro-1,3-thiazol-2-yl)-7-{3-[(5-methoxypyridin-2-yl)carbamoyl]azetidin-1-yl}-5-methyl-4-oxo-1,4-dihydro-1,8-naphthyridine-3-carboxylic acid The title compound was obtained using 7-chloro-6-fluoro-1-(5-fluoro-1,3-thiazol-2-yl)-5-methyl-4-oxo-1,4-dihydro-1,8-naphthyridine-3-carboxylic acid obtained in Example 759-(2) and N-(5-methoxypyridin-2-yl)azetidine-3-carboxamide hydrochloride obtained in Example 017 by the method described in Example 001-(3) or a method equivalent thereto.

1H-NMR (DMSO-d6): δ 2.68 (3H, d, J=3.0 Hz), 3.80 (3H, s), 3.87-3.96 (1H, m), 4.48-4.81 (4H, m), 7.45 (1H, dd, J=9.0, 3.0 Hz), 7.73 (1H, d, J=3.0 Hz), 8.05 (1H, d, J=3.0 Hz), 8.09 (1H, d, J=9.0 Hz), 9.64 (1H, s), 10.63 (1H, s)

Example 761

Compound 761

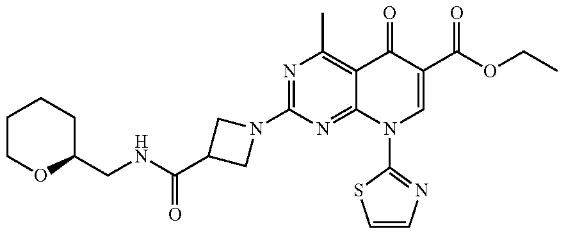

Ethyl 4-methyl-2-(3-{[(2S)-oxan-2-ylmethyl]carbamoyl}azetidin-1-yl)-5-oxo-8-(1,3-thiazol-2-yl)-5H,8H-pyrido[2,3-d]pyrimidine-6-carboxylate (1) Ethyl 2-methanesulfonyl-4-methyl-5-oxo-8-(1,3-thiazol-2-yl)-5H, 8H-pyrido[2,3-d]pyrimidine-6-carboxylate was obtained using 4-chloro-6-methyl-2-(methylsulfanyl)pyrimidine-5-carboxylic acid and 1,3-thiazol-2-amine by the method described in Journal of Medicinal Chemistry 45, 5564 (2002) or a method equivalent thereto.

1H-NMR (CDCl3): δ 1.45 (3H, t, J=7.0 Hz), 3.27 (3H, s), 3.48 (3H, s), 4.47 (2H, q, J=7.0 Hz), 7.46 (1H, d, J=3.5 Hz), 7.77 (1H, d, J=3.5 Hz), 9.97 (1H, s)

(2) The title compound was obtained using N-[(2S) oxan-2-ylmethyl]azetidine-3-carboxamide hydrochloride obtained in Example 391 and ethyl 2-methanesulfonyl-4-methyl-5-oxo-8-(1,3-thiazol-2-yl)-5H,8H-pyrido[2,3-d]pyrimidine-6-carboxylate obtained in a preceding section by the method described in Example 027-(3) or a method equivalent thereto.

1H-NMR (CDCl3): δ 0.80-0.92 (1H, m), 1.23-1.37 (3H, m), 1.43 (3H, t, J=7.0 Hz), 1.47-1.67 (1H, m), 1.84-1.91 (1H, m), 2.98 (3H, s), 3.37-3.74 (5H, m), 3.97-4.03 (1H, m), 4.42 (2H, q, J=7.0 Hz), 4.46-4.66 (4H, m), 6.00 (1H, brs), 7.23-7.29 (1H, d, J=3.0 Hz), 7.69 (1H, d, J=3.0 Hz), 9.76 (1H, s)

Example 762

Compound 762

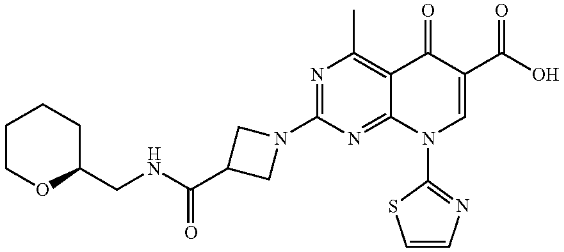

4-Methyl-2-(3-{[(2S)-oxan-2-ylmethyl]carbamoyl}azetidin-1-yl)-5-oxo-8-(1,3-thiazol-2-yl)-5H,8H-pyrido[2,3-d]pyrimidine-6-carboxylic acid The title compound was obtained from ethyl 4-methyl-2-(3-{[(2S)-oxan-2-ylmethyl]carbamoyl}azetidin-1-yl)-5-oxo-8-(1,3-thiazol-2-yl)-5H,8H-pyrido[2,3-d]pyrimidine-6-carboxylate obtained in Example 761-(2) by the method described in Example 028-(2) or a method equivalent thereto.

1H-NMR (DMSO-d6): δ 1.09-1.20 (1H, m), 1.38-1.50 (3H, m), 1.51-1.58 (1H, m), 1.71-1.81 (1H, m), 2.86 (3H, s), 3.03-3.41 (4H, m), 3.56-3.64 (1H, m), 3.83-3.90 (1H, m), 4.22-4.49 (4H, m), 7.78 (1H, d, J=3.5 Hz), 7.84 (1H, d, J=3.5 Hz), 8.22 (1H, t, J=5.5 Hz), 9.81 (1H, s), 14.69 (1H, brs)

Example 763

Compound 763

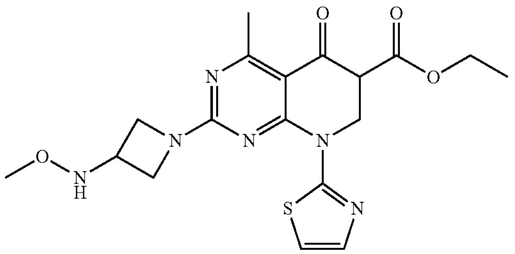

Ethyl 2-[3-(methoxyamino)azetidin-1-yl]-4-methyl-5-oxo-8-(1,3-thiazol-2-yl)-5H,8H-pyrido[2,3-d]pyrimidine-6-carboxylate The title compound was obtained using ethyl 2-methanesulfonyl-4-methyl-5-oxo-8-(1,3-thiazol-2-yl)-5H,8H-pyrido[2,3-d]pyrimidine-6-carboxylate obtained in Example 761-(1) and N-methoxyazetidin-3-amine trifluoroacetate obtained in Example 535 by the method described in Example 027-(3) or a method equivalent thereto.

1H-NMR (CDCl3): δ 1.29 (3H, t, J=7.0 Hz), 2.79 (3H, s), 3.21-3.40 (1H, m), 3.47 (3H, s), 3.95-4.18 (2H, m), 4.26 (2H, q, J=7.0 Hz), 4.29-4.44 (2H, m), 7.70 (1H, d, J=3.5 Hz), 7.78 (1H, d, J=3.5 Hz), 9.53 (1H, s)

Example 764

Compound 764

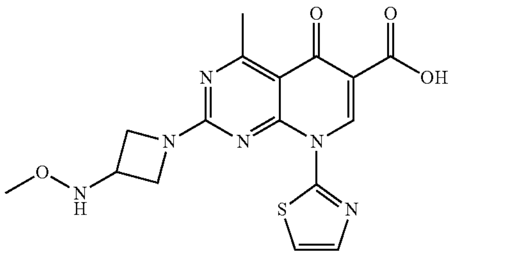

2-[3-(Methoxyamino)azetidin-1-yl]-4-methyl-5-oxo-8-(1,3-thiazol-2-yl)-5H,8H-pyrido[2,3-d]pyrimidine-6-carboxylic acid The title compound was obtained from ethyl 2-[3-(methoxyamino)azetidin-1-yl]-4-methyl-5-oxo-8-(1,3-thiazol-2-yl)-5H, 8H-pyrido[2,3-d]pyrimidine-6-carboxylate obtained in Example 763 by the method described in Example 028-(2) or a method equivalent thereto.

1H-NMR (DMSO-d6): δ 2.86 (3H, s), 3.48 (3H, s), 4.04-4.20 (3H, m), 4.35-4.48 (2H, m), 7.16 (1H, d, J=6.0 Hz), 7.80 (1H, d, J=3.0 Hz), 7.84 (1H, d, J=3.0 Hz), 9.82 (1H, s), 14.71 (1H, brs)

Example 765

Compound 765

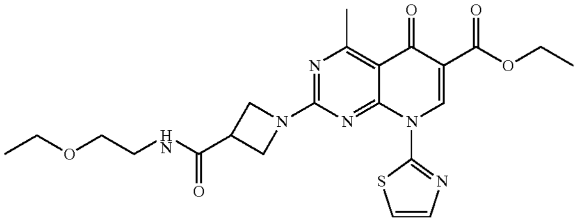

Ethyl 2-{3-[(2-ethoxyethyl)carbamoyl]azetidin-1-yl}-4-methyl-5-oxo-8-(1,3-thiazol-2-yl)-5H,8H-pyrido[2,3-d]pyrimidine-6-carboxylate The title compound was obtained using ethyl 2-methanesulfonyl-4-methyl-5-oxo-8-(1,3-thiazol-2-yl)-5H,8H-pyrido[2,3-d]pyrimidine-6-carboxylate obtained in Example 761-(1) and N-(2-ethoxyethyl)azetidine-3-carboxamide hydrochloride obtained in Example 018-(l) by the method described in Example 027-(3) or a method equivalent thereto.

1H-NMR (CDCl3): δ 1.11 (3H, t, J=7.0 Hz), 1.29 (3H, t, J=7.0 Hz), 2.80 (3H, s), 3.23-3.46 (6H, m), 3.53-3.59 (1H, m), 4.12-4.47 (6H, m), 7.68 (1H, d, J=3.5 Hz), 7.78 (1H, d, J=3.5 Hz), 8.23 (1H, t, J=5.5 Hz), 9.54 (1H, s)

Example 766

Compound 766

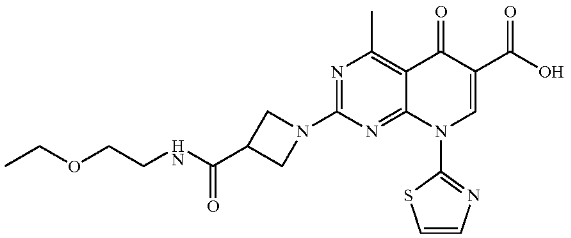

2-{3-[(2-Ethoxyethyl)carbamoyl]azetidin-1-yl}-4-methyl-5-oxo-8-(1,3-thiazol-2-yl)-5H, 8H-pyrido[2,3-d]pyrimidine-6-carboxylic acid The title compound was obtained from ethyl 2-{3-[(2-ethoxyethyl)carbamoyl]azetidin-1-yl}-4-methyl-5-oxo-8-

(1,3-thiazol-2-yl)-5H,8H-pyrido[2,3-d]pyrimidine-6-carboxylate obtained in Example 765 by the method described in Example 028-(2) or a method equivalent thereto.

1H-NMR (DMSO-d6): δ 1.11 (3H, t, J=7.5 Hz), 2.87 (3H, s), 3.23-3.47 (6H, m), 3.54-3.62 (1H, m), 4.24-4.30 (1H, m), 4.33-4.38 (1H, m), 4.39-4.51 (2H, m), 7.78 (1H, d, J=3.5 Hz), 7.84 (1H, d, J=3.5 Hz), 8.23 (1H, t, J=5.5 Hz), 9.82 (1H, s), 14.69 (1H, s)

Example 767

Compound 767

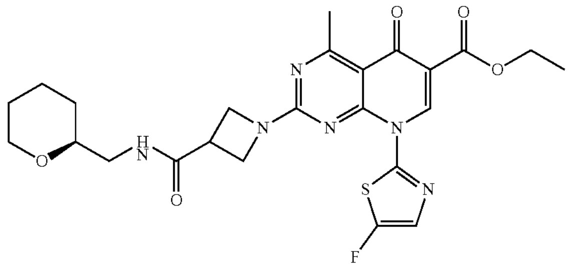

Ethyl 8-(5-fluoro-1,3-thiazol-2-yl)-4-methyl-2-(3-{[(2S)-oxan-2-ylmethyl]carbamoyl}azetidin-1-yl)-5-oxo-5H,8H-pyrido[2,3-d]pyrimidine-6-carboxylate (1) Ethyl 8-(5-fluoro-1,3-thiazol-2-yl)-2-methanesulfonyl-4-methyl-5-oxo-5H,8H-pyrido[2,3-d]pyrimidine-6-carboxylate was obtained using 4-chloro-6-methyl-2-(methylsulfanyl)pyrimidine-5-carboxylic acid and 5-fluoro-1,3-thiazol-2-amine hydrochloride by the method described in Journal of Medicinal Chemistry 45, 5564 (2002) or a method equivalent thereto.

1H-NMR (CDCl3): δ 1.43 (3H, t, J=7.0 Hz), 2.75 (3H, s), 3.08 (3H, s), 4.44 (2H, q, J=7.0 Hz), 7.33 (1H, d, J=3.0 Hz), 9.63 (1H, s)

(2) The title compound was obtained using N-[(2S)-oxan-2-ylmethyl]azetidine-3-carboxamide hydrochloride obtained in Example 391 and ethyl 8-(5-fluoro-1,3-thiazol-2-yl)-2-methanesulfonyl-4-methyl-5-oxo-5H, 8H pyrido[2,3-d]pyrimidine-6-carboxylate obtained in a preceding section by the method described in Example 027-(3) or a method equivalent thereto.

1H-NMR (CDCl3): δ 1.25-1.36 (1H, m), 1.42 (3H, t, J=7.0 Hz), 1.47-1.65 (4H, m), 1.84-1.91 (1H, m), 2.96 (3H, s), 3.03-3.14 (1H, m), 3.38-3.51 (3H, m), 3.61-3.71 (1H, m), 3.97-4.03 (1H, m), 4.42 (2H, q, J=7.0 Hz), 4.45-4.64 (4H, m), 6.00-6.05 (1H, m), 7.29 (1H, d, J=3.0 Hz), 9.59 (1H, s)

Example 768

Compound 768

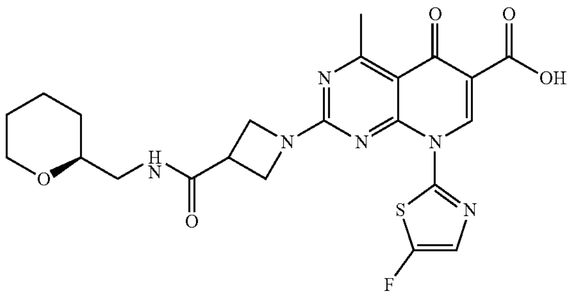

8-(5-Fluoro-1,3-thiazol-2-yl)-4-methyl-2-(3-{[(2S)-oxan-2-ylmethyl]carbamoyl}azetidin-1-yl)-5-oxo-5H, 8H-pyrido[2,3-d]pyrimidine-6-carboxylic acid The title compound was obtained from ethyl 8-(5-fluoro-1,3-thiazol-2-yl)-4-methyl-2-(3-{[(2S)-oxan-2-ylmethyl]carbamoyl}azetidin-1-yl)-5-oxo-5H, 8H-pyrido[2,3-d]pyrimidine-6-carboxylate obtained in Example 767-(2) by the method described in Example 028-(2) or a method equivalent thereto.

1H-NMR (DMSO-d6): δ 1.08-1.20 (1H, m), 1.37-1.49 (3H, m), 1.51-1.59 (1H, m), 1.71-1.81 (1H, m), 2.84 (3H, s), 2.98-3.40 (4H, m), 3.56-3.63 (1H, m), 3.81-3.91 (1H, m), 4.22-4.28 (1H, m), 4.32-4.44 (2H, m), 4.46-4.52 (1H, m), 7.74 (1H, d, J=2.5 Hz), 8.23 (1H, t, J=5.5 Hz), 9.64 (1H, s), 14.59 (1H, s)

Example 769

Compound 769

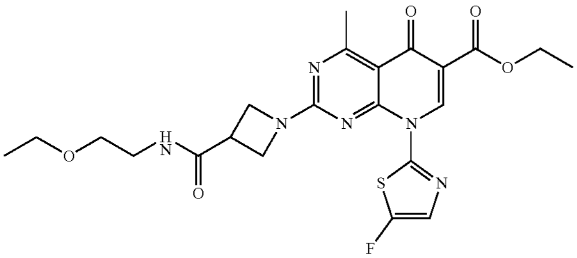

Ethyl 2-{3-[(2-ethoxyethyl)carbamoyl]azetidin-1-yl}-8-(5-fluoro-1,3-thiazol-2-yl)-4-methyl-5-oxo-5H,8H-pyrido[2,3-d]pyrimidine-6-carboxylate The title compound was obtained using ethyl 8-(5-fluoro-1,3-thiazol-2-yl)-2-methanesulfonyl-4-methyl-5-oxo-5H, 8H-pyrido[2,3-d]pyrimidine-6-carboxylate obtained in Example 767-(1) and N-(2-ethoxyethyl)azetidine-3-carboxamide hydrochloride obtained in Example 018-(1) by the method described in Example 027-(3) or a method equivalent thereto.

1H-NMR (CDCl3): δ 1.24 (3H, t, J=7.5 Hz), 1.42 (3H, t, J=7.5 Hz), 2.96 (3H, s), 3.43-3.58 (7H, m), 4.42 (2H, q, J=7.5 Hz), 4.46-4.64 (4H, m), 7.23-7.31 (1H, m), 9.60 (1H, s)

Example 770

Compound 770

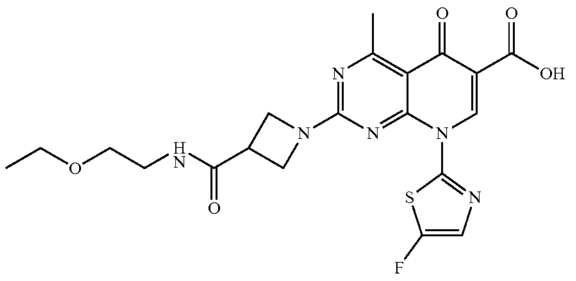

2-{3-[(2-Ethoxyethyl)carbamoyl]azetidin-1-yl}-8-(5-fluoro-1,3-thiazol-2-yl)-4-methyl-5-oxo-5H,8H-pyrido[2,3-d]pyrimidine-6-carboxylic acid The title compound was obtained from ethyl 2-{3-[(2-ethoxyethyl)carbamoyl]azetidin-1-yl}-8-(5-fluoro-1,3-thiazol-2-yl)-4-methyl-5-oxo-5H, 8H-pyrido[2,3-d]pyrimidine-6-carboxylate obtained in Example 769 by the method described in Example 028-(2) or a method equivalent thereto.

1H-NMR (DMSO-d6): δ 1.11 (3H, t, J=7.5 Hz), 2.85 (3H, s), 3.18-3.48 (6H, m), 3.54-3.61 (1H, m), 4.24-4.30 (1H, m), 4.33-4.45 (2H, m), 4.47-4.53 (1H, m), 7.75 (1H, d, J=2.5 Hz), 8.24 (1H, t, J=5.5 Hz), 9.64 (1H, s), 14.60 (1H, s)

Example 771

Compound 771

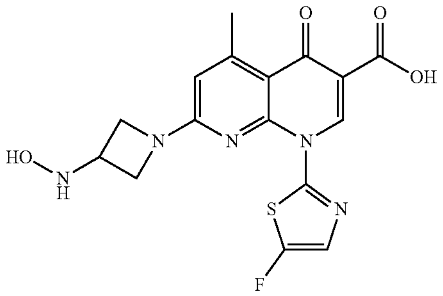

1-(5-Fluoro-1,3-thiazol-2-yl)-7-[3-(hydroxyamino) azetidin-1-yl]-5-methyl-4-oxo-1,4-dihydro-1,8-naphthyridine-3-carboxylic acid The title compound was obtained by the method described in Example 001-(3) or a method equivalent thereto using N-(azetidin-3-yl)hydroxylamine hydrochloride and 7-chloro-1-(5-fluoro-1,3-thiazol-2-yl)-5-methyl-4-oxo-1,4-dihydro-1,8-naphthyridine-3-carboxylic acid obtained in Reference Example 010-(2).

1H-NMR (DMSO-d6): δ 2.77 (3H, s), 4.19-4.63 (5H, m), 6.62 (1H, s), 7.75 (1H, d, J=2.8 Hz), 9.67 (1H, s)

Example 772

Compound 772

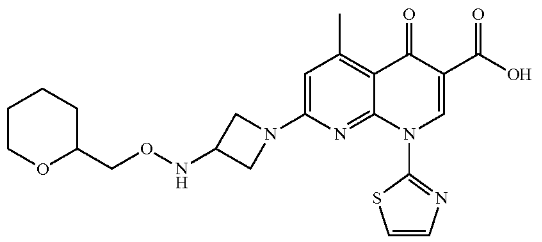

5-Methyl-7-{3-[(oxan-2-ylmethoxy)amino]azetidin-1-yl}-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-[(oxan-2-yl)methoxy]azetidin-3-amine trifluoroacetate obtained in Example 722-(2) by the method described in Example 008 or a method equivalent thereto.

1H-NMR (DMSO-d6): δ 1.18-1.19 (1H, m), 1.32-1.57 (4H, m), 1.70-1.80 (1H, m), 2.70 (3H, s), 3.44-3.57 (2H, m), 3.62 (1H, dd, J=11.0, 6.7 Hz), 3.77-3.88 (1H, m), 3.96-4.19 (3H, m), 4.21-4.42 (2H, m), 6.42 (1H, s), 7.12 (1H, d, J=6.3 Hz), 7.73 (1H, d, J=3.5 Hz), 7.80 (1H, d, J=3.5 Hz), 9.77 (1H, s), 15.29 (1H, brs)

Example 773

Compound 773

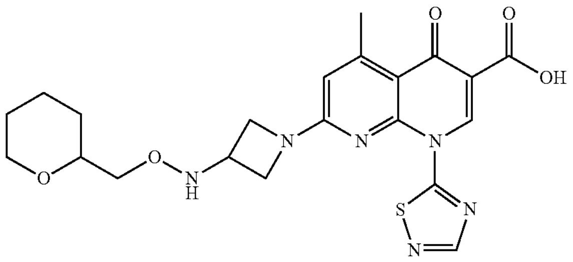

5-Methyl-7-{3-[(oxan-2-ylmethoxy)amino]azetidin-1-yl}-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-[(oxan-2-yl)methoxy]azetidin-3-amine trifluoroacetate obtained in Example 722-(2) by the method described in Example 008 or a method equivalent thereto.

1H-NMR (DMSO-d6): δ 1.07-1.22 (1H, m), 1.35-1.56 (4H, m), 1.70-1.82 (1H, m), 2.69 (3H, s), 3.48-3.67 (3H, m), 3.77-3.88 (1H, m), 3.98-4.16 (2H, m), 4.18-4.37 (2H, m), 4.40-4.51 (1H, m), 6.49 (1H, s), 7.12 (1H, d, J=6.0 Hz), 8.79 (1H, s), 9.61 (1H, s), 14.98 (1H, brs)

Example 774

Compound 774

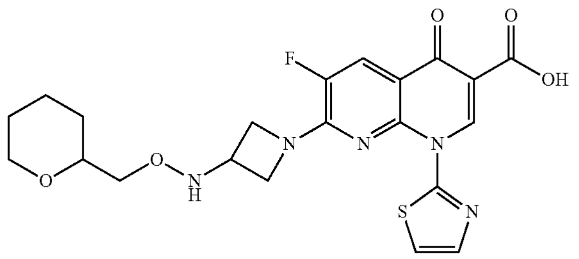

6-Fluoro-7-{3-[(oxan-2-ylmethoxy)amino]azetidin-1-yl}-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-[(oxan-2-yl)methoxy]azetidin-3-amine trifluoroacetate obtained in Example 722-(2) by the method described in Example 008 or a method equivalent thereto.

1H-NMR (DMSO-d6): δ 1.06-1.21 (1H, m), 1.31-1.57 (4H, m), 1.66-1.81 (1H, m), 3.44-3.67 (3H, m), 3.76-3.88 (1H, m), 4.06-4.18 (1H, m), 4.18-4.42 (2H, m), 4.43-4.80 (2H, m), 7.13 (1H, d, J=6.5 Hz), 7.80 (1H, d, J=3.5 Hz), 7.85 (1H, d, J=3.5 Hz), 8.07 (1H, d, J=11.5 Hz), 9.80 (1H, s), 14.72 (1H, brs)

Example 775

Compound 775

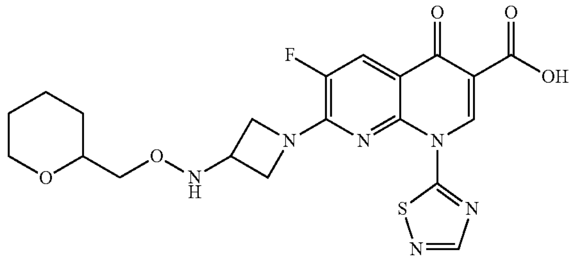

6-Fluoro-7-{3-[(oxan-2-ylmethoxy)amino]azetidin-1-yl}-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and N-[(oxan-2-yl)methoxy]azetidin-3-amine trifluoroacetate obtained in Example 722-(2) by the method described in Example 008 or a method equivalent thereto.

1H-NMR (DMSO-d6): δ 1.08-1.21 (1H, m), 1.33-1.56 (4H, m), 1.67-1.82 (1H, m), 3.49-3.67 (3H, m), 3.78-3.87 (1H, m), 4.07-4.21 (1H, m), 4.23-4.81 (4H, m), 7.13 (1H, d, J=6.0 Hz), 8.10 (1H, d, J=11.5 Hz), 8.84 (1H, s), 9.69 (1H, s), 14.41 (1H, brs)

Example 776

Compound 776

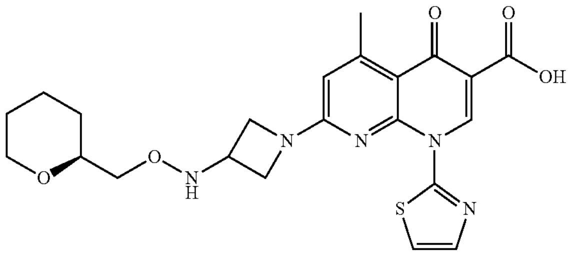

5-Methyl-7-(3-{[(2S)-oxan-2-ylmethoxy]amino}azetidin-1-yl)-4-oxo-1-(1,3-thiazol-2-yl)-1,4-dihydro-1,8-naphthyridine-3-carboxylic acid The title compound was obtained by the method described in Example 001-(3) or a method equivalent thereto using N-[(2S)-oxan-2-ylmethoxy]azetidin-3-amine trifluoroacetate obtained from [(2S)-oxan-2-yl]methanol by the methods described in Examples 735-(1) to 735-(3), 722-(1) and 001-(2) or methods equivalent thereto, and 7-chloro-5-methyl-4-oxo-1-(1,3-thiazol-2-yl)-1,4-dihydro-1,8-naphthyridine-3-carboxylic acid obtained in Reference Example 001-(2).

1H-NMR (DMSO-d6): δ 1.07-1.18 (1H, m), 1.35-1.54 (4H, m), 1.71-1.78 (1H, m), 2.75 (3H, s), 3.27-3.34 (1H, m), 3.46-3.56 (2H, m), 3.61 (1H, dd, J=11.0, 7.0 Hz), 3.77-3.86 (1H, m), 3.99-4.21 (3H, m), 4.26-4.46 (2H, m), 6.51 (1H, s), 7.14 (1H, d, J=6.5 Hz), 7.76 (1H, d, J=3.5 Hz), 7.83 (1H, d, J=3.5 Hz), 9.82 (1H, s), 15.32 (1H, brs)

Example 777

Compound 777

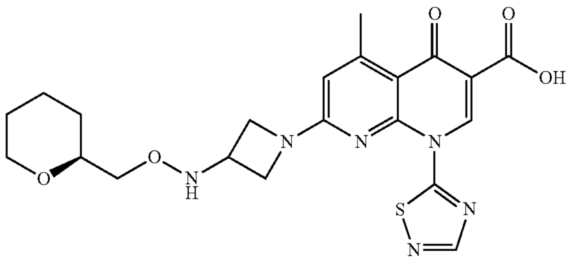

5-Methyl-7-(3-{[(2S)-oxan-2-ylmethoxy]amino}azetidin-1-yl)-4-oxo-1-(1,2,4-thiadiazol-5-yl)-1,4-dihydro-1,8-naphthyridine-3-carboxylic acid The title compound was obtained by the method described in Example 001-(3) or a method equivalent thereto using N-[(2S)-oxan-2-ylmethoxy]azetidin-3-amine trifluoroacetate obtained in Example 776, and 7-chloro-5-methyl-4-oxo-1-(1,2,4-thiadiazol-5-yl)-1,4-dihydro-1,8-naphthyridine-3-carboxylic acid obtained in Reference Example 002-(2).

1H-NMR (DMSO-d6): δ 1.07-1.19 (1H, m), 1.36-1.54 (4H, m), 1.72-1.79 (1H, m), 2.76 (3H, s), 3.28-3.35 (1H, m), 3.48-3.58 (2H, m), 3.62 (1H, dd, J=11.0, 7.0 Hz), 3.79-3.86 (1H, m), 4.06-4.17 (2H, m), 4.22-4.39 (2H, m), 4.49-4.56 (1H, m), 6.57 (1H, s), 7.15 (1H, d, J=6.0 Hz), 8.81 (1H, s), 9.72 (1H, s), 14.92 (1H, brs)

Example 778

Compound 778

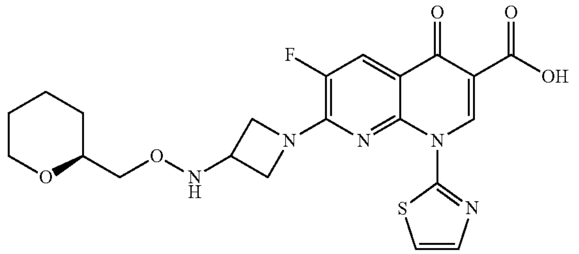

6-Fluoro-7-(3-{[(2S)-oxan-2-ylmethoxy]amino}azetidin-1-yl)-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-[(2S)-oxan-2-ylmethoxy]azetidin-3-amine trifluoroacetate obtained in Example 776 by the method described in Example 001-(3) or a method equivalent thereto.

1H-NMR (DMSO-d6): δ 1.07-1.18 (1H, m), 1.36-1.54 (4H, m), 1.71-1.78 (1H, m), 3.27-3.34 (1H, m), 3.47-3.57 (2H, m), 3.61 (1H, dd, J=11.0, 6.5 Hz), 3.78-3.85 (1H, m), 4.08-4.16 (1H, m), 4.21-4.72 (4H, m), 7.14 (1H, d, J=7.0 Hz), 7.81 (1H, d, J=3.5 Hz), 7.86 (1H, d, J=3.5 Hz), 8.09 (1H, d, J=11.5 Hz), 9.81 (1H, s), 14.70 (1H, brs)

Example 779

Compound 779

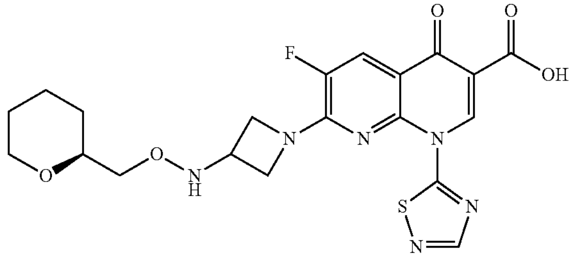

6-Fluoro-7-(3-{[(2S)-oxan-2-ylmethoxy]amino}azetidin-1-yl)-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and N-[(2S)-oxan-2-ylmethoxy]azetidin-3-amine trifluoroacetate obtained in Example 776 by the method described in Example 001-(3) or a method equivalent thereto.

1H-NMR (DMSO-d6): δ 1.08-1.19 (1H, m), 1.36-1.55 (4H, m), 1.71-1.79 (1H, m), 3.28-3.35 (1H, m), 3.49-3.59 (2H, m), 3.63 (1H, dd, J=11.0, 7.0 Hz), 3.79-3.86 (1H, m), 4.10-4.18 (1H, m), 4.28-4.78 (4H, m), 7.14 (1H, d, J=6.0 Hz), 8.14 (1H, d, J=11.5 Hz), 8.85 (1H, s), 9.74 (1H, s), 14.46 (1H, brs)

Example 780

Compound 780

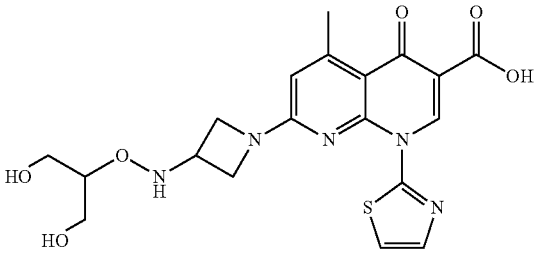

7-(3-{[(1,3-Dihydroxypropan-2-yl)oxy]amino}azetidin-1-yl)-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and 2-{([(azetidin-3-yl)amino]oxy}propane-1,3-diol trifluoroacetate obtained from 2,2,3,3,9,9,10,10-octamethyl-4,8-dioxa-3,9-disilaundecan-6-ol by the method described in Example 735-(1)~(3), Example 722-(1) and Example 001-(2) or a method equivalent thereto by the method described in Example 001-(3) or a method equivalent thereto.

1H-NMR (DMSO-d6): δ 2.73 (3H, s), 3.47 (4H, t, J=5.5 Hz), 3.58 (1H, t, J=5.5 Hz), 4.04-4.43 (5H, m), 4.49 (2H, t, J=5.5 Hz), 6.47 (1H, s), 6.96 (1H, d, J=6.5 Hz), 7.75 (1H, d, J=3.5 Hz), 7.82 (1H, d, J=3.5 Hz), 9.80 (1H, s), 15.42 (1H, brs)

Example 781

Compound 781

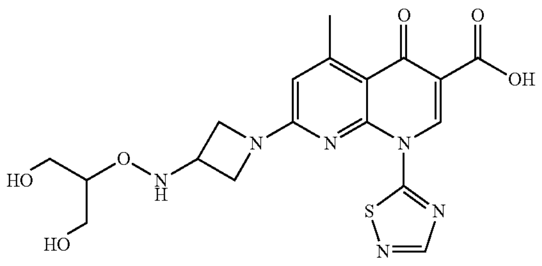

7-(3-{[(1,3-Dihydroxypropan-2-yl)oxy]amino}azetidin-1-yl)-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and 2-{[(azetidin-3-yl)amino]oxy}propane-1,3-diol trifluoroacetate obtained in Example 780 by the method described in Example 001-(3) or a method equivalent thereto.

1H-NMR (DMSO-d6): δ 2.74 (3H, s), 3.47 (4H, t, J=5.0 Hz), 3.59 (1H, t, J=5.0 Hz), 4.09-4.39 (5H, m), 4.46-4.54 (2H, m), 6.54 (1H, s), 6.98 (1H, d, J=6.0 Hz), 8.81 (1H, s), 9.70 (1H, s), 15.10 (1H, brs)

Example 782

Compound 782

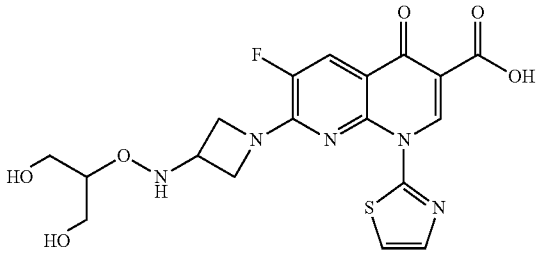

7-(3-{[(1,3-Dihydroxypropan-2-yl)oxy]amino}azetidin-1-yl)-6-fluoro-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and 2-{[(azetidin-3-yl)amino]oxy}propane-1,3-diol trifluoroacetate obtained in Example 780 by the method described in Example 001-(3) or a method equivalent thereto.

1H-NMR (DMSO-d6): δ 3.46 (4H, t, J=5.5 Hz), 3.58 (1H, t, J=5.5 Hz), 4.10-4.73 (7H, m), 6.96 (1H, d, J=7.0 Hz), 7.81 (1H, d, J=3.5 Hz), 7.86 (1H, d, J=3.5 Hz), 8.08 (1H, d, J=11.5 Hz), 9.81 (1H, s), 14.80 (1H, brs)

Example 783

Compound 783

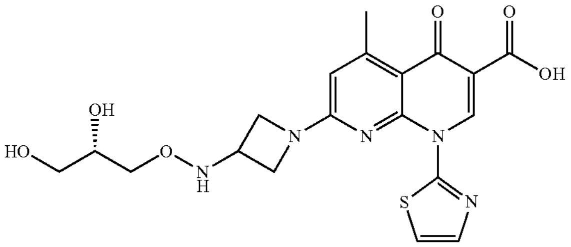

7-(3-{[(2S)-2,3-Dihydroxypropoxy]amino}azetidin-1-yl)-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and (2S)-3-{[(azetidin-3-yl)amino]oxy}propane-1,2-diol trifluoroacetate obtained from [(4R)-2, 2-dimethyl-1,3-dioxolan-4-yl]methanol by the methods described in Example 735-(1)~(3), Example 722-(1) and Example 001-(2) or methods equivalent thereto by the method described in Example 001-(3) or a method equivalent thereto.

1H-NMR (DMSO-d6): δ 2.76 (3H, d, J=1.0 Hz), 3.53-3.59 (1H, m), 3.63-3.71 (2H, m), 4.03-4.22 (3H, m), 4.29-4.45 (2H, m), 4.49 (1H, t, J=5.7 Hz), 4.62 (1H, d, J=5.1 Hz), 6.52 (1H, d, J=1.0 Hz), 7.10 (1H, d, J=6.7 Hz), 7.77 (1H, d, J=3.5 Hz), 7.84 (1H, d, J=3.5 Hz), 9.84 (1H, s), 15.33 (1H, brs)

Example 784

Compound 784

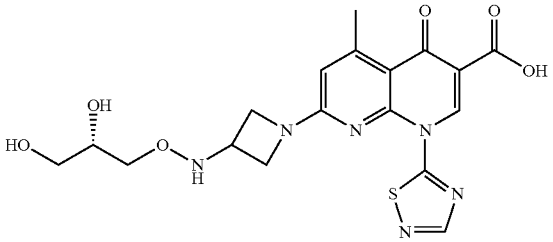

7-(3-{[(2S)-2,3-Dihydroxypropoxy]amino}azetidin-1-yl)-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and (2S)-3-{[(azetidin-3-yl)amino]oxy}propane-1,2-diol trifluoroacetate obtained in Example 783 by the method described in Example 001-(3) or a method equivalent thereto.

1H-NMR (DMSO-d6): δ 2.76 (3H, d, J=1.0 Hz), 3.57 (1H, dd, J=10.0, 6.1 Hz), 3.64-3.72 (2H, m), 4.09-4.18 (2H, m), 4.26-4.40 (2H, m), 4.49 (1H, t, J=5.7 Hz), 4.50-4.57 (1H, m), 4.63 (1H, d, J=5.0 Hz), 6.58 (1H, d, J=1.0 Hz), 7.11 (1H, d, J=6.1 Hz), 8.82 (1H, s), 9.73 (1H, s)

Example 785

Compound 785

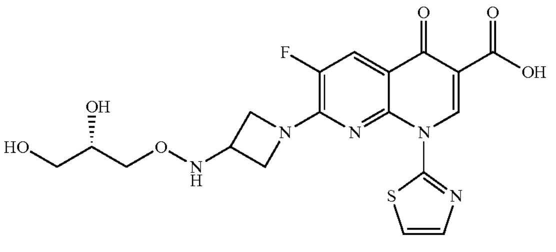

7-(3-{[(2S)-2,3-Dihydroxypropoxy]amino}azetidin-1-yl)-6-fluoro-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and (2S)-3-{[(azetidin-3-yl)amino]oxy}propane-1,2-diol trifluoroacetate obtained in Example 783 by the method described in Example 001-(3) or a method equivalent thereto.

1H-NMR (DMSO-d6): δ 3.57 (1H, dd, J=9.9, 5.9 Hz), 3.63-3.72 (2H, m), 4.11-4.18 (1H, m), 4.22-4.74 (4H, m), 4.49 (1H, t, J=5.7 Hz), 4.63 (1H, d, J=4.9 Hz), 7.10 (1H, d, J=6.9 Hz), 7.81 (1H, d, J=3.5 Hz), 7.86 (1H, d, J=3.5 Hz), 8.09 (1H, d, J=11.5 Hz), 9.81 (1H, s), 14.75 (1H, brs)

Example 786

Compound 786

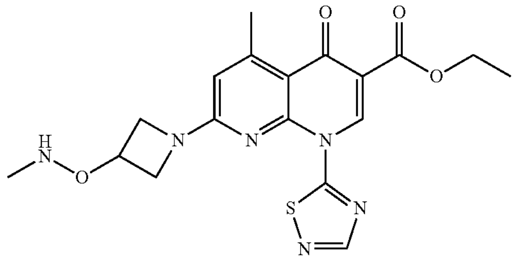

Ethyl 5-methyl-7-{3-[(methylamino)oxy]azetidin-1-yl}-4-oxo-1-(1,2,4-thiadiazol-5-yl)-1,4-dihydro-1,8-naphthyridine-3-carboxylate The title compound was obtained by the method described in Example 026-(3) or a method equivalent thereto using (azetidin-3-yloxy)(methyl)amine hydrochloride obtained in Example 552-(4), and ethyl 7-chloro-5-methyl-4-oxo-1-(1,2,4-thiadiazol-5-yl)-1,4-dihydro-1,8-naphthyridine-3-carboxylate obtained in Reference Example 002-(1).

1H-NMR (CDCl3): δ 1.43 (3H, t, J=7.5 Hz), 2.81 (3H, s), 2.88 (3H, s), 4.12-4.64 (6H, m), 4.79-4.85 (1H, m), 5.66-5.75 (1H, m), 6.12 (1H, s), 8.51 (1H, s), 9.71 (1H, s)

Example 787

Compound 787

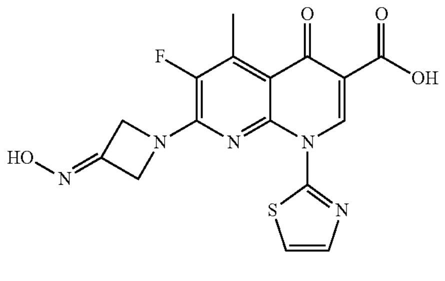

6-Fluoro-7-[3-(hydroxyimino)azetidin-1-yl]-5-methyl-4-oxo-1-(1,3-thiazol-2-yl)-1,4-dihydro-1,8-naphthyridine-3-carboxylic acid The title compound was obtained using 7-chloro-6-fluoro-5-methyl-4-oxo-1-(1,3-thiazol-2-yl)-1,4-dihydro-1,8-naphthyridine-3-carboxylic acid obtained in Reference Example 007-(2) and N-(azetidin-3-ylidene)hydroxylamine trifluoroacetate obtained in Example 595-(2) by the method described in Example 008 or a method equivalent thereto.

1H-NMR (DMSO-d6): δ 2.71 (3H, s), 5.08-5.29 (4H, m), 7.71-7.89 (2H, m), 9.80 (1H, s), 15.02 (1H, brs)

Example 788

Compound 788

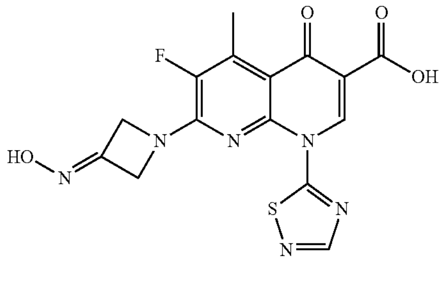

6-Fluoro-7-[3-(hydroxyimino)azetidin-1-yl]-5-methyl-4-oxo-1-(1,2,4-thiadiazol-5-yl)-1,4-dihydro-1,8-naphthyridine-3-carboxylic acid The title compound was obtained using 7-chloro-6-fluoro-5-methyl-4-oxo-1-(1,2,4-thiadiazol-5-yl)-1,4-dihydro-1,8-naphthyridine-3-carboxylic acid obtained in Reference Example 008-(2) and N-(azetidin-3-ylidene) hydroxylamine trifluoroacetate obtained in Example 595-(2) by the method described in Example 008 or a method equivalent thereto.

1H-NMR (DMSO-d6): δ 2.73 (3H, s), 5.23-5.35 (4H, m), 8.85 (1H, s), 9.78 (1H, s)

Example 789

Compound 789

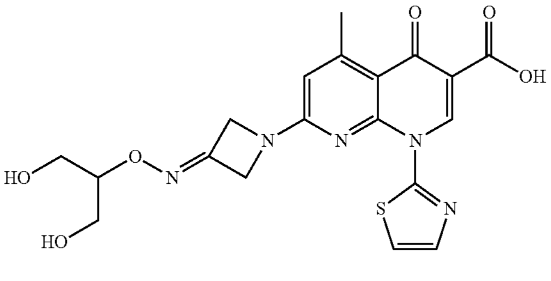

7-(3-{[(1,3-Dihydroxypropan-2-yl)oxy]imino}azetidin-1-yl)-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and 2-{[(azetidin-3-ylidene)amino]oxy}propane-1,3-diol trifluoroacetate obtained from 2,2,3,3,9,9,10,10-octamethyl-4,8-dioxa-3,9-disilaundecan-6-ol by the methods described in Example 735-(1)~(3) and Example 001-(2) or methods equivalent thereto by the method described in Example 001-(3) or a method equivalent thereto.

1H-NMR (DMSO-d6): δ 2.78 (3H, s), 3.57 (4H, t, J=5.5 Hz), 4.06 (1H, t, J=5.5 Hz), 4.66 (2H, t, J=5.5 Hz), 4.94-5.10 (4H, m), 6.66 (1H, s), 7.78 (1H, brs), 7.84 (1H, d, J=3.0 Hz), 9.83 (1H, s), 15.24 (1H, s)

Example 790

Compound 790

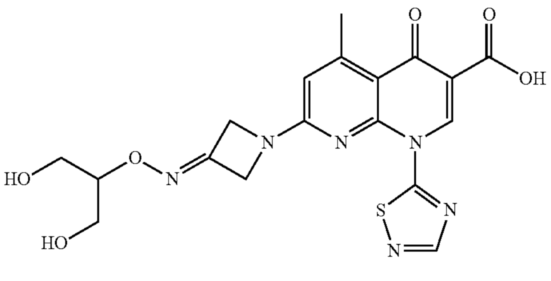

7-(3-{[(1,3-Dihydroxypropan-2-yl)oxy]imino}azetidin-1-yl)-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and 2-{[(azetidin-3-ylidene)amino]oxy}propane-1,3-diol trifluoroacetate obtained in Example 789 by the method described in Example 001-(3) or a method equivalent thereto.

1H-NMR (DMSO-d6): δ 2.80 (3H, s), 3.53-3.63 (4H, m), 4.07 (1H, t, J=5.5 Hz), 4.57-5.29 (6H, m), 6.71 (1H, s), 8.83 (1H, s), 9.76 (1H, s), 14.92 (1H, brs)

Example 791

Compound 791

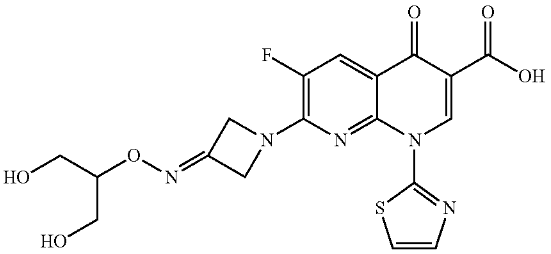

7-(3-{[(1,3-Dihydroxypropan-2-yl)oxy]imino}azetidin-1-yl)-6-fluoro-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and 2-{[(azetidin-3-ylidene)amino]oxy}propane-1,3-diol trifluoroacetate obtained in Example 789 by the method described in Example 001-(3) or a method equivalent thereto.

1H-NMR (DMSO-d6): δ 3.57 (4H, t, J=5.5 Hz), 4.05 (1H, t, J=5.5 Hz), 4.66 (2H, t, J=5.5 Hz), 5.15-5.32 (4H, m), 7.84 (1H, brs), 7.86 (1H, d, J=3.5 Hz), 8.20 (1H, d, J=11.0 Hz), 9.82 (1H, s), 14.64 (1H, brs)

Example 792

Compound 792

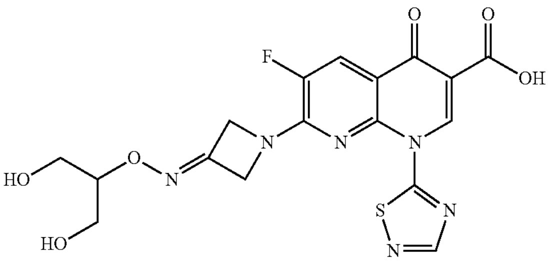

7-(3-{[(1,3-Dihydroxypropan-2-yl)oxy]imino}azetidin-1-yl)-6-fluoro-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and 2-{([(azetidin-3-ylidene)amino]oxy}propane-1,3-diol trifluoroacetate obtained in Example 789 by the method described in Example 001-(3) or a method equivalent thereto.

1H-NMR (DMSO-d6): δ 3.55-3.61 (4H, m), 4.06 (1H, t, J=5.5 Hz), 4.64-4.69 (2H, m), 5.22-5.41 (4H, m), 8.25 (1H, d, J=11.0 Hz), 8.86 (1H, s), 9.77 (1H, s), 14.35 (1H, brs)

Example 793

Compound 793

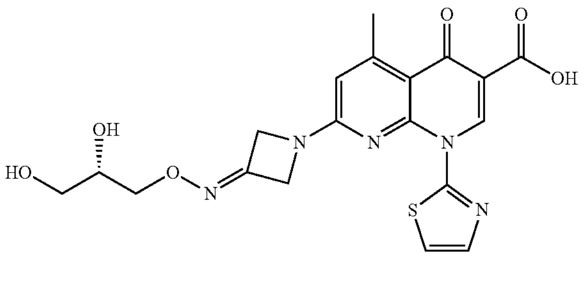

7-(3-{[(2S)-2,3-Dihydroxypropoxy]imino}azetidin-1-yl)-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and (2S)-3-{[(azetidin-3-ylidene)amino]oxy}propane-1,2-diol trifluoroacetate obtained from [(4R)-2,2-dimethyl-1,3-dioxolan-4-yl]methanol by the methods described in Example 735-(1)~(3) and Example 001-(2) or methods equivalent thereto by the method described in Example 001-(3) or a method equivalent thereto.

1H-NMR (DMSO-d6): δ 2.77 (3H, s), 3.38 (2H, t, J=5.7 Hz), 3.70-3.77 (1H, m), 3.96 (1H, dd, J=11.1, 6.8 Hz), 4.11 (1H, dd, J=11.1, 4.5 Hz), 4.60 (1H, t, J=5.7 Hz), 4.79 (1H, d, J=5.2 Hz), 4.96-5.08 (4H, m), 6.64 (1H, s), 7.77 (1H, brs), 7.83 (1H, d, J=3.5 Hz), 9.81 (1H, s), 15.22 (1H, brs)

Example 794

Compound 794

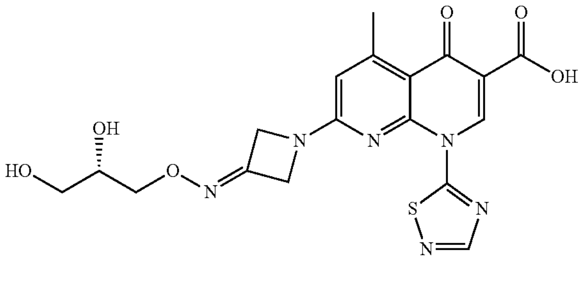

7-(3-{[(2S)-2,3-Dihydroxypropoxy]imino}azetidin-1-yl)-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and (2S)-3-{[(azetidin-3-ylidene)amino]oxy}propane-1,2-diol trifluoroacetate obtained in Example 793 by the method described in Example 001-(3) or a method equivalent thereto.

1H-NMR (DMSO-d6): δ 2.80 (3H, s), 3.39 (2H, t, J=5.5 Hz), 3.70-3.78 (1H, m), 3.97 (1H, dd, J=11.0, 6.6 Hz), 4.12 (1H, dd, J=11.0, 4.5 Hz), 4.60 (1H, t, J=5.5 Hz), 4.80 (1H, d, J=5.1 Hz), 4.98-5.28 (4H, m), 6.72 (1H, s), 8.83 (1H, s), 9.77 (1H, s), 14.93 (1H, brs)

Example 795

Compound 795

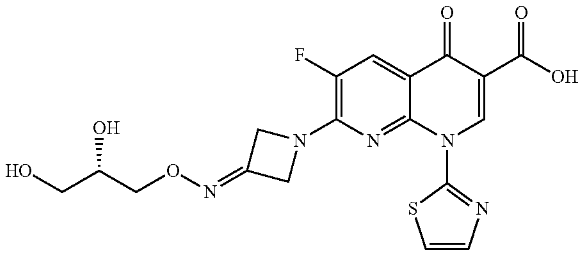

7-(3-{[(2S)-2,3-Dihydroxypropoxy]imino}azetidin-1-yl)-6-fluoro-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and (2S)-3-{[(azetidin-3-ylidene)amino]oxy}propane-1,2-diol trifluoroacetate obtained in Example 793 by the method described in Example 001-(3) or a method equivalent thereto.

1H-NMR (DMSO-d6): δ 3.38 (2H, t, J=5.6 Hz), 3.70-3.76 (1H, m), 3.95 (1H, dd, J=11.1, 6.8 Hz), 4.11 (1H, dd, J=11.1, 4.5 Hz), 4.60 (1H, t, J=5.6 Hz), 4.79 (1H, d, J=5.2 Hz), 5.16-5.30 (4H, m), 7.83 (1H, d, J=3.5 Hz), 7.86 (1H, d, J=3.5 Hz), 8.20 (1H, d, J=11.3 Hz), 9.82 (1H, s), 14.65 (1H, brs)

Example 796

Compound 796

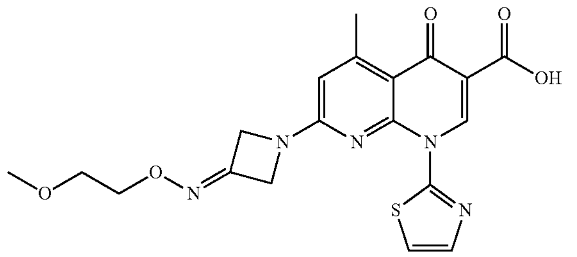

7-{3-[(2-Methoxyethoxy)imino]azetidin-1-yl}-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-(2-methoxyethoxy)azetidin-3-imine trifluoroacetate obtained from 2-methoxyethan-1-ol by the methods described in Example 735-(1)~(3) and Example 001-(2) or methods equivalent thereto by the method described in Example 008 or a method equivalent thereto.

1H-NMR (DMSO-d6): δ 2.73 (3H, d, J=0.5 Hz), 3.29 (3H, s), 3.56-3.61 (2H, m), 4.17-4.22 (2H, m), 4.92-5.08 (4H, m), 6.59 (1H, d, J=0.5 Hz), 7.75 (1H, brs), 7.80 (1H, d, J=3.5 Hz), 9.77 (1H, s), 15.19 (1H, brs)

Example 797

Compound 797

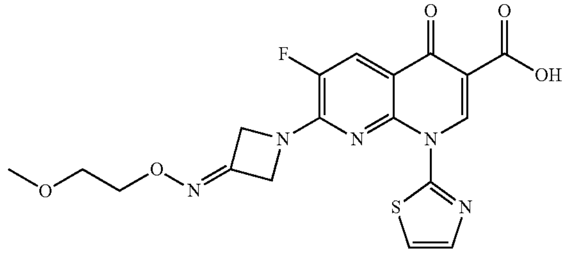

6-Fluoro-7-{3-[(2-methoxyethoxy)imino]azetidin-1-yl}-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-(2-methoxyethoxy)azetidin-3-imine trifluoroacetate obtained in Example 796 by the method described in Example 001-(3) or a method equivalent thereto.

1H-NMR (DMSO-d6): δ 3.14 (3H, s), 3.55-3.59 (2H, m), 4.16-4.21 (2H, m), 5.15-5.31 (4H, m), 7.82 (1H, d, J=3.5 Hz), 7.87 (1H, d, J=3.5 Hz), 8.21 (1H, d, J=11.5 Hz), 9.83 (1H, s), 14.64 (1H, brs)

Example 798

Compound 798

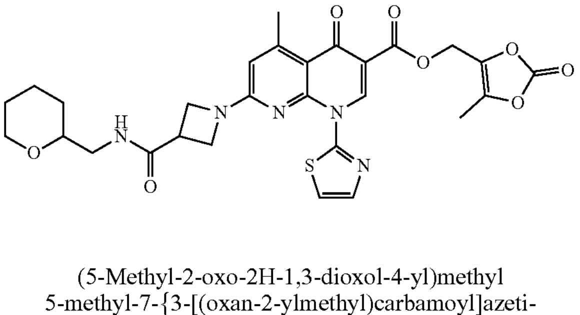

(5-Methyl-2-oxo-2H-1,3-dioxol-4-yl)methyl 5-methyl-7-{3-[(oxan-2-ylmethyl)carbamoyl]azetidin-1-yl}-4-oxo-1-(1,3-thiazol-2-yl)-1,4-dihydro-1,8-naphthyridine-3-carboxylate A mixture of 5-methyl-7-{3-[(oxan-2-ylmethyl)carbamoyl]azetidin-1-yl}-4-oxo-1-(1,3-thiazol-2-yl)-1,4-dihydro-1,8-naphthyridine-3-carboxylic acid (40 mg) obtained in Example 078-(2), potassium carbonate (11 mg), potassium iodide (3 mg), 4-chloromethyl-5-methyl-1,3-dioxol-2-one (9 DL), and DMF (1 mL) was stirred at 45° C. for 21 hours. Potassium carbonate (11 mg), potassium iodide (3 mg), and 4-chloromethyl-5-methyl-1,3-dioxol-2-one (9 μL) were further added thereto, and the mixture was stirred at the same temperature for 22 hours. To the reaction solution was added 5% sodium bicarbonate (10 mL), and the mixture was extracted with ethyl acetate. The organic layer was washed with water, dried over sodium sulfate, and concentrated. The residue was purified by silica gel column chromatography (eluent: methanol/chloroform) to obtain the title compound.

1H-NMR (CDCl3): δ 1.25-1.37 (1H, m), 1.46-1.65 (4H, m), 1.84-1.91 (1H, m), 2.28 (3H, s), 2.87 (3H, s), 3.04-3.12 (1H, m), 3.39-3.54 (3H, m), 3.62-3.69 (1H, m), 3.97-4.03 (1H, m), 4.35-4.52 (4H, m), 5.10 (2H, s), 5.99-6.05 (1H, m), 6.11 (1H, s), 7.25 (1H, d, J=3.5 Hz), 7.70 (1H, d, J=3.5 Hz), 9.83 (1H, s)

Example 799

Compound 799

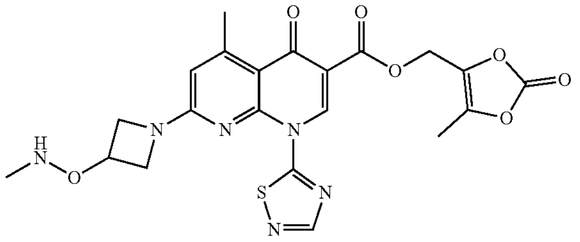

(5-Methyl-2-oxo-2H-1,3-dioxol-4-yl)methyl 5-methyl-7-{3-[(methylamino)oxy]azetidin-1-yl}-4-oxo-1-(1,2,4-thiadiazol-5-yl)-1,4-dihydro-1,8-naphthyridine-3-carboxylate The title compound was obtained by the method described in Example 798 or a method equivalent thereto from 5-methyl-7-{3-[(methylamino)oxy]azetidin-1-yl}-4-oxo-1-(1,2,4-thiadiazol-5-yl)-1,4-dihydro-1,8-naphthyridine-3-carboxylic acid obtained in Example 553.

1H-NMR (CDCl3): δ 2.23 (3H, s), 2.61 (3H, d, J=6.5 Hz), 2.69 (3H, s), 3.90-4.80 (5H, m), 5.18 (2H, s), 6.39 (1H, s), 6.89 (1H, q, J=6.5 Hz), 8.72 (1H, s), 9.48 (1H, s)

Example 800

Compound 800

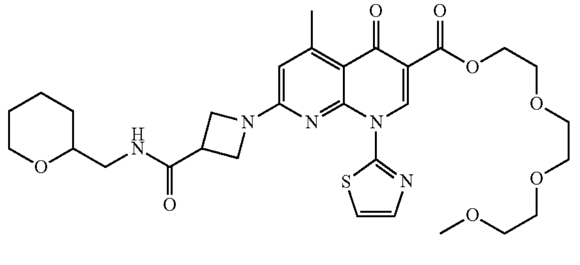

2-[2-(2-Methoxyethoxy)ethoxy]ethyl 5-methyl-7-{3-[(oxan-2-ylmethyl)carbamoyl]azetidin-1-yl}-4-oxo-1-(1,3-thiazol-2-yl)-1,4-dihydro-1,8-naphthyridine-3-carboxylate To a suspension of 5-methyl-7-{3-[(oxan-2-ylmethyl)carbamoyl]azetidin-1-yl}-4-oxo-1-(1,3-thiazol-2-yl)-1,4-dihydro-1,8-naphthyridine-3-carboxylic acid (24 mg) obtained in Example 078-(2) in methylene chloride were added oxalyl chloride (13 μL) and DMF (5 μL) under ice cooling, and the mixture was stirred at room temperature for 30 minutes. After concentration, 2-[2-(2-methoxyethoxy) ethoxy]ethan-1-ol (320 μL) was added to the residue, and the mixture was stirred at room temperature for 13 hours. To the reaction solution was added water (10 mL), and the mixture was extracted with methylene chloride. The organic layer was washed with a saturated aqueous solution of sodium bicarbonate and brine, dried over sodium sulfate, and concentrated. The residue was purified by silica gel column chromatography (eluent: methanol/methylene chloride) to obtain 8 mg of the title compound.

ESI-MS (m/z): 631 [M+H]+;

1H-NMR (CDCl3): δ 0.79-0.90 (1H, m), 1.23-1.36 (3H, m), 1.83-1.90 (1H, m), 2.86 (3H, s), 3.03-3.10 (1H, m), 3.36 (3H, s), 3.40-3.51 (1H, m), 3.52-3.56 (2H, m), 3.60-3.71 (7H, m), 3.71-3.75 (2H, m), 3.83-3.88 (2H, m), 3.96-4.02 (1H, m), 4.32-4.51 (6H, m), 6.01 (1H, brs), 6.09 (1H, s), 7.21 (1H, d, J=3.5 Hz), 7.66 (1H, d, J=3.5 Hz), 9.78 (1H, s)

Example 801

Compound 801

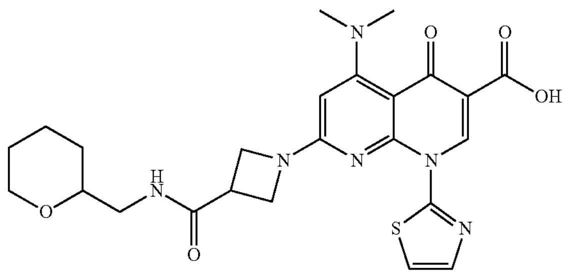

5-(Dimethylamino)-7-{3-[(oxan-2-ylmethyl)carbamoyl]azetidin-1-yl}-4-oxo-1-(1,3-thiazol-2-yl)-1,4-dihydro-1,8-naphthyridine-3-carboxylic acid The title compound was obtained using N-(oxan-2-ylmethyl)azetidine-3-carboxamide hydrochloride obtained in Example 078-(1) and 7-chloro-5-(dimethylamino)-4-oxo-1-(1,3-thiazol-2-yl)-1,4-dihydro-1,8-naphthyridine-3-carboxylic acid obtained from ethyl 5,7-dichloro-4-oxo-1-(1,3-thiazol-2-yl)-1,4-dihydro-1,8-naphthyridine-3-carboxylate and dimethylamine hydrochloride by the methods described in Example 613-(1) and Reference Example 001-(2) or methods equivalent thereto by the method described in Example 001-(3) or a method equivalent thereto.

1H-NMR (DMSO-d6): δ 1.10-1.20 (1H, m), 1.39-1.49 (3H, m), 1.52-1.58 (1H, m), 1.73-1.81 (1H, m), 2.93 (6H, s), 3.04-3.11 (1H, m), 3.15-3.21 (1H, m), 3.26-3.36 (2H, m), 3.56-3.63 (1H, m), 3.85-3.90 (1H, m), 4.16-4.40 (4H, m), 5.70 (1H, s), 7.71 (1H, d, J=3.5 Hz), 7.81 (1H, d, J=3.5 Hz), 8.16 (1H, t, J=5.7 Hz), 9.75 (1H, s), 15.65 (1H, brs)

Example 802

Compound 802

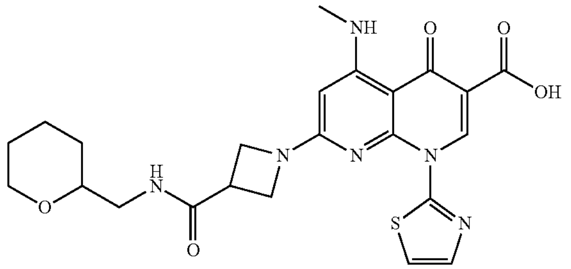

5-(Methylamino)-7-{3-[(oxan-2-ylmethyl)carbamoyl]azetidin-1-yl}-4-oxo-1-(1,3-thiazol-2-yl)-1,4-dihydro-1,8-naphthyridine-3-carboxylic acid The title compound was obtained using N-(oxan-2-ylmethyl)azetidine-3-carboxamide hydrochloride obtained in Example 078-(1) and 7-chloro-5-(methyl amino)-4-oxo-1-(1,3-thiazol-2-yl)-1,4-dihydro-1,8-naphthyridine-3-carboxylic acid obtained from ethyl 5,7-dichloro-4-oxo-1-(1,3-thiazol-2-yl)-1,4-dihydro-1,8-naphthyridine-3-carboxylate and methylamine hydrochloride by the methods described in Example 613-(1) and Reference Example 001-(2) or methods equivalent thereto by the method described in Example 001-(3) or a method equivalent thereto.

1H-NMR (DMSO-d6): δ 1.10-1.20 (1H, m), 1.39-1.49 (3H, m), 1.52-1.58 (1H, m), 1.73-1.80 (1H, m), 2.91 (3H, d, J=5.0 Hz), 3.04-3.11 (1H, m), 3.15-3.22 (1H, m), 3.28-3.36 (2H, m), 3.55-3.62 (1H, m), 3.84-3.90 (1H, m), 4.11-4.40 (4H, m), 5.33 (1H, s), 7.72 (1H, d, J=3.5 Hz), 7.81 (1H, d, J=3.5 Hz), 8.19 (1H, t, J=5.7 Hz), 9.22-9.27 (1H, m), 9.76 (1H, s), 14.88 (1H, brs)

Example 803

Compound 803

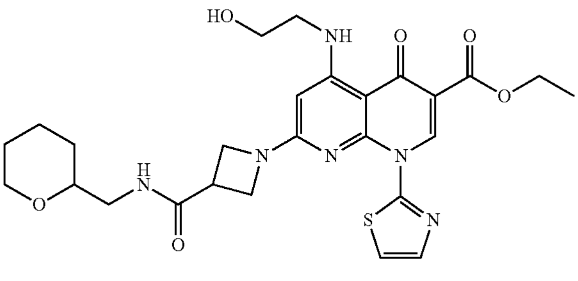

Ethyl 5-[(2-hydroxyethyl)amino]-7-{3-[(oxan-2-ylmethyl)carbamoyl]azetidin-1-yl}-4-oxo-1-(1,3-thiazol-2-yl)-1,4-dihydro-1,8-naphthyridine-3-carboxylate The title compound was obtained using N-(oxan-2-ylmethyl)azetidine-3-carboxamide hydrochloride obtained in Example 078-(1) and ethyl 7-chloro-5-[(2-hydroxy)amino]-4-oxo-1-(1,3-thiazol-2-yl)-1,4-dihydro-1,8-naphthyridine-3-carboxylate obtained from ethyl 5,7-dichloro-4-oxo-1-(1,3-thiazol-2-yl)-1,4-dihydro-1,8-naphthyridine-3-carboxylate and ethanolamine by the method described in Example 613-(1) or a method equivalent thereto by the method described in Example 002-(3) or a method equivalent thereto.

1H-NMR (DMSO-d6): δ 1.09-1.19 (1H, m), 1.29 (3H, t, J=7.1 Hz), 1.38-1.49 (3H, m), 1.52-1.57 (1H, m), 1.72-1.79 (1H, m), 3.04-3.10 (1H, m), 3.14-3.21 (1H, m), 3.25-3.33 (4H, m), 3.52-3.59 (1H, m), 3.63-3.67 (2H, m), 3.85-3.89 (1H, m), 4.11-4.19 (2H, m), 4.22-4.30 (2H, m), 4.26 (2H, q, J=7.1 Hz), 4.93 (1H, t, J=5.1 Hz), 5.37 (1H, s), 7.63 (1H, d, J=3.5 Hz), 7.76 (1H, d, J=3.5 Hz), 8.15 (1H, t, J=5.8 Hz), 9.54 (1H, s), 10.25 (1H, t, J=5.3 Hz)

Example 804

Compound 804

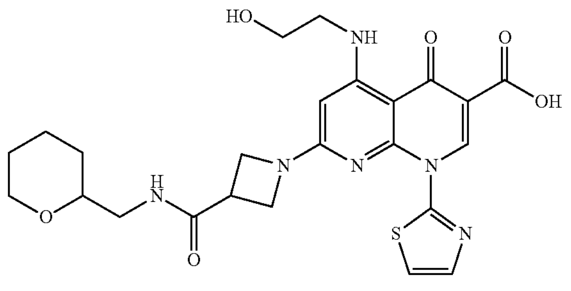

5-[(2-Hydroxyethyl)amino]-7-{3-[(oxan-2-ylmethyl)carbamoyl]azetidin-1-yl}-4-oxo-1-(1,3-thiazol-2-yl)-1,4-dihydro-1,8-naphthyridine-3-carboxylic acid The title compound was obtained from ethyl 5-[(2-hydroxyethyl)amino]-7-(3-{[(oxan-2-yl)methyl]carbamoyl}azetidin-1-yl)-4-oxo-1-(1,3-thiazol-2-yl)-1,4-dihydro-1,8-naphthyridine-3-carboxylate obtained in Example 803 by the method described in Example 028-(2) or a method equivalent thereto.

1H-NMR (DMSO-d6): δ 1.10-1.19 (1H, m), 1.39-1.49 (3H, m), 1.52-1.58 (1H, m), 1.74-1.79 (1H, m), 3.04-3.11 (1H, m), 3.15-3.21 (1H, m), 3.55-3.61 (1H, m), 3.65-3.70 (2H, m), 3.85-3.90 (1H, m), 4.11-4.39 (4H, m), 4.96-5.00 (1H, m), 5.45 (1H, s), 7.73 (1H, d, J=3.5 Hz), 7.82 (1H, d, J=3.5 Hz), 8.18 (1H, t, J=5.8 Hz), 9.52 (1H, t, J=5.1 Hz), 9.78 (1H, s), 14.87 (1H, brs)

Example 805

Compound 805

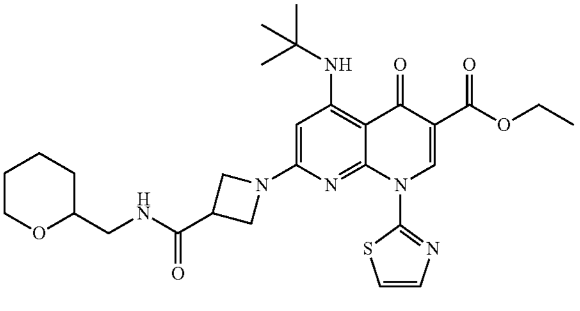

Ethyl 5-(tert-butylamino)-7-{3-[(oxan-2-ylmethyl)carbamoyl]azetidin-1-yl}-4-oxo-1-(1,3-thiazol-2-yl)-1,4-dihydro-1,8-naphthyridine-3-carboxylate The title compound was obtained using N-(oxan-2-ylmethyl)azetidine-3-carboxamide hydrochloride obtained in Example 078-(1) and ethyl 5-(tert-butyl amino)-7-chloro-4-oxo-1-(1,3-thiazol-2-yl)-1,4-dihydro-1,8-naphthyridine-3-carboxylate obtained from ethyl 5,7-dichloro-4-oxo-1-(1,3-thiazol-2-yl)-1,4-dihydro-1,8-naphthyridine-3-carboxylate and tert-butylamine by the method described in Example 613-(1) or a method equivalent thereto by the method described in Example 002-(3) or a method equivalent thereto.

1H-NMR (DMSO-d6): δ 1.10-1.20 (1H, m), 1.29 (3H, t, J=7.1 Hz), 1.36-1.49 (3H, m), 1.43 (9H, s), 1.52-1.57 (1H, m), 1.72-1.80 (1H, m), 3.04-3.10 (1H, m), 3.15-3.21 (1H, m), 3.53-3.60 (1H, m), 3.25-3.35 (2H, m), 3.85-3.89 (1H, m), 4.12-4.19 (2H, m), 4.23-4.31 (2H, m), 4.26 (2H, q, J=7.1 Hz), 5.37 (1H, s), 7.63 (1H, d, J=3.5 Hz), 7.76 (1H, d, J=3.5 Hz), 8.16 (1H, t, J=5.9 Hz), 9.52 (1H, s), 10.67 (1H, s)

Example 806

Compound 806

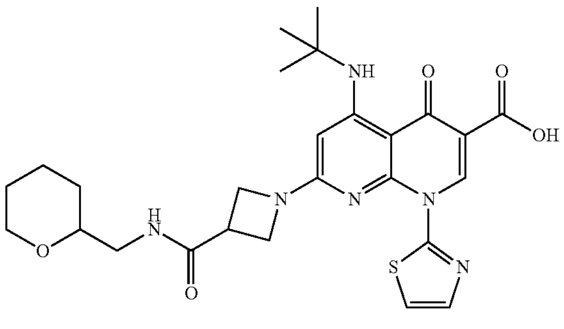

5-(tert-Butylamino)-7-{3-[(oxan-2-ylmethyl)carbamoyl]azetidin-1-yl}-4-oxo-1-(1,3-thiazol-2-yl)-1,4-dihydro-1,8-naphthyridine-3-carboxylic acid The title compound was obtained from ethyl 5-(tert-butylamino)-7-(3-{[(oxan-2-yl)methyl]carbamoyl}azetidin- 1-yl)-4-oxo-1-(1,3-thiazol-2-yl)-1,4-dihydro-1,8-naphthyridine-3-carboxylate obtained in Example 805 by the method described in Example 028-(2) or a method equivalent thereto.

1H-NMR (DMSO-d6): δ 1.10-1.19 (1H, m), 1.37-1.50 (3H, m), 1.45 (9H, s), 1.52-1.58 (1H, m), 1.73-1.80 (1H, m), 3.03-3.12 (1H, m), 3.15-3.21 (1H, m), 3.54-3.63 (1H, m), 3.85-3.90 (2H, m), 3.96-4.38 (5H, m), 5.41 (1H, s), 7.72 (1H, d, J=3.5 Hz), 7.82 (1H, d, J=3.5 Hz), 8.19 (1H, t, J=5.8 Hz), 9.77 (1H, s), 9.86 (1H, brs), 14.66 (1H, brs)

Example 807

Compound 807

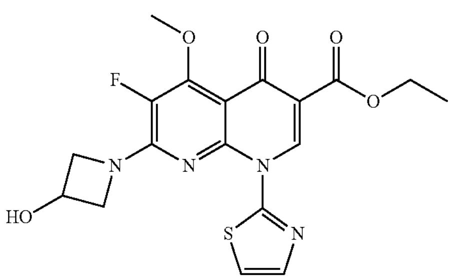

Ethyl 6-fluoro-7-(3-hydroxyazetidin-1-yl)-5-methoxy-4-oxo-1-(1,3-thiazol-2-yl)-1,4-dihydro-1,8-naphthyridine-3-carboxylate The title compound was obtained using ethyl 6,7-difluoro-5-methoxy-4-oxo-1-(1,3-thiazol-2-yl)-1,4-dihydro-1,8-naphthyridine-3-carboxylate obtained from ethyl 3-oxo-3-(2,5,6-trifluoro-4-methoxypyridin-3-yl)propanoate by the method described in Reference Example 001-(1) or a method equivalent thereto and azetidin-3-ol tartrate by the method described in Example 027-(3) or a method equivalent thereto.

1H-NMR (DMSO-d6): δ 1.29 (3H, t, J=7.0 Hz), 3.97 (3H, d, J=2.0 Hz), 4.13-4.19 (2H, m), 4.26 (2H, q, J=7.0 Hz), 4.58-4.64 (2H, m), 4.67 (1H, brs), 5.89 (1H, brs), 7.66 (1H, d, J=3.5 Hz), 7.77 (1H, d, J=3.5 Hz), 9.50 (1H, s)

Example 808

Compound 808

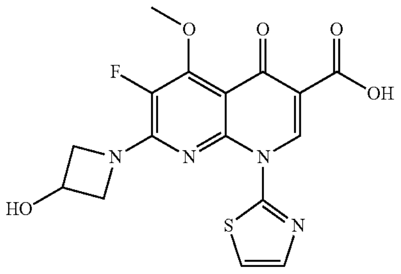

6-Fluoro-7-(3-hydroxyazetidin-1-yl)-5-methoxy-4-oxo-1-(1,3-thiazol-2-yl)-1,4-dihydro-1,8-naphthyridine-3-carboxylic acid The title compound was obtained from ethyl 6-fluoro-7-(3-hydroxyazetidin-1-yl)-5-methoxy-4-oxo-1-(1,3-thiazol-2-yl)-1,4-dihydro-1,8-naphthyridine-3-carboxylate obtained in Example 807 by the method described in Example 028-(2) or a method equivalent thereto.

1H-NMR (DMSO-d6): δ 3.94 (3H, d, J=1.0 Hz), 4.12-4.17 (2H, m), 4.55-4.61 (2H, m), 4.62-4.68 (1H, m), 7.54 (1H, d, J=3.5 Hz), 7.71 (1H, d, J=3.5 Hz), 9.20 (1H, 8)

Example 809

Compound 809

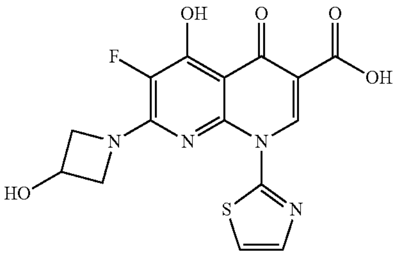

6-Fluoro-5-hydroxy-7-(3-hydroxyazetidin-1-yl)-4-oxo-1-(1,3-thiazol-2-yl)-1,4-dihydro-1,8-naphthyridine-3-carboxylic acid A mixture of 6-fluoro-7-(3-hydroxyazetidin-1-yl)-5-methoxy-4-oxo-1-(1,3-thiazol-2-yl)-1,4-dihydro-1,8-naphthyridine-3-carboxylic acid (38 mg) obtained in Example 808, and pyridine hydrochloride (336 mg) was stirred at 140° C. for 10 minutes. The reaction mixture was cooled down to room temperature, and water (2 mL) was added to the reaction product. The resulting solid was collected by filtration to obtain 33 mg of the title compound.

1H-NMR (DMSO-d6): δ 3.60-3.78 (4H, m), 4.02-4.10 (1H, m), 5.49 (1H, brs), 7.84-7.88 (2H, m), 9.72 (1H, s), 13.30 (1H, brs), 13.56 (1H, s)

Example 810

Compound 810

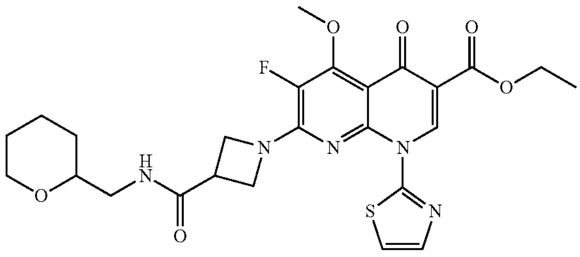

Ethyl 6-fluoro-5-methoxy-7-{3-[(oxan-2-ylmethyl)carbamoyl]azetidin-1-yl}-4-oxo-1-(1,3-thiazol-2-yl)-1,4-dihydro-1,8-naphthyridine-3-carboxylate The title compound was obtained using ethyl 6,7-difluoro-5-methoxy-4-oxo-1-(1,3-thiazol-2-yl)-1,4-dihydro-1,8-naphthyridine-3-carboxylate obtained in Example 807 and N-(oxan-2-ylmethyl)azetidine-3-carboxamide hydrochloride obtained in Example 078-(1) by the method described in Example 027-(3) or a method equivalent thereto.

1H-NMR (CDCl3): δ 1.24-1.35 (2H, m), 1.40 (3H, t, J=7.0 Hz), 1.70-1.73 (2H, m), 1.83-1.90 (1H, m), 3.03-3.11 (1H, m), 3.37-3.54 (3H, m), 3.61-3.69 (1H, m), 3.96-4.02 (1H, m), 4.14 (3H, d, J=2.5 Hz), 4.40 (2H, q, J=7.0 Hz), 4.54-4.68 (4H, m), 6.02 (1H, brs), 7.21 (1H, d, J=3.5 Hz), 7.66 (1H, d, J=3.5 Hz), 9.68 (1H, s)

Example 811

Compound 811

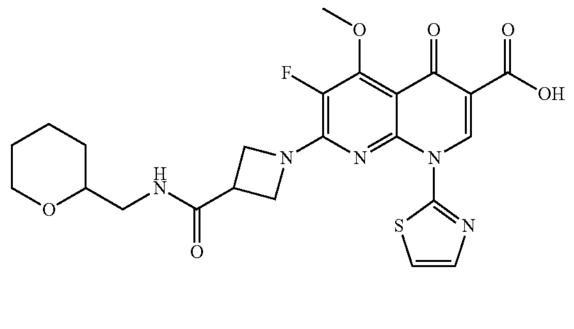

6-Fluoro-5-methoxy-7-{3-[(oxan-2-ylmethyl)carbamoyl]azetidin-1-yl}-4-oxo-1-(1,3-thiazol-2-yl)-1,4-dihydro-1,8-naphthyridine-3-carboxylic acid The title compound was obtained using from ethyl 6-fluoro-5-methoxy-7-{3-[(oxan-2-ylmethyl)carbamoyl]azetidin-1-yl}-4-oxo-1-(1,3-thiazol-2-yl)-1,4-dihydro-1,8-naphthyridine-3-carboxylate obtained in Example 810 by the method described in Example 028-(2) or a method equivalent thereto.

1H-NMR (DMSO-d6): δ 1.09-1.20 (1H, m), 1.39-1.49 (3H, m), 1.52-1.59 (1H, m), 1.73-1.81 (1H, m), 3.04-3.12 (1H, m), 3.16-3.23 (1H, m), 3.61-3.69 (1H, m), 3.85-3.90 (1H, m), 4.06 (3H, d, J=3.0 Hz), 4.36-4.75 (4H, m), 7.75 (1H, d, J=3.5 Hz), 7.83 (1H, d, J=3.5 Hz), 8.22 (1H, t, J=6.0 Hz), 9.76 (1H, s), 15.26 (1H, s)

Example 812

Compound 812

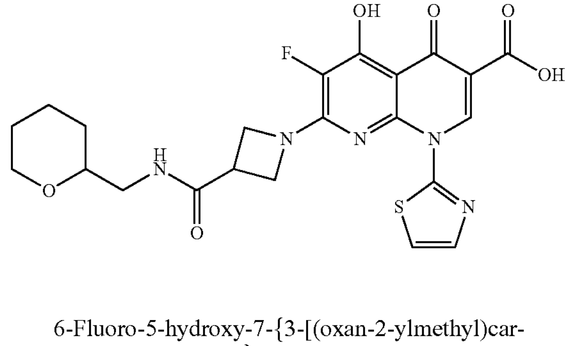

6-Fluoro-5-hydroxy-7-{3-[(oxan-2-ylmethyl)carbamoyl]azetidin-1-yl}-4-oxo-1-(1,3-thiazol-2-yl)-1,4-dihydro-1,8-naphthyridine-3-carboxylic acid The title compound was obtained using from 6-fluoro-5-methoxy-7-{3-[(oxan-2-ylmethyl)carbamoyl]azetidin-1-yl}-4-oxo-1-(1,3-thiazol-2-yl)-1,4-dihydro-1,8-naphthyridine-3-carboxylic acid obtained in Example 811 by the method described in Example 809 or a method equivalent thereto.

1H-NMR (DMSO-d6): δ 0.97-1.18 (1H, m), 1.30-1.60 (4H, m), 1.60-1.81 (1H, m), 2.96-3.05 (1H, m), 3.08-3.25 (2H, m), 3.62-3.85 (4H, m), 7.85 (1H, d, J=3.5 Hz), 7.88 (1H, d, J=3.5 Hz), 8.26 (1H, t, J=7.0 Hz), 9.74 (1H, s), 13.29 (1H, brs), 13.59 (1H, brs)

Example 813

Compound 813

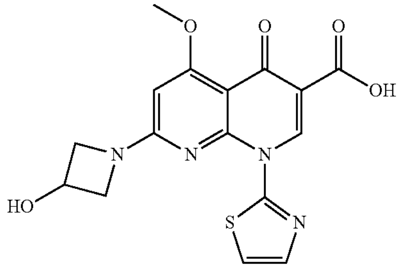

7-(3-Hydroxyazetidin-1-yl)-5-methoxy-4-oxo-1-(1,3-thiazol-2-yl)-1,4-dihydro-1,8-naphthyridine-3-carboxylic acid (1) To a suspension of ethyl 5,7-dichloro-4-oxo-1-(1,3-thiazol-2-yl)-1,4-dihydro-1,8-naphthyridine-3-carboxylate (100 mg) in toluene obtained by the method described in Journal of Medicinal Chemistry 47, 2097 (2004) or a method equivalent thereto was added a solution of 28% sodium methoxide in methanol (52 mg) in a nitrogen atmosphere, and the mixture was stirred at room temperature for 21 hours. The reaction solution was concentrated, and the residue was subjected to silica gel column chromatography (eluent: ethyl acetate/n-hexane) to obtain crude ethyl 7-chloro-5-methoxy-4-oxo-1-(1,3-thiazol-2-yl)-1,4-dihydro-1,8-naphthyridine-3-carboxylate.

(2) The title compound was obtained by the method described in Example 002-(3) or a method equivalent thereto using 7-chloro-5-methoxy-4-oxo-1-(1,3-thiazol-2-yl)-1,4-dihydro-1,8-naphthyridine-3-carboxylic acid obtained by the method described in Reference Example 001-(2) or a method equivalent thereto from crude ethyl 7-chloro-5-methoxy-4-oxo-1-(1,3-thiazol-2-yl)-1,4-dihydro-1,8-naphthyridine-3-carboxylate obtained in the preceding section, and azetidin-3-ol tartrate.

1H-NMR (DMSO-d6): δ 3.97 (3H, s), 3.99-4.15 (1H, m), 4.30-4.74 (4H, m), 5.93 (1H, d, J=6.5 Hz), 6.06 (1H, s), 7.74 (1H, d, J=3.5 Hz), 7.83 (1H, d, J=3.5 Hz), 9.80 (1H, s)

Example 814

Compound 814

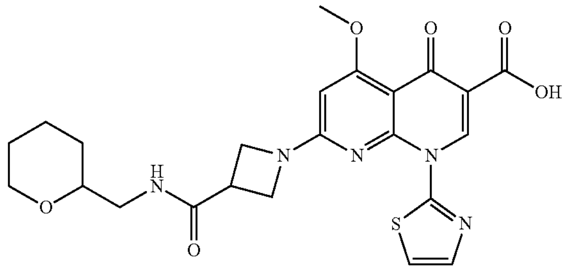

5-Methoxy-7-{3-[(oxan-2-ylmethyl)carbamoyl]azetidin-1-yl}-4-oxo-1-(1,3-thiazol-2-yl)-1,4-dihydro-1,8-naphthyridine-3-carboxylic acid The title compound was obtained using 7-chloro-5-methoxy-4-oxo-1-(1,3-thiazol-2-yl)-1,4-dihydro-1,8-naphthyridine-3-carboxylic acid obtained in Example 813-(2) and N-(oxan-2-ylmethyl)azetidine-3-carboxamide hydrochloride obtained in Example 078-(1) by the method described in Example 002-(3) or a method equivalent thereto.

1H-NMR (DMSO-d6): δ 1.08-1.22 (1H, m), 1.37-1.49 (3H, m), 1.50-1.59 (1H, m), 1.72-1.81 (1H, m), 3.03-3.12 (1H, m), 3.15-3.23 (1H, m), 3.56-3.65 (1H, s), 3.84-3.91 (2H, m), 3.97 (3H, s), 4.07-4.14 (1H, m), 4.16-4.50 (4H, m), 6.07 (1H, s), 7.81 (1H, d, J=3.0 Hz), 7.83 (1H, d, J=3.5 Hz), 8.22 (1H, t, J=6.0 Hz), 9.80 (1H, s)

Example 815

Compound 815

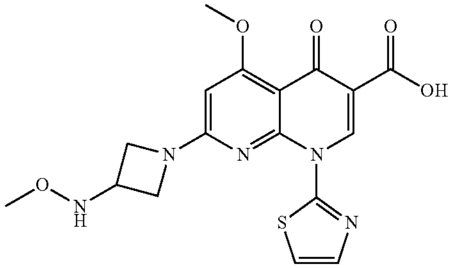

5-Methoxy-7-[3-(methoxyamino)azetidin-1-yl]-4-oxo-1-(1,3-thiazol-2-yl)-1,4-dihydro-1,8-naphthyridine-3-carboxylic acid The title compound was obtained using 7-chloro-5-methoxy-4-oxo-1-(1,3-thiazol-2-yl)-1,4-dihydro-1,8-naphthyridine-3-carboxylic acid obtained in Example 813-(2) and N-methoxyazetidin-3-amine trifluoroacetate obtained in Example 535 by the method described in Example 002-(3) or a method equivalent thereto.

1H-NMR (DMSO-d6): δ 3.49 (3H, s), 4.13 (3H, s), 4.10-4.15 (1H, m), 4.20-4.52 (4H, m), 6.06 (1H, s), 7.18 (1H, d, J=6.0 Hz), 7.76 (1H, d, J=3.0 Hz), 7.83 (1H, d, J=3.5 Hz), 9.80 (1H, s)

Example 816

Compound 816

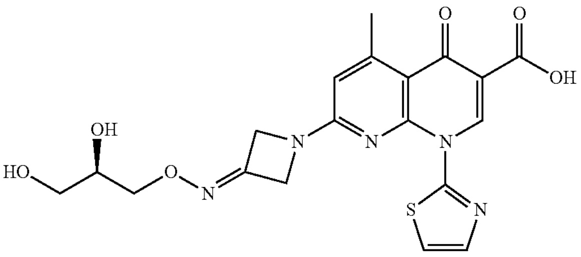

7-(3-{[(2R)-2,3-Dihydroxypropoxy]imino}azetidin-1-yl)-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and (2R)-3-{[(azetidin-3-ylidene)amino]oxy}propane-1,2-diol trifluoroacetate obtained from [(4S)-2,2-dimethyl-1,3-dioxolan-4-yl]methanol by the methods described in Example 735-(1)~(3) and Example 001-(2) or methods equivalent thereto by the method described in Example 001-(3) or a method equivalent thereto.

1H-NMR (DMSO-d6): δ 2.77 (3H, s), 3.38 (2H, t, J=5.7 Hz), 3.70-3.77 (1H, m), 3.96 (1H, dd, J=11.1, 6.8 Hz), 4.11 (1H, dd, J=11.1, 4.5 Hz), 4.60 (1H, t, J=5.7 Hz), 4.79 (1H, d, J=5.2 Hz), 4.96-5.08 (4H, m), 6.64 (1H, s), 7.77 (1H, brs), 7.83 (1H, d, J=3.5 Hz), 9.81 (1H, s), 15.13 (1H, brs)

Example 817

Compound 817

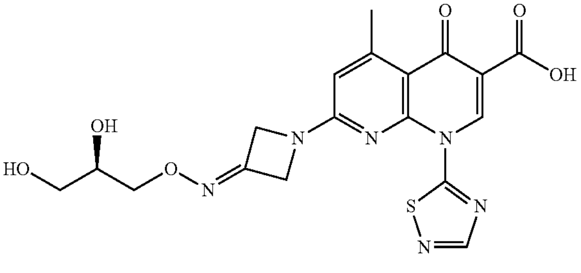

7-(3-{[(2R)-2,3-Dihydroxypropoxy]imino}azetidin-1-yl)-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and (2R)-3-{[(azetidin-3-ylidene)amino]oxy}propane-1,2-diol trifluoroacetate obtained in Example 816 by the method described in Example 001-(3) or a method equivalent thereto.

1H-NMR (DMSO-d6): δ 2.80 (3H, s), 3.39 (2H, t, J=5.5 Hz), 3.70-3.78 (1H, m), 3.97 (1H, dd, J=11.0, 6.6 Hz), 4.12

(1H, dd, J=11.0, 4.5 Hz), 4.60 (1H, t, J=5.5 Hz), 4.80 (1H, d, J=5.1 Hz), 4.98-5.28 (4H, m), 6.72 (1H, s), 8.83 (1H, s), 9.77 (1H, s), 14.91 (1H, brs)

Example 818

Compound 818

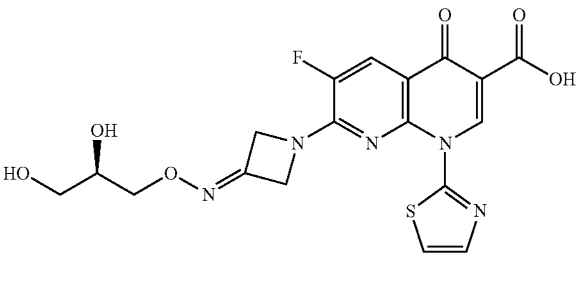

7-(3-{([2R)-2,3-Dihydroxypropoxy]imino}azetidin-1-yl)-6-fluoro-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and (2R)-3-{[(azetidin-3-ylidene)amino]oxy}propane-1,2-diol trifluoroacetate obtained in Example 816 by the method described in Example 001-(3) or a method equivalent thereto.

1H-NMR (DMSO-d6): δ 3.38 (2H, t, J=5.6 Hz), 3.70-3.76 (1H, m), 3.95 (1H, dd, J=11.1, 6.8 Hz), 4.11 (1H, dd, J=11.1, 4.5 Hz), 4.60 (1H, t, J=5.6 Hz), 4.79 (1H, d, J=5.2 Hz), 5.16-5.30 (4H, m), 7.83 (1H, d, J=3.5 Hz), 7.86 (1H, d, J=3.5 Hz), 8.20 (1H, d, J=11.3 Hz), 9.82 (1H, s), 14.61 (1H, brs)

Example 819

Compound 819

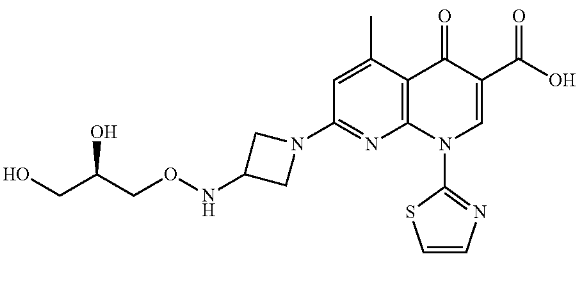

7-(3-({[(2R)-2,3-Dihydroxypropoxy]amino}azetidin-1-yl)-5-methyl-4-oxo-1-(1,3-thiazol-2-yl)-1,4-dihydro-1,8-naphthyridine-3-carboxylic acid The title compound was obtained by the method described in Example 001-(3) or a method equivalent thereto using (2R)-3-{[(azetidin-3-yl)amino]oxy}propane-1,2-diol trifluoroacetate obtained from [(4S)-2,2-dimethyl-1,3-dioxolan-4-yl]methanol by the methods described in Examples 735-(1) to 735-(3), 722-(1) and 001-(2) or methods equivalent thereto, and 7-chloro-5-methyl-4-oxo-1-(1,3-thiazol-2-yl)-1,4-dihydro-1,8-naphthyridine-3-carboxylic acid obtained in Reference Example 001-(2).

1H-NMR (DMSO-d6): δ 2.76 (3H, d, J=1.0 Hz), 3.53-3.59 (1H, m), 3.63-3.71 (2H, m), 4.03-4.22 (3H, m), 4.29-4.45 (2H, m), 4.49 (1H, t, J=5.7 Hz), 4.62 (1H, d, J=5.1 Hz), 6.52 (1H, d, J=1.0 Hz), 7.10 (1H, d, J=6.7 Hz), 7.77 (1H, d, J=3.5 Hz), 7.84 (1H, d, J=3.5 Hz), 9.84 (1H, s), 15.42 (1H, brs)

Example 820

Compound 820

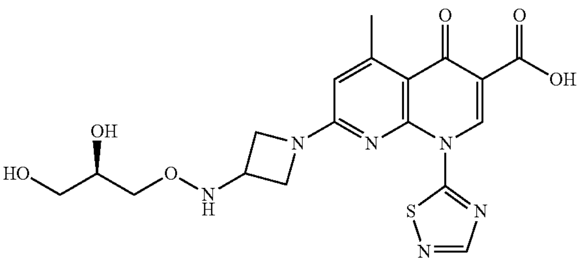

7-(3-{[(2R)-2,3-Dihydroxypropoxy]amino}azetidin-1-yl)-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and (2R)-3-{[(azetidin-3-yl)amino]oxy}propane-1,2-diol trifluoroacetate obtained in Example 819 by the method described in Example 001-(3) or a method equivalent thereto.

1H-NMR (DMSO-d6): δ 2.76 (3H, d, J=1.0 Hz), 3.57 (1H, dd, J=10.0, 6.1 Hz), 3.64-3.72 (2H, m), 4.09-4.18 (2H, m), 4.26-4.40 (2H, m), 4.49 (1H, t, J=5.7 Hz), 4.50-4.57 (1H, m), 4.63 (1H, d, J=5.0 Hz), 6.58 (1H, d, J=1.0 Hz), 7.11 (1H, d, J=6.1 Hz), 8.82 (1H, s), 9.73 (1H, s), 15.08 (1H, brs)

Example 821

Compound 821

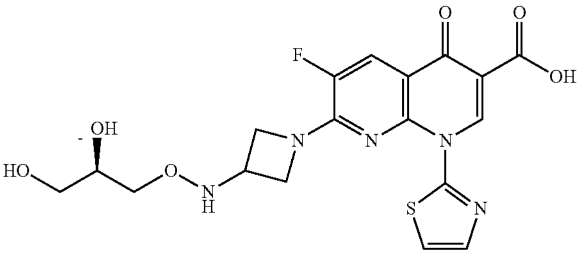

7-(3-{[(2R)-2,3-Dihydroxypropoxy]amino}azetidin-1-yl)-6-fluoro-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and (2R)-3-{[(azetidin-3-yl)amino]oxy}propane-1,2-diol trifluoroacetate obtained in Example 819 by the method described in Example 001-(3) or a method equivalent thereto.

1H-NMR (DMSO-d6): δ 3.57 (1H, dd, J=9.9, 5.9 Hz), 3.63-3.72 (2H, m), 4.11-4.18 (1H, m), 4.22-4.74 (4H, m), 4.49 (1H, t, J=5.7 Hz), 4.63 (1H, d, J=4.9 Hz), 7.10 (1H, d, J=6.9 Hz), 7.81 (1H, d, J=3.5 Hz), 7.86 (1H, d, J=3.5 Hz), 8.06 (1H, d, J=11.5 Hz), 9.81 (1H, s), 14.78 (1H, brs)

Example 822

Compound 822

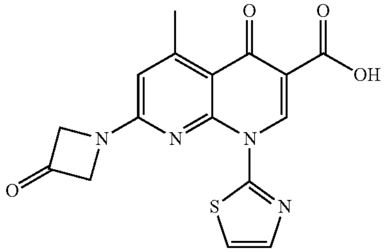

5-Methyl-4-oxo-7-(3-oxoazetidin-1-yl)-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and azetidin-3-one hydrochloride by the method described in Example 001-(3) or a method equivalent thereto.

ESI-MS (m/z): 357 [M+H]+;

1H-NMR (DMSO-d6): δ 2.80 (3H, s), 5.15 (4H, m), 6.72 (1H, d, J=0.8 Hz), 7.74 (1H, d, J=3.5 Hz), 7.84 (1H, d, J=3.5 Hz), 9.85 (1H, s), 15.38 (1H, brs)

Example 823

Compound 823

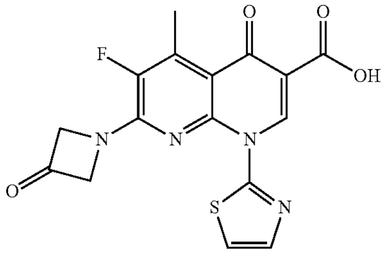

6-Fluoro-5-methyl-4-oxo-7-(3-oxoazetidin-1-yl)-1-(1,3-thiazol-2-yl)-1,4-dihydro-1,8-naphthyridine-3-carboxylic acid The title compound was obtained using 7-chloro-6-fluoro-5-methyl-4-oxo-1-(1,3-thiazol-2-yl)-1,4-dihydro-1,8-naphthyridine-3-carboxylic acid obtained in Reference Example 007-(2) and azetidin-3-one hydrochloride by the method described in Example 001-(3) or a method equivalent thereto.

ESI-MS (m/z): 375 [M+H]+;

1H-NMR (DMSO-d6): δ 2.73 (3H, d, J=2.5 Hz), 5.33 (4H, s), 7.76 (1H, d, J=3.5 Hz), 7.84 (1H, d, J=3.5 Hz), 9.80 (1H, s), 14.72-15.30 (1H, m)

Example 824

Compound 824

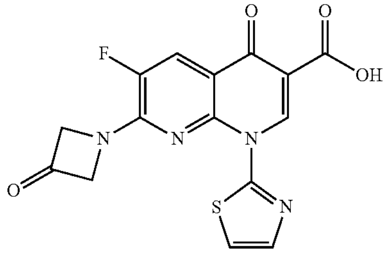

6-Fluoro-4-oxo-7-(3-oxoazetidin-1-yl)-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and azetidin-3-one hydrochloride by the method described in Example 001-(3) or a method equivalent thereto.

ESI-MS (m/z): 361 [M+H]+;

1H-NMR (DMSO-d6): δ 5.36 (4H, s), 7.79 (1H, d, J=3.5 Hz), 7.87 (1H, d, J=3.5 Hz), 8.26 (1H, d, J=11.2 Hz), 9.85 (1H, s), 14.73 (1H, brs)

Example 825

Compound 825

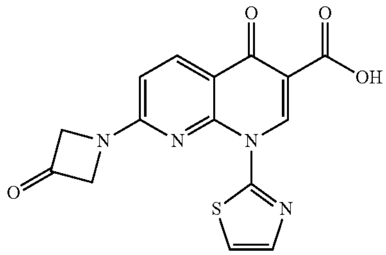

4-Oxo-7-(3-oxoazetidin-1-yl)-1-(1,3-thiazol-2-yl)-1,4-dihydro-1,8-naphthyridine-3-carboxylic acid The title compound was obtained using 7-chloro-4-oxo-1-(1,3-thiazol-2-yl)-1,4-dihydro-1,8-naphthyridine-3-carboxylic acid obtained in Reference Example 005-(2) azetidin-3-one hydrochloride by the method described in Example 001-(3) or a method equivalent thereto.

ESI-MS (m/z): 343 [M+H]+;

1H-NMR (DMSO-d6): δ 5.20 (4H, s), 6.95 (1H, d, J=8.9 Hz), 7.78 (1H, d, J=3.5 Hz), 7.86 (1H, d, J=3.5 Hz), 8.46 (1H, d, J=8.9 Hz), 9.88 (1H, s), 14.88 (1H, brs)

Example 826

Compound 826

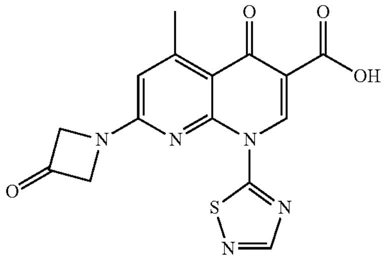

5-Methyl-4-oxo-7-(3-oxoazetidin-1-yl)-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and azetidin-3-one hydrochloride by the method described in Example 001-(3) or a method equivalent thereto.

ESI-MS (m/z): 358 [M+H]+;

1H-NMR (DMSO-d6): δ 2.82 (3H, d, J=0.6 Hz), 5.15-5.33 (4H, m), 6.77 (1H, d, J=0.6 Hz), 8.83 (1H, s), 9.79 (1H, s), 15.05 (1H, brs)

Example 827

Compound 827

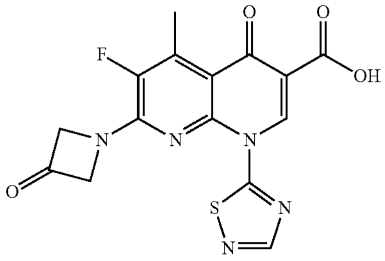

6-Fluoro-5-methyl-4-oxo-7-(3-oxoazetidin-1-yl)-1-(1,2,4-thiadiazol-5-yl)-1,4-dihydro-1,8-naphthyridine-3-carboxylic acid The title compound was obtained using 7-chloro-6-fluoro-5-methyl-4-oxo-1-(1,2,4-thiadiazol-5-yl)-1,4-dihydro-1,8-naphthyridine-3-carboxylic acid obtained in Reference Example 008-(2) and azetidin-3-one hydrochloride by the method described in Example 001-(3) or a method equivalent thereto.

Property: dark brown solid;

ESI-MS (m/z): 376 [M+H]+

Example 828

Compound 828

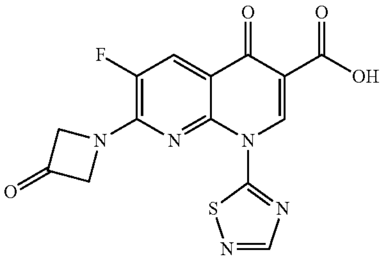

6-Fluoro-4-oxo-7-(3-oxoazetidin-1-yl)-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and azetidin-3-one hydrochloride by the method described in Example 001-(3) or a method equivalent thereto.

ESI-MS (m/z): 362 [M+H]+;

1H-NMR (DMSO-d6): δ 5.45-5.48 (4H, m), 8.29 (1H, d, J=11.0 Hz), 8.86 (1H, s), 9.79 (1H, s), 13.64-14.62 (1H, m)

Example 829

Compound 829

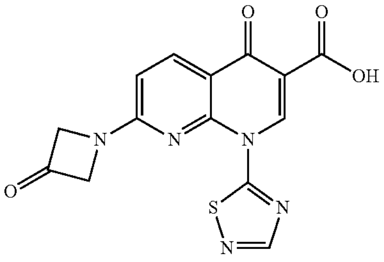

4-Oxo-7-(3-oxoazetidin-1-yl)-1-(1,2,4-thiadiazol-5-yl)-1,4-dihydro-1,8-naphthyridine-3-carboxylic acid The title compound was obtained using 7-chloro-4-oxo-1-(1,2,4-thiadiazol-5-yl)-1,4-dihydro-1,8-naphthyridine-3-carboxylic acid obtained in Reference Example 006-(2) and azetidin-3-one hydrochloride by the method described in Example 001-(3) or a method equivalent thereto.

1H-NMR (DMSO-d6): δ 5.00-5.44 (4H, m), 6.96 (1H, d, J=9.0 Hz), 8.47 (1H, d, J=9.0 Hz), 8.84 (1H, s), 9.79 (1H, s)

Example 830

Compound 830

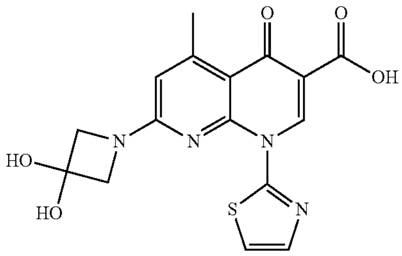

7-(3,3-Dihydroxyazetidin-1-yl)-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and azetidin-3-one hydrochloride was used and obtained a title compound by the method described in Example 001-(3) or a method equivalent thereto.

ESI-MS (m/z): 375 [M+H]+;

1H-NMR (DMSO-d6): δ 2.78 (3H, d, J=0.8 Hz), 4.16-4.22 (2H, m), 4.26-4.32 (2H, m), 6.58 (1H, d, J=0.8 Hz), 6.88 (2H, s), 7.78 (1H, d, J=3.5 Hz), 7.84 (1H, d, J=3.5 Hz), 9.88 (1H, s), 15.18 (1H, brs)

Example 831

Compound 831

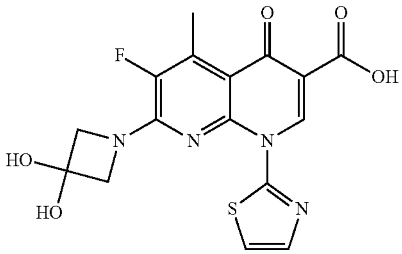

7-(3,3-Dihydroxyazetidin-1-yl)-6-fluoro-5-methyl-4-oxo-1-(1,3-thiazol-2-yl)-1,4-dihydro-1,8-naphthyridine-3-carboxylic acid The title compound was obtained using 7-chloro-6-fluoro-5-methyl-4-oxo-1-(1,3-thiazol-2-yl)-1,4-dihydro-1,8-naphthyridine-3-carboxylic acid obtained in Reference Example 007-(2) and azetidin-3-one hydrochloride by the method described in Example 001-(3) or a method equivalent thereto.

ESI-MS (m/z): 393 [M+H]+;

1H-NMR (DMSO-d6): δ 2.69 (3H, s), 4.11-4.59 (4H, m), 6.88 (2H, s), 7.79-7.87 (2H, m), 9.77 (1H, s), 14.72-15.30 (1H, m)

Example 832

Compound 832

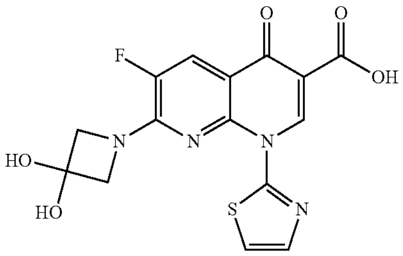

7-(3,3-Dihydroxyazetidin-1-yl)-6-fluoro-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and azetidin-3-one hydrochloride by the method described in Example 001-(3) or a method equivalent thereto.

ESI-MS (m/z): 379 [M+H]+;

1H-NMR (DMSO-d6): δ 4.34-4.52 (4H, m), 6.92 (2H, s), 7.82 (1H, d, J=3.5 Hz), 7.86 (1H, d, J=3.5 Hz), 8.11 (1H, d, J=11.4 Hz), 9.82 (1H, s), 14.73 (1H, brs)

Example 833

Compound 833

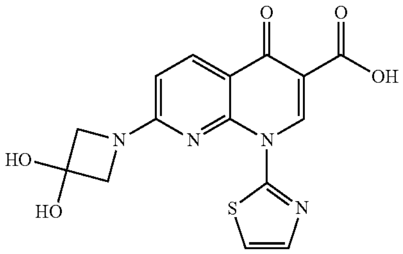

7-(3,3-Dihydroxyazetidin-1-yl)-4-oxo-1-(1,3-thiazol-2-yl)-1,4-dihydro-1,8-naphthyridine-3-carboxylic acid The title compound was obtained using 7-chloro-4-oxo-1-(1,3-thiazol-2-yl)-1,4-dihydro-1,8-naphthyridine-3-carboxylic acid obtained in Reference Example 005-(2) and azetidin-3-one hydrochloride by the method described in Example 001-(3) or a method equivalent thereto.

ESI-MS (m/z): 361 [M+H]+;

1H-NMR (DMSO-d6): δ 4.21-4.25 (2H, m), 4.30-4.33 (2H, m), 6.79 (1H, d, J=9.0 Hz), 6.90 (2H, s), 7.80 (1H, d, J=3.5 Hz), 7.85 (1H, d, J=3.5 Hz), 8.34 (1H, d, J=9.0 Hz), 9.85 (1H, s), 14.88 (1H, brs)

Example 834

Compound 834

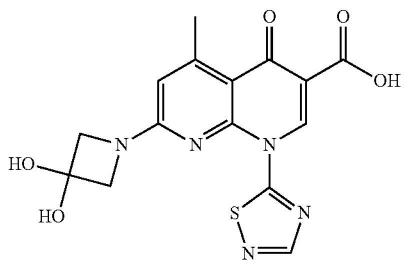

7-(3,3-Dihydroxyazetidin-1-yl)-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and azetidin-3-one hydrochloride by the method described in Example 001-(3) or a method equivalent thereto.

ESI-MS (m/z): 376 [M+H]+;

1H-NMR (DMSO-d6): δ 2.77 (3H, d, J=0.6 Hz), 4.22-4.25 (2H, m), 4.38-4.41 (2H, m), 6.62 (1H, d, J=0.6 Hz), 6.94 (2H, s), 8.82 (1H, s), 9.75 (1H, s), 15.05 (1H, brs)

Example 835

Compound 835

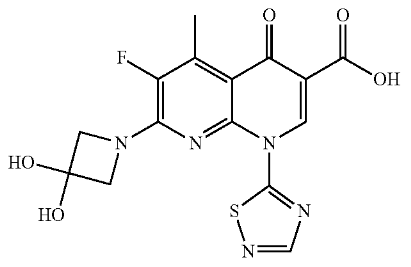

7-(3,3-Dihydroxyazetidin-1-yl)-6-fluoro-5-methyl-4-oxo-1-(1,2,4-thiadiazol-5-yl)-1,4-dihydro-1,8-naphthyridine-3-carboxylic acid The title compound was obtained using 7-chloro-6-fluoro-5-methyl-4-oxo-1-(1,2,4-thiadiazol-5-yl)-1,4-dihydro-1,8-naphthyridine-3-carboxylic acid obtained in Reference Example 008-(2) and azetidin-3-one hydrochloride and by the method described in Example 001-(3) or a method equivalent thereto.

Property: dark brown solid;

ESI-MS (m/z): 394 [M+H]+

Example 836

Compound 836

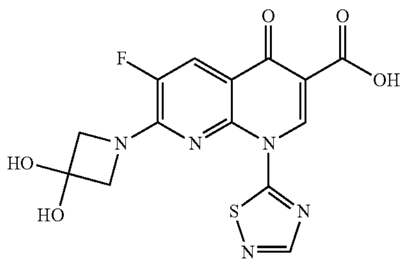

7-(3,3-Dihydroxyazetidin-1-yl)-6-fluoro-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and azetidin-3-one hydrochloride by the method described in Example 001-(3) or a method equivalent thereto.

ESI-MS (m/z): 380 [M+H]+;

1H-NMR (DMSO-d6): δ 4.22-4.65 (4H, m), 6.98 (2H, s), 8.15 (1H, d, J=11.5 Hz), 8.31 (1H, s), 9.75 (1H, s), 13.64-14.62 (1H, m)

Example 837

Compound 837

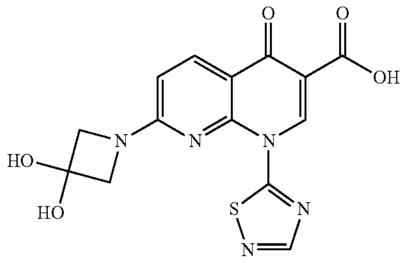

7-(3,3-Dihydroxyazetidin-1-yl)-4-oxo-1-(1,2,4-thiadiazol-5-yl)-1,4-dihydro-1,8-naphthyridine-3-carboxylic acid The title compound was obtained using 7-chloro-4-oxo-1-(1,2,4-thiadiazol-5-yl)-1,4-dihydro-1,8-naphthyridine-3-carboxylic acid obtained in Reference Example 006-(2) and azetidin-3-one hydrochloride by the method described in Example 001-(3) or a method equivalent thereto.

1H-NMR (DMSO-d6): δ 4.10-4.44 (4H, m), 6.82 (1H, d, J=9.0 Hz), 6.96 (2H, s), 8.35 (1H, d, J=9.0 Hz), 8.84 (1H, s), 9.75 (1H, s)

Example 838

Compound 838

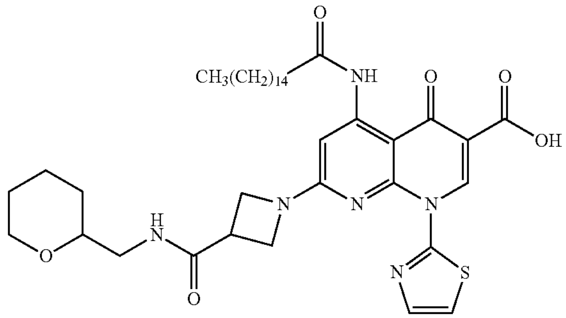

5-Hexadecanamido-7-{3-[(oxan-2-ylmethyl)carbamoyl]azetidin-1-yl}-4-oxo-1-(1,3-thiazol-2-yl)-1,4-dihydro-1,8-naphthyridine-3-carboxylic acid The title compound was obtained using 5-amino-7-(3-{[(oxan-2-yl)methyl]carbamoyl}azetidin-1-yl)-4-oxo-1-(1,3-thiazol-2-yl)-1,4-dihydro-1,8-naphthyridine-3-carboxylic acid obtained in Example 613-(2) and palmitoyl chloride by the method described in Example 002-(1) or a method equivalent thereto.

1H-NMR (CDCl3): δ 0.89 (3H, t, J=7.0 Hz), 1.13-1.47 (26H, m), 1.46-1.55 (5H, m), 1.73-1.82 (1H, m), 2.51 (2H, t, J=7.5 Hz), 2.89-2.98 (1H, m), 3.06-3.17 (1H, m), 3.33-3.46 (2H, m), 3.53-3.61 (1H, m), 3.62-3.70 (1H, m), 3.75-3.83 (1H, m), 3.83-3.91 (1H, m), 3.91-3.97 (2H, m), 6.05-6.16 (1H, m), 7.41-7.45 (1H, m), 7.77 (1H, d, J=3.5 Hz), 8.00 (1H, brs), 9.97 (1H, brs), 12.62-12.70 (1H, m), 14.24 (1H, brs)

Example 839

Compound 839

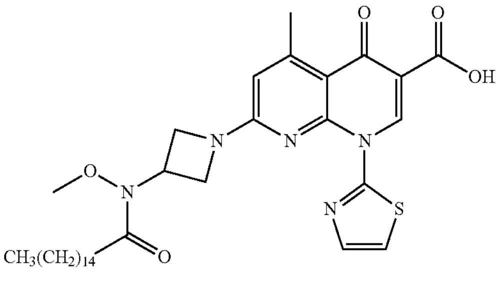

7-[3-(N-Methoxyhexadecanamido) azetidin-1-yl]-5-methyl-4-oxo-1-(1,3-thiazol-2-yl)-1,4-dihydro-1,8-naphthyridine-3-carboxylic acid The title compound was obtained using 7-[3-(methoxyamino)azetidin-1-yl]-5-methyl-4-oxo-1-(1,3-thiazol-2-yl)-1,4-dihydro-1,8-naphthyridine-3-carboxylic acid obtained in Example 546 and palmitoyl chloride by the method described in Example 002-(1) or a method equivalent thereto.

1H-NMR (CDCl3): δ 0.89 (3H, t, J=7.0 Hz), 1.22-1.44 (24H, m), 1.63-1.74 (2H, m), 2.52 (2H, t, J=7.5 Hz), 2.88 (3H, s), 3.90 (3H, s), 4.40-4.67 (4H, m), 5.29-5.36 (1H, m), 6.21 (1H, s), 7.32 (1H, d, J=3.5 Hz), 7.72 (1H, d, J=3.5 Hz), 10.11 (1H, s), 15.13 (1H, s)

Example 840

Compound 840

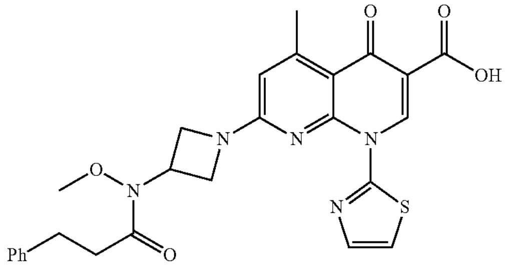

7-[3-(N-Methoxy-3-phenylpropanamido) azetidin-1-yl]-5-methyl-4-oxo-1-(1,3-thiazol-2-yl)-1,4-dihydro-1,8-naphthyridine-3-carboxylic acid The title compound was obtained by the method described in Example 002-(1) or a method equivalent thereto using 7-[3-(methoxyamino) azetidin-1-yl]-5-methyl-4-oxo-1-(1,3-thiazol-2-yl)-1,4-dihydro-1,8-naphthyridine-3-carboxylic acid obtained in Example 546, and 3-phenylpropionyl chloride.

1H-NMR (CDCl3): δ 2.85 (2H, t, J=7.5 Hz), 2.88 (3H, d, J=1.0 Hz), 3.01 (2H, t, J=7.5 Hz), 3.83 (3H, s), 4.40-4.62 (4H, m), 5.27-5.36 (1H, m), 6.20 (1H, d, J=1.0 Hz), 7.19-7.29 (3H, m), 7.30-7.34 (3H, m), 7.73 (1H, d, J=3.5 Hz), 10.13 (1H, s), 15.16 (1H, s)

Example 841

Compound 841

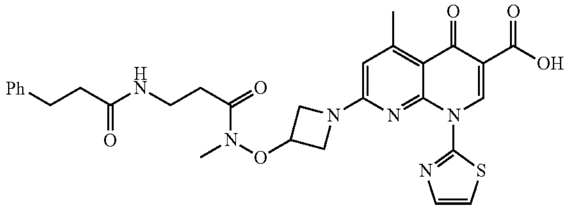

5-Methyl-7-(3-{[N-methyl-3-(3-phenylpropanamido) propanamido]oxy}azetidin-1-yl)-4-oxo-1-(1,3-thiazol-2-yl)-1,4-dihydro-1,8-naphthyridine-3-carboxylic acid The title compound was obtained by the method described in Example 724-(1) or a method equivalent thereto using 7-{3-[(3-amino-N-methylpropanamido)oxy]azetidin-1-yl}-5-methyl-4-oxo-1-(1,3-thiazol-2-yl)-1,4-dihydro-1,8-naphthyridine-3-carboxylic acid trifluoroacetate obtained in Example 724-(2), and 2,5-dioxopyrrolidin-1-yl 3-phenylpropanoate.

1H-NMR (CDCl3): δ 2.48 (2H, t, J=7.5 Hz), 2.59-2.71 (2H, m), 2.82 (3H, s), 2.96 (2H, t, J=7.5 Hz), 3.30 (3H, s), 3.52-3.58 (2H, m), 4.31-4.40 (2H, m), 4.54-4.68 (2H, m), 4.92-5.00 (1H, m), 6.15-6.21 (2H, m), 7.16-7.23 (3H, m), 7.25-7.31 (2H, m), 7.34 (1H, d, J=3.5 Hz), 7.69 (1H, d, J=3.5 Hz), 10.01 (1H, s), 15.16 (1H, brs)

Example 842

Compound 842

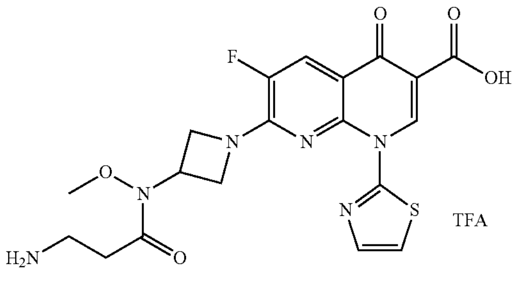

7-[3-(3-Amino-N-methoxypropanamido) azetidin-1-yl]-6-fluoro-4-oxo-1-(1,3-thiazol-2-yl)-1,4-dihydro-1,8-naphthyridine-3-carboxylic acid trifluoroacetate The title compound was obtained using 6-fluoro-7-[3-(methoxyamino)azetidin-1-yl]-4-oxo-1-(1,3-thiazol-2-yl)-1,4-dihydro-1,8-naphthyridine-3-carboxylic acid obtained in Example 539 and 3-{([(tert-butoxy) carbonyl] amino}propanoic acid by the methods described in Example 724-(1) and (2) or methods equivalent thereto.

1H-NMR (DMSO-d6): δ 2.85 (2H, t, J=6.5 Hz), 3.02-3.08 (2H, m), 3.88 (3H, s), 4.51-4.89 (4H, m), 5.18-5.29 (1H, m), 7.65 (3H, brs), 7.81 (1H, d, J=3.5 Hz), 7.88 (1H, d, J=3.5 Hz), 8.17 (1H, d, J=11.5 Hz), 9.84 (1H, s), 14.75 (1H, brs)

Example 843

Compound 843

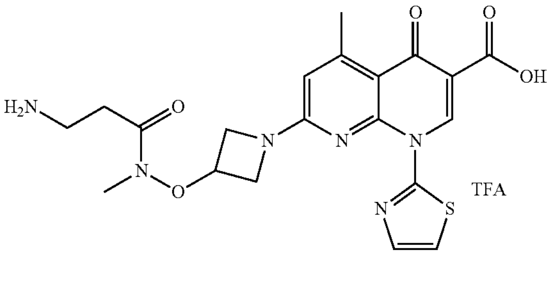

7-[3-(3-Amino-N-methoxypropanamido)azetidin-1-yl]-5-methyl-4-oxo-1-(1,3-thiazol-2-yl)-1,4-dihydro-1,8-naphthyridine-3-carboxylic acid trifluoroacetate The title compound was obtained using 5-methyl-7-{3-[(methylamino)oxy]azetidin-1-yl}-4-oxo-1-(1,2,4-thiadiazol-5-yl)-1,4-dihydro-1,8-naphthyridine-3-carboxylic acid obtained in Example 553 and 3-{[(tert-butoxy)carbonyl] amino} propanoic acid by the methods described in Example 724-(1) and (2) or methods equivalent thereto.

1H-NMR (DMSO-d6): δ 2.76-2.87 (5H, m), 3.00-3.07 (2H, m), 3.27 (3H, m), 4.27-4.93 (4H, m), 5.08-5.17 (1H, m), 6.64 (1H, s), 7.61 (3H, brs), 8.84 (1H, s), 9.79 (1H, s)

Example 844

Compound 844

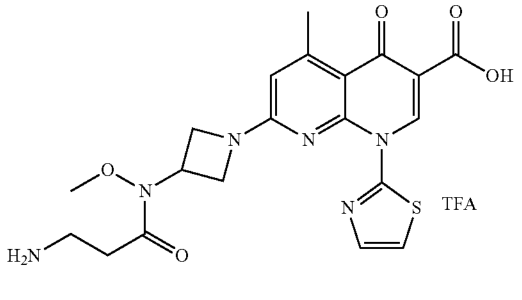

7-[3-(3-Amino-N-methoxypropanamido)azetidin-1-yl]-5-methyl-4-oxo-1-(1,3-thiazol-2-yl)-1,4-dihydro-1,8-naphthyridine-3-carboxylic acid trifluoroacetate The title compound was obtained by the methods described in Examples 724-(1) and 724-(2) or methods equivalent thereto using 7-[3-(methoxyamino)azetidin-1-yl]-5-methyl-4-oxo-1-(1,3-thiazol-2-yl)-1,4-dihydro-1,8-naphthyridine-3-carboxylic acid obtained in Example 546, and 3-{[(tert-butoxy) carbonyl]amino}propanoic acid.

1H-NMR (DMSO-d6): δ 2.81 (3H, s), 2.83-2.88 (2H, m), 3.02-3.08 (2H, m), 3.87 (3H, s), 4.39-4.70 (4H, m), 5.18-5.27 (1H, m), 6.61 (1H, s), 7.64 (3H, brs), 7.77 (1H, d, J=3.5 Hz), 7.86 (1H, d, J=3.5 Hz), 9.87 (1H, s), 15.35 (1H, brs)

Example 845

Compound 845

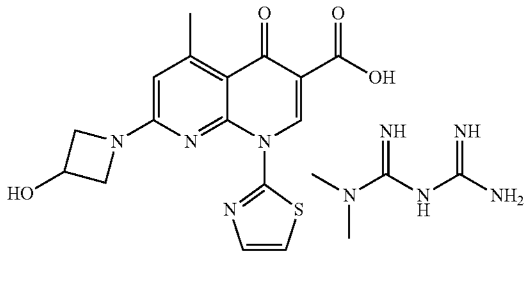

7-(3-Hydroxyazetidin-1-yl)-5-methyl-4-oxo-1-(1,3-thiazol-2-yl)-1,4-dihydro-1,8-naphthyridine-3-carboxylic acid 1-carbamimidamido-N,N-dimethylmethanimidamide salt A suspension of 7-(3-hydroxyazetidin-1-yl)-5-methyl-4-oxo-1-(1,3-thiazol-2-yl)-1,4-dihydro-1,8-naphthyridine-3-carboxylic acid (7.2 mg) obtained in Example 029, and 1-carbamimidamido-N,N-dimethylmethanimidamide (2.6 mg) in methanol (500 μL) was stirred at 60° C. for 10 minutes. Then, water (5 mL) was added thereto, and the mixture was stirred at the same temperature for 1 hour. The reaction solution was concentrated to obtain 8.0 mg of the title compound.

1H-NMR (DMSO-d6): δ 2.70 (3H, s), 2.92 (6H, s), 3.17 (1H, d, J=5.5 Hz), 3.90-4.01 (2H, m), 4.37-4.48 (2H, m), 4.61-4.69 (1H, m), 6.24 (1H, s), 6.56-7.31 (6H, m), 7.52 (1H, d, J=3.5 Hz), 7.70 (1H, d, J=3.5 Hz), 9.04-9.26 (1H, m)

Example 846

Compound 846

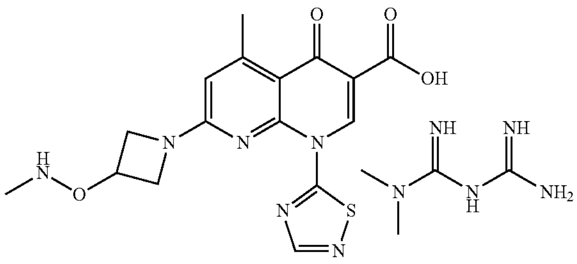

5-Methyl-7-{3-[(methylamino)oxy]azetidin-1-yl}-4-oxo-1-(1,2,4-thiadiazol-5-yl)-1,4-dihydro-1,8-naphthyridine-3-carboxylic acid 1-carbamimidamido-N,N-dimethylmethanimidamide salt The title compound was obtained using 5-methyl-7-{3-[(methylamino)oxy]azetidin-1-yl}-4-oxo-1-(1,2,4-thiadiazol-5-yl)-1,4-dihydro-1,8-naphthyridine-3-carboxylic acid obtained in Example 553 and 1-carbamimidamido-N,N-dimethylmethanimidamide by the method described in Example 845 or a method equivalent thereto.

1H-NMR (DMSO-d6): δ 2.60 (3H, d, J=6.5 Hz), 2.71 (3H, s), 2.92 (6H, s), 3.72-3.82 (1H, m), 4.05-4.27 (1H, m), 4.34-4.52 (2H, m), 4.67-4.75 (1H, m), 6.31 (1H, s), 6.64-6.99 (5H, m), 7.00-7.28 (2H, m), 8.63 (1H, s), 8.88 (1H, s)

Example 847

Compound 847

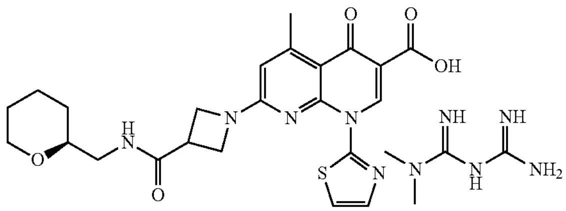

5-Methyl-7-(3-{[(2S)-oxan-2-ylmethyl]carbamoyl}azetidin-1-yl)-4-oxo-1-(1,3-thiazol-2-yl)-1,4-dihydro-1,8-naphthyridine-3-carboxylic acid 1-carbamimidamido-N, N-dimethylmethanimidamide salt The title compound was obtained using 5-methyl-7-(3-{[(2S)-oxan-2-ylmethyl]carbamoyl}azetidin-1-yl)-4-oxo-1-(1,3-thiazol-2-yl)-1,4-dihydro-1,8-naphthyridine-3-carboxylic acid obtained in Example 391 and 1-carbamimidamido-N,N-dimethylmethanimidamide by the method described in Example 845 or a method equivalent thereto.

1H-NMR (DMSO-d6): δ 1.10-1.20 (1H, m), 1.39-1.49 (3H, m), 1.52-1.59 (1H, m), 1.72-1.81 (1H, m), 2.72 (3H, s), 2.92 (6H, s), 3.00-3.24 (4H, m), 3.54-3.62 (1H, m), 3.84-3.90 (1H, m), 4.16-4.48 (4H, m), 6.27 (1H, s), 6.62-6.96 (4H, m), 7.00-7.25 (2H, m), 7.51 (1H, d, J=3.5 Hz), 7.70 (1H, d, J=3.5 Hz), 8.17 (1H, t, J=5.5 Hz), 9.08 (1H, s)

Example 848

Compound 848

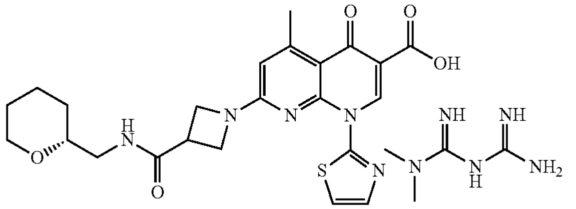

5-Methyl-7-(3-{[(2R)-oxan-2-ylmethyl]carbamoyl}azetidin-1-yl)-4-oxo-1-(1,3-thiazol-2-yl)-1,4-dihydro-1,8-naphthyridine-3-carboxylic acid 1-carbamimidamido-N, N-dimethylmethanimidamide salt The title compound was obtained using 5-methyl-7-(3-{[(2R)-oxan-2-ylmethyl]cycarbaoyl}azetidin-1-yl)-4-oxo-1-(1,3-thiazol-2-yl)-1,4-dihydro-1,8-naphthyridine-3-carboxylic acid obtained in Example 392 and 1-carbamimidamido-N,N-dimethylmethanimidamide by the method described in Example 845 or a method equivalent thereto.

1H-NMR (DMSO-d6): δ 1.10-1.20 (1H, m), 1.39-1.49 (3H, m), 1.52-1.59 (1H, m), 1.72-1.81 (1H, m), 2.72 (3H, s), 2.92 (6H, s), 3.00-3.24 (4H, m), 3.54-3.62 (1H, m), 3.84-3.90 (1H, m), 4.16-4.48 (4H, m), 6.27 (1H, s), 6.62-6.96 (4H, m), 7.00-7.25 (2H, m), 7.51 (1H, d, J=3.5 Hz), 7.70 (1H, d, J=3.5 Hz), 8.17 (1H, t, J=5.5 Hz), 9.08 (1H, s)

Example 849

Compound 849

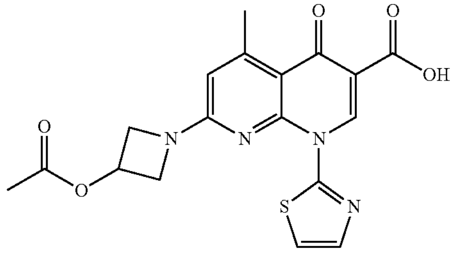

7-[3-(Acetyloxy)azetidin-1-yl]-5-methyl-4-oxo-1-(1,3-thiazol-2-yl)-1,4-dihydro-1,8-naphthyridine-3-carboxylic acid The title compound was obtained by the method described in Example 001-(3) or a method equivalent thereto using azetidin-3-yl acetate trifluoroacetate and 7-chloro-5-methyl- 4-oxo-1-(1,3-thiazol-2-yl)-1,4-dihydro-1,8-naphthyridine-3-carboxylic acid obtained in Reference Example 001-(2).

1H-NMR (DMSO-d6): δ 2.11 (3H, s), 2.77 (3H, s), 4.16-4.32 (2H, m), 4.55-4.74 (2H, m), 5.29-5.41 (1H, m), 6.57 (1H, s), 7.77 (1H, d, J=3.5 Hz), 7.84 (1H, d, J=3.5 Hz), 9.84 (1H, s), 15.33 (1H, brs)

Example 850

Compound 850

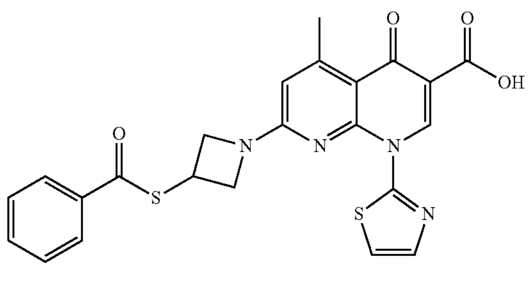

7-[3-(Benzoylsulfanyl)azetidin-1-yl]-5-methyl-4-oxo-1-(1,3-thiazol-2-yl)-1,4-dihydro-1,8-naphthyridine-3-carboxylic acid The title compound was obtained using (azetidin-3-ylsulfanyl)(phenyl)methanone trifluoroacetate and 7-chloro-5-methyl-4-oxo-1-(1,3-thiazol-2-yl)-1,4-dihydro-1,8-naphthyridine-3-carboxylic acid obtained in Reference Example 001-(2) by the method described in Example 001-(3) or a method equivalent thereto.

1H-NMR (DMSO-d6): δ 2.79 (3H, s), 4.25-4.39 (2H, m), 4.61-4.69 (1H, m), 4.79-4.94 (2H, m), 6.60 (1H, s), 7.60 (2H, t, J=7.4 Hz), 7.71-7.76 (2H, m), 7.84 (1H, d, J=3.5 Hz), 7.92-7.97 (2H, m), 9.86 (1H, s), 15.33 (1H, brs)

Example 851

Compound 851

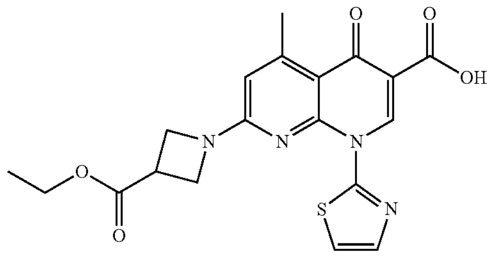

7-[3-(Ethoxycarbonyl)azetidin-1-yl]-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and ethyl azetidine-3-carboxylate trifluoroacetate by the method described in Example 001-(3) or a method equivalent thereto.

1H-NMR (DMSO-d6): δ 1.25 (3H, t, J=7.0 Hz), 2.77 (3H, s), 3.73-3.84 (1H, m), 4.18 (2H, q, J=7.0 Hz), 4.31-4.60 (4H, m), 6.56 (1H, s), 7.76 (1H, d, J=3.5 Hz), 7.83 (1H, d, J=3.5 Hz), 9.83 (1H, s), 15.32 (1H, brs)

Example 852

Compound 852

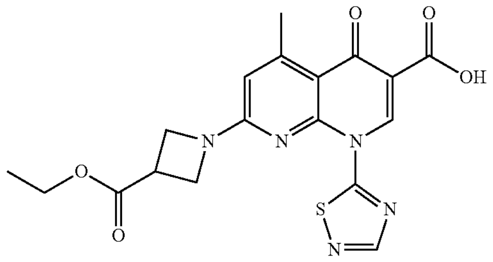

7-[3-(Ethoxycarbonyl)azetidin-1-yl]-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and ethyl azetidine-3-carboxylate trifluoroacetate by the method described in Example 001-(3) or a method equivalent thereto.

1H-NMR (DMSO-d6): δ 1.26 (3H, t, J=7.0 Hz), 2.70 (3H, s), 3.73-3.87 (1H, m), 4.21 (2H, q, J=7.0 Hz), 4.26-4.68 (4H, m), 6.52 (1H, s), 8.79 (1H, s), 9.62 (1H, S)

Example 853

Compound 853

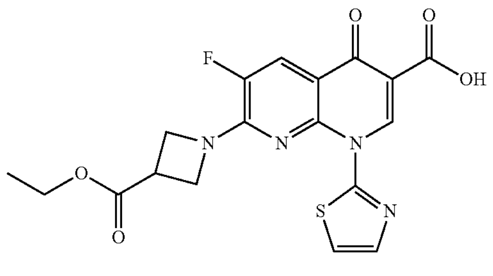

7-[3-(Ethoxycarbonyl)azetidin-1-yl]-6-fluoro-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and ethyl azetidine-3-carboxylate trifluoroacetate by the method described in Example 001-(3) or a method equivalent thereto.

1H-NMR (DMSO-d6): δ 1.26 (3H, t, J=7.2 Hz), 3.75-3.87 (1H, m), 4.18 (2H, q, J=7.2 Hz), 4.45-4.82 (4H, m), 7.81

(1H, d, J=3.5 Hz), 7.85 (1H, d, J=3.5 Hz), 8.13 (1H, d, J=11.0 Hz), 9.82 (1H, s), 14.75 (1H, brs)

Example 854

Compound 854

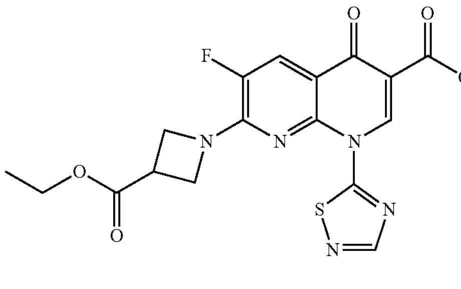

7-[3-(Ethoxycarbonyl)azetidin-1-yl]-6-fluoro-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and ethyl azetidine-3-carboxylate trifluoroacetate by the method described in Example 001-(3) or a method equivalent thereto.

1H-NMR (DMSO-d6): δ 1.25 (3H, t, J=7.2 Hz), 3.78-3.87 (1H, m), 4.20 (2H, q, J=7.2 Hz), 4.56-4.92 (4H, m), 8.15 (1H, d, J=11.5 Hz), 8.85 (1H, s), 9.74 (1H, s)

Example 855

Compound 855

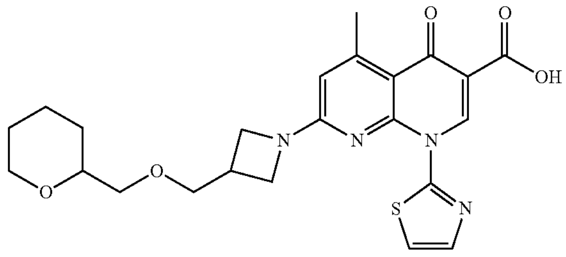

5-Methyl-7-{3-[(oxan-2-ylmethoxy)methyl]azetidin-1-yl}-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and 3-{[(oxan-2-yl)methoxy]methyl}azetidine trifluoroacetate obtained from (oxan-2-yl)methyl 4-methylbenzene-1-sulfonate and tert-butyl 3-(hydroxymethyl)azetidine-1-carboxylate by the methods described in Example 003-(1) and Example 001-(2) or methods equivalent thereto by the method described in Example 002-(3) or a method equivalent thereto.

1H-NMR (DMSO-d6): δ 1.13-1.22 (1H, m), 1.35-1.46 (3H, m), 1.49-1.55 (1H, m), 1.72-1.79 (1H, m), 2.77 (3H, s), 3.01-3.09 (1H, m), 3.39-3.47 (2H, m), 3.66 (2H, d, J=6.5 Hz), 3.80-3.87 (1H, m), 3.94-4.13 (2H, m), 4.25-4.47 (2H, m), 6.52 (1H, d, J=1.0 Hz), 7.84 (1H, d, J=3.5 Hz), 7.88 (1H, d, J=4.0 Hz), 9.85 (1H, s), 15.44 (1H, brs)

Example 856

Compound 856

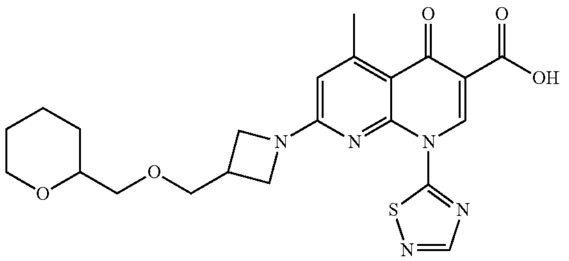

5-Methyl-7-{3-[(oxan-2-ylmethoxy)methyl]azetidin-1-yl}-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and 3-{[(oxan-2-yl)methoxy]methyl}azetidine trifluoroacetate obtained in Example 855 by the method described in Example 002-(3) or a method equivalent thereto.

1H-NMR (DMSO-d6): δ 1.13-1.23 (1H, m), 1.37-1.48 (3H, m), 1.50-1.57 (1H, m), 1.71-1.79 (1H, m), 2.76 (3H, s), 3.04-3.13 (1H, m), 3.37-3.46 (2H, m), 3.69 (2H, d, J=6.5 Hz), 3.81-3.88 (1H, m), 3.97-4.07 (1H, m), 4.12-4.21 (1H, m), 4.28-4.40 (1H, m), 4.45-4.56 (1H, m), 6.56 (1H, s), 8.82 (1H, s), 9.73 (1H, s), 15.13 (1H, brs)

Example 857

Compound 857

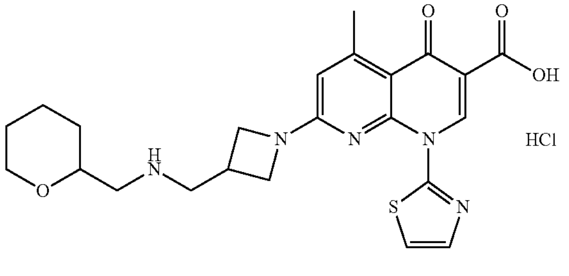

5-Methyl-7-(3-{[(oxan-2-ylmethyl)amino]methyl}azetidin-1-yl)-4-oxo-1-(1,3-thiazol-2-yl)-1,4-dihydro-1,8-naphthyridine-3-carboxylic acid hydrochloride The title compound was obtained by the method described in Example 002-(3) or a method equivalent thereto using

[(azetidin-3-yl)methyl] [(oxan-2-yl)methyl]amine trifluoroacetate and 7-chloro-5-methyl-4-oxo-1-(1,3-thiazol-2-yl)-1,4-dihydro-1,8-naphthyridine-3-carboxylic acid obtained in Reference Example 001-(2).

1H-NMR (DMSO-d6): δ 1.18-1.28 (1H, m), 1.42-1.56 (3H, m), 1.56-1.63 (1H, m), 1.77-1.86 (1H, m), 2.78 (3H, s), 2.91-2.99 (1H, m), 3.02-3.10 (1H, m), 3.18-3.24 (1H, m), 3.39-3.45 (1H, m), 3.57-3.65 (1H, m), 3.94-3.99 (1H, m), 4.00-4.27 (2H, m), 4.31-4.51 (2H, m), 6.52 (1H, d, J=1.0 Hz), 7.80 (1H, d, J=3.5 Hz), 7.87 (1H, d, J=3.5 Hz), 8.68 (2H, brs), 9.89 (1H, s), 15.37 (1H, brs)

Example 858

Compound 858

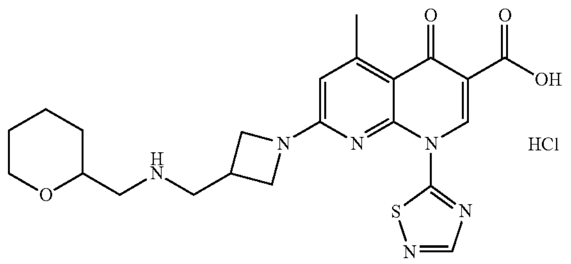

5-Methyl-7-(3-{[(oxan-2-ylmethyl)amino]methyl}azetidin-1-yl)-4-oxo-1-(1,2,4-thiadiazol-5-yl)-1,4-dihydro-1,8-naphthyridine-3-carboxylic acid hydrochloride The title compound was obtained using [(azetidin-3-yl)methyl] [(oxan-2-yl)methyl]amine trifluoroacetate and 7-chloro-5-methyl-4-oxo-1-(1,2,4-thiadiazol-5-yl)-1,4-dihydro-1,8-naphthyridine-3-carboxylic acid obtained in Reference Example 002-(2) by the method described in Example 002-(3) or a method equivalent thereto.

1H-NMR (DMSO-d6): δ 1.18-1.28 (1H, m), 1.44-1.57 (3H, m), 1.57-1.63 (1H, m), 1.80-1.87 (1H, m), 2.79 (3H, s), 2.92-3.02 (1H, m), 3.04-3.12 (1H, m), 3.19-3.27 (1H, m), 3.40-3.47 (1H, m), 3.58-3.68 (1H, m), 3.93-4.02 (1H, m), 4.03-4.12 (1H, m), 4.24-4.60 (3H, m), 6.56 (1H, d, J=1.0 Hz), 8.57-8.76 (2H, m), 8.84 (1H, s), 9.76 (1H, s), 15.07 (1H, brs)

Example 859

Compound 859

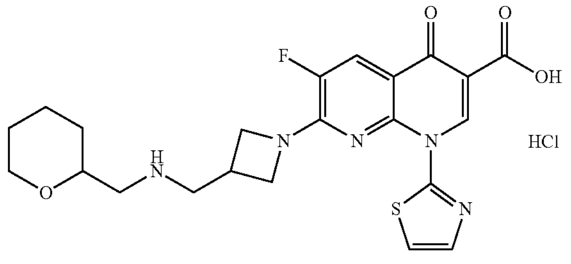

6-Fluoro-7-(3-{[(oxan-2-ylmethyl)amino]methyl}azetidin-1-yl)-4-oxo-1-(1,3-thiazol-2-yl)-1,4-dihydro-1,8-naphthyridine-3-carboxylic acid hydrochloride The title compound was obtained using [(azetidin-3-yl)methyl] [(oxan-2-yl)methyl]amine trifluoroacetate and 7-chloro-6-fluoro-4-oxo-1-(1,3-thiazol-2-yl)-1,4-dihydro-1,8-naphthyridine-3-carboxylic acid obtained in Reference Example 003-(2) by the method described in Example 002-(3) or a method equivalent thereto.

1H-NMR (DMSO-d6): δ 1.18-1.27 (1H, m), 1.44-1.56 (3H, m), 1.57-1.63 (1H, m), 1.77-1.86 (1H, m), 2.90-2.99 (1H, m), 2.99-3.02 (1H, m), 3.02-3.10 (1H, m), 3.19-3.28 (1H, m), 3.28-3.37 (1H, m), 3.38-3.44 (1H, m), 3.59-3.66 (1H, m), 3.94-3.99 (1H, m), 4.16-4.80 (4H, m), 7.84 (11H, d, J=3.5 Hz), 7.89 (1H, d, J=3.5 Hz), 8.12 (1H, d, J=11.5 Hz), 8.70 (2H, brs), 9.81 (1H, s), 14.79 (1H, brs)

Example 860

Compound 860

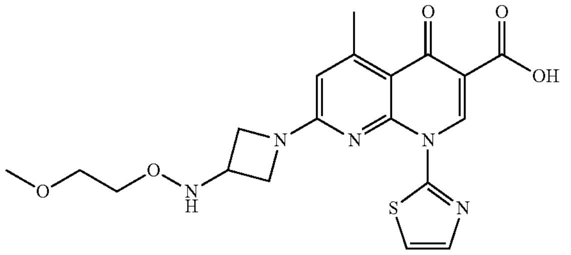

7-{3-[(2-Methoxyethoxy)amino]azetidin-1-yl}-5-methyl-4-oxo-1-(1,3-thiazol-2-yl)-1,4-dihydro-1,8-naphthyridine-3-carboxylic acid The title compound was obtained by the method described in Example 001-(3) or a method equivalent thereto using N-(2-methoxyethoxy)azetidin-3-amine trifluoroacetate obtained from 2-methoxyethan-1-ol by the methods described in Examples 735-(1) to 735-(3), 722-(1) and 001-(2) or methods equivalent thereto, and 7-chloro-5-methyl-4-oxo-1-(1,3-thiazol-2-yl)-1,4-dihydro-1,8-naphthyridine-3-carboxylic acid obtained in Reference Example 001-(2).

1H-NMR (DMSO-d6): δ 2.73 (3H, d, J=1.0 Hz), 3.23 (3H, s), 3.45-3.50 (2H, m), 3.73-3.79 (2H, m), 3.97-4.21 (3H, m), 4.24-4.45 (2H, m), 6.48 (1H, d, J=1.0 Hz), 7.12 (1H, brs), 7.75 (1H, d, J=3.5 Hz), 7.82 (1H, d, J=3.5 Hz), 9.80 (1H, s), 15.41 (1H, brs)

Example 861

Compound 861

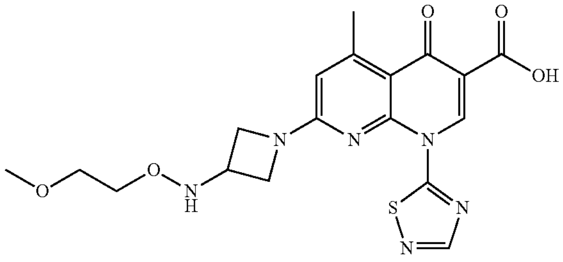

7-{3-[(2-Methoxyethoxy)amino]azetidin-1-yl}-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-(2-methoxyethoxy)azetidin-3-amine trifluoroacetate obtained in Example 860 by the method described in Example 001-(3) or a method equivalent thereto.

1H-NMR (DMSO-d6): δ 2.74 (3H, d, J=1.0 Hz), 3.24 (3H, s), 3.46-3.51 (2H, m), 3.75-3.81 (2H, m), 4.02-4.57 (5H, m), 6.55 (1H, d, J=1.0 Hz), 7.13 (1H, brs), 8.81 (1H, s), 9.70 (1H, s), 15.09 (1H, brs)

Example 862

Compound 862

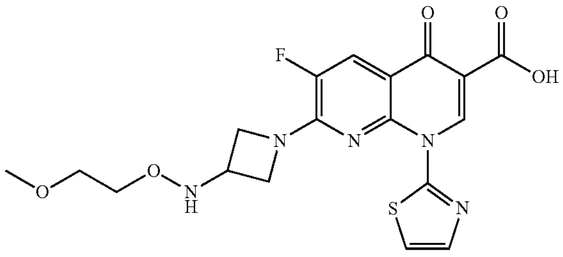

6-Fluoro-7-{3-[(2-methoxyethoxy)amino]azetidin-1-yl}-4-oxo-1-(1,3-thiazol-2-yl)-1,4-dihydro-1,8-naphthyridine-3-carboxylic acid The title compound was obtained using 7-chloro-6-fluoro-4-oxo-1-(1,3-thiazol-2-yl)-1,4-dihydro-1,8-naphthyridine-3-carboxylic acid obtained in Reference Example 003-(2) and N-(2-methoxyethoxy) azetidin-3-amine trifluoroacetate obtained in Example 860 by the method described in Example 001-(3) or a method equivalent thereto.

1H-NMR (DMSO-d6): δ 3.23 (3H, s), 3.45-3.51 (2H, m), 3.74-3.80 (2H, m), 4.06-4.77 (5H, m), 7.13 (1H, d, J=7.0 Hz), 7.81 (1H, d, J=3.0 Hz), 7.85 (1H, d, J=3.0 Hz), 8.08 (1H, d, J=11.0 Hz), 9.80 (1H, s)

Example 863

Compound 863

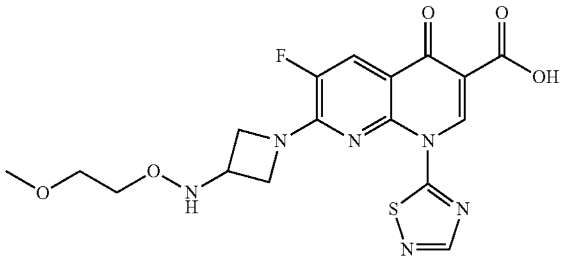

6-Fluoro-7-{3-[(2-methoxyethoxy)amino]azetidin-1-yl}-4-oxo-1-(1,2,4-thiadiazol-5-yl)-1,4-dihydro-1,8-naphthyridine-3-carboxylic acid The title compound was obtained using 7-chloro-6-fluoro-4-oxo-1-(1,2,4-thiadiazol-5-yl)-1,4-dihydro-1,8-naphthyridine-3-carboxylic acid obtained in Reference Example 004-(2) and N-(2-methoxyethoxy)azetidin-3-amine trifluoroacetate obtained in Example 860 by the method described in Example 001-(3) or a method equivalent thereto.

1H-NMR (DMSO-d6): δ 3.24 (3H, s), 3.45-3.53 (2H, m), 3.75-3.82 (2H, m), 4.10-4.21 (1H, m), 4.27-4.84 (4H, m), 7.13 (1H, d, J=5.5 Hz), 8.12 (1H, d, J=11.5 Hz), 8.84 (1H, s), 9.71 (1H, s), 14.48 (1H, brs)

Example 864

Compound 864

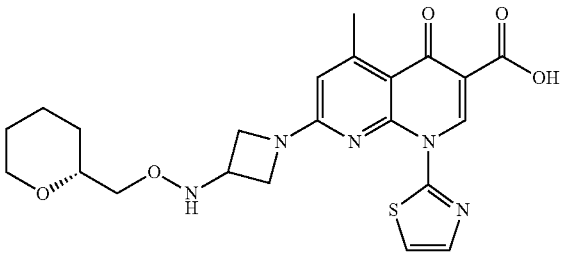

5-Methyl-7-(3-{[(2R)-oxan-2-ylmethoxy]amino}azetidin-1-yl)-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and N-[(2R)-oxan-2-ylmethoxy]azetidin-3-amine trifluoroacetate obtained from [(2R)-oxan-2-yl]methanol by the methods described in Example 735-(1)~(3), Example 722-(1) and Example 001-(2) or methods equivalent thereto by the method described in Example 001-(3) or a method equivalent thereto.

1H-NMR (DMSO-d6): δ 1.07-1.17 (1H, m), 1.31-1.57 (4H, m), 1.70-1.82 (1H, m), 2.75 (3H, s), 3.44-3.57 (2H, m), 3.58-3.65 (1H, m), 3.77-3.88 (1H, m), 3.98-4.22 (3H, m), 4.26-4.46 (2H, m), 6.50 (1H, s), 7.13 (1H, d, J=6.5 Hz), 7.76 (1H, d, J=3.5 Hz), 7.83 (1H, d, J=3.5 Hz), 9.82 (1H, s)

Example 865

Compound 865

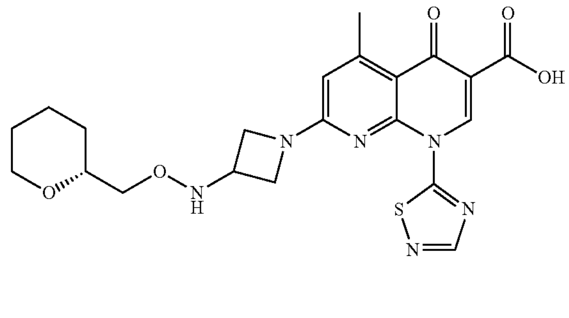

5-Methyl-7-(3-{[(2R)-oxan-2-ylmethoxy]amino}azetidin-1-yl)-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and N-[(2R)-oxan-2-ylmethoxy]azetidin-3-amine trifluoroacetate obtained in Example 864 by the method described in Example 001-(3) or a method equivalent thereto.

1H-NMR (DMSO-d6): δ 1.07-1.19 (1H, m), 1.33-1.56 (4H, m), 1.71-1.81 (1H, m), 2.76 (3H, s), 3.47-3.58 (2H, m), 3.59-3.66 (1H, m), 3.79-3.87 (1H, m), 4.05-4.18 (2H, m), 4.20-4.40 (2H, m), 4.49-4.58 (1H, m), 6.58 (1H, s), 7.13 (1H, d, J=6.0 Hz), 8.82 (1H, s), 9.73 (1H, s), 15.10 (1H, brs)

Example 866

Compound 866

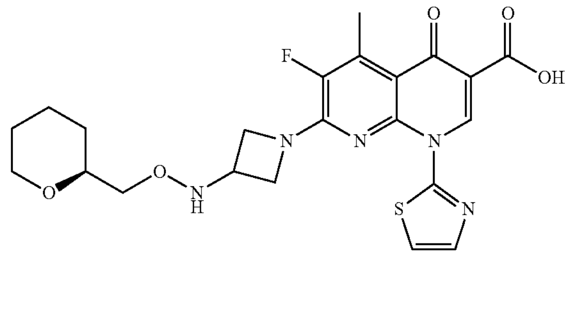

6-Fluoro-5-methyl-7-(3-{[(2S)-oxan-2-ylmethoxy]amino}azetidin-1-yl)-4-oxo-1-(1,3-thiazol-2-yl)-1,4-dihydro-1,8-naphthyridine-3-carboxylic acid The title compound was obtained using 7-chloro-6-fluoro-5-methyl-4-oxo-1-(1,3-thiazol-2-yl)-1,4-dihydro-1,8-naphthyridine-3-carboxylic acid obtained in Reference Example 007-(2) and N-[(2S)-oxan-2-ylmethoxy]azetidin-3-amine trifluoroacetate obtained in Example 776 by the method described in Example 001-(3) or a method equivalent thereto.

1H-NMR (DMSO-d6): δ 1.07-1.17 (1H, m), 1.35-1.54 (4H, m), 1.71-1.79 (1H, m), 2.68 (3H, d, J=2.5 Hz), 3.26-3.34 (1H, m), 3.47-3.56 (2H, m), 3.60 (1H, d, J=11.0, 6.5 Hz), 3.78-3.85 (1H, m), 4.06-4.14 (1H, m), 4.17-4.71 (4H, m), 7.12 (1H, d, J=6.5 Hz), 7.79 (1H, d, J=3.5 Hz), 7.85 (1H, d, J=3.5 Hz), 9.79 (1H, s), 15.11 (1H, brs)

Example 867

Compound 867

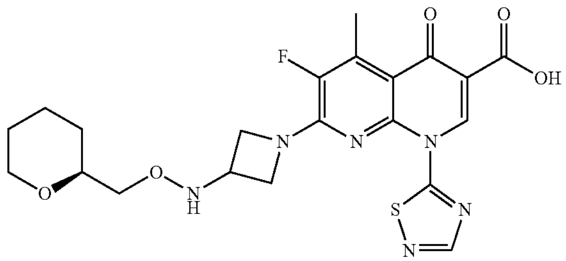

6-Fluoro-5-methyl-7-(3-{[(2S)-oxan-2-ylmethoxy]amino}azetidin-1-yl)-4-oxo-1-(1,2,4-thiadiazol-5-yl)-1,4-dihydro-1,8-naphthyridine-3-carboxylic acid The title compound was obtained using 7-chloro-6-fluoro-5-methyl-4-oxo-1-(1,2,4-thiadiazol-5-yl)-1,4-dihydro-1,8-naphthyridine-3-carboxylic acid obtained in Reference Example 008-(2) and N-[(2S)-oxan-2-ylmethoxy]azetidin-3-amine trifluoroacetate obtained in Example 776 by the method described in Example 001-(3) or a method equivalent thereto.

1H-NMR (DMSO-d6): δ 1.08-1.18 (1H, m), 1.36-1.54 (4H, m), 1.71-1.79 (1H, m), 2.68 (3H, d, J=3.0 Hz), 3.28-3.35 (1H, m), 3.50-3.58 (2H, m), 3.63 (1H, dd, J=11.0, 6.5 Hz), 3.79-3.85 (1H, m), 4.09-4.15 (1H, m), 4.29-4.78 (4H, m), 7.13 (1H, d, J=6.0 Hz), 8.84 (1H, s), 9.74 (1H, s), 14.86 (1H, brs)

Example 868

Compound 868

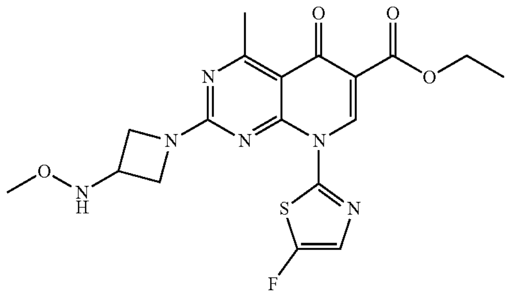

Ethyl 8-(5-fluoro-1,3-thiazol-2-yl)-2-[3-(methoxyamino)azetidin-1-yl]-4-methyl-5-oxo-5H,8H-pyrido[2,3-d]pyrimidine-6-carboxylate The title compound was obtained using ethyl 8-(5-fluoro-1,3-thiazol-2-yl)-2-methanesulfonyl-4-methyl-5-oxo-5H, 8H-pyrido[2,3-d]pyrimidine-6-carboxylate obtained in Example 767-(1) and N-methoxyazetidin-3-amine trifluoroacetate obtained in Example 535 by the method described in Example 027-(3) or a method equivalent thereto.

1H-NMR (CDCl3): δ 1.42 (3H, t, J=7.0 Hz), 2.97 (3H, s), 3.65 (3H, s), 4.15-4.63 (7H, m), 5.79 (1H, d, J=6.0 Hz), 7.29 (1H, d, J=3.0 Hz), 9.59 (1H, s)

Example 869

Compound 869

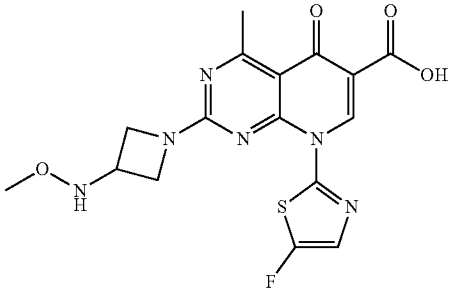

8-(5-Fluoro-1,3-thiazol-2-yl)-2-[3-(methoxyamino)azetidin-1-yl]-4-methyl-5-oxo-5H,8H-pyrido[2,3-d]pyrimidine-6-carboxylic acid The title compound was obtained from ethyl 8-(5-fluoro-1,3-thiazol-2-yl)-2-[3-(methoxyamino)azetidin-1-yl]-4-methyl-5-oxo-5H,8H-pyrido[2,3-d]pyrimidine-6-carboxylate obtained in Example 868 by the method described in Example 028-(2) or a method equivalent thereto.

Property: dark brown solid;

ESI-MS (m/z): 407 [M+H]+

Example 870

Compound 870

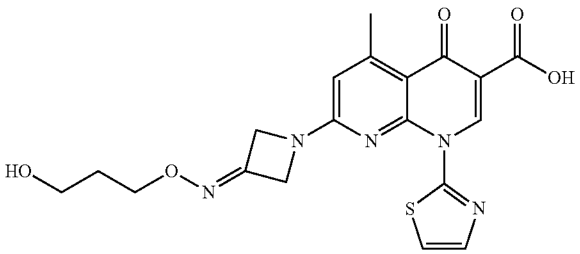

7-{3-[(3-Hydroxypropoxy)imino]azetidin-1-yl}-5-methyl-4-oxo-1-(1,3-thiazol-2-yl)-1,4-dihydro-1,8-naphthyridine-3-carboxylic acid The title compound was obtained using 7-chloro-5-methyl-4-oxo-1-(1,3-thiazol-2-yl)-1,4-dihydro-1,8-naphthyridine-3-carboxylic acid obtained in Reference Example 001-(2) and 3-{[(azetidin-3-ylidene)amino]oxy}propan-1-ol trifluoroacetate obtained from propane-1,3-diol by the methods described in Example 735-(1)~(3) and Example 001-(2) or methods equivalent thereto by the method described in Example 001-(3) or a method equivalent thereto.

1H-NMR (DMSO-d6): δ 1.74-1.86 (2H, m), 2.77 (3H, s), 3.44-3.56 (2H, m), 4.12-4.15 (2H, m), 4.93-5.10 (4H, m), 6.63 (1H, s), 7.75-7.78 (1H, m), 7.82 (1H, d, J=3.5 Hz), 9.82 (1H, s), 15.22 (1H, brs)

Example 871

Compound 871

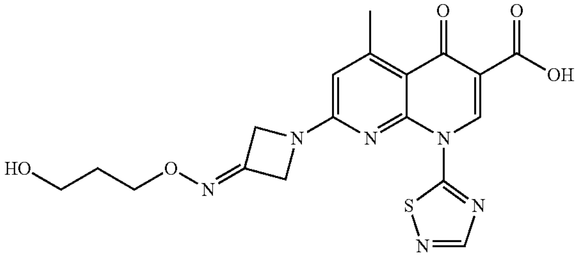

7-{3-[(3-Hydroxypropoxy)imino]azetidin-1-yl}-5-methyl-4-oxo-1-(1,2,4-thiadiazol-5-yl)-1,4-dihydro-1,8-naphthyridine-3-carboxylic acid The title compound was obtained using 7-chloro-5-methyl-4-oxo-1-(1,2,4-thiadiazol-5-yl)-1,4-dihydro-1,8-naphthyridine-3-carboxylic acid obtained in Reference Example 002-(2) and 3-{[(azetidin-3-ylidene)amino]oxy}propan-1-ol trifluoroacetate obtained in Example 870 by the method described in Example 001-(3) or a method equivalent thereto.

1H-NMR (DMSO-d6): δ 1.74-1.87 (2H, m), 2.80 (3H, s), 3.45-3.57 (2H, m), 4.09-4.20 (2H, m), 4.92-5.34 (4H, m), 6.72 (1H, s), 8.83 (1H, s), 9.79 (1H, s), 14.95 (1H, brs)

Example 872

Compound 872

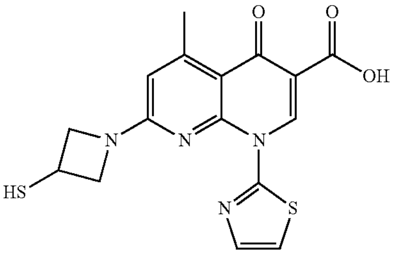

5-Methyl-4-oxo-7-(3-sulfanylazetidin-1-yl)-1-(1,3-thiazol-2-yl)-1,4-dihydro-1,8-naphthyridine-3-carboxylic acid (1) To a solution of tert-butyl 3-(benzoylsulfanyl)azetidine-1-carboxylate (290 mg) in methanol (2.5 mL) was added sodium methoxide (54 mg), and the mixture was stirred at room temperature for 21 hours. To the reaction solution was added a saturated aqueous solution of sodium bicarbonate, and the mixture was extracted with ethyl acetate. The organic layer was washed with water and brine, then dried over sodium sulfate, and concentrated. The residue was purified by silica gel column chromatography (eluent: ethyl acetate/n-hexane) to obtain 100 mg of tert-butyl 3-({1-[(tert-butoxy)carbonyl]azetidin-3-yl}disulfanyl) azetidine-1-carboxylate.

1H-NMR (DMSO-d6): δ 1.44 (18H, s), 3.70-3.77 (2H, m), 3.83-3.88 (4H, m), 4.21-4.28 (4H, m)

(2) 7-[3-({1-[6-Carboxy-4-methyl-5-oxo-8-(1,3-thiazol-2-yl)-5,8-dihydro-1,8-naphthyridin-2-yl]pyrimidin-4-yl}azetidin-3-yl)disulfanyl]azetidin-1-yl]-5-methyl-4-oxo-1-(1,3-thiazol-2-yl)-1,4-dihydro-1,8-naphthyridine-3-carboxylic acid was obtained by the method described in Example 008 or a method equivalent thereto using 3-(azetidin-3-yldisulfanyl)azetidine trifluoroacetate obtained by the method described in Example 001-(2) or a method equivalent thereto from tert-butyl 3-({1-[(tert-butoxy) carbonyl]azetidin-3-yl}disulfanyl)azetidine-1-carboxylate obtained in the preceding section, and 7-chloro-5-methyl-4-oxo-1-(1,3-thiazol-2-yl)-1,4-dihydro-1,8-naphthyridine-3-carboxylic acid obtained in Reference Example 001-(2).

1H-NMR (DMSO-d6): δ 2.73 (6H, s), 4.13-4.45 (8H, m), 4.56-4.80 (2H, m), 6.52 (2H, s), 7.54-7.78 (4H, m), 9.78 (2H, sa), 15.26 (2H, brs)

(3) To a suspension of 7-[3-({1-[6-carboxy-4-methyl-5-oxo-8-(1,3-thiazol-2-yl)-5,8-dihydro-1,8-naphthyridin-2-yl] pyrimidin-4-yl}azetidin-3-yl)disulfanyl]azetidin-1-yl]-5-methyl-4-oxo-1-(1,3-thiazol-2-yl)-1,4-dihydro-1,8-naphthyridine-3-carboxylic acid (30 mg) obtained in the preceding section in methanol (4 mL) were added dithiothreitol (13 mg) and triethylamine (6 μL), and the mixture was stirred at room temperature for 20 hours in a nitrogen atmosphere. Precipitates were collected by filtration, washed with methanol and diethyl ether, and then dried to obtain 22 mg of the title compound.

1H-NMR (DMSO-d6): δ 2.79 (3H, s), 3.95-4.26 (3H, m), 4.59-4.85 (2H, m), 6.56 (1H, s), 7.76 (1H, d, J=3.6 Hz), 7.84 (1H, d, J=3.6 Hz), 9.86 (1H, s), 15.37 (1H, brs)

Example 873

Compound 873

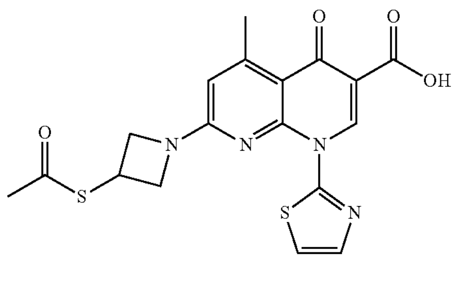

7-[3-(Acetylsulfanyl)azetidin-1-yl]-5-methyl-4-oxo-1-(1,3-thiazol-2-yl)-1,4-dihydro-1,8-naphthyridine-3-carboxylic acid To a mixture of 5-methyl-4-oxo-7-(3-sulfanylazetidin-1-yl)-1-(1,3-thiazol-2-yl)-1,4-dihydro-1,8-naphthyridine-3-carboxylic acid (8 mg) obtained in Example 872-(3), acetic anhydride (8 μL), and methylene chloride (100 μL) was added 4-dimethylaminopyridine (2 mg), and the mixture was stirred at room temperature for 21 hours. To the reaction solution was added 1 mol/L hydrochloric acid, and the mixture was extracted with methylene chloride. The organic layer was dried over sodium sulfate and concentrated to obtain 3 mg of the title compound.

1H-NMR (DMSO-d6): δ 2.40 (3H, s), 2.74 (3H, s), 4.09-4.25 (2H, m), 4.39-4.50 (1H, m), 4.67-4.83 (2H, m), 6.52 (1H, s), 7.75 (1H, d, J=3.5 Hz), 7.82 (1H, d, J=3.5 Hz), 9.81 (1H, s), 15.31 (1H, brs)

Example 874

Compound 874

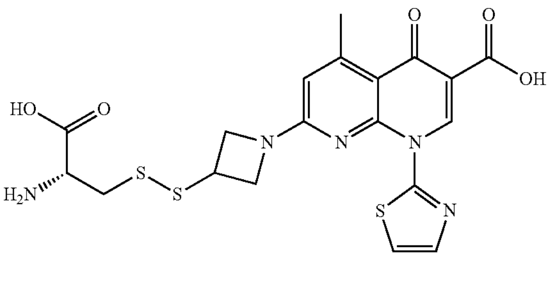

7-(3-{[(2R)-2-Amino-2-carboxyethyl] disulfanyl}azetidin-1-yl)-5-methyl-4-oxo-1-(1,3-thiazol-2-yl)-1,4-dihydro-1,8-naphthyridine-3-carboxylic acid A suspension of 5-methyl-4-oxo-7-(3-sulfanylazetidin-1-yl)-1-(1,3-thiazol-2-yl)-1,4-dihydro-1,8-naphthyridine-3-carboxylic acid (7 mg) obtained in Example 872-(3), and cysteine (5 mg) in methanol (100 μL) was stirred at room temperature to 40° C. for 2 hours. An aqueous hydrogen peroxide solution was added thereto, and the mixture was stirred at 40° C. for 18 hours. Precipitates were collected by filtration, washed with methanol, and then dried to obtain 2 mg of the title compound.

Property: white solid;

ESI-MS (m/z): 494 [M+H]+

Test Examples

The antitumor effect and growth inhibitory activity against normal cells of the compound of the present invention will be described below with reference to Test Examples. "1,4-Dihydro-7-(3-methoxy-4-methylamino-1-pyrrolidinyl)-4-oxo-1-(2-thiazolyl)-1,8-naphthyridine-3-carboxylic acid" (compound A) described in Patent Literature 1 was used as a positive control compound.

Test Example 1: In Vitro Cell Growth Inhibition Test Against NCI-H460 (Human Non-Small Cell Lung Cancer Cell Line)

An NCI-H460 cell suspension was inoculated at $4\times10^3$ cells/100 μL/well (0.1 mL) to a 96-well flat-bottomed multiplate using RPMI-1640 (Sigma-Aldrich Co. LLC, R8758) medium containing 10% PBS (fetal bovine serum, Thermo Fisher Scientific Inc.), and cultured at 37° C. for 1 day in an incubator containing 5% carbon dioxide. The compound of the present invention was dissolved at a concentration of 1 mM in dimethyl sulfoxide and further diluted into 5.00, 2.50, 1.25, 0.63, 0.31, 0.16, 0.078, and 0.039 μM (final concentrations) using dimethyl sulfoxide and RPMI-1640 medium. Each of these dilutions was added at 0.1 mL/well to the culture plate of the NCI-H460 cells mentioned above after removal of the medium, and the cells were cultured at 37° C. for 3 days in an incubator containing 5% carbon dioxide.

After the culture, Cell Counting Kit-8 (Dojindo Laboratories), which adopts WST-8 [2-(2-methoxy-4-nitrophenyl)-3-(4-nitrophenyl)-5-(2,4-disulfophenyl)-2H-tetrazolium monosodium salt] as a chromogenic substrate, was added at 10 μL/well, and the cells were cultured under the same conditions as above for 1 hour, followed by measurement of absorbance at 450 nm. A cell survival rate was calculated in terms of 50% growth inhibition concentration ($IC_{50}$ (μM)) by the least square method with that of a control group defined as 100%. The results are shown in Table 1.

TABLE 1

| Compound No. | $IC_{50}$ (μM) |
|---|---|
| 078 | 0.092 |
| 173 | 0.26 |
| 006 | 0.11 |
| 243 | 0.22 |
| 414 | 0.40 |
| 218 | 0.26 |
| 083 | 0.19 |
| 499 | 0.20 |
| 489 | 0.26 |
| 487 | 0.16 |
| 020 | 0.34 |
| 549 | 0.19 |
| 541 | 0.39 |
| 553 | 0.38 |
| 561 | 0.90 |
| 586 | 0.41 |
| 584 | 0.21 |
| Compound A | 0.37 |

From the results in Table 1, the compound of the present invention was confirmed to have an excellent antitumor effect as compared with compound A.

Test Example 2: In Vitro Cell Growth Inhibition Test Against MV4-11 (Human Acute Myeloid Leukemia Cell Line)

The compound of the present invention was dissolved at a concentration of 1 mM in dimethyl sulfoxide and further diluted into 10.00, 2.50, 0.625, 0.156, 0.039, 0.0098, 0.0024, and 0.00061 μM (final concentrations) using dimethyl sulfoxide and IMDM (Thermo Fisher Scientific Inc., 12440-053) medium. Each of these dilutions was added at 0.05 mL/well to a 96-well flat-bottomed multiplate. An MV4-11 cell suspension was diluted into $1\times10^6$ cells/μL using IMDM (Thermo Fisher Scientific Inc., 12440-053) medium containing 101 FBS (fetal bovine serum, Thermo Fisher Scientific Inc.), and this dilution was added at 0.05 mL/well to the compound-containing 96-well flat-bottomed multiplate mentioned above, and cultured at 37° C. for 3 days in an incubator containing 5% carbon dioxide.

After the culture, Cell Counting Kit-8 (Dojindo Laboratories), which adopts WST-8 as a chromogenic substrate, was added at 10 μL/well, and the cells were cultured under the same conditions as above for 6 hours, followed by measurement of absorbance at 450 nm. A cell survival rate was calculated in terms of 50% growth inhibition concentration ($IC_{50}$ (μM)) by the least square method with that of a control group defined as 100%. The results are shown in Table 2.

TABLE 2

| Compound No. | $IC_{50}$ (μM) |
|---|---|
| 078 | 1.4 |
| Compound A | 10.3 |

From the results in Table 2, the compound of the present invention was confirmed to have an excellent antitumor effect as compared with compound A.

Test Example 3: In Vivo Antitumor Effect Test Against PC-3 (Human Prostate Cancer Cell Line)

A suspension of cancer cells ($1\times10^7$ cells/mL) prepared in RPMI culture medium (Sigma-Aldrich Co. LLC, R8758) was subcutaneously inoculated in an amount of 200 μL to the right abdomen of each female Balb/c nu-nu mouse (Charles River Laboratories Japan, Inc.). After tumor engraftment, animals having a sufficient tumor size were randomly assigned to an active (compound A or compound 078) group and a control (vehicle) group.

Each test compound (drug) was dissolved at each administration concentration in physiological saline containing 12.5 mM sodium hydroxide. The administration of the compound or a vehicle was started on the day of randomization and continued once a week for 21 days. During the test period, the body weights were measured twice a week throughout the treatment period, and tumors were measured twice a week using calipers. The tumor volumes were measured according to the expression $V=L\times W^2/2$ (V: volume, mm3; L: length, mm; W: width, mm). Using the following expression:

% TGI=100−((Average tumor volume of the treatment group Average tumor volume of the control group)×100), tumor growth inhibition was calculated on the basis of the average tumor volume of the vehicle group. The results are shown in Table 3.

TABLE 3

| Compound No. | Dose mg/kg | Route, regimen | % TGI |
|---|---|---|---|
| 078 | 20 | IV, Q7D ×3 | 49.2 |
| Compound A | 20 | IV, Q7D ×3 | 21.7 |

The compound of the present invention was confirmed to strongly inhibit tumor growth in PC-3 (human prostate cancer cell line) xenograft models after intravenous administration of 20 mg/kg, as compared with compound A.

Test Example 4: In Vitro Cell Growth Inhibition Test Against WI-38 (Human Fetal Lung Fibroblast Cell Line)

A WI-38 cell suspension was inoculated at $5\times10^3$ cells/100 μL/well (0.1 mL) to a 96-well flat-bottomed multiplate using DMEM (Sigma-Aldrich Co. LLC, D6429) medium containing 10% FBS (fetal bovine serum, Nichirei Biosciences Inc.), and cultured at 37° C. for 1 day in an incubator containing 5% carbon dioxide. Compound A or the compound of the present invention was dissolved at a concentration of 10 mM in dimethyl sulfoxide and further diluted into 12.5 μM (final concentration) using dimethyl sulfoxide and RPMI-1640 medium. This dilution was added at 0.1 mL/well to the culture plate of the WI-38 cells mentioned above after removal of the medium, and the cells were cultured at 37° C. for 3 days in an incubator containing 5% carbon dioxide.

After the culture, Cell Counting Kit-8 (Dojindo Laboratories), which adopts WST-8 as a chromogenic substrate, was added at 10 μL/well, and the cells were cultured under the same conditions as above for 1 hour, followed by measurement of absorbance at 450 nm. A cell survival rate was calculated with that of a control group defined as 100%. The results are shown in Table 4.

TABLE 4

| Compound No. | Cell survival rate (%) |
|---|---|
| 078 | 68 |
| Compound A | 26 |

From the results of Table 4, the compound of the present invention was confirmed to be very low toxic.

The invention claimed is:

1. A pyridone carboxylic acid derivative of formula (1) or a salt thereof:

(1)

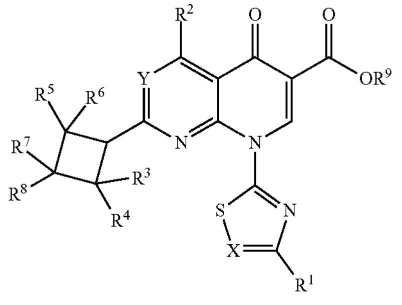

wherein $R^1$ represents a hydrogen atom, a halogen atom, a nitrile group, an optionally substituted lower alkyl group, an optionally substituted lower alkoxy group, an optionally substituted lower alkylamino group, a cyclo lower alkyl group, a cyclic amino group, an optionally substituted aryl group or an optionally substituted heteroaryl group;

$R^2$ represents a hydrogen atom, a halogen atom, a nitro group, a hydroxy group, an optionally substituted lower alkyl group, a lower alkoxy group, an amino group, an optionally substituted lower alkylamino group, a cyclo lower alkyl group, an optionally substituted 4- to 7-membered cyclic amino group or a $C_{1-17}$ alkanoylamino group;

$R^3$ to $R^6$ are the same or different and each represent a hydrogen atom, an optionally substituted lower alkyl group, a carboxy group, a lower alkoxy carbonyl group or an optionally substituted carbamoyl group;

$R^7$ represents a hydrogen atom, a halogen atom, a hydroxy group, an optionally substituted amino group, a carboxy group, a nitrile group, an optionally substituted lower alkyl group or a lower alkoxy group;

$R^8$ represents a hydrogen atom, a halogen atom, a hydroxy group, an optionally substituted lower alkyl group, an optionally substituted lower alkenyl group, an optionally substituted cyclo lower alkyl group, an optionally substituted lower alkoxy group, an optionally substituted lower alkylaminocarbonylalkyl group, a lower alkanoyloxy group, a lower alkanoylthio group, an arylcarbonylthio group, a thiol group, —SS—$R^{8a}$, wherein $R^{8a}$ represents an optionally substituted lower alkyl group or a group represented by any of following 1), 2), 4) and 5):

1) formula (a):

(a)

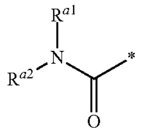

wherein $R^{a1}$ and $R^{a2}$ are the same or different and each represent a hydrogen atom, a hydroxy group, an optionally substituted lower alkyl group, an optionally substituted lower alkenyl group, an optionally substituted lower alkynyl group, an optionally substituted lower alkoxy group, an optionally substituted $C_{2-12}$ alkyl or alkoxy group having an ether bond(s), an optionally substituted heteroarylamino group, an optionally substituted nitrogen-containing bicyclic heteroaryl group, —$R^{a3}$-$Cy^1$, wherein $R^{a3}$ represents a single bond, an optionally halogen atom-substituted divalent hydrocarbon group or an oxy group, and $Cy^1$ represents an optionally substituted cyclo lower alkyl group, an optionally substituted 4- to 7-membered cyclic ether group, a N-substituted morpholinyl group, an oxazinanyl group or an isoxazolinyl group, an optionally substituted 5- or 6-membered heteroaryl group, an optionally substituted heteroaralkyl group, or following group:

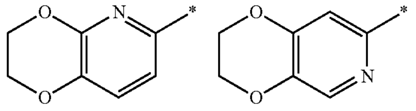

or $R^{a1}$ and $R^{a2}$ form an optionally substituted 4- to 9-membered cyclic amino group together with the adjacent nitrogen atom, and * represents a bonding site;

2) formula (b):

(b)

$(R^{b1})_m$—Het—* wherein Het represents a 4- to 6-membered heterocyclyl group, $R^{b1}$ is a substituent on the hetero ring wherein when a plurality of $R^{b1}$ are present, these moieties are the same or different and each represent a halogen atom, a hydroxy group, an amino group, a nitro group, an amide group, a lower alkylamide group, a carboxy group, an optionally substituted lower alkyl group, an optionally substituted lower alkoxy group, a lower alkoxycarbonyl group, an optionally substituted 4- to 7-membered cyclic ether group, a lower alkylamino group, a lower alkanoylamino group or an oxy group, m represents an integer of 0 to 2, and * represents a bonding site;

4) formula (d):

(d)

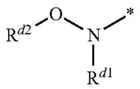

wherein $R^{d1}$ represents a hydrogen atom, an optionally substituted lower alkyl group or an optionally substituted $C_{1-17}$ alkanoyl group, $R^{d2}$ represents a hydrogen atom, an optionally substituted lower alkyl group, an optionally substituted aralkyl group or an optionally substituted heteroaralkyl group, and * represents a bonding site; and 5) formula (e):

(e)

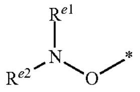

wherein $R^{e1}$ and $R^{e2}$ are the same or different and each represent a hydrogen atom, an optionally substituted lower alkyl group, an optionally substituted lower alkanoyl group, an optionally substituted aralkyl group or an optionally substituted 5- or 6-membered heteroaryl group, and * represents a bonding site;

or $R^7$ and $R^8$ together represent $=N-OR^{10}$, wherein $R^{10}$ represents a hydrogen atom, or $=O$, or $R^7$ and $R^8$ form an optionally substituted 4- to 6-membered saturated hetero ring together with the adjacent carbon atom;

$R^9$ represents a hydrogen atom or an ester residue;

X represents a nitrogen atom or $C-R^{11}$, wherein $R^{11}$ represents a hydrogen atom, a halogen atom, a nitrile group, a nitro group, a lower alkyl group, a lower alkoxy group, an optionally substituted thienyl group, or an optionally substituted phenyl group, or $R^1$ and $R^{11}$ form a benzene ring or a naphthalene ring together with the adjacent carbon atom; and Y represents a nitrogen atom or $C-R^{12}$, wherein $R^{12}$ represents a hydrogen atom, a halogen atom, a nitrile group or an optionally substituted lower alkyl group, except for the case where $R^7$ is an amino group and $R^8$ is a hydrogen atom and the case where $R^7$ is a hydrogen atom and $R^8$ is a methylamino group.

2. The pyridone carboxylic acid derivative according to claim 1 or a salt thereof, wherein $R^8$ is a group of the formula (a).

3. The pyridone carboxylic acid derivative according to claim 2 or a salt thereof, wherein in the formula (a), any one of $R^{a1}$ and $R^{a2}$ is a hydrogen atom, and the other moiety is an optionally substituted $C_{2-12}$ alkyl group having an ether bond(s), $-R^{a3}$-$Cy^1$ or an optionally substituted 5- or 6-membered heteroaryl group.

4. The pyridone carboxylic acid derivative according to claim 1 or a salt thereof, wherein $R^8$ is a group of the formula (e).

5. The pyridone carboxylic acid derivative according to claim 4 or a salt thereof, wherein in the formula (e), $R^{e1}$ is a hydrogen atom or an optionally substituted lower alkyl group, and $R^{e2}$ is an optionally substituted lower alkyl group.

6. The pyridone carboxylic acid derivative according to claim 1 or a salt thereof, wherein $R^8$ is a group of the formula (d).

7. The pyridone carboxylic acid derivative according to claim 6 or a salt thereof, wherein in the formula (d), $R^{d1}$ is a hydrogen atom, and $R^{d2}$ is an optionally substituted $C_{1-7}$ alkyl group.

8. The pyridone carboxylic acid derivative according to claim 1 or a salt thereof, wherein in the formula (1), $R^1$ is a hydrogen atom or a halogen atom, $R^2$ is a hydrogen atom or an optionally substituted $C_{1-7}$ alkyl group, each of $R^3$ to $R^6$ is a hydrogen atom, $R^7$ is a hydrogen atom, $R^9$ is a hydrogen atom, and Y is $C-R^{12}$.

9. A medicament comprising the pyridone carboxylic acid derivative according to claim 1 or a salt thereof and a pharmaceutically acceptable carrier.

10. An antitumor agent comprising the pyridone carboxylic acid derivative according to claim 1 or a salt thereof as an active ingredient.

11. An antitumor agent, comprising the pyridone carboxylic acid derivative according to claim 1 or a salt thereof.

12. A method for treating a cancer, the method comprising:

administering the pyridone carboxylic acid derivative according to claim 1 or a salt thereof to a subject in need thereof, wherein said cancer is at least one selected from the group consisting of rectal cancer, large intestine cancer, familial polyposis coli, hereditary non-polyposis, colorectal cancer-kidney cancer, stromal cancer of the kidney, ovary cancer, uterine corpus cancer, pancreatic cancer, prostate cancer, breast cancer, urinary organ cancer, malignant melanoma, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, diffuse large B-cell lymphoma (DLBCL), myelodysplastic syndrome (MDS), small-cell lung cancer, non-small cell lung cancer, multiple myeloma, choroidal malignant melanoma, rhabdomyosarcoma, osteosarcoma chondrosarcoma, myosarcoma, liposarcoma, fibrosarcoma, and Ewing's sarcoma.

13. The pyridone carboxylic acid derivative according to claim 1 or a salt thereof, wherein $R^8$ is a group represented by the formula (b).

14. The pyridone carboxylic acid derivative according to claim 8 or a salt thereof, wherein $R^8$ is a group represented by the formula (b) wherein m is 0, and Het is a 6π-electron system nitrogen-containing heterocyclyl group.

* * * * *

UNITED STATES PATENT AND TRADEMARK OFFICE

CERTIFICATE OF CORRECTION

PATENT NO. : 11,286,255 B2
APPLICATION NO. : 16/496145
DATED : March 29, 2022
INVENTOR(S) : Yamaguchi et al.

It is certified that error appears in the above-identified patent and that said Letters Patent is hereby corrected as shown below:

In the Claims

Column 595, Line 56, Claim 1, "a lower alkoxy carbonyl" should read -- a lower alkoxycarbonyl group --.

Column 598, Line 37, Claim 12, "cancer-kidney cancer," should read -- cancer, kidney cancer, --.

Signed and Sealed this
Fifth Day of July, 2022

Katherine Kelly Vidal
*Director of the United States Patent and Trademark Office*